US012528781B2

(12) United States Patent
Meng et al.

(10) Patent No.: US 12,528,781 B2
(45) **Date of Patent: *Jan. 20, 2026**

(54) HETEROCYCLIC GLP-1 AGONISTS

(71) Applicant: Gasherbrum Bio, Inc., South San Francisco, CA (US)

(72) Inventors: Qinghua Meng, Shanghai (CN); Hui Lei, Shanghai (CN); Haizhen Zhang, Shanghai (CN); Xichen Lin, Shanghai (CN); Andrew Jennings, South San Francisco, CA (US)

(73) Assignee: Gasherbrum Bio, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/534,517

(22) Filed: Dec. 8, 2023

(65) Prior Publication Data

US 2024/0376061 A1 Nov. 14, 2024

Related U.S. Application Data

(63) Continuation of application No. 18/106,378, filed on Feb. 6, 2023, now Pat. No. 11,897,851, which is a continuation of application No. PCT/CN2021/111193, filed on Aug. 6, 2021.

(30) Foreign Application Priority Data

Aug. 6, 2020 (WO) ................ PCT/CN2020/107437
Jan. 27, 2021 (WO) ................ PCT/CN2021/073958

(51) Int. Cl.
*C07D 273/01* (2006.01)
*A61K 9/00* (2006.01)
*A61K 45/06* (2006.01)

(52) U.S. Cl.
CPC .......... *C07D 273/01* (2013.01); *A61K 9/0053* (2013.01); *A61K 45/06* (2013.01)

(58) Field of Classification Search
CPC ..... C07D 273/01; A61K 9/0053; A61K 45/06
See application file for complete search history.

(56) References Cited

U.S. PATENT DOCUMENTS

| | | | |
|---|---|---|---|
| 11,926,626 B2 | 3/2024 | Meng et al. |
| 2008/0280933 A1 | 11/2008 | Efremov et al. |
| 2018/0170908 A1 | 6/2018 | Aspnes et al. |
| 2019/0276465 A1 | 9/2019 | Xu |
| 2019/0382384 A1 | 12/2019 | Aspnes et al. |
| 2019/0382387 A1 | 12/2019 | Aspnes et al. |
| 2023/0071840 A1 | 3/2023 | Meng et al. |
| 2023/0107793 A1 | 4/2023 | Meng et al. |
| 2023/0165846 A1 | 6/2023 | Meng et al. |
| 2023/0192633 A1 | 6/2023 | Meng et al. |
| 2023/0295154 A1 | 9/2023 | Meng et al. |
| 2023/0391760 A1 | 12/2023 | Meng et al. |
| 2024/0083886 A1 | 3/2024 | Meng et al. |
| 2024/0246962 A1 | 7/2024 | Meng et al. |

FOREIGN PATENT DOCUMENTS

| | | |
|---|---|---|
| CN | 108017636 | 5/2018 |
| CN | 108430998 | 8/2018 |
| CN | 109790161 A | 5/2019 |
| CN | 110325530 | 10/2019 |
| CN | 112533674 A | 3/2021 |
| CN | 113480534 | 10/2021 |
| CN | 113493447 | 10/2021 |
| CN | 113773310 | 12/2021 |
| CN | 113801136 | 12/2021 |
| CN | 113816948 | 12/2021 |
| CN | 113831337 | 12/2021 |
| CN | 114591296 | 6/2022 |
| CN | 114591308 | 6/2022 |
| CN | 114634510 | 6/2022 |
| CN | 114716423 | 7/2022 |
| CN | 114761395 A | 7/2022 |

(Continued)

OTHER PUBLICATIONS

Database Registry Chemical Abstracts Service; Sep. 21, 2008, Anonymous: "1-Ethyl-2-[[[5-[[5-(3-thienyl)-2H-tetrazol-2-yl]methyl]-1, 3, 4-oxadiazol-2-yl]thio]methyl]-1H-benzimidazole-5-carboxylic acid" Database accession No. 1051103-45-7.
ACS STN. RN 1290110-76-7, 1228633-44-0, 1228554-41-3. STN Registry. May 4, 2011. 2 pages.
GLP-1 Receptor Agonists—The Johns Hopkins Patient Guide to Diabetes (hopkinsdiabetesinfo.org), https://hopkinsdiabetesinfo.org/medications-for-type-2-diabetes-glp-1-agonists/.
GLP-1 agonists: Diabetes drugs and weight loss—Mayo Clinic.
International Search Report and Written Opinion for PCT/CN2021/111193 dated Nov. 8, 2021, 9 pages.

*Primary Examiner* — Jared Barsky
(74) *Attorney, Agent, or Firm* — Sheppard Mullin Richter & Hampton LLP

(57) ABSTRACT

This disclosure relates to GLP-1 agonists of Formula I:

Formula I

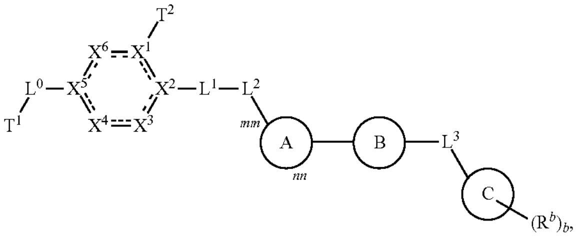

including pharmaceutically acceptable salts and solvates thereof, and pharmaceutical compositions including the same.

21 Claims, No Drawings

(56) References Cited

FOREIGN PATENT DOCUMENTS

| | | | |
|---|---|---|---|
| CN | 114763352 | | 7/2022 |
| CN | 114907351 | | 8/2022 |
| CN | 115594669 | A | 1/2023 |
| CN | 115884969 | A | 3/2023 |
| WO | WO 2004/026305 | | 4/2004 |
| WO | WO 2005/002503 | A2 | 1/2005 |
| WO | WO 2006/102610 | | 9/2006 |
| WO | WO 2007/146122 | | 12/2007 |
| WO | WO 2008/137770 | A1 | 11/2008 |
| WO | WO 2008/153701 | | 12/2008 |
| WO | WO 2009/143039 | A2 | 11/2009 |
| WO | WO 2010/065674 | A1 | 6/2010 |
| WO | WO 2011/068821 | | 6/2011 |
| WO | WO 2018/056453 | A1 | 3/2018 |
| WO | WO 2018/085148 | A1 | 5/2018 |
| WO | WO 2018/109607 | A1 | 6/2018 |
| WO | WO 2018/157857 | A1 | 9/2018 |
| WO | WO 2019/239319 | A1 | 12/2019 |
| WO | WO 2019/239371 | | 12/2019 |
| WO | WO 2020/103815 | | 5/2020 |
| WO | WO 2020/207474 | | 10/2020 |
| WO | WO 2020/234726 | | 11/2020 |
| WO | WO 2020/263695 | | 12/2020 |
| WO | WO 2021/018023 | | 2/2021 |
| WO | WO 2021/081207 | | 4/2021 |
| WO | WO 2021/096284 | | 5/2021 |
| WO | WO 2021/096304 | | 5/2021 |
| WO | WO 2021/112538 | | 6/2021 |
| WO | WO 2021/154796 | | 8/2021 |
| WO | WO 2021/160127 | | 8/2021 |
| WO | WO 2021/187886 | | 9/2021 |
| WO | WO 2021/197464 | | 10/2021 |
| WO | WO 2021/219019 | | 11/2021 |
| WO | WO 2021/244645 | | 12/2021 |
| WO | WO 2021/249492 | | 12/2021 |
| WO | WO 2021/254470 | | 12/2021 |
| WO | WO 2021/259309 | A1 | 12/2021 |
| WO | WO 2022/007979 | | 1/2022 |
| WO | WO 2022/028572 | | 2/2022 |
| WO | WO 2022/031994 | | 2/2022 |
| WO | WO 2022/040600 | | 2/2022 |
| WO | WO 2022/042691 | | 3/2022 |
| WO | WO 2022/048665 | A1 | 3/2022 |
| WO | WO 2022/068772 | | 4/2022 |
| WO | WO 2022/078152 | | 4/2022 |
| WO | WO 2022/078380 | | 4/2022 |
| WO | WO 2022/078407 | | 4/2022 |
| WO | WO 2022/109182 | | 5/2022 |
| WO | WO 2022/111624 | | 6/2022 |
| WO | WO 2022/135572 | | 6/2022 |
| WO | WO 2022/165076 | | 8/2022 |
| WO | WO 2022/192428 | | 9/2022 |
| WO | WO 2022/192430 | | 9/2022 |
| WO | WO 2022/199458 | | 9/2022 |
| WO | WO 2022/199661 | | 9/2022 |
| WO | WO 2022/202864 | | 9/2022 |
| WO | WO 2022/216094 | | 10/2022 |
| WO | WO-2022219495 | A1 * | 10/2022 ........... A61K 31/454 |
| WO | WO 2022/228490 | A1 | 11/2022 |
| WO | WO 2023/138684 | A1 | 7/2023 |
| WO | WO 2023/151574 | A1 | 8/2023 |
| WO | WO 2023/151575 | A1 | 8/2023 |
| WO | WO 2023/179542 | A1 | 9/2023 |
| WO | WO 2023/198140 | A1 | 10/2023 |

* cited by examiner

HETEROCYCLIC GLP-1 AGONISTS

CROSS REFERENCE TO RELATED APPLICATIONS

The application is a continuation of U.S. application Ser. No. 18/106,378, filed Feb. 6, 2023, which is a continuation of International Patent Application Number PCT/CN2021/111193, filed on Aug. 6, 2021, which claims the benefit of International Patent Application Number PCT/CN2020/107437, filed on Aug. 6, 2020, and International Patent Application Number PCT/CN2021/073958, filed on Jan. 27, 2021, each of which is incorporated herein by reference in its entirety.

TECHNICAL FIELD

This disclosure relates to GLP-1 agonists, pharmaceutical compositions, and methods of use thereof.

BACKGROUND

Incretin metabolic hormones, including glucagon-like peptide-1 (GLP-1) and glucose-dependent insulinotropic polypeptide (GIP), are important in the regulation of glucose homeostasis. Medicaments targeting this family of intestinal peptides, such as GLP-1 agonists, have been shown to suppress glucagon production, decrease gastric motility, and increase satiety.

Diabetes mellitus refers to a group of metabolic disorders characterized by persistent hyperglycemia. The most common form, type 2 diabetes mellitus (T2DM) is an acquired condition that accounts for more than 90% of diabetes cases. Typical onset occurs in obese or otherwise sedentary adults and begins with insulin resistance. Though lifestyle changes can be useful in management of this disorder, patients with T2DM may be required to take anti-diabetic medications, including dipeptidyl peptidase-4 inhibitors, SGLT2 inhibitors, and sulfonylureas, among others.

In healthy individuals, the incretin hormones glucose-dependent insulinotropic polypeptide (GIP) and glucagon-like peptide 1 (GLP-1) provide tandem modulation of insulin secretory response to glucose ingestion. While this incretin effect is significantly diminished (if at all present) in cases of T2DM, GLP-1 retains insulinotropic properties, even as endocrine pancreatic response to GIP is effectively halted. As such, incretin mimetics and other GLP-1-based therapies can help stimulate insulin production in T2DM patients.

SUMMARY

The present application describes heterocyclic GLP-1 agonists, as well as pharmaceutical compositions comprising the compounds disclosed herein. Also provided are methods for treating GLP-1-associated diseases, disorders, and conditions.

Accordingly, provided herein are compounds of Formula I:

Formula I

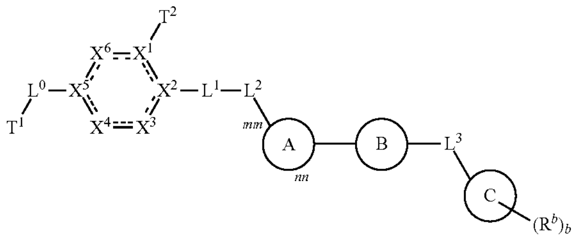

or a pharmaceutically acceptable salt or solvate thereof, wherein:

$X^1$, $X^2$, and $X^5$ are independently C or N;

$X^3$ and $X^4$ are independently selected from the group consisting of: N, $NR^x$, $CR^y$, C(=O), O, and S;

$X^6$ is selected from the group consisting of: a bond, N, $NR^x$, $CR^y$, and C(=O);

each ⎓ is a single bond or a double bond, provided that at least one of $X^1$-$X^6$ is an independently selected heteroatom or heteroatomic group; at least one of $X^1$-$X^6$ is C or $CR^y$; and the ring including $X^1$-$X^6$ is aromatic;

each RX is independently selected from the group consisting of: hydrogen, $(C_1$-$C_6)$alkyl, $(C_1$-$C_6)$haloalkyl, C(=O)$(C_1$-$C_6)$alkyl, $S(O)_2(C_1$-$C_6)$alkyl, and C(=O)O$(C_1$-$C_6)$alkyl;

each BY is independently selected from the group consisting of: hydrogen, —OH, $(C_1$-$C_6)$alkyl, $(C_1$-$C_6)$haloalkyl, $(C_1$-$C_6)$alkoxy, $(C_1$-$C_6)$haloalkoxy, CN, and halogen;

$L^0$ is a bond or #—$P^0$-$P^1$, wherein #represents the point of attachment to $X^5$;

—$P^0$ is a bond, —NH—, —N$(C_1$-$C_6$ alkyl)-, —O—, or $S(O)_{0-2}$;

—$P^1$ is selected from the group consisting of: $(C_1$-$C_6)$alkylene, $(C_2$-$C_6)$alkenylene, $(C_2$-$C_6)$alkynylene, $(C_3$-$C_8)$cycloalkylene, and 4- to 8-membered heterocycloalkylene, each of which is optionally substituted with 1-3 $R^0$;

each $R^0$ is independently selected from the group consisting of: halogen, CN, $(C_1$-$C_6)$alkyl, $(C_1$-$C_6)$haloalkyl, $(C_1$-$C_6)$alkoxy, and $(C_1$-$C_6)$haloalkoxy;

$T^1$ is C(=O)OH or a carboxylic acid bioisostere;

$T^2$ is hydrogen, CN, $(C_1$-$C_6)$haloalkyl, $(C_1$-$C_6)$hydroxyalkyl or $(C_1$-$C_6)$alkyl which is optionally substituted with $(C_1$-$C_6)$alkoxy, $(C_1$-$C_6)$thioalkoxy, $(C_1$-$C_6)$haloalkoxy, $S(O)_2(C_1$-$C_6$ alkyl), —N$(C_1$-$C_6$ alkyl)-$S(O)_2(C_1$-$C_6$ alkyl), —NH—$S(O)_2(C_1$-$C_6$ alkyl), $(C_3$-$C_6)$cycloalkyl, $(C_3$-$C_6)$cycloalkoxy, 3- to 6-membered heterocycloalkyl, phenyl, or 5- to 6-membered heteroaryl, wherein each of the $(C_3$-$C_6)$cycloalkyl, 3- to 6-membered heterocycloalkyl, phenyl, or 5- to 6-membered heteroaryl is optionally substituted with 1-4 $R^T$;

each $R^T$ is independently selected from the group consisting of OH, SH, CN, $NO_2$, halogen, =O, $(C_1$-$C_6)$alkyl, $(C_2$-$C_6)$alkenyl, $(C_2$-$C_6)$alkynyl, $(C_1$-$C_6)$haloalkyl, $(C_1$-$C_6)$cyanoalkyl, $(C_1$-$C_6)$hydroxyalkyl, $(C_1$-$C_6)$alkoxy, $(C_1$-$C_6)$haloalkoxy, $(C_3$-$C_6)$cycloalkyl, amino, $(C_1$-$C_6)$alkylamino, $(C_1$-$C_6)$alkylamino$(C_1$-$C_6$ alkyl)-C(O)—$C_1$-$C_6$ alkyl, $S(O)_2(C_1$-$C_6$ alkyl) and di$(C_1$-$C_6)$alkylamino;

$L^1$ is a bond or $(C_1$-$C_3)$alkylene which is optionally substituted with 1-3 $R^L$;

$L^2$ is a bond, —O—, —$S(O)_{0-2}$—, or —NH—;

each $R^L$ is independently selected from the group consisting of: halogen, $(C_1\text{-}C_3)$alkyl, and $(C_1\text{-}C_3)$haloalkyl; or a pair of $R^L$ on the same or on adjacent carbon atoms, taken together with the atom(s) to which each is attached, forms a $(C_3\text{-}C_6)$cycloalkyl ring;

Ring A is selected from the group consisting of:

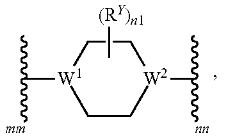

wherein n1 is O, 1, or 2, $W^1$ is $CR^{Y1}$ or N and $W^2$ is $CR^{Y2}$ or N;

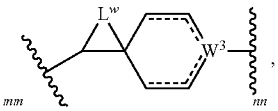

wherein $W^3$ is C, $CR^{Y3}$ or N, $L^W$ is $(C_1\text{-}C_3)$alkylene, and each ═══ is independently a single bond or a double bond, as allowed by valence;

phenylene optionally substituted with 1-4 $R^Y$;

5- to 6-membered heteroarylene optionally substituted with 1-3 $R^Y$;

partially unsaturated monocyclic $(C_5\text{-}C_8)$cycloalkylene optionally substituted with 1-4 $R^Y$; and partially unsaturated monocyclic 5- to 8-membered heterocycloalkylene optionally substituted with 1-4 $R^Y$;

wherein mm represents the point of attachment to $L^2$, and nn represents the point of attachment to Ring B;

each occurrence of $R^Y$ is independently selected from the group consisting of halogen, CN, —OH, oxo, $(C_1\text{-}C_6)$alkyl, $(C_1\text{-}C_3)$haloalkyl, $(C_1\text{-}C_3)$alkoxy, and $(C_1\text{-}C_3)$haloalkoxy;

$R^{Y1}$, $R^{Y2}$, and $R^{Y3}$ are each independently selected from the group consisting of hydrogen, halogen, CN, —OH, $(C_1\text{-}C_6)$alkyl, $(C_1\text{-}C_3)$haloalkyl, $(C_1\text{-}C_3)$alkoxy, and $(C_1\text{-}C_3)$haloalkoxy; or when $W^1$ is $CR^{Y1}$ and $W^2$ is $CR^{Y2}$, the $R^{Y1}$ and $R^{Y2}$ groups taken together can form $(C_1\text{-}C_4)$alkylene, wherein one of the $CH_2$ units of the $(C_1\text{-}C_4)$alkylene is optionally replaced by a heteroatom selected from the group consisting of O, S, NH, and $N(C_{1\text{-}3})$alkyl;

Ring B is selected from the group consisting of: (B-I), (B-II), (B-III), (B-IV), (B-V), and (B-VI);

(B-I)

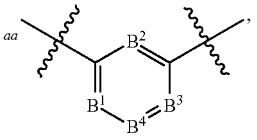

(B-II)

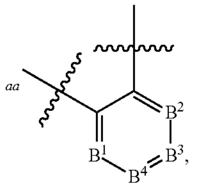

-continued (B-III)

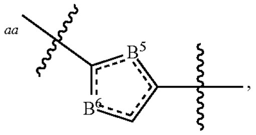

(B-IV)

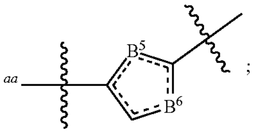

wherein aa represents the point of attachment to Ring A;

each of $B^1$, $B^2$, $B^3$, and $B^4$ is independently selected from the group consisting of $CR^1$ and N;

each of $B^5$ and $B^6$ is independently selected from the group consisting of N, $NR^1$, C, $CR^1$, O, and S, provided that the ring containing $B^5$ and $B^6$ is heteroaryl;

(B-V)

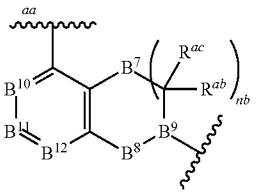

and (B-VI)

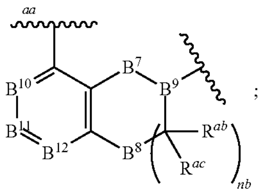

wherein aa represents the point of attachment to Ring A;

$B^7$ and $B^8$ are independently selected from the group consisting of: —O—, —$NR^N$—, and —$C(R')_2$—; $B^9$ is N or $CR^{aa}$;

nb is 0 or 1;

$B^{10}$, $B^{11}$ and $B^{12}$ are independently selected from the group consisting of $CR^1$ and N;

each $R^1$ is independently selected from the group consisting of hydrogen, halogen, CN, $(C_1\text{-}C_6)$alkyl, $(C_1\text{-}C_6)$haloalkyl; $(C_1\text{-}C_3)$alkyl$(C_3\text{-}C_6)$cycloalkyl, $(C_1\text{-}C_3)$alkyl(3- to 5-membered heterocycloalkyl), and —$C(O)NR^2R^3$;

each $R^2$ and $R^3$ is independently selected from the group consisting of H and $(C_1\text{-}C_6)$alkyl;

each $R^N$ is independently selected from the group consisting of hydrogen, $(C_1\text{-}C_6)$alkyl, $(C_1\text{-}C_6)$haloalkyl, $C({=}O)(C_1\text{-}C_6)$alkyl, $S(O)_2(C_1\text{-}C_6)$alkyl, and $C({=}O)O(C_1\text{-}C_6)$alkyl;

$R^{aa}$, $R^{ab}$, and $R^{ac}$ are each independently selected from the group consisting of H, $(C_1\text{-}C_6)$alkyl, and $(C_1\text{-}C_6)$haloalkyl;

$L^3$ is a bond or —$Z^1$—$Z^2$—*, wherein * represents the point of attachment to Ring C;

—$Z^1$ is a bond, NH, $N(C_1\text{-}C_6$ alkyl), O, or $S(O)_{0\text{-}2}$;

—$Z^2$ is $C_{1\text{-}3}$ alkylene optionally substituted with 1-2 $R^c$;

each $R^c$ is independently selected from the group consisting of halogen, $(C_1-C_6)$alkyl, and $(C_1-C_3)$haloalkyl;

Ring C is selected from the group consisting of phenyl, 5- to 6-membered heteroaryl, $(C_3-C_6)$cycloalkyl, $(C_5-C_{10})$ bicycloalkyl, 5- to 10-membered bicycloheteroaryl, and 3- to 6-membered heterocycloalkyl;

each $R^b$ is independently selected from the group consisting of $(C_1-C_6)$alkyl, $(C_1-C_6)$haloalkyl, $(C_1-C_6)$alkoxy, $(C_1-C_6)$haloalkoxy, halogen, $(C_3-C_6)$cycloalkyl, and CN; and b is an integer selected from 0-3.

Also provided herein are pharmaceutical compositions comprising a compound of Formula I, or a pharmaceutically acceptable salt or solvate thereof, and a pharmaceutically acceptable excipient.

Also provided herein are methods for treating type 2 diabetes mellitus in a patient in need thereof, the methods comprising administering to the patient a therapeutically effective amount of a compound of Formula I, or a pharmaceutically acceptable salt or solvate thereof, or a pharmaceutical composition thereof.

Also provided herein are methods for treating type 2 diabetes mellitus in a patient, the methods comprising administering to a patient identified or diagnosed as having type 2 diabetes mellitus a therapeutically effective amount of a compound of Formula I, or a pharmaceutically acceptable salt or solvate thereof, or a pharmaceutical composition thereof.

Also provided herein are methods for treating diabetes mellitus in a patient, the methods comprising determining that the patient has type 2 diabetes mellitus; and administering to the patient a therapeutically effective amount of a compound of Formula I, or a pharmaceutically acceptable salt or solvate thereof, or a pharmaceutical composition thereof. In some embodiments, the step of determining that the patient has type 2 diabetes mellitus includes performing an assay to determine the level of an analyte in a sample from the patient, wherein the analyte is selected from the group consisting of hemoglobin A1c (HbA1c), fasting plasma glucose, non-fasting plasma glucose, or any combination thereof. In some embodiments, the level of HbA1c is greater than or about 6.5%. In some embodiments, the level of fasting plasma glucose is greater than or about 126 mg/dL. In some embodiments, the level of non-fasting plasma glucose is greater than or about 200 mg/dL.

In some embodiments, the methods further comprise obtaining a sample from the patient. In some embodiments, the sample is a body fluid sample. In some embodiments, the patient is about 40 to about 70 years old and is overweight or obese. In some embodiments, the patient has a body mass index (BMI) greater than or about 22 kg/$m^2$. In some embodiments, the patient has a BMI greater than or about 30 kg/$m^2$.

In some embodiments, the methods for the treatment of type 2 diabetes mellitus comprise a reduction in fasting plasma glucose levels. In some embodiments, the fasting plasma glucose levels are reduced to about or below 100 mg/dL.

In some embodiments, the methods for the treatment of type 2 diabetes mellitus comprise a reduction in HbA1c levels. In some embodiments, the HbA1c levels are reduced to about or below 5.7%.

In some embodiments, the methods for the treatment of type 2 diabetes mellitus comprise a reduction in glucagon levels.

In some embodiments, the methods for the treatment of type 2 diabetes mellitus comprise an increase in insulin levels.

In some embodiments, the methods for the treatment of type 2 diabetes mellitus comprise a decrease in BMI. In some embodiments, the BMI is decreased to about or below 25 kg/$m^2$.

In some embodiments, the compound of Formula I, or a pharmaceutically acceptable salt or solvate thereof, or a pharmaceutical composition thereof, is administered orally.

In some embodiments, the methods of treatment for type 2 diabetes mellitus further comprise administering an additional therapy or therapeutic agent to the patient. In some embodiments, the additional therapy or therapeutic agent is selected from the group consisting of an anti-diabetic agent, an anti-obesity agent, a GLP-1 receptor agonist, an agent to treat non-alcoholic steatohepatitis (NASH), gastric electrical stimulation, dietary monitoring, physical activity, or any combinations thereof. In some embodiments, the anti-diabetic agent is selected from the group consisting of a biguanide, a sulfonylurea, a glitazar, a thiazolidinedione, a dipeptidyl peptidase 4 (DPP-4) inhibitor, a meglitinide, a sodium-glucose linked transporter 2 (SGLT2) inhibitor, a glitazone, a GRP40 agonist, a glucose-dependent insulinotropic peptide (GIP), an insulin or insulin analogue, an alpha glucosidase inhibitor, a sodium-glucose linked transporter 1 (SGLT1) inhibitor, or any combinations thereof. In some embodiments, the biguanide is metformin. In some embodiments, the anti-obesity agent is selected from the group consisting of neuropeptide Y receptor type 2 (NPYR2) agonist, a NPYR1 or NPYR5 antagonist, a human proislet peptide (HIP), a cannabinoid receptor type 1 (CB 1R) antagonist, a lipase inhibitor, a melanocortin receptor 4 agonist, a farnesoid X receptor (FXR) agonist, phentermine, zonisamide, a norepinephrine/dopamine reuptake inhibitor, a GDF-15 analog, an opioid receptor antagonist, a cholecystokinin agonist, a serotonergic agent, a methionine aminopeptidase 2 (MetAP2) inhibitor, diethylpropion, phendimetrazine, benzphetamine, a fibroblast growth factor receptor (FGFR) modulator, an AMP-activated protein kinase (AMPK) activator, or any combinations thereof. In some embodiments, the GLP-1 receptor agonist is selected from the group consisting of liraglutide, exenatide, dulaglutide, albiglutide, taspoglutide, lixisenatide, semaglutide, or any combinations thereof. In some embodiments, the agent to treat NASH is selected from the group consisting of an FXR agonist, PF-05221304, a synthetic fatty acid-bile conjugate, an anti-lysyl oxidase homologue 2 (LOXL2) monoclonal antibody, a caspase inhibitor, a MAPKS inhibitor, a galectin 3 inhibitor, a fibroblast growth factor 21 (FGF21) agonist, a niacin analogue, a leukotriene D4 (LTD4) receptor antagonist, an acetyl-CoA carboxylase (ACC) inhibitor, a ketohexokinase (KHK) inhibitor, an ileal bile acid transporter (IBAT) inhibitor, an apoptosis signal-regulating kinase 1 (ASK1) inhibitor, or any combinations thereof. In some embodiments, the compound of Formula I, or a pharmaceutically acceptable salt or solvate thereof, or a pharmaceutical composition thereof, and the additional therapeutic agent are administered as separate dosages sequentially in any order.

Also provided herein are methods for modulating insulin levels in a patient in need of such modulating, the method comprising administering to the patient an effective amount of a compound of Formula I, or a pharmaceutically acceptable salt or solvate thereof, or a pharmaceutical composition thereof. In some embodiments, the modulation results in an increase of insulin levels.

Also provided herein are methods for modulating glucose levels in a patient in need of such modulating, the method comprising administering to the patient an effective amount of a compound of Formula I, or a pharmaceutically acceptable salt or solvate thereof, or a pharmaceutical composition thereof. In some embodiments, the modulation results in a decrease of glucose levels.

Also provided herein are methods for treating a GLP-1 associated disease, disorder, or condition, the method comprising administering to a patient in need thereof an effective amount of a compound of Formula I, or a pharmaceutically acceptable salt or solvate thereof, or a pharmaceutical composition thereof. In some embodiments, the disease, disorder, or condition is selected from the group consisting of type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity, weight gain from use of other agents, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, Polycystic Ovary Syndrome (PCOS), or any combination thereof. In some embodiments, the disease, disorder, or condition is selected from the group consisting of type 2 diabetes mellitus, early onset type 2 diabetes mellitus, obesity, weight gain from use of other agents, gout, excessive sugar craving, hypertriglyceridemia, dyslipidemia, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non alcoholic steatohepatitis (NASH), non-alcoholic fatty liver disease (NAFLD), short bowel syndrome, Parkinson's disease, Polycystic Ovary Syndrome (PCOS), or any combination thereof. In some embodiments, the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

Other features and advantages of the invention will be apparent from the following detailed description and figures, and from the claims.

DETAILED DESCRIPTION

Provided herein are heterocyclic GLP-1 agonists for use in the management of T2DM and other conditions where activation of GLP-1 activity is useful.

DEFINITIONS

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

As used herein, the term "halo" or "halogen" means —F (sometimes referred to herein as "fluoro" or "fluoros"), —Cl (sometimes referred to herein as "chloro" or "chloros"), —Br (sometimes referred to herein as "bromo" or "bromos"), and —I (sometimes referred to herein as "iodo" or "iodos").

As used herein, the term "alkyl" refers to saturated linear or branched-chain monovalent hydrocarbon radicals, containing the indicated number of carbon atoms. For example, "($C_1$-$C_6$)alkyl" refers to saturated linear or branched-chain monovalent hydrocarbon radicals of one to six carbon atoms. Non-limiting examples of alkyl include methyl, ethyl, 1-propyl, isopropyl, 1-butyl, isobutyl, sec-butyl, tert-butyl, 2-methyl-2-propyl, pentyl, neopentyl, and hexyl.

As used herein, the term "alkylene" refers to a divalent alkyl containing the indicated number of carbon atoms. For example, "($C_1$-$C_3$)alkylene" refers to a divalent alkyl having one to three carbon atoms (e.g., $—CH_2—$, $—CH(CH_3)—$, $—CH_2CH_2—$, or $—CH_2CH_2CH_2—$). Similarly, the terms "cycloalkylene", "heterocycloalkylene", "arylene", and "heteroarylene" mean divalent cycloalkyl, heterocycloalkyl, aryl, and heteroaryl, respectively.

As used herein, the term "alkenyl" refers to a linear or branched mono unsaturated hydrocarbon chain, containing the indicated number of carbon atoms. For example, "($C_2$-$C_6$)alkenyl" refers a linear or branched mono unsaturated hydrocarbon chain of two to six carbon atoms. Non-limiting examples of alkenyl include ethenyl, propenyl, butenyl, or pentenyl.

As used herein, the term "alkynyl" refers to a linear or branched di-unsaturated hydrocarbon chain, containing the indicated number of carbon atoms. For example, "($C_2$-$C_6$) alkynyl" refers to a linear or branched di-unsaturated hydrocarbon chain having two to six carbon atoms. Non-limiting examples of alkynyl include ethynyl, propynyl, butynyl, or pentynyl.

As used herein, the term "cycloalkyl" refers to a saturated or partially unsaturated cyclic hydrocarbon, containing the indicated number of carbon atoms. For example, "($C_3$-$C_6$) cycloalkyl" refers to a saturated or partially unsaturated cyclic hydrocarbon having three to six ring carbon atoms. Non-limiting examples of cycloalkyl include cyclopropyl, cyclobutyl, cyclopentyl, and cyclohexyl. Cycloalkyl may be partially unsaturated. Non-limiting examples of partially unsaturated cycloalkyl include cyclohexenyl, cyclopentenyl, cycloheptenyl, cyclooctenyl, and the like. Cycloalkyl may include multiple fused and/or bridged rings. Non-limiting examples of fused/bridged cycloalkyl includes: bicyclo[1.1.0]butane, bicyclo[2.1.0]pentane, bicyclo[1.1.1]pentane, bicyclo[3.1.0]hexane, bicyclo[2.1.1]hexane, bicyclo[3.2.0]heptane, bicyclo[4.1.0]heptane, bicyclo[2.2.1]heptane, bicyclo[3.1.1]heptane, bicyclo[4.2.0]octane, bicyclo[3.2.1]octane, bicyclo[2.2.2]octane, and the like. Cycloalkyl also includes spirocyclic rings (e.g., spirocyclic bicycle wherein two rings are connected through just one atom). Non-limiting examples of spirocyclic cycloalkyls include spiro[2.2]pentane, spiro[2.5]octane, spiro[3.5]nonane, spiro[3.5]nonane, spiro[3.5]nonane, spiro[4.4]nonane, spiro[2.6]nonane, spiro[4.5]decane, spiro[3.6]decane, spiro[5.5]undecane, and the like.

As used herein, the term "heterocycloalkyl" refers to a mon-, bi-, tri-, or polycyclic nonaromatic ring system containing indicated number of ring atoms (e.g., 3-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, the heteroatoms selected from O, N, S, or $S(O)_{1-2}$ (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocycloalkyl groups include piperazinyl, pyrrolidinyl, dioxanyl, morpholinyl, tetrahydrofuranyl, and the like. Heterocycloalkyl groups may be partially unsaturated. Non-limiting examples of partially unsaturated heterocycloalkyl include dihydropyrrolyl, dihydropyridinyl, tetrahydropyridinyl, dihydrofuranyl, dihydropyranyl, and the like. Heterocycloalkyl may include multiple fused and bridged rings. Non-limiting examples of fused/bridged heteorocyclyl includes: 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, 3-azabicyclo[3.2.1]octane, 2-oxabicyclo[1.1.0]butane, 2-oxabicyclo[2.1.0]pentane, 2-oxabicyclo[1.1.1]pentane, 3-oxabicyclo[3.1.0]hexane, 5-oxabicyclo[2.1.1]hexane, 3-oxabicyclo[3.2.0]heptane, 3-oxabicyclo[4.1.0]heptane, 7-oxabicyclo[2.2.1]heptane, 6-oxabicyclo[3.1.1]heptane, 7-oxabicyclo[4.2.0]octane, 2-oxabicyclo[2.2.2]octane, 3-oxabicyclo[3.2.1]octane, and the like. Heterocycloalkyl also includes spirocyclic rings (e.g., spirocyclic bicycle wherein two rings are connected through just one atom). Non-limiting examples of spirocyclic heterocycloalkyl include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 7-azaspiro[4.5]decane 2,5-diazaspiro[3.6]decane, 3-azaspiro[5.5]undecane, 2-oxaspiro[2.2]pentane, 4-oxaspiro[2.5]octane, 1-oxaspiro[3.5]nonane, 2-oxaspiro[3.5]nonane, 7-oxaspiro[3.5]nonane, 2-oxaspiro[4.4]nonane, 6-oxaspiro[2.6]nonane, 1,7-dioxaspiro[4.5]decane, 2,5-dioxaspiro[3.6]decane, 1-oxaspiro[5.5]undecane, 3-oxaspiro[5.5]undecane, 3-oxa-9-azaspiro[5.5]undecane and the like.

As used herein, the term "aryl" refers to a mono-, bi-, tri- or polycyclic hydrocarbon group containing the indicated numbers of carbon atoms, wherein at least one ring in the system is aromatic (e.g., $C_6$ monocyclic, $C_{10}$ bicyclic, or $C_{14}$ tricyclic aromatic ring system). Examples of aryl groups include phenyl, naphthyl, tetrahydronaphthyl, and the like.

As used herein, the term "heteroaryl" refers to a mono-, bi-, tri- or polycyclic group having indicated numbers of ring atoms (e.g., 5-6 ring atoms; e.g., 5, 6, 9, 10, or 14 ring atoms); wherein at least one ring in the system is aromatic (but does not have to be a ring which contains a heteroatom, e.g. tetrahydroisoquinolinyl, e.g., tetrahydroquinolinyl), and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others.

As used herein, the term "haloalkyl" refers to an alkyl radical as defined herein, wherein one or more hydrogen atoms is replaced with one or more halogen atoms. Non-limiting examples include fluoromethyl, difluoromethyl, trifluoromethyl, 2-fluoroethyl, 2,2-difluoroethyl, 2,2,2-trifluoroethyl, chloromethyl, dichloromethyl, chloroethyl, trichloroethyl, bromomethyl, and iodomethyl.

As used herein, the term "hydroxyalkylalkyl" refers to an alkyl radical as defined herein, wherein one or more hydrogen atoms is replaced with one or more hydroxyl (—OH) groups.

As used herein, the term "alkoxy" refers to an —O-alkyl radical, wherein the radical is on the oxygen atom. For example, "$C_{1-6}$ alkoxy" refers to an —O—($C_{1-6}$ alkyl) radical, wherein the radical is on the oxygen atom. Examples of alkoxy include methoxy, ethoxy, propoxy, isopropoxy, butoxy and tert-butoxy. Accordingly, as used herein, the term "haloalkoxy" refers to an —O-haloalkyl radical, wherein the radical is on the oxygen atom.

As used herein, "- - -" indicates an optional single or double bond, as allowed by valence. As used herein, "~" indicates the point of attachment to the parent molecule.

As used herein, the term "compound," is meant to include all stereoisomers, geometric isomers, tautomers, and isotopes of the structures depicted. Compounds herein identified by name or structure as one particular tautomeric form are intended to include other tautomeric forms unless otherwise specified.

As used herein, when a ring is described as being "aromatic", it means the ring has a continuous, delocalized π-electron system. Typically, the number of out of plane π-electrons corresponds to the Hückel rule (4n+2). Examples of such rings include: benzene, pyridine, pyrimidine, pyrazine, pyridazine, pyridone, pyrrole, pyrazole, oxazole, thioazole, isoxazole, isothiazole, and the like. When a ring system comprising at least two rings is described as "aromatic", it means the ring system comprises one or more aromatic ring(s). Accordingly, when a ring system comprising at least two rings is described as "non-aromatic", none of the constituent rings of the ring system is aromatic.

As used herein, when a ring is described as being "partially unsaturated", it means the ring has one or more additional degrees of unsaturation (in addition to the degree of unsaturation attributed to the ring itself, e.g., one or more double bonds between constituent ring atoms), provided that the ring is not aromatic. Examples of such rings include: cyclopentene, cyclohexene, cycloheptene, dihydropyridine, tetrahydropyridine, dihydropyrrole, dihydrofuran, dihydrothiophene, and the like. When a ring system comprising at least two rings is described as "partially unsaturated", it means the ring system comprises one or more partially unsaturated ring(s), provided that none of the constituent rings of the ring system is aromatic.

As used herein, the term "carboxylic acid bioisostere" means a group which has chemical and physical similarities producing broadly similar biological properties to a carboxylic acid (see Lipinski, Annual Reports in Medicinal Chemistry, 1986, 21, p 283 "Bioisosterism In Drug Design"; Yun, Hwahak Sekye, 1993, 33, pages 576-579 "Application Of Bioisosterism To New Drug Design"; Zhao, Huaxue Tongbao, 1995, pages 34-38 25 "Bioisosteric Replacement And Development Of Lead Compounds In Drug Design"; Graham, Theochem, 1995, 343, pages 105-109 "Theoretical Studies Applied To Drug Design: ab initio Electronic Distributions In Bioisosteres"). Examples of suitable carboxylic acid bioisostere include: sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer.

The term "GLP-1R" or "GLP-1 receptor" as used herein is meant to include, without limitation, nucleic acids, polynucleotides, oligonucleotides, sense and antisense polynucleotide strands, complementary sequences, peptides, polypeptides, proteins, homologous, and/or orthologous GLP-1R molecules, isoforms, precursors, mutants, variants, derivatives, splice variants, alleles, different species, and active fragments thereof.

The term "GLP-1 associated disease" as used herein is meant to include, without limitation, all those diseases, disorders, or conditions in which modulating glucagon-like peptide-1 (GLP-1) receptor signaling can alter the pathology and/or symptoms and/or progression of the disease, disorder, or condition.

The term "GLP-1 agonist" or "GLP-1 RA" as used herein refers to an agonist of the glucagon-like peptide-1 (GLP-1) receptor. GLP-1 RAs enhance glucose-dependent insulin secretion; suppress inappropriately elevated glucagon levels, both in fasting and postprandial states; and slow gastric emptying. Karla et al., Glucagon-like peptide-1 receptor agonists in the treatment of type 2 diabetes: Past, present, and future, *Indian J Endocrinol Metab.* 2016 March-April; 20(2): 254-267. GLP-1 RAs have been shown to treat type 2 diabetes. Examples of GLP-1RAs include, but are not limited to, albiglutide (TANZEUM®), dulaglutide (LY2189265, TRULICITY®), efpeglenatide, exenatide (BYETTA®, BYDUREON®, Exendin-4), liraglutide (VICTOZA®, NN2211), lixisenatide (LYXUMIA®), semaglutide (OZEMPIC®), tirzepatide, ZP2929, NNCO113-0987, BPI-3016, and TT401. See, also, for example, additional GLP-1 receptor agonists described in U.S. Pat. Nos. 10,370,426; 10,308,700; 10,259,823; 10,208,019; 9,920,106; 9,839,664; 8,129,343; 8,536,122; 7,919,598; 6,414,126; 6,628,343; and RE45313; and International Publication Nos. WO 2019/239319; WO 2019/239371; WO 2020/103815; WO 2020/207474; WO 20202/34726; WO 2020/044266; WO 2020117987; and WO 2020263695.

The term "pharmaceutically acceptable" as used herein indicates that the compound, or salt or composition thereof is compatible chemically and/or toxicologically with the other ingredients comprising a formulation and/or the patient being treated therewith.

The term "therapeutic compound" as used herein is meant to include, without limitation, all compounds of Formula I, or pharmaceutically acceptable salts or solvates thereof (e.g., a compound of any one of Formulas (I-A1), (I-A2), (I-A3), (I-A4), (I-A4-1), (I-B1), or (I-A5), (I-A6), (I-A7), (I-A8), and (I-B2), or a pharmaceutically acceptable salt or solvate thereof), and all compositions (e.g., pharmaceutical compositions) wherein a compound of Formula I, or a pharmaceutically acceptable salt or solvate thereof (e.g., a compound of any one of Formulas I-A1), (I-A2), (I-A3), (I-A4), (I-A4-1), (I-B1), or (I-A5), (I-A6), (I-A7), (I-A8), and (I-B2), or a pharmaceutically acceptable salt or solvate thereof) is a component of the composition.

The term "administration" or "administering" refers to a method of giving a dosage of a compound or pharmaceutical composition to a vertebrate or invertebrate, including a mammal, a bird, a fish, or an amphibian. The method of administration can vary depending on various factors, e.g., the components of the pharmaceutical composition, the site of the disease, and the severity of the disease.

The terms "effective amount" or "effective dosage" or "pharmaceutically effective amount" or "therapeutically effective amount," as used herein, refer to a sufficient amount of a chemical entity (e.g., a compound of Formula I, or a pharmaceutically acceptable salt or solvate thereof (e.g., a compound of any one of Formulas I-A1), (I-A2), (I-A3), (I-A4), (I-A4-1), (I-B), or (I-A5), (I-A6), (I-A7), (I-A8), and (I-B2), or a pharmaceutically acceptable salt or solvate thereof)) being administered which will relieve to some extent one or more of the symptoms of the disease or condition being treated, and can include curing the disease. "Curing" means that the symptoms of active disease are eliminated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study. In some embodiments, a "therapeutically effective amount" of a compound as provided herein refers to an amount of the compound that is effective as a monotherapy or combination therapy.

The term "excipient" or "pharmaceutically acceptable excipient" means a pharmaceutically-acceptable material, composition, or vehicle, such as a liquid or solid filler, diluent, carrier, solvent, or encapsulating material. In some embodiments, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Remington: The Science and Practice of Pharmacy, 21st ed.; Lippincott Williams & Wilkins: Philadelphia, PA, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, FL, 2009.

The term "pharmaceutical composition" refers to a mixture of a compound of Formula I, or a pharmaceutically acceptable salt or solvate thereof (e.g., a compound of any one of Formulas I-A1), (I-A2), (I-A3), (I-A4), (I-A4-1), (I-B1), or (I-A5), (I-A6), (I-A7), (I-A8), and (I-B2), or a pharmaceutically acceptable salt or solvate thereof) as described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to, rectal, oral, intravenous, aerosol, parenteral, ophthalmic, pulmonary, and topical administration.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "preventing", as used herein, is the prevention of the onset, recurrence or spread, in whole or in part, of the disease or condition as described herein, or a symptom thereof.

The terms "subject", "patient" or "individual", as used herein, are used interchangeably and refers to any animal, including mammals such as mice, rats, other rodents, rabbits, dogs, cats, swine, cattle, sheep, horses, primates, and humans. In some embodiments, the term refers to a subject, particularly a mammalian subject, for whom diagnosis, prognosis, or therapy is desired or needed. In some embodiments, the patient is a human. In some embodiments, the subject has experienced and/or exhibited at least one symptom of the disease, disorder, or condition to be treated and/or prevented.

The terms "treatment regimen" and "dosing regimen" are used interchangeably to refer to the dose and timing of administration of each therapeutic agent in a combination of the invention.

The term "pharmaceutical combination", as used herein, refers to a pharmaceutical treatment resulting from the mixing or combining of more than one active ingredient and includes both fixed and non-fixed combinations of the active ingredients.

The term "combination therapy" as used herein refers to a dosing regimen of two different therapeutically active agents (i.e., the components or combination partners of the combination), wherein the therapeutically active agents are administered together or separately in a manner prescribed by a medical care taker or according to a regulatory agency as defined herein.

The term "modulation", as used herein, refers to a regulation or an adjustment (e.g., increase or decrease) and can include, for example agonism, partial agonism or antagonism.

Compounds

Accordingly, provided herein are compounds of Formula I:

Formula I

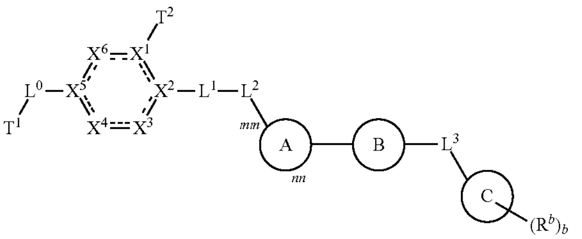

or a pharmaceutically acceptable salt or solvate thereof, wherein:

$X^1$, $X^2$, and $X^5$ are independently C or N;

$X^3$ and $X^4$ are independently selected from the group consisting of: N, $NR^x$, $CR^y$, C(=O), 0, and S;

$X^6$ is selected from the group consisting of: a bond, N, $NR^x$, $CR^y$, and C(=O);

each ---- is a single bond or a double bond, provided that at least one of $X^1$-$X^6$ is an independently selected heteroatom or heteroatomic group; at least one of $X^1$-$X^6$ is C or $CR^y$; and the ring including $X^1$-$X^6$ is aromatic;

each $R^x$ is independently selected from the group consisting of: hydrogen, $(C_1\text{-}C_6)$alkyl, $(C_1\text{-}C_6)$haloalkyl, $C(=O)(C_1\text{-}C_6)$alkyl, $S(O)_2(C_1\text{-}C_6)$alkyl, and $C(=O)O(C_1\text{-}C_6)$alkyl;

each $R^y$ is independently selected from the group consisting of: hydrogen, —OH, $(C_1\text{-}C_6)$alkyl, $(C_1\text{-}C_6)$haloalkyl, $(C_1\text{-}C_6)$alkoxy, $(C_1\text{-}C_6)$haloalkoxy, CN, and halogen;

$L^0$ is a bond or #—$P^0$-$P^1$, wherein #represents the point of attachment to $X^5$;

—$P^0$ is a bond, —NH—, —N($C_1$-$C_6$ alkyl)-, —O—, or $S(O)_{0\text{-}2}$;

—$P^1$ is selected from the group consisting of: $(C_1\text{-}C_6)$alkylene, $(C_2\text{-}C_6)$alkenylene, $(C_2\text{-}C_6)$alkynylene, ($C_3$-

$C_8$)cycloalkylene, and 4- to 8-membered heterocycloalkylene, each of which is optionally substituted with 1-3 $R^0$;

each $R^0$ is independently selected from the group consisting of: halogen, CN, ($C_1$-$C_6$)alkyl, ($C_1$-$C_6$)haloalkyl, ($C_1$-$C_6$)alkoxy, and ($C_1$-$C_6$)haloalkoxy;

$T^1$ is C(═O)OH or a carboxylic acid bioisostere;

$T^2$ is hydrogen, CN, ($C_1$-$C_6$)haloalkyl, ($C_1$-$C_6$)hydroxyalkyl or ($C_1$-$C_6$)alkyl which is optionally substituted with ($C_1$-$C_6$)alkoxy, ($C_1$-$C_6$)thioalkoxy, ($C_1$-$C_6$)haloalkoxy, $S(O)_2$($C_1$-$C_6$ alkyl), —N($C_1$-$C_6$ alkyl)-$S(O)_2$($C_1$-$C_6$ alkyl), —NH-$S(O)_2$($C_1$-$C_6$ alkyl), ($C_3$-$C_6$)cycloalkyl, ($C_3$-$C_6$)cycloalkoxy, 3- to 6-membered heterocycloalkyl, phenyl, or 5- to 6-membered heteroaryl, wherein each of the ($C_3$-$C_6$)cycloalkyl, 3- to 6-membered heterocycloalkyl, phenyl, or 5- to 6-membered heteroaryl is optionally substituted with 1-4 $R^T$;

each $R^T$ is independently selected from the group consisting of OH, SH, CN, $NO_2$, halogen, ═O, ($C_1$-$C_6$)alkyl, ($C_2$-$C_6$)alkenyl, ($C_2$-$C_6$)alkynyl, ($C_1$-$C_6$)haloalkyl, ($C_1$-$C_6$)cyanoalkyl, ($C_1$-$C_6$)hydroxyalkyl, ($C_1$-$C_6$)alkoxy, ($C_1$-$C_6$)haloalkoxy, ($C_3$-$C_6$)cycloalkyl, amino, ($C_1$-$C_6$)alkylamino, ($C_1$-$C_6$)alkylamino($C_1$-$C_6$ alkyl)-C(O)—$C_1$-$C_6$ alkyl, $S(O)_2$($C_1$-$C_6$ alkyl), and di($C_1$-$C_6$)alkylamino;

$L^1$ is a bond or ($C_1$-$C_3$)alkylene which is optionally substituted with 1-3 $R^L$;

$L^2$ is a bond, —O—, —$S(O)_{0-2}$—, or —NH—;

each $R^L$ is independently selected from the group consisting of: halogen, ($C_1$-$C_3$)alkyl, and ($C_1$-$C_3$)haloalkyl; or a pair of $R^L$ on the same or on adjacent carbon atoms, taken together with the atom(s) to which each is attached, forms a ($C_3$-$C_6$)cycloalkyl ring;

Ring A is selected from the group consisting of:

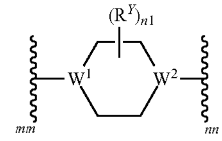

, wherein n1 is 0, 1, or 2, $W^1$ is $CR^{Y1}$ or N, and $W^2$ is $CR^{Y2}$ or N;

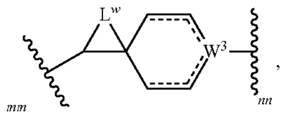

, wherein $W^3$ is C, $CR^{Y3}$, or N, $L^w$ is ($C_1$-$C_3$)alkylene, and each ═ is independently a single bond or a double bond, as allowed by valence;

phenylene optionally substituted with 1-4 $R^Y$;

5- to 6-membered heteroarylene optionally substituted with 1-3 $R^Y$;

partially unsaturated monocyclic ($C_5$-$C_8$)cycloalkylene optionally substituted with 1-4 $R^Y$; and partially unsaturated monocyclic 5- to 8-membered heterocycloalkylene optionally substituted with 1-4 $R^Y$;

wherein mm represents the point of attachment to $L^2$, and nn represents the point of attachment to Ring B;

each occurrence of $R^Y$ is independently selected from the group consisting of halogen, CN, —OH, oxo, ($C_1$-$C_6$)alkyl, ($C_1$-$C_3$)haloalkyl, ($C_1$-$C_3$)alkoxy, and ($C_1$-$C_3$)haloalkoxy;

$R^{Y1}$, $R^{Y2}$, and $R^{Y3}$ are each independently selected from the group consisting of hydrogen, halogen, CN, —OH, ($C_1$-$C_6$)alkyl, ($C_1$-$C_3$)haloalkyl, ($C_1$-$C_3$)alkoxy, and ($C_1$-$C_3$)haloalkoxy; or when $W^1$ is $CR^{Y1}$ and $W^2$ is $CR^{Y2}$, the $R^{Y1}$ and $R^{Y2}$ groups taken together can form ($C_1$-$C_4$)alkylene, wherein one of the $CH_2$ units of the ($C_1$-$C_4$)alkylene is optionally replaced by a heteroatom selected from the group consisting of O, S, NH, and N($C_{1-3}$)alkyl;

Ring B is selected from the group consisting of: (B-I), (B-II), (B-III), (B-IV), (B-V), and (B-VI):

(B-I)

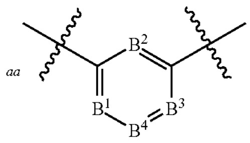

, (B-II)

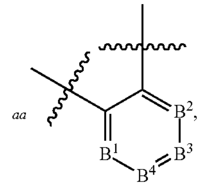

(B-III)

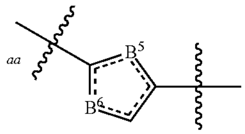

, (B-IV)

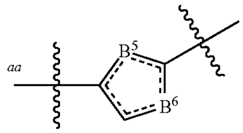

;

wherein aa represents the point of attachment to Ring A;

each of $B^1$, $B^2$, $B^3$, and $B^4$ is independently selected from the group consisting of $CR^1$ and N;

each of $B^5$ and $B^6$ is independently selected from the group consisting of N, $NR^1$, C, $CR^1$, O, and S, provided that the ring containing $B^5$ and $B^6$ is heteroaryl;

(B-V)

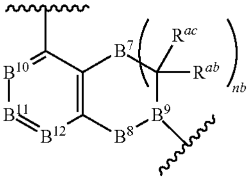

and (B-VI)

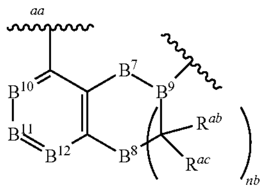

;

wherein aa represents the point of attachment to Ring A;

$B^7$ and $B^8$ are independently selected from the group consisting of: —O—, —$NR^N$—, and —$C(R')_2$—; $B^9$ is N or $CR^{aa}$;

nb is 0 or 1;

$B^{10}$, $B^{11}$ and $B^{12}$ are independently selected from the group consisting of $CR^1$ and N;

each $R^1$ is independently selected from the group consisting of hydrogen, halogen, CN, $(C_1-C_6)$alkyl, $(C_1-C_6)$haloalkyl; $(C_1-C_3)$alkyl$(C_3-C_6)$cycloalkyl, $(C_1-C_3)$alkyl(3- to 5-membered heterocycloalkyl), and —C(O)$NR^2R^3$;

each $R^2$ and $R^3$ is independently selected from the group consisting of H and $(C_1-C_6)$alkyl;

each $R^N$ is independently selected from the group consisting of hydrogen, $(C_1-C_6)$alkyl, $(C_1-C_6)$haloalkyl, $C(=O)(C_1-C_6)$alkyl, $S(O)_2(C_1-C_6)$alkyl, and $C(=O)O(C_1-C_6)$alkyl;

$R^{aa}$, $R^{ab}$, and $R^{ac}$ are each independently selected from the group consisting of H, $(C_1-C_6)$alkyl, and $(C_1-C_6)$haloalkyl;

$L^3$ is a bond or —$Z^1$-$Z^2$—*, wherein * represents the point of attachment to Ring C;

—$Z^1$ is a bond, NH, $N(C_1-C_6$ alkyl), 0, or $S(O)_{0-2}$;

—$Z^2$ is $C_1$-3 alkylene optionally substituted with 1-2 $R^c$;

each $R^c$ is independently selected from the group consisting of halogen, $(C_1-C_6)$alkyl, and $(C_1-C_3)$haloalkyl;

Ring C is selected from the group consisting of phenyl, 5- to 6-membered heteroaryl, $(C_3-C_6)$cycloalkyl, $(C_5-C_{10})$bicycloalkyl, 5- to 10-membered bicycloheteroaryl, and 3- to 6-membered heterocycloalkyl;

each $R^b$ is independently selected from the group consisting of $(C_1-C_6)$alkyl, $(C_1-C_6)$haloalkyl, $(C_1-C_6)$alkoxy, $(C_1-C_6)$haloalkoxy, halogen, $(C_3-C_6)$cycloalkyl, and CN; and b is an integer selected from 0-3.

Also provided herein are compounds of Formula I:

Formula I

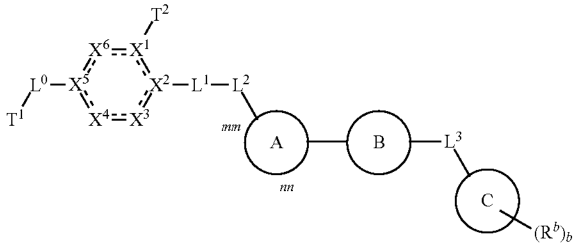

or a pharmaceutically acceptable salt or solvate thereof, wherein:

$X^1$, $X^2$, and $X^5$ are independently C or N;

$X^3$ and $X^4$ are independently selected from the group consisting of: N, $NR^x$, $CR^y$, C(=O), O, and S;

$X^6$ is selected from the group consisting of: a bond, N, $NR^x$, $CR^y$, and C(=O);

each ---- is a single bond or a double bond, provided that at least one of $X^1$-$X^6$ is an independently selected heteroatom or heteroatomic group; at least one of $X^1$-$X^6$ is C or $CR^y$; and the ring including $X^1$-$X^6$ is aromatic;

each $R^x$ is independently selected from the group consisting of: hydrogen, $(C_1-C_6)$alkyl, $(C_1-C_6)$haloalkyl, $C(=O)(C_1-C_6)$alkyl, $S(O)_2(C_1-C_6)$alkyl, and $C(=O)O(C_1-C_6)$alkyl;

each $R^y$ is independently selected from the group consisting of: hydrogen, —OH, $(C_1-C_6)$alkyl, $(C_1-C_6)$haloalkyl, $(C_1-C_6)$alkoxy, $(C_1-C_6)$haloalkoxy, CN, and halogen;

$L^0$ is a bond or #—$P^0$-$P^1$, wherein #represents the point of attachment to $X^5$;

—$P^0$ is a bond, —NH—, —$N(C_1-C_6$ alkyl)-, —O—, or $S(O)_{0-2}$;

$P^1$ is selected from the group consisting of: $(C_1-C_6)$alkylene, $(C_2-C_6)$alkenylene, $(C_2-C_6)$alkynylene, $(C_3-C_8)$cycloalkylene, and 4- to 8-membered heterocycloalkylene, each of which is optionally substituted with 1-3 $R^0$;

each $R^0$ is independently selected from the group consisting of: halogen, CN, $(C_1-C_6)$alkyl, $(C_1-C_6)$haloalkyl, $(C_1-C_6)$alkoxy, and $(C_1-C_6)$haloalkoxy;

$T^1$ is C(=O)OH or a carboxylic acid bioisostere;

$T^2$ is hydrogen or $(C_1-C_6)$alkyl which is optionally substituted with $(C_1-C_6)$alkoxy, $(C_1-C_6)$thioalkoxy, $(C_1-C_6)$haloalkoxy, $S(O)_2(C_1-C_6$ alkyl), $(C_3-C_6)$cycloalkyl, 3- to 6-membered heterocycloalkyl, phenyl, or 5- to 6-membered heteroaryl, wherein each of the $(C_3-C_6)$cycloalkyl, 3- to 6-membered heterocycloalkyl, phenyl, or 5- to 6-membered heteroaryl is optionally substituted with 1-4 $R^T$;

each $R^T$ is independently selected from the group consisting of OH, SH, CN, $NO_2$, halogen, $(C_1-C_6)$alkyl, $(C_2-C_6)$alkenyl, $(C_2-C_6)$alkynyl, $(C_1-C_6)$haloalkyl, $(C_1-C_6)$cyanoalkyl, $(C_1-C_6)$hydroxyalkyl, $(C_1-C_6)$alkoxy, $(C_1-C_6)$haloalkoxy, $(C_3-C_6)$cycloalkyl, amino, $(C_1-C_6)$alkylamino, and di$(C_1-C_6)$alkylamino;

$L^1$ is a bond or $(C_1-C_3)$alkylene which is optionally substituted with 1-3 $R^L$;

$L^2$ is a bond, —O—, —$S(O)_{0-2}$—, or —NH—;

each $R^L$ is independently selected from the group consisting of: halogen, $(C_1-C_3)$alkyl, and $(C_1-C_3)$haloalkyl; or a pair of $R^L$ on the same or on adjacent carbon atoms, taken together with the atom(s) to which each is attached, forms a $(C_3-C_6)$cycloalkyl ring;

Ring A is selected from the group consisting of:

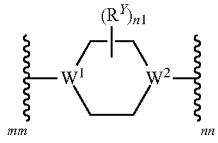
, wherein n1 is 0, 1, or 2, $W^1$ is $CR^{Y1}$ or N, and $W^2$ is $CR^{Y2}$ or N;

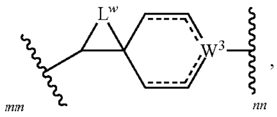
, wherein $W^3$ is C, $CR^{Y3}$ or N, $L^w$ is $(C_1-C_3)$alkylene and each ---- is independently a single bond or a double bond, as allowed by valence;

phenylene optionally substituted with 1-4 $R^Y$;

5- to 6-membered heteroarylene optionally substituted with 1-3 $R^Y$;

partially unsaturated monocyclic $(C_5-C_8)$cycloalkylene optionally substituted with 1-4 $R^Y$; and partially unsaturated monocyclic 5- to 8-membered heterocycloalkylene optionally substituted with 1-4 $R^Y$;

wherein mm represents the point of attachment to $L^2$, and nn represents the point of attachment to Ring B;

each occurrence of $R^Y$ is independently selected from the group consisting of halogen, CN, —OH, oxo, $(C_1\text{-}C_6)$alkyl, $(C_1\text{-}C_3)$haloalkyl, $(C_1\text{-}C_3)$alkoxy, and $(C_1\text{-}C_3)$haloalkoxy;

$R^{Y1}$, $R^{Y2}$, and $R^{Y3}$ are each independently selected from the group consisting of hydrogen, halogen, CN, —OH, $(C_1\text{-}C_6)$alkyl, $(C_1\text{-}C_3)$haloalkyl, $(C_1\text{-}C_3)$alkoxy, and $(C_1\text{-}C_3)$haloalkoxy; or when $W^1$ is $CR^{Y1}$ and $W^2$ is $CR^{Y2}$, the $R^{Y1}$ and $R^{Y2}$ groups taken together can form $(C_1\text{-}C_4)$alkylene, wherein one of the $CH_2$ units of the $(C_1\text{-}C_4)$alkylene is optionally replaced by a heteroatom selected from the group consisting of O, S, NH, and $N(C_{1\text{-}3})$alkyl;

Ring B is selected from the group consisting of: (B-I), (B-II), (B-III), (B-IV), (B-V) and (B-VI)

(B-I)

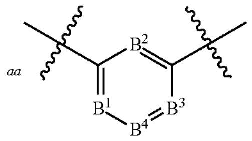

, (B-II)

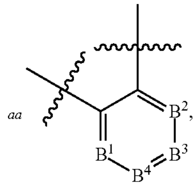

(B-III)

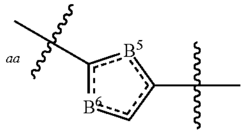

, (B-IV)

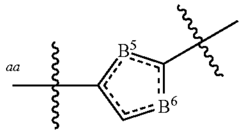

;

wherein aa represents the point of attachment to Ring A;

each of $B^1$, $B^2$, $B^3$, and $B^4$ is independently selected from the group consisting of $CR^1$ and N;

each of $B^5$ and $B^6$ is independently selected from the group consisting of N, $NR^1$, C, $CR^1$, O, and S, provided that the ring containing $B^5$ and $B^6$ is heteroaryl;

(B-V)

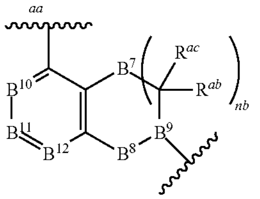

and

-continued (B-VI)

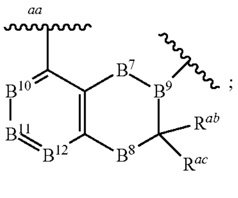

;

wherein aa represents the point of attachment to Ring A;

$B^7$ and $B^8$ are independently selected from the group consisting of: —O—, —$NR^N$—, and —$C(R')_2$—;

$B^9$ is N or $CR^a$;

nb is 0 or 1;

$B^{10}$, $B^{11}$, and $B^{12}$ are independently selected from the group consisting of $CR^1$ and N;

each $R^1$ is independently selected from the group consisting of hydrogen, halogen, CN, $(C_1\text{-}C_6)$alkyl, $(C_1\text{-}C_6)$haloalkyl; $(C_1\text{-}C_3)$alkyl$(C_3\text{-}C_6)$cycloalkyl, $(C_1\text{-}C_3)$alkyl(3- to 5-membered heterocycloalkyl), and —$C(O)NR^2R^3$;

each $R^2$ and $R^3$ is independently selected from the group consisting of H and $(C_1\text{-}C_6)$alkyl;

each $R^N$ is independently selected from the group consisting of hydrogen, $(C_1\text{-}C_6)$alkyl, $(C_1\text{-}C_6)$haloalkyl, $C(=O)(C_1\text{-}C_6)$alkyl, $S(O)_2(C_1\text{-}C_6)$alkyl, and $C(=O)O(C_1\text{-}C_6)$alkyl;

$R^{aa}$, $R^{ab}$, and $R^{ac}$ are each independently selected from the group consisting of H, $(C_1\text{-}C_6)$alkyl, and $(C_1\text{-}C_6)$haloalkyl;

$L^3$ is a bond or —$Z^1$-$Z^2$—*, wherein * represents the point of attachment to Ring C;

—$Z^1$ is a bond, NH, $N(C_1\text{-}C_6$ alkyl), O, or $S(O)_{0\text{-}2}$;

—$Z^2$ is $C_1$-3 alkylene optionally substituted with 1-2 $R^c$;

each $R^c$ is independently selected from the group consisting of halogen, $(C_1\text{-}C_6)$alkyl, and $(C_1\text{-}C_3)$haloalkyl;

Ring C is selected from the group consisting of phenyl, 5- to 6-membered heteroaryl, $(C_3\text{-}C_6)$cycloalkyl, $(C_5\text{-}C_{10})$bicycloalkyl, 5- to 10-membered bicycloheteroaryl, and 3- to 6-membered heterocycloalkyl;

each $R^b$ is independently selected from the group consisting of $(C_1\text{-}C_6)$alkyl, $(C_1\text{-}C_6)$haloalkyl, $(C_1\text{-}C_6)$alkoxy, $(C_1\text{-}C_6)$haloalkoxy, halogen, $(C_3\text{-}C_6)$cycloalkyl, and CN; and b is an integer selected from 0-3.

Also provided herein are compounds of Formula I

Formula I

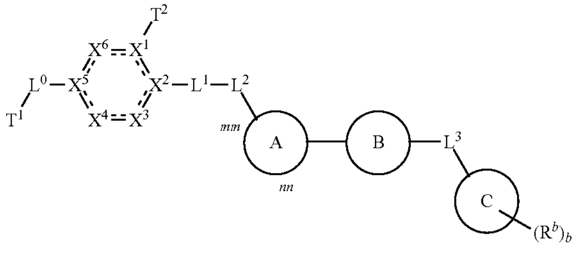

or a pharmaceutically acceptable salt or solvate thereof, wherein:

$X^1$, $X^2$, and $X^5$ are independently C or N;

$X^3$ and $X^4$ are independently selected from the group consisting of: N, $NR^x$, $CR^y$, C(=O), 0, and S;

$X^6$ is selected from the group consisting of: a bond, N, $NR^x$, $CR^y$, and C(═O);

each ---- is a single bond or a double bond, provided that at least one of $X^1$-$X^6$ is an independently selected heteroatom or heteroatomic group; at least one of $X^1$-$X^6$ is C or $CR^y$; and the ring including $X^1$-$X^6$ is aromatic;

each $R^x$ is independently selected from the group consisting of: hydrogen, $(C_1$-$C_6)$alkyl, $(C_1$-$C_6)$haloalkyl, C(═O)$(C_1$-$C_6)$alkyl, $S(O)_2(C_1$-$C_6)$alkyl, and C(═O)O$(C_1$-$C_6)$alkyl;

each $R^y$ is independently selected from the group consisting of: hydrogen, —OH, $(C_1$-$C_6)$alkyl, $(C_1$-$C_6)$haloalkyl, $(C_1$-$C_6)$alkoxy, $(C_1$-$C_6)$haloalkoxy, CN, and halogen;

$L^0$ is a bond or #—$P^0$-$P^1$, wherein #represents the point of attachment to $X^5$;

—$P^0$ is a bond, —NH—, —N($C_1$-$C_6$ alkyl)-, —O—, or $S(O)_{0-2}$;

—$P^1$ is selected from the group consisting of: $(C_1$-$C_6)$alkylene, $(C_2$-$C_6)$alkenylene, $(C_2$-$C_6)$alkynylene, $(C_3$-$C_8)$cycloalkylene, and 4- to 8-membered heterocycloalkylene, each of which is optionally substituted with 1-3 $R^0$;

each $R^0$ is selected from the group consisting of: halogen, CN, $(C_1$-$C_6)$alkyl, $(C_1$-$C_6)$haloalkyl, $(C_1$-$C_6)$alkoxy, and $(C_1$-$C_6)$haloalkoxy;

$T^1$ is C(═O)OH or a carboxylic acid bioisostere;

$T^2$ is hydrogen or $(C_1$-$C_6)$alkyl which is optionally substituted with $(C_1$-$C_6)$alkoxy, $(C_1$-$C_6)$thioalkoxy, $(C_1$-$C_6)$haloalkoxy, $S(O)_2(C_1$-$C_6$ alkyl), $(C_3$-$C_6)$cycloalkyl, 3- to 6-membered heterocycloalkyl, phenyl, or 5- to 6-membered heteroaryl, wherein each of the $(C_3$-$C_6)$cycloalkyl, 3- to 6-membered heterocycloalkyl, phenyl, or 5- to 6-membered heteroaryl is optionally substituted with 1-4 $R^T$;

each $R^T$ is independently selected from the group consisting of OH, SH, CN, $NO_2$, halogen, $(C_1$-$C_6)$alkyl, $(C_2$-$C_6)$alkenyl, $(C_2$-$C_6)$alkynyl, $(C_1$-$C_6)$haloalkyl, $(C_1$-$C_6)$cyanoalkyl, $(C_1$-$C_6)$hydroxyalkyl, $(C_1$-$C_6)$alkoxy, $(C_1$-$C_6)$haloalkoxy, $(C_3$-$C_6)$cycloalkyl, amino, $(C_1$-$C_6)$alkylamino, and di$(C_1$-$C_6)$alkylamino;

$L^1$ is a bond or $(C_1$-$C_3)$alkylene which is optionally substituted with 1-3 $R^L$;

$L^2$ is a bond, —O—, —$S(O)_{0-2}$-, or —NH—;

each $R^L$ is independently selected from the group consisting of: halogen, $(C_1$-$C_3)$alkyl, and $(C_1$-$C_3)$haloalkyl; or a pair of $R^L$ on the same or on adjacent carbon atoms, taken together with the atom(s) to which each is attached, forms a $(C_3$-$C_6)$cycloalkyl ring;

Ring A is selected from the group consisting of:

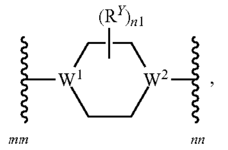

wherein n1 is 0, 1, or 2; $W^1$ is $CR^{Y1}$ or N; and $W^2$ is $CR^{Y2}$ or N:

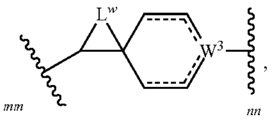

wherein $W^3$ is C, $CR^{Y3}$ or N, $L^w$ is $(C_1$-$C_3)$alkylene and each ---- is independently a single bond or a double bond, as allowed by valence;

phenylene optionally substituted with 1-4 $R^Y$;

5- to 6-membered heteroarylene optionally substituted with 1-3 $R^Y$;

partially unsaturated monocyclic $(C_5$-$C_8)$cycloalkylene optionally substituted with 1-4 $R^Y$; and partially unsaturated monocyclic 5- to 8-membered heterocycloalkylene optionally substituted with 1-4 $R^Y$;

wherein mm represents the point of attachment to $L^2$, and nn represents the point of attachment to Ring B;

each occurrence of $R^Y$ is independently selected from the group consisting of halogen, CN, —OH, oxo, $(C_1$-$C_6)$alkyl, $(C_1$-$C_3)$haloalkyl, $(C_1$-$C_3)$alkoxy, and $(C_1$-$C_3)$haloalkoxy;

$R^{Y1}$, $R^{Y2}$, and $R^{Y3}$ are each independently selected from the group consisting of hydrogen, halogen, CN, —OH, $(C_1$-$C_6)$alkyl, $(C_1$-$C_3)$haloalkyl, $(C_1$-$C_3)$alkoxy, and $(C_1$-$C_3)$haloalkoxy; or when $W^1$ is $CR^{Y1}$ and $W^2$ is $CR^{Y2}$, the $R^{Y1}$ and $R^{Y2}$ groups taken together form $(C_1$-$C_4)$alkylene, wherein one of the $CH_2$ units of the $(C_1$-$C_4)$alkylene is optionally replaced by a heteroatom selected from the group consisting of O, S, NH, and $N(C_{1-3})$alkyl;

Ring B is selected from the group consisting of: (B-I), (B-II), (B-III), (B-IV), (B-V), and (B-VI):

(B-I)

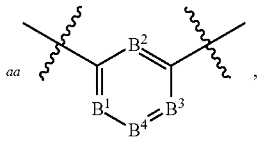

(B-II)

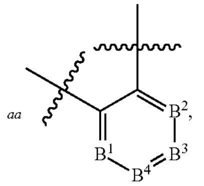

(B-III)

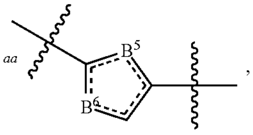

(B-IV)

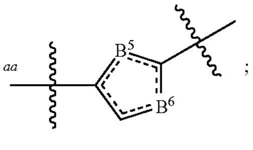

wherein aa represents the point of attachment to Ring A; each of $B^1$, $B^2$, $B^3$, and $B^4$ is independently selected from the group consisting of $CR^1$ and N;

each of $B^5$ and $B^6$ is independently selected from the group consisting of N, $NR^1$, C, $CR^1$, O, and S, provided that the ring containing $B^4$ and $B^5$ is heteroaryl;

(B-V)

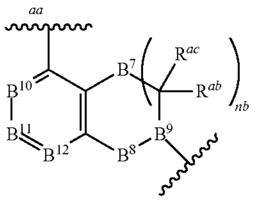

and (B-VI)

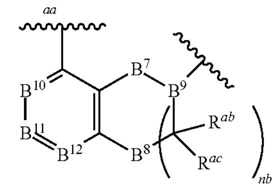

;

wherein aa represents the point of attachment to Ring A;

$B^7$ and $B^8$ are independently selected from the group consisting of: —O—, —$NR^N$—, and —C(R')$_2$—; $B^9$ is N or $CR^a$;

nb is 0 or 1;

$B^{10}$, $B^{11}$, and $B^{12}$ are independently selected from the group consisting of $CR^1$ and N;

each $R^1$ is selected from the group consisting of hydrogen, halogen, CN, $(C_1$-$C_6)$alkyl, $(C_1$-$C_6)$haloalkyl; $(C_1$-$C_3)$alkyl$(C_3$-$C_6)$cycloalkyl, $(C_1$-$C_3)$alkyl(3- to 5-membered heterocycloalkyl), and —C(O)$NR^2R^3$;

each $R^2$ and $R^3$ is independently selected from the group consisting of H and $(C_1$-$C_6)$alkyl;

each $R^N$ is selected from the group consisting of hydrogen, $(C_1$-$C_6)$alkyl, $(C_1$-$C_6)$haloalkyl, C(═O)$(C_1$-$C_6)$alkyl, $S(O)_2(C_1$-$C_6)$alkyl, and C(═O)O$(C_1$-$C_6)$alkyl;

$R^{aa}$, $R^{ab}$, and $R^{ac}$ are each independently selected from the group consisting of H, $(C_1$-$C_6)$alkyl, and $(C_1$-$C_6)$haloalkyl; $L^3$ is a bond or —$Z^1$—$Z^2$—*, wherein * represents the point of attachment to Ring C;

—$Z^1$ is a bond, NH, N($C_1$-$C_6$ alkyl), 0, or $S(O)_{0-2}$;

—$Z^2$ is $C_1$-3 alkylene optionally substituted with 1-2 $R^c$;

each $R^c$ is independently selected from the group consisting of halogen, $(C_1$-$C_6)$alkyl, and $(C_1$-$C_3)$haloalkyl;

Ring C is selected from the group consisting of phenyl, 5- to 6-membered heteroaryl, $(C_3$-$C_6)$cycloalkyl, $(C_5$-$C_{10})$bicycloalkyl, 5- to 10-membered bicycloheteroaryl, and 3- to 6-membered heterocycloalkyl;

each $R^b$ is independently selected from the group consisting of $(C_1$-$C_6)$alkyl, $(C_1$-$C_6)$haloalkyl, $(C_1$-$C_6)$alkoxy, $(C_1$-$C_6)$haloalkoxy, halogen, $(C_3$-$C_6)$cycloalkyl, and CN; and b is an integer selected from 0-3.

Embodiments can include any one or more of the features delineated below and/or in the claims.

In some embodiments, $X^3$ is N.

In some embodiments, $X^6$ is a bond. For avoidance of doubt, when $X^6$ is a bond, $X^1$ is directly attached to $X^5$ (e.g., via a single bond or double bond), thereby providing a 5-membered heteroaromatic ring.

In some embodiments, $X^3$ is N; and $X^6$ is a bond.

In some embodiments, the ring including $X^1$-$X^6$ is:

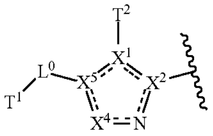

.

In some embodiments, $X^2$ is C. In some embodiments, $X^1$ is N. In some embodiments, $X^5$ is C. In some embodiments, $X^4$ is $CR^y$. In some embodiments, $X^4$ is CH. In some embodiments, $X^4$ is N.

In some embodiments, $X^1$ is N; $X^2$ is C; and $X^5$ is C. In some embodiments, the ring including $X^1$-$X^6$ is

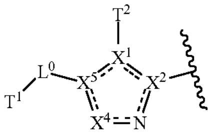

, wherein $X^1$ is N; and $X^2$ is C. In some embodiments, $X^4$ is CH. In some embodiments, $X^4$ is N.

In some embodiments, $X^1$ is N; $X^2$ is C; $X^3$ is N; $X^4$ is $CR^y$ or N; $X^5$ is C; and $X^6$ is a bond. In some embodiments, $X^4$ is CH or N. As a non-limiting example of the foregoing embodiments, $X^1$ is N; $X^2$ is C; $X^3$ is N; $X^4$ is CH; $X^5$ is C; and $X^6$ is a bond. As another non-limiting example, $X^1$ is N; $X^2$ is C; $X^3$ is N; $X^4$ is N; $X^5$ is C; and $X^6$ is a bond.

In some embodiments, $X^6$ is selected from the group consisting of: N, $NR^x$, $CR^y$, and C(═O). In some embodiments, $X^3$ is N; and $X^6$ is selected from the group consisting of: N, $NR^x$, $CR^y$, and C(═O).

In some embodiments, the ring including $X^1$-$X^6$ is:

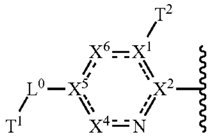

, wherein $X^6$ is selected from the group consisting of: N, $NR^x$, $CR^y$, and C(═O). In some embodiments, $X^1$ is C. In some embodiments, $X^2$ is C. In some embodiments, $X^5$ is C.

In some embodiments, $X^6$ is $CR^y$. For example, $X^6$ can be CH. In some embodiments, $X^4$ is $CR^y$. For example, $X^4$ can be CH.

In some embodiments, $X^1$, $X^2$, and $X^5$ are C; $X^4$ and $X^6$ are independently N or $CR^y$. In some embodiments, $X^4$ and $X^6$ are independently selected $CR^y$. As a non-limiting example of the foregoing embodiments, $X^4$ and $X^6$ can be CH.

In some embodiments, $L^0$ is a bond. In some embodiments, $L^0$ is #—$P^0$-$P^1$; and $P^0$ is a bond.

In some embodiments, $L^0$ is #—$P^0$-$P^1$; and $P^0$ is —NH—, —N($C_1$-$C_6$ alkyl)-, —O—, or $S(O)_{0-2}$. In some embodiments, $P^0$ is —O—. In some embodiments, $P^0$ is —NH—.

In some embodiments, $P^1$ is $(C_1$-$C_6)$alkylene which is optionally substituted with 1-3 $R^0$. In some embodiments, $P^1$ is $(C_1$-$C_3)$alkylene which is optionally substituted with 1-3 $R^0$. In some embodiments, $P^1$ is $(C_1$-$C_3)$alkylene. In some embodiments, $P^1$ is —$CH_2CH_2$—, —$CH_2$—, —CH(Me)- or —$C(Me)_2$-. For example, $P^1$ can be —$CH_2CH_2$—. As another non-limiting example, $P^1$ can be —$CH_2$—. As further non-limiting examples, $P^1$ can be —CH(Me)- or —$C(Me)_2$-.

In some embodiments, $P^1$ is ($C_2$-$C_6$)alkenylene or ($C_2$-$C_6$)alkynylene, each of which is optionally substituted with 1-3 $R^0$. In some embodiments, $P^1$ is ($C_2$-$C_6$)alkenylene which is optionally substituted with 1-3 $R^0$. In some embodiments, $P^1$ is ($C_2$-$C_4$)alkenylene (e.g., ($C_2$-$C_3$)alkenylene, such as $C_2$ alkenylene) which is optionally substituted with 1-3 $R^0$.

In some embodiments, $P^1$ is

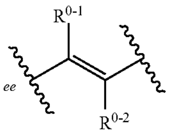

or

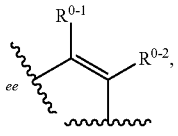

wherein $R^{0-1}$ and $R^{0-2}$ are independently H or $R^0$; and ee is the point of attachment to $T^1$. In some embodiments, $P^1$ is

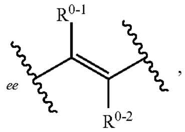

wherein $R^{0-1}$ and $R^{0-2}$ are independently H or $R^0$; and ee is the point of attachment to $T^1$. In some embodiments, $P^1$ is

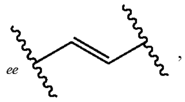

wherein ee is the point of attachment to $T^1$. In some embodiments, $P^1$ is

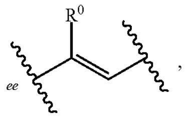

wherein ee is the point of attachment to $T^1$. For example, $P^1$ can be

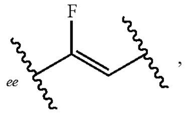

wherein ee is the point of attachment to $T^1$. As another non-limiting example, $P^1$ can be

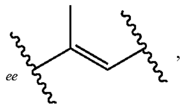

wherein ee is the point of attachment to $T^1$. In some embodiments, $P^1$ is

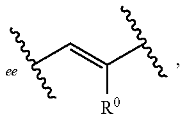

wherein ee is the point of attachment to $T^1$. For example, $P^1$ can be

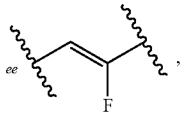

wherein ee is the point of attachment to $T^1$. As another non-limiting example, $P^1$ can be

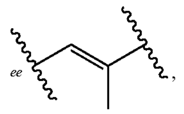

wherein ee is the point of attachment to $T^1$.

In some embodiments, $P^1$ is

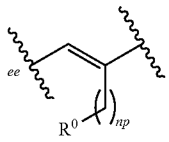

or

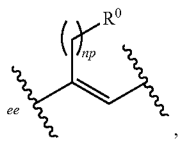

wherein np is 1, 2, or 3; and ee is the point of attachment to $T^1$. In some embodiments, $P^1$ is

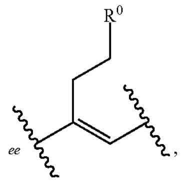

wherein ee is the point of attachment to $T^1$. For example, $P^1$ can be

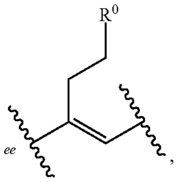

wherein $R^0$ is $(C_1\text{-}C_6)$alkoxy or $(C_1\text{-}C_6)$haloalkoxy; and ee is the point of attachment to $T^1$.

In some embodiments, $P^1$ is selected from the group consisting of: $(C_3\text{-}C_8)$cycloalkylene, and 4- to 8-membered heterocycloalkylene, each of which is optionally substituted with 1-3 $R^0$.

In some embodiments, $P^1$ is $(C_3\text{-}C_8)$cycloalkylene, which is optionally substituted with 1-3 $R^0$. In some embodiments, $P^1$ is $(C_3\text{-}C_6)$cycloalkylene, which is optionally substituted with 1-3 $R^0$. In some embodiments, $P^1$ is $(C_3\text{-}C_4)$cycloalkylene. As a non-limiting example foregoing embodiments, $P^1$ can be

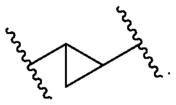 [SMILES: *C1CC1*]

In some embodiments, $P^1$ is 4- to 8-membered heterocycloalkylene, which is optionally substituted with 1-3 $R^0$. In some embodiments, $P^1$ is

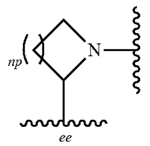

which is optionally substituted with 1-2 $R^0$, wherein np is 1, 2, or 3; and ee is the point of attachment to $T^1$. In some embodiments, $P^1$ is

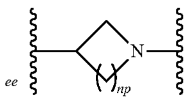

which is optionally substituted with 1-2 $R^0$, wherein np is 1, 2, or 3; and ee is the point of attachment to $T^1$.

In some embodiments, $L^0$ is #—$P^0$-$P^1$; $P^0$ is a bond; and $P^1$ is $(C_1\text{-}C_3)$alkylene which is optionally substituted with 1-3 $R^0$. In some embodiments, $P^1$ is $(C_1\text{-}C_3)$alkylene. For example, $P^1$ can be $CH_2CH_2$. As another example, $P^1$ can be $CH_2$.

In some embodiments, $L^0$ is #—$P^0$-$P^1$; $P^0$ is —NH—, —N($C_1$-$C_3$ alkyl) or —O—; and $P^1$ is $(C_1\text{-}C_3)$alkylene which is optionally substituted with 1-3 $R^0$. In some embodiments, $P^1$ is $(C_1\text{-}C_3)$alkylene. As non-limiting examples of the foregoing embodiments, $P^1$ can be $CH_2$, CH(Me), or $C(Me)_2$.

In some embodiments, $L^0$ is #—$P^0$-$P^1$; $P^0$ is a bond; and $P^1$ is $(C_2\text{-}C_4)$alkenylene which is optionally substituted with 1-3 $R^0$. In some embodiments, $P^1$ is

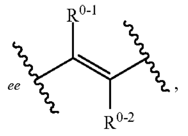

wherein $R^{0\text{-}1}$ and $R^{0\text{-}2}$ are independently H or $R^0$; and ee is the point of attachment to $T^1$. As non-limiting examples of the foregoing embodiments, $P^1$ can be

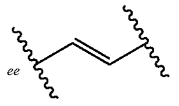

or

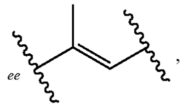

, wherein ee is the point of attachment to $T^1$.

In some embodiments, $L^0$ is #—$P^0$-$P^1$; $P^0$ is a bond; and $P^1$ is $(C_3\text{-}C_6)$cycloalkylene, which is optionally substituted with 1-3 $R^0$. In some embodiments, $P^1$ is

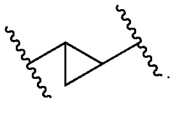 [SMILES: *C1CC1*]

In some embodiments, $L^0$ is #—$P^0$-$P^1$; $P^0$ is a bond; and $P^1$ is

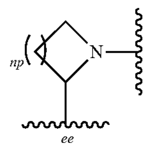

or

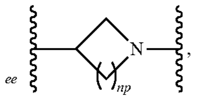

, each of which is optionally substituted with 1-2 $R^0$, wherein np is 1, 2, or 3; and ee is the point of attachment to $T^1$.

In some embodiments, $T^1$ is C(O)OH.

In some embodiments, $T^1$ is a carboxylic acid bioisostere.

In some embodiments, $T^1$ is tetrazolyl optionally substituted with $(C_1\text{-}C_3)$alkyl.

In some embodiments, $T^1$ is tetrazolyl, which is optionally substituted with from 1-2 substituents each independently selected from the group consisting of hydroxy, $(C_1\text{-}C_6)$alkyl, $(C_1\text{-}C_6)$haloalkyl, and halogen. For example, $T^1$ is selected from the group consisting of:

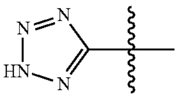

and

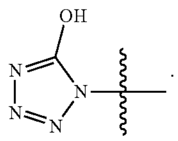

.

In some embodiments, $T^1$ is triazolyl substituted with from 1-2 substituents each independently selected from $(C_1\text{-}C_6)$alkyl and hydroxy. For example, $T^1$ is

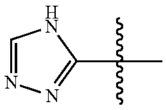 or 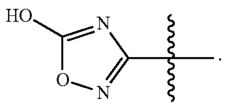.

In some embodiments, $T^1$ is triazolyl, which is optionally substituted with from 1-2 substituents each independently selected from $(C_1\text{-}C_6)$haloalkyl, CN. For example, $T^1$ is

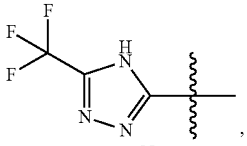, 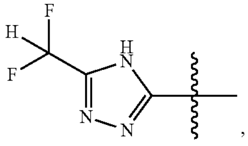, 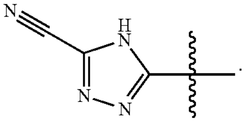.

In some embodiments, $T^1$ is a ring (e.g., a 4-6 membered ring, e.g., a 5 membered ring) including from 0-3 heteroatoms each independently selected from the group consisting of N, O, and S, wherein the ring is substituted with from 1-2 oxo and further optionally substituted from 1-2 substituent each independently selected from the group consisting of hydroxy, $(C_1\text{-}C_6)$alkyl, $(C_1\text{-}C_6)$haloalkyl, and halogen. For example, $T^1$ is

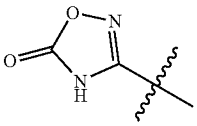 or 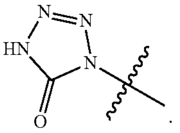.

In some embodiments, $T^1$ is $(C_1\text{-}C_6)$alkyl which is substituted with from 1-3 hydroxy and further optionally substituted with from 1-10 fluoro. In certain of these 20 embodiments, $T^1$ is $(C_1\text{-}C_6)$alkyl which is substituted with from 1-3 hydroxy and further substituted with from 1-10 fluoro. For example, $T^1$ is

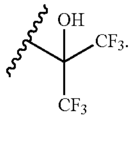

In some embodiments, $T^1$ is $C(=O)NHS(O)_2(C_1\text{-}C_4)$ alkyl. For example, $T^1$ is $C(=O)NHS(O)_2Me$.

In some embodiments, $T^1$ is selected from the group consisting of the following:

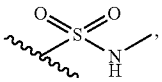, 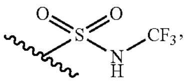, 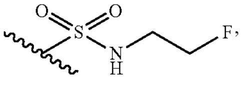, 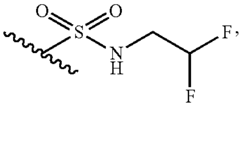,

-continued

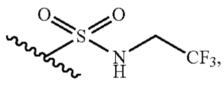, 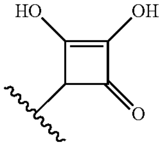,

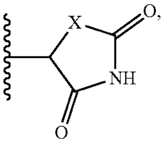, 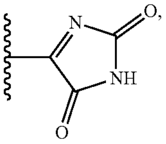, 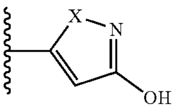,

X = O, S

X = O, S, NMe

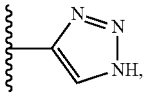, 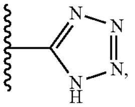, and 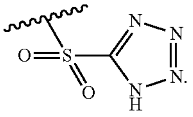.

In some embodiments, $T^2$ is hydrogen or $(C_1\text{-}C_6)$alkyl which is optionally substituted with $(C_1\text{-}C_6)$alkoxy, $(C_1\text{-}C_6)$ thioalkoxy, $(C_1\text{-}C_6)$haloalkoxy, $S(O)_2(C_1\text{-}C_6$ alkyl), $(C_3\text{-}C_6)$ cycloalkyl, 3- to 6-membered heterocycloalkyl, phenyl, or 5- to 6-membered heteroaryl, wherein each of the $(C_3\text{-}C_6)$ cycloalkyl, 3- to 6-membered heterocycloalkyl, phenyl, or 5- to 6-membered heteroaryl is optionally substituted with 1-4 $R^T$.

In some embodiments, each $R^T$ is independently selected from the group consisting of OH, SH, CN, $NO_2$, halogen, $(C_1\text{-}C_6)$alkyl, $(C_2\text{-}C_6)$alkenyl, $(C_2\text{-}C_6)$alkynyl, $(C_1\text{-}C_6)$haloalkyl, $(C_1\text{-}C_6)$cyanoalkyl, $(C_1\text{-}C_6)$hydroxyalkyl, $(C_1\text{-}C_6)$ alkoxy, $(C_1\text{-}C_6)$haloalkoxy, $(C_3\text{-}C_6)$cycloalkyl, amino, $(C_1\text{-}C_6)$alkylamino, and di$(C_1\text{-}C_6)$alkylamino.

In some embodiments, $T^2$ is hydrogen or $(C_1\text{-}C_6)$alkyl which is optionally substituted with $(C_1\text{-}C_6)$alkoxy, $(C_1\text{-}C_6)$ thioalkoxy, $(C_1\text{-}C_6)$haloalkoxy, $S(O)_2(C_1\text{-}C_6$ alkyl), $(C_3\text{-}C_6)$ cycloalkyl, 3- to 6-membered heterocycloalkyl, phenyl, or 5- to 6-membered heteroaryl, wherein each of the $(C_3\text{-}C_6)$ cycloalkyl, 3- to 6-membered heterocycloalkyl, phenyl, or 5- to 6-membered heteroaryl is optionally substituted with 1-4 $R^T$; and each $R^T$ is independently selected from the group consisting of OH, SH, CN, $NO_2$, halogen, $(C_1\text{-}C_6)$ alkyl, $(C_2\text{-}C_6)$alkenyl, $(C_2\text{-}C_6)$alkynyl, $(C_1\text{-}C_6)$haloalkyl, $(C_1\text{-}C_6)$cyanoalkyl, $(C_1\text{-}C_6)$hydroxyalkyl, $(C_1\text{-}C_6)$alkoxy, $(C_1\text{-}C_6)$haloalkoxy, $(C_3\text{-}C_6)$cycloalkyl, amino, $(C_1\text{-}C_6)$alkylamino, and di$(C_1\text{-}C_6)$alkylamino.

In some embodiments, $T^2$ is hydrogen, CN, $(C_1\text{-}C_6)$ haloalkyl, $(C_1\text{-}C_6)$hydroxyalkyl or $(C_1\text{-}C_6)$alkyl which is optionally substituted with $(C_1\text{-}C_6)$alkoxy, $(C_1\text{-}C_6)$thioalkoxy, $(C_1\text{-}C_6)$haloalkoxy, $S(O)_2(C_1\text{-}C_6$ alkyl), $-N(C_1\text{-}C_6$ alkyl)-$S(O)_2(C_1\text{-}C_6$ alkyl), $-NH\text{-}S(O)_2(C_1\text{-}C_6$ alkyl), $(C_3\text{-}C_6)$cycloalkyl, $(C_3\text{-}C_6)$cycloalkoxy, 3- to 6-membered heterocycloalkyl, phenyl, or 5- to 6-membered heteroaryl, wherein each of the $(C_3\text{-}C_6)$cycloalkyl, 3- to 6-membered heterocycloalkyl, phenyl, or 5- to 6-membered heteroaryl is optionally substituted with 1-4 $R^T$.

In some embodiments, each $R^T$ is independently selected from the group consisting of OH, SH, CN, $NO_2$, halogen, $=O$, $(C_1\text{-}C_6)$alkyl, $(C_2\text{-}C_6)$alkenyl, $(C_2\text{-}C_6)$alkynyl, $(C_1\text{-}C_6)$ haloalkyl, $(C_1\text{-}C_6)$cyanoalkyl, $(C_1\text{-}C_6)$hydroxyalkyl, $(C_1\text{-}C_6)$alkoxy, $(C_1\text{-}C_6)$haloalkoxy, $(C_3\text{-}C_6)$cycloalkyl, amino, $(C_1\text{-}C_6)$alkylamino, $(C_1\text{-}C_6)$alkylamino$(C_1\text{-}C_6$ alkyl)-C(O)—$C_1\text{-}C_6$ alkyl, $S(O)_2(C_1\text{-}C_6$ alkyl) and di$(C_1\text{-}C_6)$alkylamino.

In some embodiments, $T^2$ is hydrogen, CN, $(C_1\text{-}C_6)$ haloalkyl, $(C_1\text{-}C_6)$hydroxyalkyl or $(C_1\text{-}C_6)$alkyl which is optionally substituted with ($C_1$-$C_6$)alkoxy, ($C_1$-$C_6$)thioalkoxy, ($C_1$-$C_6$)haloalkoxy, $S(O)_2$($C_1$-$C_6$ alkyl), —N($C_1$-$C_6$ alkyl)-$S(O)_2$($C_1$-$C_6$ alkyl), —NH-$S(O)_2$($C_1$-$C_6$ alkyl), ($C_3$-$C_6$)cycloalkyl, ($C_3$-$C_6$)cycloalkoxy, 3- to 6-membered heterocycloalkyl, phenyl, or 5- to 6-membered heteroaryl, wherein each of the ($C_3$-$C_6$)cycloalkyl, 3- to 6-membered heterocycloalkyl, phenyl, or 5- to 6-membered heteroaryl is optionally substituted with 1-4 $R^T$; and each $R^T$ is independently selected from the group consisting of OH, SH, CN, $NO_2$, halogen, =O, ($C_1$-$C_6$)alkyl, ($C_2$-$C_6$)alkenyl, ($C_2$-$C_6$)alkynyl, ($C_1$-$C_6$)haloalkyl, ($C_1$-$C_6$)cyanoalkyl, ($C_1$-$C_6$)hydroxyalkyl, ($C_1$-$C_6$)alkoxy, ($C_1$-$C_6$)haloalkoxy, ($C_3$-$C_6$)cycloalkyl, amino, ($C_1$-$C_6$)alkylamino, ($C_1$-$C_6$)alkylamino ($C_1$-$C_6$ alkyl)-C(O)—$C_1$-$C_6$ alkyl, $S(O)_2$($C_1$-$C_6$ alkyl) and di($C_1$-$C_6$)alkylamino.

In some embodiments, $T^2$ is hydrogen.

In some embodiments, $T^2$ is CN.

In some embodiments, $T^2$ is ($C_1$-$C_6$)alkyl. In some embodiments, $T^2$ is methyl.

In some embodiments, $T^2$ is ($C_1$-$C_6$)alkyl which is substituted with ($C_1$-$C_6$)alkoxy. In some embodiments, $T^2$ is ($C_1$-$C_3$)alkyl which is substituted with ($C_1$-$C_3$)alkoxy. For example, $T^2$ can be

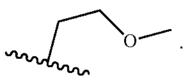

In some embodiments, $T^2$ is ($C_1$-$C_6$)alkyl which is substituted with $S(O)_2$($C_1$-$C_6$ alkyl). In some embodiments, $T^2$ is ($C_1$-$C_3$)alkyl which is substituted with $S(O)_2$($C_1$-$C_3$ alkyl). For example, $T^2$ can be

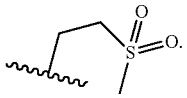 [SMILES: *CCS(C)(=O)=O]

In some embodiments, $T^2$ is ($C_1$-$C_6$)alkyl which is substituted with ($C_3$-$C_6$)cycloalkyl. In some embodiments, $T^2$ is ($C_1$-$C_3$)alkyl which is substituted with ($C_3$-$C_6$)cycloalkyl. In some embodiments, $T^2$ is ($C_1$-$C_3$)alkyl which is substituted with cyclobutyl. For example, $T^2$ can be

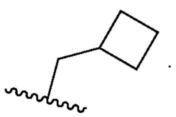 [SMILES: *CC1CCC1]

In some embodiments, $T^2$ is ($C_1$-$C_6$)alkyl which is substituted with 3- to 6-membered heterocycloalkyl. In some embodiments, $T^2$ is ($C_1$-$C_3$)alkyl which is substituted with 3- to 5-membered heterocycloalkyl. In some embodiments, $T^2$ is ($C_1$-$C_3$)alkyl which is substituted with oxetanyl. For example, $T^2$ can be

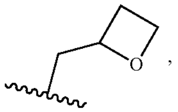 [SMILES: *CC1CCO1]

optionally wherein the stereogenic center in

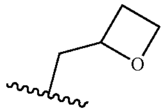 [SMILES: *CC1CCO1]

has (S)-configuration. In some embodiments, $T^2$ is ($C_1$-$C_3$) alkyl which is substituted with tetrahydrofuranyl. For example, $T^2$ can be

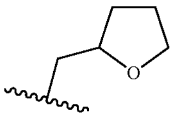

or

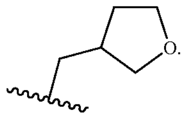

In some embodiments, $T^2$ is ($C_1$-$C_6$)alkyl which is substituted with 5- to 6-membered heteroaryl, wherein the 5- to 6-membered heteroaryl is optionally substituted with 1-4 $R^T$. In some embodiments, $T^2$ is ($C_1$-$C_3$)alkyl which is substituted with 5-membered heteroaryl, wherein the 5-membered heteroaryl is optionally substituted with 1-2 $R^T$. In some embodiments, $T^2$ is ($C_1$-$C_3$)alkyl which is substituted with imidazolyl, wherein the imidazolyl is optionally substituted with $R^T$. For example, $T^2$ can be

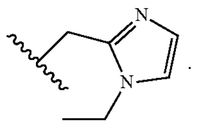 [SMILES: *Cc1nccn1CC]

As another non-limiting example, $T^2$ can be

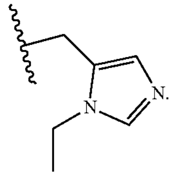 [SMILES: *Cc1cncn1CC]

In some embodiments, $T^2$ is ($C_1$-$C_6$)alkyl which is substituted with ($C_3$-$C_6$)cycloalkoxy.

In some embodiments, $T^2$ is ($C_1$-$C_6$)alkyl which is substituted with 3- to 6-membered heterocycloalkyl, wherein the 3- to 6-membered heterocycloalkyl is optionally substituted with 1-4 $R^T$. In certain of these embodiments, $R^T$ is $S(O)_2$($C_1$-$C_6$ alkyl).

In some embodiments, $T^2$ is ($C_1$-$C_6$)alkyl, which is substituted with —N($C_1$-$C_6$ alkyl)-$S(O)_2$($C_1$-$C_6$ alkyl).

In some embodiments, $T^2$ is ($C_1$-$C_6$)alkyl, which is substituted with —NH-$S(O)_2$($C_1$-$C_6$ alkyl).

In some embodiments, $T^2$ is ($C_1$-$C_6$)hydroxyalkyl.

In some embodiments, $T^2$ is ($C_1$-$C_6$)haloalkyl.

In some embodiments, $L^2$ is a bond.

In some embodiments, $L^1$ is $CH_2$. In some embodiments, $L^1$ is a bond.

In some embodiments, $L^2$ is a bond; and $L^1$ is $CH_2$.

In some embodiments, $L^1$ is a bond; and $L^2$ is a bond.

In some embodiments, Ring A is

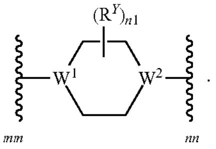

In some embodiments, $W^1$ is N. In some embodiments, $W^2$ is $CR^{Y2}$. In some embodiments, $R^{Y2}$ is hydrogen. In some embodiments, $W^2$ is N. In some embodiments, n1 is 0. For example, Ring A can be

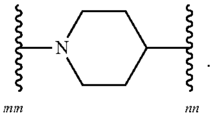

As another non-limiting example, Ring A can be

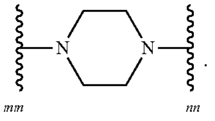

In some embodiments, n1 is 1. For example, Ring A can be

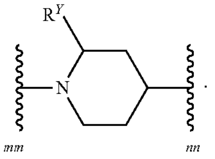

In some embodiments, Ring A is

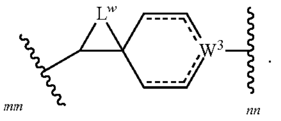

In some embodiments, Ring A is

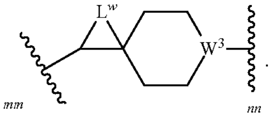

In some embodiments, $L^w$ is $CH_2$. In some embodiments, $W^3$ is N. As a non-limiting example of the foregoing embodiments, Ring A can be

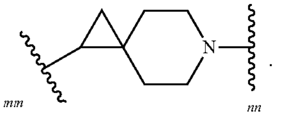

In some embodiments, $L^2$ is a bond; $L^1$ is $CH_2$; and Ring A is

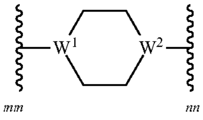
or
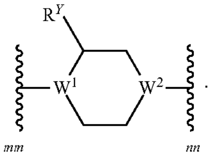

In some embodiments, Ring A is

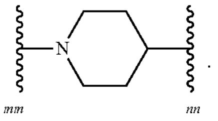

In some embodiments, Ring A is

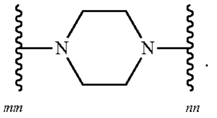

In some embodiments, $L^2$ is a bond; $L^1$ is a bond; and Ring A is

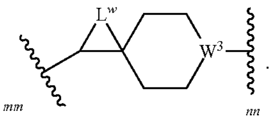

In some embodiments, Ring A is

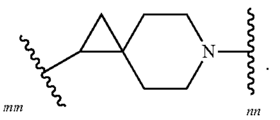

In some embodiments, Ring B is (B-I)

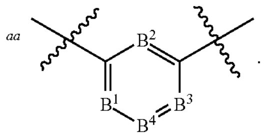

In some embodiments, $B^4$ is $CR^1$. For example, $B^4$ can be CH. In some embodiments, $B^1$ is $CR^1$. For example, $B^1$ can be CH. In some embodiments, $B^3$ is $CR^1$. For example, $B^3$ can be CH. In some embodiments, $B^2$ is N. In some embodiments, Ring B is

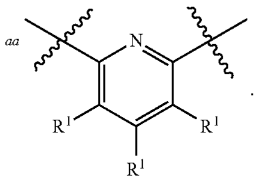

For example, Ring B can be

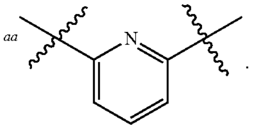 [SMILES: *c1cccc(*)n1]

In some embodiments, Ring B is (B-II)

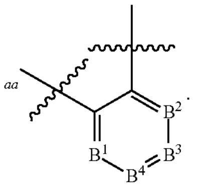

In some embodiments, $B^4$ and $B^3$ are independently selected $CR^1$. As non-limiting examples of the foregoing embodiments, $B^4$ and $B^3$ can be CH. In some embodiments, $B^1$ is $CR^1$. For example, $B^1$ can be CH. In some embodiments, $B^2$ is N. In some embodiments, Ring B is

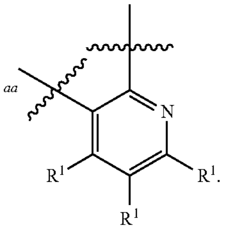

For example, Ring B can be

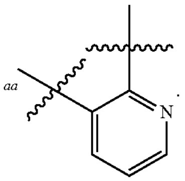 [SMILES: *c1cccnc1*]

In some embodiments, Ring B is (B-V)

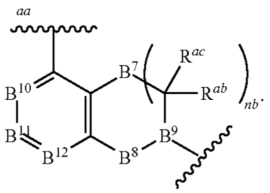

In some embodiments, $B^9$ is $CR^{aa}$. In some embodiments, $R^{aa}$ is H. In some embodiments, R is $(C_1\text{-}C_6)$alkyl. In some embodiments, $R^{aa}$ is $(C_1\text{-}C_3)$alkyl. For example, $R^{aa}$ can be methyl. In some embodiments, nb is 0. In some embodiments, nb is 1. In some embodiments, when $B^9$ is CRS, the carbon atom to which $B^8$ and $R^{aa}$ are both attached has (R)-configuration. In some embodiments, when $B^9$ is CRS, the carbon atom to which $B^8$ and $R^{aa}$ are both attached has (S)-configuration.

In some embodiments, Ring B is

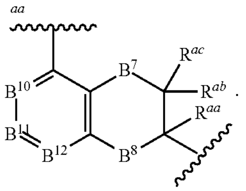

In some embodiments, $B^7$ is —O—. In some embodiments, $B^8$ is —O—. In some embodiments, $B^7$ is —O—; and $B^8$ is —O—. In some embodiments, $R^{aa}$ is H. In some embodiments, $R^{aa}$ is $(C_1\text{-}C_6)$alkyl. In some embodiments, $R^{aa}$ is $(C_1\text{-}C_3)$alkyl. For example, $R^{aa}$ can be methyl. In some embodiments, $R^{ab}$ is H. In some embodiments, $R^{ac}$ is H. In some embodiments, $R^{aa}$, $R^{ab}$, and $R^{ac}$ are each H. In some embodiments, $R^{aa}$ is $(C_1\text{-}C_3)$alkyl; and $R^{ab}$ and $R^{ac}$ are H. In some embodiments, $B^{10}$ is $CR^1$. For example, $B^{10}$ can be CH. In some embodiments, $B^{11}$ is $CR^1$. For example, $B^{11}$ can be CH. In some embodiments, $B^{12}$ is $CR^1$. For example, $B^{1t}$ can be CH. In some embodiments, $B^{10}$, $B^{11}$, and $B^{12}$ are each independently selected $CR^1$. In some embodiments, $B^{10}$, $B^{11}$, and $B^{12}$ are CH. In some embodiments, the carbon atom to which $B^8$ and $R^{aa}$ are both attached has (R)-configuration. In some embodiments, the carbon atom to which $B^8$ and $R^{aa}$ are both attached has (S)-configuration.

In some embodiments, B is

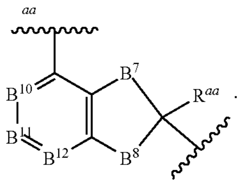

In some embodiments, $B^7$ is —O—. In some embodiments, $B^8$ is —O—. In some embodiments, $B^7$ is —O—; and $B^8$ is —O—. In some embodiments, $R^{aa}$ is H. In some embodiments, $R^{aa}$ is $(C_1\text{-}C_6)$alkyl. In some embodiments, $R^{aa}$ is $(C_1\text{-}C_3)$alkyl. For example, $R^{aa}$ can be methyl. In some embodiments, $B^{10}$ is $CR^1$. For example, $B^{10}$ can be CH. In some embodiments, $B^{11}$ is $CR^1$. For example, $B^{11}$ can be CH. In some embodiments, $B^{12}$ is $CR^1$. For example, $B^{12}$ can be CH. In some embodiments, $B^{10}$, $B^{11}$, and $B^{12}$ are each independently selected $CR^1$. In some embodiments, $B^{10}$, $B^{11}$ and $B^{12}$ are CH. In some embodiments, the carbon atom to which $B^8$ and $R^{aa}$ are both attached has (R)-configuration. In some embodiments, the carbon atom to which $B^8$ and $R^{aa}$ are both attached has (S)-configuration.

In some embodiments, Ring B is

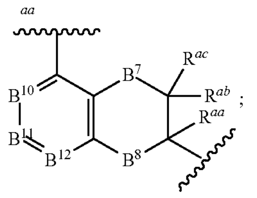

$B^7$ and $B^8$ are —O—; and $R^{aa}$ is H or $(C_1\text{-}C_3)$alkyl, such as H or methyl. In some embodiments, $R^{ab}$ and $R^{ac}$ are H. In some embodiments, $R^{aa}$ is H. In some embodiments, $R^{aa}$ is $(C_1\text{-}C_3)$alkyl, such as methyl. In some embodiments, $B^{10}$, $B^{11}$, and $B^{12}$ are each independently selected $CR^1$. In some embodiments, $B^{10}$, $B^{11}$, and $B^{12}$ are CH. In some embodiments, the carbon atom to which $B^8$ and $R^{aa}$ are both attached has (R)-configuration. In some embodiments, the carbon atom to which $B^8$ and $R^{aa}$ are both attached has (S)-configuration.

In some embodiments, Ring B is

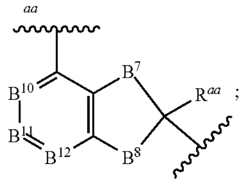

$B^7$ and $B^8$ are —O—; and $R^{aa}$ is H or $(C_1\text{-}C_3)$alkyl. In some embodiments, $R^{aa}$ is H. In some embodiments, $R^{aa}$ is $(C_1\text{-}C_3)$alkyl, such as methyl. In some embodiments, $B^{10}$, $B^{11}$, and $B^{12}$ are each independently selected $CR^1$. In some embodiments, $B^{10}$, $B^{11}$, and $B^{12}$ are CH. In some embodiments, the carbon atom to which $B^8$ and $R^{aa}$ are both attached has (R)-configuration. In some embodiments, the carbon atom to which $B^8$ and $R^{aa}$ are both attached has (S)-configuration.

In some embodiments, Ring B is

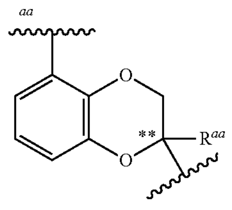

or

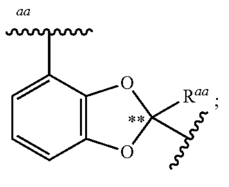

and the carbon atom labelled with ** has (R)-configuration.

In some embodiments, Ring B is

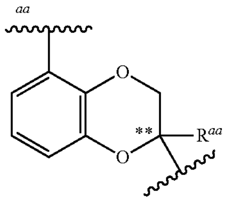

or

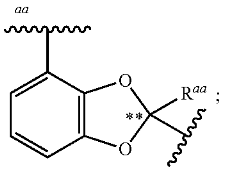

and the carbon atom labelled with ** has (S)-configuration.

In some embodiments, Ring B is

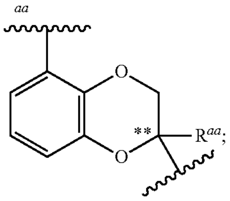

and the carbon atom labelled with ** has (R)-configuration.

In some embodiments, Ring B is

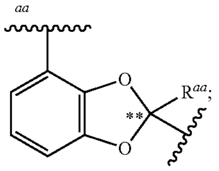

and the carbon atom labelled with ** has (S)-configuration. In some embodiments, $R^{aa}$ is $(C_1\text{-}C_3)$alkyl. For example, $R^{aa}$ can be methyl. For example, Ring B can be

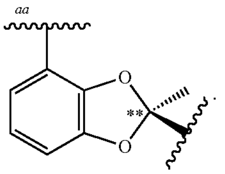 [SMILES: *c1cccc2c1O[C@](*)(C)O2]

In some embodiments, Ring B is

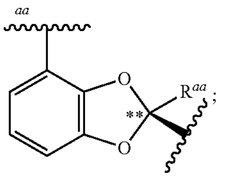

and the carbon atom labelled with ** has (R)-configuration. In some embodiments, $R^{aa}$ is $(C_1\text{-}C_3)$alkyl. For example, $R^{aa}$ can be methyl. For example, Ring B can be

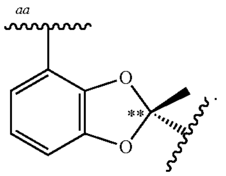 [SMILES: *c1cccc2c1O[C@@](*)(C)O2]

In some embodiments, $L^3$ is a bond. In some embodiments, Ring B is selected from the group consisting of (B-V) and (B-VI); and $L^3$ is a bond. In some embodiments, Ring B is (B-V) (e.g., Ring B is as defined in one or more embodiments, supra); and $L^3$ is a bond.

In some embodiments, $L^3$ is $—Z^1\text{-}Z^2—*$, wherein * represents the point of attachment to Ring C. In some embodiments, Ring B is selected from the group consisting of (B-I), (B-II), (B-III), and (B-IV), $L^3$ is $—Z^1\text{-}Z^2—*$, wherein * represents the point of attachment to Ring C. For example, Ring B is (B-I) or (B-II); and $L^3$ is $—Z^1\text{-}Z^2—$.

In some embodiments, $Z^1$ is —O—.

In some embodiments, $Z^2$ is $—CH_2—$ optionally substituted with 1-2 $R^c$. In some embodiments, $Z^2$ is $—CH_2—$.

In some embodiments, $L^3$ is $—O—CH_2—*$, wherein * represents the point of attachment to Ring C.

In some embodiments, Ring C is selected from the group consisting of: phenyl, 5- to 6-membered heteroaryl, and 5- to 10-membered bicycloheteroaryl. In some embodiments, Ring C is selected from the group consisting of: phenyl and 6-membered heteroaryl (e.g., pyridyl).

In some embodiments, b is 1-3. In some embodiments, b is 2. In some embodiments, b is 1. In some embodiments, b is 0.

In some embodiments, Ring C is phenyl. In some embodiments, Ring C is phenyl; and b is 2. In some embodiments,

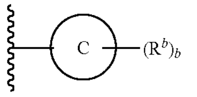 is 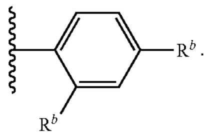

In some embodiments, Ring C is phenyl; and b is 1. In some embodiments,

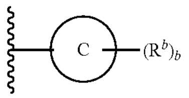 is 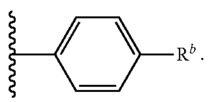

In some embodiments, Ring C is phenyl; and b is 0.

In some embodiments, each occurrence of $R^b$ is independently selected from the group consisting of: $(C_1\text{-}C_6)$alkyl, $(C_1\text{-}C_6)$haloalkyl, $(C_1\text{-}C_6)$alkoxy, $(C_1\text{-}C_6)$haloalkoxy, halogen, and CN. In some embodiments, each occurrence of $R^b$ is independently selected from the group consisting of —F, $—C_1$, $CF_3$, and CN.

In some embodiments, the compound is a compound of Formula (I-A1) or a pharmaceutically acceptable salt thereof:

Formula (I-A1)

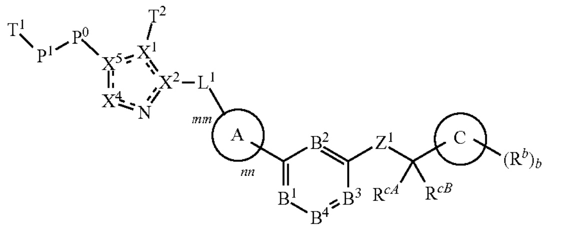

wherein $R^{cA}$ and $R^{cB}$ are independently selected from the group consisting of H and $R^c$.

In some embodiments of Formula (I-A1), the ring containing $B^1$, $B^2$, $B^3$, and $B^4$ is

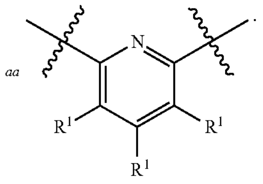

For example, the ring containing $B^1$, $B^2$, $B^3$, and $B^4$ can be

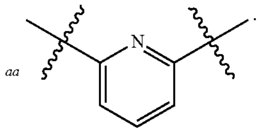 [SMILES: *c1cccc(*)n1]

In some embodiments, the compound is a compound of Formula (I-A2) or a pharmaceutically acceptable salt thereof:

Formula (I-A2)

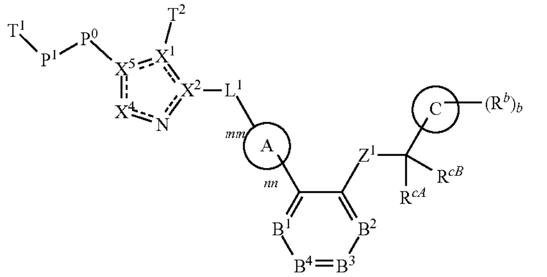

wherein $R^{cA}$ and $R^{cB}$ are independently selected from the group consisting of H and $R^c$.

In some embodiments of Formula (I-A2), the ring containing $B^1$, $B^2$, $B^3$, and $B^4$ is

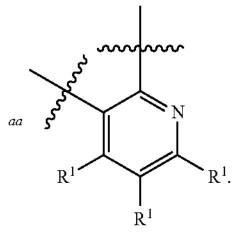

For example, the ring containing $B^1$, $B^2$, $B^3$, and $B^4$ can be

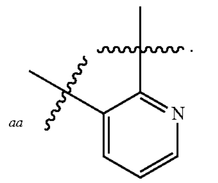 [SMILES: *c1cccnc1*]

In some embodiments of Formulae (I-A1) or (I-A2), $Z^1$ is —O—. In some embodiments of Formulae (I-A1) or (I-A2), $R^{cA}$ is H. In some embodiments of Formulae (I-A1) or (I-A2), $R^{cB}$ is H.

In some embodiments, the compound is a compound of Formula (I-A3):

Formula (I-A3)

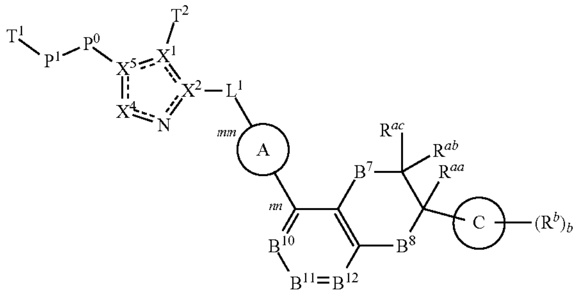

or a pharmaceutically acceptable salt thereof.

In some embodiments of Formula (I-A3), $R^{ab}$ and $R^{ac}$ are H.

In some embodiments, the compound is a compound of Formula (I-A4):

Formula (I-A4)

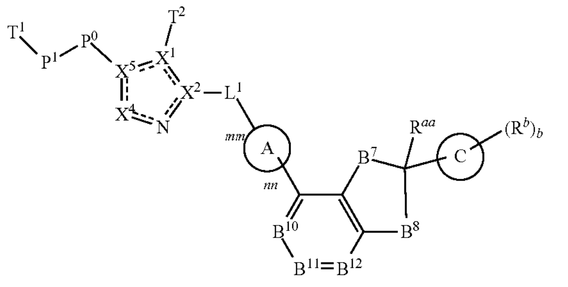

or a pharmaceutically acceptable salt thereof.

In some embodiments of Formula (I-A4), $B^7$ is —O—; and $B^8$ is —O—.

In some embodiments of Formulae (I-A3) or (I-A4), $R^{aa}$ is H. In some embodiments, $R^{aa}$ is $(C_1$-$C_3)$alkyl. For example, $R^{aa}$ can be methyl.

In some embodiments of Formulae (I-A3) or (I-A4), $B^{10}$, $B^{11}$, and $B^{12}$ are independently selected $CR^1$. In some embodiments, $B^{10}$, $B^{11}$, and $B^{12}$ are CH.

In some embodiments of Formulae (I-A1), (I-A2), (I-A3), or (I-A4), $X^1$ is N.

In some embodiments of Formulae (I-A1), (I-A2), (I-A3), or (I-A4), $X^2$ is C.

In some embodiments of Formulae (I-A1), (I-A2), (I-A3), or (I-A4), $X^5$ is C.

In some embodiments of Formulae (I-A1), (I-A2), (I-A3), or (I-A4), $X^4$ is N. In some embodiments of Formulae (I-A1), (I-A2), (I-A3), or (I-A4), $X^4$ is $CR^y$, such as CH.

In some embodiments of Formulae (I-A1), (I-A2), (I-A3), or (I-A4), the

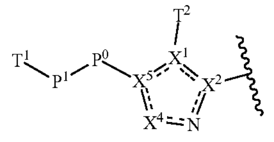

moiety is

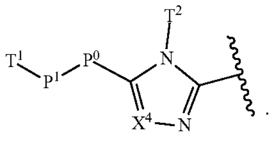

In some embodiments, $X^4$ is N. In some embodiments, $X^4$ is $CR^y$. For example, $X^4$ can be CH.

In some embodiments, the compound is a compound of Formula (I-B), or a pharmaceutically acceptable salt thereof:

Formula (I-B1)

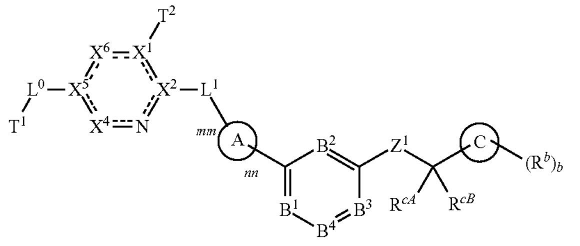

wherein $X^6$ is selected from the group consisting of: N, $NR^x$, $CR^y$, and C(═O); and $R^{cA}$ and $R^{cB}$ are independently selected from the group consisting of H and $R^c$.

In some embodiments of Formula (I-B), $X^1$ is C. In some embodiments of Formula (I-B), $X^2$ and $X^5$ are C. In some embodiments of Formula (I-B1), $X^4$ and $X^6$ are independently selected $CR^y$. For example, $X^4$ and $X^6$ can be CH.

In some embodiments of Formula (I-B1), the

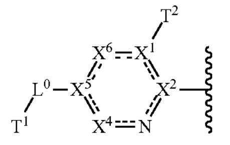

moiety is

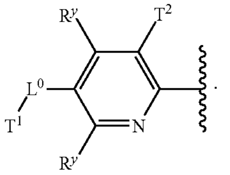

In some embodiments, each $R^y$ is H.

In some embodiments of Formula (I-B1), $L^0$ is #—$P^0$-$P^1$.

In some embodiments of Formula (I-B), $Z^1$ is —O—. In some embodiments of Formula (I-B1), $R^{cA}$ is H; and $R^{cB}$ is H.

In some embodiments of Formulae (I-A1), (I-A2), (I-A3), (I-A4), or (I-B), $P^0$ is a bond; and $P^1$ is $(C_1$-$C_3)$alkylene which is optionally substituted with 1-3 $R^0$. In some embodiments, $P^1$ is $(C_1$-$C_3)$alkylene. For example, $P^1$ can be —$CH_2CH_2$—.

In some embodiments of Formulae (I-A1), (I-A2), (I-A3), (I-A4), or (I-B), $P^0$ is —NH—, —N($C_1$-$C_3$ alkyl) or —O—; and $P^1$ is $(C_1$-$C_3)$alkylene which is optionally substituted with 1-3 $R^0$. In some embodiments, $P^1$ is $(C_1$-$C_3)$alkylene. For example, $P^1$ can be $CH_2$, CH(Me), or $C(Me)_2$.

In some embodiments of Formulae (I-A1), (I-A2), (I-A3), (I-A4), or (I-B), $P^0$ is a bond; and $P^1$ is $(C_2$-$C_4)$alkenylene which is optionally substituted with 1-3 $R^0$. In some embodiments, $P^1$ is

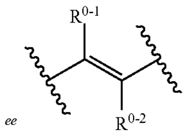, wherein $R^{0-1}$ and $R^{0-2}$ are independently H or $R^0$; and ee is the point of attachment to $T^1$. In some embodiments, $P^1$ is

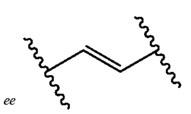 or 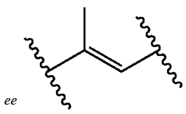, wherein ee is the point of attachment to $T^1$.

In some embodiments of Formulae (I-A1), (I-A2), (I-A3), (I-A4), or (I-B), $P^0$ is a bond; and $P^1$ is $(C_3$-$C_6)$cycloalkylene, which is optionally substituted with 1-3 $R^0$. In some embodiments, P1 is

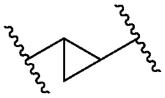.

In some embodiments of Formulae (I-A1), (I-A2), (I-A3), (I-A4), or (I-B), $P^0$ is a bond; and $P^1$ is

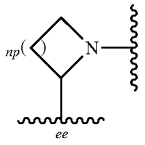 or 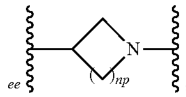, each of which is optionally substituted with 1-2 $R^0$, wherein np is 1, 2, or 3; and ee is the point of attachment to $T^1$.

In some embodiments of Formulae (I-A1), (I-A2), (I-A3), (I-A4), or (I-B), $T^1$ is C(O)OH.

In some embodiments of Formulae (I-A1), (I-A2), (I-A3), (I-A4), or (I-B), $T^2$ is H or $(C_1$-$C_3)$alkyl.

In some embodiments of Formulae (I-A1), (I-A2), (I-A3), (I-A4), or (I-B), $T^2$ is $(C_1$-$C_3)$alkyl which is substituted with $(C_1$-$C_3)$alkoxy. For example, $T^2$ can be

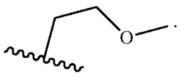 [SMILES: *CCOC].

In some embodiments of Formulae (I-A1), (I-A2), (I-A3), (I-A4), or (I-B), $T^2$ is $(C_1$-$C_3)$alkyl which is substituted with $S(O)_2(C_1$-$C_3$ alkyl). For example, $T^2$ can be

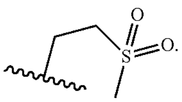 [SMILES: *CCS(C)(=O)=O].

In some embodiments of Formulae (I-A1), (I-A2), (I-A3), (I-A4), or (I-B), $T^2$ is $(C_1$-$C_3)$alkyl which is substituted with $(C_3$-$C_6)$cycloalkyl. For example, $T^2$ can be

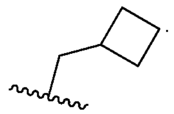 [SMILES: *CC1CCC1].

In some embodiments of Formulae (I-A1), (I-A2), (I-A3), (I-A4), or (I-B), $T^2$ is $(C_1$-$C_3)$alkyl which is substituted with 3- to 5-membered heterocycloalkyl. In some embodiments, $T^2$ is $(C_1$-$C_3)$alkyl which is substituted with oxetanyl. For example, $T^2$ can be

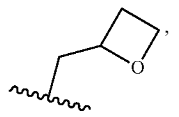 [SMILES: *CC1CCO1], optionally wherein the stereogenic center in

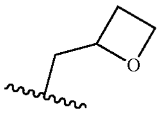 [SMILES: *CC1CCO1]

has (S)-configuration. In some embodiments, $T^2$ is ($C_1$-$C_3$) alkyl which is substituted with tetrahydrofuranyl. In some embodiments, T2 is

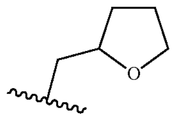

or

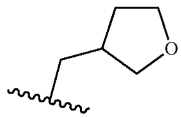

In some embodiments of Formulae (I-A1), (I-A2), (I-A3), (I-A4), or (I-B), $T^2$ is ($C_1$-$C_3$)alkyl which is substituted with 5-membered heteroaryl, wherein the 5-membered heteroaryl is optionally substituted with 1-2 $R^T$. In some embodiments, $T^2$ is ($C_1$-$C_3$)alkyl which is substituted with imidazolyl, wherein the imidazolyl is optionally substituted with $R^T$. For example, $T^2$ can be

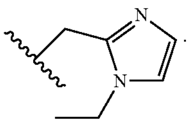 [SMILES: *Cc1nccn1CC]

As another non-limiting example, $T^2$ can be

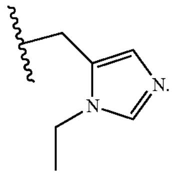 [SMILES: *Cc1cncn1CC]

In some embodiments of Formulae (I-A1), (I-A2), (I-A3), (I-A4), or (I-B), $L^1$ is $CH_2$; and Ring A is

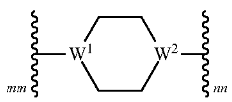

or

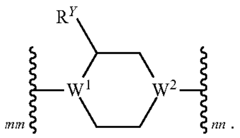

In some embodiments of Formulae (I-A1), (I-A2), (I-A3), (I-A4), or (I-B), $L^1$ is $CH_2$; and Ring A is

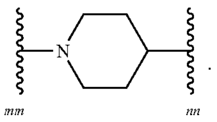

In some embodiments of Formulae (I-A1), (I-A2), (I-A3), (I-A4), or (I-B), $L^1$ is $CH_2$; and Ring A is

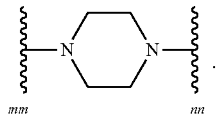

In some embodiments of Formulae (I-A1), (I-A2), (I-A3), (I-A4), or (I-B), $L^1$ is a bond; and Ring A is

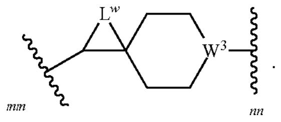

In some embodiments, Ring A is

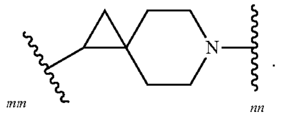 [SMILES: *C1CC12CCN(*)CC2]

In some embodiments of Formulae (I-A1), (I-A2), (I-A3), (I-A4), or (I-B), Ring C is selected from the group consisting of: phenyl and 6-membered heteroaryl (e.g., pyridyl such as 2-pyridyl, 3-pyridyl, or 4-pyridyl).

In some embodiments of Formulae (I-A1), (I-A2), (I-A3), (I-A4), or (I-B),

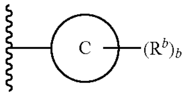

is

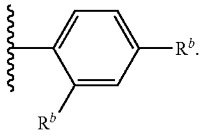

In some embodiments of Formulae (I-A1), (I-A2), (I-A3), (I-A4), or (I-B),

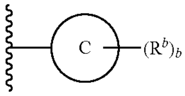

is

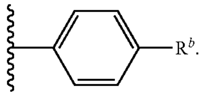

In some embodiments of Formulae (I-A1), (I-A2), (I-A3), (I-A4), or (I-B1), each occurrence of $R^b$ is independently selected from the group consisting of: ($C_1$-$C_6$)alkyl, ($C_1$-$C_6$) haloalkyl, ($C_1$-$C_6$)alkoxy, ($C_1$-$C_6$)haloalkoxy, halogen, and CN.

In some embodiments of Formulae (I-A1), (I-A2), (I-A3), (I-A4), or (I-B1), $R^b$ is independently selected from the group consisting of —F, —Cl, $CF_3$, and CN.

In some embodiments, the compound of Formula (I) is a compound of Formula (I-A4-1), or a pharmaceutically acceptable salt thereof:

Formula (I-A4-1)

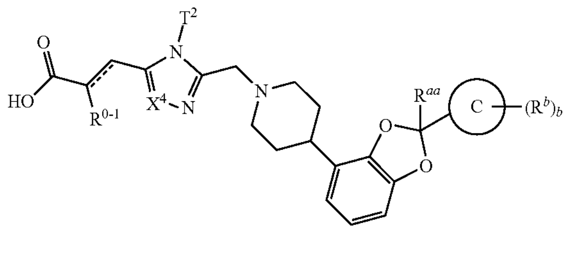

wherein:

is a single bond or a double bond;

$R^{0-1}$ is selected from the group consisting of hydrogen and ($C_1$-$C_3$)alkyl;

$X^4$ is selected from the group consisting of N and $CR^y$;

$T^2$ is ($C_1$-$C_3$)alkyl which is substituted with a substituent selected from the group consisting of ($C_1$-$C_3$)alkoxy, $S(O)_2$($C_1$-$C_3$ alkyl), ($C_3$-$C_6$)cycloalkyl, 3- to 6-membered heterocycloalkyl, phenyl, and 5- to 6-membered heteroaryl, wherein the phenyl or 5- to 6-membered heteroaryl are each optionally substituted with halogen or ($C_1$-$C_3$)alkyl;

$R^{aa}$ is selected from the group consisting of hydrogen and ($C_1$-$C_3$)alkyl;

Ring C is selected from the group consisting of: phenyl and 6-membered heteroaryl;

b is 0, 1, or 2; and each occurrence of $R^b$ is independently selected from the group consisting of:

($C_1$-$C_6$)alkyl, ($C_1$-$C_6$)haloalkyl, ($C_1$-$C_6$)alkoxy, ($C_1$-$C_6$) haloalkoxy, halogen, and CN.

In some embodiments of Formula (I-A4-1), is a double bond.

In some embodiments of Formula (I-A4-1), is a single bond.

In some embodiments of Formula (I-A4-1), $R^{0-1}$ is hydrogen.

In some embodiments of Formula (I-A4-1), $R^{0-1}$ is ($C_1$-$C_3$)alkyl. For example, $R^{0-1}$ can be methyl.

In some embodiments of Formula (I-A4-1), is a double bond; and $R^{0-1}$ is hydrogen.

In some embodiments of Formula (I-A4-1), is a double bond; and $R^{0-1}$ is methyl.

In some embodiments of Formula (I-A4-1), is a single bond; and $R^{0-1}$ is hydrogen.

In some embodiments of Formula (I-A4-1), $X^4$ is CH.

In some embodiments of Formula (I-A4-1), $X^4$ is N.

In some embodiments of Formula (I-A4-1), $T^2$ is ($C_1$-$C_3$) alkyl which is substituted with 3- to 6-membered heterocycloalkyl. In some embodiments, $T^2$ is ($C_1$-$C_3$)alkyl which is substituted with oxetanyl. For example, $T^2$ can be

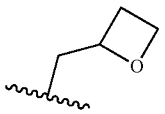 [SMILES: *CC1CCO1]

(e.g., the stereogenic center in $T^2$ can have (S)-configuration). In some embodiments, $T^2$ is ($C_1$-$C_3$)alkyl which is substituted with tetrahydrofuranyl. For example, $T^2$ can be

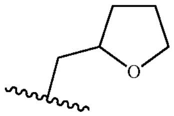

or

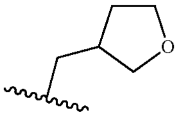

(e.g., the stereogenic center in $T^2$ can have (S)-configuration).

In some embodiments of Formula (I-A4-1), $T^2$ is ($C_1$-$C_3$) alkyl which is substituted with 5-membered heteroaryl, wherein the 5-membered heteroaryl is optionally substituted with ($C_1$-$C_3$)alkyl. In some embodiments, $T^2$ is ($C_1$-$C_3$)alkyl which is substituted with imidazolyl, wherein the imidazolyl is optionally substituted with ($C_1$-$C_3$)alkyl. For example, $T^2$ can be

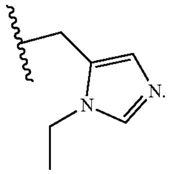 [SMILES: *Cc1cncn1CC]

As another non-limiting example, $T^2$ can be

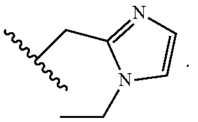 [SMILES: *Cc1nccn1CC]

In some embodiments of Formula (I-A4-1), $T^2$ is ($C_1$-$C_3$) alkyl which is substituted with ($C_1$-$C_3$)alkoxy. For example, $T^2$ can be

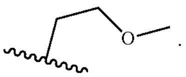 [SMILES: *CCOC]

In some embodiments of Formula (I-A4-1), $R^{aa}$ is ($C_1$-$C_3$)alkyl. For example, $R^{aa}$ is methyl.

In some embodiments of Formula (I-A4-1), $R^{aa}$ is hydrogen.

In some embodiments of Formula (I-A4-1), the carbon to which both $R^{aa}$ and Ring C are attached has (S)-configuration.

In some embodiments of Formula (I-A4-1), $R^{aa}$ is ($C_1$-$C_3$)alkyl; and the carbon to which both $R^{aa}$ and Ring C are attached has (S)-configuration. In some embodiments, $R^{aa}$ is methyl.

In some embodiments of Formula (I-A4-1), Ring C is phenyl.

In some embodiments of Formula (I-A4-1), b is 1 or 2.

In some embodiments of Formula (I-A4-1),

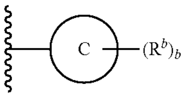

is

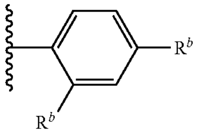

-continued (e.g., 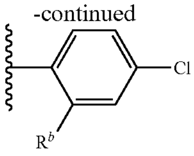 ).

In some Formula I-A4-1),

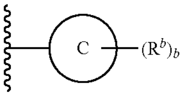 is 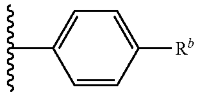

(e.g., 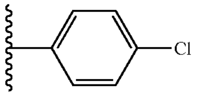 ).

In some embodiments of Formula (I-A4-1), each $R^b$ is independently selected from the group consisting of: —F, —Cl, and —CN. In some embodiments, each $R^b$ is independently selected from the group consisting of: —F and —Cl. For example, each $R^b$ can be independently —F or —Cl.

In some embodiments of Formula (I-A4-1):

$R^{0-1}$ is hydrogen or methyl;

$X^4$ is N or CH;

$T^2$ is selected from the group consisting of:

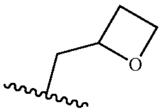 , 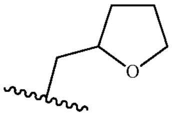 , 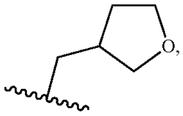

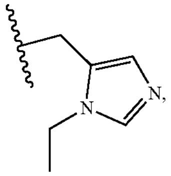 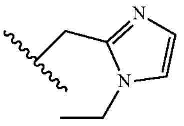 , and

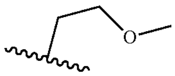 ;

$R^{aa}$ is $(C_1\text{-}C_3)$alkyl, wherein the carbon to which both $R^{aa}$ and Ring C are attached has (S)-configuration;

Ring C is phenyl; and b is 1 or 2.

In some embodiments, $R^{aa}$ is methyl. In some embodiments, $X^4$ is CH. In some embodiments, $X^4$ is N. In some embodiments, each $R^b$ is independently —F or —Cl.

In some embodiments, the compound of Formula I (e.g., Formulae (I-A1), (I-A2), (I-A3), (I-A4), or (I-B)) is selected from the group consisting of the compounds in Table Cl, or a pharmaceutically acceptable salt or solvate thereof.

In some embodiments, the compound of Formula I is selected from the group consisting of compounds 101, 102, 102a, 103, 103a, 104, 105, 106, 107, 108, 109, 110, 112, 113, 114, 114a, 115, 115a, 116, 116a, 117, 119, 120, 123, 125, 126, 127, 128, and 129, as depicted in Table Cl, or a pharmaceutically acceptable salt or solvate thereof.

In some embodiments, the compound of Formula I (e.g., Formulae (I-A4) or (I-A4-1)) is selected from the group consisting of compounds 131, 131a, 131b, 132, 132a, 133, 133a, 133b, 134, 134a, 134b, 135, 135a, 135b, 136, 136a, 137, 137a, 138, 138a, 138b, 139, 139a, 139b, 140, 140a, 141, 142, 143, and 144, as depicted in Table Cl, or a pharmaceutically acceptable salt or solvate thereof.

In some embodiments, the compound is a compound of Formula (I-A1) or a pharmaceutically acceptable salt thereof:

Formula (I-A5)

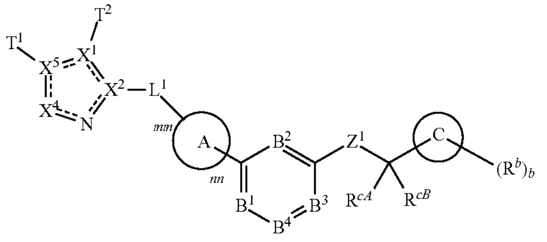

wherein $R^{cA}$ and $R^{cB}$ are independently selected from the group consisting of H and $R^c$.

In some embodiments of Formula (I-A5), the ring containing $B^1$, $B^2$, $B^3$, and $B^4$ is

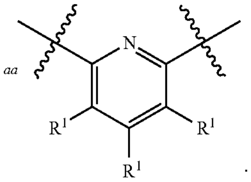 .

For example, the ring containing $B^1$, $B^2$, $B^3$, and $B^4$ can be

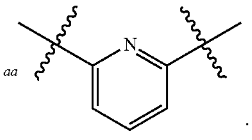 [SMILES: *c1cccc(*)n1] .

In some embodiments, the compound is a compound of Formula (I-A2) or a pharmaceutically acceptable salt thereof:

Formula (I-A6)

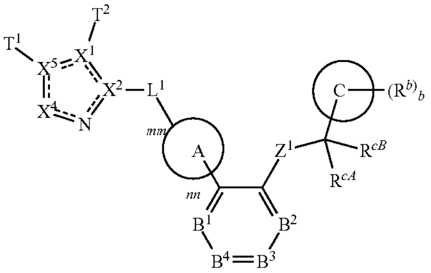

wherein $R^{cA}$ and $R^{cB}$ are independently selected from the group consisting of H and $R^c$.

In some embodiments of Formula (I-A6), the ring containing $B^1$, $B^2$, $B^3$, and $B^4$ is

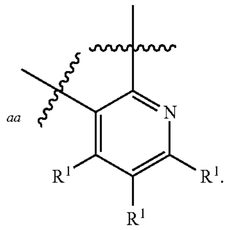

For example, the ring containing $B^1$, $B^2$, $B^3$, and $B^4$ can be

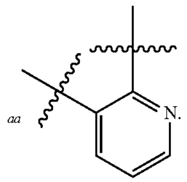 [SMILES: *c1cccnc1*]

In some embodiments of Formulae (I-A1) or (I-A2), $Z^1$ is —O—. In some embodiments of Formulae (I-A1) or (I-A2), $R^{cA}$ is H. In some embodiments of Formulae (I-A1) or (I-A2), $R^{cB}$ is H.

In some embodiments, the compound is a compound of Formula (I-A3):

Formula (I-A7)

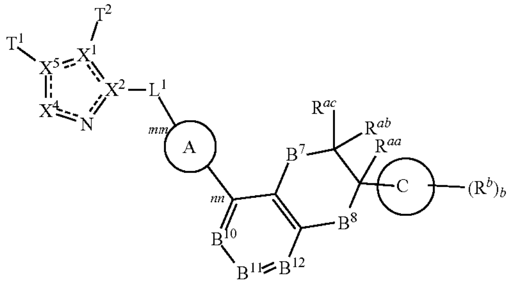

or a pharmaceutically acceptable salt thereof.

In some embodiments of Formula (I-A7), $R^{ab}$ and $R^{ac}$ are H.

In some embodiments, the compound is a compound of Formula (I-A4):

Formula (I-A8)

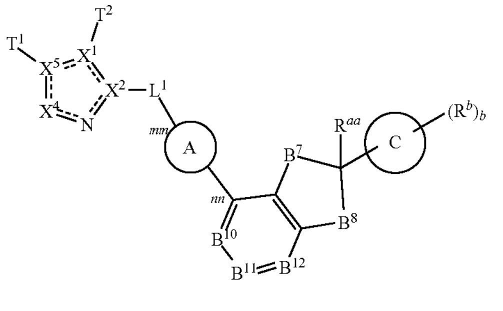

or a pharmaceutically acceptable salt thereof.

In some embodiments of Formula (I-A8), $B^7$ is —O—; and $B^8$ is —O—.

In some embodiments of Formulae (I-A7) or (I-A8), $R^{aa}$ is H. In some embodiments, $R^{aa}$ is $(C_1$-$C_3)$alkyl. For example, $R^{aa}$ can be methyl.

In some embodiments of Formulae (I-A7) or (I-A8), $B^{10}$, $B^{11}$, and $B^{12}$ are independently selected $CR^1$. In some embodiments, $B^{10}$, $B^{11}$, and $B^{12}$ are CH.

In some embodiments of Formulae (I-A5), (I-A6), (I-A7), or (I-A8), $X^1$ is N.

In some embodiments of Formulae (I-A5), (I-A6), (I-A7), or (I-A8), $X^2$ is C.

In some embodiments of Formulae (I-A5), (I-A6), (I-A7), or (I-A8), $X^5$ is C.

In some embodiments of Formulae (I-A5), (I-A6), (I-A7), or (I-A8), $X^4$ is N.

In some embodiments of Formulae (I-A5), (I-A6), (I-A7), or (I-A8), $X^4$ is $CR^y$, such as CH.

In some embodiments of Formulae (I-A5), (I-A6), (I-A7), or (I-A8), the

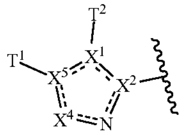

moiety is

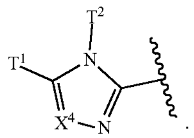

In some embodiments, $X^4$ is N. In some embodiments, $X^4$ is $CR^y$. For example, $X^4$ can be CH.

In some embodiments, the compound is a compound of Formula (I-B2), or a pharmaceutically acceptable salt thereof:

Formula (I-B2)

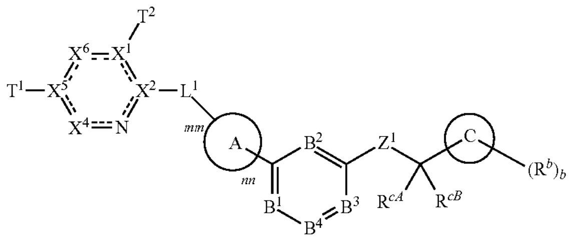

wherein $X^6$ is selected from the group consisting of: N, $NR^x$, $CR^y$, and C(═O); and $R^{cA}$ and $R^{cB}$ are independently selected from the group consisting of H and R.

In some embodiments of Formula (I-B2), $X^1$ is C. In some embodiments of Formula (I-B2), $X^2$ and $X^5$ are C. In some embodiments of Formula (I-B2), $X^4$ and $X^6$ are independently selected $CR^y$. For example, $X^4$ and $X^6$ can be CH.

In some embodiments of Formula (I-B2), the

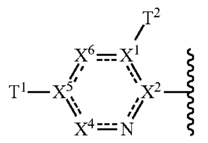

moiety is

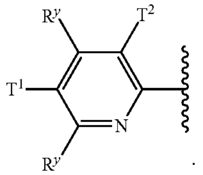

In some embodiments, each $R^y$ is H.

In some embodiments of Formula (I-B2), $L^0$ is #—$P^0$-$P^1$.

In some embodiments of Formula (I-B2), $Z^1$ is —O—. In some embodiments of Formula (I-B2), $R^{cA}$ is H; and $R^{cB}$ is H.

In some embodiments of Formulae (I-A5), (I-A6), (I-A7), (I-A8), or (I-B2), $T^1$ is C(O)OH.

In some embodiments of Formulae (I-A5), (I-A6), (I-A7), (I-A8), or (I-B2), $T^1$ is a carboxylic acid bioisostere (e.g., tetrazolyl, optional substituted triazolyl).

In some embodiments of Formulae (I-A5), (I-A6), (I-A7), (I-A8), or (I-B2), $T^2$ is H or $(C_1$-$C_3)$alkyl.

In some embodiments of Formulae (I-A5), (I-A6), (I-A7), (I-A8), or (I-B2), $T^2$ is $(C_1$-$C_3)$alkyl which is substituted with $(C_1$-$C_3)$alkoxy. For example, $T^2$ can be

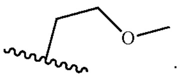 [SMILES: *CCOC]

In some embodiments of Formulae (I-A5), (I-A6), (I-A7), (I-A8), or (I-B2), $T^2$ is $(C_1$-$C_3)$alkyl which is substituted with $S(O)_2(C_1$-$C_3$ alkyl). For example, $T^2$ can be

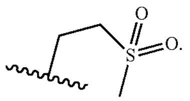 [SMILES: *CCS(C)(=O)=O]

In some embodiments of Formulae (I-A5), (I-A6), (I-A7), (I-A8), or (I-B2), $T^2$ is $(C_1$-$C_3)$alkyl which is substituted with $(C_3$-$C_6)$cycloalkyl. For example, $T^2$ can be

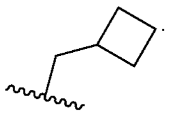 [SMILES: *CC1CCC1]

In some embodiments of Formulae (I-A5), (I-A6), (I-A7), (I-A8), or (I-B2), $T^2$ is $(C_1$-$C_3)$alkyl which is substituted with 3- to 5-membered heterocycloalkyl. In some embodiments, $T^2$ is $(C_1$-$C_3)$alkyl which is substituted with oxetanyl. For example, $T^2$ can be

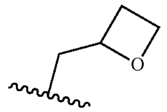 [SMILES: *CC1CCO1]

optionally wherein the stereogenic center in

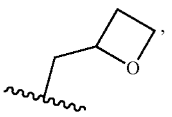 [SMILES: *CC1CCO1]

has (S)-configuration. In some embodiments, $T^2$ is $(C_1$-$C_3)$ alkyl which is substituted with tetrahydrofuranyl. In some embodiments, $T^2$ is

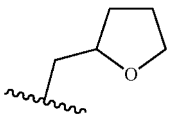

or

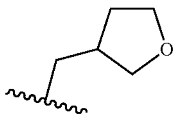

.

In some embodiments of Formulae (I-A5), (I-A6), (I-A7), (I-A8), or (I-B2), $T^2$ is $(C_1$-$C_3)$alkyl which is substituted with 5-membered heteroaryl, wherein the 5-membered heteroaryl is optionally substituted with 1-2 $R^T$. In some embodiments, $T^2$ is $(C_1$-$C_3)$alkyl which is substituted with imidazolyl, wherein the imidazolyl is optionally substituted with $R^T$. For example, $T^2$ can be

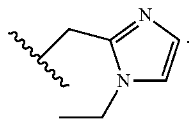 [SMILES: *Cc1nccn1CC]

As another non-limiting example, $T^2$ can be

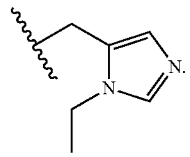 [SMILES: *Cc1cncn1CC]

In some embodiments of Formulae (I-A5), (I-A6), (I-A7), (I-A8), or (I-B2), $L^1$ is $CH_2$; and Ring A is

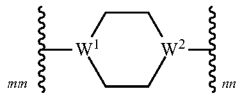

or

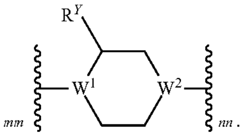

In some embodiments of Formulae (I-A5), (I-A6), (I-A7), (I-A8), or (I-B2), $L^1$ is $CH_2$; and Ring A is

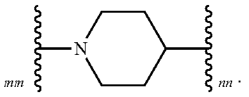

In some embodiments of Formulae (I-A5), (I-A6), (I-A7), (I-A8), or (I-B2), $L^1$ is $CH_2$; and Ring A is

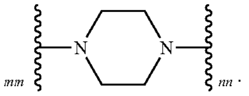

In some embodiments of Formulae (I-A5), (I-A6), (I-A7), (I-A8), or (I-B2), $L^1$ is a bond; and Ring A is

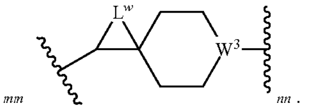

In some embodiments, Ring A is

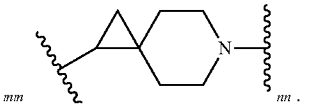

In some embodiments of Formulae (I-A5), (I-A6), (I-A7), (I-A8), or (I-B2), Ring C is selected from the group consisting of: phenyl and 6-membered heteroaryl (e.g., pyridyl such as 2-pyridyl, 3-pyridyl, or 4-pyridyl).

In some embodiments of Formulae (I-A5), (I-A6), (I-A7), (I-A8), or (I-B2),

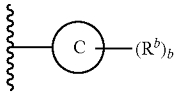 is 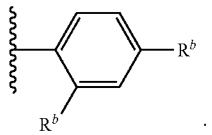.

In some embodiments of Formulae (I-A5), (I-A6), (I-A7), (I-A8), or (I-B2),

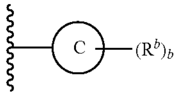 is 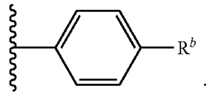.

In some embodiments of Formulae (I-A5), (I-A6), (I-A7), (I-A8), or (I-B2), each occurrence of $R^b$ is independently selected from the group consisting of: $(C_1\text{-}C_6)$alkyl, $(C_1\text{-}C_6)$haloalkyl, $(C_1\text{-}C_6)$alkoxy, $(C_1\text{-}C_6)$haloalkoxy, halogen, and CN.

In some embodiments of Formulae (I-A5), (I-A6), (I-A7), (I-A8), or (I-B2), $R^b$ is independently selected from the group consisting of —F, —Cl, $CF_3$, and CN.

TABLE C1

| Compound No. | Structure |
|---|---|
| 101 | 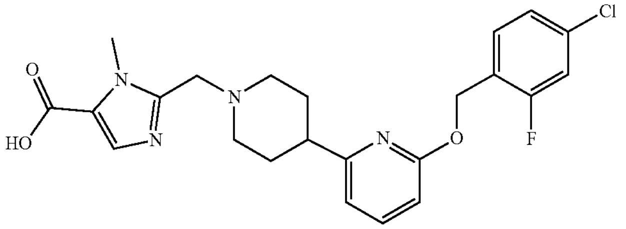 [SMILES: Cn1c(C(=O)O)cnc1CN1CCC(c2cccc(OCc3ccc(Cl)cc3F)n2)CC1] |
| 102 | 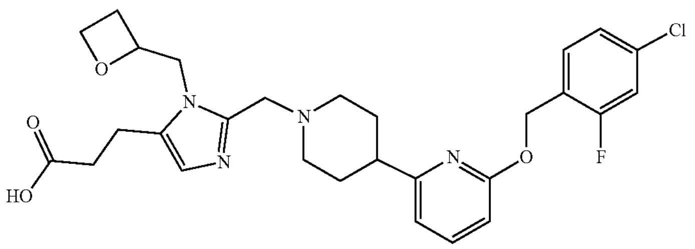 [SMILES: O=C(O)CCc1cnc(CN2CCC(c3cccc(OCc4ccc(Cl)cc4F)n3)CC2)n1CC1CCO1] |

TABLE C1-continued
| Compound No. | Structure |
|---|---|
| 102a | 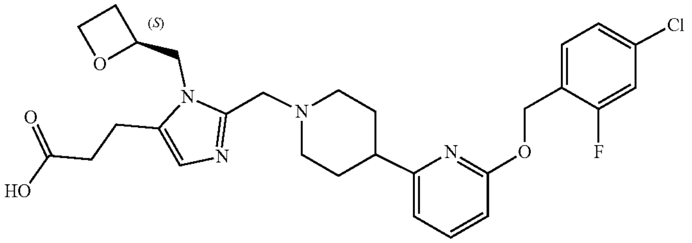 |
| 103 | 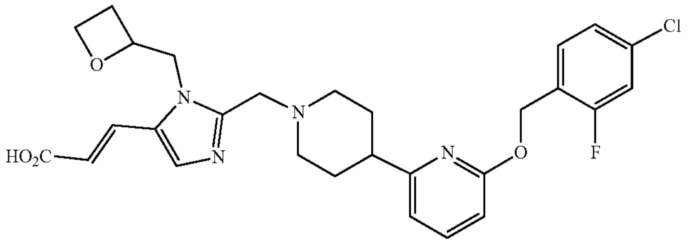 [SMILES: O=C(O)/C=C/c1cnc(CN2CCC(c3cccc(OCc4ccc(Cl)cc4F)n3)CC2)n1CC1CCO1] |
| 103a | 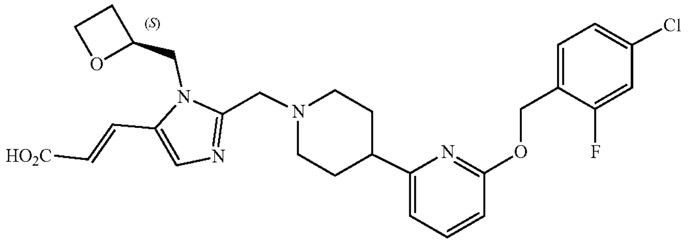 |
| 104 | 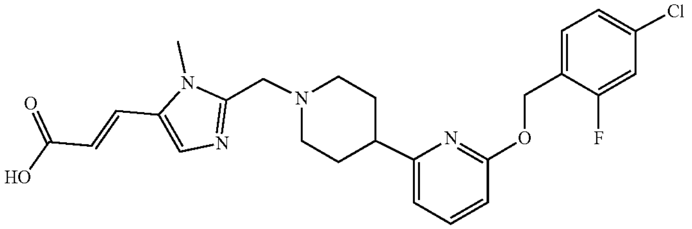 [SMILES: Cn1c(/C=C/C(=O)O)cnc1CN1CCC(c2cccc(OCc3ccc(Cl)cc3F)n2)CC1] |
| 105 | 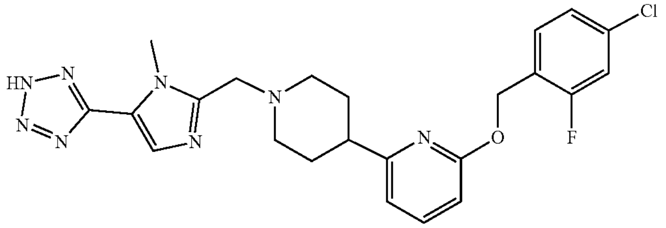 [SMILES: Cn1c(-c2nn[nH]n2)cnc1CN1CCC(c2cccc(OCc3ccc(Cl)cc3F)n2)CC1] |
| 106 | 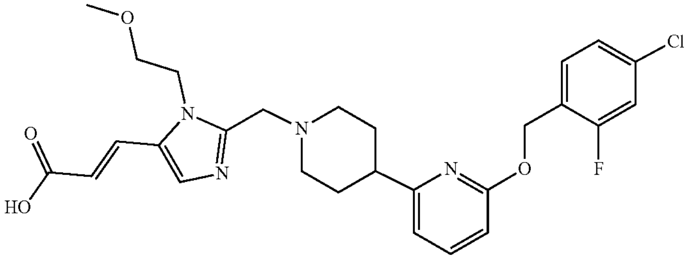 [SMILES: COCCn1c(/C=C/C(=O)O)cnc1CN1CCC(c2cccc(OCc3ccc(Cl)cc3F)n2)CC1] |

TABLE C1-continued
| Compound No. | Structure |
|---|---|
| 107 | 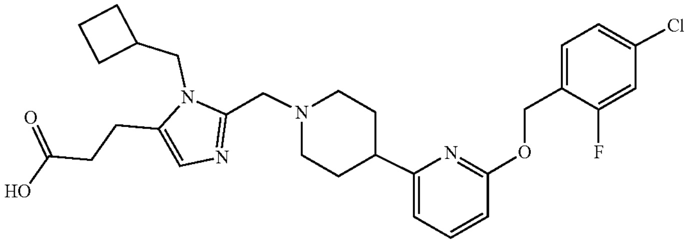 [SMILES: O=C(O)CCc1cnc(CN2CCC(c3cccc(OCc4ccc(Cl)cc4F)n3)CC2)n1CC1CCC1] |
| 108 | 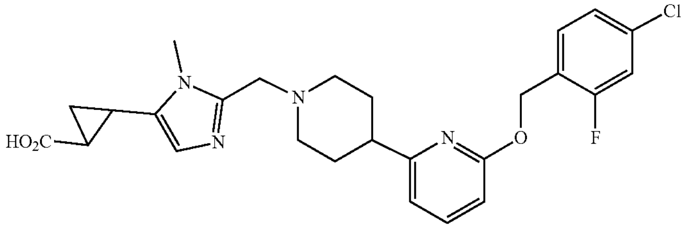 [SMILES: Cn1c(C2CC2C(=O)O)cnc1CN1CCC(c2cccc(OCc3ccc(Cl)cc3F)n2)CC1] |
| 109 | 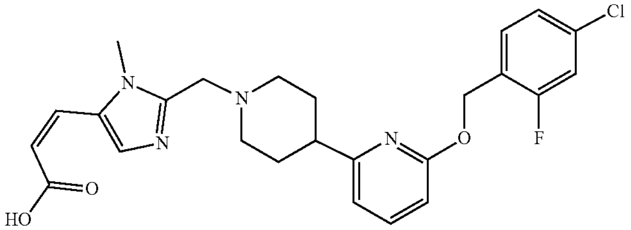 [SMILES: Cn1c(/C=C\C(=O)O)cnc1CN1CCC(c2cccc(OCc3ccc(Cl)cc3F)n2)CC1] |
| 110 | 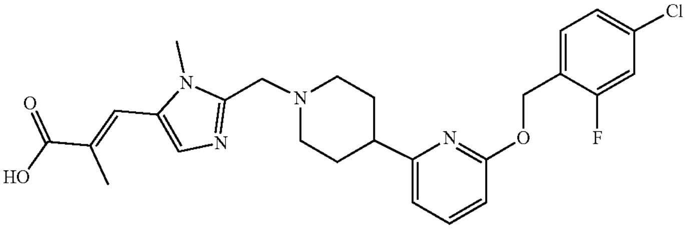 [SMILES: C/C(=C\c1cnc(CN2CCC(c3cccc(OCc4ccc(Cl)cc4F)n3)CC2)n1C)C(=O)O] |
| 112 | 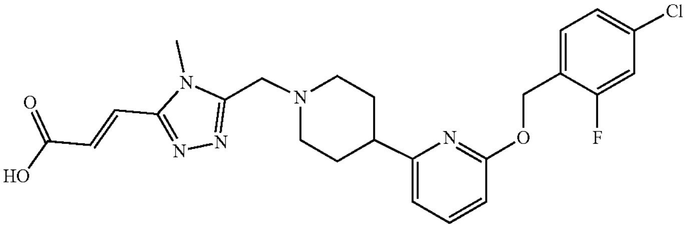 |
| 113 | 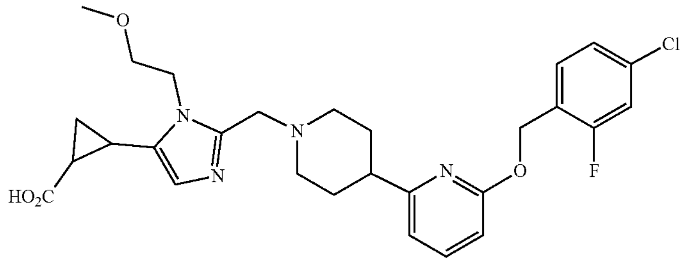 [SMILES: COCCn1c(C2CC2C(=O)O)cnc1CN1CCC(c2cccc(OCc3ccc(Cl)cc3F)n2)CC1] |

TABLE C1-continued
| Compound No. | Structure |
|---|---|
| 114 | 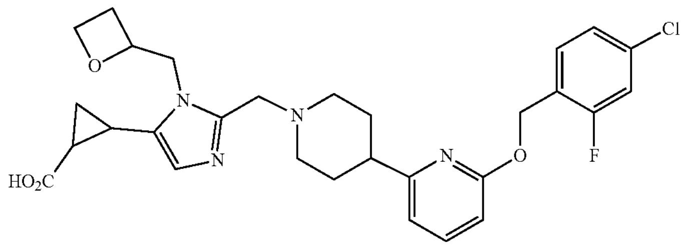 [SMILES: O=C(O)C1CC1c1cnc(CN2CCC(c3cccc(OCc4ccc(Cl)cc4F)n3)CC2)n1CC1CCO1] |
| 114a | 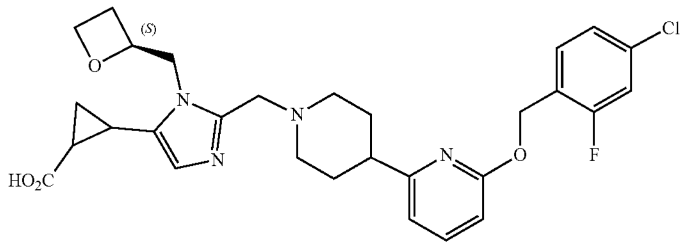 |
| 115 | 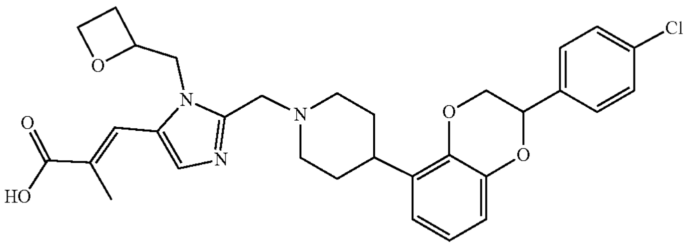 [SMILES: C/C(=C\c1cnc(CN2CCC(c3cccc4c3OCC(c3ccc(Cl)cc3)O4)CC2)n1CC1CCO1)C(=O)O] |
| 115a | 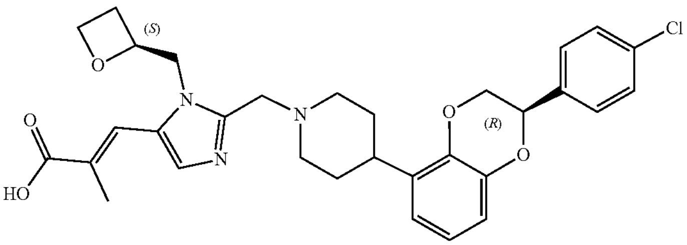 |
| 116 | 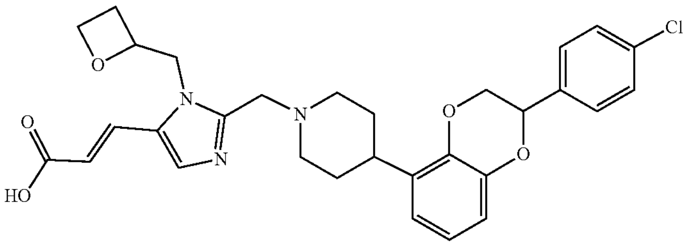 [SMILES: O=C(O)/C=C/c1cnc(CN2CCC(c3cccc4c3OCC(c3ccc(Cl)cc3)O4)CC2)n1CC1CCO1] |
| 116a | 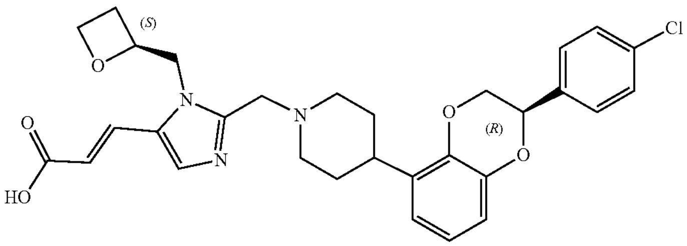 |

TABLE C1-continued
| Compound No. | Structure |
|---|---|
| 117 | 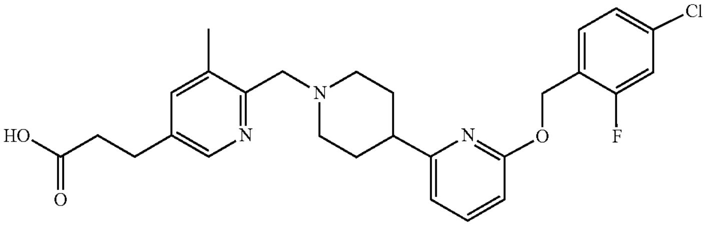 [SMILES: Cc1cc(CCC(=O)O)cnc1CN1CCC(c2cccc(OCc3ccc(Cl)cc3F)n2)CC1] |
| 118 | 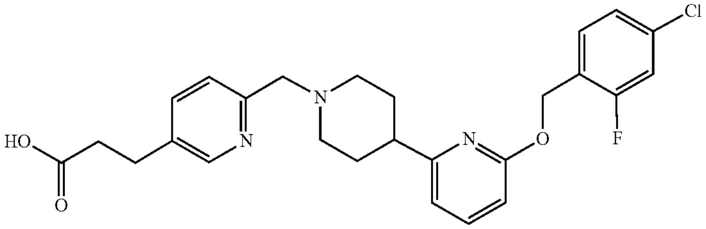 [SMILES: O=C(O)CCc1ccc(CN2CCC(c3cccc(OCc4ccc(Cl)cc4F)n3)CC2)nc1] |
| 119 | 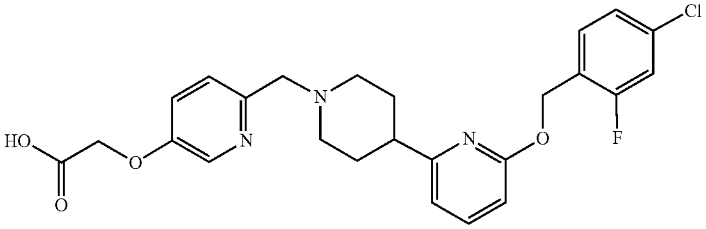 [SMILES: O=C(O)COc1ccc(CN2CCC(c3cccc(OCc4ccc(Cl)cc4F)n3)CC2)nc1] |
| 120 | 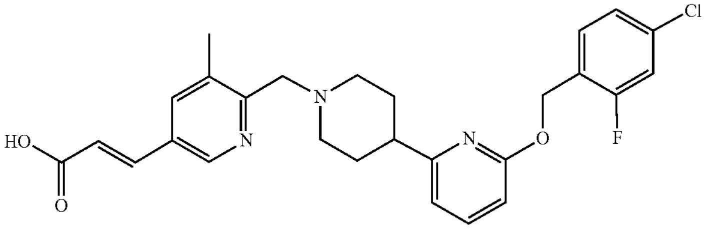 [SMILES: Cc1cc(/C=C/C(=O)O)cnc1CN1CCC(c2cccc(OCc3ccc(Cl)cc3F)n2)CC1] |
| 121 | 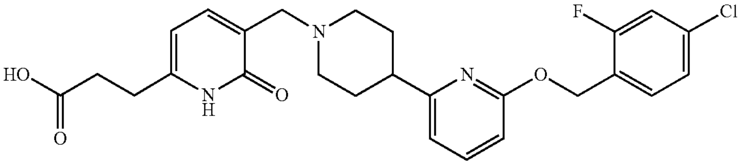 [SMILES: O=C(O)CCc1ccc(CN2CCC(c3cccc(OCc4ccc(Cl)cc4F)n3)CC2)c(=O)[nH]1] |
| 122 | 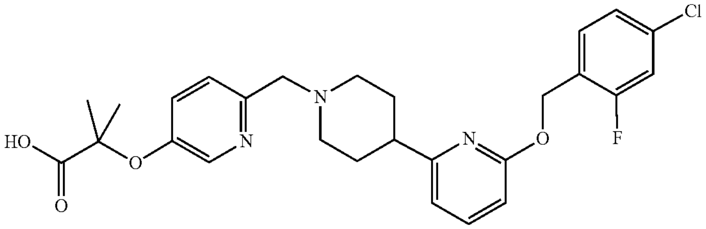 [SMILES: CC(C)(Oc1ccc(CN2CCC(c3cccc(OCc4ccc(Cl)cc4F)n3)CC2)nc1)C(=O)O] |

TABLE C1-continued
| Compound No. | Structure |
| --- | --- |
| 123 | 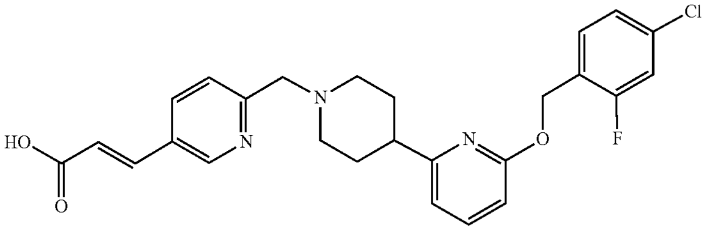 [SMILES: O=C(O)/C=C/c1ccc(CN2CCC(c3cccc(OCc4ccc(Cl)cc4F)n3)CC2)nc1] |
| 124 | 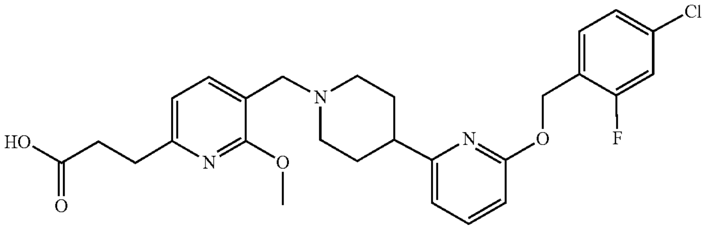 [SMILES: COc1nc(CCC(=O)O)ccc1CN1CCC(c2cccc(OCc3ccc(Cl)cc3F)n2)CC1] |
| 125 | 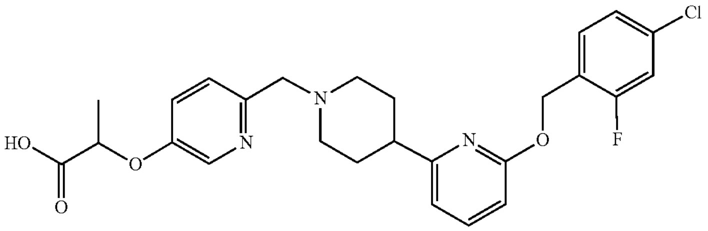 [SMILES: CC(Oc1ccc(CN2CCC(c3cccc(OCc4ccc(Cl)cc4F)n3)CC2)nc1)C(=O)O] |
| 126 | 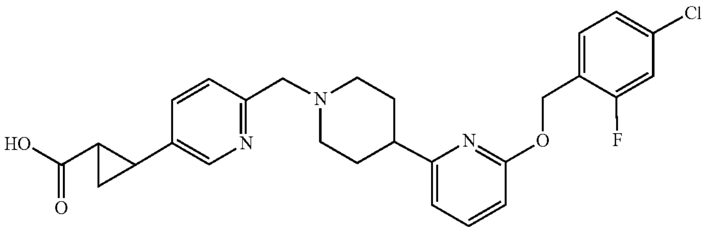 [SMILES: O=C(O)C1CC1c1ccc(CN2CCC(c3cccc(OCc4ccc(Cl)cc4F)n3)CC2)nc1] |
| 127 | 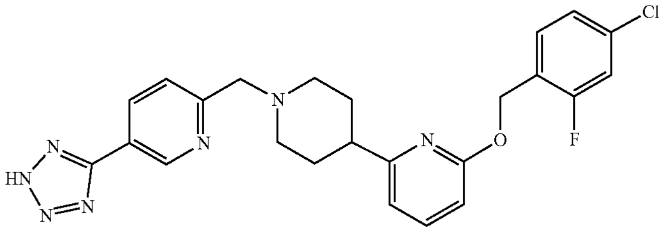 [SMILES: Fc1cc(Cl)ccc1COc1cccc(C2CCN(Cc3ccc(-c4nn[nH]n4)cn3)CC2)n1] |
| 128 | 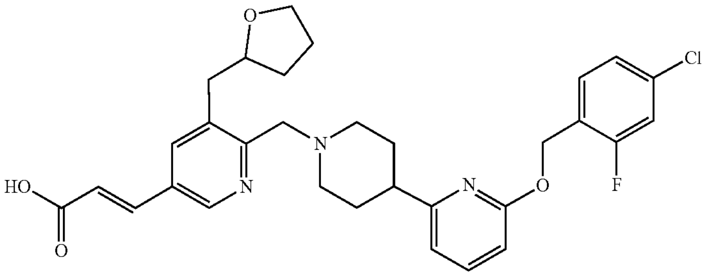 [SMILES: O=C(O)/C=C/c1cnc(CN2CCC(c3cccc(OCc4ccc(Cl)cc4F)n3)CC2)c(CC2CCCO2)c1] |

TABLE C1-continued
| Compound No. | Structure |
|---|---|
| 129 | 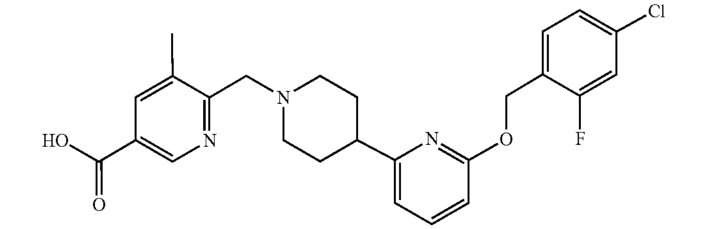 [SMILES: Cc1cc(C(=O)O)cnc1CN1CCC(c2cccc(OCc3ccc(Cl)cc3F)n2)CC1] |
| 130 | 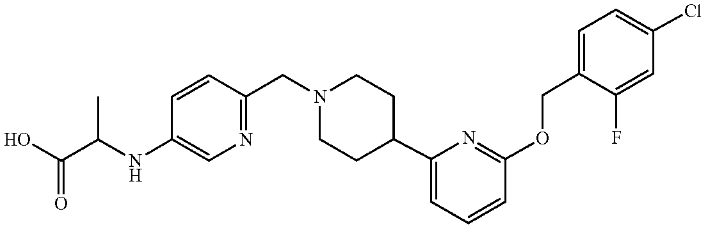 [SMILES: CC(Nc1ccc(CN2CCC(c3cccc(OCc4ccc(Cl)cc4F)n3)CC2)nc1)C(=O)O] |
| 131 | 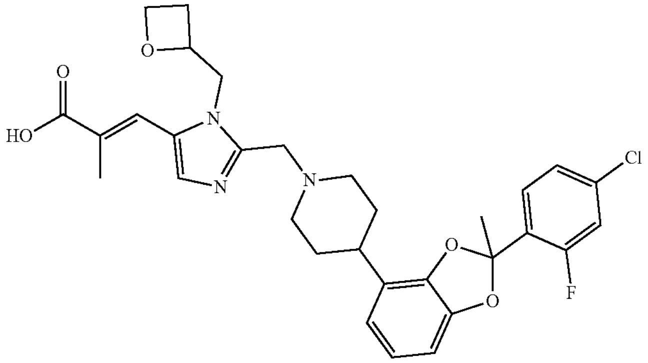 [SMILES: C/C(=C\c1cnc(CN2CCC(c3cccc4c3OC(C)(c3ccc(Cl)cc3F)O4)CC2)n1CC1CCO1)C(=O)O] |
| 131a | 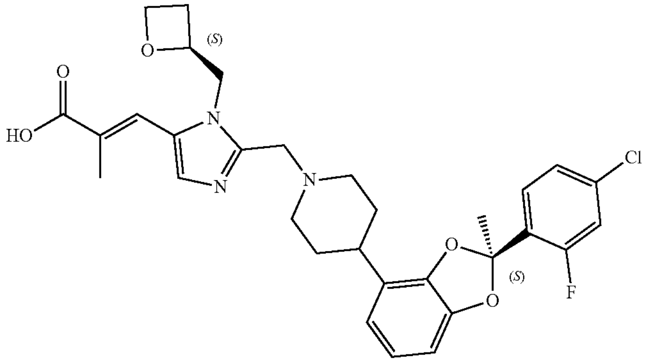 |
| 131b | 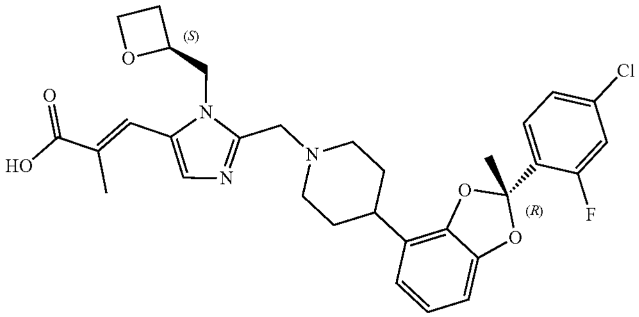 |

TABLE C1-continued
| Compound No. | Structure |
|---|---|
| 132 | 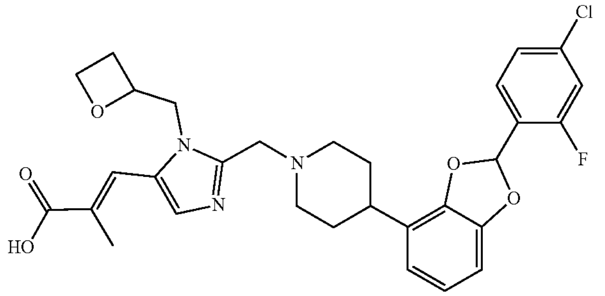 [SMILES: C/C(=C\c1cnc(CN2CCC(c3cccc4c3OC(c3ccc(Cl)cc3F)O4)CC2)n1CC1CCO1)C(=O)O] |
| 132a | 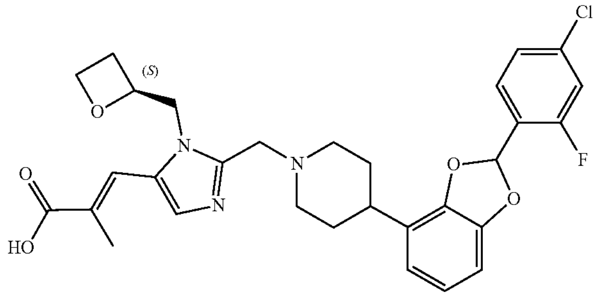 |
| 133 | 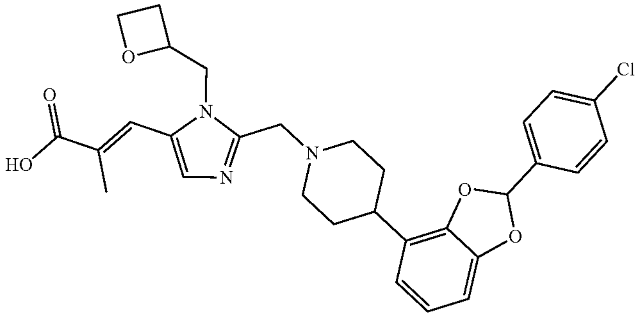 [SMILES: C/C(=C\c1cnc(CN2CCC(c3cccc4c3OC(c3ccc(Cl)cc3)O4)CC2)n1CC1CCO1)C(=O)O] |
| 133a | 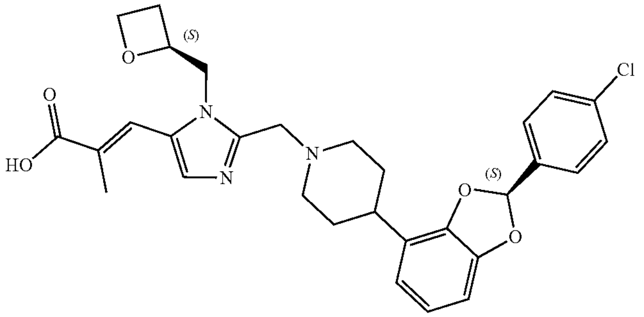 |
| 133b | 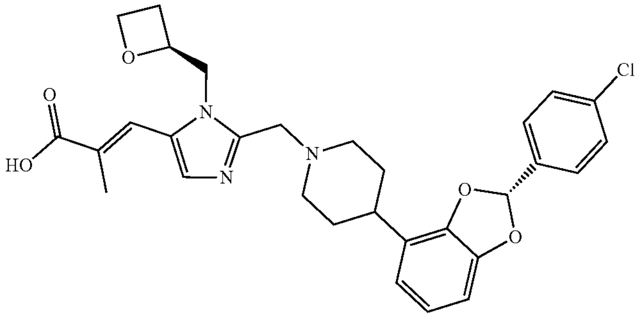 [SMILES: C/C(=C\c1cnc(CN2CCC(c3cccc4c3O[C@H](c3ccc(Cl)cc3)O4)CC2)n1C[C@@H]1CCO1)C(=O)O] |

TABLE C1-continued
| Compound No. | Structure |
|---|---|
| 134 | 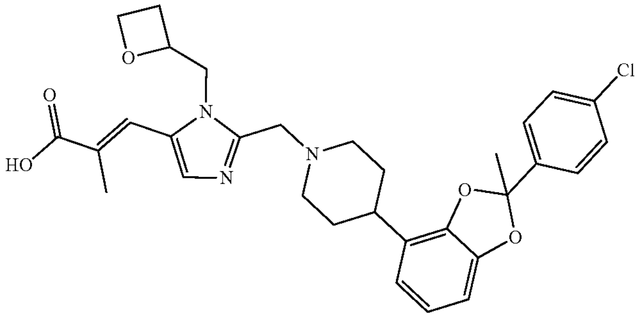 [SMILES: C/C(=C\c1cnc(CN2CCC(c3cccc4c3OC(C)(c3ccc(Cl)cc3)O4)CC2)n1CC1CCO1)C(=O)O] |
| 134a | 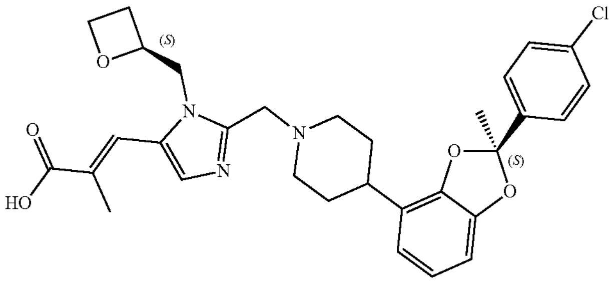 |
| 134b | 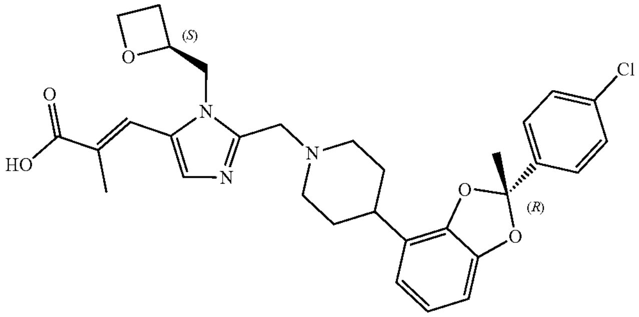 |
| 135 | 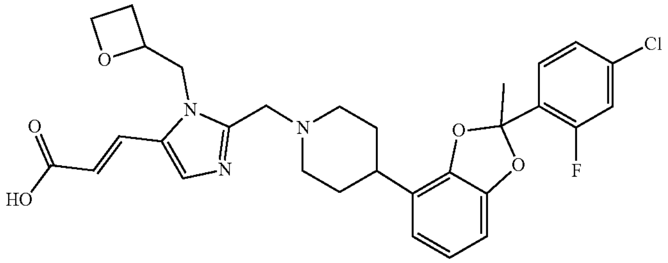 [SMILES: CC1(c2ccc(Cl)cc2F)Oc2cccc(C3CCN(Cc4ncc(/C=C/C(=O)O)n4CC4CCO4)CC3)c2O1] |
| 135a | 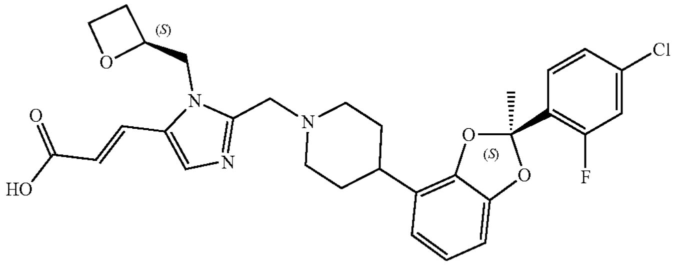 |

TABLE C1-continued
| Compound No. | Structure |
|---|---|
| 135b | 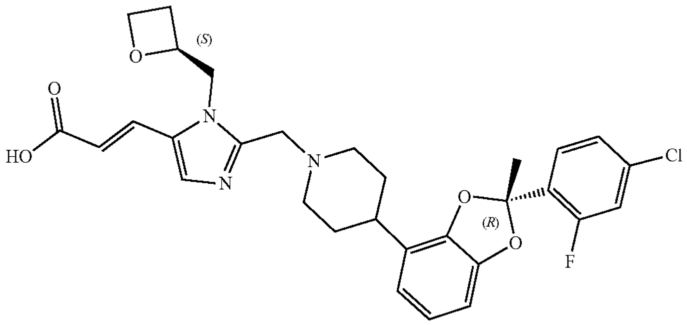 |
| 136 | 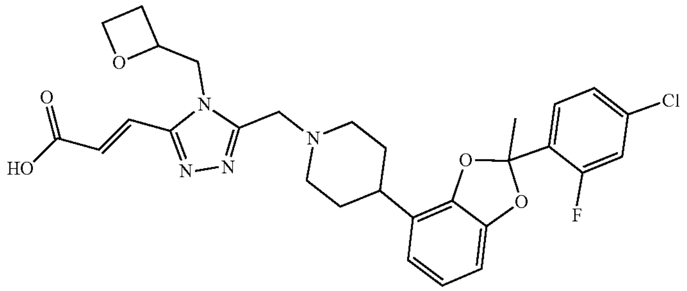 [SMILES: CC1(c2ccc(Cl)cc2F)Oc2cccc(C3CCN(Cc4nnc(/C=C/C(=O)O)n4CC4CCO4)CC3)c2O1] |
| 136a | 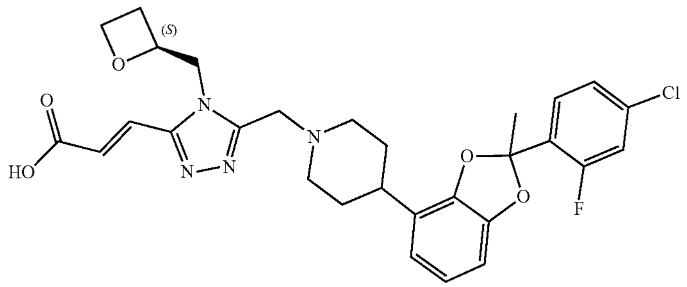 |
| 137 | 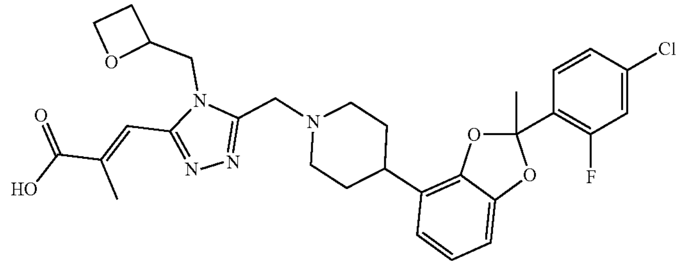 [SMILES: C/C(=C\c1nnc(CN2CCC(c3cccc4c3OC(C)(c3ccc(Cl)cc3F)O4)CC2)n1CC1CCO1)C(=O)O] |
| 137a | 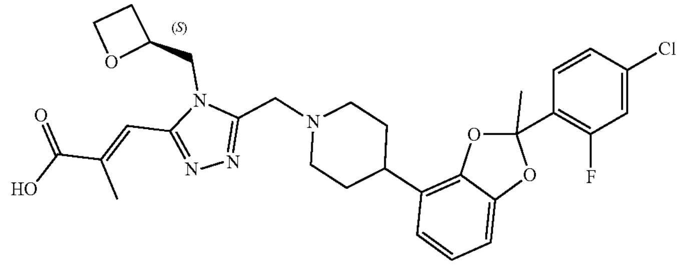 |

TABLE C1-continued
| Compound No. | Structure |
|---|---|
| 138 | 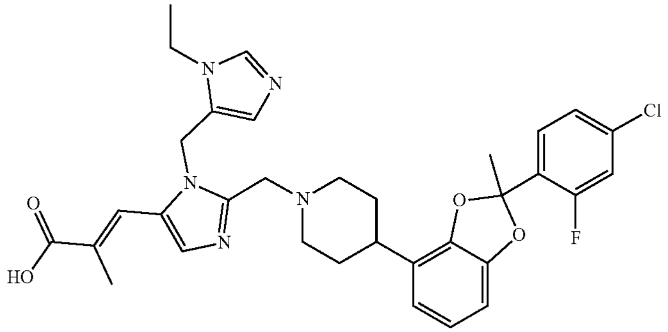 [SMILES: CCn1cncc1Cn1c(/C=C(\C)C(=O)O)cnc1CN1CCC(c2cccc3c2OC(C)(c2ccc(Cl)cc2F)O3)CC1] |
| 138a | 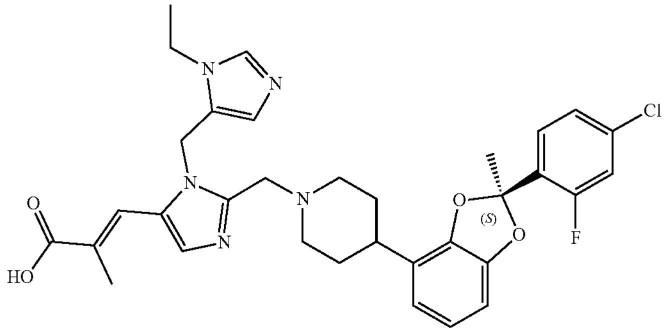 |
| 138b | 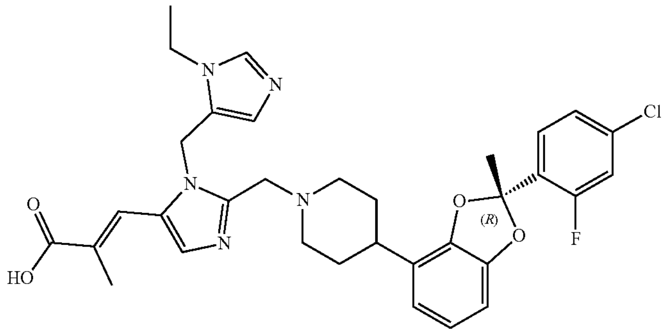 |
| 139 | 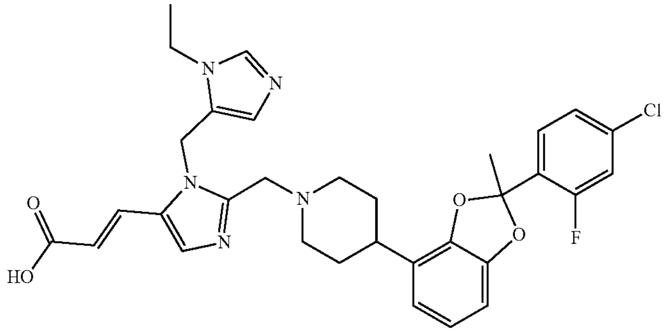 [SMILES: CCn1cncc1Cn1c(/C=C/C(=O)O)cnc1CN1CCC(c2cccc3c2OC(C)(c2ccc(Cl)cc2F)O3)CC1] |

TABLE C1-continued
| Compound No. | Structure |
|---|---|
| 139a | 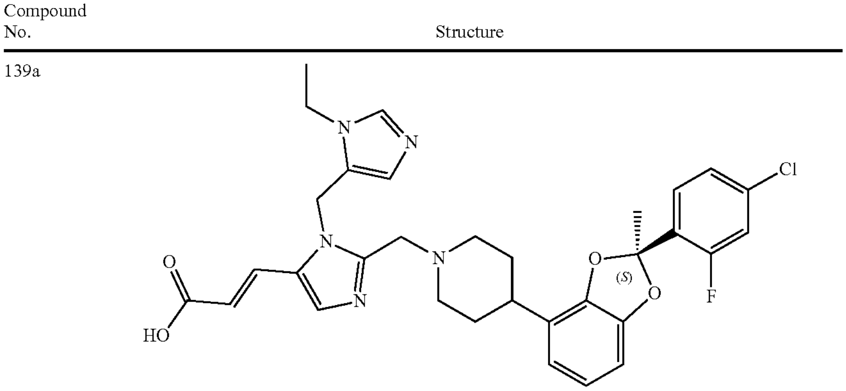 |
| 139b | 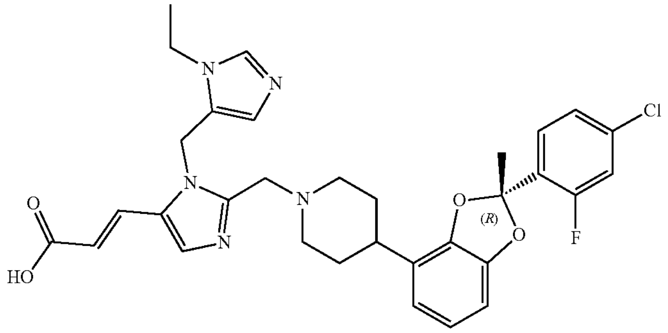 |
| 140 | 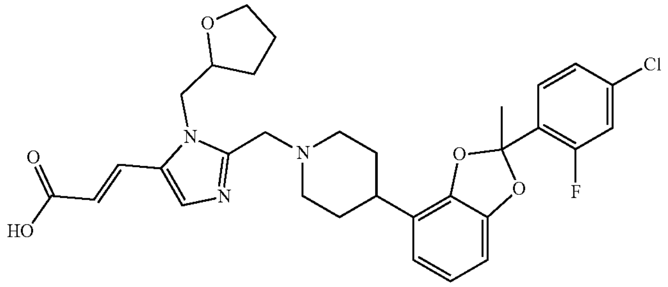 [SMILES: CC1(c2ccc(Cl)cc2F)Oc2cccc(C3CCN(Cc4ncc(/C=C/C(=O)O)n4CC4CCCO4)CC3)c2O1] |
| 140a | 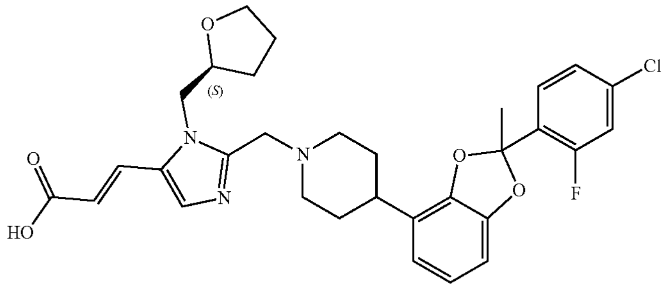 |
| 141 | 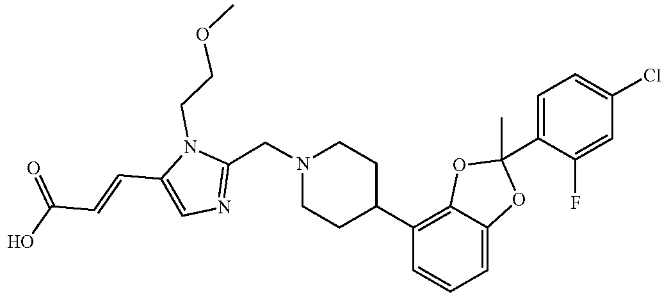 [SMILES: COCCn1c(/C=C/C(=O)O)cnc1CN1CCC(c2cccc3c2OC(C)(c2ccc(Cl)cc2F)O3)CC1] |

TABLE C1-continued
| Compound No. | Structure |
|---|---|
| 142 | 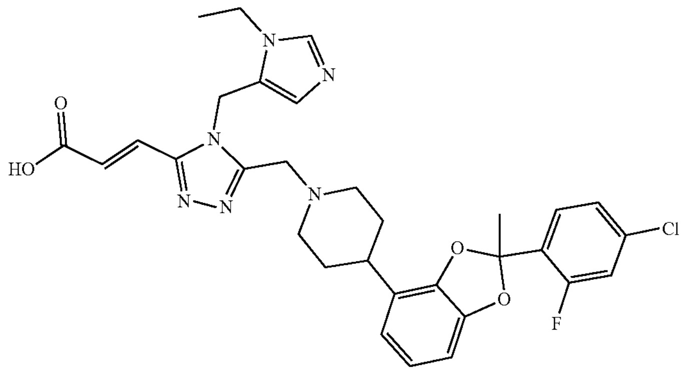 [SMILES: CCn1cncc1Cn1c(/C=C/C(=O)O)nnc1CN1CCC(c2cccc3c2OC(C)(c2ccc(Cl)cc2F)O3)CC1] |
| 143 | 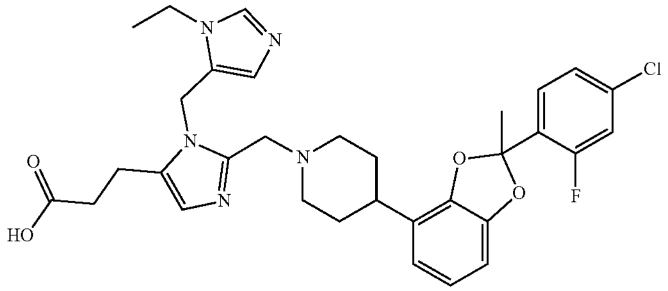 [SMILES: CCn1cncc1Cn1c(CCC(=O)O)cnc1CN1CCC(c2cccc3c2OC(C)(c2ccc(Cl)cc2F)O3)CC1] |
| 144 | 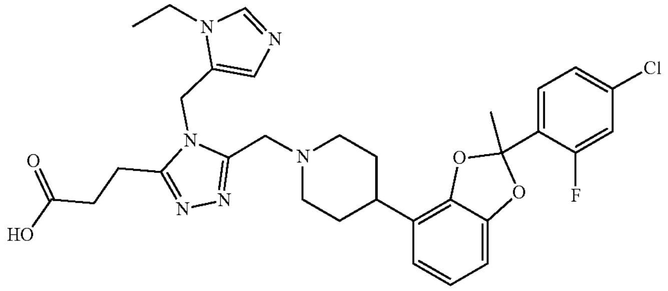 [SMILES: CCn1cncc1Cn1c(CCC(=O)O)nnc1CN1CCC(c2cccc3c2OC(C)(c2ccc(Cl)cc2F)O3)CC1] |
| 145 | 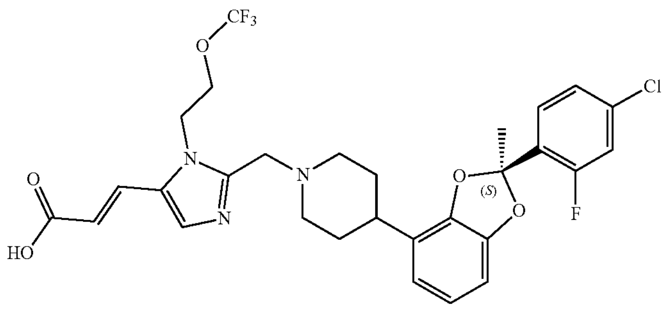 |

TABLE C1-continued
| Compound No. | Structure |
|---|---|
| 146 | 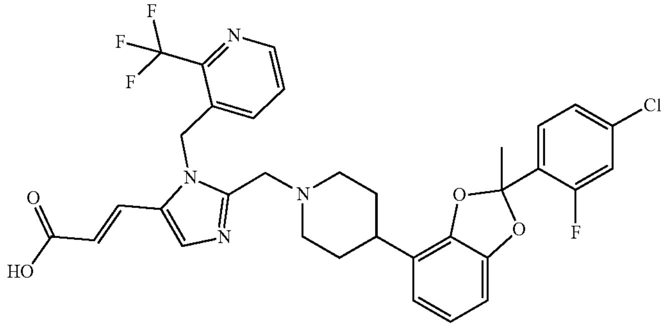 [SMILES: CC1(c2ccc(Cl)cc2F)Oc2cccc(C3CCN(Cc4ncc(/C=C/C(=O)O)n4Cc4cccnc4C(F)(F)F)CC3)c2O1] |
| 147 | 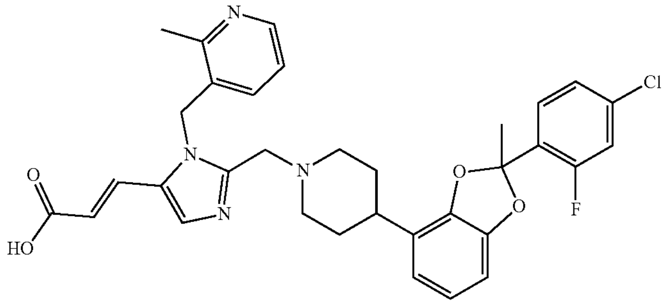 [SMILES: Cc1ncccc1Cn1c(/C=C/C(=O)O)cnc1CN1CCC(c2cccc3c2OC(C)(c2ccc(Cl)cc2F)O3)CC1] |
| 148 | 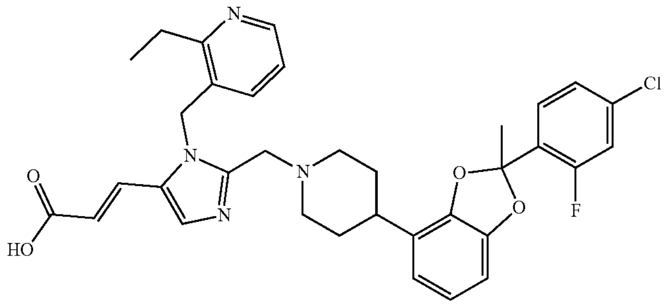 [SMILES: CCc1ncccc1Cn1c(/C=C/C(=O)O)cnc1CN1CCC(c2cccc3c2OC(C)(c2ccc(Cl)cc2F)O3)CC1] |
| 149 | 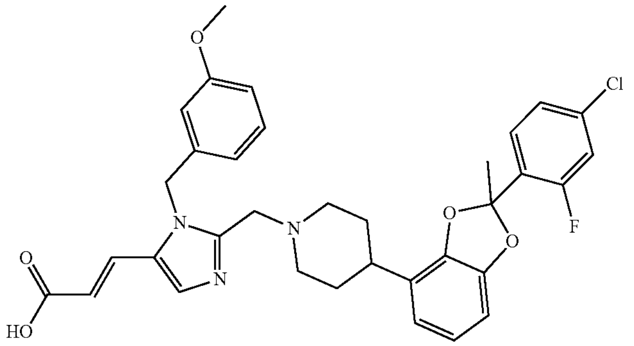 [SMILES: COc1cccc(Cn2c(/C=C/C(=O)O)cnc2CN2CCC(c3cccc4c3OC(C)(c3ccc(Cl)cc3F)O4)CC2)c1] |

TABLE C1-continued
| Compound No. | Structure |
|---|---|
| 150 | 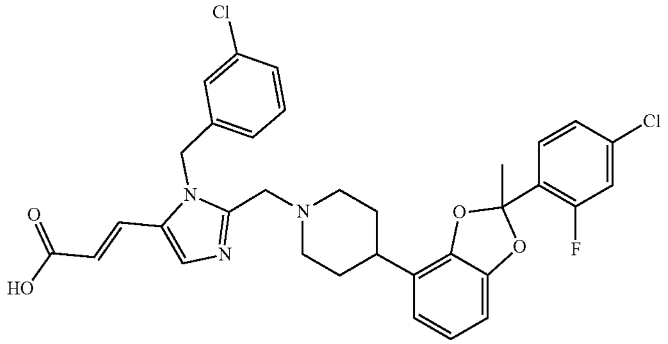 [SMILES: CC1(c2ccc(Cl)cc2F)Oc2cccc(C3CCN(Cc4ncc(/C=C/C(=O)O)n4Cc4cccc(Cl)c4)CC3)c2O1] |
| 151 | 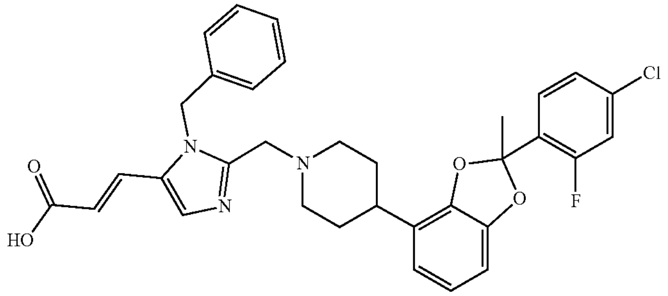 [SMILES: CC1(c2ccc(Cl)cc2F)Oc2cccc(C3CCN(Cc4ncc(/C=C/C(=O)O)n4Cc4ccccc4)CC3)c2O1] |
| 152 | 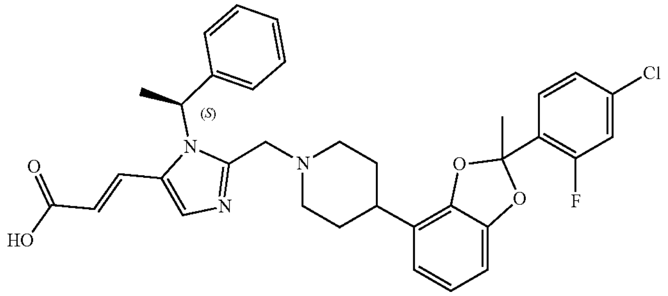 |
| 153 | 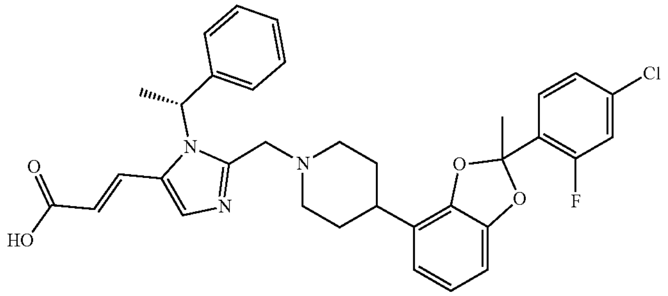 [SMILES: C[C@H](c1ccccc1)n1c(/C=C/C(=O)O)cnc1CN1CCC(c2cccc3c2OC(C)(c2ccc(Cl)cc2F)O3)CC1] |
| 154 | 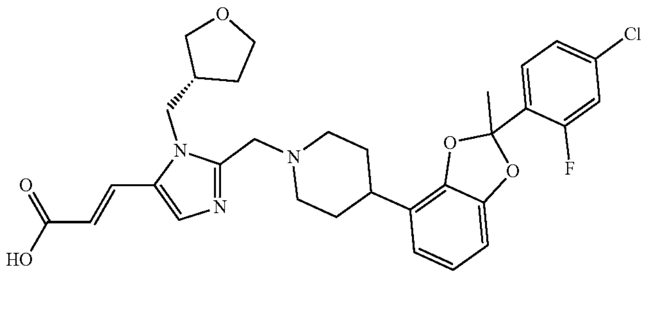 [SMILES: CC1(c2ccc(Cl)cc2F)Oc2cccc(C3CCN(Cc4ncc(/C=C/C(=O)O)n4C[C@H]4CCOC4)CC3)c2O1] |

TABLE C1-continued
| Compound No. | Structure |
|---|---|
| 155 | 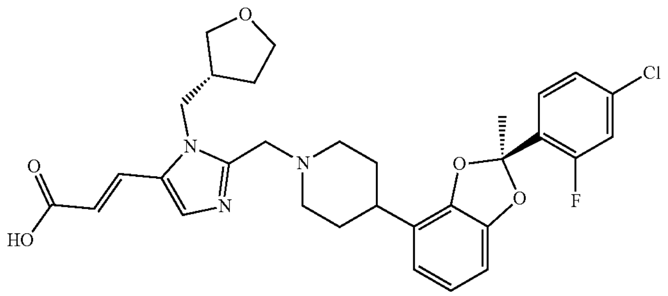 [SMILES: C[C@]1(c2ccc(Cl)cc2F)Oc2cccc(C3CCN(Cc4ncc(/C=C/C(=O)O)n4C[C@H]4CCOC4)CC3)c2O1] |
| 156 | 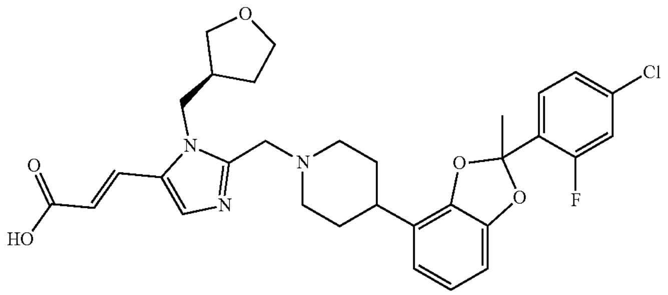 [SMILES: CC1(c2ccc(Cl)cc2F)Oc2cccc(C3CCN(Cc4ncc(/C=C/C(=O)O)n4C[C@@H]4CCOC4)CC3)c2O1] |
| 157 | 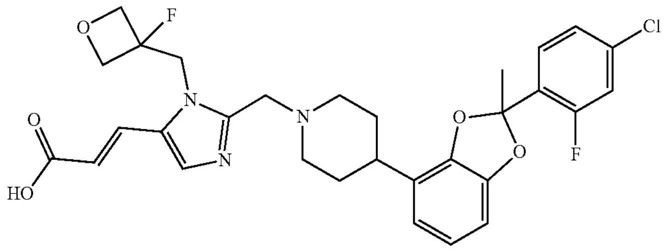 [SMILES: CC1(c2ccc(Cl)cc2F)Oc2cccc(C3CCN(Cc4ncc(/C=C/C(=O)O)n4CC4(F)COC4)CC3)c2O1] |
| 158 | 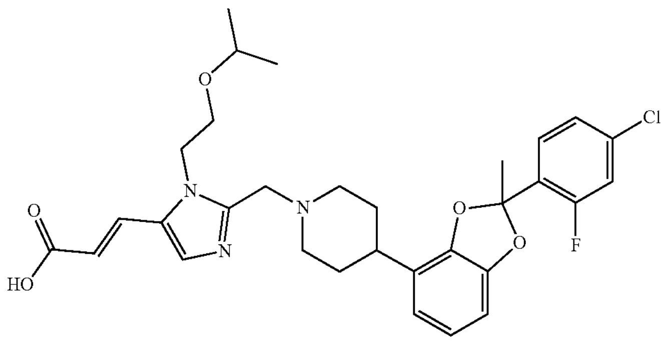 [SMILES: CC(C)OCCn1c(/C=C/C(=O)O)cnc1CN1CCC(c2cccc3c2OC(C)(c2ccc(Cl)cc2F)O3)CC1] |

TABLE C1-continued
| Compound No. | Structure |
|---|---|
| 159 | 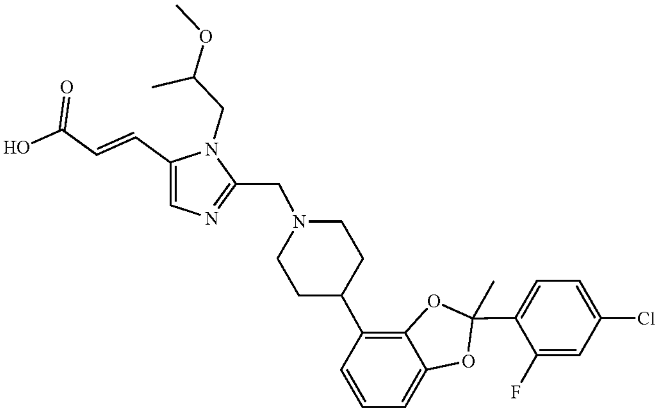 [SMILES: COC(C)Cn1c(/C=C/C(=O)O)cnc1CN1CCC(c2cccc3c2OC(C)(c2ccc(Cl)cc2F)O3)CC1] |
| 160 | 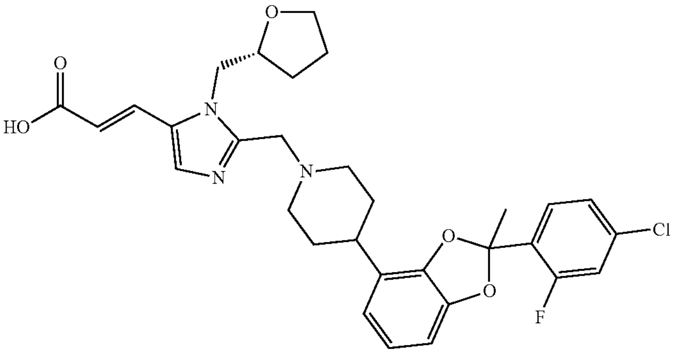 [SMILES: CC1(c2ccc(Cl)cc2F)Oc2cccc(C3CCN(Cc4ncc(/C=C/C(=O)O)n4C[C@H]4CCCO4)CC3)c2O1] |
| 161 | 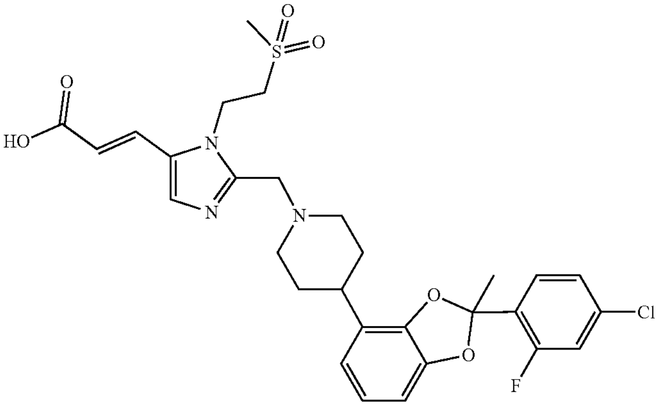 [SMILES: CC1(c2ccc(Cl)cc2F)Oc2cccc(C3CCN(Cc4ncc(/C=C/C(=O)O)n4CCS(C)(=O)=O)CC3)c2O1] |
| 162 | 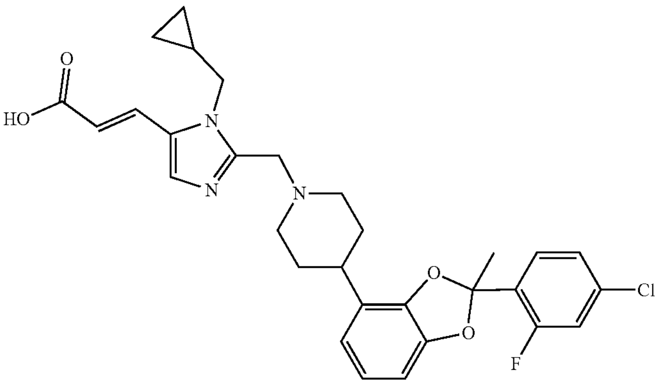 [SMILES: CC1(c2ccc(Cl)cc2F)Oc2cccc(C3CCN(Cc4ncc(/C=C/C(=O)O)n4CC4CC4)CC3)c2O1] |

TABLE C1-continued
| Compound No. | Structure |
|---|---|
| 163 | 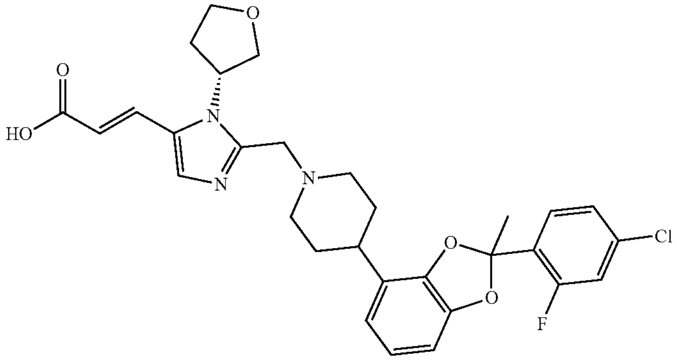 [SMILES: CC1(c2ccc(Cl)cc2F)Oc2cccc(C3CCN(Cc4ncc(/C=C/C(=O)O)n4[C@@H]4CCOC4)CC3)c2O1] |
| 164 | 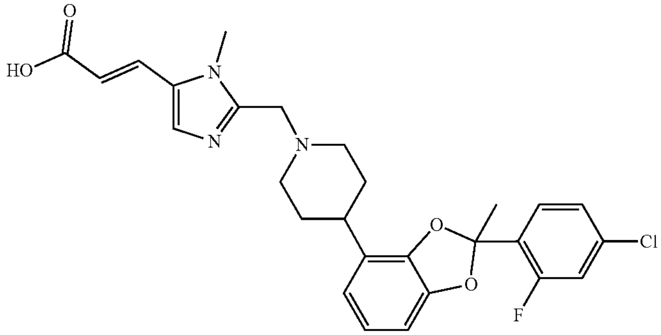 [SMILES: Cn1c(/C=C/C(=O)O)cnc1CN1CCC(c2cccc3c2OC(C)(c2ccc(Cl)cc2F)O3)CC1] |
| 165 | 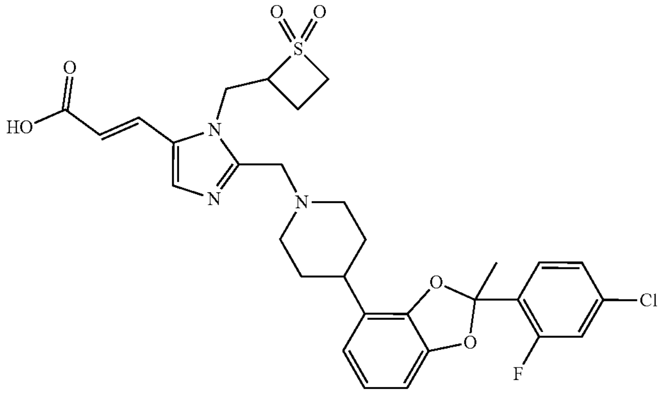 [SMILES: CC1(c2ccc(Cl)cc2F)Oc2cccc(C3CCN(Cc4ncc(/C=C/C(=O)O)n4CC4CCS4(=O)=O)CC3)c2O1] |
| 166 | 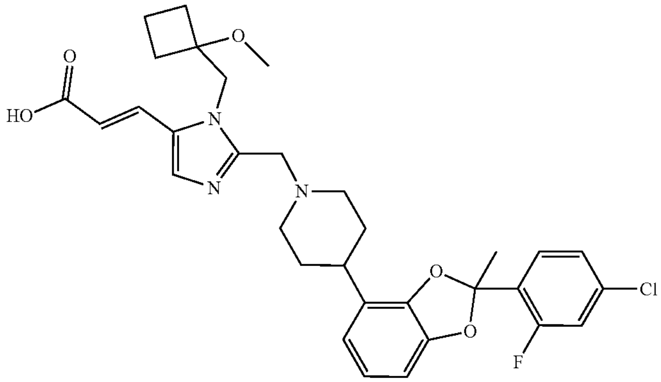 [SMILES: COC1(Cn2c(/C=C/C(=O)O)cnc2CN2CCC(c3cccc4c3OC(C)(c3ccc(Cl)cc3F)O4)CC2)CCC1] |

TABLE C1-continued
| Compound No. | Structure |
|---|---|
| 167 | 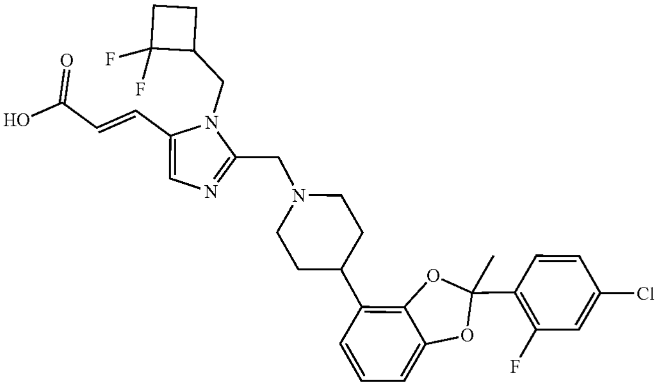 [SMILES: CC1(c2ccc(Cl)cc2F)Oc2cccc(C3CCN(Cc4ncc(/C=C/C(=O)O)n4CC4CCC4(F)F)CC3)c2O1] |
| 168 | 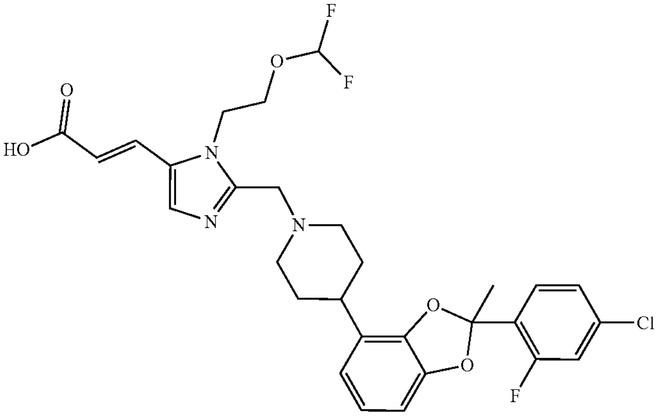 [SMILES: CC1(c2ccc(Cl)cc2F)Oc2cccc(C3CCN(Cc4ncc(/C=C/C(=O)O)n4CCOC(F)F)CC3)c2O1] |
| 169a | 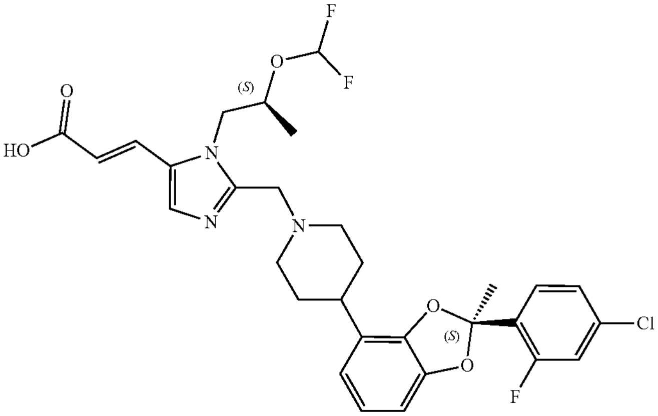 |

TABLE C1-continued
| Compound No. | Structure |
|---|---|
| 169b | 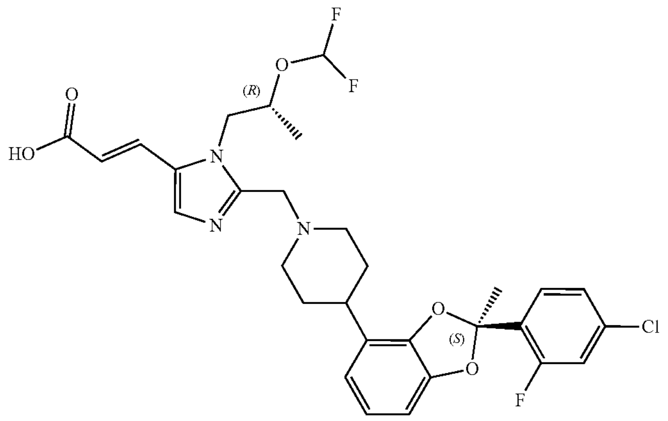 |
| 170b | 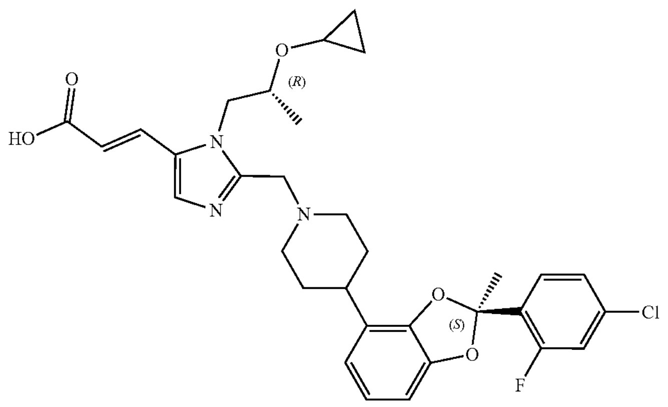 |
| 170a | 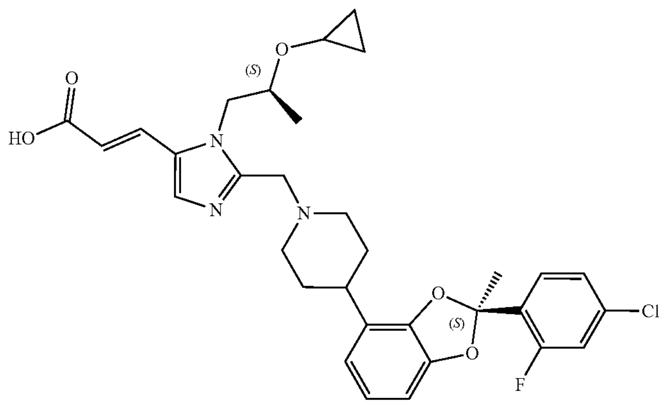 |

TABLE C1-continued
| Compound No. | Structure |
|---|---|
| 171b | 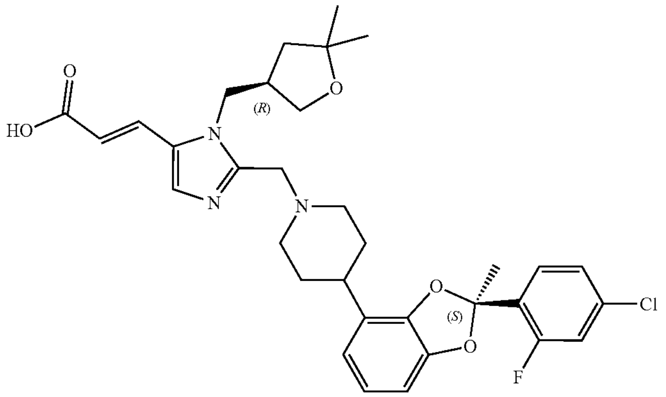 |
| 171a | 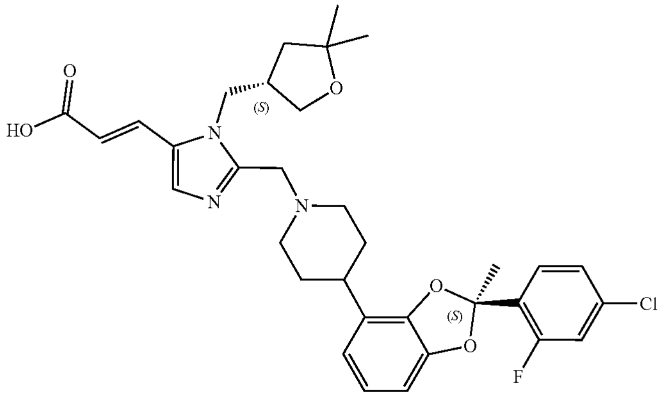 |
| 172a | 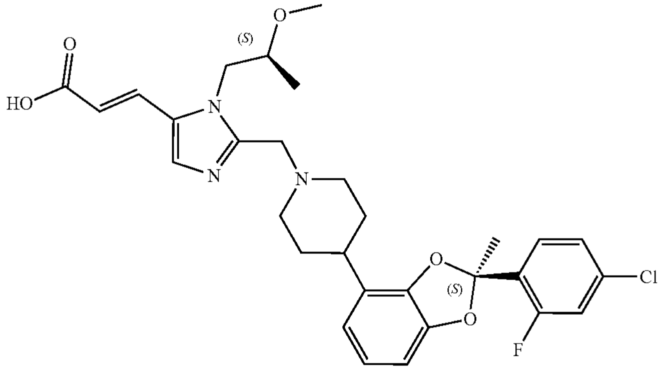 |
| 172b | 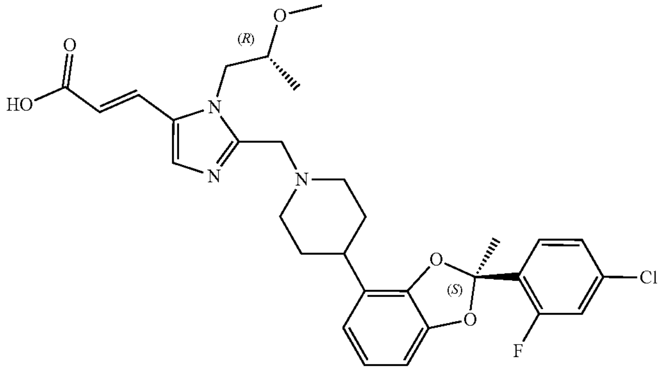 |

TABLE C1-continued
| Compound No. | Structure |
|---|---|
| 173a | 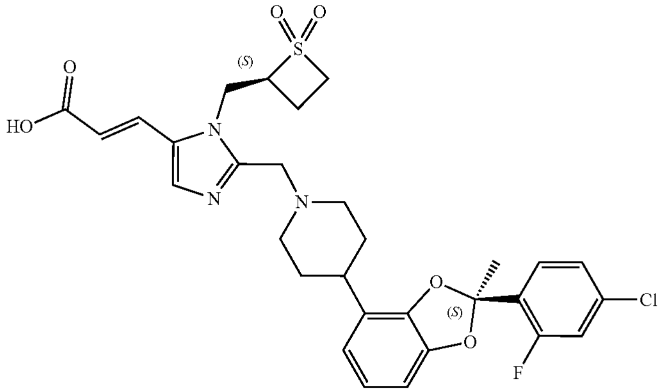 |
| 173b | 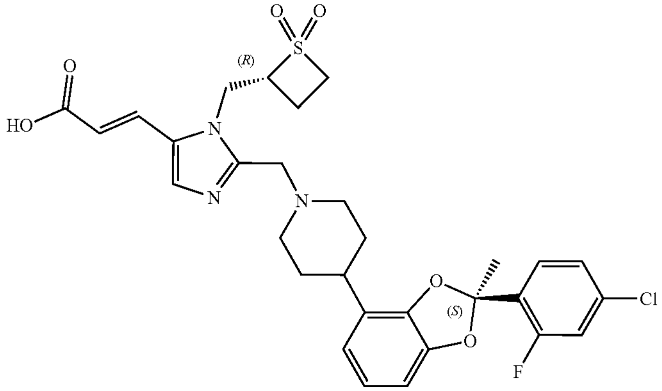 |
| 174 | 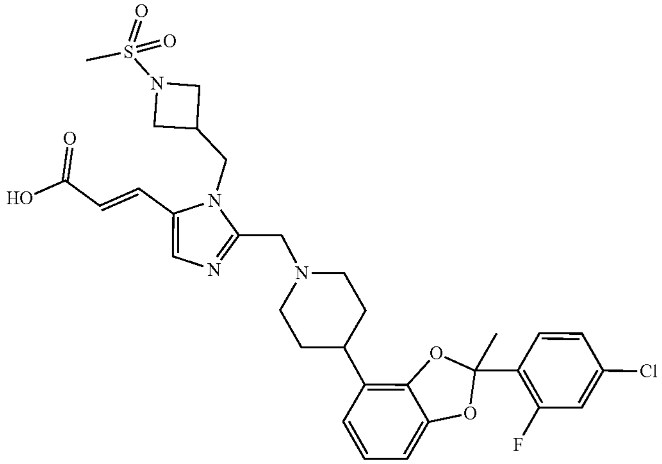 [SMILES: CC1(c2ccc(Cl)cc2F)Oc2cccc(C3CCN(Cc4ncc(/C=C/C(=O)O)n4CC4CN(S(C)(=O)=O)C4)CC3)c2O1] |

TABLE C1-continued
| Compound No. | Structure |
|---|---|
| 175 | 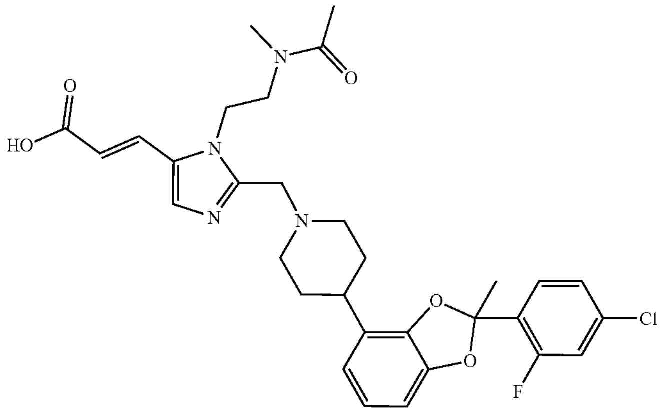 [SMILES: CC(=O)N(C)CCn1c(/C=C/C(=O)O)cnc1CN1CCC(c2cccc3c2OC(C)(c2ccc(Cl)cc2F)O3)CC1] |
| 176 | 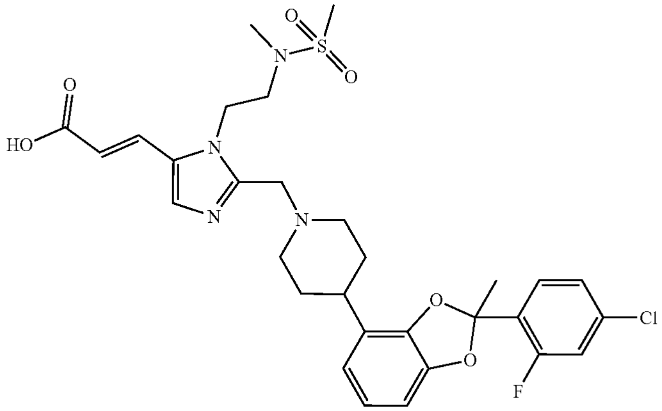 [SMILES: CN(CCn1c(/C=C/C(=O)O)cnc1CN1CCC(c2cccc3c2OC(C)(c2ccc(Cl)cc2F)O3)CC1)S(C)(=O)=O] |
| 177 | 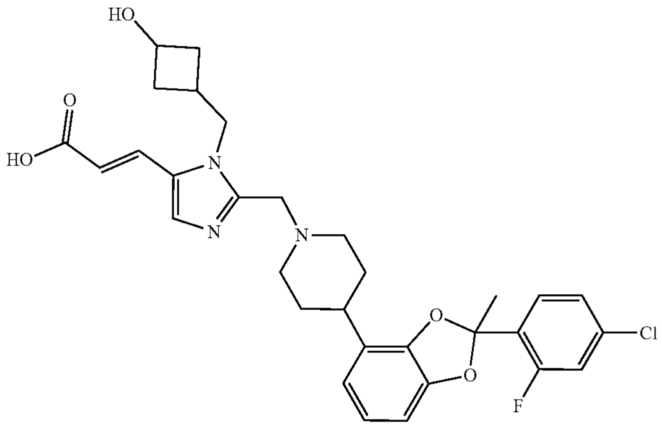 [SMILES: CC1(c2ccc(Cl)cc2F)Oc2cccc(C3CCN(Cc4ncc(/C=C/C(=O)O)n4CC4CC(O)C4)CC3)c2O1] |

TABLE C1-continued
| Compound No. | Structure |
|---|---|
| 178 | 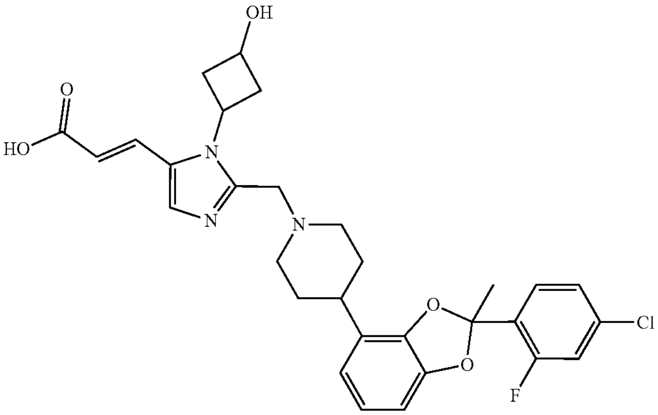 [SMILES: CC1(c2ccc(Cl)cc2F)Oc2cccc(C3CCN(Cc4ncc(/C=C/C(=O)O)n4C4CC(O)C4)CC3)c2O1] |
| 179 | 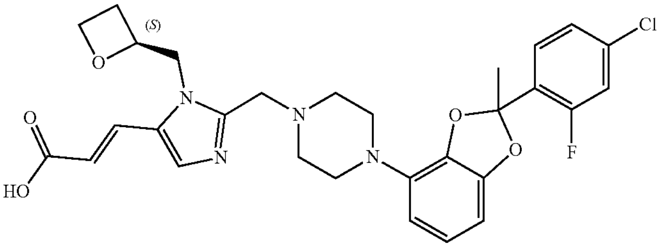 |
| 180 | 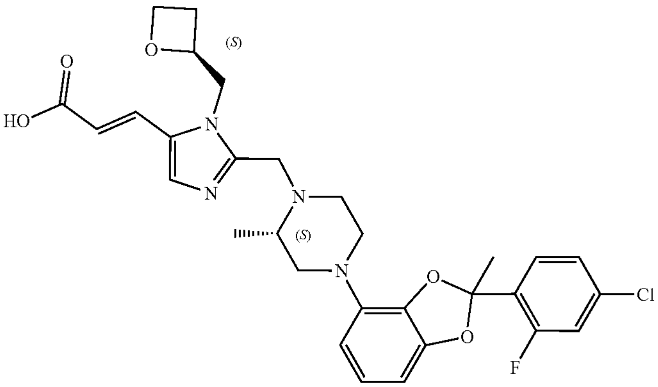 |
| 181 | 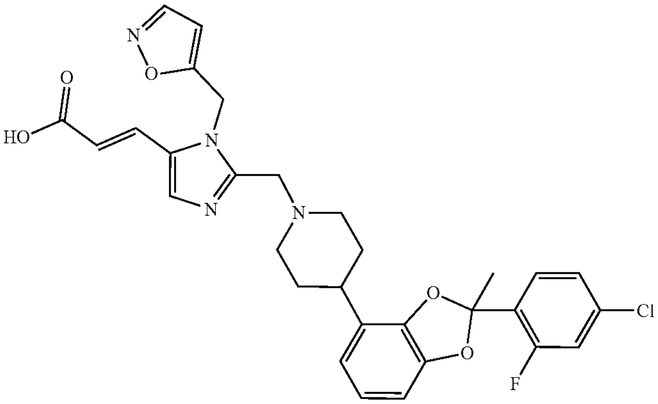 [SMILES: CC1(c2ccc(Cl)cc2F)Oc2cccc(C3CCN(Cc4ncc(/C=C/C(=O)O)n4Cc4ccno4)CC3)c2O1] |

TABLE C1-continued
| Compound No. | Structure |
| --- | --- |
| 182 | 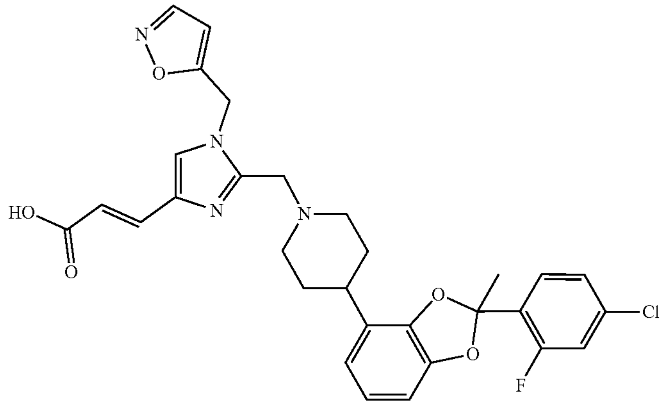 [SMILES: CC1(c2ccc(Cl)cc2F)Oc2cccc(C3CCN(Cc4nc(/C=C/C(=O)O)cn4Cc4ccno4)CC3)c2O1] |
| 183 | 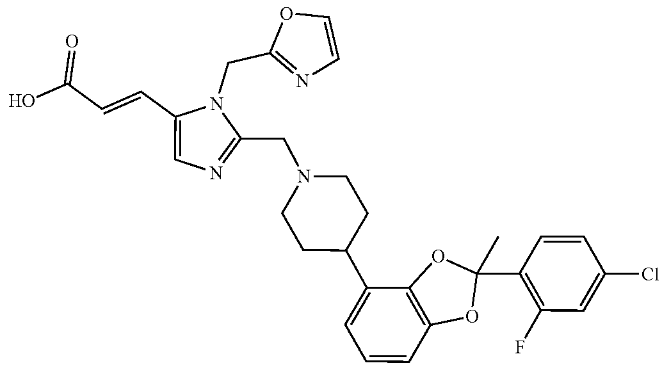 [SMILES: CC1(c2ccc(Cl)cc2F)Oc2cccc(C3CCN(Cc4ncc(/C=C/C(=O)O)n4Cc4ncco4)CC3)c2O1] |
| 184 | 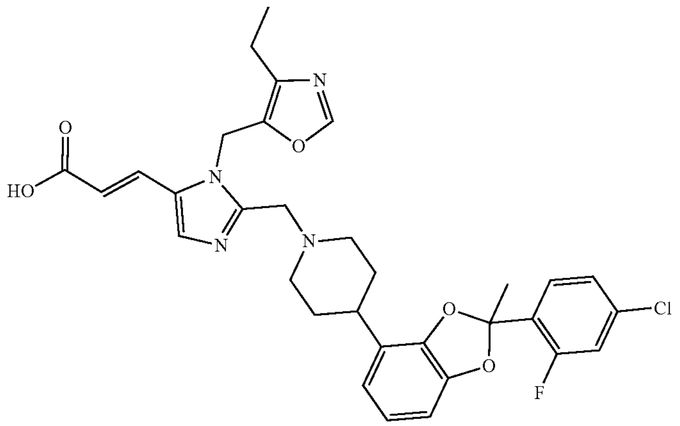 [SMILES: CCc1ncoc1Cn1c(/C=C/C(=O)O)cnc1CN1CCC(c2cccc3c2OC(C)(c2ccc(Cl)cc2F)O3)CC1] |

TABLE C1-continued
| Compound No. | Structure |
| --- | --- |
| 185 | 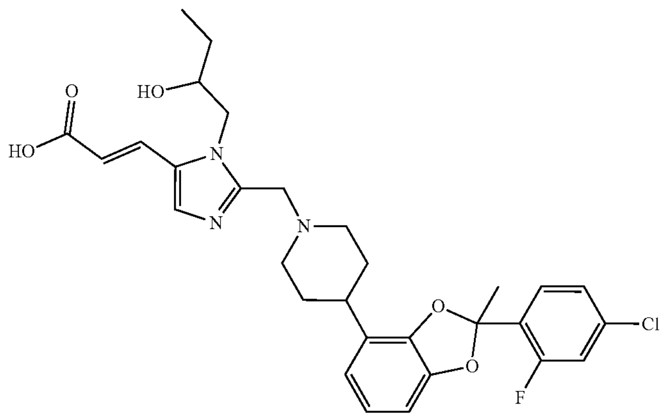 [SMILES: CCC(O)Cn1c(/C=C/C(=O)O)cnc1CN1CCC(c2cccc3c2OC(C)(c2ccc(Cl)cc2F)O3)CC1] |
| 186a | 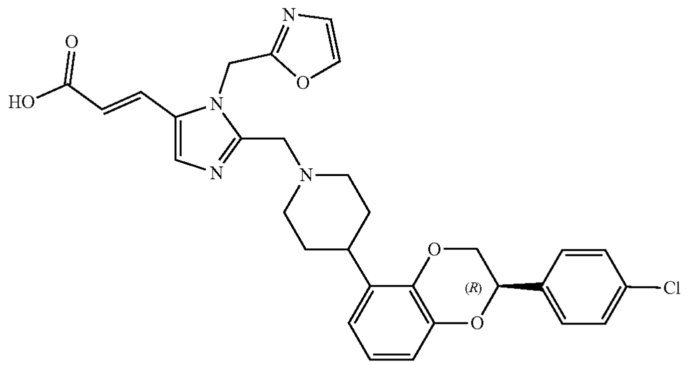 |
| 187a | 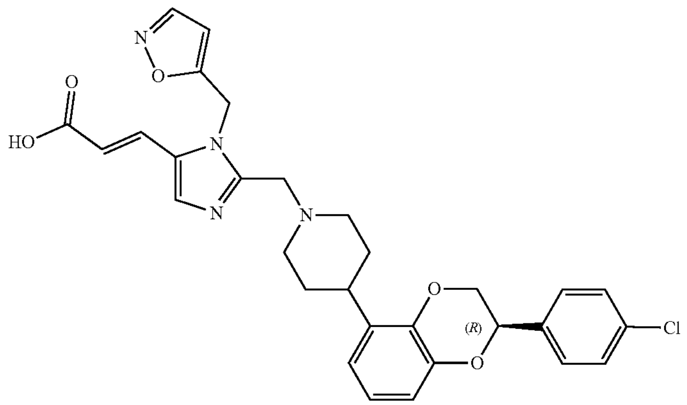 |

TABLE C1-continued
| Compound No. | Structure |
|---|---|
| 188 | 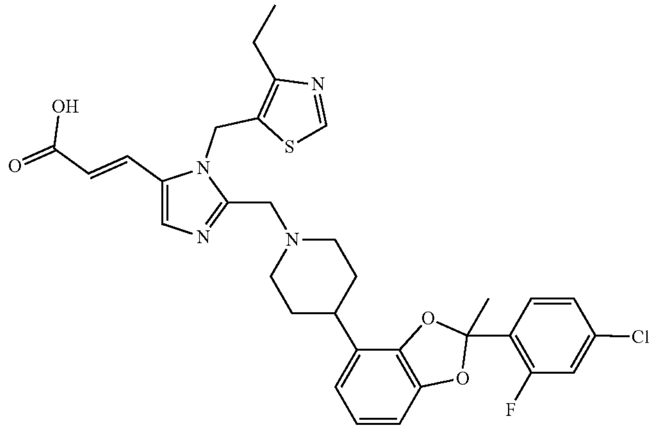 [SMILES: CCc1ncsc1Cn1c(/C=C/C(=O)O)cnc1CN1CCC(c2cccc3c2OC(C)(c2ccc(Cl)cc2F)O3)CC1] |
| 189 | 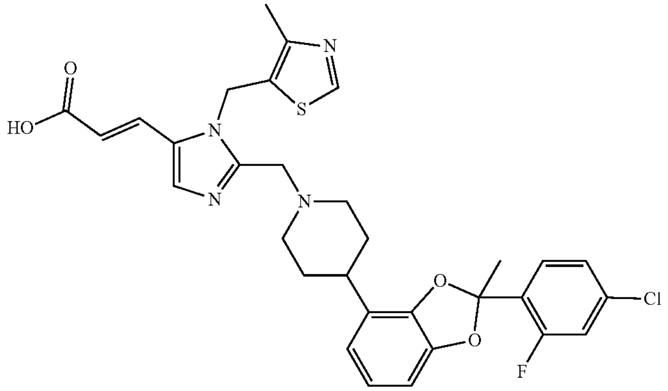 [SMILES: Cc1ncsc1Cn1c(/C=C/C(=O)O)cnc1CN1CCC(c2cccc3c2OC(C)(c2ccc(Cl)cc2F)O3)CC1] |
| 190 | 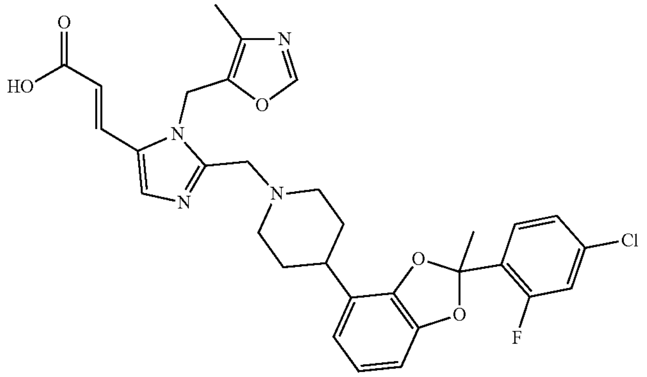 [SMILES: Cc1ncoc1Cn1c(/C=C/C(=O)O)cnc1CN1CCC(c2cccc3c2OC(C)(c2ccc(Cl)cc2F)O3)CC1] |

TABLE C1-continued
| Compound No. | Structure |
| --- | --- |
| 191 | 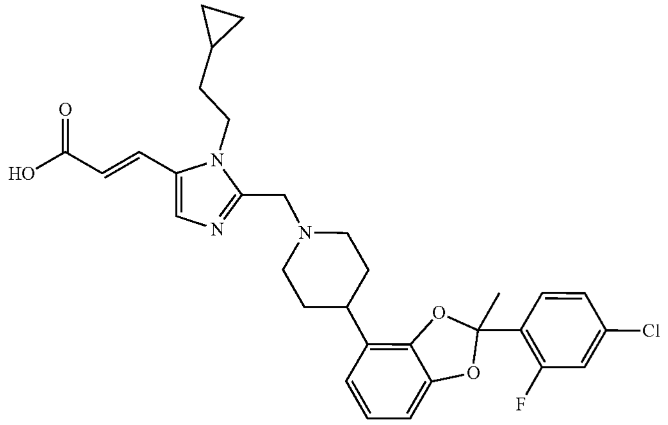 [SMILES: CC1(c2ccc(Cl)cc2F)Oc2cccc(C3CCN(Cc4ncc(/C=C/C(=O)O)n4CCC4CC4)CC3)c2O1] |
| 192 | 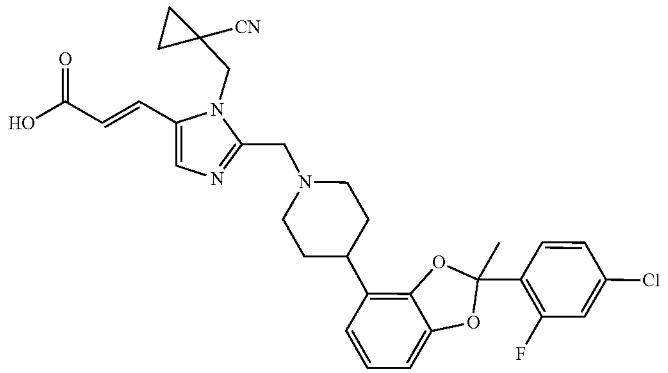 [SMILES: CC1(c2ccc(Cl)cc2F)Oc2cccc(C3CCN(Cc4ncc(/C=C/C(=O)O)n4CC4(C#N)CC4)CC3)c2O1] |
| 193 | 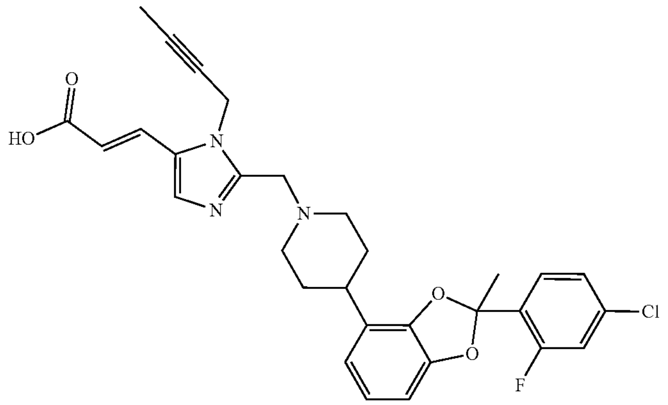 [SMILES: CC#CCn1c(/C=C/C(=O)O)cnc1CN1CCC(c2cccc3c2OC(C)(c2ccc(Cl)cc2F)O3)CC1] |
| 194 | 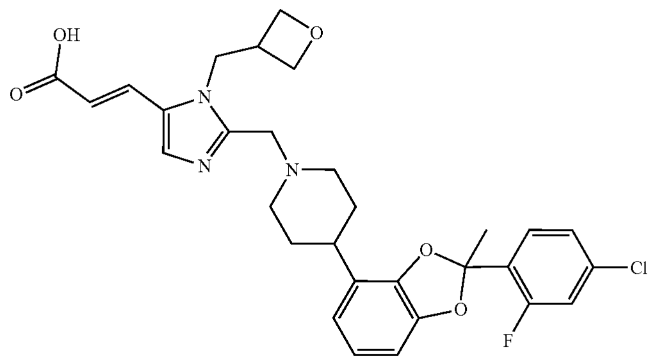 [SMILES: CC1(c2ccc(Cl)cc2F)Oc2cccc(C3CCN(Cc4ncc(/C=C/C(=O)O)n4CC4COC4)CC3)c2O1] |

TABLE C1-continued
| Compound No. | Structure |
|---|---|
| 195 | 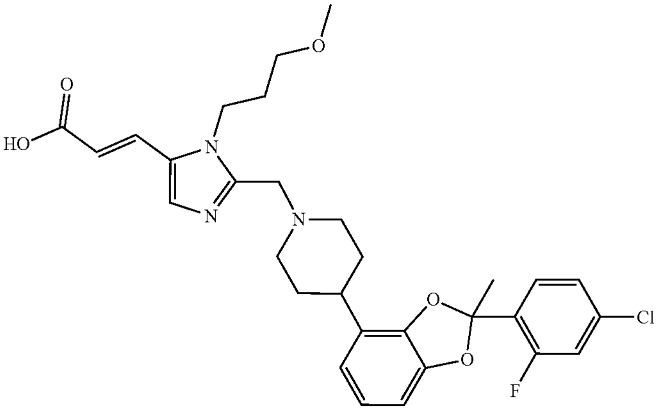 [SMILES: COCCCn1c(/C=C/C(=O)O)cnc1CN1CCC(c2cccc3c2OC(C)(c2ccc(Cl)cc2F)O3)CC1] |
| 196 | 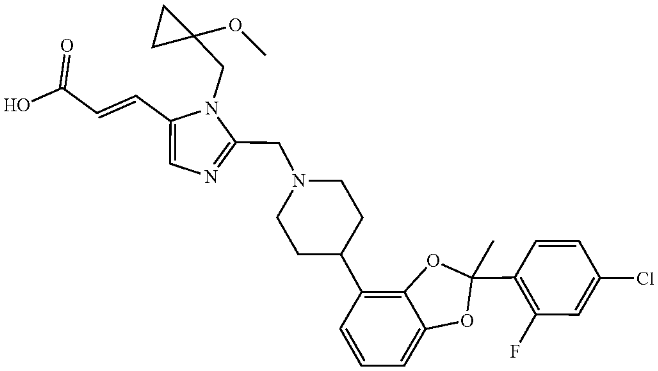 [SMILES: COC1(Cn2c(/C=C/C(=O)O)cnc2CN2CCC(c3cccc4c3OC(C)(c3ccc(Cl)cc3F)O4)CC2)CC1] |
| 197 | 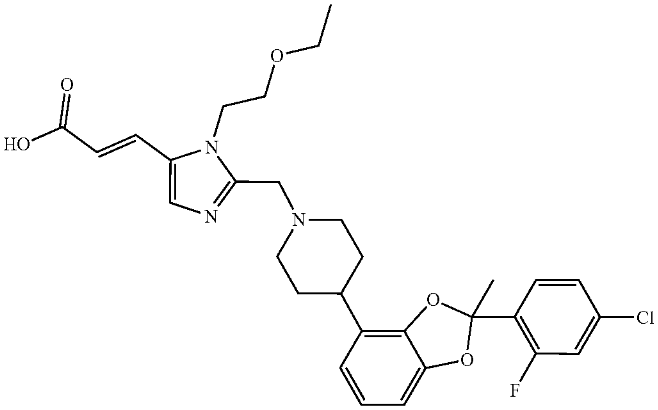 [SMILES: CCOCCn1c(/C=C/C(=O)O)cnc1CN1CCC(c2cccc3c2OC(C)(c2ccc(Cl)cc2F)O3)CC1] |

TABLE C1-continued
| Compound No. | Structure |
| --- | --- |
| 198a | 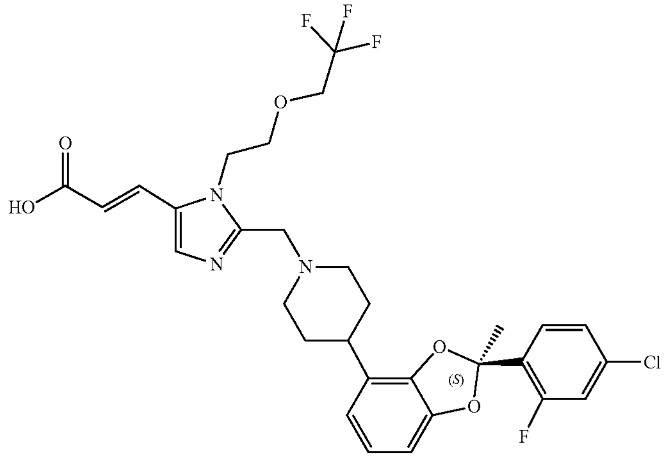 |
| 199a | 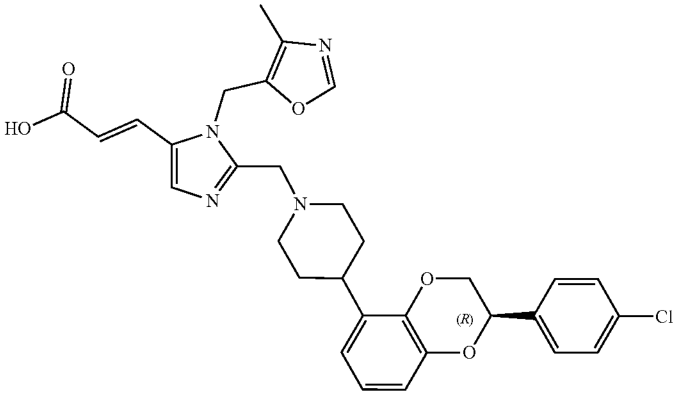 |
| 200 | 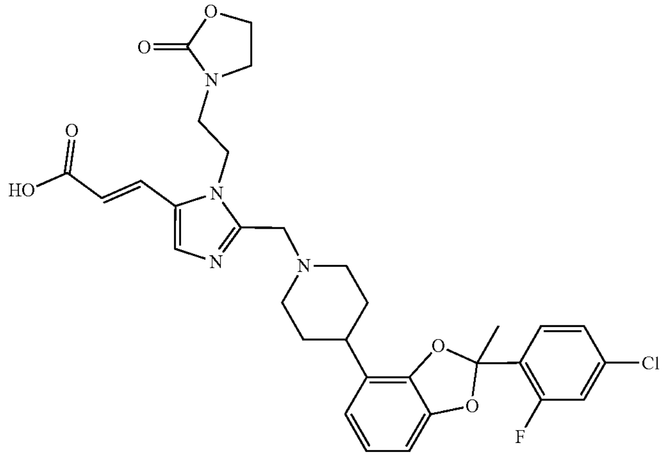 [SMILES: CC1(c2ccc(Cl)cc2F)Oc2cccc(C3CCN(Cc4ncc(/C=C/C(=O)O)n4CCN4CCOC4=O)CC3)c2O1] |

TABLE C1-continued
| Compound No. | Structure |
|---|---|
| 201 | 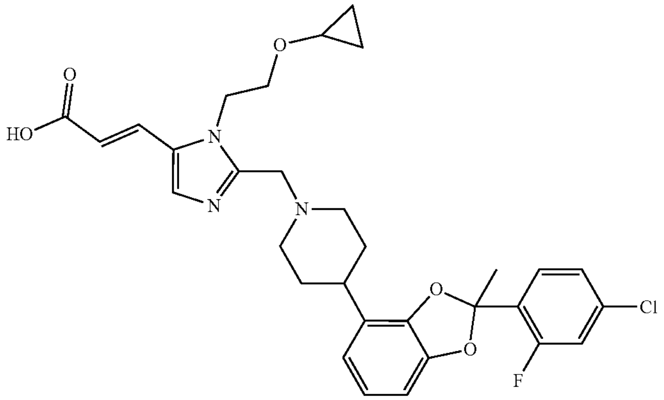 [SMILES: CC1(c2ccc(Cl)cc2F)Oc2cccc(C3CCN(Cc4ncc(/C=C/C(=O)O)n4CCOC4CC4)CC3)c2O1] |
| 202 | 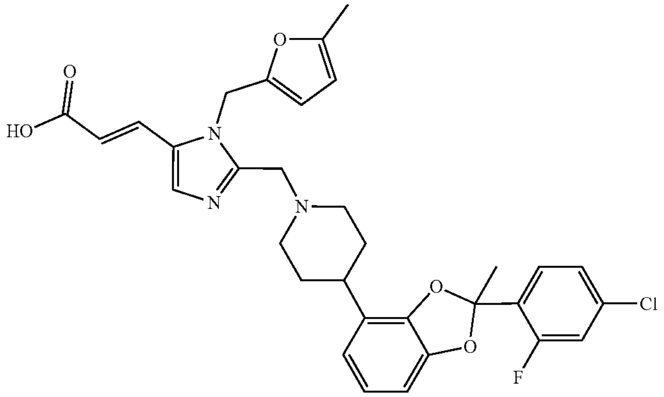 [SMILES: Cc1ccc(Cn2c(/C=C/C(=O)O)cnc2CN2CCC(c3cccc4c3OC(C)(c3ccc(Cl)cc3F)O4)CC2)o1] |
| 203 | 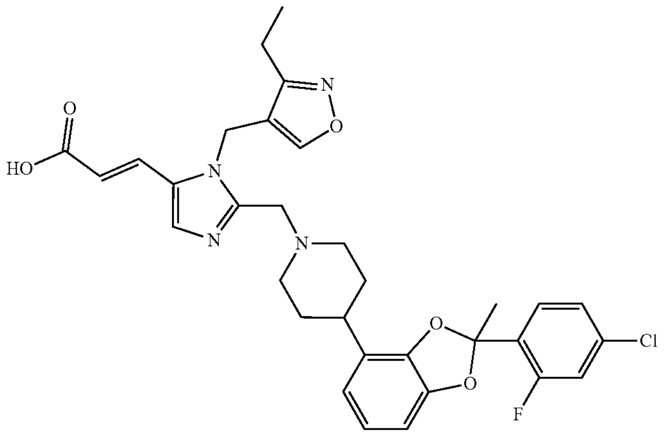 [SMILES: CCc1nocc1Cn1c(/C=C/C(=O)O)cnc1CN1CCC(c2cccc3c2OC(C)(c2ccc(Cl)cc2F)O3)CC1] |

TABLE C1-continued
| Compound No. | Structure |
| --- | --- |
| 204 | 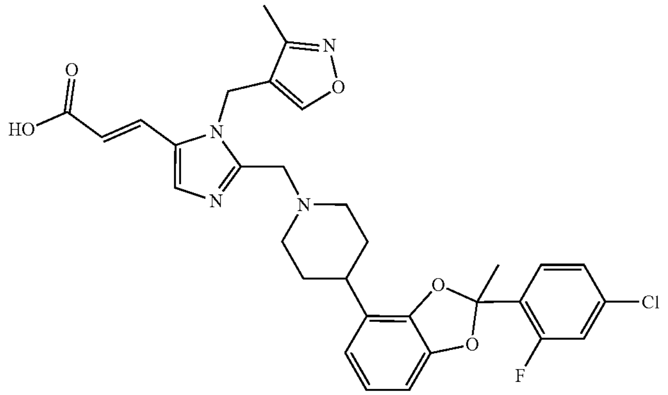 [SMILES: Cc1nocc1Cn1c(/C=C/C(=O)O)cnc1CN1CCC(c2cccc3c2OC(C)(c2ccc(Cl)cc2F)O3)CC1] |
| 205a | 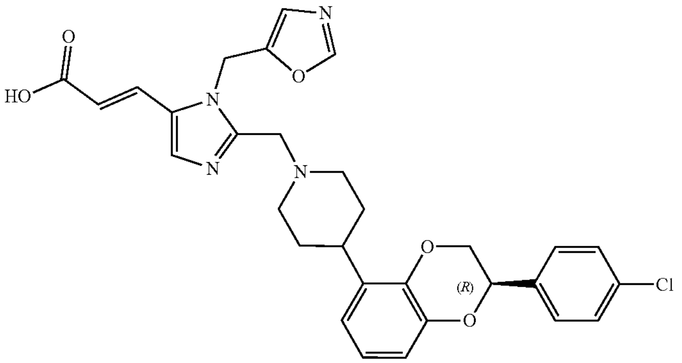 |
| 206a | 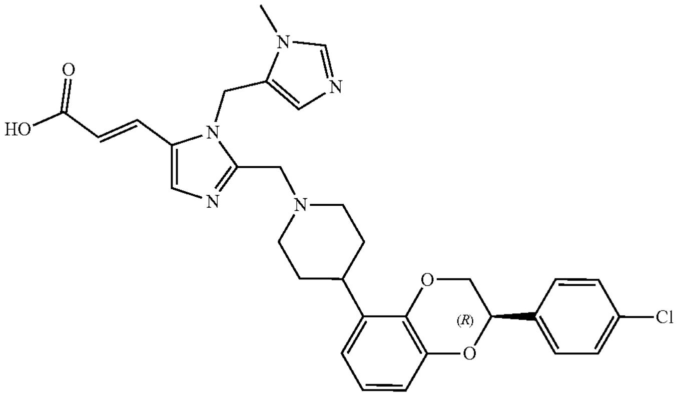 |
| 207a | 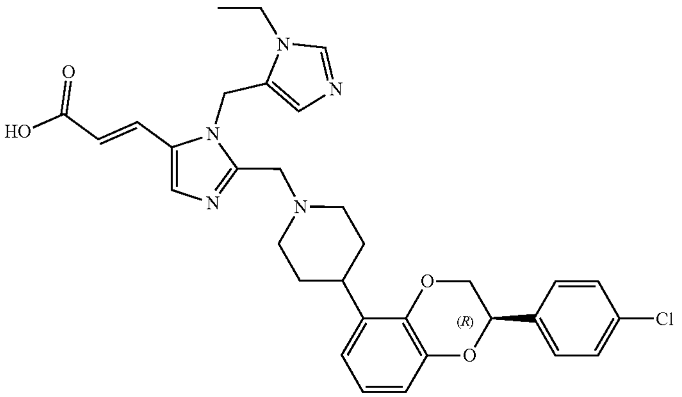 |

TABLE C1-continued
| Compound No. | Structure |
|---|---|
| 208a | 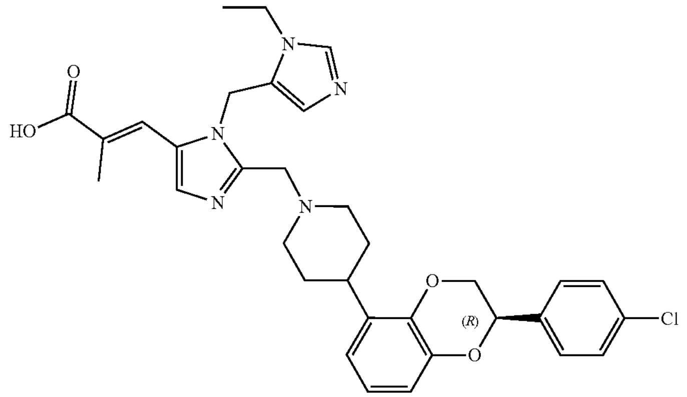 |
| 209a | 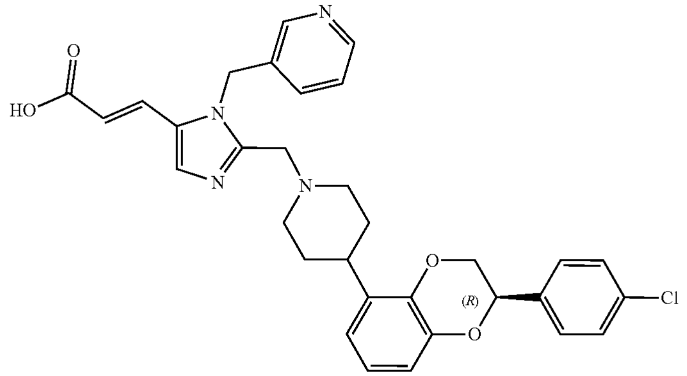 |
| 210a | 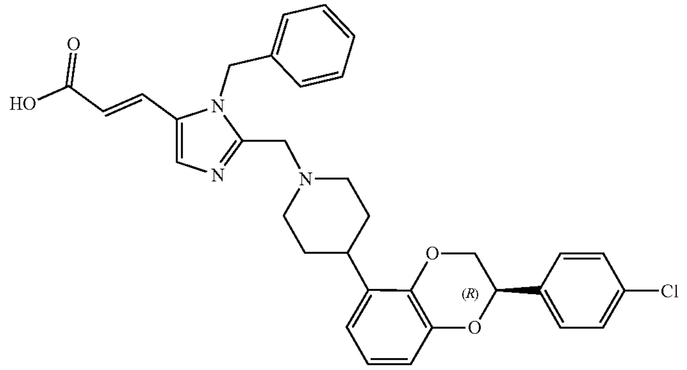 |
| 211 | 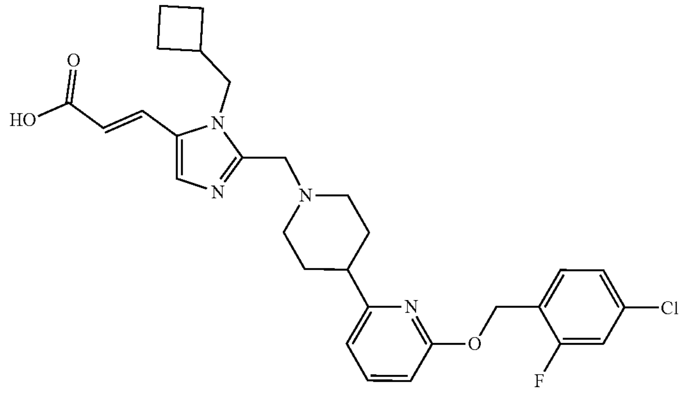 [SMILES: O=C(O)/C=C/c1cnc(CN2CCC(c3cccc(OCc4ccc(Cl)cc4F)n3)CC2)n1CC1CCC1] |

TABLE C1-continued
| Compound No. | Structure |
| --- | --- |
| 212 | 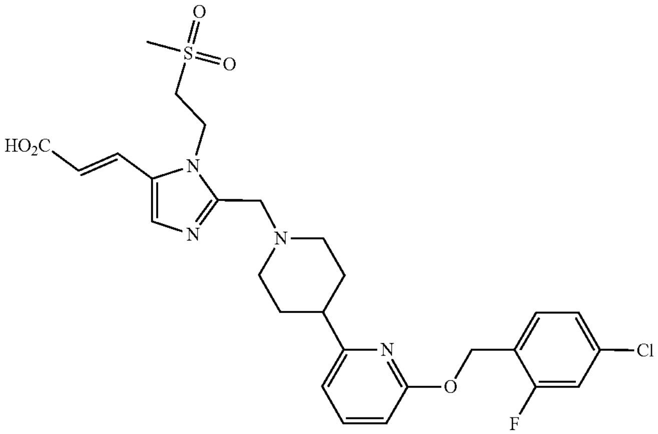 [SMILES: CS(=O)(=O)CCn1c(/C=C/C(=O)O)cnc1CN1CCC(c2cccc(OCc3ccc(Cl)cc3F)n2)CC1] |
| 213 | 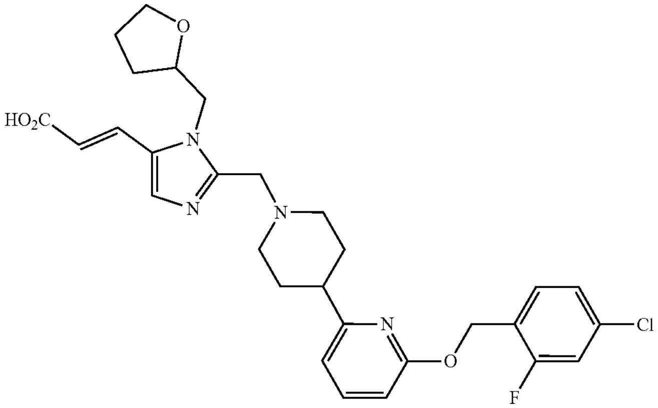 [SMILES: O=C(O)/C=C/c1cnc(CN2CCC(c3cccc(OCc4ccc(Cl)cc4F)n3)CC2)n1CC1CCCO1] |
| 214 | 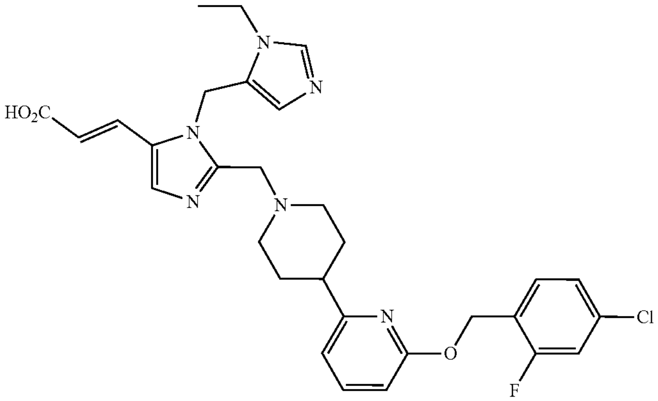 [SMILES: CCn1cncc1Cn1c(/C=C/C(=O)O)cnc1CN1CCC(c2cccc(OCc3ccc(Cl)cc3F)n2)CC1] |

TABLE C1-continued
| Compound No. | Structure |
|---|---|
| 215a | 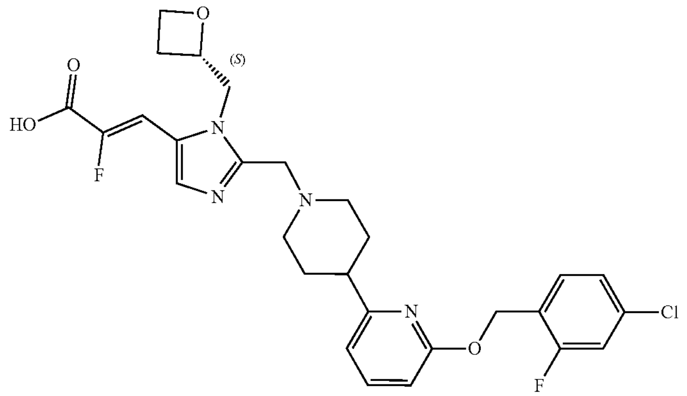 |
| 216a | 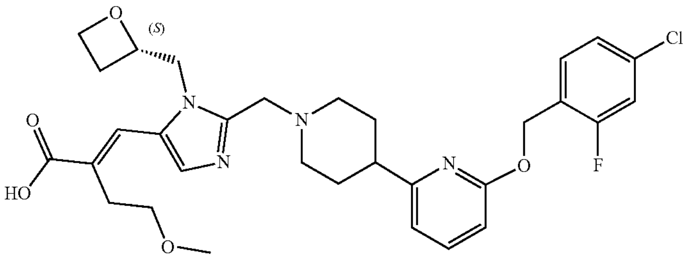 |
| 217a | 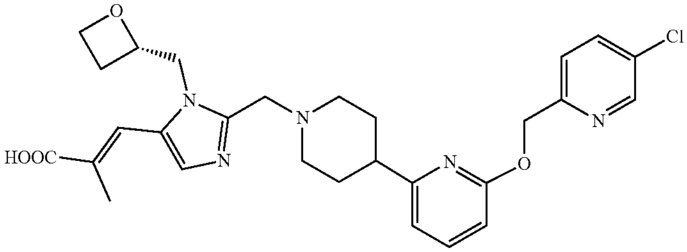 [SMILES: C/C(=C\c1cnc(CN2CCC(c3cccc(OCc4ccc(Cl)cn4)n3)CC2)n1C[C@@H]1CCO1)C(=O)O] |
| 218a | 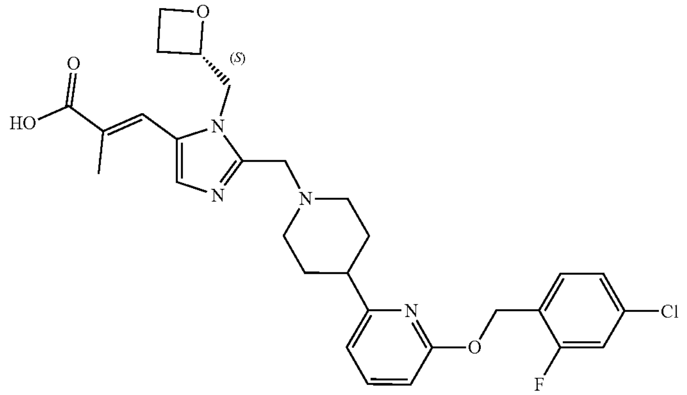 |

TABLE C1-continued
| Compound No. | Structure |
| --- | --- |
| 219 | 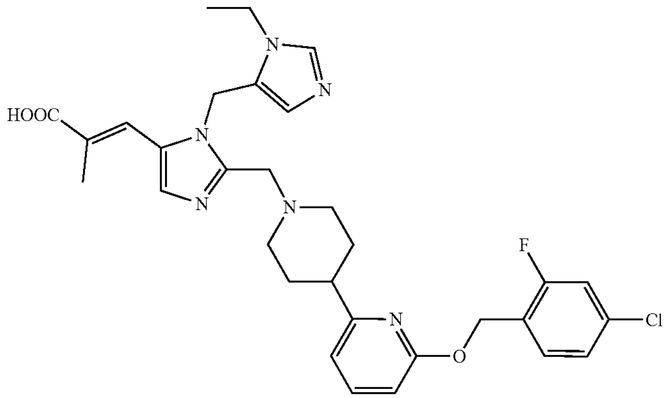 [SMILES: CCn1cncc1Cn1c(/C=C(\C)C(=O)O)cnc1CN1CCC(c2cccc(OCc3ccc(Cl)cc3F)n2)CC1] |
| 220 | 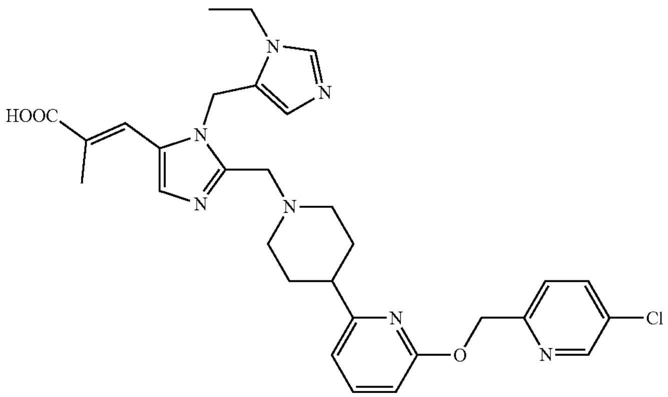 [SMILES: CCn1cncc1Cn1c(/C=C(\C)C(=O)O)cnc1CN1CCC(c2cccc(OCc3ccc(Cl)cn3)n2)CC1] |
| 221 | 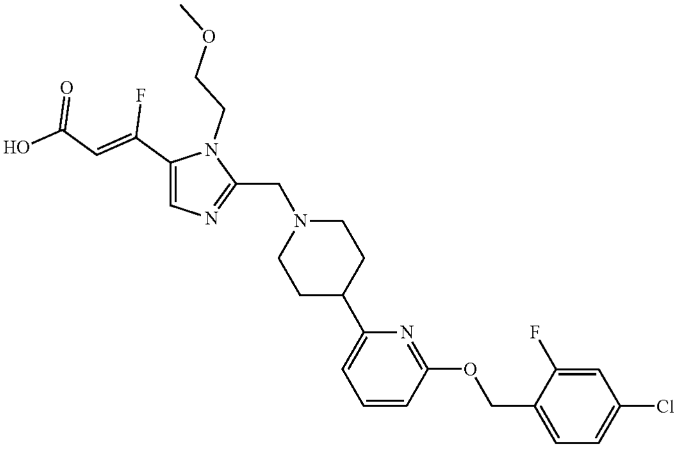 [SMILES: COCCn1c(/C(F)=C/C(=O)O)cnc1CN1CCC(c2cccc(OCc3ccc(Cl)cc3F)n2)CC1] |

TABLE C1-continued
| Compound No. | Structure |
|---|---|
| 222a | 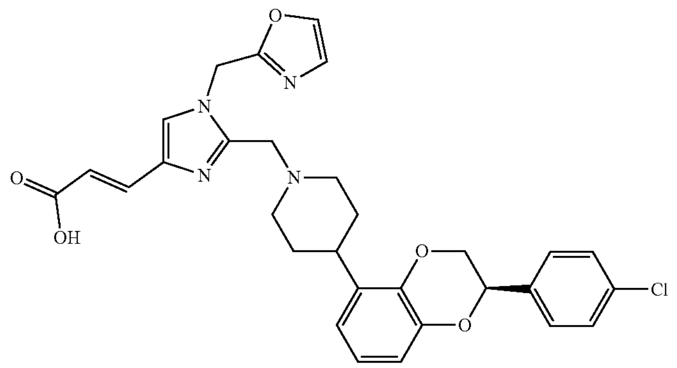 [SMILES: O=C(O)/C=C/c1cn(Cc2ncco2)c(CN2CCC(c3cccc4c3OC[C@@H](c3ccc(Cl)cc3)O4)CC2)n1] |
| 223 | 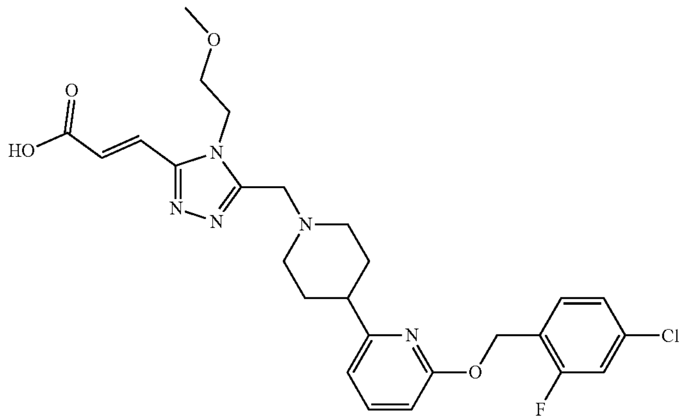 [SMILES: COCCn1c(/C=C/C(=O)O)nnc1CN1CCC(c2cccc(OCc3ccc(Cl)cc3F)n2)CC1] |
| 224 | 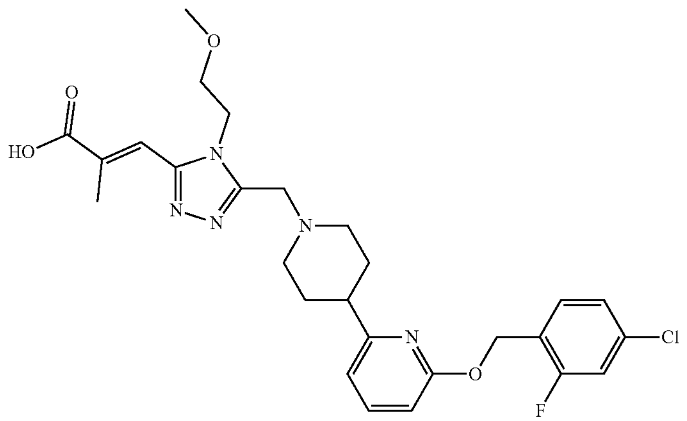 [SMILES: COCCn1c(/C=C(\C)C(=O)O)nnc1CN1CCC(c2cccc(OCc3ccc(Cl)cc3F)n2)CC1] |

TABLE C1-continued
| Compound No. | Structure |
| --- | --- |
| 225a | 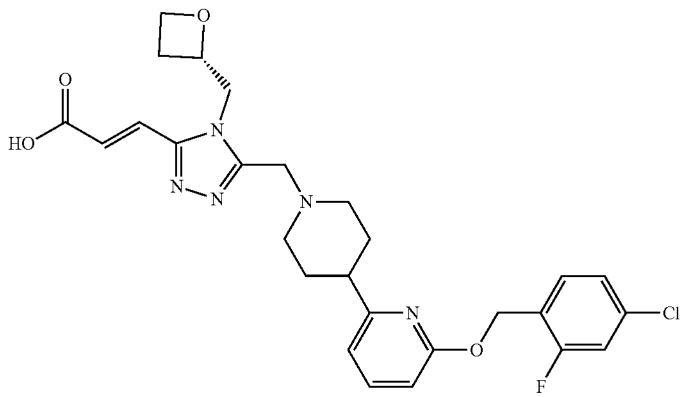 [SMILES: O=C(O)/C=C/c1nnc(CN2CCC(c3cccc(OCc4ccc(Cl)cc4F)n3)CC2)n1C[C@@H]1CCO1] |
| 226a | 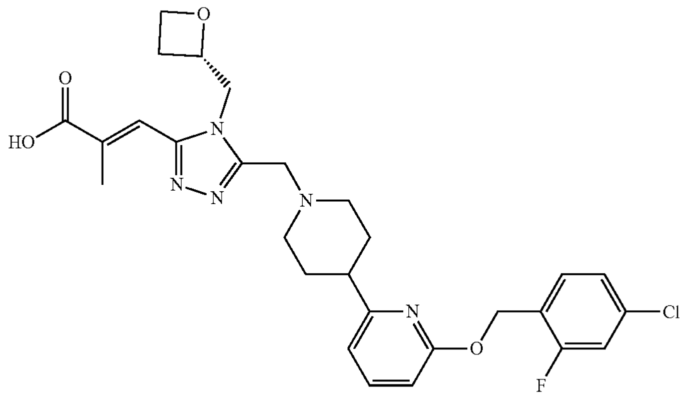 [SMILES: C/C(=C\c1nnc(CN2CCC(c3cccc(OCc4ccc(Cl)cc4F)n3)CC2)n1C[C@@H]1CCO1)C(=O)O] |
| 227 | 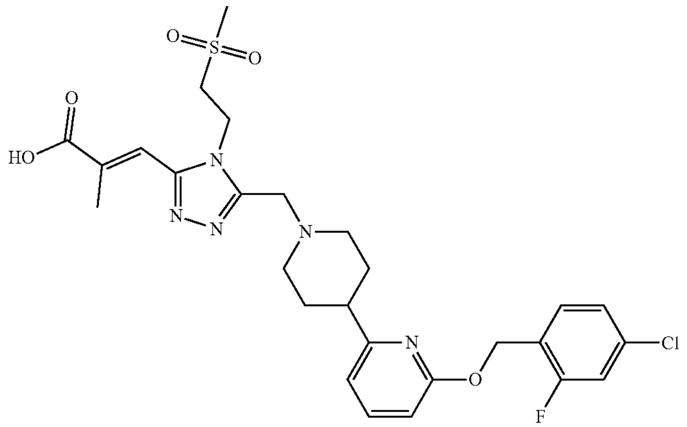 [SMILES: C/C(=C\c1nnc(CN2CCC(c3cccc(OCc4ccc(Cl)cc4F)n3)CC2)n1CCS(C)(=O)=O)C(=O)O] |

TABLE C1-continued
| Compound No. | Structure |
|---|---|
| 228 | 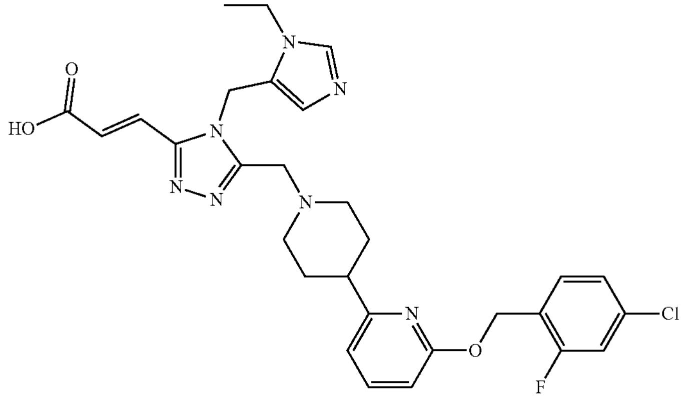 [SMILES: CCn1cncc1Cn1c(/C=C/C(=O)O)nnc1CN1CCC(c2cccc(OCc3ccc(Cl)cc3F)n2)CC1] |
| 229 | 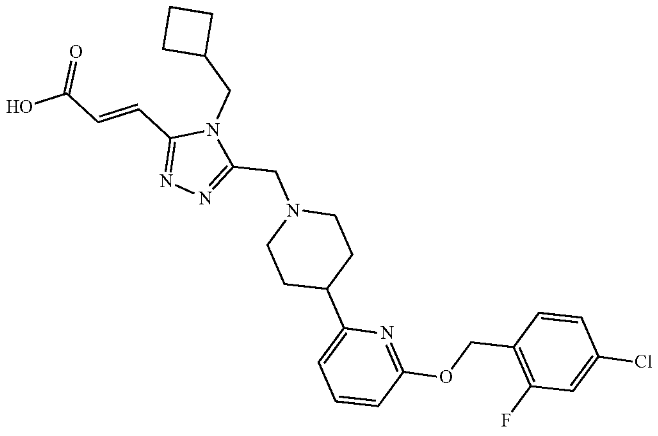 [SMILES: O=C(O)/C=C/c1nnc(CN2CCC(c3cccc(OCc4ccc(Cl)cc4F)n3)CC2)n1CC1CCC1] |
| 230 | 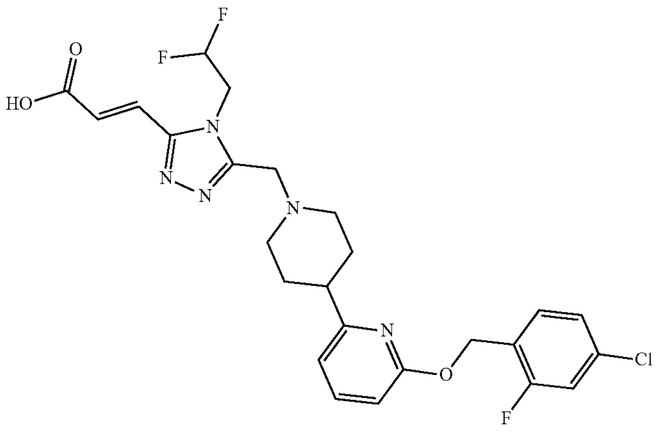 [SMILES: O=C(O)/C=C/c1nnc(CN2CCC(c3cccc(OCc4ccc(Cl)cc4F)n3)CC2)n1CC(F)F] |

TABLE C1-continued
| Compound No. | Structure |
|---|---|
| 231 | 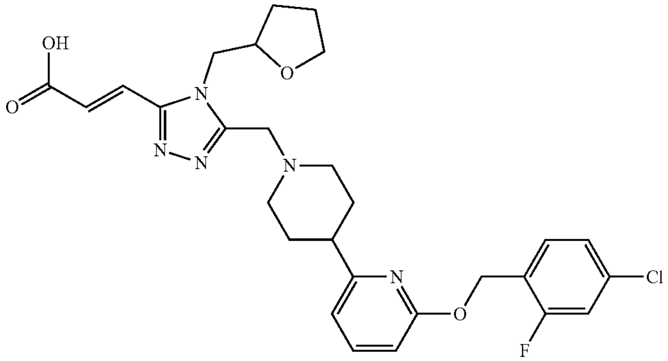 [SMILES: O=C(O)/C=C/c1nnc(CN2CCC(c3cccc(OCc4ccc(Cl)cc4F)n3)CC2)n1CC1CCCO1] |
| 232 | 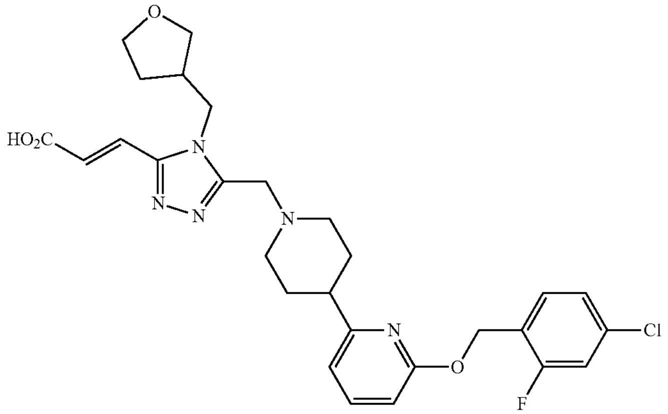 [SMILES: O=C(O)/C=C/c1nnc(CN2CCC(c3cccc(OCc4ccc(Cl)cc4F)n3)CC2)n1CC1CCOC1] |
| 233 | 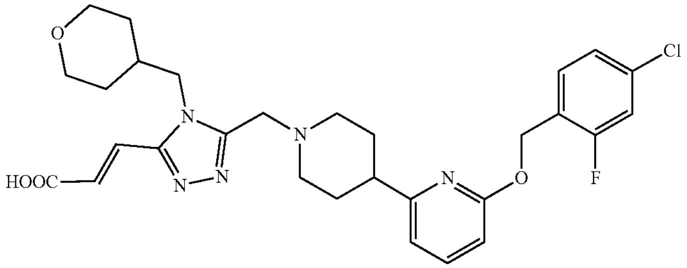 [SMILES: O=C(O)/C=C/c1nnc(CN2CCC(c3cccc(OCc4ccc(Cl)cc4F)n3)CC2)n1CC1CCOCC1] |
| 234a | 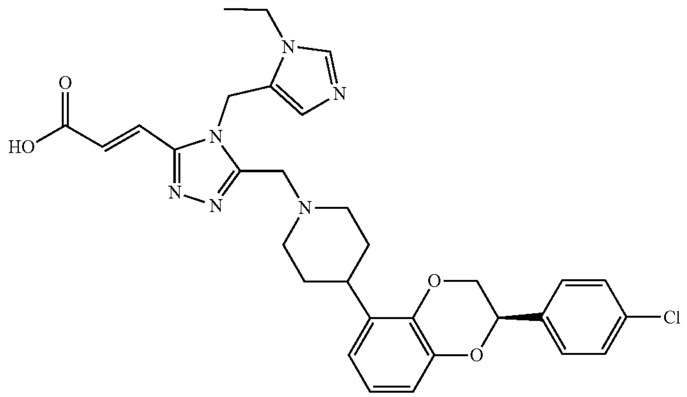 [SMILES: CCn1cncc1Cn1c(/C=C/C(=O)O)nnc1CN1CCC(c2cccc3c2OC[C@@H](c2ccc(Cl)cc2)O3)CC1] |

TABLE C1-continued
| Compound No. | Structure |
|---|---|
| 235 | 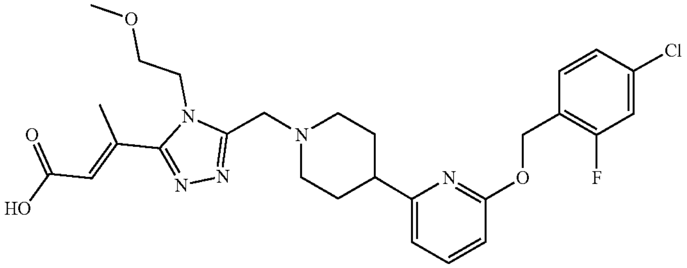 [SMILES: COCCn1c(CN2CCC(c3cccc(OCc4ccc(Cl)cc4F)n3)CC2)nnc1/C(C)=C/C(=O)O] |
| 236 | 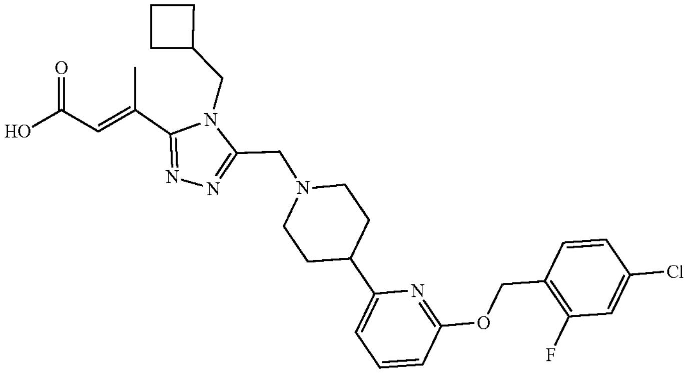 [SMILES: C/C(=C\C(=O)O)c1nnc(CN2CCC(c3cccc(OCc4ccc(Cl)cc4F)n3)CC2)n1CC1CCC1] |
| 237 | 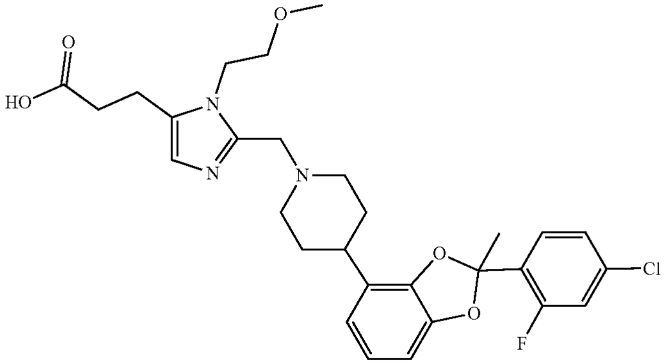 [SMILES: COCCn1c(CCC(=O)O)cnc1CN1CCC(c2cccc3c2OC(C)(c2ccc(Cl)cc2F)O3)CC1] |
| 238 | 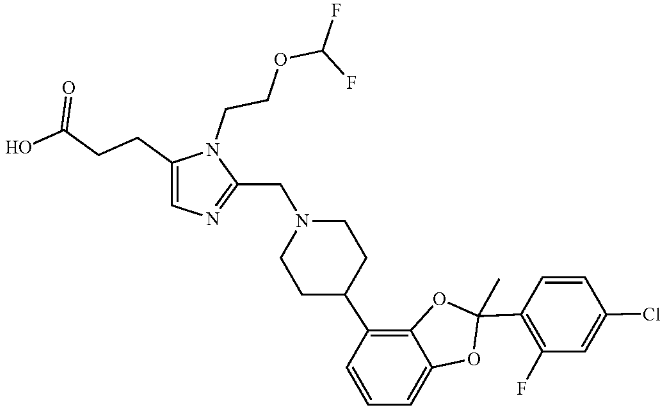 [SMILES: CC1(c2ccc(Cl)cc2F)Oc2cccc(C3CCN(Cc4ncc(CCC(=O)O)n4CCOC(F)F)CC3)c2O1] |

TABLE C1-continued
| Compound No. | Structure |
|---|---|
| 239 | 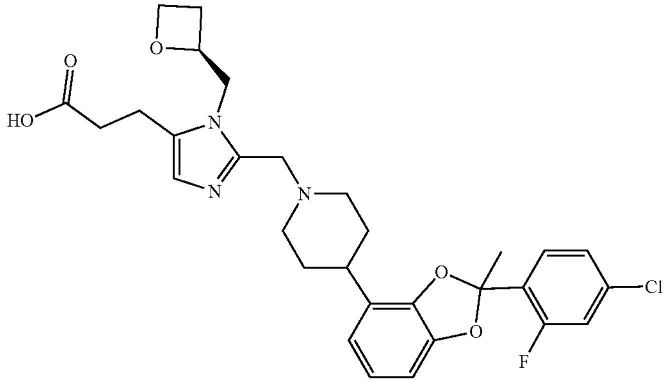 [SMILES: CC1(c2ccc(Cl)cc2F)Oc2cccc(C3CCN(Cc4ncc(CCC(=O)O)n4C[C@@H]4CCO4)CC3)c2O1] |
| 240 | 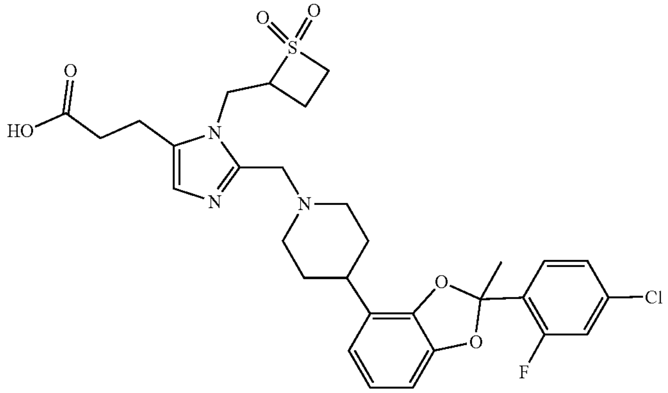 [SMILES: CC1(c2ccc(Cl)cc2F)Oc2cccc(C3CCN(Cc4ncc(CCC(=O)O)n4CC4CCS4(=O)=O)CC3)c2O1] |
| 241 | 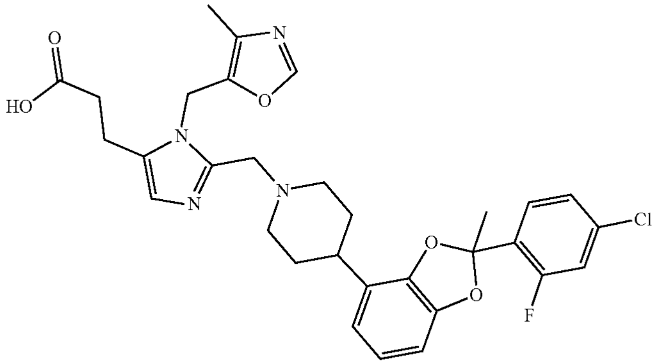 [SMILES: Cc1ncoc1Cn1c(CCC(=O)O)cnc1CN1CCC(c2cccc3c2OC(C)(c2ccc(Cl)cc2F)O3)CC1] |
| 242 | 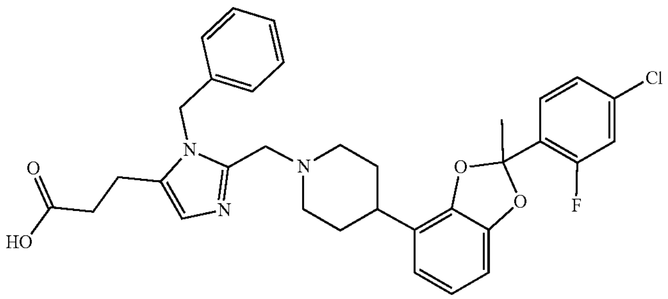 [SMILES: CC1(c2ccc(Cl)cc2F)Oc2cccc(C3CCN(Cc4ncc(CCC(=O)O)n4Cc4ccccc4)CC3)c2O1] |

TABLE C1-continued
| Compound No. | Structure |
|---|---|
| 243 | 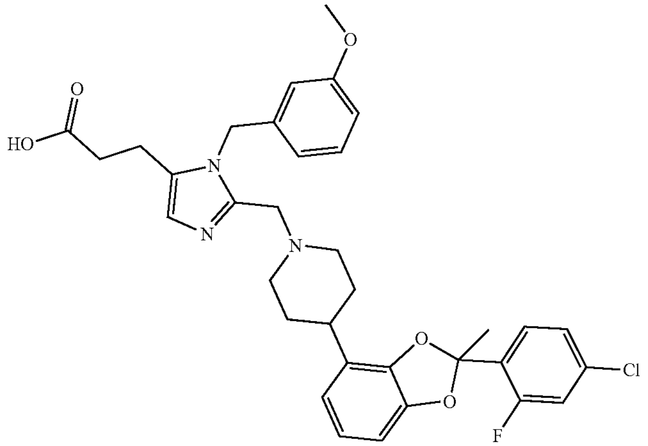 [SMILES: COc1cccc(Cn2c(CCC(=O)O)cnc2CN2CCC(c3cccc4c3OC(C)(c3ccc(Cl)cc3F)O4)CC2)c1] |
| 244 | 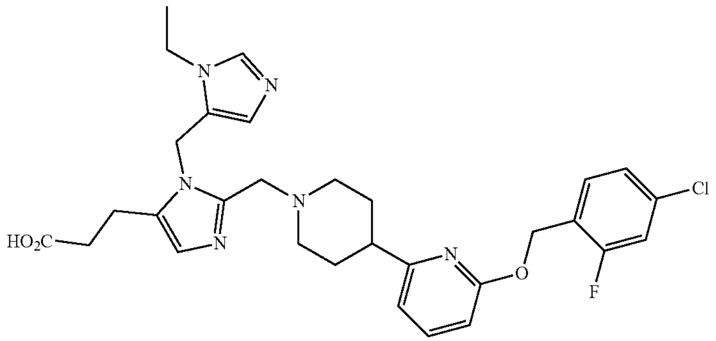 [SMILES: CCn1cncc1Cn1c(CCC(=O)O)cnc1CN1CCC(c2cccc(OCc3ccc(Cl)cc3F)n2)CC1] |
| 245 | 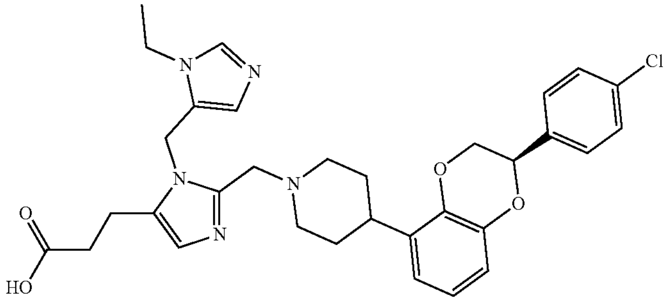 [SMILES: CCn1cncc1Cn1c(CCC(=O)O)cnc1CN1CCC(c2cccc3c2OC[C@@H](c2ccc(Cl)cc2)O3)CC1] |
| 246 | 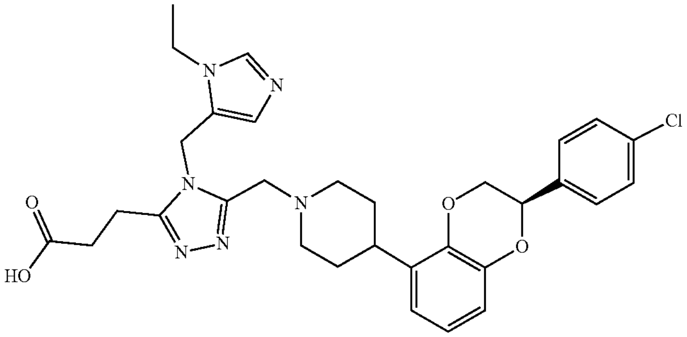 [SMILES: CCn1cncc1Cn1c(CCC(=O)O)nnc1CN1CCC(c2cccc3c2OC[C@@H](c2ccc(Cl)cc2)O3)CC1] |

TABLE C1-continued
| Compound No. | Structure |
|---|---|
| 247 | 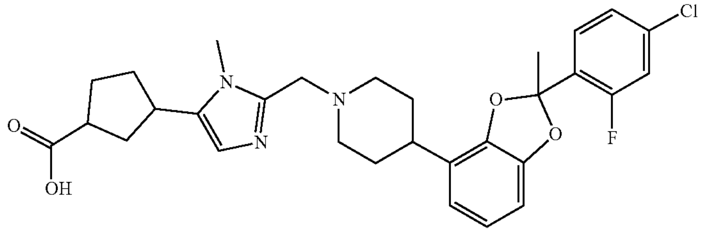 [SMILES: Cn1c(C2CCC(C(=O)O)C2)cnc1CN1CCC(c2cccc3c2OC(C)(c2ccc(Cl)cc2F)O3)CC1] |
| 248 | 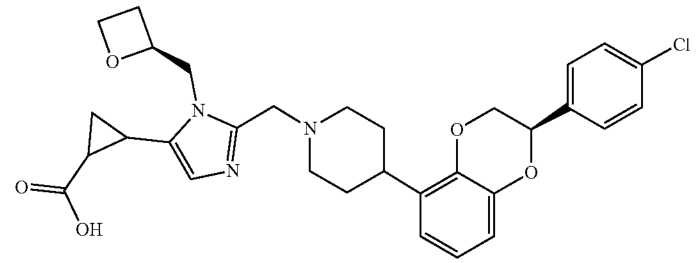 [SMILES: O=C(O)C1CC1c1cnc(CN2CCC(c3cccc4c3OC[C@@H](c3ccc(Cl)cc3)O4)CC2)n1C[C@@H]1CCO1] |
| 249a | 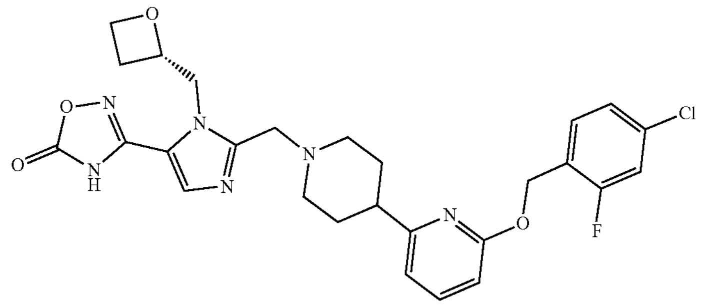 [SMILES: O=c1[nH]c(-c2cnc(CN3CCC(c4cccc(OCc5ccc(Cl)cc5F)n4)CC3)n2C[C@@H]2CCO2)no1] |
| 250 | 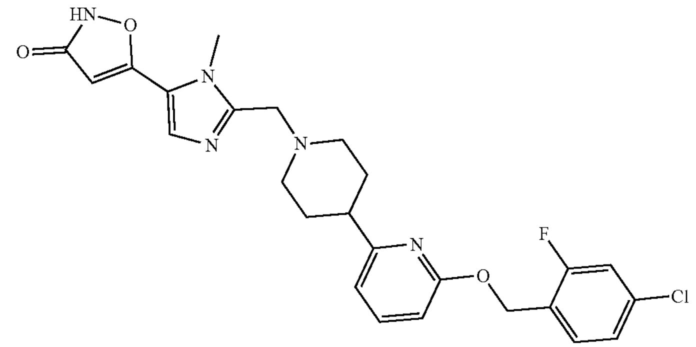 [SMILES: Cn1c(-c2cc(=O)[nH]o2)cnc1CN1CCC(c2cccc(OCc3ccc(Cl)cc3F)n2)CC1] |
| 251 | 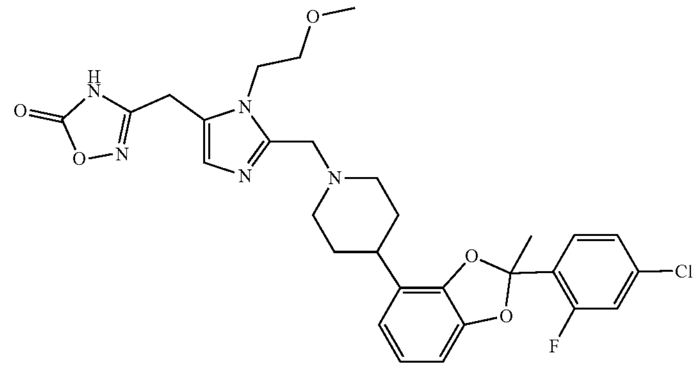 [SMILES: COCCn1c(Cc2noc(=O)[nH]2)cnc1CN1CCC(c2cccc3c2OC(C)(c2ccc(Cl)cc2F)O3)CC1] |

TABLE C1-continued
| Compound No. | Structure |
| --- | --- |
| 252 | 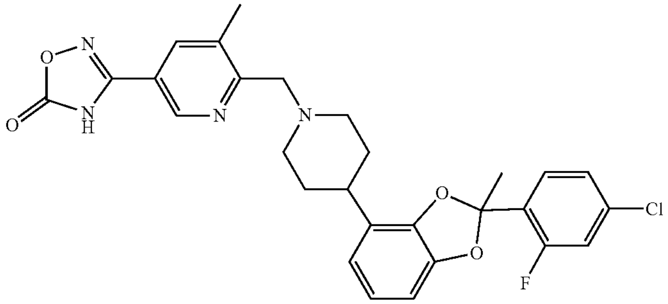 [SMILES: Cc1cc(-c2noc(=O)[nH]2)cnc1CN1CCC(c2cccc3c2OC(C)(c2ccc(Cl)cc2F)O3)CC1] |
| 253 | 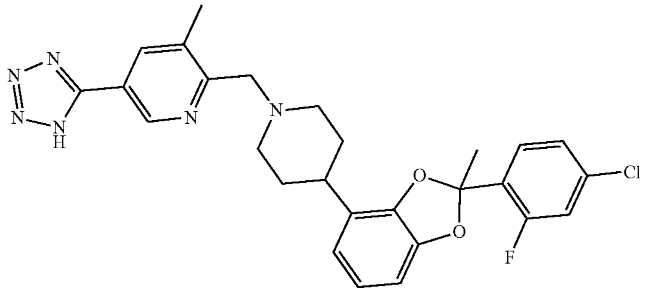 [SMILES: Cc1cc(-c2nnn[nH]2)cnc1CN1CCC(c2cccc3c2OC(C)(c2ccc(Cl)cc2F)O3)CC1] |
| 254 | 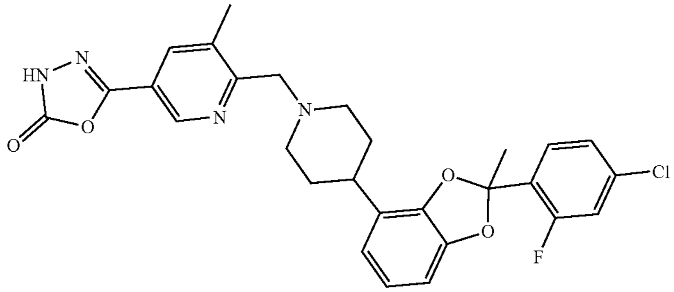 [SMILES: Cc1cc(-c2n[nH]c(=O)o2)cnc1CN1CCC(c2cccc3c2OC(C)(c2ccc(Cl)cc2F)O3)CC1] |
| 255 | 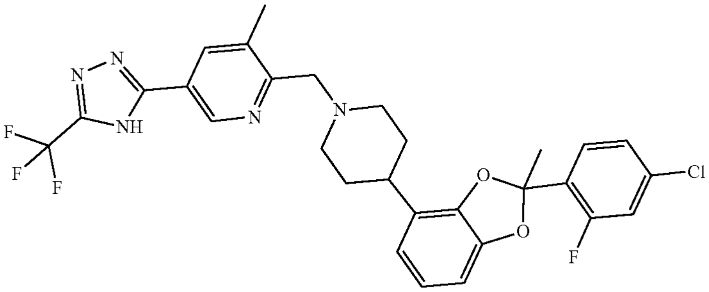 [SMILES: Cc1cc(-c2nnc(C(F)(F)F)[nH]2)cnc1CN1CCC(c2cccc3c2OC(C)(c2ccc(Cl)cc2F)O3)CC1] |
| 256 | 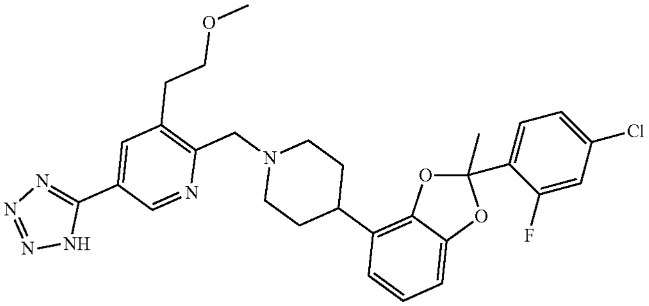 [SMILES: COCCc1cc(-c2nnn[nH]2)cnc1CN1CCC(c2cccc3c2OC(C)(c2ccc(Cl)cc2F)O3)CC1] |

TABLE C1-continued
| Compound No. | Structure |
| --- | --- |
| 257 | 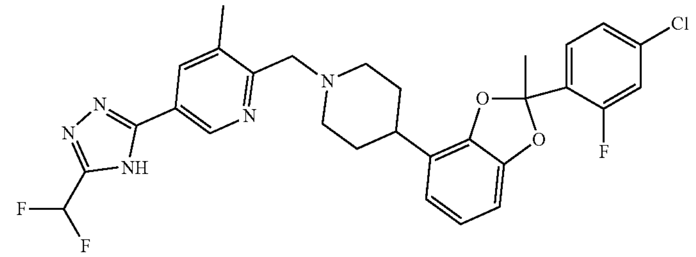 [SMILES: Cc1cc(-c2nnc(C(F)F)[nH]2)cnc1CN1CCC(c2cccc3c2OC(C)(c2ccc(Cl)cc2F)O3)CC1] |
| 258 | 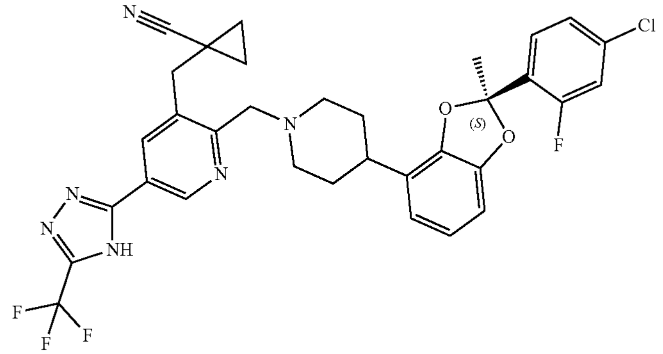 |
| 259 | 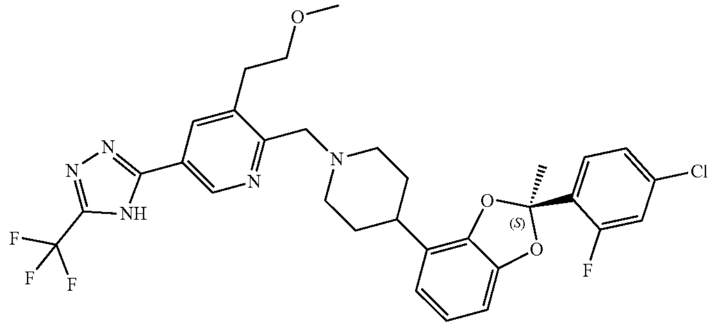 |
| 260 | 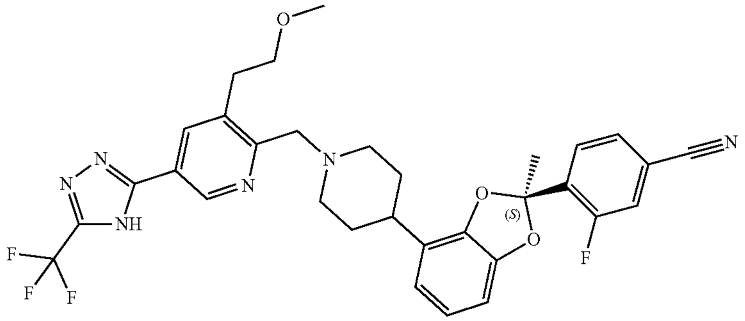 |

TABLE C1-continued
| Compound No. | Structure |
|---|---|
| 261 | 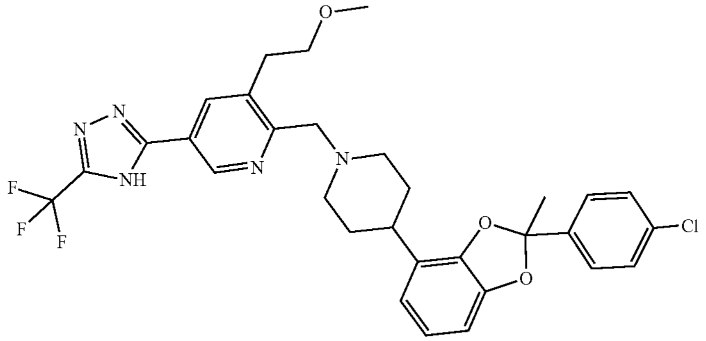 [SMILES: COCCc1cc(-c2nnc(C(F)(F)F)[nH]2)cnc1CN1CCC(c2cccc3c2OC(C)(c2ccc(Cl)cc2)O3)CC1] |
| 262 | 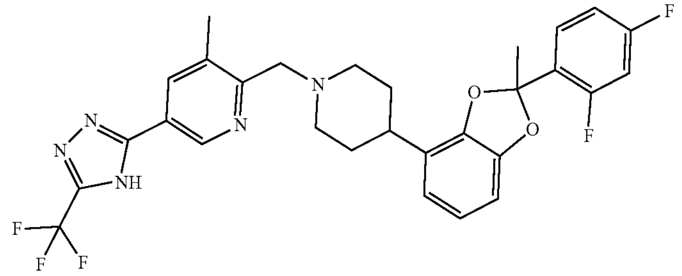 [SMILES: Cc1cc(-c2nnc(C(F)(F)F)[nH]2)cnc1CN1CCC(c2cccc3c2OC(C)(c2ccc(F)cc2F)O3)CC1] |
| 263 | 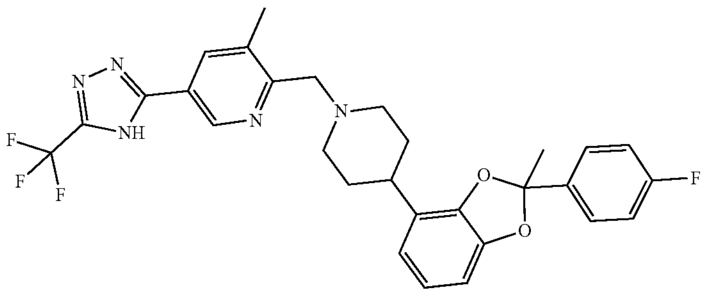 [SMILES: Cc1cc(-c2nnc(C(F)(F)F)[nH]2)cnc1CN1CCC(c2cccc3c2OC(C)(c2ccc(F)cc2)O3)CC1] |
| 264 | 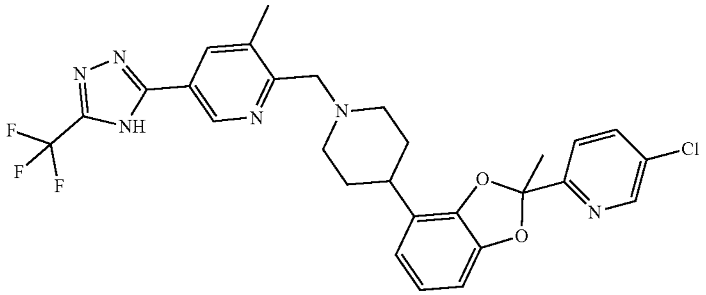 [SMILES: Cc1cc(-c2nnc(C(F)(F)F)[nH]2)cnc1CN1CCC(c2cccc3c2OC(C)(c2ccc(Cl)cn2)O3)CC1] |
| 265 | 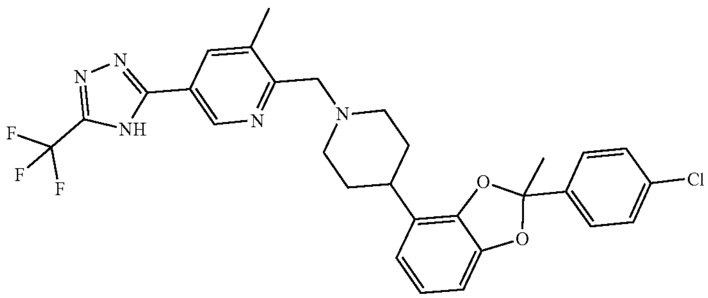 [SMILES: Cc1cc(-c2nnc(C(F)(F)F)[nH]2)cnc1CN1CCC(c2cccc3c2OC(C)(c2ccc(Cl)cc2)O3)CC1] |

TABLE C1-continued
| Compound No. | Structure |
|---|---|
| 266 | 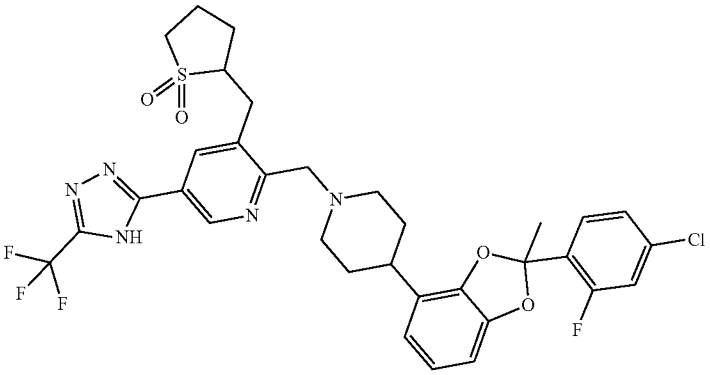 [SMILES: CC1(c2ccc(Cl)cc2F)Oc2cccc(C3CCN(Cc4ncc(-c5nnc(C(F)(F)F)[nH]5)cc4CC4CCCS4(=O)=O)CC3)c2O1] |
| 267 | 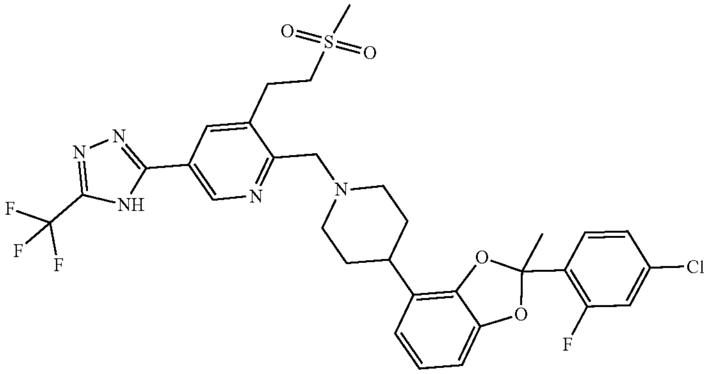 [SMILES: CC1(c2ccc(Cl)cc2F)Oc2cccc(C3CCN(Cc4ncc(-c5nnc(C(F)(F)F)[nH]5)cc4CCS(C)(=O)=O)CC3)c2O1] |
| 268 | 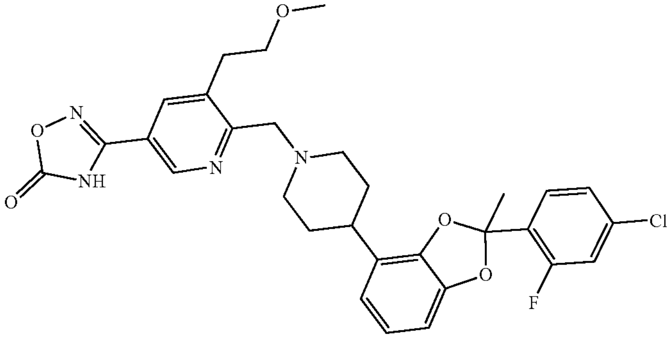 [SMILES: COCCc1cc(-c2noc(=O)[nH]2)cnc1CN1CCC(c2cccc3c2OC(C)(c2ccc(Cl)cc2F)O3)CC1] |
| 269 | 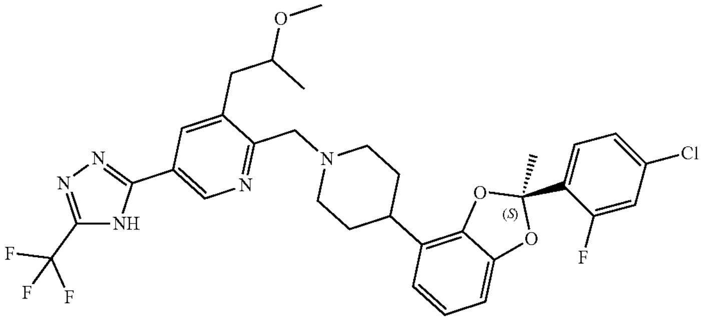 |

TABLE C1-continued
| Compound No. | Structure |
|---|---|
| 269a | 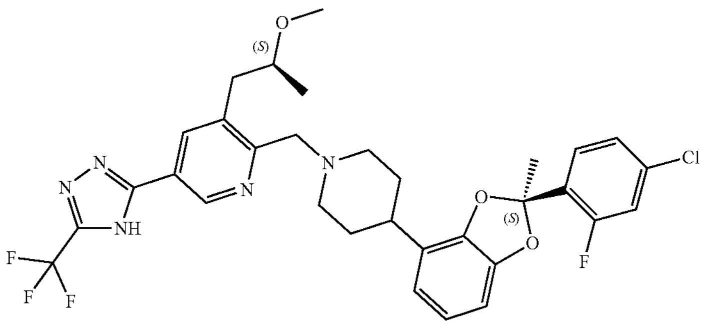 |
| 269b | 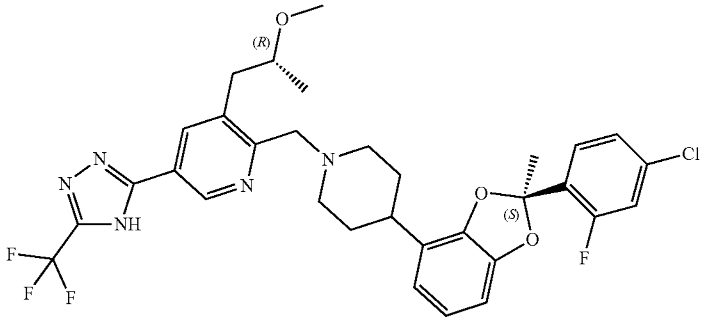 |
| 270 | 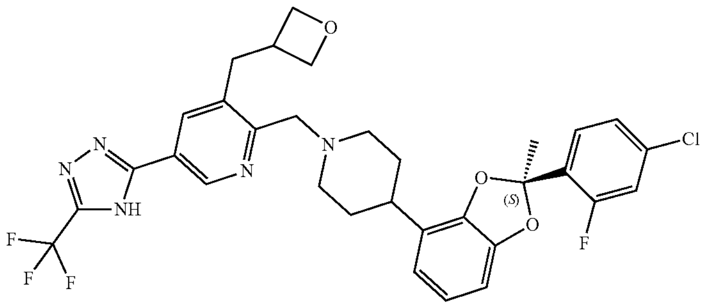 |
| 271 | 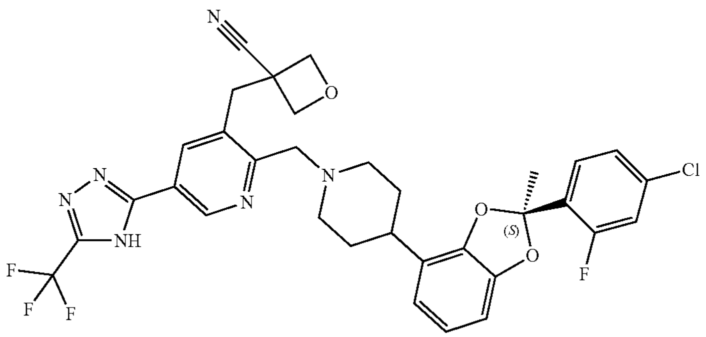 |

TABLE C1-continued
| Compound No. | Structure |
|---|---|
| 272 | 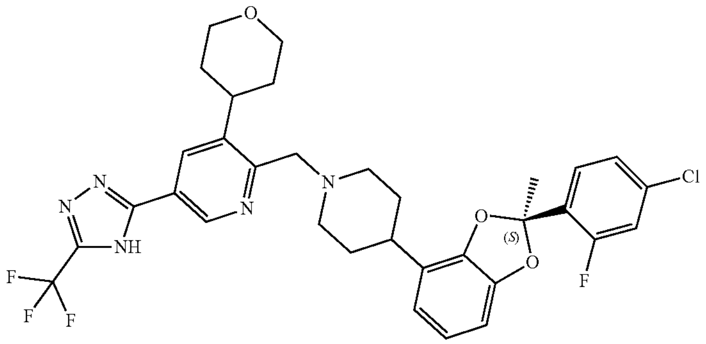 |
| 273 | 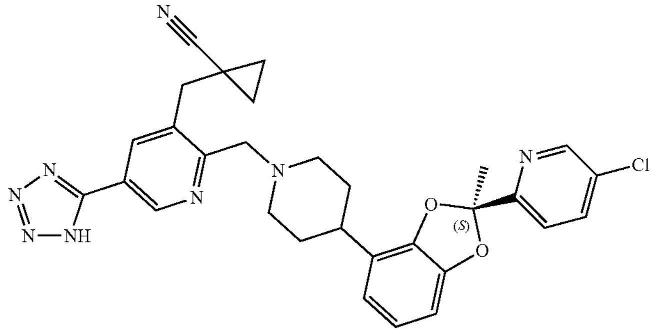 |
| 274 | 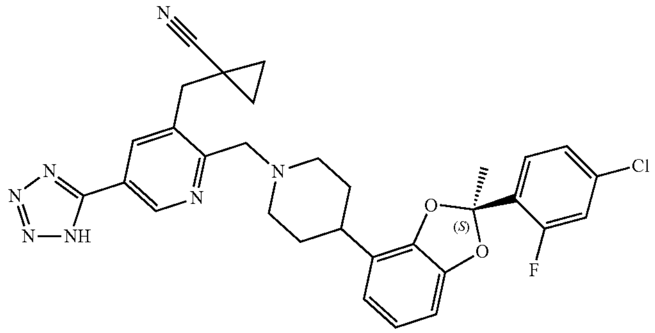 |
| 275 | 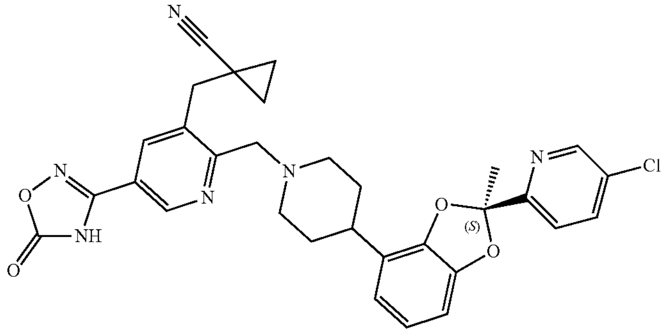 |

TABLE C1-continued
| Compound No. | Structure |
| --- | --- |
| 276 | 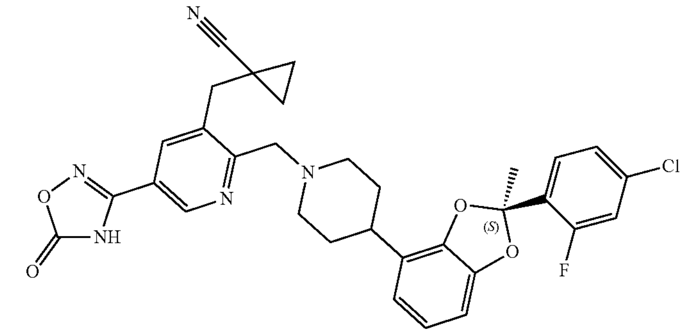 |
| 277 | 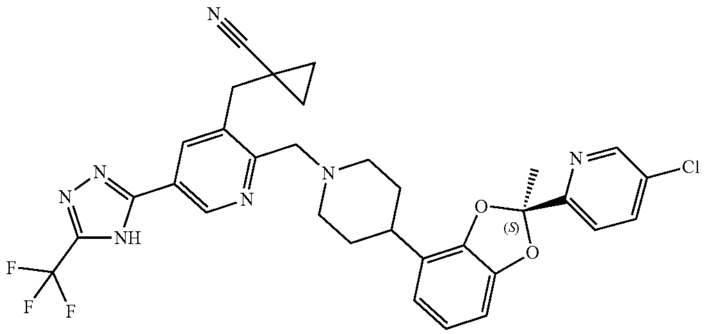 |
| 278 | 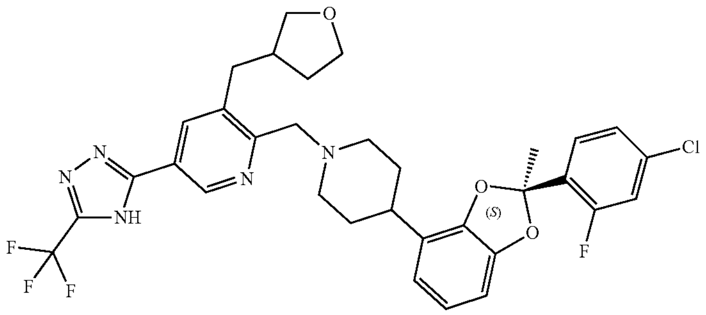 |
| 279 | 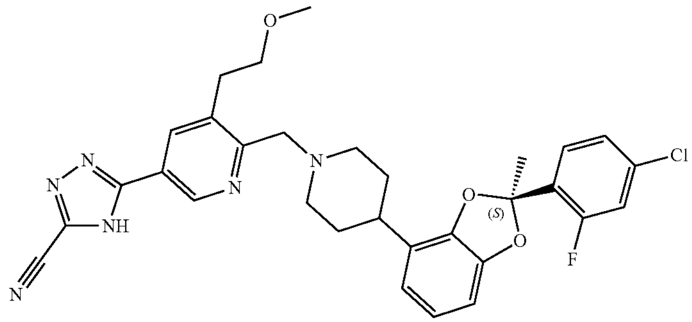 |
| 280 | 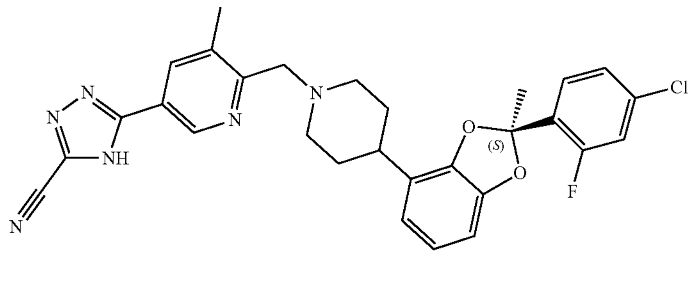 |

TABLE C1-continued
| Compound No. | Structure |
| --- | --- |
| 281 | 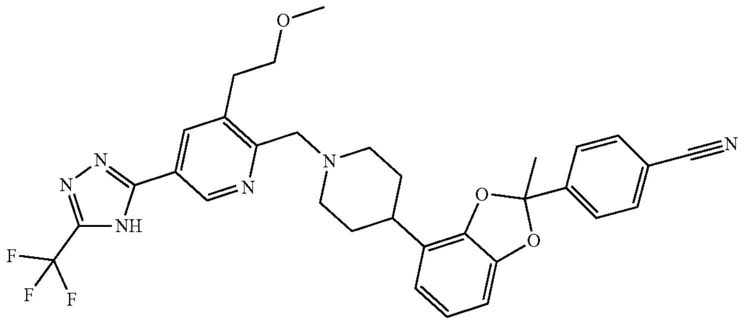 [SMILES: COCCc1cc(-c2nnc(C(F)(F)F)[nH]2)cnc1CN1CCC(c2cccc3c2OC(C)(c2ccc(C#N)cc2)O3)CC1] |
| 282 | 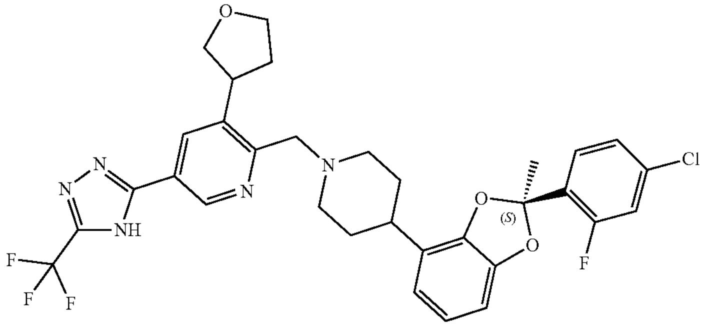 |
| 283 | 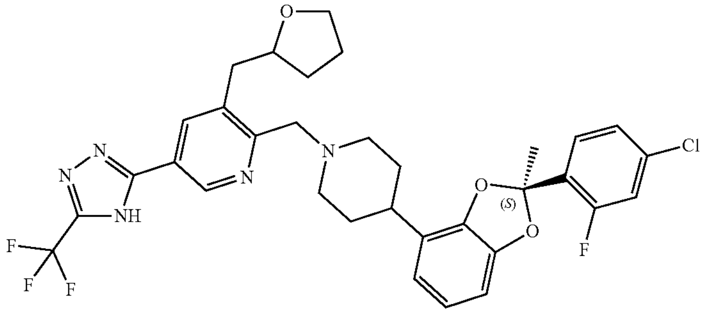 |
| 284 | 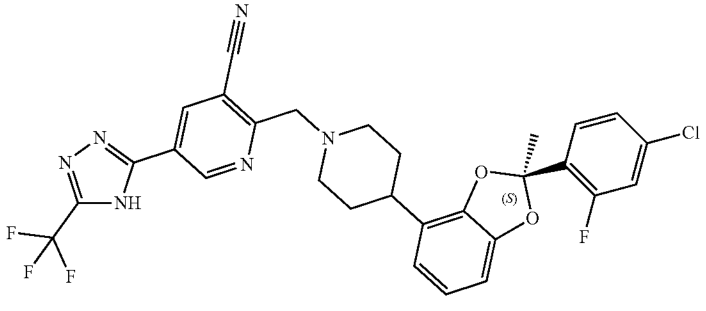 |

TABLE C1-continued
| Compound No. | Structure |
|---|---|
| 285 | 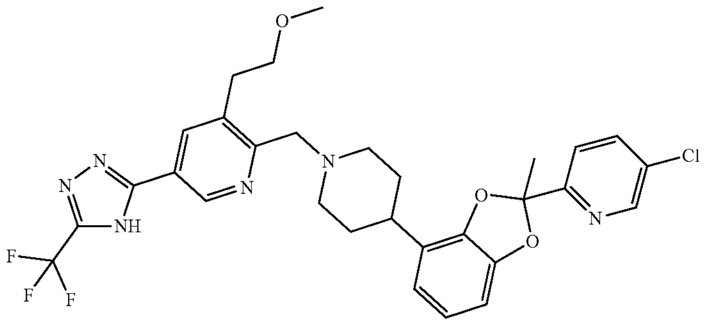 [SMILES: COCCc1cc(-c2nnc(C(F)(F)F)[nH]2)cnc1CN1CCC(c2cccc3c2OC(C)(c2ccc(Cl)cn2)O3)CC1] |
| 286 | 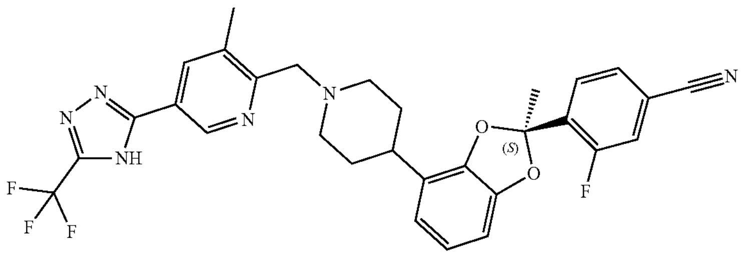 |
| 287 | 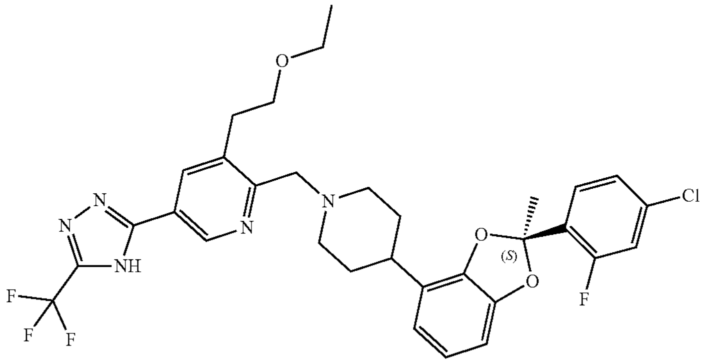 |
| 288 | 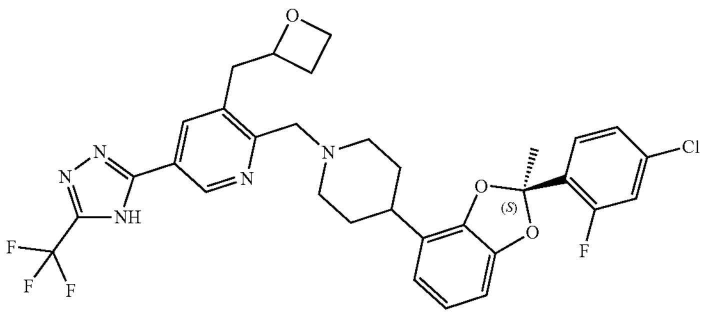 |

TABLE C1-continued

| Compound No. | Structure |
|---|---|
| 289 | 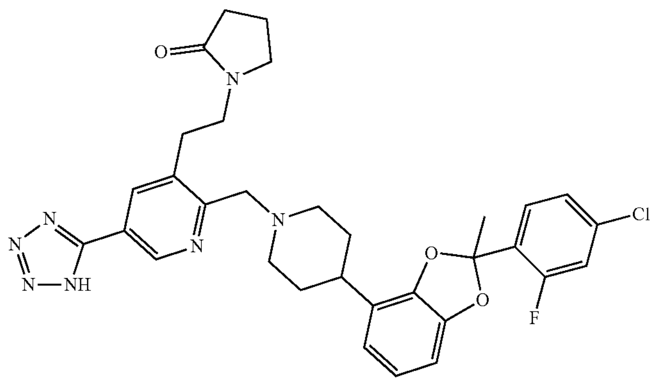 [SMILES: CC1(c2ccc(Cl)cc2F)Oc2cccc(C3CCN(Cc4ncc(-c5nnn[nH]5)cc4CCN4CCCC4=O)CC3)c2O1] |
| 290 | 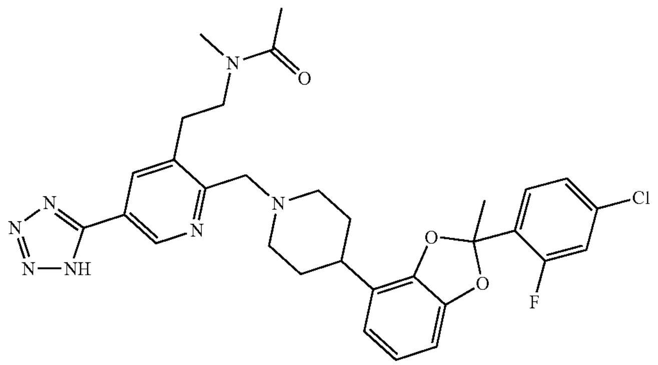 [SMILES: CC(=O)N(C)CCc1cc(-c2nnn[nH]2)cnc1CN1CCC(c2cccc3c2OC(C)(c2ccc(Cl)cc2F)O3)CC1] |
| 291 | 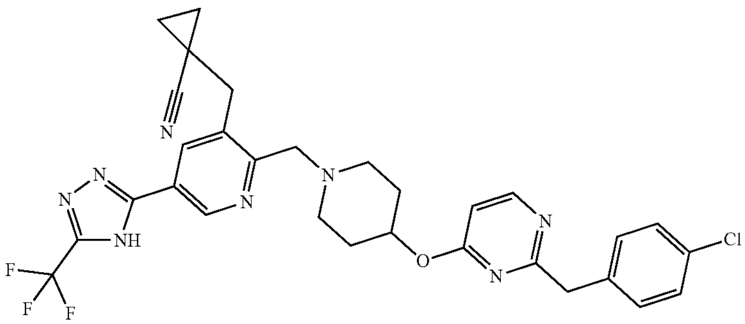 [SMILES: N#CC1(Cc2cc(-c3nnc(C(F)(F)F)[nH]3)cnc2CN2CCC(Oc3ccnc(Cc4ccc(Cl)cc4)n3)CC2)CC1] |
| 292 | 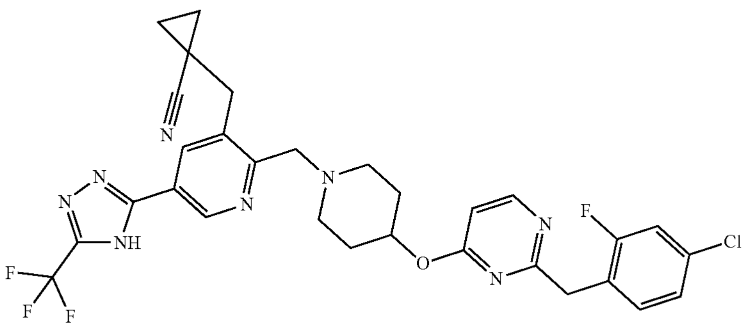 [SMILES: N#CC1(Cc2cc(-c3nnc(C(F)(F)F)[nH]3)cnc2CN2CCC(Oc3ccnc(Cc4ccc(Cl)cc4F)n3)CC2)CC1] |

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of pharmaceutically acceptable salts of compounds of Formula I include trifluoroacetic acid salts.

It will further be appreciated that the compounds of Formula I or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

Pharmaceutical Compositions and Administration

When employed as pharmaceuticals, the compounds of Formula I, including pharmaceutically acceptable salts or solvates thereof can be administered in the form of a pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula I, or a pharmaceutically acceptable salt or solvate thereof, in combination with one or more pharmaceutically acceptable excipients (carriers). For example, a pharmaceutical composition prepared using a compound of Formula I, or a pharmaceutically acceptable salt or solvate thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula I, or a pharmaceutically acceptable salt or solvate thereof with a pharmaceutically acceptable excipient. Pharmaceutical compositions containing a compound of Formula I, or a pharmaceutically acceptable salt or solvate thereof as the active ingredient can be prepared by intimately mixing the compound of Formula I, or a pharmaceutically acceptable salt or solvate thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In some embodiments, the compound or pharmaceutical composition can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, $22^{nd}$ Edition (Pharmaceutical Press, London, U K. 2012).

In some embodiments, the compounds and pharmaceutical compositions described herein or a pharmaceutical composition thereof can be administered to patient in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal (e.g., intranasal), nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In some embodiments, a preferred route of administration is parenteral (e.g., intratumoral).

In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B1), or (I-A5), (I-A6), (I-A7), (I-A8), and (I-B2), or a pharmaceutically acceptable salt or solvate thereof) as described herein or pharmaceutical compositions thereof can be formulated for parenteral administration, e.g., formulated for injection via the intraarterial, intrasternal, intracranial, intravenous, intramuscular, subcutaneous, or intraperitoneal routes. For example, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure. In some embodiments, devices are used for parenteral administration. For example, such devices may include needle injectors, microneedle injectors, needle-free injectors, and infusion techniques.

In some embodiments, the pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In some embodiments, the form must be sterile and must be fluid to the extent that it may be easily injected. In some embodiments, the form should be stable under the conditions of manufacture and storage and must be preserved against the contaminating action of microorganisms, such as bacteria and fungi.

In some embodiments, the carrier also can be a solvent or dispersion medium containing, for example, water, ethanol, polyol (for example, glycerol, propylene glycol, and liquid polyethylene glycol, and the like), suitable mixtures thereof, and vegetable oils. In some embodiments, the proper fluidity can be maintained, for example, by the use of a coating, such as lecithin, by the maintenance of the required particle size in the case of dispersion, and by the use of surfactants. In some embodiments, the prevention of the action of microorganisms can be brought about by various antibacterial and antifungal agents, for example, parabens, chlorobutanol, phenol, sorbic acid, thimerosal, and the like. In some embodiments, isotonic agents, for example, sugars or sodium chloride are included. In some embodiments, prolonged absorption of the injectable compositions can be brought about by the use in the compositions of agents delaying absorption, for example, aluminum monostearate and gelatin.

In some embodiments, sterile injectable solutions are prepared by incorporating a compound of Formula I, or a pharmaceutically acceptable salt or solvate thereof (e.g., a compound of any one of Formulas (I-A1), (I-A2), (I-A3), (I-A4), (I-A4-1), and (I-B1), or (I-A5), (I-A6), (I-A7), (I-A8), and (I-B2), or a pharmaceutically acceptable salt or solvate thereof) in the required amount in the appropriate solvent with various of the other ingredients enumerated above, as required, followed by filtered sterilization. In some embodiments, dispersions are prepared by incorporating the various sterilized active ingredients into a sterile vehicle which contains the basic dispersion medium and the required other ingredients from those enumerated above. In some embodiments, sterile powders are used for the preparation of sterile injectable solutions. In some embodiments, the methods of preparation are vacuum-drying and freeze-drying techniques, which yield a powder of the active ingredient, plus any additional desired ingredient from a previously sterile-filtered solution thereof.

In some embodiments, pharmacologically acceptable excipients usable in a rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol, Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In some embodiments, suppositories can be prepared by mixing a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof) or pharmaceutical compositions as described herein with suitable non-irritating excipients or carriers such as cocoa butter, polyethylene glycol or a suppository wax which are solid at ambient temperature but liquid at body temperature and therefore melt in the rectum and release the active compound. In some embodiments, compositions for rectal administration are in the form of an enema.

In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof) as described herein or a pharmaceutical composition thereof is formulated for local delivery to the digestive or GI tract by way of oral administration (e.g., solid or liquid dosage forms.).

In some embodiments, solid dosage forms for oral administration include capsules, tablets, pills, powders, and granules. In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof) is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For example, in the case of capsules, tablets and pills, the dosage form may also comprise buffering agents. In some embodiments, solid compositions of a similar type may also be employed as fillers in soft and hard-filled gelatin capsules using such excipients as lactose or milk sugar as well as high molecular weight polyethylene glycols and the like.

In some embodiments, the pharmaceutical compositions will take the form of a unit dosage form such as a pill or tablet and thus the composition may contain, along with a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof) as provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In some embodiments, another solid dosage form, a powder, marume, solution or suspension (e.g., in propylene carbonate, vegetable oils, PEG's, poloxamer 124 or triglycerides) is encapsulated in a capsule (gelatin or cellulose base capsule). In some embodiments, unit dosage forms in which one or more compounds and pharmaceutical compositions as provided herein or additional active agents are physically separated are also contemplated; e.g., capsules with granules (or tablets in a capsule) of each drug; two-layer tablets; two-compartment gel caps, etc. In some embodiments, enteric coated or delayed release oral dosage forms are also contemplated.

In some embodiments, other physiologically acceptable compounds may include wetting agents, emulsifying agents, dispersing agents or preservatives that are particularly useful for preventing the growth or action of microorganisms. For example, various preservatives are well known and include, for example, phenol and ascorbic acid.

In some embodiments, the excipients are sterile and generally free of undesirable matter. For example, these compositions can be sterilized by conventional, well-known sterilization techniques. In some embodiments, for various oral dosage form excipients such as tablets and capsules, sterility is not required. For example, the United States Pharmacopeia/National Formulary (USP/NF) standard can be sufficient.

In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof) as described herein or a pharmaceutical composition thereof is formulated for ocular administration. In some embodiments, ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof) as described herein or a pharmaceutical composition thereof is formulated for topical administration to the skin or mucosa (e.g., dermally or transdermally). In some embodiments, topical compositions can include ointments and creams. In some embodiments, ointments are semisolid preparations that are typically based on petrolatum or other petroleum derivatives. In some embodiments, creams containing the selected active agent are typically viscous liquid or semisolid emulsions, often either oil-in-water or water-in-oil. For example, cream bases are typically water-washable, and contain an oil phase, an emulsifier and an aqueous phase. For example, the oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. In some embodiments, the emulsifier in a cream formulation is generally a nonionic, anionic, cationic or amphoteric surfactant. In some embodiments, as with other carriers or vehicles, an ointment base should be inert, stable, nonirritating and non-sensitizing.

In any of the foregoing embodiments, pharmaceutical compositions as described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

In some embodiments, the dosage for a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof), is determined based on a multiple factors including, but not limited to, type, age, weight, sex, medical condition of the patient, severity of the medical condition of the patient, route of administration, and activity of the compound or pharmaceutically acceptable salt or solvate thereof. In some embodiments, proper dosage for a particular situation can be determined by one skilled in the medical arts. In some embodiments, the total daily dosage may be divided and administered in portions throughout the day or by means providing continuous delivery.

In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof), is administered at a dose from about 0.01 to about 1000 mg. For example, from about 0.1 to about 30 mg, about 10 to about 80 mg, about 0.5 to about 15 mg, about 50 mg to about 200 mg, about 100 mg to about 300 mg, about 200 to about 400 mg, about 300 mg to about 500 mg, about 400 mg to about 600 mg, about 500 mg to about 800 mg, about 600 mg to about 900 mg, or about 700 mg to about 1000 mg. In some embodiments, the dose is a therapeutically effective amount.

In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof) as described herein is administered at a dosage of from about 0.0002 mg/Kg to about 100 mg/Kg (e.g., from about 0.0002 mg/Kg to about 50 mg/Kg; from about 0.0002 mg/Kg to about 25 mg/Kg; from about 0.0002 mg/Kg to about 10 mg/Kg; from about 0.0002 mg/Kg to about 5 mg/Kg; from about 0.0002 mg/Kg to about 1 mg/Kg; from about 0.0002 mg/Kg to about 0.5 mg/Kg; from about 0.0002 mg/Kg to about 0.1 mg/Kg; from about 0.001 mg/Kg to about 50 mg/Kg; from about 0.001 mg/Kg to about 25 mg/Kg; from about 0.001 mg/Kg to about 10 mg/Kg; from about 0.001 mg/Kg to about 5 mg/Kg; from about 0.001 mg/Kg to about 1 mg/Kg; from about 0.001 mg/Kg to about 0.5 mg/Kg; from about 0.001 mg/Kg to about 0.1 mg/Kg; from about 0.01 mg/Kg to about 50 mg/Kg; from about 0.01 mg/Kg to about 25 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 50 mg/Kg; from about 0.1 mg/Kg to about 25 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg). In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B1), or (I-A5), (I-A6), (I-A7), (I-A8), and (I-B2), or a pharmaceutically acceptable salt or solvate thereof) as described herein is administered as a dosage of about 100 mg/Kg.

In some embodiments, the foregoing dosages of a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof), can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof) as described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof) is administered to a patient for a period of time followed by a separate period of time where administration of the compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof) is stopped. In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B1), or (I-A5), (I-A6), (I-A7), (I-A8), and (I-B2), or a pharmaceutically acceptable salt or solvate thereof) is administered for a first period and a second period following the first period, with administration stopped during the second period, followed by a third period where administration of the compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof) is started and then a fourth period following the third period where administration is stopped. For example, the period of administration of a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof) followed by a period where administration is stopped is repeated for a determined or undetermined period of time. In some embodiments, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof), is orally administered to the patient one or more times per day (e.g., one time per day, two times per day, three times per day, four times per day per day or a single daily dose).

In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B1), or (I-A5), (I-A6), (I-A7), (I-A8), and (I-B2), or a pharmaceutically acceptable salt or solvate thereof), is administered by parenteral administration to the patient one or more times per day (e.g., 1 to 4 times one time per day, two times per day, three times per day, four times per day or a single daily dose).

In some embodiments, a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof), is administered by parenteral administration to the patient weekly.

Methods of Treatment

In some embodiments, this disclosure features methods for treating a patient (e.g., a human) having a disease, disorder, or condition in which modulation of GLP-1R (e.g., repressed or impaired and/or elevated or unwanted GLP-1R) is beneficial for the treatment of the underlying pathology and/or symptoms and/or progression of the disease, disorder, or condition. In some embodiments, the methods described herein can include or further include treating one or more conditions associated, co-morbid or sequela with any one or more of the conditions described herein.

Provided herein is a method for treating a GLP-1 associated disease, disorder, or condition, the method comprising administering to a patient in need thereof an effective amount of a compound of Formula I, or a pharmaceutically acceptable salt or solvate thereof (e.g., a compound of any one of Formulas (I-A1), (I-A2), (I-A3), (I-A4), (I-A4-1), and (I-B1), or (I-A5), (I-A6), (I-A7), (I-A8), and (I-B2), or a pharmaceutically acceptable salt or solvate thereof), or a pharmaceutical composition as disclosed herein.

In some embodiments, the disease, disorder, or condition includes, but is not limited to type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity (including hypothalamic obesity and monogenic obesity), weight gain from use of other agents, idiopathic intracranial hypertension, Wolfram syndrome, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, and Polycystic Ovary Syndrome (PCOS).

In some embodiments, the disease, disorder, or condition includes, but is not limited to type 2 diabetes mellitus, early onset type 2 diabetes mellitus, obesity, idiopathic intracranial hypertension, Wolfram syndrome, weight gain from use of other agents, gout, excessive sugar craving, hypertriglyceridemia, dyslipidemia, gestational diabetes, kidney disease (e.g., acute kidney disorder, tubular dysfunction, proinflammatory changes to the proximal tubules), adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), non alcoholic fatty liver disease (NAFLD), short bowel syndrome, Parkinson's disease, Polycystic Ovary Syndrome (PCOS), or any combination thereof.

In some embodiments, the disease, disorder, or condition includes, but is not limited to, type 2 diabetes mellitus, early onset type 2 diabetes mellitus, obesity, idiopathic intracranial hypertension, Wolfram syndrome, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

In some embodiments, the compounds and pharmaceutical compositions and methods for treating a patient described herein induce one or more of a reduction of blood glucose levels (e.g., reduce blood glucose levels), a reduction of blood hemoglobin A1c (HbA1c) levels, a promotion of insulin synthesis, a stimulation of insulin secretion, an increase in the mass of β-cells, a modulation of gastric acid secretion, a modulation of gastric emptying, a decrease in the body mass index (BMI), and/or a decrease in glucagon production (e.g., level). In some embodiments, the compounds and pharmaceutical compositions and methods for treating a patient described herein can reduce blood glucose levels, reduce blood hemoglobin A1c (HbA1c) levels, promote insulin synthesis, stimulate insulin secretion, increase the mass of β-cells, modulate gastric acid secretion, modulate gastric emptying, decrease the body mass index (BMI), decrease glucagon production (e.g., level), or any combination thereof. In certain embodiments, the compounds and pharmaceutical compositions and methods for treating a patient described herein stabilize serum glucose and serum insulin levels (e.g., serum glucose and serum insulin concentrations). Also provided herein are methods for modulating glucose or insulin levels in a patient in need of such modulating, the method comprising administering to the patient an effective amount of a compound of Formula I, or a pharmaceutically acceptable salt or solvate thereof (e.g., a compound of any one of Formulas (I-A1), (I-A2), (I-A3), (I-A4), (I-A4-1), and (I-B1), or (I-A5), (I-A6), (I-A7), (I-A8), and (I-B2), or a pharmaceutically acceptable salt or solvate thereof), or a pharmaceutical composition as disclosed herein.

In some embodiments, provided herein is a method for reducing the risk (e.g., by about at least 20%, at least 30%, at least 40%, at least 50%, at least 60%, at least 70%, or at least 80%) of major adverse cardiovascular events (MACE) in a patient in need thereof, the method comprising administering to the patient an effective amount of a compound of Formula I, or a pharmaceutically acceptable salt or solvate thereof (e.g., a compound of any one of Formulas (I-A1), (I-A2), (I-A3), (I-A4), (I-A4-1), and (I-B), or (I-A5), (I-A6), (I-A7), (I-A8), and (I-B2), or a pharmaceutically acceptable salt or solvate thereof), or a pharmaceutical composition as disclosed herein. In certain of these embodiments, the patient is an adult that has been diagnosed with type 2 diabetes (T2D). In certain embodiments, the patient is an adult that has been diagnosed with a heart disease. In certain embodiments, the patient is an adult that has been diagnosed with type 2 diabetes (T2D) and a heart disease. In certain embodiments, the patient is an adult that has type 2 diabetes (T2D). In certain embodiments, the patient is an adult that has a heart disease. In certain embodiments, the patient has type 2 diabetes (T2D) and a heart disease.

Indications

Obesity

In some embodiments, the condition, disease or disorder is obesity and conditions, diseases or disorders that are associated with or related to obesity. Non-limiting examples of obesity and obesity related conditions include symptomatic obesity, simple obesity, childhood obesity, morbid obesity, and abdominal obesity (central obesity characterized by abdominal adiposity). Non-limiting examples of symptomatic obesity include endocrine obesity (e.g., Cushing syndrome, hypothyroidism, insulinoma, obese type II diabetes, pseudohypoparathyroidism, hypogonadism), hypothalamic obesity, hereditary obesity (e.g., Prader-Willi syndrome, Laurence-Moon-Biedl syndrome), and drug-induced obesity (e.g., steroid, phenothiazine, insulin, sulfonylurea agent, or β-blocker-induced obesity).

In some embodiments, the condition, disease or disorder is associated with obesity. Examples of such conditions, diseases or disorders include, without limitation, glucose tolerance disorders, diabetes (e.g., type 2 diabetes, obese diabetes), lipid metabolism abnormality, hyperlipidemia, hypertension, cardiac failure, hyperuricemia, gout, fatty liver (including non-alcoholic steatohepatitis (NASH)), coronary heart disease (e.g., myocardial infarction, angina pectoris), cerebral infarction (e.g., brain thrombosis, transient cerebral ischemic attack), bone or articular disease (e.g., knee osteoarthritis, hip osteoarthritis, spondylitis deformans, lumbago), sleep apnea syndrome, obesity hypoventilation syndrome (Pickwickian syndrome), menstrual disorder (e.g., abnormal menstrual cycle, abnormality of menstrual flow and cycle, amenorrhea, abnormal catamenial symptom), visceral obesity syndrome, urine incontinence, and metabolic syndrome. In some embodiments, the chemical compound and pharmaceutical compositions described herein can be used to treat patients exhibiting symptoms of both obesity and insulin deficiency.

Diabetes

In some embodiments, the condition, disease or disorder is diabetes. Non-limiting examples of diabetes include type 1 diabetes mellitus, type 2 diabetes mellitus (e.g., diet-treated type 2-diabetes, sulfonylurea-treated type 2-diabetes, a far-advanced stage type 2-diabetes, long-term insulin-treated type 2-diabetes), diabetes mellitus (e.g., non-insulin-dependent diabetes mellitus, insulin-dependent diabetes mellitus), gestational diabetes, obese diabetes, autoimmune diabetes, and borderline type diabetes. In some embodiments, the condition, disease or disorder is type 2 diabetes mellitus (e.g., diet-treated type 2-diabetes, sulfonylurea-treated type 2-diabetes, a far-advanced stage type 2-diabetes, long-term insulin-treated type 2-diabetes).

Provided herein is a method of treating a diabetes mellitus in a patient, the method comprising (a) determining that the patient has type 2 diabetes mellitus, and (b) administering to the patient a therapeutically effective amount of a compound of Formula I, or a pharmaceutically acceptable salt or solvate thereof (e.g., a compound of any one of a compound of any one of Formulas (I-A1), (I-A2), (I-A3), (I-A4), (I-A4-1), and (I-B1), or (I-A5), (I-A6), (I-A7), (I-A8), and (I-B2), or a pharmaceutically acceptable salt or solvate thereof, or a pharmaceutically acceptable salt or solvate thereof) or a pharmaceutical composition as disclosed herein.

Provided herein is a method for treating type 2 diabetes mellitus in a patient, the method comprising administering to a patient identified or diagnosed as having type 2 diabetes mellitus a therapeutically effective amount of a compound of Formula I, or a pharmaceutically acceptable salt or solvate thereof (e.g., a compound of any one of a compound of any one of Formulas (I-A1), (I-A2), (I-A3), (I-A4), (I-A4-1), and (I-B1), or (I-A5), (I-A6), (I-A7), (I-A8), and (I-B2), or a pharmaceutically acceptable salt or solvate thereof, or a pharmaceutically acceptable salt or solvate thereof), or a pharmaceutical composition as disclosed herein.

Also provided herein is a method of treating type 2 diabetes mellitus in a patient in need thereof, the method comprising administering to the patient a therapeutically effective amount of a compound of Formula I, or a pharmaceutically acceptable salt or solvate thereof (e.g., a compound of any one of a compound of any one of Formulas (I-A1), (I-A2), (I-A3), (I-A4), (I-A4-1), and (I-B1), or (I-A5), (I-A6), (I-A7), (I-A8), and (I-B2), or a pharmaceutically acceptable salt or solvate thereof, or a pharmaceutically acceptable salt or solvate thereof), or a pharmaceutical composition as disclosed herein.

In some embodiments, the compounds and pharmaceutical compositions and methods for treating a patient with a condition, disease, or disorder (e.g., type 2 diabetes mellitus) described herein reduce fasting plasma glucose levels. In some embodiments, the compounds and pharmaceutical compositions and methods for treating a patient with a condition, disease, or disorder (e.g., type 2 diabetes mellitus) described herein reduce non-fasting plasma glucose levels. In some embodiments, the compounds and pharmaceutical compositions and methods for treating a patient with a condition, disease, or disorder (e.g., type 2 diabetes mellitus) described herein reduce HbA1c levels. In some embodiments, the compounds and pharmaceutical compositions and methods for treating a patient with a condition, disease, or disorder (e.g., type 2 diabetes mellitus) described herein reduce glucagon levels. In some embodiments, the compounds and pharmaceutical compositions and methods for treating a patient with a condition, disease, or disorder (e.g., type 2 diabetes mellitus) described herein increase insulin levels. In some embodiments, the compounds and pharmaceutical compositions and methods for treating a patient with a condition, disease, or disorder (e.g., type 2 diabetes mellitus) described herein reduce BMI.

In some embodiments, a reduction in fasting plasma glucose levels of about 5% to about 95% indicates treatment of type 2 diabetes mellitus. In some embodiments, a reduction in fasting plasma glucose levels of about 15% to about 80% indicates treatment of type 2 diabetes mellitus. In some embodiments, a reduction in fasting plasma glucose levels of about 25% to about 60% indicates treatment of type 2 diabetes mellitus. In some embodiments, a reduction in fasting plasma glucose levels to about or below 126 mg/dL, about or below 110 mg/dL, or about or below 90 mg/dL indicates treatment of the type 2 diabetes mellitus.

In some embodiments, a reduction in non-fasting plasma glucose levels of about 5% to about 95% indicates treatment of type 2 diabetes mellitus. In some embodiments, a reduction in non-fasting plasma glucose levels of about 15% to about 80% indicates treatment of type 2 diabetes mellitus. In some embodiments, a reduction in non-fasting plasma glucose levels of about 25% to about 60% indicates treatment of type 2 diabetes mellitus. In some embodiments, a reduction in non-fasting plasma glucose levels to about or below 200 mg/dL, about or below 150 mg/dL, or about or below 130 mg/dL indicates treatment of type 2 diabetes mellitus.

In some embodiments, a reduction in HbA1c levels of about 5% to about 95% indicates treatment of type 2 diabetes mellitus. In some embodiments, a reduction in HbA1c levels of about 15% to about 80% indicates treatment of type 2 diabetes mellitus. In some embodiments, a reduction in HbA1c levels of about 25% to about 60% indicates treatment of type 2 diabetes mellitus. In some embodiments, reduction in HbA1c levels to about or below 6.5%, about or below 6.0%, or about or below 5.0% indicates treatment of type 2 diabetes mellitus.

In some embodiments, a reduction in glucagon levels of about 5% to about 95% indicates treatment of type 2 diabetes mellitus. In some embodiments, a reduction in glucagon levels of about 15% to about 80% indicates treatment of type 2 diabetes mellitus. In some embodiments, a reduction in glucagon levels of about 25% to about 60% indicates treatment of type 2 diabetes mellitus. In some embodiments, an increase in insulin levels of about 5% to about 95% indicates treatment of type 2 diabetes mellitus. In some embodiments, an increase in insulin levels of about 15% to about 80% indicates treatment of type 2 diabetes mellitus. In some embodiments, an increase in insulin levels of about 25% to about 60% indicates treatment of type 2 diabetes mellitus.

In some embodiments, a reduction in BMI of about 5% to about 95% indicates treatment of type 2 diabetes mellitus. In some embodiments, a reduction in BMI of about 15% to about 80% indicates treatment of the type 2 diabetes mellitus. In some embodiments, a reduction in BMI of about 25% to about 60% indicates treatment of type 2 diabetes mellitus. In some embodiments, a reduction in BMI of about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% indicates treatment of type 2 diabetes mellitus. In some embodiments, a reduction in BMI to about or below 40, about or below 30, or about or below 20 indicates treatment of type 2 diabetes mellitus.

In some embodiments, the condition, disease or disorder is associated with diabetes (e.g., a complication of diabetes). Non-limiting examples of disorders associated with diabetes include obesity, obesity-related disorders, metabolic syndrome, neuropathy, nephropathy (e.g., diabetic nephropathy), retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, diabetic cachexia, delayed wound healing, diabetic dyslipidemia peripheral blood circulation disorder, cardiovascular risk factors. (e.g., coronary artery disease, peripheral artery disease, cerebrovascular disease, hypertension, and risk factors related to unmanaged cholesterol and/or lipid levels, and/or inflammation), NASH, bone fracture, and cognitive dysfunction Other non-limiting examples of disorders related to diabetes include pre-diabetes, hyperlipidemia (e.g., hypertriglyceridemia, hypercholesterolemia, high LDL-cholesterolemia, low HDL-cholesterolemia, postprandial hyperlipemia), metabolic syndrome (e.g., metabolic disorder where activation of GLP-1R is beneficial, metabolic syndrome X), hypertension, impaired glucose tolerance (IGT), insulin resistance, and sarcopenia.

In some embodiments, the condition, disease or disorder is diabetes and obesity (diabesity). In some embodiments, the compounds described herein are useful in improving the therapeutic effectiveness of metformin.

Disorders of Metabolically Important Tissues

In some embodiments, the condition, disease or disorder is a disorder of a metabolically important tissue. Non-limiting examples of metabolically important tissues include liver, fat, pancreas, kidney, and gut.

In some embodiments, the condition, disease or disorder is a fatty liver disease. Fatty liver diseases include, but are not limited to, non-alcoholic fatty acid liver disease (NAFLD), steatohepatitis, non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, hyperlipoproteinemia, glycogen storage diseases, Weber-Christian disease, Wolman disease, acute fatty liver of pregnancy, and lipodystrophy.

Non-alcoholic fatty liver disease (NAFLD) represents a spectrum of disease occurring in the absence of alcohol abuse and is typically characterized by the presence of steatosis (fat in the liver). NAFLD is believed to be linked to a variety of conditions, e.g., metabolic syndrome (including obesity, diabetes and hypertriglyceridemia) and insulin resistance. It can cause liver disease in adults and children and can ultimately lead to cirrhosis (Skelly et al., *J Hepatol* 2001; 35: 195-9; Chitturi et al., Hepatology 2002; 35(2): 373-9). The severity of NAFLD ranges from the relatively benign isolated predominantly macrovesicular steatosis (i.e., nonalcoholic fatty liver or NAFL) to non alcoholic steatohepatitis (NASH) (Angulo et al., *J Gastroenterol Hepatol* 2002; 17 Suppl: S186-90).

Other non-limiting examples of disorders in metabolically important tissues include joint disorders (e.g., osteoarthritis, secondary osteoarthritis), steatosis (e.g., in the liver); fibrosis (e.g., in the liver); cirrhosis (e.g., in the liver); gall stones; gallbladder disorders; gastroesophageal reflux; sleep apnea; hepatitis; fatty liver; bone disorder characterized by altered bone metabolism, such as osteoporosis, including post menopausal osteoporosis, poor bone strength, osteopenia, Paget's disease, osteolytic metastasis in cancer patients, osteodistrophy in liver disease and the altered bone metabolism caused by renal failure or haemodialysis, bone fracture, bone surgery, aging, pregnancy, protection against bone fractures, and malnutritionpolycystic ovary syndrome; renal disease (e.g., chronic renal failure, glomerulonephritis, glomerulosclerosis, nephrotic syndrome, hypertensive nephrosclerosis, end-stage renal disease); muscular dystrophy, angina pectoris, acute or chronic diarrhea, testicular dysfunction, respiratory dysfunction, frailty, sexual dysfunction (e.g., erectile dysfunction), and geriatric syndrome. In some embodiments, the compounds and pharmaceutical compositions described herein can be used for treating surgical trauma by improving recovery after surgery and/or by preventing the catabolic reaction caused by surgical trauma.

Cardiovascular and Vascular Diseases

In some embodiments, the condition, disease or disorder is a cardiovascular disease. Non-limiting examples of cardiovascular disease include congestive heart failure, atherosclerosis, arteriosclerosis, coronary heart disease, coronary artery disease, congestive heart failure, coronary heart disease, hypertension, cardiac failure, cerebrovascular disorder (e.g., cerebral infarction), vascular dysfunction, myocardial infarction, elevated blood pressure (e.g., 130/85 mm Hg or higher), and prothrombotic state (exemplified by high fibrinogen or plasminogen activator inhibitor in the blood).

In some embodiments, the condition, disease or disorder is related to a vascular disease. Non-limiting examples of vascular diseases include peripheral vascular disease, macrovascular complications (e.g., stroke), vascular dysfunction, peripheral artery disease, abdominal aortic aneurysm, carotid artery disease, cerebrovascular disorder (e.g., cerebral infarction), pulmonary embolism, chronic venous insufficiency, critical limb ischemia, retinopathy, nephropathy, and neuropathy.

Neurological Diseases

In some embodiments, the condition, disease or disorder is a neurological disorder (e.g., neurodegenerative disorder) or a psychiatric disorder. Non-limiting examples of neurological disorders include idiopathic intracranial hypertension (IIH), brain insulin resistance, mild cognitive impairment (MCI), Alzheimer's disease (AD), Parkinson's disease (PD), anxiety, dementia (e.g., senile dementia), traumatic brain injury, Huntington's chores, tardive dyskinesia, hyperkinesia, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis (ALS), glaucoma, and apoptosis-mediated degenerative diseases of the central nervous system (e.g., Creutzfeld-Jakob Disease, bovine spongiform encephalopathy (mad cow disease), and chronic wasting syndrome). See, e.g., U.S. Publication No. 20060275288A1.

In some embodiments, the condition, disease or disorder is idiopathic intracranial hypertension. Idiopathic intracranial hypertension is characterized by increased intracranial pressure and papilloedema. See, e.g., Virdee et al. *Ophthalmol Ther.* 2020; 9(4):767-781. In some embodiments, the compounds and pharmaceutical compositions and methods described herein reduce cerebrospinal fluid secretion in a patient with idiopathic intracranial hypertension. In some embodiments, the compounds and pharmaceutical compositions and methods described herein reduce intracranial pressure in a patient with idiopathic intracranial hypertension. In some embodiments, the compounds and pharmaceutical compositions and methods described herein reduce one or more symptoms in a patient with idiopathic intracranial hypertension. Symptoms of idiopathic intracranial hypertension can include severe headaches and visual impairment. In some embodiments, the patient with idiopathic intracranial hypertension is female. In some embodiments, the patient with idiopathic intracranial hypertension is about 20 to about 30 years old. In some embodiments, the patient with idiopathic intracranial hypertension is obese.

In some embodiments, the condition, disease or disorder is Wolfram syndrome. Wolfram syndrome is caused by biallelic mutations of the Wolframin ER transmembrane glycoprotein (Wfsl) gene. See, e.g., Seppa et al. *Sci Rep* 9, 15742 (2019). Wolfram syndrome can first appear as diabetes mellitus, followed by optic nerve atrophy, deafness, and symptoms of neurodegeneration. Patients with Wolfram syndrome can have symptoms of ataxia, sleep apnea, dysphagia, hearing loss, and loss of taste due to brainstem atrophy. In some embodiments, the compounds and pharmaceutical compositions and methods described herein reduce neuroinflammation in a patient with Wolfram syndrome. In some embodiments, the neuroinflammation is reduced in the inferior olive in the patient. In some embodiments, the compounds and pharmaceutical compositions and methods described herein reduce retinal ganglion cell death in a patient with Wolfram syndrome. In some embodiments, the compounds and pharmaceutical compositions and methods described herein reduce axonal degeneration in a patient with Wolfram syndrome. In some embodiments, the compounds and pharmaceutical compositions and methods described herein reduce one or more symptoms (e.g., any of the symptoms described herein) in a patient with Wolfram syndrome.

Non-limiting examples of psychiatric disorders include drug dependence/addiction (narcotics and amphetamines and attention deficit/hyperactivity disorder (ADHD). The compounds and pharmaceutical compositions described herein can be useful in improving behavioral response to addictive drugs, decreasing drug dependence, prevention drug abuse relapse, and relieving anxiety caused by the absence of a given addictive substance. See, e.g., U.S. Publication No. 20120021979A1.

In some embodiments, the compounds and pharmaceutical compositions described herein are useful in improving learning and memory by enhancing neuronal plasticity and facilitation of cellular differentiation, and also in preserving dopamine neurons and motor function in Morbus Parkinson.

Insulin Related

In some embodiments, the condition, disease or disorder is impaired fasting glucose (IFG), impaired fasting glycemia (IFG), hyperglycemia, insulin resistance (impaired glucose homeostasis), hyperinsulinemia, elevated blood levels of fatty acids or glycerol, a hypoglycemic condition, insulin resistant syndrome, paresthesia caused by hyperinsulinemia, hyperlipidaemia, hypercholesteremia, impaired wound healing, leptin resistance, glucose intolerance, increased fasting glucose, dyslipidemia (e.g., hyperlipidemia, atherogenic dyslipidemia characterized by high triglycerides and low HDL cholesterol), glucagonoma, hyperuricacidemia, hypoglycemia (e.g., nighttime hypoglycemia), and concomitant comatose endpoint associated with insulin.

In some embodiments, the compounds and pharmaceutical compositions described herein can reduce or slow down the progression of borderline type, impaired fasting glucose or impaired fasting glycemia into diabetes.

Autoimmune Disorders

In some embodiments, the condition, disease or disorder is an autoimmune disorder. Non-limiting examples of autoimmune disorders include multiple sclerosis, experimental autoimmune encephalomyelitis, autoimmune disorder is associated with immune rejection, graft versus host disease, uveitis, optic neuropathies, optic neuritis, transverse myelitis, inflammatory bowel disease, rheumatoid arthritis, ankylosing spondylitis, systemic lupus erythematosus, myasthenia gravis, and Graves disease. See, e.g., U.S. Publication No. 20120148586A1.

Stomach and Intestine-Related Disorders

In some embodiments, the condition, disease or disorder is a stomach or intestine related disorder. Non-limiting examples of these disorders include ulcers of any etiology (e.g. peptic ulcers, Zollinger-Ellison syndrome, drug-induced ulcers, ulcers related to infections or other pathogens), digestion disorders, malabsorption, short bowel syndrome, cul-de-sac syndrome, inflammatory bowel diseases (Crohn's disease and ulcerative colitis), celiac sprue, hypogammaglobulinemic sprue, chemotherapy and/or radiation therapy-induced mucositis and diarrhea, gastrointestinal inflammation, short bowel syndrome, colitis ulcerosa, gastric mucosal injury (e.g., gastric mucosal injury caused by aspirin), small intestinal mucosal injury, and cachexia (e.g., cancerous cachexia, tuberculous cachexia, cachexia associated with blood disease, cachexia associated with endocrine disease, cachexia associated with infectious disease, and cachexia caused by acquired immunodeficiency syndrome).

Body Weight

In some embodiments, the compounds and pharmaceutical compositions described herein can be used to reduce body weight (e.g., excess body weight), prevent body weight gain, induce weight loss, decrease body fat, or reduce food intake in a patient (e.g., a patient in need thereof). In some embodiments, the weight increase in a patient may be attributed to excessive ingestion of food or unbalanced diets, or may be weight increase derived from a concomitant drug (e.g., insulin sensitizers having a PPARγ agonist-like action, such as troglitazone, rosiglitazone, englitazone, ciglitazone, pioglitazone and the like). In some embodiments, the weight increase may be weight increase before reaching obesity, or may be weight increase in an obese patient. In some embodiments, the weight increase may also be medication-induced weight gain or weight gain subsequent to cessation of smoking. In some embodiments, the weight gain is induced by the use of steroids or antipsychotics.

In some embodiments, the condition, disease or disorder is an eating disorder, such as hyperphagia, binge eating, bulimia, compulsive eating, or syndromic obesity such as Prader-Willi and Bardet-Biedl syndromes.

Inflammatory Diseases

In some embodiments, the condition, disease or disorder is an inflammatory disorder. Non-limiting examples of inflammatory disorders include chronic rheumatoid arthritis, spondylitis deformans, arthritis deformans, lumbago, gout, post-operational or post-traumatic inflammation, bloating, neuralgia, laryngopharyngitis, cystitis, pneumonia, pancreatitis, enteritis, inflammatory bowel disease (including inflammatory large bowel disease), inflammation in metabolically important tissues including liver, fat, pancreas, kidney and gut, and a proinflammatory state (e.g., elevated levels of proinflammatory cytokines or markers of inflammation-like C-reactive protein in the blood).

Cancer

In some embodiments, the condition, disease or disorder is cancer. Suitable examples of cancer include breast cancer (e.g., invasive ductal breast cancer, noninvasive ductal breast cancer, inflammatory breast cancer), prostate cancer (e.g., hormone-dependent prostate cancer, hormone-independent prostate cancer), pancreatic cancer (e.g., ductal pancreatic cancer), gastric cancer (e.g., papillary adenocarcinoma, mucous adenocarcinoma, adenosquamous carcinoma), lung cancer (e.g., non-small cell lung cancer, small-cell lung cancer, malignant mesothelioma), colon cancer (e.g., gastrointestinal stromal tumor), rectal cancer (e.g., gastrointestinal stromal tumor), colorectal cancer (e.g., familial colorectal cancer, hereditary non-polyposis colorectal cancer, gastrointestinal stromal tumor), small intestinal cancer (e.g., non-Hodgkin's lymphoma, gastrointestinal stromal tumor), esophageal cancer, duodenal cancer, tongue cancer, pharyngeal cancer (e.g., nasopharyngeal cancer, oropharynx cancer, hypopharyngeal cancer), salivary gland cancer, brain tumor (e.g., pineal astrocytoma, pilocytic astrocytoma, diffuse astrocytoma, anaplastic astrocytoma), neurilemmoma, liver cancer (e.g., primary liver cancer, extrahepatic bile duct cancer), renal cancer (e.g., renal cell cancer, transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential), bladder cancer, urethral cancer, skin cancer (e.g., intraocular (ocular) melanoma, Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, soft tissue sarcoma), angiofibroma, sarcoma of the retina, penis cancer, testicular tumor, pediatric solid tumor (e.g., Wilms' tumor, childhood kidney tumor), Kaposi's sarcoma, Kaposi's sarcoma caused by AIDS, tumor of maxillary sinus, fibrous histiocytoma, leiomyosarcoma, rhabdomyosarcoma, and leukemia (e.g., acute myeloid leukemia, acute lymphoblastic leukemia).

Hypothalamic Pituitary Disorders

In some embodiments, the condition, disease or disorder is related to the hypothalamic-pituitary-gonadal axis. For example, the condition, disease or disorder is related to the hypothalamus-pituitary-ovary axis. In another example, the condition, disease or disorder is related to the hypothalamus-pituitary-testis axis. Hypothalamic-pituitary-gonadal axis diseases include, but are not limited to, hypogonadism, polycystic ovary syndrome, hypothyroidism, hypopituitarism, sexual dysfunction, and Cushing's disease.

In some embodiments, the condition, disease or disorder associated with diabetes is related to the hypothalamic-pituitary-gonadal axis.

Pulmonary Disease

In some embodiments, the condition, disease or disorder is related to a pulmonary disease. Pulmonary diseases include, but are not limited to, asthma, idiopathic pulmonary fibrosis, pulmonary hypertension, obstructive sleep apnoea-hypopnoea syndrome, and chronic obstructive pulmonary disease (COPD) (e.g., emphysema, chronic bronchitis, and refractory (non-reversible) asthma).

In some embodiments, the condition, disease or disorder associated with diabetes is a pulmonary disease.

Combination Therapy

In some embodiments, this disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the methods described herein include administering a compound described herein in combination with one or more of a diet therapy (e.g., dietary monitoring, diet therapy for diabetes), an exercise therapy (e.g., physical activity), blood sugar monitoring, gastric electrical stimulation (e.g., TANTALUS®), and diet modifications.

In some embodiments, the compounds of Formula I (e.g., a compound of any one of Formulas (I-A1), (I-A2), (I-A3), (I-A4), (I-A4-1), and (I-B1), or (I-A5), (I-A6), (I-A7), (I-A8), and (I-B2), or a pharmaceutically acceptable salt or solvate thereof), or a pharmaceutically acceptable salt or solvate thereof as described herein can be administered in combination with one or more additional therapeutic agents.

Representative additional therapeutic agents include, but are not limited to, anti-obesity agents, therapeutic agents for diabetes, therapeutic agents for diabetic complications, therapeutic agents for hyperlipidemia, antihypertensive agents, diuretics, chemotherapeutics, immunotherapeutics, anti-inflammatory drugs, antithrombotic agents, anti-oxidants, therapeutic agents for osteoporosis, vitamins, antidementia drugs, erectile dysfunction drugs, therapeutic drugs for urinary frequency or urinary incontinence, therapeutic agents for NAFLD, therapeutic agents for NASH, and therapeutic agents for dysuria.

In some embodiments, the one or more additional therapeutic agents include those useful, for example, as anti-obesity agents. Non-limiting examples include monoamine uptake inhibitors (e.g., tramadol, phentermine, sibutramine, mazindol, fluoxetine, tesofensine), serotonin 2C receptor agonists (e.g., lorcaserin), serotonin 6 receptor antagonists, histamine H3 receptor modulator, GABA modulator (e.g., topiramate), including GABA receptor agonists (e.g., gabapentin, pregabalin), neuropeptide Y antagonists (e.g., velneperit), peptide YY or an analogue thereof, cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498, naltrexone), orexin receptor antagonists, melanocortin 4 receptor agonists, 1β-hydroxysteroid dehydrogenase inhibitors (e.g., AZD-4017, BVT-3498, INCB-13739), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors (e.g., compounds described in International Publication Nos. WO 2020/234726, WO 2020/044266, and U.S. Pat. No. 8,859,577), stearoyl-CoA desaturated enzyme inhibitors, microsomal triglyceride transfer protein inhibitors (e.g., R-256918), sodium-glucose cotransporter 2 (SGLT-2) inhibitors (e.g., JNJ-28431754, dapagliflozin, AVE2268, TS-033, YM543, TA-7284, ASP1941, remogliflozin, empagliflozin, canagliflozin, ipragliflozin, tofogliflozin, sergliflozin etabonate, remogliflozin etabonate, or ertugliflozin), SGLT-1 inhibitors, MCR-4 agonists, monoamine reuptake inhibitors, melanocytestimulating hormone analogs, 5HT2c agonists, galanin antagonists, anorectic agents (such as a bombesin agonist), thyromimetic agents, dehydroepiandrosterone or analogs thereof, human agouti-related protein (AGRP) inhibitors, neuromedin U agonists, NFK inhibitors (e.g., HE-3286), PPAR agonists (e.g., GFT-505, DRF-11605, gemfibrozil, fenofibrate, balaglitazone, ciglitazone, darglitazone, englitazone, isaglitazone, pioglitazone, rosiglitazone, CLX-0940, GW-1536, GW-1929, GW-2433, KRP-297, L-796449, LR-90, MK-0767, and SB-219994), phosphotyrosine phosphatase inhibitors (e.g., sodium vanadate, trodusquemin), GPR119 agonists (e.g., PSN-821, MBX-2982, APD597, compounds described in International Publication Nos. WO 2010/140092, WO 2010/128425, WO 2010/128414, WO 2010/106457), glucokinase activators (e.g., piragliatin, AZD-1656, AZD6370, TTP-355, TTP-399, TTP547, ARRY403, MK-0599, TAK-329, AZD5658 or GKM-001 compounds described in International Publication Nos. WO 2010/103437, WO 2010/103438, WO 2010/013161, WO 2007/122482, WO 2006/112549, WO 2007/028135, WO 2008/047821, WO 2008/050821, WO 2008/136428 and WO 2008/156757), leptin, leptin derivatives (e.g., metreleptin), leptin resistance improving drugs, CNTF (ciliary neurotrophic factor), BDNF (brain-derived neurotrophic factor), cholecystokinin agonists, amylin preparations (e.g., pramlintide, AC-2307), neuropeptide Y agonists (e.g., PYY3-36, derivatives of PYY3-36, obineptide, TM-30339, TM-30335), oxyntomodulin (OXM) preparations, appetite suppressants (e.g. ephedrine), FGF21 preparations (e.g., animal FGF21 preparations extracted from the pancreas of bovine or swine; human FGF21 preparations genetically synthesized using *Escherichia coli* or yeast; fragments or derivatives of FGF21), anorexigenic agents (e.g., P-57), human proislet peptide (HIP), melanocortin receptor 4 agonist (e.g., setmelanotide), melanin concentrating hormone receptor 1 antagonist, serotonergic agents (e.g. sibutramine, lorcaserin), farnesoid X receptor (FXR) agonist (e.g., obeticholic acid, tropifexor, cilofexor, LY2562175, Met409, TERN-101, EDP305, compounds described in International Publication Nos. WO 2020/234726 and WO 2020/044266), phentermine, zonisamide, norepinephrine/dopamine reuptake inhibitor (e.g., buproprion), GDF-15 analog, methionine aminopeptidase 2 (MetAP2) inhibitor (e.g., beloranib or ZGN-1061), diethylpropion, phendimetrazine, benzphetamine, fibroblast growth factor receptor (FGFR) modulator, biotin, a MAS receptor modulator, glucagon receptor agonist, CCKa agonists (e.g., compounds described in International Publication No. WO 2005/116034 and U.S. Publication No. 2005/0287100), and AMP-activated protein kinase (AMPK) activator.

In some embodiments, the one or more additional therapeutic agents include those useful, for example, as anti-diabetic agents. Non-limiting examples include insulin and insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation, synthetic human insulin), insulin sensitizers (e.g., pioglitazone or a salt thereof), biguanides (e.g., metformin, buformin or a salt thereof (e.g., hydrochloride, fumarate, succinate)), glucagon analogs (e.g., any of glucagon analogs described, e.g., in WO 2010/011439), agents which antagonize the actions of or reduce secretion of glucagon, sulfonylurea agents (e.g., chlorpropamide, tolazamide, glimepiride, tolbutamide, glibenclamide, gliclazide, acetohexamide, glyclopyramide, glybuzole, glyburide, glipizide), thiazolidinedione agents (e.g. rosiglitazone, lobeglitazone, troglitazone, balaglitazone, rivoglitazone, lobeglitazone or pioglitazone), glitazars (e.g., aleglitazar, chiglitazar, saroglitazar, muraglitazar, tesaglitazar), SGLT2 inhibitors (e.g., JNJ-28431754, dapagliflozin, AVE2268, TS-033, YM543, TA-7284, ASP1941, THR1474, TS-071, ISIS388626, LX4211, remogliflozin, empagliflozin, canagliflozin, ipragliflozin, tofogliflozin, sergliflozin etabonate, remogliflozin etabonate, ertugliflozin, compounds described in WO 2010/023594), GPR40 agonists (e.g., a FFAR1/FFA1 agonist, e.g. fasiglifam), a-glucosidase inhibitors (e.g., adiposin, camiglibose, pradimicin-Q, salbostatin, voglibose, acarbose, miglitol, emiglitate), insulin secretagogues, such as prandial glucose regulators (sometimes called "short-acting secretagogues"), e.g., meglitinides (e.g. repaglinide and nateglinide), cholinesterase inhibitors (e.g., donepezil, galantamine, rivastigmine, tacrine), NMDA receptor antagonists, dual GLP-1/GIP receptor agonists (e.g., LBT-2000, ZPD1-70), GLP-1R agonists (e.g., exenatide, liraglutide, albiglutide, dulaglutide, abiglutide, taspoglutide, lixisenatide, semaglutide, AVE-0010, S4P and Boc5), and dipeptidyl peptidase IV (DPP-4) inhibitors (e.g., vildagliptin, dutogliptin, gemigliptin, alogliptin, saxagliptin, sitagliptin, linagliptin, berberine, adogliptin, anagliptin (SK-0403), teneligliptin, omarigliptin, BI1356, GRC8200, MP-513, PF-00734200, PHX1149, ALS2-0426, TA-6666, TS-021, KRP-104, trelagliptin).

In some embodiments, the one or more additional therapeutic agents include those useful, for example, for treating NAFL and NASH. Non-limiting examples include FXR agonists (e.g., obeticholic acid), PF-05221304, PPAR a/6 agonists (e.g., elafibranor), a synthetic fatty acid-bile conjugate (e.g., aramchol), an anti-lysyl oxidase homologue 2 (LOXL2) monoclonal antibody (e.g., simtuzumab), a caspase inhibitor (e.g., emricasan), a MAPK5 inhibitor (e.g., GS-4997), a galectin 3 inhibitor (e.g., GR-MD-02), a fibroblast growth factor 21 (FGF21) (e.g., BMS-986036), a niacin analogue (e.g., ARJ 3037MO), a leukotriene D4

(LTD4) receptor antagonist (e.g., tipelukast), an acetyl-CoA carboxylase (ACC) inhibitor (e.g., NDI 010976 amd compounds described in International Publication Nos. WO 2009/144554, WO 2003/072197, WO 2009/144555, and WO 2008/065508), a ketohexokinase (KHK) inhibitor (e.g., compounds described in WO 2020/234726), an apoptosis signal-regulating kinase 1 (ASK1) inhibitor, an ileal bile acid transporter (IBAT) inhibitor, a dual antagonist of chemokine receptor 2 (CCR2) and CCR5 (e.g., cenicriviroc), diacylglyceryl acyltransferase 2 (DGAT2) inhibitor (e.g., compounds described in WO 2020/234726 and U.S. Publication No. 20180051012), a CB 1 receptor antagonist, an anti-CB 1R antibody, glycyrrhizin, schisandra extract, ascorbic acid, glutathione, silymarin, lipoic acid, and d-alpha-tocopherol, ascorbic acid, glutathione, vitamin B-complex, glitazones/thiazolidinediones (e.g., troglitazone, rosiglitazone, pioglitazone, balaglitazone, rivoglitazone, lobeglitazone), metformin, cysteamine, sulfonylureas, alpha-glucosidase inhibitors, meglitinides, vitamin E, tetrahydrolipstatin, milk thistle protein, anti-virals, and anti-oxidants.

In some embodiments, the one or more additional therapeutic agents include those useful, for example, for treating diabetic complications. Non-limiting examples include aldose reductase inhibitors (e.g., tolrestat, epalrestat, zopolrestat, fidarestat, CT-112, ranirestat, lidorestat), neurotrophic factor and increasing agents thereof (e.g., NGF, NT-3, BDNF, neurotrophic production/secretion promoting agents described in WO01/14372 (e.g., 4-(4-chlorophenyl)-2-(2-methyl-1-imidazolyl)-5-[3-(2-methylphenoxyl)propyl]oxazole), compounds described in WO2004/039365), PKC inhibitors (e.g., ruboxistaurin mesylate), AGE inhibitors (e.g., ALT946, N-phenacylthiazolium bromide (ALT766), EXO-226, pyridorin, pyridoxamine), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), and apoptosis signal regulating kinase-1 (ASK-1) inhibitors.

In some embodiments, the one or more additional therapeutic agents include those useful, for example, for treating hyperlipidemia. Non-limiting examples include HMG-COA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compounds described in WO97/10224, e.g., N-[[(3R,5S)-1-(3-acetoxy-2,2-dimethylpropyl)-7-chloro-5-(2,3-dimethoxyphenyl)-2-oxo-1,2,3,5-tetrahydro-4, 1-benzoxazepin-3-yl]acetyl]piperidin-4-acetic acid), fibratecompounds (e.g., bezafibrate, clofibrate, simfibrate, clinofibrate), anion exchange resin (e.g., colestyramine), nicotinic acid drugs (e.g., nicomol, niceritrol, niaspan), phytosterols (e.g., soysterol, gamma oryzanol (y-oryzanol)), cholesterol absorption inhibitors (e.g., zechia), CETP inhibitors (e.g., dalcetrapib, anacetrapib) and w-3 fatty acid preparations (e.g., w-3-fatty acid ethyl esters 90).

In some embodiments, the one or more additional therapeutic agents include those useful, for example, as anti-hypertensive agents. Non-limiting examples include angiotensin converting enzyme inhibitors (e.g., captopril, zofenopril, fbsinopril, enalapril, ceranopril, cilazopril, delapril, pentopril, quinapril, ramipril, lisinopril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine) and β-blockers (e.g., metoprolol, atenolol, propranolol, carvedilol, pindolol). Further non-limiting examples of antihypertensive agents include: diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone), alpha adrenergic blockers, beta adrenergic blockers, calcium channel blockers (e.g., diltiazem, verapamil, nifedipine and amlodipine), vasodilators (e.g., hydralazine), renin inhibitors, AT-1 receptor antagonists (e.g., losartan, irbesartan, valsartan), ET receptor antagonists (e.g., sitaxsentan, atrsentan, compounds disclosed in U.S. Pat. Nos. 5,612,359 and 6,043,265), dual ET/AII antagonist (e.g., compounds disclosed in WO 2000/01389), neutral endopeptidase (NEP) inhibitors, If channel blocker ivabradinand, vasopepsidase inhibitors (dual NEP-ACE inhibitors) (e.g., gemopatrilat and nitrates).

In some embodiments, the one or more additional therapeutic agents include those useful, for example, as diuretics. Non-limiting examples include_xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penfluthiazide, polythiazide, methyclothiazide), antialdosterone preparations (e.g., spironolactone, triamterene), carbonic anhydrase inhibitors (e.g., acetazolamide) and chlorobenzenesulfonamide agents (e.g., chlortalidone, mefruside, indapamide).

In some embodiments, the one or more additional therapeutic agents include those useful, for example, as immunotherapeutic agents. Non-limiting examples include microbial or bacterial compounds (e.g., muramyl dipeptide derivative, picibanil), polysaccharides having immunoenhancing activity (e.g., lentinan, sizofiran, krestin), cytokines obtained by genetic engineering approaches (e.g., interferon, interleukin (IL) such as IL-1, IL-2, IL-12), and colony-stimulating factors (e.g., granulocyte colony-stimulating factor, erythropoietin).

In some embodiments, the one or more additional therapeutic agents include those useful, for example, as anti-thrombotic agents. Non-limiting examples include heparins (e.g., heparin sodium, heparin calcium, enoxaparin sodium, dalteparin sodium) warfarin (e.g., warfarin potassium); anti-thrombin drugs (e.g., aragatroban, dabigatran, boroarginine derivatives, boropeptides, heparins, hirudin, and melagatran), FXa inhibitors (e.g., rivaroxaban, apixaban, edoxaban, YM150, compounds described in WO02/06234, WO2004/048363, WO2005/030740, WO2005/058823, and WO2005/113504) thrombolytic agents (e.g., anistreplase, streptokinase, tenecteplase (TNK), lanoteplase (nPA), urokinase, tisokinase, alteplase, nateplase, monteplase, pamiteplase, factor VIIa inhibitors, PAI-1 inhibitors, alpha2-antiplasmin inhibitors, and anisoylated plasminogen streptokinase activator complex), and platelet aggregation inhibitors (e.g., ticlopidine hydrochloride, clopidogrel, prasugrel, E5555, SHC530348, cilostazol, ethyl icosapentate, beraprost sodium, and sarpogrelate hydrochloride).

In some embodiments, the one or more additional therapeutic agents include those useful, for example, for treating osteoporosis. Non-limiting examples include alfacalcidol, calcitriol, elcatonin, calcitonin salmon, estriol, ipriflavone, pamidronate disodium, alendronate sodium hydrate, incadronate disodium, and risedronate disodium. Suitable examples of vitamins include vitamin B1 and vitamin B12. Suitable examples of erectile dysfunction drugs include apomorphine and sildenafil citrate. Suitable examples of therapeutic agents for urinary frequency or urinary incontinence include flavorxate hydrochloride, oxybutynin hydrochloride and propiverine hydrochloride. Suitable examples of therapeutic agents for dysuria include acetylcholine esterase inhibitors (e.g., distigmine). Suitable examples of anti-inflammatory agents include nonsteroidal anti-inflammatory drugs such as aspirin, acetaminophen, indomethacin.

Other exemplary additional therapeutic agents include agents that modulate hepatic glucose balance (e.g., fructose 1,6-bisphosphatase inhibitors, glycogen phosphorylase inhibitors, glycogen synthase kinase inhibitors, glucokinase activators), agents designed to treat the complications of prolonged hyperglycemia, such as aldose reductase inhibitors (e.g. epalrestat and ranirestat), agents used to treat complications related to micro-angiopathies, anti-dyslipidemia agents, such as HMG-CoA reductase inhibitors (statins, e.g. rosuvastatin pravastatin, pitavastatin, lovastatin, atorvastatin, simvastatin, fluvastatin, itavastatin, ZD-4522), HMG-CoA synthase inhibitors, cholesterol-lowering agents, bile acid sequestrants (e.g., cholestyramine, questran, colestipol, and colesevelam), cholesterol absorption inhibitors (e.g. plant sterols such as phytosterols), cholesteryl ester transfer protein (CETP) inhibitors, inhibitors of the ileal bile acid transport system (IBAT inhibitors), diacylglyceryl acyltransferase 1 (DGAT1) inhibitors (e.g., AZD7687, LCQ908, compounds described in WO 2009/016462, WO 2010/086820), monoacylglycerol O-acyltransferase inhibitors, a-amylase inhibitors (e.g., tendamistat, trestatin, AL-3688), a-glucoside hydrolase inhibitors, SIRT-1 activators, c-Jun N-terminal kinase (JNK) inhibitors, a VPAC2 receptor agonist, TGRS receptor modulators (e.g., compounds described in), GPBARI receptor modulators, GPR120 modulators, high affinity nicotinic acid receptor (HM74A) activators, carnitine palmitoyl transferase enzyme inhibitors, mineralocorticoid receptor inhibitors, inhibitors of TORC2, fatty acid synthetase inhibitors, serine palmitoyl transferase inhibitors, GPR81 modulators, GPR39 modulators, GPR43 modulators, GPR41 modulators, GPR105 modulators, Kv1.3 modulators, retinol binding protein 4 modulators, somatostain receptor modulators, PDHK2 modulators, PDHK4 modulators, MAP4K4 inhibitors, IL 1 family modulators (e.g., ILI beta modulators), ACAT inhibitors, MTP inhibitors (e.g., diriotapide, mitratapide, and implitapide), lipooxygenase inhibitors, PCSK9 modulators (e.g., alirocumab and evolocumab), RXRalpha modulators, cysteamine, cystamine, an RNA anti sense construct to inhibit protein tyrosine phosphatase PTPRU, vitamin B complex, pentraxin proteins, a protein tyrosine phosphatase-1 B (PTP-1 B) inhibitor (e.g., trodusquemine, hyrtiosal extract, and compounds described by Zhang et al. *Drug Discovery Today.* 2007, 12(9-10): 373-381), ezitimbe, betaine, pentoxifylline, alpha delta-9 desaturase, BCKDK inhibitors, branched-chain alpha keto acid dehydrogenase kinase (BCBK) inhibitors, PNPLA3 inhibitors, FGF19 analogs, SCD1 inhibitors, bile acid binding resins, nicotinic acid (niacin) and analogues thereof, anti-oxidants (e.g., probucol), omega-3 fatty acids, antihypertensive agents, including adrenergic receptor antagonists, such as beta blockers (e.g. atenolol), alpha blockers (e.g. doxazosin), and mixed alpha/beta blockers (e.g. labetalol), adrenergic receptor agonists, including alpha-2 agonists (e.g. clonidine), angiotensin converting enzyme (ACE) inhibitors (e.g. lisinopril), calcium channel blockers, such as dihydropridines (e.g. nifedipine), phenylalkylamines (e.g. verapamil), and benzothiazepines (e.g. diltiazem), angiotensin II receptor antagonists (e.g. candesartan), aldosterone receptor antagonists (e.g. eplerenone, spironolactone), centrally acting adrenergic drugs, such as central alpha agonists (e.g. clonidine), diuretic agents (e.g. furosemide, torsemide, bemetanide, ethacrynic acid, thiazide-type diuretics (e.g., chlorothiazide, hydrochlorothiazide, benzthiazide, hydroflumethiazide, bendroflumethiazide, methychlorthiazide, polythiazide, trichlormethiazide, indapamide), phthalimidine-type diuretics (e.g., chlorthalidone, metolazone), quinazoline-type diuretics (e.g., quinethazone), potassium-sparing diuretics (e.g., triamterene and amiloride), thyroid receptor agonists (e.g., compounds described in WO 2020/117987), haemostasis modulators, including antithrombotics (e.g., activators of fibrinolysis), thrombin antagonists, factor VIIa inhibitors, anticoagulants (e.g., vitamin K antagonists such as warfarin), heparin and low molecular weight analogues thereof, factor Xa inhibitors, and direct thrombin inhibitors (e.g. argatroban), antiplatelet agents (e.g., cyclooxygenase inhibitors (e.g. aspirin), non-steroidal anti-inflammatory drugs (NSAIDS), thromboxane-A2-receptor antagonists (e.g., ifetroban), thromboxane-A2-synthetase inhibitors, PDE inhibitors (e.g., Pletal, dipyridamole)), antagonists of purinergic receptors (e.g., P2Y1 and P2Y12), adenosine diphosphate (ADP) receptor inhibitors (e.g. clopidogrel), phosphodiesterase inhibitors (e.g. cilostazol), glycoprotein IIB/IIA inhibitors (e.g. tirofiban, eptifibatide, and abcixima), adenosine reuptake inhibitors (e.g. dipyridamole), noradrenergic agents (e.g. phentermine), serotonergic agents (e.g. sibutramine, lorcaserin), diacyl glycerolacyltransferase (DGAT) inhibitors, feeding behavior modifying agents, pyruvate dehydrogenase kinase (PDK) modulators, serotonin receptor modulators, monoamine transmission-modulating agents, such as selective serotonin reuptake inhibitors (S SRI) (e.g. fluoxetine), noradrenaline reuptake inhibitors (NARI), noradrenaline-serotonin reuptake inhibitors (SNRI), and monoamine oxidase inhibitors (MAOI) (e.g. toloxatone and amiflamine), compounds described in WO 2007/013694, WO 2007/018314, WO 2008/093639 and WO 2008/099794, GPR40 agonists (e.g., fasiglifam or a hydrate thereof, compounds described in WO 2004/041266, WO 2004/106276, WO 2005/063729, WO 2005/063725, WO 2005/087710, WO 2005/095338, WO 2007/013689 and WO 2008/001931), SGLT1 inhibitors, adiponectin or agonist thereof, IKK inhibitors (e.g., AS-2868), somatostatin receptor agonists, ACC2 inhibitors, cachexia-ameliorating agents, such as a cyclooxygenase inhibitors (e.g., indomethacin), progesterone derivatives (e.g., megestrol acetate), glucocorticoids (e.g., dexamethasone), metoclopramide agents, tetrahydrocannabinol agents, agents for improving fat metabolism (e.g., eicosapentaenoic acid), growth hormones, IGF-1, antibodies against a cachexia-inducing factor TNF-$\alpha$, LIF, IL-6, and oncostatin M, metabolism-modifying proteins or peptides such as glucokinase (GK), glucokinase regulatory protein (GKRP), uncoupling proteins 2 and 3 (UCP2 and UCP3), peroxisome proliferator-activated receptor a (PPARa), MC4r agonists, insulin receptor agonist, PDE 5 inhibitors, glycation inhibitors (e.g., ALT-711), nerve regeneration-promoting drugs (e.g., Y-128, VX853, prosaptide), antidepressants (e.g., desipramine, amitriptyline, imipramine), antiepileptic drugs (e.g., lamotrigine, trileptal, keppra, zonegran, pregabalin, harkoseride, carbamazepine), antiarrhythmic drugs (e.g., $K^+$ channel openers, mexiletine, propafenone, metoprolol, atenolol, carvadiol, propranolol, sotalol, dofetilide, amiodarone, azimilide, ibutilide, ditiazem, and verapamil), acetylcholine receptor ligands (e.g., ABT-594), endothelin receptor antagonists (e.g., ABT-627), narcotic analgesics (e.g., morphine), a2 receptor agonists (e.g., clonidine), local analgesics (e.g., capsaicin), antianxiety drugs (e.g., benzothiazepine), phosphodiesterase inhibitors (e.g., sildenafil), dopamine receptor agonists (e.g., apomorphine), cytotoxic antibodies (e.g., T-cell receptor and IL-2 receptor-specific antibodies), B cell depleting therapies (e.g., anti-CD20 antibody (e.g., rituxan), i-BLyS antibody), drugs affecting T cell migration (e.g., anti-integrin alpha 4/beta 1 antibody (e.g., tysabri), drugs that act on immunophilins (e.g., cyclosporine, tacrolimus, sirolimus, rapamicin), interferons (e.g., IFN-β), immunomodulators (e.g., glatiramer), TNF-binding proteins (e.g., circulating receptors), immunosupressants (e.g., mycophenolate), metaglidasen, AMG-131, balaglitazone, MBX-2044, rivoglitazone, aleglitazar, chiglitazar, saroglitazar, muraglitazar, tesaglitazar, lobeglitazone, PLX-204, PN-2034, GFT-505, THR-0921, exenatide, exendin-4, memantine, midazolam, ketoconazole, ethyl icosapentate, clonidine, azosemide, isosorbide, ethacrynic acid, piretanide, bumetanide, etoposide, piroxicam, NO donating agents (e.g., organonitrates), NO promoting agents (e.g., phosphodiesterase inhibitors).

In some embodiments, the one or more additional therapeutic agents include those useful, for example, as anti-emetic agents. As used herein, an "anti-emetic" agent refers to any agent that counteracts (e.g., reduces or removes) nausea or emesis (vomiting). While not wishing to be bound by theory, it is believed that administering one or more anti-emetic agents in combination with the formula (I) compounds described herein may allow higher dosages of the formula (I) compounds to be administered, e.g., because the patient may be able to have a normal food intake and thereby respond faster to the treatment.

Non-limiting examples of anti-emetic agents include 5HT3-receptor antagonists (serotonin receptor antagonists), neuroleptics/anti-psychotics, antihistamines, anticholinergic agents, steroids (e.g., corticosteroids), NK1-receptor antagonists (e.g., Neurokinin 1 substance P receptor antagonists), antidopaminergic agents/dopamine receptor antagonists, benzodiazepines, and cannabinoids.

For example, the antiemetic agent can be selected from the group consisting of, neuroleptics, antihistamines, anticholinergic agents, steroids, 5HT-3-receptor antagonists, NK1-receptor antagonists, anti-dopaminergic agents/dopamine receptor antagonists, benzodiazepines and non-psychoactive cannabinoids.

In some embodiments, the anti-emetic agent is a 5HT3-receptor antagonist (serotonin receptor antagonist). Non-limiting examples of 5HT3-receptor antagonists (serotonin receptor antagonists) include: Granisetron (Kytril), Dolasetron, Ondansetron (Zofran), Tropisetron, Ramosetron, Palonosetron, Alosetron, azasetron, Bemesetron, Zatisetron, Batanopirde, MDL-73147EF; Metoclopramide, N-3389 (endo-3,9-dimethyl-3,9-diazabicyclo[3,3,1]non-7-yl-1H-indazole-3-carboxamide dihydrochloride), Y-25130 hydrochloride, MDL 72222, Tropanyl-3,5-dimethylbenzoate, 3-(4-Allylpiperazin-1-yl)-2-quinoxalinecarbonitrile maleate, Zacopride hydrochloride, and Mirtazepine. Other non-limiting examples of 5HT3-receptor antagonists (serotonin receptor antagonists) include: cilansetron, clozapine, cyproheptadine, dazopride, hydroxyzine, lerisetron, metoclopramide, mianserin, olanzapine, palonosetron (+netupitant), quetiapine, qamosetron, ramosteron, ricasetron, risperidone, ziprasidone, and zatosetron.

In certain embodiments, the 5HT-3-receptor antagonist is Granisetron, Dolasetron, Ondansetron hydrochloride, Tropisetron, Ramosetron, Palonosetron, Alosetron, Bemesetron, Zatisetron, Batanopirde, MDL-73147EF, Metoclopramide, N-3389, Y-25130 hydrochloride, MDL 72222, Tropanyl-3,5-dimethylbenzoate 3-(4-AIIyI-piperazin-1-yl)-2-quinoxalinecarbonitrile maleate, Zacopride hydrochloride and Mirtazepine.

In certain embodiments, the 5HT-3-receptor antagonist is Granisetron, Dolasetron, Ondansetron hydrochloride, Tropisetron, Ramosetron, Palonosetron, Alosetron, Bemesetron, and Zatisetron.

In certain embodiments, the 5HT-3-receptor antagonist is Granisetron, Dolasetron and Ondansetron.

In certain embodiments, the 5HT-3-receptor antagonist is Granisetron.

In certain embodiments, the 5HT-3-receptor antagonist is Ondansetron.

In some embodiments, the anti-emetic agent is an antihistamine. Non-limiting examples of antihistamines include: piperazine derivatives (e.g., cyclizine, meclizine, and cinnarizine); Promethazine; Dimenhydrinate (Dramamine, Gravol); Diphenhydramine; Hydroxyzine; Buclizine; and Meclizine hydrochloride (Bonine, Antivert), doxylamine, and mirtazapine.

In some embodiments, the anti-emetic agent is an anticholinergic agent (Inhibitors of the acetylcholine receptors). Non-limiting examples of anticholinergic agents include: atropine, Scopolamine, Glycopyrron, Hyoscine, Artane (Trihexy-5 trihexyphenidyl hydrochloride), Cogentin (benztropine mesylate), Akineton (biperiden hydrochloride), Disipal (Norflex orphenadrine citrate), diphenhydramine, hydroxyzine, hyoscyamine, and Kemadrin (procyclidine hydrochloride).

In some embodiments, the anti-emetic agent is a steroid (e.g., a corticosteroid). Non-limiting examples of steroids include: betamethasone, Dexamethasone, Methylprednisolone, Prednisone®, and Trimethobenzamide (Tigan).

In some embodiments, the anti-emetic agent is an NK1-receptor antagonists (e.g., Neurokinin 1 substance P receptor antagonists). Non-limiting examples of NK1-receptor antagonists include: aprepitant, casopitant, ezlopitant, fosaprepitant, maropitant, netupitant, rolapitant, and vestipitant.

Other non-limiting examples of NK1-receptor antagonists include: MPC-4505, GW597599, MPC-4505, GR205171, L-759274, SR 140333, CP-96,345, BIIF 1149, NKP 608C, NKP 608A, CGP 60829, SR 140333 (Nolpitantium besilate/chloride), LY 303870 (Lanepitant), MDL-105172A, MDL-103896, MEN-11149, MEN-11467, DNK 333A, YM-49244, YM-44778, ZM-274773, MEN-10930, S-19752, Neuronorm, YM-35375, DA-5018, MK-869, L-754030, CJ-11974, L-758298, DNK-33A, 6b-1, CJ-11974 j. Benserazide and carbidopa k. TAK-637 [(aR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthyridine-6,13-dione], PD 154075, ([(2-benzofuran)-CH2OCO]—(R)-alpha-MeTrp-(S)—NHCH($CH_3$) Ph), FK888, and (D-Pro4, D-Trp7,9,10, Phe11)SP4-11.

In some embodiments, the anti-emetic agent is an anti-dopaminergic agents/dopamine receptor antagonist (e.g., dopamine receptor antagonist, e.g., D2 or D3 antagonists). Non-limiting examples include phenothiazines (e.g., promethazine, chlorpromazine, prochlorperazine, perphenazine, hydroxyzine, thiethylperazine, metopimazine,); benzamides (e.g., Metoclopramide, domperidone), butyrophenones (e.g., haloperidol, droperidol); alizapride, bromopride, clebopride, domperidone, itopride, metoclopramide, trimethobenzamide, and amisulpride.

In some embodiments, the anti-emetic agent is a non-psychoactive cannabinoids (e.g., Cannabidiol (CBD), Cannabidiol dimethylheptyl (CBD-DMH), Tetra-hydro-cannabinol (THC), Cannabinoid agonists such as WIN 55-212 (a CB 1 and CB2 receptor agonist), Dronabinol (Marinol®), and Nabilone (Cesamet)).

Other exemplary anti-emetic agents include: c-9280 (Merck); benzodiazepines (diazepam, midazolam, lorazepam); neuroleptics/anti-psychotics (e.g., dixyrazine, haloperidol, and Prochlorperazine (Compazine®)); cerium oxalate; propofol; sodium citrate; dextrose; fructose (Nauzene); orthophosphoric acid; fructose; glucose (Emetrol); bismuth subsalicylate (Pepto Bismol); ephedrine; vitamin B6; peppermint, lavender, and lemon essential oils; and ginger.

Still other exemplary anti-emetic agents include those disclosed in US 20120101089A1; U.S. Pat. No. 10,071,088 B2; U.S. Pat. No. 6,673,792 B1; U.S. Pat. No. 6,197,329 B1; U.S. Pat. No. 10,828,297 B2; U.S. Pat. No. 10,322,106 B2; U.S. Pat. No. 10,525,033 B2; WO 2009080351 A1; WO 2019203753 A2; WO 2002020001 A2; U.S. Pat. No. 8,119,697 B2; U.S. Pat. No. 5,039,528; US20090305964A1; and WO 2006/111169, each of which is incorporated by reference in its entirety.

In some embodiments, the additional therapeutic agent or regimen is administered to the patient prior to contacting with or administering the compounds and pharmaceutical compositions (e.g., about one hour prior, or about 6 hours prior, or about 12 hours prior, or about 24 hours prior, or about 48 hours prior, or about 1 week prior, or about 1 month prior).

In some embodiments, the additional therapeutic agent or regimen is administered to the patient at about the same time as contacting with or administering the compounds and pharmaceutical compositions. By way of example, the additional therapeutic agent or regimen and the compounds and pharmaceutical compositions are provided to the patient simultaneously in the same dosage form. As another example, the additional therapeutic agent or regimen and the compounds and pharmaceutical compositions are provided to the patient concurrently in separate dosage forms.

In some embodiments, the methods described herein further include the step of identifying a patient (e.g., a subject) in need of such treatment (e.g., by way of blood assay, body mass index, or other conventional method known in the art).

In some embodiments, the methods described herein further include the step of identifying a patient (e.g., patient) that has a disease, disorder, or condition as provided here (e.g., a GLP-1 associated disease, disorder, or condition).

In some embodiments, the methods described herein further include the step of identifying a patient (e.g., patient) that has type 2 diabetes mellitus. In some embodiments, determining if the patient has type 2 diabetes mellitus includes performing an assay to determine the level of hemoglobin A1c (HbA1c), fasting plasma glucose, non-fasting plasma glucose, or any combination thereof. In some embodiments, the level of HbA1c is about 6.5% to about 24.0%. In some embodiments, the level of HbA1c is greater than or about 6.5%. In some embodiments, the level of HbA1c is greater than or about 8.0%. In some embodiments, the level of HbA1c is greater than or about 10.0%. In some embodiments, the level of HbA1c is greater than or about 12.0%. In some embodiments, the level of HbA1c is greater than or about 14.0%. In some embodiments, the level of HbA1c is greater than or about 16.0%. In some embodiments, the level of HbA1c is greater than or about 18.0%. In some embodiments, the level of HbA1c is greater than or about 20.0%. In some embodiments, the level of HbA1c is greater than or about 22.0%. In some embodiments, the level of HbA1c is greater than or about 24.0%.

In some embodiments, the level of fasting plasma glucose is greater than or about 120 mg/dL to greater than or about 750 mg/dL. In some embodiments, the level of fasting plasma glucose is greater than or about 200 mg/dL to greater than or about 500 mg/dL. In some embodiments, the level of fasting plasma glucose is greater than or about 300 mg/dL to greater than or about 700 mg/dL.

In some embodiments, the level of non-fasting plasma glucose is greater than or about 190 mg/dL to greater than or about 750 mg/dL. In some embodiments, the level of non-fasting plasma glucose is greater than or about 250 mg/dL to greater than or about 450 mg/dL. In some embodiments, the level of non-fasting plasma glucose is greater than or about 400 mg/dL to greater than or about 700 mg/dL.

In some embodiments, determining if the patient has type 2 diabetes mellitus further includes determining the patient's BMI. In some embodiments, the BMI of the patient is greater than or about 22 $kg/m^2$ to greater than or about 100 $kg/m^2$. In some embodiments, the BMI of the patient is greater than or about 30 $kg/m^2$ to greater than or about 90 $kg/m^2$. In some embodiments, the BMI of the patient is greater than or about 40 $kg/m^2$ to greater than or about 80 $kg/m^2$. In some embodiments, the BMI of the patient is greater than or about 50 $kg/m^2$ to greater than or about 70 $kg/m^2$.

In some embodiments, additional factors (e.g. risk factors) used for determining if the patient has type 2 diabetes mellitus further includes age and ethnicity of the patient. In some embodiments, the patient's age is greater than or about 10 years. In some embodiments, the patient's age is greater than or about 15 years. In some embodiments, the patient's age is greater than or about 20 years. In some embodiments, the patient's age is greater than or about 25 years. In some embodiments, the patient's age is greater than or about 30 years. In some embodiments, the patient's age is greater than or about 35 years. In some embodiments, the patient's age is greater than or about 40 years. In some embodiments, the patient's age is greater than or about 42 years. In some embodiments, the patient's age is greater than or about 44 years. In some embodiments, the patient's age is greater than or about 46 years. In some embodiments, the patient's age is greater than or about 48 years. In some embodiments, the patient's age is greater than or about 50 years. In some embodiments, the patient's age is greater than or about 52 years. In some embodiments, the patient's age is greater than or about 54 years. In some embodiments, the patient's age is greater than or about 56 years. In some embodiments, the patient's age is greater than or about 58 years. In some embodiments, the patient's age is greater than or about 60 years. In some embodiments, the patient's age is greater than or about 62 years. In some embodiments, the patient's age is greater than or about 64 years. In some embodiments, the patient's age is greater than or about 66 years. In some embodiments, the patient's age is greater than or about 68 years. In some embodiments, the patient's age is greater than or about 70 years. In some embodiments, the patient's age is greater than or about 72 years. In some embodiments, the patient's age is greater than or about 74 years. In some embodiments, the patient's age is greater than or about 76 years. In some embodiments, the patient's age is greater than or about 78 years. In some embodiments, the patient's age is greater than or about 80 years. In some embodiments, the patient's age is greater than or about 85 years. In some embodiments, the patient's age is greater than or about 90 years. In some embodiments, the patient's age is greater than or about 95 years. In some embodiments, the ethnicity of the patient may be African American, American Indian or Alaska Native, Asian American, Hispanics or Latinos, or Native Hawaiian or Pacific Islander.

In some embodiments, the patient is a pediatric patient. The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age. In some embodiments, the patient is an adult patient.

EXAMPLES

The invention is further described in the following examples, which do not limit the scope of the invention described in the claims.

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (100-200 mesh). Solvent systems were reported as mixtures by volume. NMR spectra were recorded on a Bruker 400 or Varian (400 MHz) spectrometer. $^{1}H$ chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration. LCMS spectra were obtained on SHIMADZU LC20-MS2020 or Agilent 1260 series 6125B mass spectrometer or Agilent 1200 series, 6110 or 6120 mass spectrometer with electrospray ionization and excepted as otherwise indicated.

Example 1

(S,E)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)acrylic acid (Compound 103a)

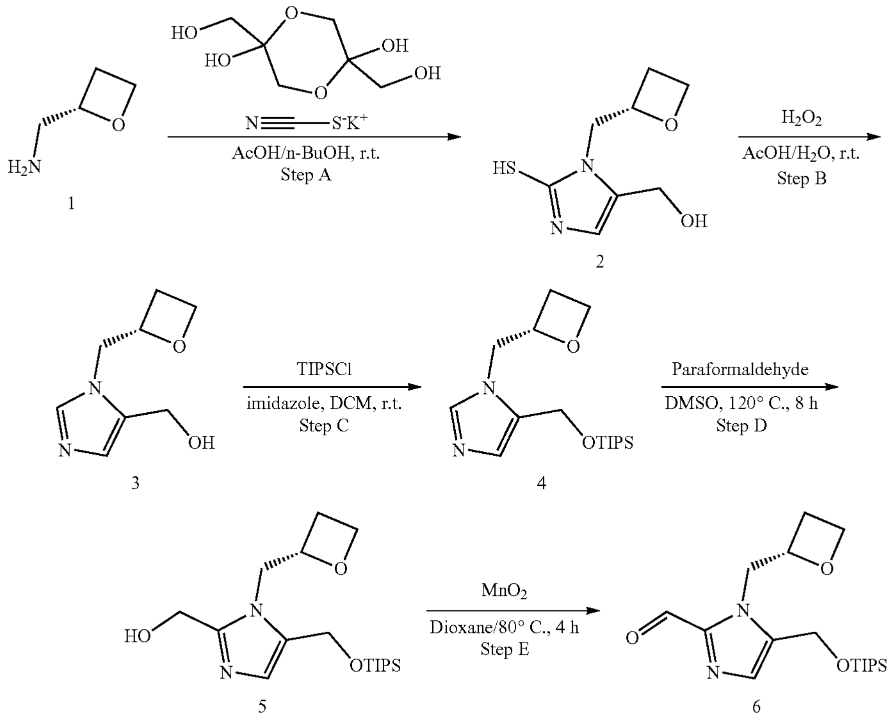

1 2 3 4 5 6

-continued
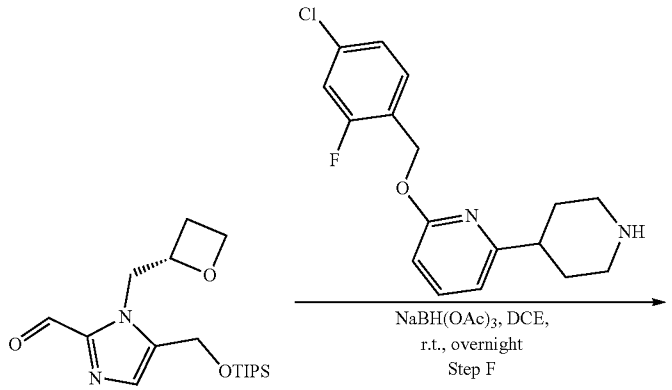
6
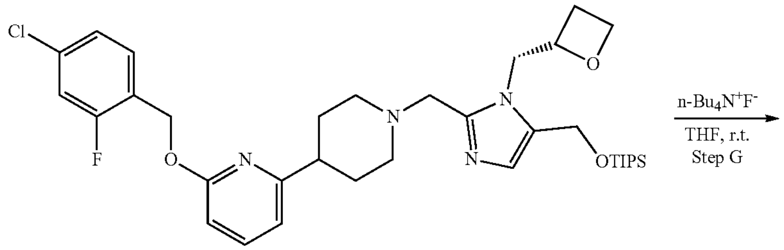
7
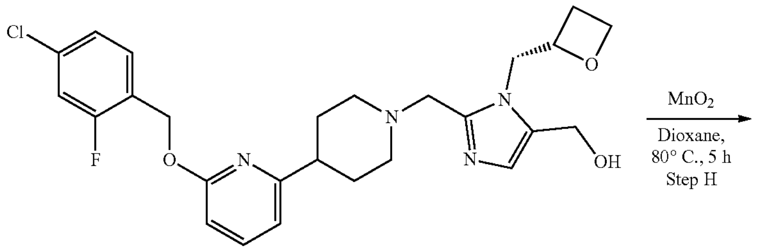
8
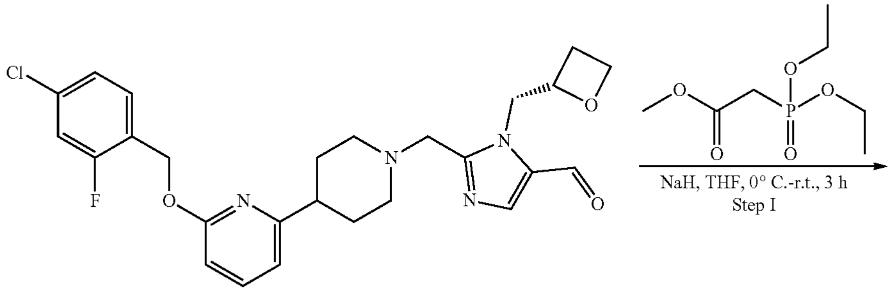
9
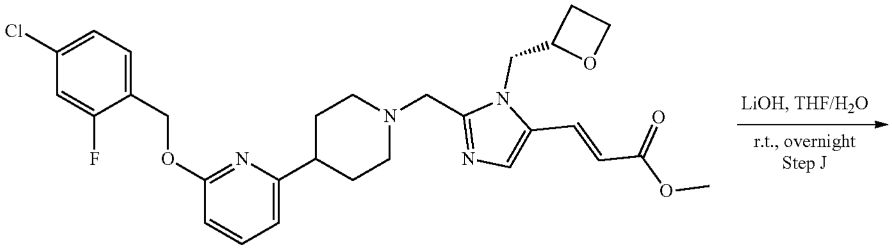
10

-continued

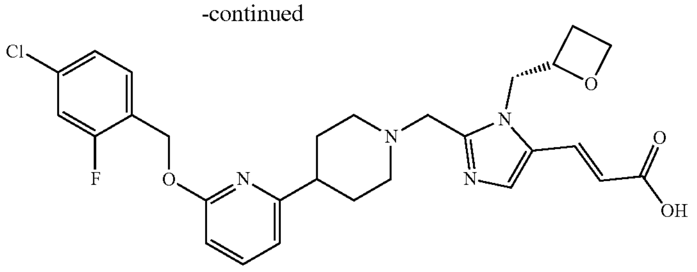

Compound 103a

Step A: (S)-(2-mercapto-1-(oxetan-2-ylmethyl)-1H-imidazol-5-yl)methanol

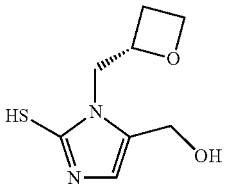

A solution of (S)-oxetan-2-ylmethanamine-2-methanol 4-toluenesulfonate (5.00 g, 19.3 mmol), 2,5-bis(hydroxymethyl)-1,4-dioxane-2,5-diol (3.50 g, 193 mmol) and potassium thiocyanate (1.88 g, 19.3 mmol) in AcOH/1-butanol (7.5 mL/50 mL) was stirred at room temperature overnight. The mixture was poured into water (500 mL), and extracted with EA (100 mL*3). The combined organic phase was dried over anhydrous $Na_2SO_4$ and concentrated. The residue was purified by flash chromatography (eluted with DCM/MeOH=10/1) to afford the title compound (S)-(2-mercapto-1-(oxetan-2-ylmethyl)-1H-imidazol-5-yl)methanol (1.48 g, 38% yield) as a white solid. $^1$H NMR (400 MHz, DMSO-d6) δ 12.08 (s, 1H), 6.81 (d, J=2.4 Hz, 1H), 5.15 (br.s, 1H), 4.99-5.06 (m, 1H), 4.47-4.51 (m, 1H), 4.40-4.44 (m, 2H), 4.34-4.39 (m, 1H), 4.34-4.23 (m, 2H), 2.52-2.69 (m, 2H). LC-MS: m/z 201.2 $(M+H)^+$ Step B: (S)-(1-(oxetan-2-ylmethyl)-1H-imidazol-5-yl)methanol

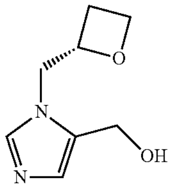 [SMILES: OCc1cncn1C[C@@H]1CCO1]

To a solution of compound (S)-(2-mercapto-1-(oxetan-2-ylmethyl)-1H-imidazol-5-yl)methanol (1.48 g, 7.40 mmol) in 20 mL AcOH was added 2 mL 30% hydrogen peroxide aqueous solution. The reaction was allowed to be stirred at room temperature for 3h. Then the reaction was quenched with saturated $Na_2SO_3$ solution at 0° C. The mixture was filtered. The filtrate was extracted with ethyl acetate. The combined organic layers were dried over $Na_2SO_4$, filtered, and concentrated in vacuo to provide compound (S)-(1-(oxetan-2-ylmethyl)-1H-imidazol-5-yl)methanol (2.00 g, crude), which was used in next step without further purification. LC-MS: m/z 169.07 $(M+H)^+$ Step C: (S)-1-(oxetan-2-ylmethyl)-5-(((triisopropylsilyl)oxy)methyl)-1H-imidazole

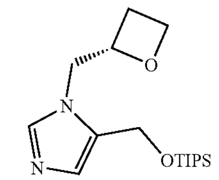

To a stirred solution of (S)-(1-(oxetan-2-ylmethyl)-1H-imidazol-5-yl)methanol (1.00 g, 5.94 mmo) and imidazole (808 mg, 11.9 mmol) in $CH_2Cl_2$ (20 mL) was slowly added solution of TIPSCl (1.70 g, 8.92 mmol, 1.5 equiv) in $CH_2Cl_2$ (5 mL) at 0° C. The reaction was warmed to room temperature and stirred for 2 d until the reaction was completed. The reaction mixture was concentrated under reduced pressure and purified by flash chromatography (eluted with DCM/MeOH=20/1) to afford the title compound (S)-1-(oxetan-2-ylmethyl)-5-(((triisopropylsilyl)oxy)methyl)-1H-imidazole as a white solid (760 mg, 39% yield). $^1$H NMR (400 MHz, $CDCl_3$) δ 7.69 (s, 1H), 6.95 (s, 1H), 5.04-5.19 (m, 1H), 4.75 (s, 2H), 4.62-4.64 (m, 1H), 4.35-4.41 (m, 1H), 4.21-4.31 (m, 2H), 2.65-2.73 (m, 1H), 2.32-2.39 (m, 1H), 1.08-1.17 (m, 3H), 1.02-1.07 (m, 18H). LC-MS: m/z 325.1 $(M+H)^+$.

Step D: (S)-(1-(oxetan-2-ylmethyl)-5-(((triisopropylsilyl)oxy)methyl)-1H-imidazol-2-yl)methanol

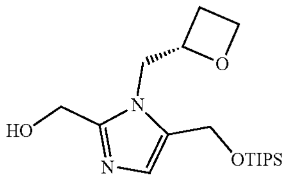

A solution of (S)-1-(oxetan-2-ylmethyl)-5-(((triisopropylsilyl)oxy)methyl)-1H-imidazole (850 mg, 2.60 mmol) and paraformaldehyde (1.20 g, 13.3 mmol) are added to dimethylsulfoxide (2 mL), and the resulting solution was sealed into a glass-lined tube. The solution is heated at 120° C. and stirred for 8 hours. The mixture was cooled to room temperature and filtered. The organic phase was purified by reverse chromatography (eluted with McOH/$H_2O$=10/1) to afford the (S)-(1-(oxetan-2-ylmethyl)-5-(((triisopropylsilyl)oxy)methyl)-1H-imidazol-2-yl)methanol (750 mg, 81% yield). $^1H$ NMR (400 MHz, DMSO-$d_6$) δ 6.72 (s, 1H), 5.21 (dd, J=6.4, 4.8 Hz, 1H), 5.00-5.06 (m, 1H), 4.79 (d, J=12.8 Hz, 1H), 4.70 (d, J=12.8 Hz, 1H), 4.42-4.56 (m, 4H), 4.35-4.40 (m, 1H), 4.24 (dd, J=14.8, 2.8 Hz), 2.59-2.67 (m, 1H), 2.33-2.41 (m, 1H), 1.08-1.17 (m, 3H), 1.04 (d, J=6.4 Hz, 18H). LC-MS: m/z 355.2 $(M+H)^+$.

Step E: (S)-1-(oxetan-2-ylmethyl)-5-(((triisopropylsilyl)oxy)methyl)-1H-imidazole-2-carbaldehyde

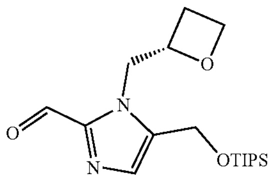

A solution of (S)-(1-(oxetan-2-ylmethyl)-5-(((triisopropylsilyl)oxy)methyl)-1H-imidazol-2-yl)methanol (750 mg, 2.12 mmol) in dioxane (20 mL) was added $MnO_2$ (922 mg, 10.6 mmol). The resulting mixture was stirred for 4 h at 80° C. The reaction mixture was cooled to room temperature and filtered. The filtrate was concentrated in vacuo to give (S)-1-(oxetan-2-ylmethyl)-5-(((triisopropylsilyl)oxy)methyl)-1H-imidazole-2-carbaldehyde (760 mg, crude) as a yellow oil, which was used in next step without further purification. LC-MS: m/z 353.1 $(M+H)^+$.

Step F: (S)-2-((4-chloro-2-fluorobenzyl)oxy)-6-(1-((oxetan-2-ylmethyl)-5-(((triisopropylsilyl)oxy)methyl)-1H-imidazol-2-yl)methyl)piperidin-4-yl)pyridine

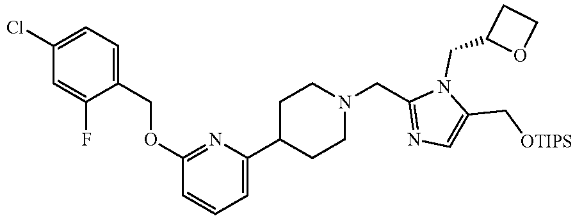

A mixture of (S)-1-(oxetan-2-ylmethyl)-5-(((triisopropylsilyl)oxy)methyl)-1H-imidazole-2-carbaldehyde (670 mg, 1.90 mmol), 2-((4-chloro-2-fluorobenzyl)oxy)-6-(piperidin-4-yl)pyridine (611 mg, 1.90 mmol), and sodium triacetoxyborohydride (807 mg, 3.80 mmol) in 1,2-dichloroethane (10 mL) was stirred at room temperature overnight. The reaction mixture was diluted with saturated aqueous solution of $NaHCO_3$ and extracted with DCM. The combined organic extracts were washed with water, dried over $Na_2SO_4$, filtered, and concentrated. The residue was purified by flash chromatography (DCM/MeOH=15/1) to give the title compound (S)-2-((4-chloro-2-fluorobenzyl)oxy)-6-(1-((1-(oxetan-2-ylmethyl)-5-(((triisopropylsilyl)oxy)methyl)-1H-imidazol-2-yl)methyl)piperidin-4-yl)pyridine (820 mg, 66% yield) as a white solid. LC-MS: m/z 657.3 $(M+H)^+$.

Step G: (S)-(2-((4-(6-((4-chloro-2-fluorobenzyl)oxy)pyridin-2-yl)piperidin-1-yl)methyl)-1-(oxetan-2-ylmethyl)-1H-imidazol-5-yl)methanol

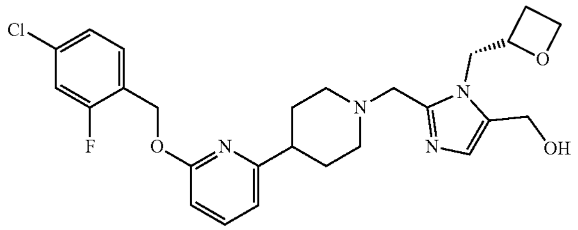

To a solution of (S)-2-((4-chloro-2-fluorobenzyl)oxy)-6-(1-((1-(oxetan-2-ylmethyl)-5-(((triisopropylsilyl)oxy)methyl)-1H-imidazol-2-yl)methyl)piperidin-4-yl)pyridine (820 mg, 1.25 mmol) in THF (20 ml) was added tetrabutylammonium fluoride 1 M in THF (2 ml, 2 mmol). The solution was stirred at room temperature for 3 h. Then $H_2O$ (15 mL) was added, and the mixture was extracted with AcOEt. The organic phase was washed with water, brine and dried over $MgSO_4$. The solvent was removed under reduced pressure and the resulting oil was purified by flash chromatography on silica gel (DCM/MeOH: 10/1) to give the title compound (S)-(2-((4-(6-((4-chloro-2-fluorobenzyl)oxy)pyridin-2-yl)piperidin-1-yl)methyl)-1-(oxetan-2-ylmethyl)-1H-imidazol-5-yl)methanol as a white solid (490 mg, 78% yield). $^1H$ NMR (400 MHz, DMSO-$d_6$) δ 7.63 (dd, J=8.4, 7.2 Hz, 4H), 7.57 (t, J=8.0 Hz, 1H), 7.46 (dd, J=10.0, 2.4 Hz, 1H), 7.30 (dd, J=8.0, 1.6 Hz, 1H), 6.87 (d, J=7.2 Hz, 1H), 6.69 (s, 1H), 6.67 (d, J=8.0 Hz, 1H), 6.28 (d, J=16.0 Hz, 1H), 5.38 (s, 2H), 5.02-5.08 (m, 1H), 4.99 (t, J=5.6 Hz, 1H), 4.60-4.62 (m, 1H), 4.55-4.57 (m, 1H), 4.41-4.47 (m, 3H), 4.26-4.30 (m, 1H), 3.72 (d, J=13.2 Hz, 1H), 3.43 (d, J=13.6 Hz, 1H), 2.95 (d, J=11.2 Hz, 1H), 2.81 (d, J=11.2 Hz, 1H), 2.64-2.69 (m, 2H), 2.36-2.45 (m, 1H), 2.12-2.17 (m, 2H), 1.63-1.78 (m, 4H). LC-MS: m/z 501.2 $(M+H)^+$.

Step H: (S)-2-((4-(6-((4-chloro-2-fluorobenzyl)oxy)pyridin-2-yl)piperidin-1-yl)methyl)-1-(oxetan-2-ylmethyl)-1H-imidazole-5-carbaldehyde

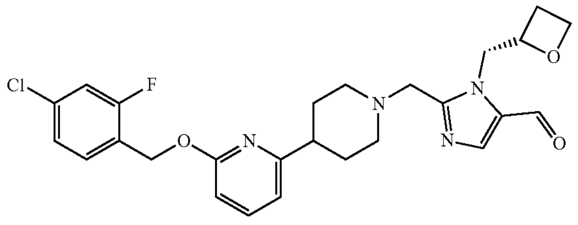

The mixture of (S)-(2-((4-(6-((4-chloro-2-fluorobenzyl)oxy)pyridin-2-yl)piperidin-1-yl)methyl)-1-(oxetan-2-ylmethyl)-1H-imidazol-5-yl)methanol (440 mg, 0.880 mmol) and $MnO_2$ (383 mg, 4.40 mmol) in 15 mL of 1,4-dioxane was heated at 80° C. for 5 h under an atmosphere of argon. LCMS showed the reaction was completed. The mixture was filtered through a celite pad, and the filtrate was concentrated. The residue was purified with silica gel column chromatography (PE/EA=2:1) to give (S)-2-((4-(6-((4-chloro-2-fluorobenzyl)oxy)pyridin-2-yl)piperidin-1-yl)

methyl)-1-(oxetan-2-ylmethyl)-1H-imidazole-5-carbaldehyde (130 mg, 0.261 mmol, 30% yield) as a pale white solid. $^1$H NMR (400 MHz, DMSO-$d_6$) δ 9.70 (s, 1H), 7.83 (s, 1H), 7.63 (dd, J=8.0, 7.2 Hz, 1H), 7.56 (t, J=8.0 Hz, 1H), 7.45 (dd, J=10.0, 2.0 Hz, 1H), 7.29 (dd, J=8.4, 2.0 Hz, 1H), 6.87 (d, J=7.2 Hz, 1H), 6.67 (d, J=7.6 Hz, 1H), 5.37 (s, 2H), 4.93-4.98 (m, 1H), 4.56-4.66 (m, 2H), 4.40-4.49 (m, 1H), 4.31-4.38 (m, 1H), 3.81 (d, J=13.6 Hz, 1H), 3.66 (d, J=13.6 Hz, 1H), 2.94 (d, J=11.2 Hz, 1H), 2.82 (d, J=10.8 Hz, 1H), 2.66-2.71 (m, 1H), 2.55-2.64 (m, 1H), 2.32-2.40 (m, 1H), 2.11-2.22 (m, 2H), 1.66-1.78 (m, 4H). LCMS: m/z=499.0, 501.0 (M+H)$^+$.

Step I: ethyl S,E)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)acrylate

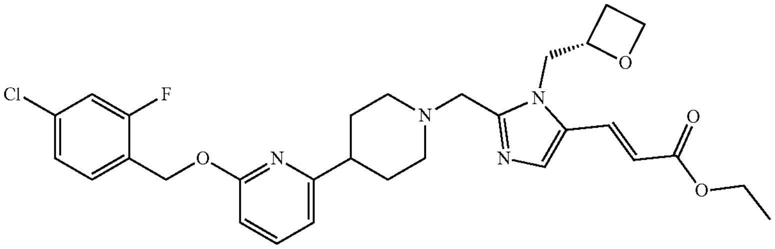 [SMILES: CCOC(=O)/C=C/c1cnc(CN2CCC(c3cccc(OCc4ccc(Cl)cc4F)n3)CC2)n1C[C@@H]1CCO1]

To a solution of (S)-2-((4-(6-((4-chloro-2-fluorobenzyl)oxy)pyridin-2-yl)piperidin-1-yl)methyl)-1-(oxetan-2-ylmethyl)-1H-imidazole-5-carbaldehyde (40.0 mg, 0.0800 mmol) in 2 mL of THF was added NaH (60% in oil, 13.0 mg, 0.320 mmol) at 0° C. After the mixture was stirred at 0° C. for 30 mins, ethyl 2-(diethoxyphosphoryl)acetate (53.8 mg, 0.240 mmol) was added. The mixture was stirred at room temperature for 3 h. LCMS showed the reaction was completed. The mixture was quenched by the saturated aqueous $NH_4Cl$, and extracted with DCM (30 mL). The organic layer was washed with water (20 mL), dried and concentrated. The residue was purified by prep-HPLC to give ethyl (S,E)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)acrylate (40.0 mg, 0.0700 mmol, 88% yield) as a white solid. LCMS: m/z=569.0, 571.0 (M+H)$^+$.

Step J: (S,E)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)acrylic acid

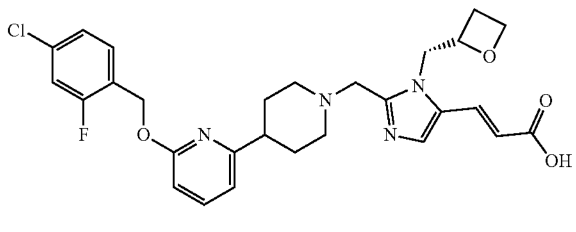

The mixture of ethyl (S,E)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)acrylate (40.0 mg, 0.0700 mmol) and LiOH (8.00 mg, 0.280 mmol) in THF/$H_2O$=2:1 (3 mL) was stirred at room temperature for 12 h when LCMS showed the reaction was completed. The mixture was adjusted to pH=5 with formic acid, and purified by prep-HPLC to give (S,E)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)acrylic acid (23.6 mg, 0.0440 mmol, 63% yield). $^1$H NMR (400 MHz, DMSO-$d_6$) δ 12.24 (br.s, 1H), 7.53-7.66 (m, 4H), 7.46 (dd, J=10.0, 2.0 Hz, 1H), 7.30 (dd, J=8.4, 2.0 Hz, 1H), 6.87 (d, J=7.2 Hz, 1H), 6.67 (d, J=8.4 Hz, 1H), 6.28 (d, J=16.0 Hz, 1H), 5.37 (s, 2H), 4.88-5.00 (m, 1H), 4.54 (dd, J=15.6, 7.2 Hz, 1H), 4.39-4.49 (m, 2H), 4.30-4.36 (m, 1H), 3.69 (d, J=13.6 Hz, 1H), 3.52 (d, J=13.6 Hz, 1H), 2.93 (d, J=10.8 Hz, 1H), 2.78 (d, J=11.2 Hz, 1H), 2.64-2.71 (m, 1H), 2.55-2.61 (m, 1H), 2.35-2.42 (m, 1H), 2.10 (dt, J=21.6, 10 Hz, 2H), 1.63-1.80 (m, 4H). LCMS: m/z=541.2, 543.2 (M+H)$^+$.

(E)-3-(2-((4-(6-((4-Chloro-2-fluorobenzyl)oxy)pyridin-2-yl)piperidin-1-yl)methyl)-1-(2-methoxyethyl)-1H-imidazol-5-yl)acrylic acid (Compound 106) was synthesized 2-methoxyethanamine in step A.

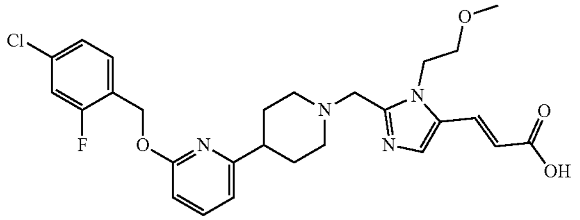 [SMILES: COCCn1c(/C=C/C(=O)O)cnc1CN1CCC(c2cccc(OCc3ccc(Cl)cc3F)n2)CC1]

$^1$H NMR (400 MHz, DMSO-$d_6$) δ: 12.23 (br.s, 1H), 7.64 (t, J=8.0 Hz, 1H), 7.56 (t, J=8.0 Hz, 1H), 7.41-7.53 (m, 3H), 7.30 (dd, J=8.4, 1.6 Hz, 1H), 6.87 (d, J=7.2 Hz, 1H), 6.68 (d, J=8.0 Hz, 1H), 6.29 (d, J=15.6 Hz, 1H), 5.37 (s, 2H), 4.36 (t, J=5.2 Hz, 2H), 3.65 (t, J=5.2 Hz, 2H), 3.61 (s, 2H), 3.23 (s, 3H), 2.86 (d, J=10.8 Hz, 2H), 2.59-2.52 (m, 1H), 2.11 (t, J=10.4 Hz, 2H), 1.55-1.83 (m, 4H). LC-MS: m/z 529.2 (M+H)$^+$ (E)-3-(2-((4-((R)-2-(4-Chlorophenyl)-2,3-dihydrobenzo[b][1,4]dioxin-5-yl)piperidin-1-yl)methyl)-1-(((S)-oxetan-2-yl)methyl)-1H-imidazol-5-yl)acrylic acid (Compound 116a) was synthesized following the route of Example 1, using (R)-4-(2-(4-chlorophenyl)-2,3-dihydrobenzo[b][1,4]dioxin-5-yl)piperidin-1-ium chloride in step F.

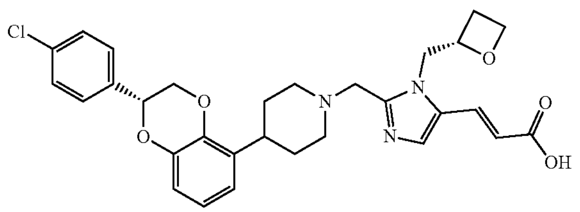 [SMILES: O=C(O)/C=C/c1cnc(CN2CCC(c3cccc4c3OC[C@@H](c3ccc(Cl)cc3)O4)CC2)n1C[C@@H]1CCO1]

$^1$H NMR (400 MHz, $CD_3OD$) δ 7.55 (d, J=16.0 Hz, 1H), 7.45 (s, 1H), 7.73 (dd, J=15.6, 8.4 Hz, 4H), 6.78-6.83 (m, 3H), 6.39 (d, J=15.6 Hz, 1H), 5.11-5.15 (m, 2H), 4.62-4.67 (m, 2H), 4.43-4.51 (m, 3H), 3.91-4.02 (m, 3H), 3.19 (d, J=11.2 Hz, 1H), 3.12 (d, J=10.4 Hz, 1H), 3.00 (t, J=12.0 Hz, 1H), 2.75-2.87 (m, 1H), 2.49-2.55 (m, 3H), 1.78-1.93 (m, 4H). LC-MS: m/z 550.0 $(M+H)^+$.

(E)-3-(2-((4-((R)-2-(4-chlorophenyl)-2,3-dihydrobenzo[b][1,4]dioxin-5-yl)piperidin-1-yl)methyl)-1-(((S)-oxetan-2-yl)methyl)-1H-imidazol-5-yl)-2-methylacrylic acid (Compound 115a) was synthesized following the route of example 1, using (R)-4-(2-(4-chlorophenyl)-2,3-dihydrobenzo[b][1,4]dioxin-5-yl)piperidin-1-ium chloride in step F and methyl 2-(diethoxyphosphoryl)propanoate in step I.

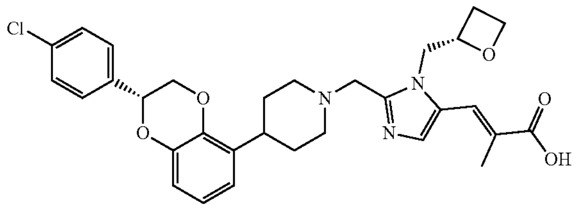 [SMILES: C/C(=C\c1cnc(CN2CCC(c3cccc4c3OC[C@@H](c3ccc(Cl)cc3)O4)CC2)n1C[C@@H]1CCO1)C(=O)O]

LC-MS: m/z 564.6 $(M+H)^+$ $^1$H NMR (400 MHz, DMSO) δ 7.55 (s, 1H), 7.50 (s, 4H), 7.21 (s, 1H), 6.77-6.86 (m, 3H), 5.25 (d, J=7.6 Hz, 1H), 4.93-4.95 (m, 1H), 4.44-4.55 (m, 3H), 4.34-4.42 (m, 2H), 3.99-4.11 (m, 1H), 3.70 (d, J=13.2 Hz, 1H), 3.56 (d, J=13.2 Hz, 1H), 2.94 (d, J=10.6 Hz, 1H), 2.81-2.84 (m, 2H), 2.64-2.73 (m, 1H), 2.33-2.43 (m, 1H), 2.03-2.19 (m, 2H), 2.00 (s, 3H), 1.74 (d, J=11.2 Hz, 1H), 1.52-1.69 (m, 3H).

Example 2

(S)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)propanoic acid (Compound 102a)

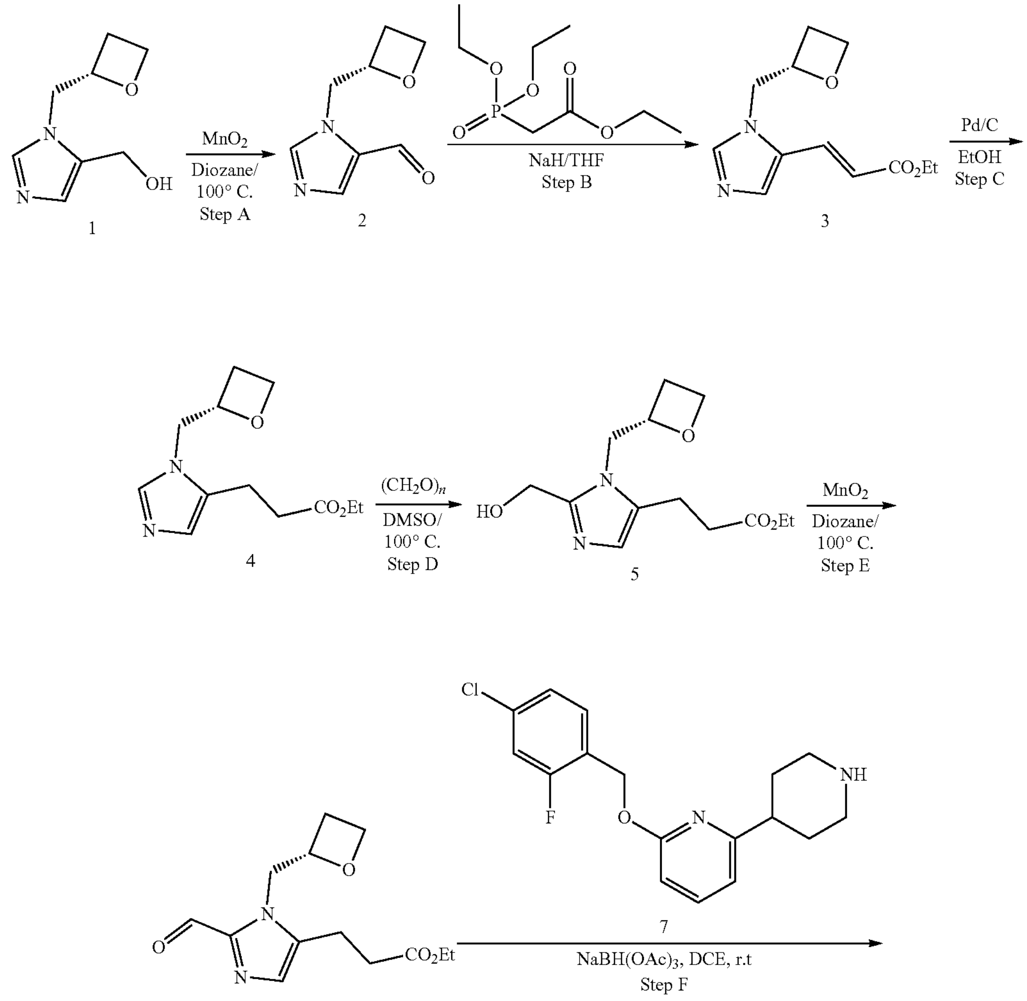

1 2 3 4 5 6 7

-continued

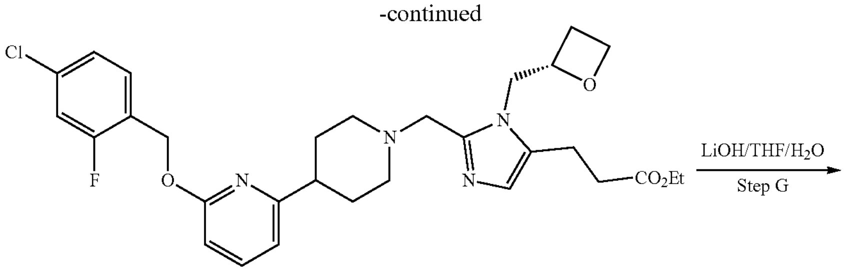

8

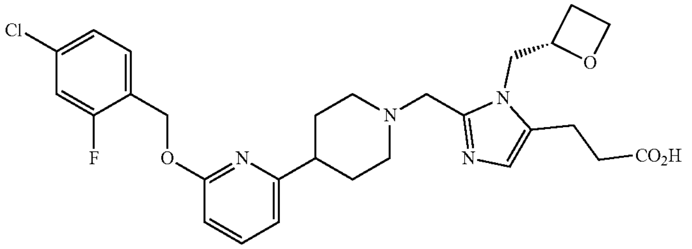

Compound 102a

Step A: (S)-1-(oxetan-2-ylmethyl)-1H-imidazole-5-carbaldehyde

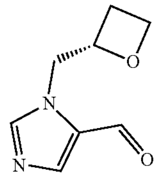 [SMILES: O=Cc1cncn1C[C@@H]1CCO1]

To a mixture of (S)-(1-(oxetan-2-ylmethyl)-1H-imidazol-5-yl)methanol (300 mg, 1.78 mmol) in dioxane (8 mL) was added $MnO_2$ (780 mg, 8.90 mmol). The mixture was stirred at 100° C. for 12h. LCMS showed the reaction was completed. The mixture was filtered and concentrated. The residue was purified by flash chromatography (eluted with DCM/MeOH=10/1) to afford the title compound (S)-1-(oxetan-2-ylmethyl)-1H-imidazole-5-carbaldehyde (260 mg, 1.56 mmol, 88% yield) as yellow oil. $^1$H NMR (400 MHz, DMSO-$d_6$) δ 9.74 (d, J=1.2 Hz, 1H), 8.04 (s, 1H), 7.91 (d, J=0.8 Hz, 1H), 4.87-4.93 (m, 1H), 4.59-4.64 (m, 1H), 4.44-4.52 (m, 2H), 4.23-4.33 (m, 3H), 2.59-2.68 (m, 1H), 2.23-2.31 (m, 1H). LCMS: m/z=167.0 $(M+H)^+$.

Step B: ethyl (S,E)-3-(oxetan-2-ylmethyl)-1H-imidazol-5-yl)acrylate

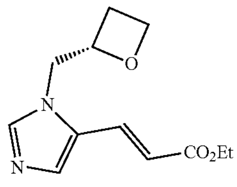 [SMILES: CCOC(=O)/C=C/c1cncn1C[C@@H]1CCO1]

To a solution of ethyl 2-(diethoxyphosphoryl)acetate (702 mg, 3.13 mmol) in THF (5 mL) was added NaH (60% in oil, 125 mg, 3.13 mmol). The mixture was stirred at room temperature for 0.5 h and then (S)-1-(oxetan-2-ylmethyl)-1H-imidazole-5-carbaldehyde (260 mg, 1.56 mmol) was added. The mixture was stirred at room temperature for 2 h. LCMS showed the reaction was completed. The mixture was quenched by $H_2O$ (10 mL), and extracted with EA (2×10 mL). The combined organic phase was dried over anhydrous $Na_2SO_4$ and concentrated. The residue was purified by flash chromatography (eluted with DCM/MeOH=10/1) to afford the title compound ethyl (S,E)-3-(1-(oxetan-2-ylmethyl)-1H-imidazol-5-yl)acrylate (306 mg, 1.29 mmol, 83% yield) as colorless oil. $^1$H NMR (400 MHz, DMSO-$d_6$) δ 7.82 (s, 1H), 7.66 (s, 1H), 7.58 (d, J=16 Hz, 1H), 6.40 (d, J=15.6 Hz, 1H), 4.85-4.91 (m, 1H), 4.41-4.47 (m, 1H), 4.34-4.37 (m, 2H), 4.16-4.21 (m, 3H), 2.60-2.68 (m, 1H), 2.22-2.30 (m, 1H), 1.19 (t, J=7.2 Hz, 3H). LCMS: m/z=237.1 $(M+H)^+$.

Step C: ethyl S)-3-(oxetan-2-ylmethyl)-1H-imidazol-5-yl)propanoate

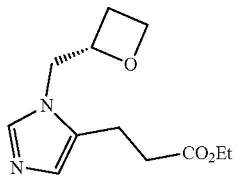 [SMILES: CCOC(=O)CCc1cncn1C[C@@H]1CCO1]

To a mixture of ethyl (S,E)-3-(1-(oxetan-2-ylmethyl)-1H-imidazol-5-yl)acrylate (300 mg, 1.27 mmol) in EtOH (6 mL) was added Pd/C (30 mg). The mixture was stirred at room temperature under $H_2$ atmosphere for 12h. LCMS showed the reaction was completed. The mixture was filtered and concentrated to afford the title compound ethyl (S)-3-(1-(oxetan-2-ylmethyl)-1H-imidazol-5-yl)propanoate (300 mg, 99% yield) as yellow oil. $^1$H NMR (400 MHz, $CDCl_3$) δ 7.57 (s, 1H), 6.82 (s, 1H), 5.01-5.07 (m, 1H), 4.59-4.64 (m, 1H), 4.32-4.37 (m, 1H), 4.12-4.23 (m, 4H), 2.87-2.90 (m, 2H), 2.65-2.71 (m, 3H), 2.19-2.36 (m, 1H), 1.26 (t, J=7.2 Hz, 3H). LCMS: m/z=239.1 $(M+H)^+$.

Step D: ethyl (S)-3-(2-(hydroxymethyl)-1-(oxetan-2-ylmethyl)-1H-imidazol-5-yl)propanoate

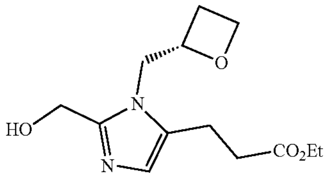 [SMILES: CCOC(=O)CCc1cnc(CO)n1C[C@@H]1CCO1]

To a solution of ethyl (S)-3-(1-(oxetan-2-ylmethyl)-1H-imidazol-5-yl)propanoate (300 mg, 1.26 mmol) in DMSO (3 mL) was added paraformaldehyde (283 mg, 3.15 mmol) at room temperature. The mixture was stirred at 100° C. for 12h. LCMS showed the reaction was completed. The mixture was filtered and purified by reverse phase column flash to afford ethyl (S)-3-(2-(hydroxymethyl)-1-(oxetan-2-ylmethyl)-1H-imidazol-5-yl)propanoate (100 mg, 30% yield) as yellow oil. $^1$H NMR (400 MHz, $CDCl_3$) δ 6.92 (br.s, 1H), 5.05-5.10 (m, 1H), 4.83-4.85 (m, 2H), 4.62-4.68 (m, 1H), 4.42-4.48 (m, 2H), 4.26-4.30 (m, 1H), 4.17 (q, J=7.2 Hz, 2H), 2.97 (t, J=7.2 Hz, 2H), 2.75-2.83 (m, 1H), 2.68 (t, J=7.2 Hz, 2H), 2.42-2.49 (m, 1H), 1.25-1.27 (m, 3H). LCMS: m/z=269.1 $(M+H)^+$.

Step E: ethyl S)-3-(2-formyl-1-(oxetan-2-ylmethyl)-1H-imidazol-5-yl)propanoate

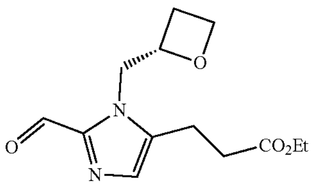 [SMILES: CCOC(=O)CCc1cnc(C=O)n1C[C@@H]1CCO1]

To a solution of ethyl (S)-3-(2-(hydroxymethyl)-1-(oxetan-2-ylmethyl)-1H-imidazol-5-yl)propanoate (100 mg, 0.370 mmol) in dioxane (5 mL) was added $MnO_2$ (162 mg, 1.86 mmol). The mixture was stirred at 100° C. for 12h. LCMS showed the reaction was completed. The mixture was cooled to room temperature. The mixture was filtered and concentrated. The residue was purified by Prep-TLC (eluted with DCM/MeOH=10/1) to afford the title compound ethyl (S)-3-(2-formyl-1-(oxetan-2-ylmethyl)-1H-imidazol-5-yl) propanoate (40 mg, 41% yield) as colorless oil. $^1$H NMR (400 MHz, $CDCl_3$) δ 9.73 (s, 1H), 7.12 (s, 1H), 5.05-5.09 (m, 1H), 4.64 (d, J=4.8 Hz, 2H), 4.57-4.61 (m, 1H), 4.35-4.41 (m, 1H), 4.16 (q, J=7.2 Hz, 2H), 3.06-3.11 (m, 2H), 2.70-2.77 (m, 3H), 2.35-2.40 (m, 1H), 1.26 (t, J=7.2 Hz, 3H). LCMS: m/z=267.2 $(M+H)^+$.

Step F: ethyl (S)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)propanoate

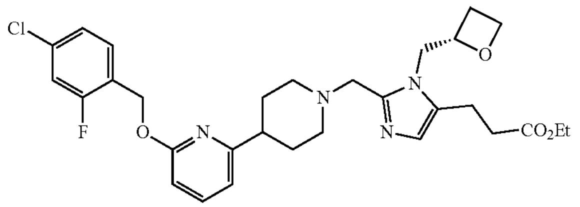 [SMILES: CCOC(=O)CCc1cnc(CN2CCC(c3cccc(OCc4ccc(Cl)cc4F)n3)CC2)n1C[C@@H]1CCO1]

To a mixture of ethyl (S)-3-(2-formyl-1-(oxetan-2-ylmethyl)-1H-imidazol-5-yl)propanoate (40.0 mg, 0.150 mmol) in DCE (3 mL) were added 2-((4-chloro-2-fluorobenzyl) oxy)-6-(piperidin-4-yl)pyridine (48.0 mg, 0.150 mmol) and $NaBH(OAc)_3$ (48.0 mg, 0.230 mmol) at room temperature. The mixture was stirred at room temperature for 5h. LCMS showed the reaction was completed. The mixture was quenched by $H_2O$ (5 mL). The mixture was extracted with DCM (2×15 mL). The combined organic phase was dried over anhydrous $Na_2SO_4$ and concentrated. The residue was purified by Prep-TLC (eluted with DCM/MeOH=10/1) to afford the title compound ethyl (S)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)propanoate (70.0 mg, 82% yield) as colorless oil. LCMS: m/z=571.3 $(M+H)^+$.

Step G: (S)-3-(2-((4-(6-((4-chloro-2-fluorobenzyl) oxy)pyridin-2-yl)piperidin-1-yl)methyl)-1-(oxetan-2-ylmethyl)-1H-imidazol-5-yl)propanoic acid

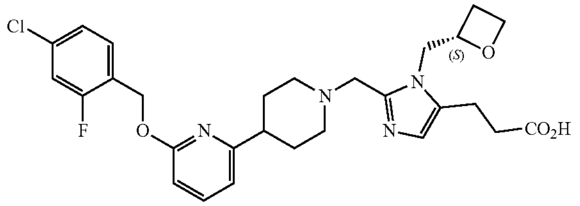

To a mixture of ethyl (S)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)propanoate (70.0 mg, 0.120 mmol) in THF/$H_2O$ (4 mL/1 mL) was added LiOH (24.0 mg, 0.980 mmol) at room temperature. The mixture was stirred at room temperature for 12h. LCMS showed the reaction was completed. HCOOH (1 mL) was added into the mixture. The mixture was concentrated. The residue was purified by Prep-HPLC to afford the title compound (S)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)propanoic acid (30.0 mg, 46% yield) as white solid. $^1$H NMR (400 MHz, $CD_3OD$) δ7.59 (t, J=8.0 Hz, 1H), 7.48 (t, J=8.0 Hz, 1H), 7.17-7.23 (m, 2H), 6.88 (s, 1H), 6.83 (d, J=7.2 Hz, 1H), 6.65 (d, J=8.4 Hz, 1H), 5.41 (s, 2H), 5.11-5.16 (m, 1H), 4.49-4.69 (m, 3H), 4.38 (dd, J=13.6-2.0 Hz, 1H), 3.96 (q, J=14.4 Hz, 2H). 3.10-3.17 (m, 2H), 2.91 (t, J=7.2 Hz, 2H), 2.72-2.83 (m, 2H), 2.60 (t, J=7.2 Hz, 2H), 2.48-2.55 (m, 3H), 1.86-1.92 (m, 4H). LCMS: m/z=543.2 $(M+H)^+$.

Example 3
(E)-3-(6-((4-(6-((4-chloro-2-fluorobenzyl)oxy)pyridin-2-yl)piperidin-1-yl)methyl)pyridin-3-yl)acrylic acid (Compound 123)
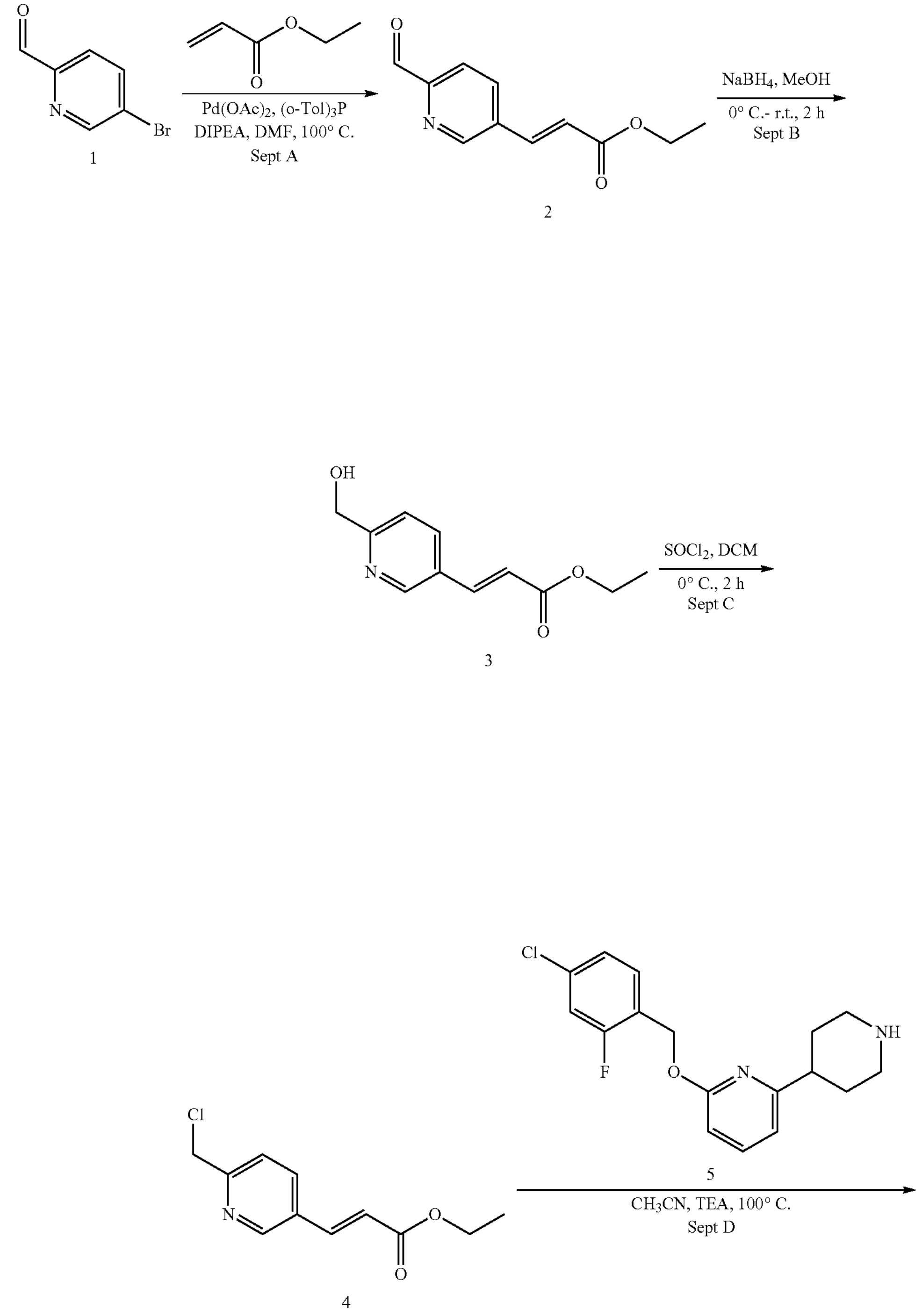

-continued

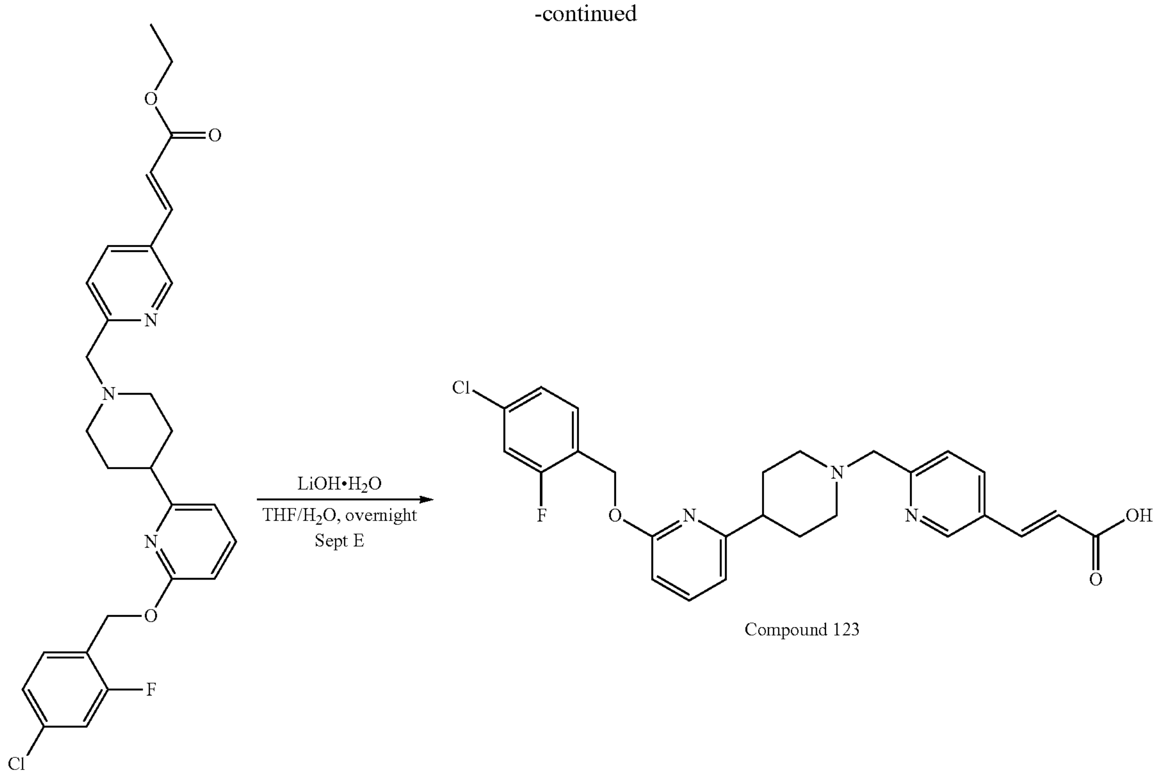

6

Compound 123

Step A: ethyl E)-3-(6-formylpyridin-3-yl)acrylate

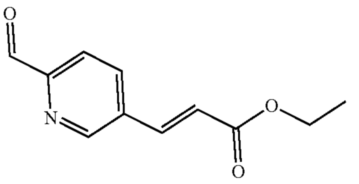

A mixture of compound 5-bromopicolinaldehyde (2.00 g, 10.8 mmol), ethyl acrylate (5.72 mL, 53.8 mmol), $Pd(OAc)_2$ (604 mg, 1.08 mmol), $P(o\text{-tol})_3$ (656 mg, 2.05 mmol) and DIPEA (5.32 mL, 32.2 mmol) in dry DMF (80 mL) was stirred at 100° C. overnight under $N_2$ atmosphere. The reaction mixture was filtered through celite and diluted with EtOAc (3×100 mL). The combined organic phase was washed with brine (80 mL), dried over anhydrous $Na_2SO_4$, filtered and concentrated. The residue was purified by flash chromatography (PE/EtOAc=10/1) to afford the title compound ethyl (E)-3-(6-formylpyridin-3-yl)acrylate (870 mg, 39% yield) as a yellow solid. LC-MS: m/z 206.2 $(M+H)^+$.

Step B: ethyl E)-3-(6-(hydroxymethyl)pyridin-3-yl)acrylate

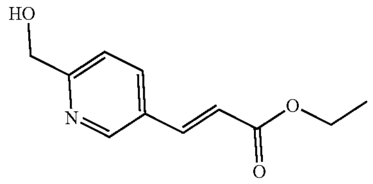

To a solution of ethyl (E)-3-(6-formylpyridin-3-yl)acrylate (870 mg, 4.24 mmol) in MeOH (5 mL) was added $NaBH_4$ (482 mg, 12.7 mmol) at 0° C. The resulting mixture was stirred at room temperature for 2 h. Then the reaction was quenched with water (30 mL) and extracted with EtOAc (3×20 mL). The combined organic layers were washed with brine (30 mL), dried over anhydrous $Na_2SO_4$ and concentrated. The residue was purified by flash chromatography (eluted with PE/EtOAc=1/1) to afford the title compound ethyl (E)-3-(6-(hydroxymethyl)pyridin-3-yl)acrylate as a yellow solid (700 mg, 80% yield). LC-MS: m/z 208.2 $(M+H)^+$.

Step C: ethyl E)-3-(6-(chloromethyl)pyridin-3-yl)acrylate

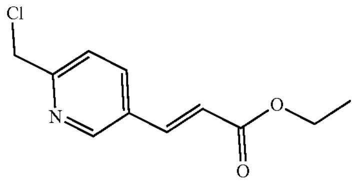

To a solution of ethyl (E)-3-(6-(hydroxymethyl)pyridin-3-yl)acrylate (700 mg, 3.38 mmol) in DCM (10 mL) was added $SOCl_2$ (0.50 mL, 6.76 mmol) at 0° C. The resulting mixture was stirred at 0° C. for 2 hours. The solution was quenched with water (30 mL) and extracted with EtOAc (3×20 mL). The combined organic layers were washed with brine (30 mL), dried over anhydrous $Na_2SO_4$ and concentrated. The residue was purified by flash chromatography (eluted with PE/EtOAc=2/1) to afford the title compound ethyl (E)-3-(6-(chloromethyl)pyridin-3-yl)acrylate as a white solid (750 mg, 88% yield). LC-MS: m/z 226.1 $(M+H)^+$.

Step D: ethyl E)-3-(6-((4-(6-((4-chloro-2-fluorobenzyl)oxy)pyridin-2-yl)piperidin-1-yl)methyl)pyridin-3-yl)acrylate

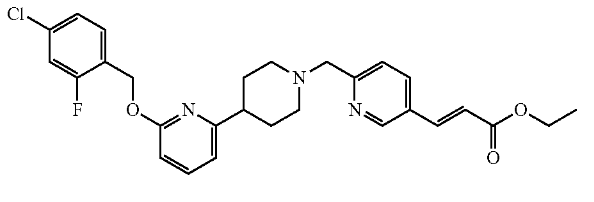 [SMILES: CCOC(=O)/C=C/c1ccc(CN2CCC(c3cccc(OCc4ccc(Cl)cc4F)n3)CC2)nc1]

A solution of ethyl (E)-3-(6-(chloromethyl)pyridin-3-yl) acrylate (300 mg, 1.33 mmol,), 2-((4-chloro-2-fluorobenzyl) oxy)-6-(piperidin-4-yl)pyridine (427 mg, 1.33 mmol) and $Et_3N$ (0.55 mL, 4.00 mmol) in $CH_3CN$ (2 mL) was stirred at 100° C. overnight under $N_2$ atmosphere. The reaction mixture was diluted with water (20 mL) and extracted with EtOAc (3×20 mL). The combined organic phase was washed with brine (20 mL), dried over anhydrous $Na_2SO_4$ and concentrated. The residue was purified by flash chromatography (eluted with DCM/MeOH=50/1) to afford the title compound ethyl (E)-3-(6-((4-(6-((4-chloro-2-fluorobenzyl)oxy)pyridin-2-yl)piperidin-1-yl)methyl)pyridin-3-yl)acrylate (552 mg, 54% yield) as a colorless oil. LC-MS: m/z 510.2 $(M+H)^+$.

Step E: (E)-3-(6-((4-(6-((4-chloro-2-fluorobenzyl) oxy)pyridin-2-yl)piperidin-1-yl)methyl)pyridin-3-yl) acrylic acid

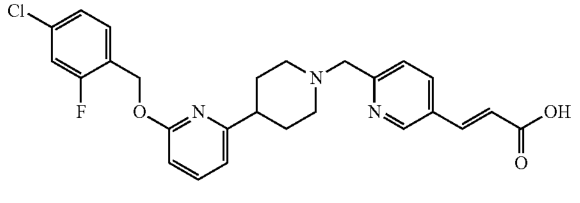 [SMILES: O=C(O)/C=C/c1ccc(CN2CCC(c3cccc(OCc4ccc(Cl)cc4F)n3)CC2)nc1]

To a solution of ethyl (E)-3-(6-((4-(6-((4-chloro-2-fluorobenzyl)oxy)pyridin-2-yl)piperidin-1-yl)methyl)pyridin-3-yl)acrylate (100 mg, 0.220 mmol) in $THF/H_2O$ (1 mL/1 mL) was added $LiOH \cdot H_2O$ (18.0 mg, 0.440 mmol). The resulting mixture was stirred at room temperature overnight. Then the reaction mixture was adjusted to pH=5-6 with 1 M HCl solution. The mixture was extracted with EtOAc (3×10 mL). The combined organic layers were washed with water (10 mL) and brine (10 mL), dried over $Na_2SO_4$, concentrated and purified with Prep-HPLC to afford (E)-3-(6-((4-(6-((4-chloro-2-fluorobenzyl)oxy)pyridin-2-yl)piperidin-1-yl) methyl)pyridin-3-yl)acrylic acid as white solid (20.0 mg, 19% yield).

$^1H$ NMR (400 MHz, $CD_3OD$) δ 8.75 (d, J=2.0 Hz, 1H), 8.08 (dd, J=8.4, 2.4 Hz, 1H), 7.58-7.65 (m, 1H), 7.44-7.56 (m, 3H), 7.16-7.27 (m, 2H), 6.87 (d, J=7.2 Hz, 1H), 6.63-6.69 (m, 2H), 5.43 (s, 2H), 4.21 (s, 2H), 3.42 (d, J=12.2 Hz, 2H), 2.86-2.91 (m, 3H), 2.03-2.13 (m, 4H). LC-MS: m/z 482.1 $(M+H)^+$.

Example 4

3-(6-((4-(6-((4-chloro-2-fluorobenzyl)oxy)pyridin-2-yl)piperidin-1-yl)methyl)pyridin-3-yl)propanoic acid (Compound 118)

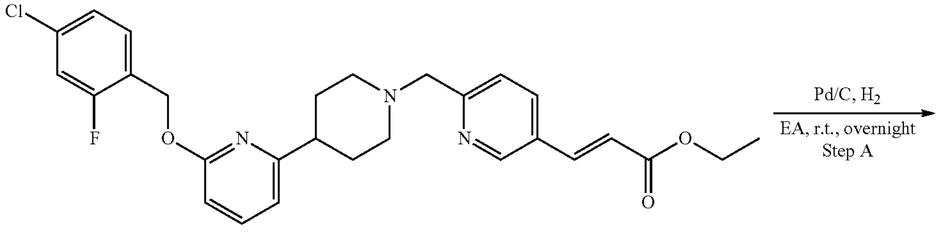

1

-continued

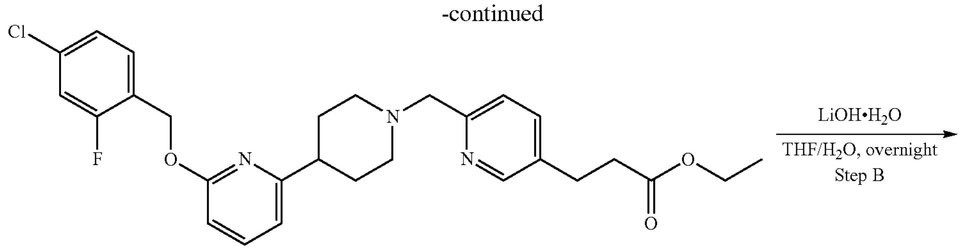

2

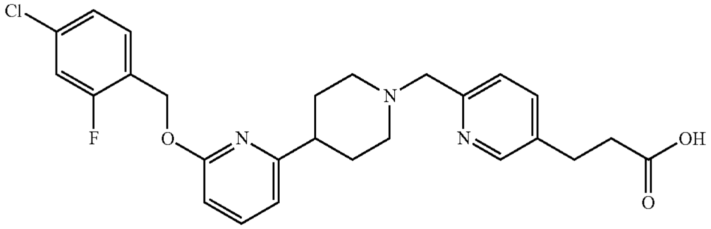

Compound 118

Step A: ethyl 3-(6-((4-(6-((4-chloro-2-fluorobenzyl)oxy)pyridin-2-yl)piperidin-1-yl)methyl)pyridin-3-yl)propanoate

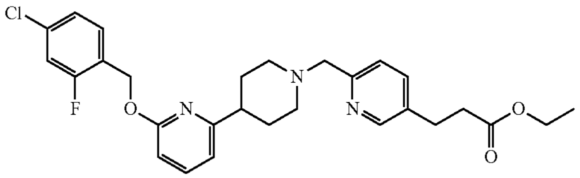 [SMILES: CCOC(=O)CCc1ccc(CN2CCC(c3cccc(OCc4ccc(Cl)cc4F)n3)CC2)nc1]

To a solution of ethyl (E)-3-(6-((4-(6-((4-chloro-2-fluorobenzyl)oxy)pyridin-2-yl)piperidin-1-yl)methyl)pyridin-3-yl)acrylate (100 mg, 0.200 mmol) in EtOH (2 mL) was added Pd/C (10.0 mg) under $H_2$. The resulting mixture was degassed and refilled with $H_2$ for three times. Then the mixture was stirred at room temperature for 12 h under $H_2$ atmosphere. The reaction mixture was filtered through celite and concentrated to afford the title compound ethyl 3-(6-((4-(6-((4-chloro-2-fluorobenzyl)oxy)pyridin-2-yl)piperidin-1-yl)methyl)pyridin-3-yl)propanoate (10.0 mg, 100% yield, overweight). The title compound was used in next step directly without purification. LC-MS: m/z 512.2 $(M+H)^+$.

Step B: 3-(6-((4-(6-((4-chloro-2-fluorobenzyl)oxy)pyridin-2-yl)piperidin-1-yl)methyl)pyridin-3-yl)propanoic acid

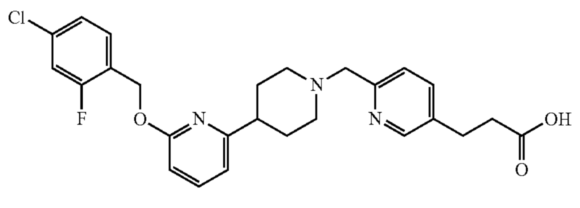 [SMILES: O=C(O)CCc1ccc(CN2CCC(c3cccc(OCc4ccc(Cl)cc4F)n3)CC2)nc1]

To a solution of ethyl 3-(6-((4-(6-((4-chloro-2-fluorobenzyl)oxy)pyridin-2-yl)piperidin-1-yl)methyl)pyridin-3-yl)propanoate (100 mg, 0.190 mmol) in THF/$H_2O$ (2 mL/2 mL) was added LiOH·$H_2O$ (16.0 mg, 0.390 mmol). The resulting mixture was stirred at room temperature overnight. Then the reaction mixture was adjusted to pH=5~6 with 1 M HCl solution. The mixture was extracted with EtOAc (3×10 mL). The organic combined layers were washed with water (10 mL) and brine (10 mL), dried over $Na_2SO_4$, concentrated and purified with Prep-HPLC to afford 3-(6-((4-(6-((4-chloro-2-fluorobenzyl)oxy)pyridin-2-yl)piperidin-1-yl)methyl)pyridin-3-yl)propanoic acid as white solid (19.8 mg, 21% yield). 1H NMR (400 MHz, $CD_3OD$) δ 8.57 (d, J=2.0 Hz, 1H), 7.79 (dd, J=7.6, 2.4 Hz, 1H), 7.61-7.67 (m, 1H), 7.50 (t, J=8.0 Hz, 1H), 7.44 (d, J=8.0 Hz, 1H), 7.20-7.25 (m, 2H), 6.89 (d, J=7.2 Hz, 1H), 6.71 (d, J=8.4 Hz, 1H), 5.44 (s, 2H), 4.34 (s, 2H), 3.54 (d, J=12.4 Hz, 2H), 3.09-3.14 (m, 2H), 2.93-3.00 (m, 3H), 2.62 (t, J=7.6 Hz, 2H), 2.09-2.18 (m, 4H). LC-MS: m/z 484.2 $(M+H)^+$.

Example 5

(E)-3-(2-((4-(6-((4-chloro-2-fluorobenzyl)oxy)pyridin-2-yl)piperidin-1-yl)methyl)-1-methyl-1H-imidazol-5-yl)acrylic acid (Compound 104)

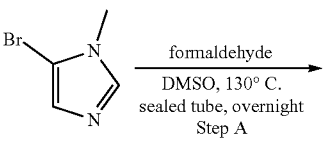

1

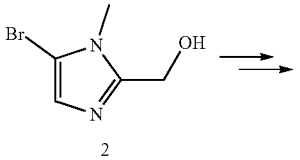

2

-continued

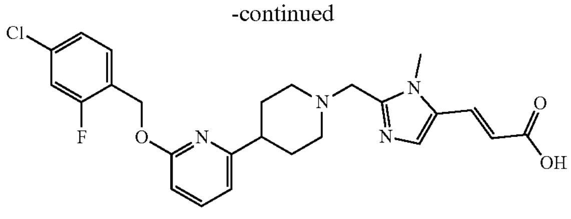

Compound 104

Step A: (2-bromo-1-methyl-1H-imidazol-5-yl)methanol

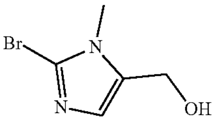

A solution of 5-bromo-1-methyl-1H-imidazole (1.50 g, 9.31 mmol) in DMSO (5 mL) was added paraldehyde (4.20 g, 46.6 mmol). The resulting mixture was stirred at 130° C. in a sealed tube for 12 hours. Filtered and the liquid was concentrated to afford a residue. The residue was purified by reverse phase chromatography to afford (2-bromo-1-methyl-1H-imidazol-5-yl)methanol (1.23 g, 69% yield) as a colorless oil. $^1H$ NMR (400 MHz, DMSO-$d_6$) b 6.91 (s, 1H), 5.37 (t, J=5.6 Hz, 1H), 4.48 (d, J=5.6 Hz, 2H), 3.58 (s, 3H).

(E)-3-(2-((4-(6-((4-Chloro-2-fluorobenzyl)oxy)pyridin-2-yl)piperidin-1-yl)methyl)-1-methyl-1H-imidazol-5-yl) acrylic acid (Compound 104) was synthesized following the route of Example 3, using (2-bromo-1-methyl-1H-imidazol-5-yl)methanol in step A.

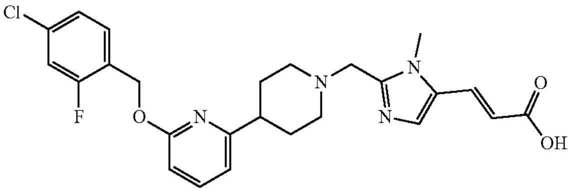

$^1H$ NMR (400 MHz, $CD_3OD$) δ: 8.24 (s, 1H), 7.89 (t, J=8.0 Hz, 1H), 7.62 (d, J=16.0 Hz, 1H), 7.57 (t, J=8.0 Hz, 1H), 7.19-7.30 (m, 2H), 7.08 (d, J=7.6 Hz, 1H), 6.98 (d, J=8.4 Hz, 1H), 6.70 (d, J=16.0 Hz, 1H), 5.48 (s, 2H), 4.88 (s, 2H), 4.08 (s, 3H), 3.77 (d, J=12.0 Hz, 2H), 3.38-3.49 (m, 2H), 3.02-3.14 (m, 1H), 2.20-2.37 (m, 4H). LC-MS: m/z 485.4 $(M+H)^+$

Example 6

(E)-3-(5-((4-(2-(4-chloro-2-fluorophenyl)-2-methylbenzo[d][1,3]dioxol-4-yl)piperidin-1-yl)methyl)-4-(((S)-oxetan-2-yl)methyl)-4H-1,2,4-triazol-3-yl) acrylic acid (Compound 136a)

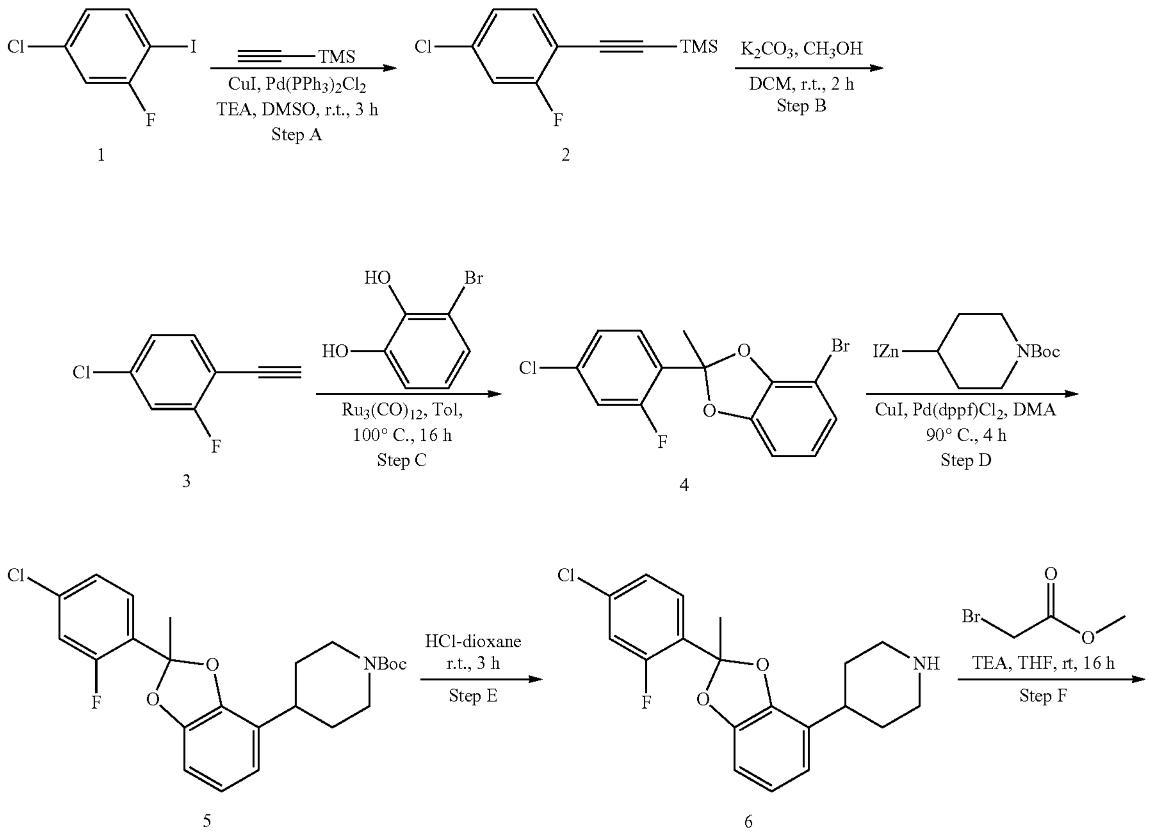

-continued
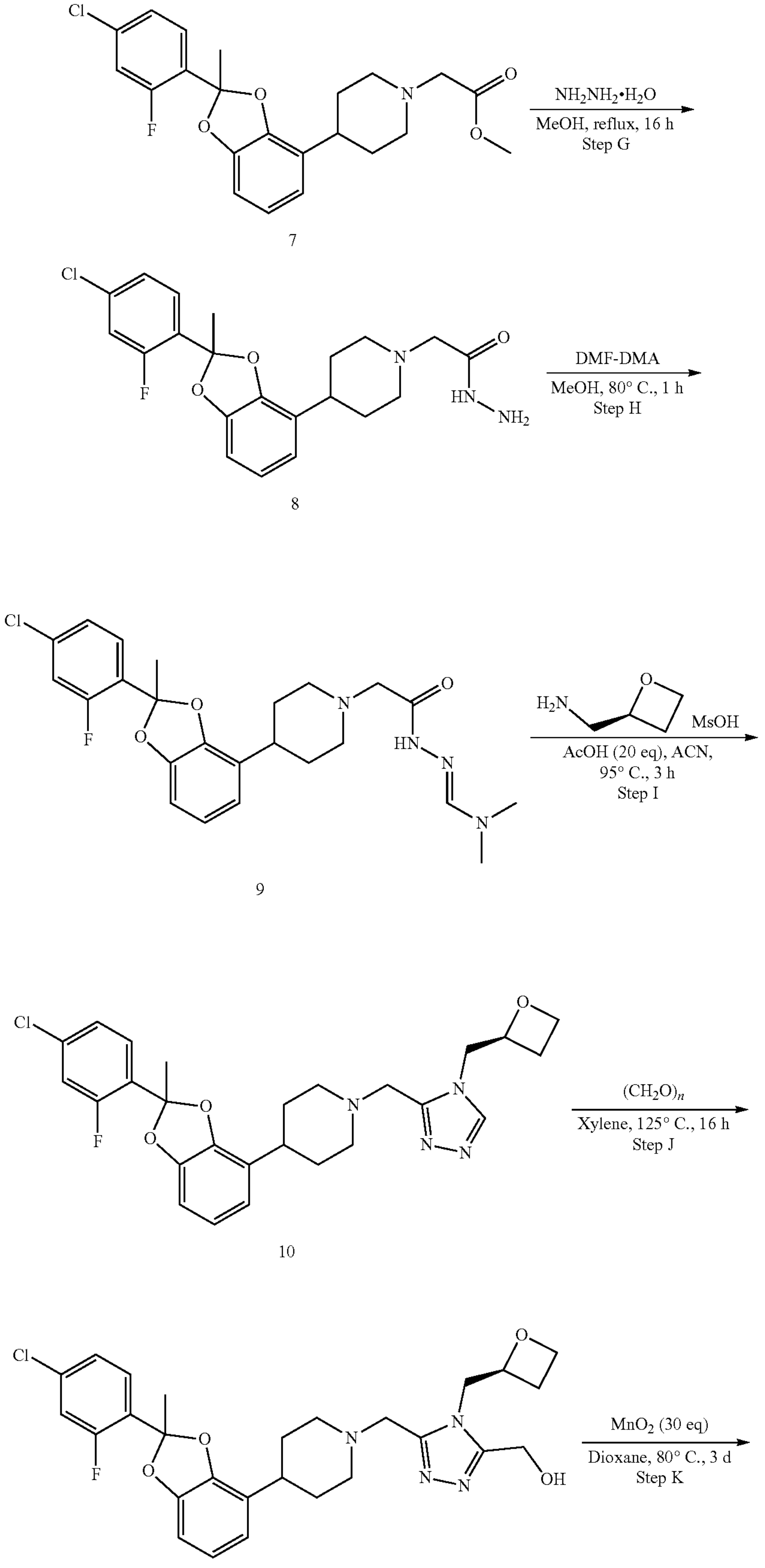
7
8
9
10
11

-continued

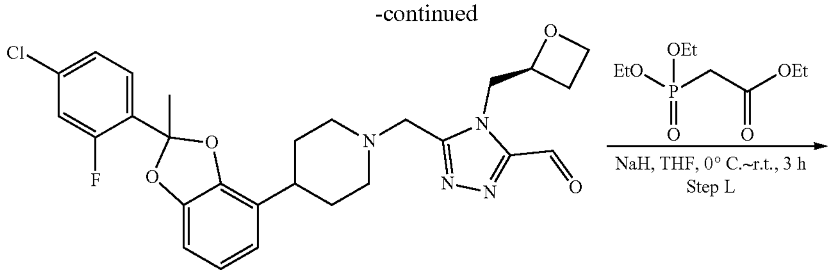

12

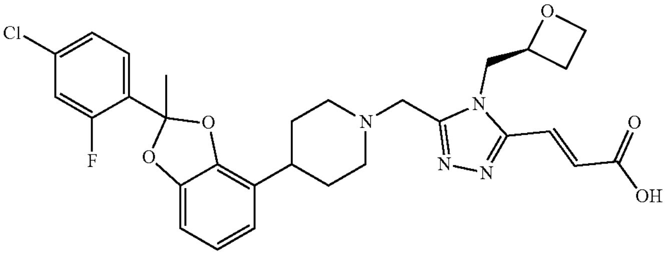

Compound 136a

Step A: ((4-chloro-2-fluorophenyl)ethynyl)trimethylsilane

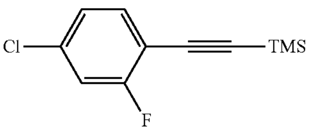 [SMILES: C[Si](C)(C)C#Cc1ccc(Cl)cc1F]

To a solution of 4-chloro-2-fluoro-1-iodobenzene (10.0 g, 39.0 mmol) in DMSO (50 mL) were added ethynyl(trimethyl)silane (4.60 g, 46.8 mmol), copper iodide (0.15 g, 0.78 mmol), bis(triphenylphosphine) palladium(II) chloride (1.09 g, 1.56 mmol) and TEA (5 mL). The reaction mixture was stirred at room temperature for 3 hours. The reaction mixture was added into water (100 mL) and filtered through celite bed. The mixture was extracted with EtOAc (3×50 mL). The organic layer was washed with brine, dried over $Na_2SO_4$, filtered, and concentrated. The residue was purified by silica gel column chromatography (PE: 100%) to afford ((4-chloro-2-fluorophenyl) ethynyl)trimethylsilane (9.00 g, crude) as a white solid. $^1H$ NMR (400 MHz, $CDCl_3$) δ 7.34-7.40 (t, J=8.0 Hz, 1H), 7.05-7.12 (m, 2H), 0.26 (s, 9H).

Step B: 4-chloro-1-ethynyl-2-fluorobenzene

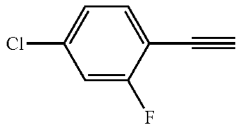

To a solution of ((4-chloro-2-fluorophenyl)ethynyl)trimethylsilane (8.50 g, 37.5 mmol, crude) in DCM (50 mL) was added $K_2CO_3$ (26.0 g 187 mmol) and MeOH (50 mL). The reaction mixture was stirred for 2 hours at room temperature. The mixture was filtered and the filter cake was washed with DCM. The filtrate was concentrated to afford 4-chloro-1-ethynyl-2-fluorobenzene as a white solid (4.80 g, 84.6% over two steps). $^1H$ NMR (400 MHz, $CDCl_3$) δ 7.41 (dd, J=8.4, 7.6 Hz, 1H), 7.09-7.15 (m, 2H), 3.33 (s, 1H).

Step C: 4-bromo-2-(4-chloro-2-fluorophenyl)-2-methylbenzo[d][1,3]dioxole

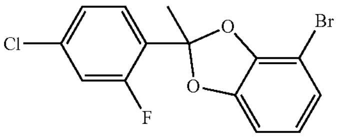 [SMILES: CC1(c2ccc(Cl)cc2F)Oc2cccc(Br)c2O1]

A mixture of 4-chloro-1-ethynyl-2-fluorobenzene (1.00 g, 6.47 mmol), 3-bromobenzene-1,2-diol (1.22 g, 6.47 mmol), and triruthenium dodecacarbonyl (83.0 mg, 0.129 mmol) in toluene (4 mL) was degassed for 1 minute and then heated at 100° C. for 16 hours. The reaction mixture was diluted with EtOAc (30 mL) and filtered through a pad of diatomaceous earth. The filtrate was concentrated in vacuo and purified by silica gel column chromatography (PE: 100%) to afford 4-bromo-2-(4-chloro-2-fluorophenyl)-2-methylbenzo[d][1,3]dioxole as a yellow oil (1.00 g, 45%). $^1H$ NMR (400 MHz, $CDCl_3$) δ 7.54 (t, J=8.4 Hz, 1H), 7.11-7.18 (m, 2H), 6.95 (dd, J=8.0, 1.6 Hz, 1H), 6.66-6.78 (m, 2H), 2.11 (d, J=0.8 Hz, 3H).

Step D: tert-butyl 4-(2-(4-chloro-2-fluorophenyl)-2-methylbenzo[d][1,3]dioxol-4-yl) piperidine-1-carboxylate

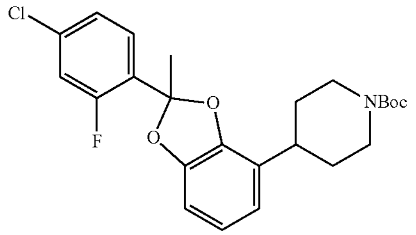 [SMILES: CC(C)(C)OC(=O)N1CCC(c2cccc3c2OC(C)(c2ccc(Cl)cc2F)O3)CC1]

Zinc dust (11.5 g, 175 mmol) was suspended in dimethylaceamide (DMA, 30 mL) and a mixture of trimethylsilyl chloride/1,2-dibromoethane (7:5 w/w, 3.10 g) was added via syringe over several minutes. The temperature rose to 60° C. and stirring was continued for 15 minutes. The reaction mixture was cooled back to room temperature and a solution of tert-butyl 4-iodopiperidine-1-carboxylate (49.5 g, 158.7 mmol) in DMA (80 mL) was added from a syringe over 5 minutes. The temperature rose again to 66° C. Stirring was continued for 2 hours and the mixture was cooled back to room temperature again to give a 1.2 M Zinc reagent solution in DMA.

4-Bromo-2-(4-chloro-2-fluorophenyl)-2-methylbenzo[d][1,3]dioxole (660 mg, 1.92 mmol) was dissolved in DMA (2 mL) and PdCl2(dppf) (47.0 mg, 0.058 mmol) and CuI (22.0 mg, 0.12 mmol) was added. The mixture was degassed with alternate $N_2$/high vacuum (3 times) and a 1.2 M solution of the above zinc reagent solution (5 mL) was added. The mixture was heated to 90° C. for 4 hours, and then cooled in an ice bath. The sat. aq. $NH_4Cl$ (10 mL) and EtOAc (10 mL) were added. The mixture was filtered through Celite and washed with water and EtOAc. The organic layers were separated and the aqueous layer was extracted with EtOAc (2×10 mL). The combined extracts were washed with $NaHCO_3$ solution and brine, dried over $Na_2SO_4$, filtered and concentrated. The resulting oil was purified by silica gel column chromatography (PE/EtOAc=8/10~3/10) to afford tert-butyl 4-(2-(4-chloro-2-fluorophenyl)-2-methylbenzo[d][1,3]dioxol-4-yl)piperidine-1-carboxylate (570 mg, 66.2%) as an yellow oil. LC-MS: m/z 392.2 $(M-56+H)^+$.

Step E: 4-(2-(4-chloro-2-fluorophenyl)-2-methylbenzo[d][1,3]dioxol-4-yl)piperidine

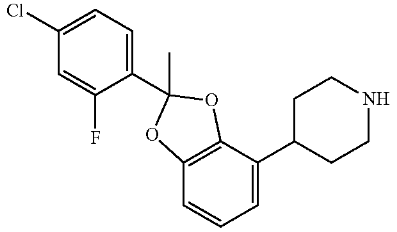 [SMILES: CC1(c2ccc(Cl)cc2F)Oc2cccc(C3CCNCC3)c2O1]

To a solution of tert-butyl 4-(2-(4-chloro-2-fluorophenyl)-2-methylbenzo[d][1,3]dioxol-4-yl)piperidine-1-carboxylate (570 mg, 1.27 mmol) in 1,4-dioxane (4 mL) was added HCl-1,4-dioxane solution (4 M, 4 mL). The mixture was stirred at room temperature for 3 hours. Then the reaction mixture was concentrated and purified by prep-HPLC to afford 4-(2-(4-chloro-2-fluorophenyl)-2-methylbenzo[d][1,3]dioxol-4-yl)piperidine (390 mg, 88.3%) as an yellow oil. $^1H$ NMR (400 MHz, $CDCl_3$) δ 7.53 (t, J=8.0 Hz, 1H), 7.09-7.16 (m, 2H), 6.74-6.80 (m, 1H), 6.67-6.72 (m, 2H), 3.15-3.26 (m, 2H), 2.73-2.85 (m, 3H), 2.05 (s, 3H), 1.75 (m, 4H). LC-MS: m/z 348.3 $(M+H)^+$.

Step F: methyl 2-(4-(2-(4-chloro-2-fluorophenyl)-2-methylbenzo[d][1,3]dioxol-4-yl) piperidin-1-yl)acetate

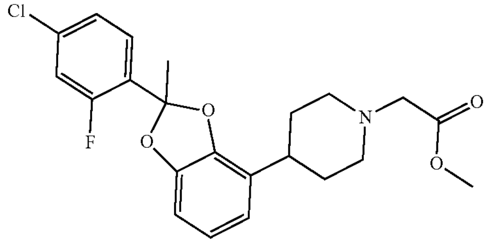 [SMILES: COC(=O)CN1CCC(c2cccc3c2OC(C)(c2ccc(Cl)cc2F)O3)CC1]

To a mixture of 4-(2-(4-chloro-2-fluorophenyl)-2-methylbenzo[d][1,3]dioxol-4-yl) piperidine (500 mg, 1.44 mmol) in THF (10 mL) were added methyl 2-bromoacetate (330 mg, 2.16 mmol) and TEA (0.56 ml, 4.32 mmol). The mixture was stirred at room temperature overnight. The reaction was quenched with water and extracted with DCM (3×50 mL). The organic layers were dried over $Na_2SO_4$, concentrated and purified by silica gel column chromatography (PE/EtOAc=10/1) to afford methyl 2-(4-(2-(4-chloro-2-fluorophenyl)-2-methylbenzo[d][1,3]dioxol-4-yl)piperidin-1-yl) acetate (530 mg, 87%) as a white solid. $^1H$ NMR (400 MHz, DMSO-$d_6$) δ 7.57 (dd, J=10.0, 6.8 Hz, 2H), 7.35 (dd, J=8.4, 1.6 Hz, 1H), 6.69-6.87 (m, 3H), 3.62 (s, 3H), 3.25 (s, 2H), 2.92 (d, J=10.4 Hz, 2H), 2.54-2.63 (m, 1H), 2.28 (dd, J=11.2, 8.4 Hz, 2H), 2.03 (s, 3H), 1.65-1.81 (m, 4H). LC-MS: m/z 420.2 $(M+H)^+$.

Step G: 2-(4-(2-(4-chloro-2-fluorophenyl)-2-methylbenzo[d][1,3]dioxol-4-yl) piperidin-1-yl)acetohydrazide

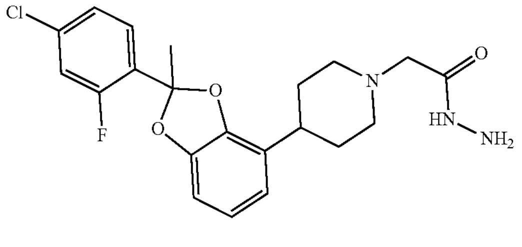 [SMILES: CC1(c2ccc(Cl)cc2F)Oc2cccc(C3CCN(CC(=O)NN)CC3)c2O1]

To a mixture of methyl 2-(4-(2-(4-chloro-2-fluorophenyl)-2-methylbenzo[d][1,3]dioxol-4-yl)piperidin-1-yl)acetate (530 mg, 1.26 mmol) in THF (10 mL) was added hydrazine (190 mg, 3.79 mmol). The mixture was stirred at 80° C. overnight. After cooled down to room temperature, the solvent was evaporated and the residue was purified by silica gel column chromatography (DCM/MeOH=20/1) to afford 2-(4-(2-(4-chloro-2-fluorophenyl)-2-methylbenzo[d][1,3]dioxol-4-yl)piperidin-1-yl)acetohydrazide (509 mg, 96%) as light yellow oil. $^1H$ NMR (400 MHz, DMSO-$d_6$) δ 8.89 (s, 1H), 7.56 (dd, J=13.6, 5.2 Hz, 2H), 7.35 (dd, J=8.4, 1.6 Hz, 1H), 6.74-6.80 (m, 3H), 4.23 (s, 2H), 2.93 (s, 2H), 2.89 (d, J=10.4 Hz, 2H), 2.55-2.64 (m, 1H), 2.16 (dd, J=11.6, 9.6 Hz, 2H), 2.03 (s, 3H), 1.65-1.85 (m, 4H). LC-MS: m/z 420.2 $(M+H)^+$.

Step H: (E)-N'-2-(4-(2-(4-chloro-2-fluorophenyl)-2-methylbenzo[d][1,3]dioxol-4-yl) piperidin-1-yl) acetyl)-N,N-dimethylformohydrazonamide

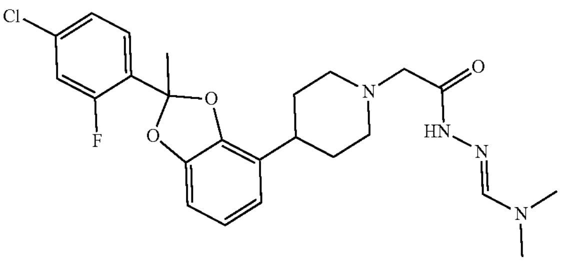 [SMILES: CN(C)/C=N/NC(=O)CN1CCC(c2cccc3c2OC(C)(c2ccc(Cl)cc2F)O3)CC1]

To a mixture of 2-(4-(2-(4-chloro-2-fluorophenyl)-2-methylbenzo[d][1,3]dioxol-4-yl) piperidin-1-yl)acetohydrazide (400 mg, 1.00 mmol) in MeOH (2 mL) was added DMF-DMA (119 mg, 1.00 mmol). The mixture was stirred at 80° C. for 1 hour. After cooled down to room temperature, the mixture was concentrated under vacuum to afford (E)-N'-(2-(4-(2-(4-chloro-2-fluorophenyl)-2-methylbenzo[d][1,3]dioxol-4-yl) piperidin-1-yl)acetyl)-N,N-dimethylformohydrazonamide (462 mg, crude) which was used directly for the next step without further purification. LC-MS: m/z 475.2 $(M+H)^+$.

Step I: 4-(2-(4-chloro-2-fluorophenyl)-2-methylbenzo[d][1,3]dioxol-4-yl)-1-((4-(((S)-oxetan-2-yl)methyl)-4H-1,2,4-triazol-3-yl)methyl)piperidine

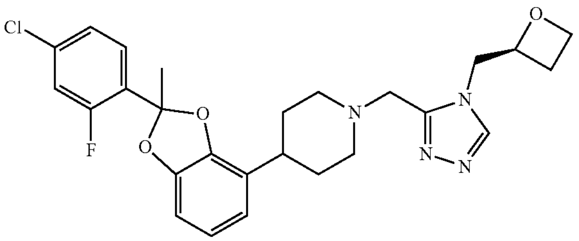 [SMILES: CC1(c2ccc(Cl)cc2F)Oc2cccc(C3CCN(Cc4nncn4C[C@@H]4CCO4)CC3)c2O1]

To a mixture of [(2S)-oxetan-2-yl]methanamine (220 mg, 1.20 mmol, MsOH salt) and (E)-N'-(2-(4-(2-(4-chloro-2-fluorophenyl)-2-methylbenzo[d][1,3]dioxol-4-yl)piperidin-1-yl)acetyl)-N,N-dimethylformohydrazonamide (460 mg, 1.00 mmol) in $CH_3CN$ (5 mL) was added AcOH (1.21 g, 20.0 mmol). The mixture was stirred at 95° C. for 3 hours under nitrogen. After cooled down to room temperature, to the mixture was added 1 N NaOH aq. solution until pH=7. The mixture was diluted with water (40 mL) and extracted with EtOAc (3×30 mL). The combined organic layer was dried over anhydrous $Na_2SO_4$, filtered and concentrated under vacuum. The residue was purified by silica gel column chromatography (DCM/MeOH=25/1) to afford 4-(2-(4-chloro-2-fluorophenyl)-2-methylbenzo[d][1,3]dioxol-4-yl)-1-((4-(((S)-oxetan-2-yl)methyl)-4H-1,2,4-triazol-3-yl)methyl)piperidine (336 mg, 68%) as light yellow oil. LC-MS: m/z 499.2 $(M+H)^+$.

Step J: (5-((4-(2-(4-chloro-2-fluorophenyl)-2-methylbenzo[d][1,3]dioxol-4-yl) piperidin-1-yl)methyl)-4-(((S)-oxetan-2-yl)methyl)-4H-1,2,4-triazol-3-yl) methanol

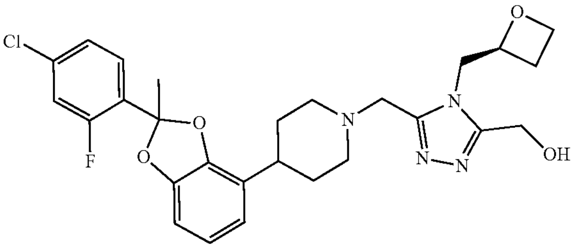 [SMILES: CC1(c2ccc(Cl)cc2F)Oc2cccc(C3CCN(Cc4nnc(CO)n4C[C@@H]4CCO4)CC3)c2O1]

To a mixture of 4-(2-(4-chloro-2-fluorophenyl)-2-methylbenzo[d][1,3]dioxol-4-yl)-1-((4-(((S)-oxetan-2-yl) methyl)-4H-1,2,4-triazol-3-yl)methyl)piperidine (100 mg, 0.20 mmol) in xylene (2 mL) was added paraformaldehyde (120 mg, 4.00 mmol). The mixture was stirred at 125° C. for 16 hours. After cooled down to room temperature, the solvent was removed under vacuum. The residue was diluted with water (10 mL) and extracted with EtOAc (3×20 mL). The organic layer was dried over anhydrous $Na_2SO_4$, concentrated and purified by silica gel column chromatography (DCM/MeOH=10/1) to afford (5-((4-(2-(4-chloro-2-fluorophenyl)-2-methylbenzo [d][1,3]dioxol-4-yl)piperidin-1-yl) methyl)-4-(((S)-oxetan-2-yl)methyl)-4H-1,2,4-triazol-3-yl) methanol (46.0 mg, 45%) as light yellow oil. LC-MS: m/z 529.2 $(M+H)^+$.

Step K: 5-((4-(2-(4-chloro-2-fluorophenyl)-2-methylbenzo[d][1,3]dioxol-4-yl) piperidin-1-yl)methyl)-4-(((S)-oxetan-2-yl)methyl)-4H-1,2,4-triazole-3 carbaldehyde

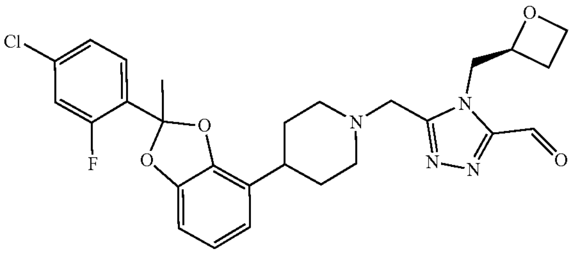 [SMILES: CC1(c2ccc(Cl)cc2F)Oc2cccc(C3CCN(Cc4nnc(C=O)n4C[C@@H]4CCO4)CC3)c2O1]

To a mixture of (5-((4-(2-(4-chloro-2-fluorophenyl)-2-methylbenzo[d][1,3]dioxol-4-yl) piperidin-1-yl)methyl)-4-(((S)-oxetan-2-yl)methyl)-4H-1,2,4-triazol-3-yl)methanol (46.0 mg, 0.08 mmol) in dioxane (2 mL) was added $MnO_2$ (75.0 mg, 0.80 mmol). The mixture was stirred at 80° C. for 72 hours. After cooled down to room temperature, the mixture was filtered through a celite and washed with DCM (4×20 mL). The resulting filtrate was concentrated under vacuum to afford 5-((4-(2-(4-chloro-2-fluorophenyl)-2-methylbenzo[d][1,3]dioxol-4-yl)piperidin-1-yl)methyl)-4-

(((S)-oxetan-2-yl)methyl)-4H-1,2,4-triazole-3 carbaldehyde (43.0 mg, 95%) as light yellow oil. LC-MS: m/z 527.2 $(M+H)^+$.

Step L: (E)-3-(5-((4-(2-(4-chloro-2-fluorophenyl)-2-methylbenzo[d][1,3]dioxol-4-yl) piperidin-1-yl) methyl)-4-(((S)-oxetan-2-yl)methyl)-4H-1,2,4-triazol-3-yl)acrylic acid

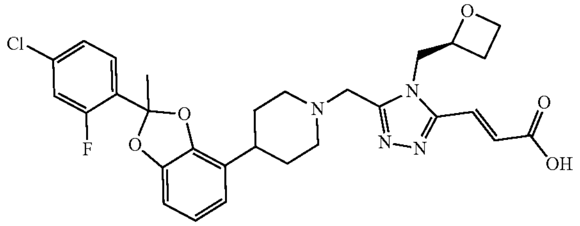 [SMILES: CC1(c2ccc(Cl)cc2F)Oc2cccc(C3CCN(Cc4nnc(/C=C/C(=O)O)n4C[C@@H]4CCO4)CC3)c2O1]

To a solution of ethyl 2-(diethoxyphosphoryl)acetate (56.0 mg, 0.250 mmol) in THF (2 mL) was added NaH (13.0 mg, 0.33 mmol, 60% in oil) at 0° C. After stirring at 0° C. for 30 minutes, (5-((4-(2-(4-chloro-2-fluorophenyl)-2-methylbenzo[d][1,3]dioxol-4-yl)piperidin-1-yl)methyl)-4-(((S)-oxetan-2-yl)methyl)-4H-1,2,4-triazol-3-yl)methanol (43.0 mg, 0.082 mmol) was added. The mixture was stirred at room temperature for 3 hours. After quenched by the sat. aq. $NH_4Cl$ solution (1 mL), the reaction mixture was adjusted to pH=5 with formic acid, and purified by Prep-HPLC to afford (E)-3-(5-((4-25 (2-(4-chloro-2-fluorophenyl)-2-methylbenzo[d][1,3]dioxol-4-yl) piperidin-1-yl)methyl)-4-(((S)-oxetan-2-yl)methyl)-4H-1,2,4-triazol-3-yl)acrylic acid (12.4 mg, 87%) as a white solid. $^1$H NMR (400 MHz, DMSO-$d_6$) δ 12.74 (br.s, 1H), 7.50-7.66 (m, 3H), 7.34 (d, J=8.4 Hz, 1H), 6.68-6.84 (m, 4H), 4.91-5.03 (m, 1H), 4.61 (dd, J=15.2, 6.8 Hz, 1H), 4.33-4.47 (m, 3H), 3.78 (d, J=13.6 Hz, 1H), 3.67 (d, J=13.6 Hz, 1H), 2.96 (d, J=10.4 Hz, 1H), 2.80 (d, J=10.8 Hz, 1H), 2.60-2.72 (m, 2H), 2.31-2.42 (m, 1H), 2.08-2.21 (m, 2H), 2.02 (s, 3H), 1.72 (d, J=9.2 Hz, 4H). LC-MS: m/z 569.2 $(M+H)^+$.

(E)-3-(5-((4-(2-(4-chloro-2-fluorophenyl)-2-methylbenzo[d][1,3]dioxol-4-yl)piperidin-1-yl)methyl)-4-(((S)-oxetan-2-yl)methyl)-4H-1,2,4-triazol-3-yl)-2-methylacrylic acid (Compound 137a) was synthesized following the method described in Example 1 (step I to step J) from 5-((4-(2-(4-chloro-2-fluorophenyl)-2-methyl benzo[d][1,3]dioxol-4-yl) piperidin-1-yl)methyl)-4-(((S)-oxetan-2-yl)methyl)-4H-1,2,4-triazole-3 carbaldehyde and methyl 2-(diethoxyphosphoryl)propanoate.

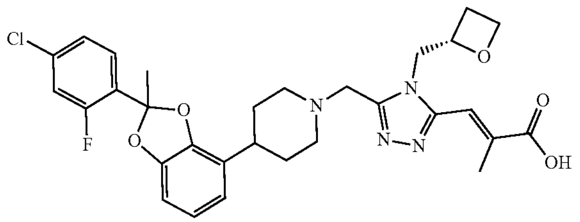 [SMILES: C/C(=C\c1nnc(CN2CCC(c3cccc4c3OC(C)(c3ccc(Cl)cc3F)O4)CC2)n1C[C@@H]1CCO1)C(=O)O]

$^1$H NMR (400 MHz, DMSO-$d_6$) δ 12.78 (br.s, 1H), 7.53-7.59 (m, 2H), 7.49 (dd, J=3.2, 1.6 Hz, 1H), 7.34 (d, J=8.4 Hz, 1H), 6.77-6.80 (m, 2H), 6.71-6.76 (m, 1H), 4.93-5.02 (m, 1H), 4.49-4.57 (m, 1H), 4.31-4.48 (m, 3H), 3.75-3.82 (m, 1H), 3.63-3.70 (m, 1H), 2.96 (d, J=8.0 Hz, 1H), 2.80 (d, J=10.4 Hz, 1H), 2.59-2.72 (m, 2H), 2.35-2.43 (m, 1H), 2.31 (d, J=0.8 Hz, 2H), 2.12-2.19 (m, 2H), 2.07 (d, J=1.2 Hz, 1H), 2.02 (s, 3H), 1.72-1.74 (m, 4H). LCMS: m/z 583.2 $(M+H)^+$.

Example 7

(E)-3-(5-((4-(2-(4-chloro-2-fluorophenyl)-2-methylbenzo[d][1,3]dioxol-4-yl)piperidin-1-yl)methyl)-4-((1-ethyl-1H-imidazol-5-yl)methyl)-4H-1,2,4-triazol-3-yl)acrylic acid (Compound 142)

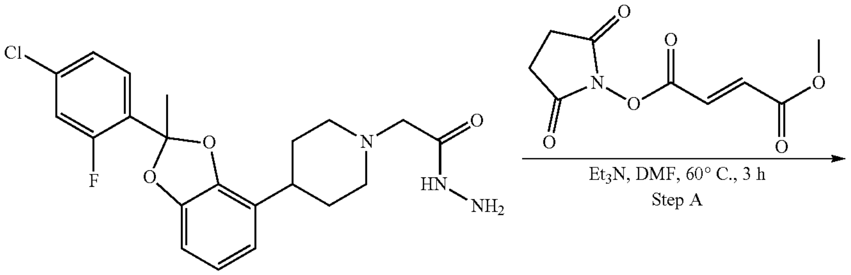

1

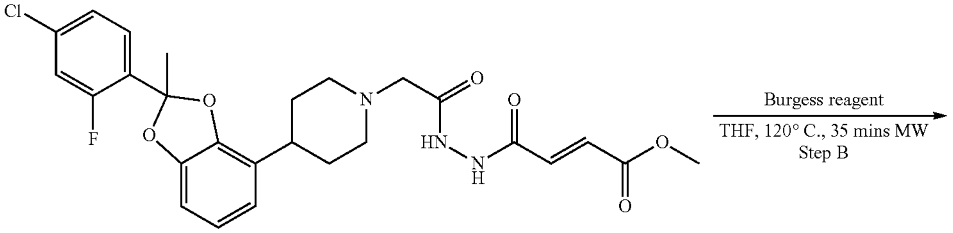

2

-continued

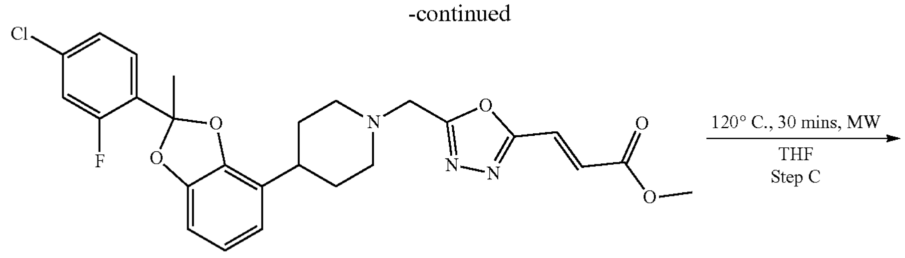

3

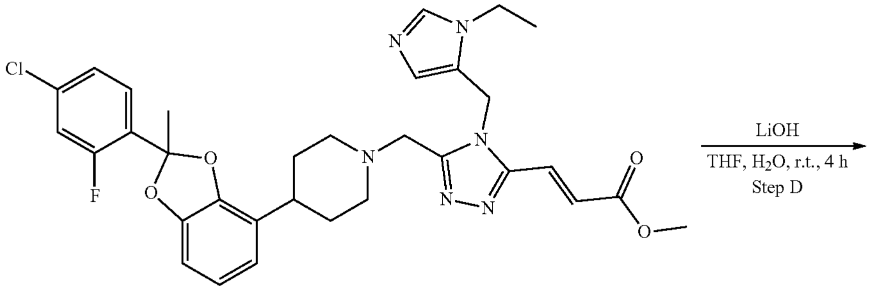

4

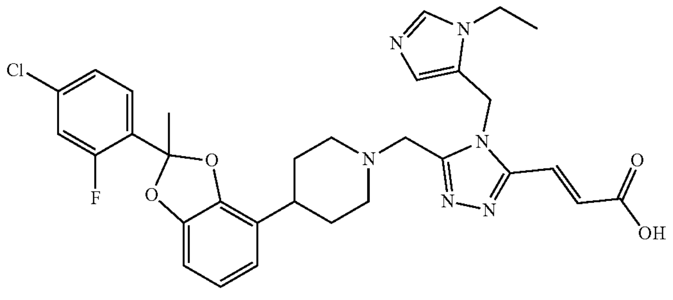

Compound 142

Step A: methyl (E)-4-(2-(2-(4-(2-(4-chloro-2-fluorophenyl)-2-methylbenzo[d][1,3]dioxol-4-yl)piperidin-1-yl)acetyl)hydrazinyl)-4-oxobut-2-enoate

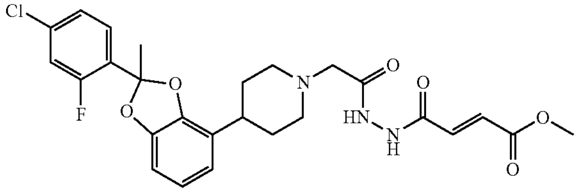 [SMILES: COC(=O)/C=C/C(=O)NNC(=O)CN1CCC(c2cccc3c2OC(C)(c2ccc(Cl)cc2F)O3)CC1]

To a solution of 2-(4-(2-(4-chloro-2-fluorophenyl)-2-methylbenzo[d][1,3]dioxol-4-yl)piperidin-1-yl)acetohydrazide (500 mg, 1.19 mmol) in DMF (5 mL) was added TEA (362 mg, 3.57 mmol) and 2,5-dioxopyrrolidin-1-yl methyl fumarate (298 mg, 1.31 mmol). The reaction mixture was stirred at 60° C. for 3 hours and then diluted with water (20 mL). The mixture was extracted with DCM (3×20 mL). The combined organic layers were washed with water (25 mL), brine (25 mL), dried over anhydrous $Na_2SO_4$, concentrated and purified by silica gel column chromatography (DCM/MeOH=10/1) afford methyl (E)-4-(2-(2-(4-(2-(4-chloro-2-fluorophenyl)-2-methylbenzo[d][1,3]dioxol-4-yl) piperidin-1-yl)acetyl)hydrazinyl)-4-oxobut-2-enoate (460 mg, 73%) as a yellow solid. LC-MS: m/z 532.2 $(M+H)^+$.

Step B: methyl E)-3-(5-((4-(2-(4-chloro-2-fluorophenyl)-2-methylbenzo[d][1,3]dioxol-4-yl)piperidin-1-yl)methyl)-1,3,4-oxadiazol-2-yl)acrylate

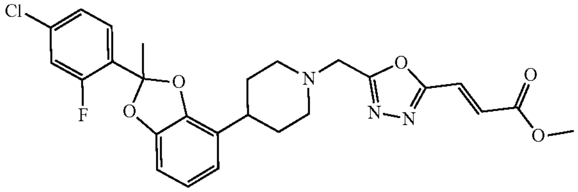 [SMILES: COC(=O)/C=C/c1nnc(CN2CCC(c3cccc4c3OC(C)(c3ccc(Cl)cc3F)O4)CC2)o1]

A solution of methyl (E)-4-(2-(2-(4-(2-(4-chloro-2-fluorophenyl)-2-methylbenzo [d][1,3]dioxol-4-yl)piperidin-1-yl)acetyl)hydrazinyl)-4-oxobut-2-enoate (450 mg, 0.847 mmol), methyl N-(triethylammoniumsulfonyl)carbamate [Burgess reagent] (607 mg, 2.55 mmol) in THF (4 mL) was stirred at 120° C. for 35 minutes under microwave irradiation. After cooled down to room temperature, THF was removed, and the residue was purified by Prep-HPLC to afford methyl (E)-3-(5-((4-(2-(4-chloro-2-fluorophenyl)-2-methylbenzo[d][1,3]dioxol-4-yl)piperidin-1-yl)methyl)-1,3,4-oxadiazol-2-yl)acrylate (300 mg, 69) as a white solid. LC-MS: m/z 514.2 $(M+H)^+$.

Step C: methyl E)-3-(5-((4-(2-(4-chloro-2-fluorophenyl)-2-methylbenzo[d][1,3]dioxol-4-yl)piperidin-1-yl)methyl)-4-((1-ethyl-1H-imidazol-5-yl)methyl)-4H-1,2,4-triazol-3-yl)acrylate

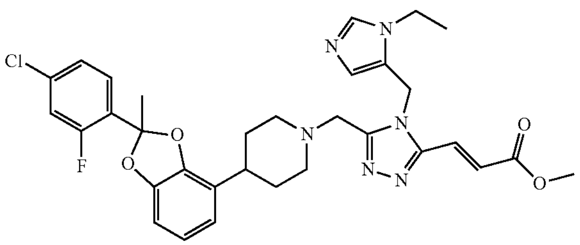 [SMILES: CCn1cncc1Cn1c(/C=C/C(=O)OC)nnc1CN1CCC(c2cccc3c2OC(C)(c2ccc(Cl)cc2F)O3)CC1]

To a mixture of methyl (E)-3-(5-((4-(2-(4-chloro-2-fluorophenyl)-2-methylbenzo [d][1,3]dioxol-4-yl)piperidin-1-yl)methyl)-1,3,4-oxadiazol-2-yl)acrylate (170 mg, 0.33 mmol) and acetic acid (199 mg, 3.31 mmol) in MeCN (2 mL) were added (1-Ethyl-1H-imidazol-5-yl)methanamine dihydrochloride (655 mg, 3.31 mmol) and TEA (669 mg, 6.62 mmol). The reaction was stirred at 120° C. for 2 days. The mixture was concentrated and purified by silica gel column chromatography (DCM/MeOH=10/1) to afford methyl (E)-3-(5-((4-(2-(4-chloro-2-fluorophenyl)-2-methylbenzo [d][1,3]dioxol-4-yl)piperidin-1-yl)methyl)-4-((1-ethyl-1H-imidazol-5-yl)methyl)-4H-1,2,4-triazol-3-yl)acrylate (100 mg, 49) as a white solid. LC-MS: m/z 621.2 $(M+H)^+$.

Step D: (E)-3-(5-((4-(2-(4-chloro-2-fluorophenyl)-2-methylbenzo[d][1,3]dioxol-4-yl) piperidin-1-yl) methyl)-4-((1-ethyl-1H-imidazol-5-yl)methyl)-4H-1,2,4-triazol-3-yl)acrylic acid

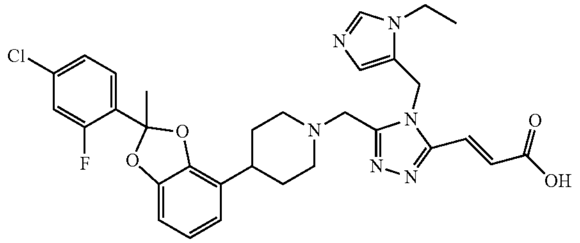 [SMILES: CCn1cncc1Cn1c(/C=C/C(=O)O)nnc1CN1CCC(c2cccc3c2OC(C)(c2ccc(Cl)cc2F)O3)CC1]

To a mixture of methyl (E)-3-(5-((4-(2-(4-chloro-2-fluorophenyl)-2-methylbenzo [d][1,3]dioxol-4-yl)piperidin-1-yl)methyl)-4-((1-ethyl-1H-imidazol-5-yl)methyl)-4H-1,2,4-triazol-3-yl)acrylate (40.0 mg, 0.0645 mmol) in THF (4 mL) was added lithium hydroxide (7.75 mg, 0.32 mmol) in water (2 mL). The mixture was stirred at room temperature for 3 hours. The mixture was adjusted to pH=4 with formic acid and concentrated under 40° C. to remove THF. The residue was extracted with DCM (2×20 mL) and the organic layer was dried over $Na_2SO_4$ and concentrated. The residue was purified by Prep-HPLC (0.1% formic acid in water and acetonitrile) to afford (E)-3-(5-((4-(2-(4-chloro-2-fluorophenyl)-2-methylbenzo[d][1,3]dioxol-4-yl)piperidin-1-yl) methyl)-4-((1-ethyl-1H-imidazol-5-yl)methyl)-4H-1,2,4-triazol-3-yl)acrylic acid as a white solid (7.30 mg, 19%). $^1H$ NMR (400 MHz, DMSO-$d_6$) δ 7.66 (s, 1H), 7.50-7.60 (m, 2H), 7.31-7.42 (m, 2H), 6.74-6.81 (m, 3H), 6.62 (dd, J=6.4, 2.4 Hz, 1H), 6.29 (s, 1H), 5.54 (s, 2H), 4.02 (q, J=7.2 Hz, 2H), 3.71 (s, 2H), 2.75-2.79 (m, 2H), 2.56-2.61 (m, 1H), 2.05-2.09 (m, 2H), 2.02 (s, 3H), 1.58-1.64 (m, 2H), 1.30-1.44 (m, 2H), 1.26 (t, J=7.2 Hz, 3H). LC-MS: m/z 607.2 $(M+H)^+$.

Example 8

(E)-3-(5-((4-(6-((4-chloro-2-fluorobenzyl)oxy)pyridin-2-yl)piperidin-1-yl)methyl)-4-methyl-4H-1,2,4-triazol-3-yl)acrylic acid (Compound 112)

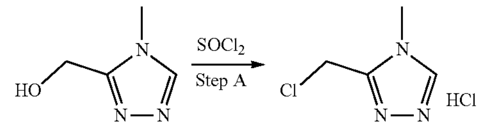

5 4

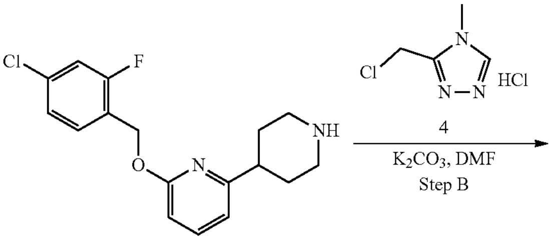

1

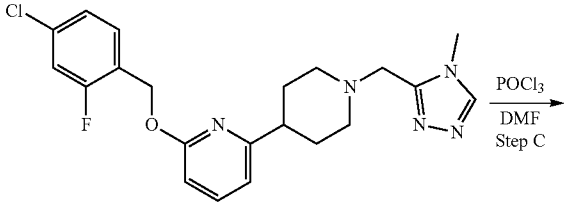

2

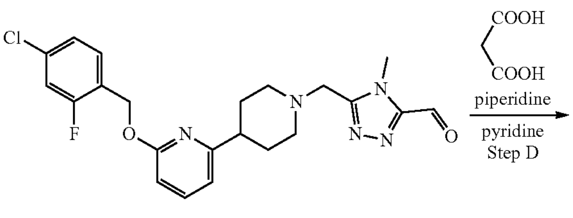

3

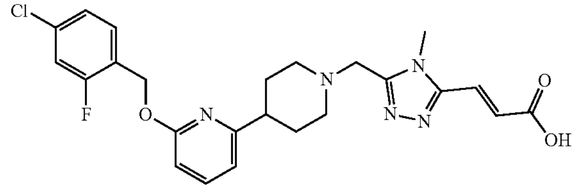

Compound 112

Step A: 3-(chloromethyl)-4-methyl-4H-1,2,4-triazole hydrochloride

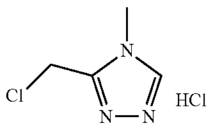

$SOCl_2$ (4.21 g, 35.4 mmol, 2.57 mL) was added to (4-methyl-1,2,4-triazol-3-yl) methanol (200 mg, 1.77 mmol) at 0° C., the resulting mixture was heated at 90° C. for 1 hour. After cooled down to room temperature, the solvent was removed under reduced pressure to afford 3-(chloromethyl)-4-methyl-4H-1,2,4-triazole hydrochloride (280 mg, 94.3%) as a white solid.

$^1H$ NMR (400 MHz, DMSO-$d_6$) δ 9.29 (s, 1H), 5.13-5.04 (m, 2H), 3.81 (s, 3H).

Step B: 2-((4-chloro-2-fluorobenzyl)oxy)-6-(1-((4-methyl-4H-1,2,4-triazol-3-yl) methyl)piperidin-4-yl) pyridine

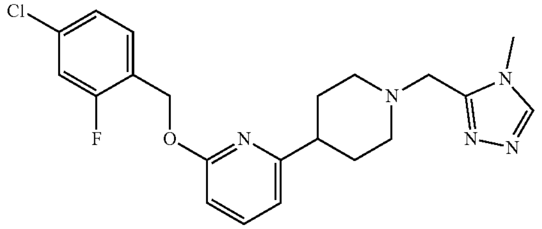 [SMILES: Cn1cnnc1CN1CCC(c2cccc(OCc3ccc(Cl)cc3F)n2)CC1]

A mixture of 2-[(4-chloro-2-fluoro-phenyl)methoxy]-6-(4-piperidyl)pyridine (200 mg, 623 umol) and 3-(chloromethyl)-4-methyl-1,2,4-triazole hydrochloride (105 mg, 623 umol) in DMF (7 mL) was added $K_2CO_3$ (259 mg, 1.87 mmol), the resulting mixture was stirred at 50° C. for 12 hours. After cooled down to room temperature, the reaction mixture was diluted with water (80 mL) and extracted with EtOAc (3x80 mL), the combined organic phase was dried over anhydrous $Na_2SO_4$, filtered and evaporated to afford 2-((4-chloro-2-fluorobenzyl)oxy)-6-(1-((4-methyl-4H-1,2,4-triazol-3-yl)methyl) piperidin-4-yl)pyridine (219 mg, 84.5%) as a yellow oil. $^1H$ NMR (400 MHz, $CDCl_3$) δ 8.15-8.09 (m, 1H), 7.54-7.39 (m, 2H), 7.16-7.08 (m, 2H), 6.74 (d, J=7.2 Hz, 1H), 6.62 (d, J=8.4 Hz, 1H), 5.41 (s, 2H), 3.93-3.69 (m, 5H), 2.53-2.69 (m, 1H), 2.20-2.36 (m, 1H), 1.75-1.95 (m, 3H), 1.33-1.22 (m, 2H), 1.21-1.07 (m, 1H), 0.96-0.80 (m, 1H). LC-MS: m/z 416.1 $(M+H)^+$.

Step C: 5-(4-(6-((4-chloro-2-fluorobenzyl)oxy)pyridin-2-yl)piperidin-1-yl)methyl)-4-methyl-4H-1,2,4-triazole-3-carbaldehyde

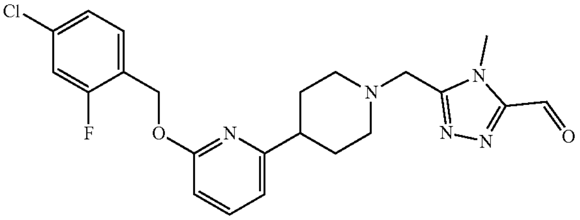 [SMILES: Cn1c(C=O)nnc1CN1CCC(c2cccc(OCc3ccc(Cl)cc3F)n2)CC1]

$POCl_3$ (404 mg, 2.63 mmol, 245 uL) was added dropwise to DMF (10 mL) at 0° C., after stirring for 1 hr at 0° C., 2-((4-chloro-2-fluorobenzyl)oxy)-6-(1-((4-methyl-4H-1,2,4-triazol-3-yl)methyl)piperidin-4-yl)pyridine (219 mg, 527 umol) in DMF (2 mL) was added, the resulting mixture was stirred at 0° C. for 2 hours and then stirred at 25° C. for 12 hours. The reaction mixture was poured into sat. aq. $NaHCO_3$ solution (100 mL) and extracted with EtOAc (5x50 mL), the combined organic phase was dried over anhydrous $Na_2SO_4$, filtered and evaporated to afford 5-((4-(6-((4-chloro-2-fluorobenzyl)oxy)pyridin-2-yl)piperidin-1-yl)methyl)-4-methyl-4H-1,2,4-triazole-3-carbaldehyde (232 mg, 99.3%) as a yellow oil. LC-MS: m/z 462.2 $(M+H_2O+H)^+$.

Step D: (E)-3-(5-((4-(6-((4-chloro-2-fluorobenzyl) oxy)pyridin-2-yl)piperidin-1-yl) methyl)-4-methyl-4H-1,2,4-triazol-3-yl)acrylic acid

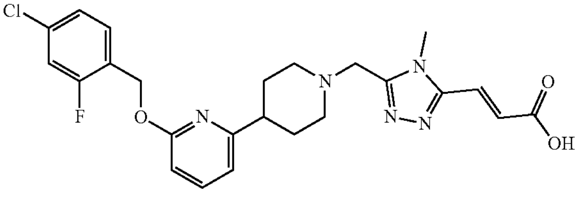 [SMILES: Cn1c(/C=C/C(=O)O)nnc1CN1CCC(c2cccc(OCc3ccc(Cl)cc3F)n2)CC1]

To a solution of 5-((4-(6-((4-chloro-2-fluorobenzyl)oxy) pyridin-2-yl)piperidin-1-yl) methyl)-4-methyl-4H-1,2,4-triazole-3-carbaldehyde (230 mg, 518 umol) and malonic acid (53.9 mg, 518 umol, 53.9 uL) in pyridine (2 mL) was added piperidine (35.3 mg, 414 umol), the resulting mixture was stirred at 80° C. for 12 hours. After cooled down to room temperature, the reaction mixture was adjusted to pH=8 with 1N HCl aqueous and the solvent was removed under reduced pressure to give a residue. The residue was purified by prep-HPLC (Column: Phenomenex Gemini-NX C18 75x30 mmx3 um; 13% to 43% (v/v) water (0.04% $NH_3 \cdot H_2O$+10 mM $NH_4HCO_3$)-ACN) to afford (E)-3-(5-((4-(6-((4-chloro-2-fluorobenzyl)oxy)pyridin-2-yl)piperidin-1-yl)methyl)-4-methyl-4H-1,2,4-triazol-3-yl)acrylic acid (8.72 mg, 3.20%) as a white solid.

$^1H$ NMR (400 MHz, $CD_3OD$) δ 7.62-7.45 (m, 3H), 7.23-7.16 (m, 2H), 6.92 (d, J 16.0 Hz, 1H), 6.82 (d, J=7.4 Hz, 1H), 6.63 (d, J=8.4 Hz, 1H), 5.40 (s, 2H), 3.89-3.81 (m, 5H), 3.09-2.99 (m, 2H), 2.72-2.60 (m, 1H), 2.43-2.26 (m, 2H), 1.92-1.81 (m, 4H). LC-MS: m/z 486.2 $(M+H)^+$.

Example 9
(E)-3-(2-((4-((R)-2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)-2-methylacrylic acid (Compound 131b) and (E)-3-(2-((4-((S)-2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)-2-methylacrylic acid (Compound 131a)
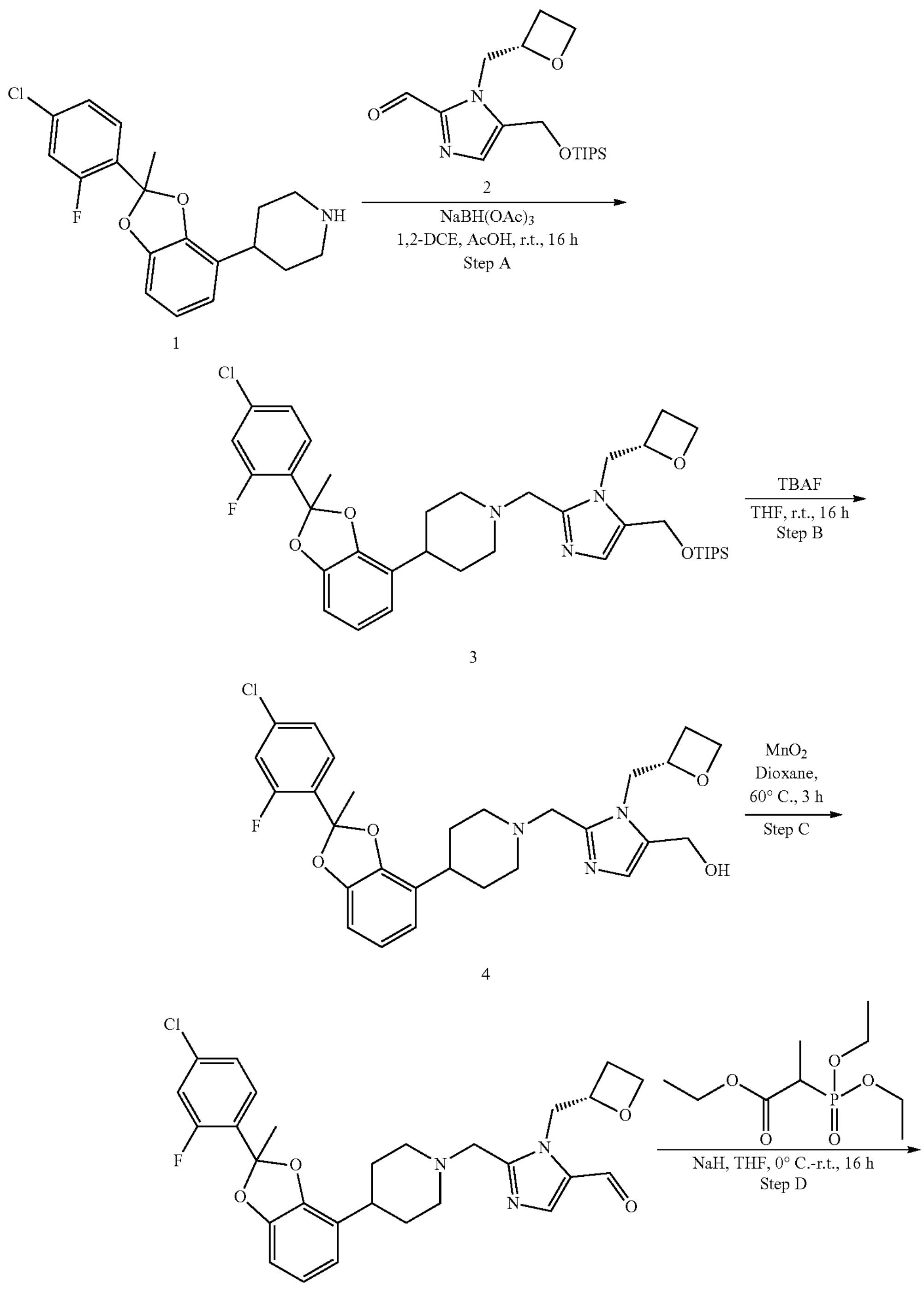
5

-continued

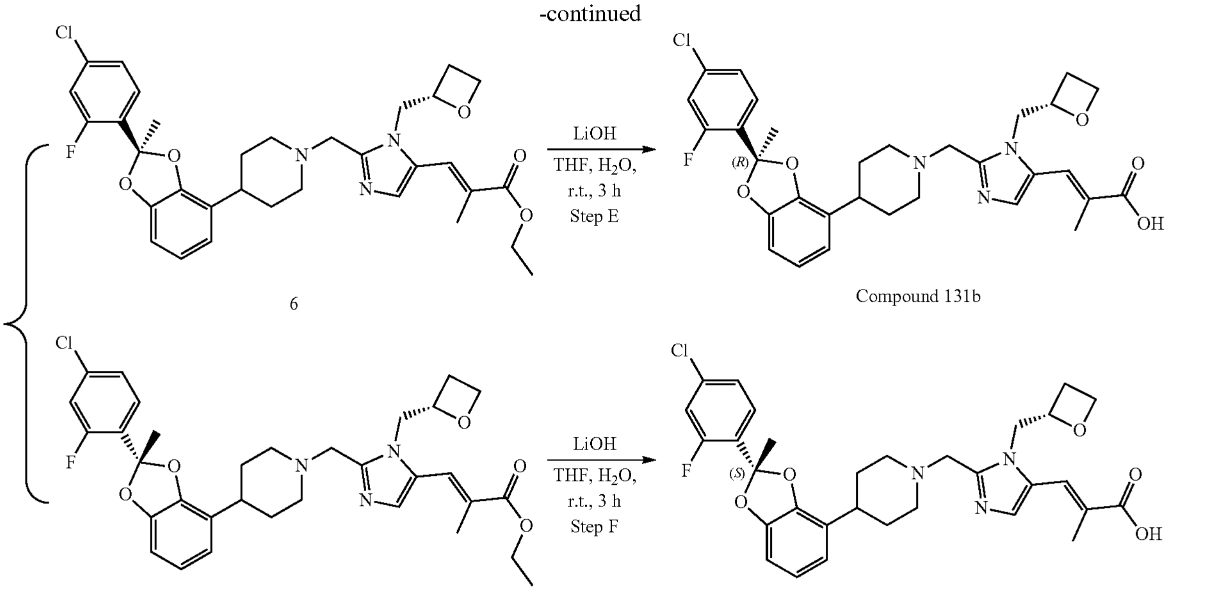

6

Compound 131b

7

Compound 131a

Step A: 4-(2-(4-chloro-2-fluorophenyl)-2-methylbenzo[d][1,3]dioxol-4-yl)-1-((1-(((S)-oxetan-2-yl)methyl)-5-(((triisopropylsilyl)oxy)methyl)-1H-imidazol-2-yl)methyl)piperidine

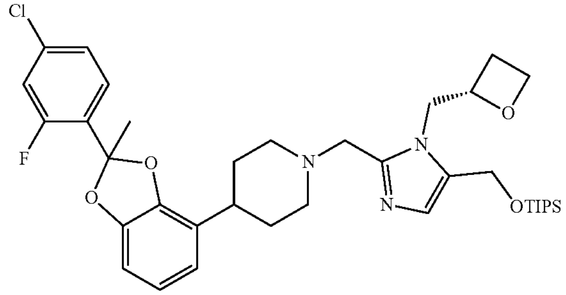

To a solution of 4-(2-(4-chloro-2-fluorophenyl)-2-methylbenzo[d][1,3]dioxol-4-yl) piperidine (170 mg, 0.49 mmol) in 1,2-DCE (10 mL) were added (S)-1-(oxetan-2-ylmethyl)-5-(((triisopropylsilyl)oxy)methyl)-1H-imidazole-2-carbaldehyde (190 mg, 0.54 mmol) and AcOH (9 drops). The resulting mixture was stirred at room temperature for 1 hour. Then $NaBH(OAc)_3$ (311 mg, 1.47 mmol) was added. The reaction mixture was stirred at room temperature for 16 hours. It was mixed with water (15 mL) and extracted with EtOAc (3×20 mL). The organic layers were washed with brine (30 ml), dried over $Na_2SO_4$, filtered, concentrated and purified by silica gel column chromatography (DCM:DCM/MeOH (10/1)=40%-55%) to afford 4-(2-(4-chloro-2-fluorophenyl)-2-methylbenzo[d][1,3]dioxol-4-yl)-1-((1-(((S)-oxetan-2-yl)methyl)-5-(((triisopropylsilyl)oxy)methyl)-1H-imidazol-2-yl)methyl)piperidine (265 mg, 79%) as an orange gum. LC-MS: m/z 684.4 $(M+H)^+$.

Step B: (2-((4-(2-(4-chloro-2-fluorophenyl)-2-methylbenzo[d][1,3]dioxol-4-yl) piperidin-1-yl)methyl)-1-(((S)-oxetan-2-yl)methyl)-1H-imidazol-5-yl)methanol

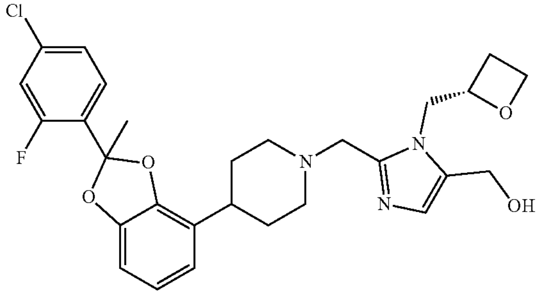 [SMILES: CC1(c2ccc(Cl)cc2F)Oc2cccc(C3CCN(Cc4ncc(CO)n4C[C@@H]4CCO4)CC3)c2O1]

To a solution of 4-(2-(4-chloro-2-fluorophenyl)-2-methylbenzo[d][1,3]dioxol-4-yl)-1-((1-(((S)-oxetan-2-yl)methyl)-5-(((triisopropylsilyl)oxy)methyl)-1H-imidazol-2-yl)methyl)piperidine (265 mg, 0.387 mmol) in THF (10 mL) was added TBAF (1 mL, 1 M in THF, 1 mmol). The reaction mixture was stirred at room temperature for 16 hours. The mixture was diluted with water (15 mL) and extracted with EtOAc (3×20 mL). The organic layers were washed with brine (30 mL), dried over $Na_2SO_4$, filtered, concentrated and purified by silica gel column chromatography (DCM:DCM/MeOH (10/1)=25%-40%) to afford (2-((4-(2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)methanol as a colorless gum (170 mg, 83%). LC-MS: m/z 528.2 $(M+H)^+$.

Step C: 2-((4-(2-(4-chloro-2-fluorophenyl)-2-methylbenzo[d][1,3]dioxol-4-yl) piperidin-1-yl)methyl)-1-(((S)-oxetan-2-yl)methyl)-1H-imidazole-5-carbaldehyde

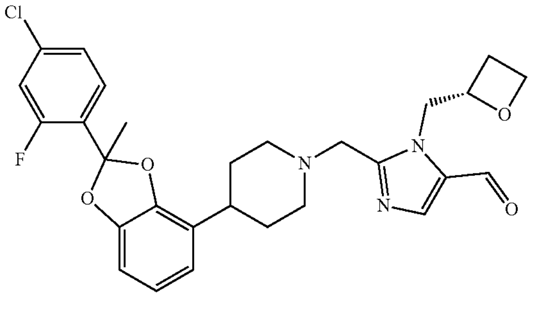 [SMILES: CC1(c2ccc(Cl)cc2F)Oc2cccc(C3CCN(Cc4ncc(C=O)n4C[C@@H]4CCO4)CC3)c2O1]

To a solution of (2-((4-(2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)methanol (170 mg, 0.322 mmol) in dioxane (13 mL) was added $MnO_2$ (280 mg, 3.22 mmol). The mixture was stirred at 60° C. for 3 hours. Then the mixture was filtered and the filtrate was concentrated to afford 2-((4-(2-(4-chloro-2-fluorophenyl)-2-methylbenzo[d][1,3] dioxol-4-yl)piperidin-1-yl)methyl)-1-(((S)-oxetan-2-yl)methyl)-1H-imidazole-5-carbaldehyde (170 mg, 100%) as a gum. LC-MS: m/z 526.2 $(M+H)^+$.

Step D: ethyl E)-3-(2-((4-((R)-2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)-2-methylacrylate and ethyl E)-3-(2-((4-((S)-2-(4-chloro-2-fluorophenyl)-2-methyl benzo[d][1,3]dioxol-4-yl)piperidin-1-yl)methyl)-1-(((S)-oxetan-2-yl)methyl)-1H-imidazol-5-yl)-2-methylacrylate

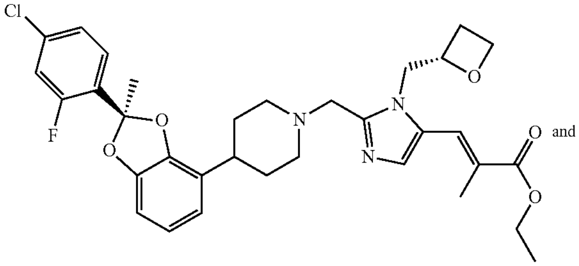

and

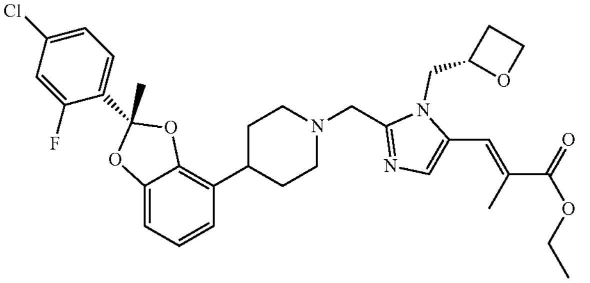

To a solution of 2-((4-(2-(4-chloro-2-fluorophenyl)-2-methylbenzo[d][1,3]dioxol-4-yl)piperidin-1-yl)methyl)-1-(((S)-oxetan-2-yl)methyl)-1H-imidazole-5-carbaldehyde (170 mg, 0.32 mmol) in THF (4.5 mL) was added 60% NaH (26.0 mg, 0.65 mmol) at 0° C. The reaction mixture was stirred at 0° C. for 1 hour, and then a solution of ethyl 2-(diethoxyphosphoryl)propanoate in THF (3 mL) was added. The mixture was stirred at room temperature for 16 hours. The reaction mixture was quenched by water (15 mL) and extracted with EtOAc (3×20 mL). The organic layers were washed with brine (30 mL), dried over $Na_2SO_4$, filtered, concentrated, and purified by silica gel column chromatography (DCM:DCM/MeOH (10/1)=20%-45%) to afford a mixture of the diastereomeric products as a yellow gum. Separation into the two products was carried out via SFC. The first-eluting diastereomer, obtained as a white solid, was designated as ethyl(E)-3-(2-((4-((R)-2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)-2-methylacrylate (30.0 mg, 15%), LC-MS: m/z 610.2 $(M+H)^+$. The second-eluting diastereomer, obtained as a white solid, was designated as ethyl (E)-3-(2-((4-((S)-2-(4-chloro-2-fluorophenyl)-2-methylbenzo[d][1,3]dioxol-4-yl) piperidin-1-yl)methyl)-1-(((S)-oxetan-2-yl)methyl)-1H-imidazol-5-yl)-2-methylacrylate (39.0 mg, 20%), LC-MS: m/z 610.2 $(M+H)^+$).

Step E: (E)-3-(2-((4-((RR)-2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)-2-methylacrylic acid

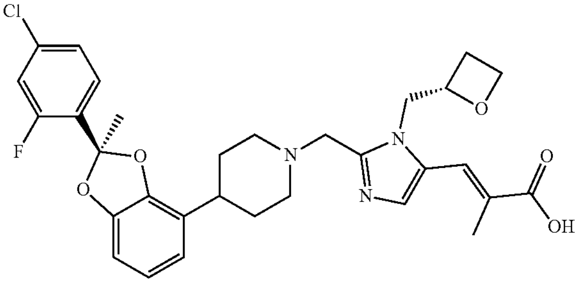 [SMILES: C/C(=C\c1cnc(CN2CCC(c3cccc4c3O[C@](C)(c3ccc(Cl)cc3F)O4)CC2)n1C[C@@H]1CCO1)C(=O)O]

To a solution of ethyl (E)-3-(2-((4-((R)-2-(4-chloro-2-fluorophenyl)-2-methylbenzo [d][1,3]dioxol-4-yl)piperidin-1-yl)methyl)-1-(((S)-oxetan-2-yl)methyl)-1H-imidazol-5-yl)-2-methylacrylate (30.0 mg, 0.049 mmol) in THF (1.5 mL) and $H_2O$ (1.5 mL) was added LiOH (5.88 mg, 0.25 mmol). The reaction mixture was stirred at room temperature for 3 hours. Then the reaction solution was adjusted to pH to 5-6 with formic acid. Then the mixture was purified by Prep-HPLC to afford (E)-3-(2-((4-((R)-2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)-2-methylacrylic acid (14.6 mg, 51%) as a white solid. $^1H$ NMR (400 MHz, DMSO-$d_6$) δ 7.49-7.62 (m, 3H), 7.34 (dd, J=8.4, 2.0 Hz, 1H), 7.20 (s, 1H), 6.71-6.81 (m, 3H), 4.93-4.99 (m, 1H), 4.33-4.53 (m, 4H), 3.72 (d, J=13.2 Hz, 1H), 3.55 (d, J=13.2 Hz, 1H), 2.95 (d, J=10.8 Hz, 1H), 2.82 (d, J=11.2 Hz, 1H), 2.60-2.70 (m, 2H), 2.37-2.45 (m, 1H), 2.11-2.19 (m, 1H), 2.06-2.09 (m, 1H), 2.02 (s, 3H), 2.00 (s, 3H), 1.64-1.78 (m, 4H). LC-MS: m/z 582.2 $(M+H)^+$.

Step F: (E)-3-(2-((4-((S)-2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)-2-methylacrylic acid

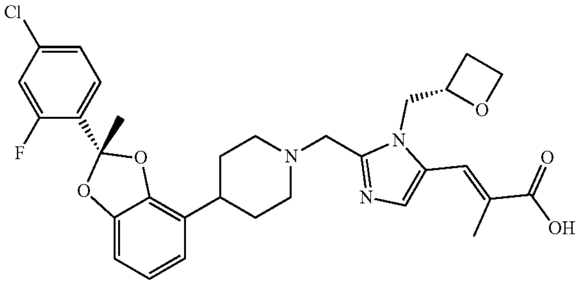 [SMILES: C/C(=C\c1cnc(CN2CCC(c3cccc4c3O[C@@](C)(c3ccc(Cl)cc3F)O4)CC2)n1C[C@@H]1CCO1)C(=O)O]

To a solution of ethyl (E)-3-(2-((4-((S)-2-(4-chloro-2-fluorophenyl)-2-methylbenzo [d][1,3]dioxol-4-yl)piperidin-1-yl)methyl)-1-(((S)-oxetan-2-yl)methyl)-1H-imidazol-5-yl)-2-methylacrylate (39.0 mg, 0.064 mmol) in THF (1.5 mL) and $H_2O$ (1.5 mL) was added LiOH (7.68 mg, 0.32 mmol). The reaction mixture was stirred at room temperature for 3 hours. The reaction solution was adjusted to pH=5-6 with formic acid and purified by Prep-HPLC to afford (E)-3-(2-((4-((S)-2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)-2-methylacrylic acid (17.2 mg, 46%) as a white solid.

$^1H$ NMR (400 MHz, DMSO-$d_6$) δ 7.51-7.60 (m, 3H), 7.34 (dd, J=8.4, 2.0 Hz, 1H), 7.18 (s, 1H), 6.70-6.81 (m, 3H), 4.93-4.95 (m, 1H), 4.43-4.53 (m, 2H), 4.33-4.40 (m, 2H), 3.73 (d, J=13.2 Hz, 1H), 3.54 (d, J=13.2 Hz, 1H), 2.96 (d, J=11.2 Hz, 1H), 2.81 (d, J=10.8 Hz, 1H), 2.58-2.71 (m, 2H), 2.36-2.46 (m, 1H), 2.12-2.19 (m, 1H), 2.05-2.12 (m, 1H), 2.02 (s, 3H), 2.00 (s, 3H), 1.62-1.81 (m, 4H). LC-MS: m/z 582.2 $(M+H)^+$.

Note: In the example above, the absolute configuration of the stereogenic center at the dioxolane ring was assigned tentatively based on relative potencies of stereoisomers epimeric at this position. This assignment of stereochemistry was applied to dioxolane-containing analogs in this application.

(E)-3-(2-((4-((S)-2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)acrylic acid (Compound 135a) and (E)-3-(2-((4-((R)-2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)acrylic acid (Compound 135b) were synthesized following the method described in Example 9 (step A to step F) by using methyl 2-(diethoxyphosphoryl)acetate in step D:

(E)-3-(2-((4-((S)-2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)acrylic acid (Compound 135a)

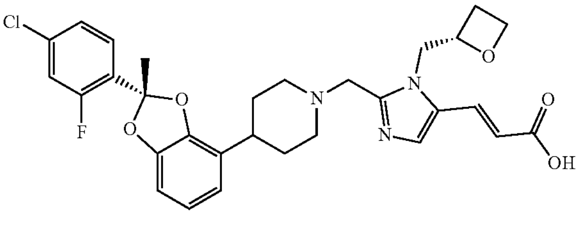 [SMILES: C[C@]1(c2ccc(Cl)cc2F)Oc2cccc(C3CCN(Cc4ncc(/C=C/C(=O)O)n4C[C@@H]4CCO4)CC3)c2O1]

$^1H$ NMR (400 MHz, DMSO-$d_6$) δ 12.32 (br.s, 1H), 8.14 (s, 1H), 7.53-7.65 (m, 3H), 7.34 (dd, J=8.4, 1.6 Hz, 1H), 6.79 (d, J=4.0 Hz, 2H), 6.71-6.77 (m, 1H), 6.30 (d, J=16.0 Hz, 1H), 4.91-5.01 (m, 1H), 4.31-4.58 (m, 4H), 3.72-3.76 (m, 1H), 3.55-3.59 (m, 1H), 2.98 (d, J=10.4 Hz, 1H), 2.84 (d, J=9.6 Hz, 1H), 2.59-2.74 (m, 2H), 2.32-2.44 (m, 1H), 2.08-2.27 (m, 2H), 2.02 (s, 3H), 1.63-1.79 (m, 4H). LC-MS: m/z 568.2 $(M+H)^+$.

(E)-3-(2-((4-((R)-2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)acrylic acid (Compound 135b)

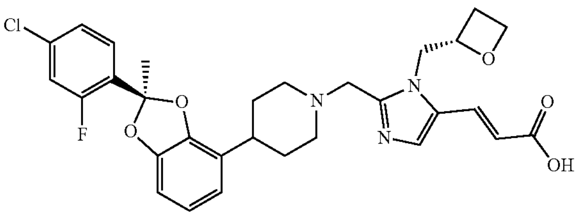 [SMILES: C[C@@]1(c2ccc(Cl)cc2F)Oc2cccc(C3CCN(Cc4ncc(/C=C/C(=O)O)n4C[C@@H]4CCO4)CC3)c2O1]

$^1H$ NMR (400 MHz, DMSO-$d_6$) δ 8.22 (s, 1H), 7.53-5.58 (m, 3H), 7.34 (dd, J=8.4, 1.6 Hz, 1H), 6.79 (d, J=4.4 Hz, 2H), 6.71-6.77 (m, 1H), 6.29 (d, J=16.0 Hz, 1H), 4.90-5.00 (m, 1H), 4.29-4.58 (m, 4H), 3.69-3.73 (m, 1H), 3.50-3.54 (m, 1H), 2.95 (d, J=11.2 Hz, 1H), 2.79 (d, J=11.2 Hz, 1H), 2.58-2.72 (m, 2H), 2.34-2.41 (m, 1H), 2.08-2.21 (m, 2H), 2.02 (s, 3H), 1.62-1.79 (m, 4H). LC-MS: m/z 568.2 $(M+H)^+$.

(E)-3-(2-((4-((R)-2-(4-chlorophenyl)-2-methylbenzo[d][1,3]dioxol-4-yl)piperidin-1-yl)methyl)-1-(((S)-oxetan-2-yl)methyl)-1H-imidazol-5-yl)-2-methylacrylic acid (Compound 134b) and (E)-3-(2-((4-((S)-2-(4-chlorophenyl)-2-methylbenzo[d][1,3]dioxol-4-yl)piperidin-1-yl)methyl)-1-(((S)-oxetan-2-yl)methyl)-1H-imidazol-5-yl)-2-methylacrylic acid (Compound 134a) were synthesized following the method described in step A to step F in Example 9 starting from 4-(2-(4-chlorophenyl)-2-methylbenzo[d][1,3]dioxol-4-yl)piperidine which is obtained after two step conversion of 4-bromo-2-(4-chloro-2-fluorophenyl)benzo[d][1,3]dioxole analogous to step D and E in Example 6.

(E)-3-(2-((4-((R)-2-(4-chlorophenyl)-2-methylbenzo[d][1,3]dioxol-4-yl)piperidin-1-yl)methyl)-1-(((S)-oxetan-2-yl)methyl)-1H-imidazol-5-yl)-2-methylacrylic acid (Compound 134b)

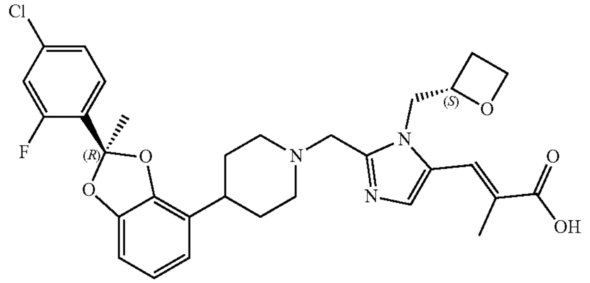

$^1$H NMR (400 MHz, DMSO-$d_6$) δ 12.32 (br.s, 1H), 7.58-7.68 (m, 3H), 7.49-7.51 (m, 2H), 7.23 (s, 1H), 6.73-7.76 (m, 3H), 4.96-4.97 (m, 1H), 4.34-4.58 (m, 4H), 3.72 (d, J=13.6 Hz, 1H), 3.55 (d, J=13.6 Hz, 1H), 2.95 (d, J=10.0 Hz, 1H), 2.82 (d, J=10.0 Hz, 1H), 2.58-2.73 (m, 2H), 2.33-2.48 (m, 1H), 2.02-2.20 (m, 2H), 2.01 (s, 3H), 1.96 (s, 3H), 1.60-1.82 (m, 4H). LC-MS: m/z 564.2 $(M+H)^+$.

(E)-3-(2-((4-((S)-2-(4-chlorophenyl)-2-methylbenzo[d][1,3]dioxol-4-yl)piperidin-1-yl)methyl)-1-(((S)-oxetan-2-yl)methyl)-1H-imidazol-5-yl)-2-methylacrylic acid (Compound 134a)

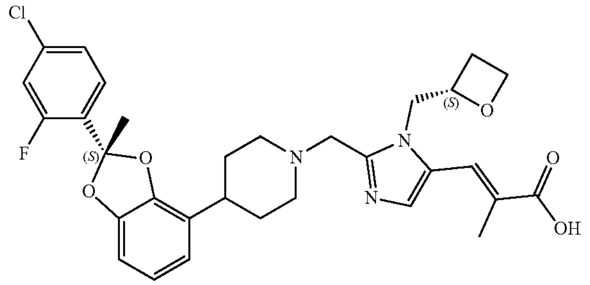

$^1$H NMR (400 MHz, DMSO-$d_6$) δ 12.32 (br.s, 1H), 7.57-7.63 (m, 3H), 7.43-7.54 (m, 2H), 7.23 (s, 1H), 6.61-6.88 (m, 3H), 4.91-4.99 (m, 1H), 4.29-4.59 (m, 4H), 3.73 (d, J=13.6 Hz, 1H), 3.55 (d, J=13.6 Hz, 1H), 2.96 (d, J=11.2 Hz, 1H), 2.81 (d, J=10.8 Hz, 1H), 2.57-2.73 (m, 2H), 2.31-2.45 (m, 1H), 2.03-2.23 (m, 2H), 1.93-2.03 (m, 6H), 1.57-1.86 (m, 4H). LC-MS: m/z 564.2 $(M+H)^+$.

Example 10

(E)-3-(2-((4-(2-(4-chloro-2-fluorophenyl)benzo[d][1,3]dioxol-4-yl)piperidin-1-yl)methyl)-1-((S)-oxetan-2-ylmethyl)-1H-imidazol-5-yl)-2-methylacrylic acid (Compound 132a)

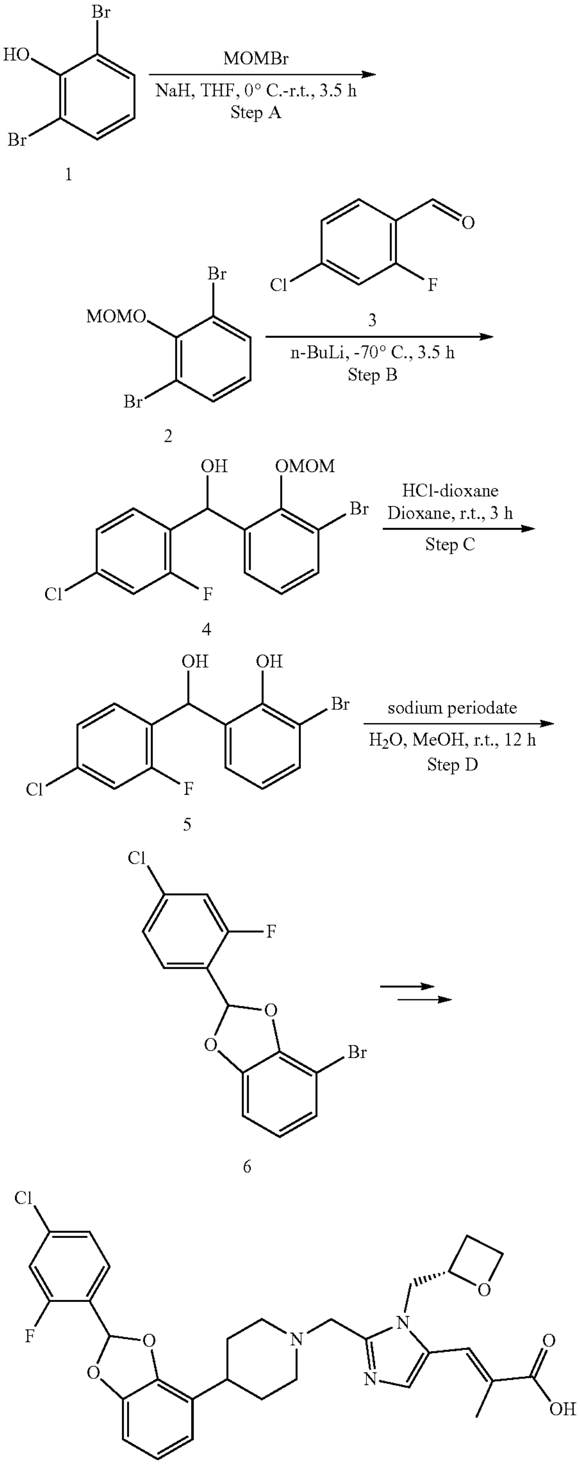

Step A: 1,3-dibromo-2-(methoxymethoxy)benzene

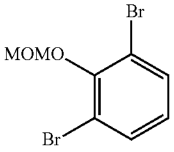

To a solution of 2,6-dibromophenol (2.52 g, 1.24 mmol) in THF (20 mL) was added sodium hydride (645 mg, 16.1 mmol, 60% dispersion in mineral oil) at 0° C. The mixture was stirred at 0° C. for 0.5 hour. Then bromo(methoxy) methane (2.01 g, 16.1 mmol) was added into the mixture dropwise at room temperature and stirred for another 3 hours. The reaction mixture was quenched with sat. aq. $NH_4Cl$ solution (10 mL) and extracted with EtOAc (3×100 mL). The organic layer was washed by brine, dried over $Na_2SO_4$, filtered and concentrated. The residue was purified by silica gel column chromatography (PE/EtOAc=20/1) to afford 1,3-dibromo-2-(methoxymethoxy)benzene (2.50 g, 84%) as a colorless oil. $^1H$ NMR (400 MHz, $CDCl_3$) δ 7.52 (d, J=8.0 Hz, 2H), 6.88 (t, J=8.0 Hz, 1H), 5.18 (s, 2H), 3.73 (s, 3H).

Step B: (3-bromo-2-(methoxymethoxy)phenyl)(4-chloro-2-fluorophenyl)methanol

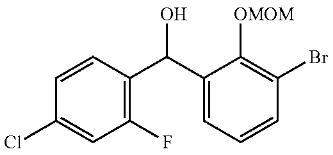

To a solution of 1,3-dibromo-2-(methoxymethoxy)benzene (740 mg, 2.50 mmol) in THF (8 mL) was added n-BuLi (1.30 mL, 3.25 mmol, 2.5M in hexane) at −70° C. under $N_2$. The mixture was stirred at −70° C. for 1.2 hours. Then 4-chloro-2-fluorobenzaldehyde (515 mg, 3.25 mmol) was added into the mixture dropwise at −70° C. over 30 minutes and the mixture was stirred for another 3 hours at −70° C.-−30° C. under $N_2$. The mixture was quenched with sat. aq. $NH_4Cl$ solution (10 mL) and extracted with EtOAc (3×20 mL). The organic layer was washed by brine, dried over $Na_2SO_4$, filtered and concentrated. The residue was purified by silica gel column chromatography (PE/EtOAc=10/1) to afford (3-bromo-2-(methoxymethoxy) phenyl)(4-chloro-2-fluorophenyl)methanol (500 mg, 53%) as a colorless oil. LC-MS: m/z 375.1, 377.1 $(M+H)^+$.

Step C: 2-bromo-6-((4-chloro-2-fluorophenyl)(hydroxy)methyl)phenol

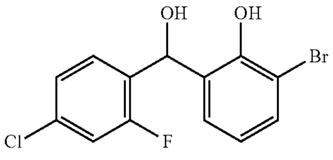 [SMILES: Oc1c(Br)cccc1C(O)c1ccc(Cl)cc1F]

To a solution of (3-bromo-2-(methoxymethoxy)phenyl) (4-chloro-2-fluorophenyl) methanol (230 mg, 0.612 mmol) in 1,4-dioxane (3 mL) was added HCl-dioxane solution (3 mL, 12.0 mmol, 4M in dioxane) at 0° C. dropwise. The mixture was stirred at room temperature for 2 hours. Then the reaction mixture was concentrated to afford 2-bromo-6-((4-chloro-2-fluorophenyl)(hydroxy)methyl)phenol (150 mg, 74%) as a white solid, which was used directly for the next step without further purification. LC-MS: m/z 313.1, 315.1 $(M-18+H)^+$.

Step D: 4-bromo-2-(4-chloro-2-fluorophenyl)benzo [d][1,3]dioxole

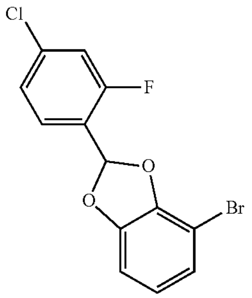 [SMILES: Fc1cc(Cl)ccc1C1Oc2cccc(Br)c2O1]

To a solution of 2-bromo-6-((4-chloro-2-fluorophenyl) (hydroxy)methyl)phenol (150 mg, 0.479 mmol) in MeOH (6 mL) was added a solution of sodium periodate (256 mg, 1.20 mmol) in $H_2O$ (1.5 mL). The reaction was stirred at room temperature for 16 hours. MeOH was removed in vacuum and the reaction mixture was extracted with EtOAc (3×20 mL). The organic layers were washed with brine (20 mL), dried over $Na_2SO_4$, filtered, concentrated and purified by silica gel column chromatography (PE=100% to PE/EtOAc=100/1) to afford 4-bromo-2-(4-chloro-2-fluorophenyl)benzo [d][1,3]dioxole (80.0 mg, 51%) as a colorless oil. $^1H$ NMR (400 MHz, $CDCl_3$) δ 7.54 (t, J=8.0 Hz, 1H), 7.25 (s, 1H), 7.20 (dt, J=10.0, 2.0 Hz, 1H), 7.00 (dd, J=8.0, 1.6 Hz, 1H), 6.71-6.83 (m, 2H).

Compound 132a was synthesized following the method described in Example 1 (step F to step J) starting from 4-(2-(4-chloro-2-fluorophenyl)benzo[d][1,3]dioxol-4-yl) piperidine which was obtained after two step conversion of 4-bromo-2-(4-chloro-2-fluorophenyl)benzo[d][1,3]dioxole analogous to step D and E in Example 6.

(E)-3-(2-((4-(2-(4-chloro-2-fluorophenyl)benzo[d][1,3]dioxol-4-yl)piperidin-1-yl)methyl)-1-((S)-oxetan-2-ylmethyl)-1H-imidazol-5-yl)-2-methylacrylic acid (Compound 132a)

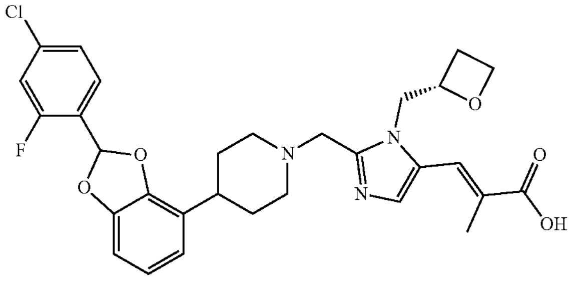 [SMILES: C/C(=C\c1cnc(CN2CCC(c3cccc4c3OC(c3ccc(Cl)cc3F)O4)CC2)n1C[C@@H]1CCO1)C(=O)O]

$^1$H NMR (400 MHz, $CD_3OD$) δ 7.51-7.62 (m, 2H), 7.24-7.37 (m, 3H), 7.20 (s, 1H), 6.72-6.83 (m, 3H), 5.08-5.10 (m, 1H), 4.39-4.70 (m, 4H), 3.74-3.96 (m, 2H), 2.98-3.11 (m, 2H), 2.69-2.73 (m, 2H), 2.21-2.49 (m, 3H), 2.10 (s, 3H), 1.86-1.97 (m, 4H). LC-MS: m/z 568.3 $(M+H)^+$.

Example 11

(E)-3-(2-((4-((S)-2-(4-chlorophenyl)benzo[d][1,3]dioxol-4-yl)piperidin-1-yl)methyl)-1-(((S)-oxetan-2-yl)methyl)-1H-imidazol-5-yl)-2-methylacrylic acid (Compound 133a) and (E)-3-(2-((4-((R)-2-(4-chlorophenyl)benzo[d][1,3]dioxol-4-yl) piperidin-1-yl) methyl)-1-(((S)-oxetan-2-yl)methyl)-1H-imidazol-5-yl)-2-methylacrylic acid (Compound 133b)

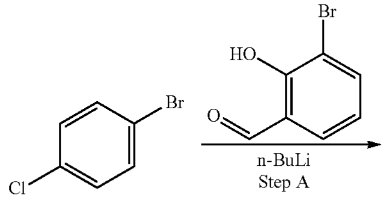

1

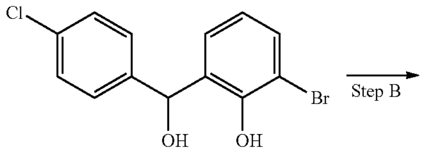

2

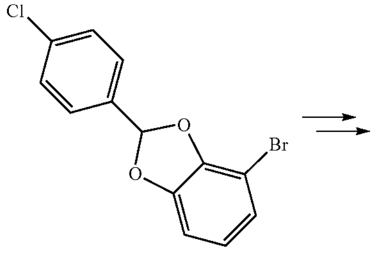

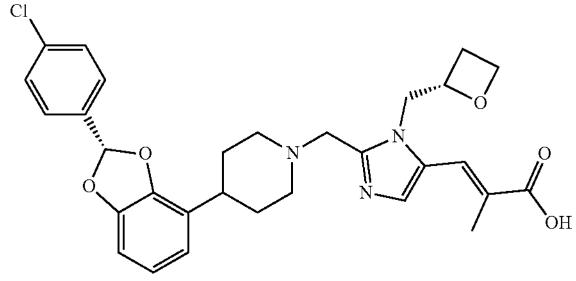

Compound 133a

-continued

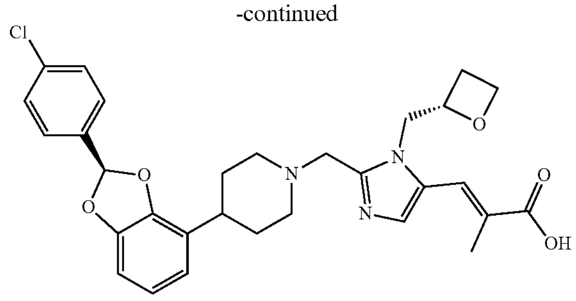

Compound 133b

Step A: 2-bromo-6-((4-chlorophenyl)(hydroxy)methyl)phenol

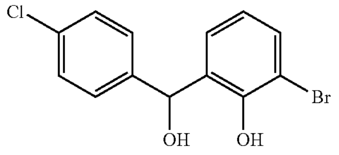 [SMILES: Oc1c(Br)cccc1C(O)c1ccc(Cl)cc1]

To a solution of 1-bromo-4-chlorobenzene (2.86 g, 14.9 mmol) in THF (12 mL) was added n-BuLi (6 mL, 14.9 mmol, 2.5M in hexane) dropwise at −78° C. The reaction was stirred at −78° C. for 0.5 hour, and a solution of 3-bromo-2-hydroxybenzaldehyde (1.00 g, 4.98 mmol) in THF (13 mL) was added dropwise at −78° C. The reaction mixture was stirred at −78° C. for another 0.5 hour, and quenched by sat. aq. $NH_4Cl$ solution (40 mL). The mixture was extracted with EtOAc (3×30 mL). The organic layers were washed with brine (50 ml), dried over $Na_2SO_4$, filtered, concentrated and purified by silica gel column chromatography (PE/EtOAc=5%-10%) to afford 2-bromo-6-((4-chlorophenyl)(hydroxy)methyl)phenol (1.38 g, 88%) as a white solid. LC-MS: m/z 296.1, 298.1 $(M-18+H)^+$.

Step B: 4-bromo-2-(4-chlorophenyl)benzo[d][1,3]dioxole

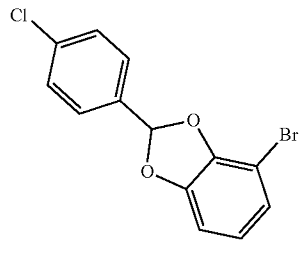 [SMILES: Clc1ccc(C2Oc3cccc(Br)c3O2)cc1]

The title compound was obtained from 2-bromo-6-((4-chlorophenyl)(hydroxy)methyl)phenol following the method described in step D in Example 10.

Compound 133a and Compound 133b were then synthesized following the method described in step A to step F in Example 9 starting from 4-(2-(4-chlorophenyl)-2-methyl-benzo[d][1,3]dioxol-4-yl)piperidine which is obtained after two step conversion of 4-bromo-2-(4-chlorophenyl)benzo[d][1,3]dioxole analogous to step D and E in Example 6.

(E)-3-(2-((4-((S)-2-(4-chlorophenyl)benzo[d][1,3]dioxol-4-yl)piperidin-1-yl)methyl)-1-(((S)-oxetan-2-yl)methyl)-1H-imidazol-5-yl)-2-methylacrylic acid (Compound 133a)

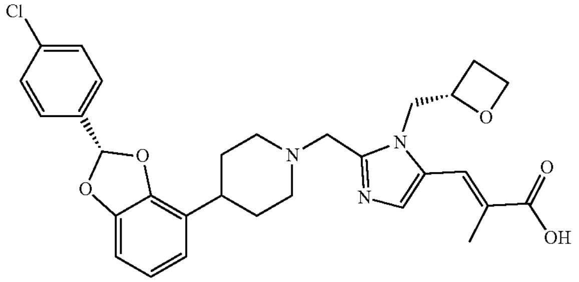 [SMILES: C/C(=C\c1cnc(CN2CCC(c3cccc4c3O[C@@H](c3ccc(Cl)cc3)O4)CC2)n1C[C@@H]1CCO1)C(=O)O]

$^1$H NMR (400 MHz, DMSO-$d_6$) δ 12.32 (br. s, 1H), 7.49-7.63 (m, 5H), 7.23 (s, 1H), 7.16 (s, 1H), 6.66-6.90 (m, 3H), 4.89-4.95 (m, 1H), 4.25-4.53 (m, 4H), 3.70 (d, J=13.6 Hz, 1H), 3.53 (d, J=13.6 Hz, 1H), 2.93 (d, J=11.2 Hz, 1H), 2.79 (d, J=11.2 Hz, 1H), 2.55-2.70 (m, 2H), 2.28-2.41 (m, 1H), 2.02-2.18 (m, 2H), 2.00 (s, 3H), 1.63-1.80 (m, 4H). LC-MS: m/z 550.2 $(M+H)^+$.

(E)-3-(2-((4-((R)-2-(4-chlorophenyl)benzo[d][1,3]dioxol-4-yl)piperidin-1-yl)methyl)-1-(((S)-oxetan-2-yl)methyl)-1H-imidazol-5-yl)-2-methylacrylic acid (Compound 133b)

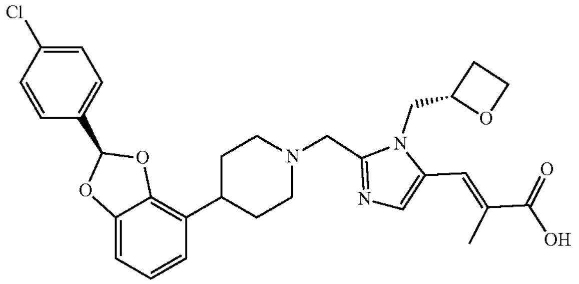 [SMILES: C/C(=C\c1cnc(CN2CCC(c3cccc4c3O[C@H](c3ccc(Cl)cc3)O4)CC2)n1C[C@@H]1CCO1)C(=O)O]

$^1$H NMR (400 MHz, DMSO-$d_6$) δ 12.33 (br. s, 1H), 7.48-7.65 (m, 5H), 7.23 (s, 1H), 7.16 (s, 1H), 6.70-6.89 (m, 3H), 4.88-4.94 (m, 1H), 4.47 (dd, J=15.6, 7.2 Hz, 1H), 4.27-4.40 (m, 3H), 3.71 (d, J=13.6 Hz, 1H), 3.51 (d, J=13.6 Hz, 1H), 2.94 (d, J=11.2 Hz, 1H), 2.78 (d, J=11.2 Hz, 1H), 2.55-2.69 (m, 2H), 2.30-2.42 (m, 1H), 2.01-2.17 (m, 2H), 2.00 (s, 3H), 1.61-1.85 (m, 4H). LC-MS: m/z 550.2 $(M+H)^+$.

Example 12

(E)-3-(2-((4-(2-(4-chloro-2-fluorophenyl)-2-methylbenzo[d][1,3]dioxol-4-yl)piperidin-1-yl)methyl)-1-((1-ethyl-1H-imidazol-5-yl)methyl)-1H-imidazol-5-yl)-2-methylacrylic acid (Compound 138), (S,E)-3-(2-((4-(2-(4-chloro-2-fluorophenyl)-2-methylbenzo[d][1,3]dioxol-4-yl)piperidin-1-yl)methyl)-1-((1-ethyl-1H-imidazol-5-yl)methyl)-1H-imidazol-5-yl)-2-methylacrylic acid (Compound 138a) and (R,E)-3-(2-((4-(2-(4-chloro-2-fluorophenyl)-2-methylbenzo[d][1,3]dioxol-4-yl) piperidin-1-yl) methyl)-1-((1-ethyl-1H-imidazol-5-yl)methyl)-1H-imidazol-5-yl)-2-methylacrylic acid (Compound 138b)

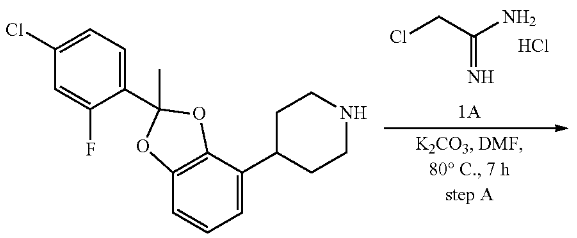

1

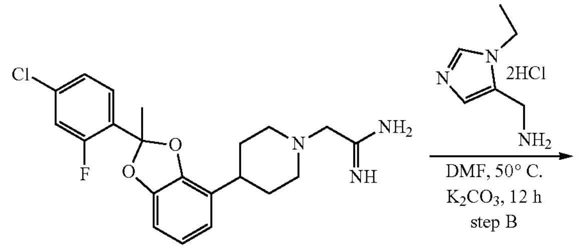

2

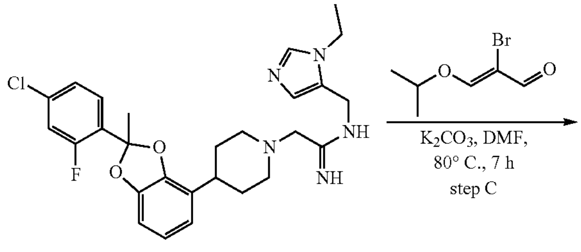

3

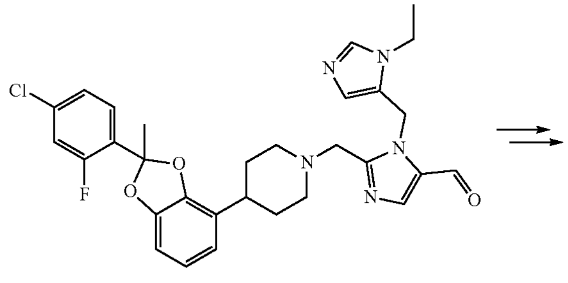

4

-continued

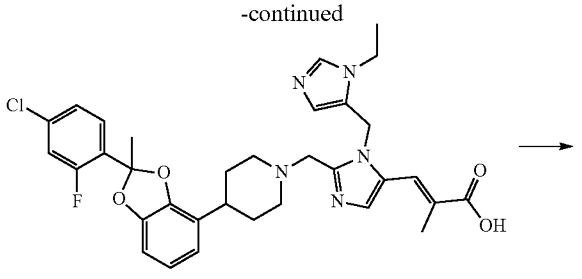

Compound 138

Compound 138a
Compound 138b

Step A: 2-(4-(2-(4-chloro-2-fluorophenyl)-2-methylbenzo[d][1,3]dioxol-4-yl) piperidin-1-yl)acetimidamide

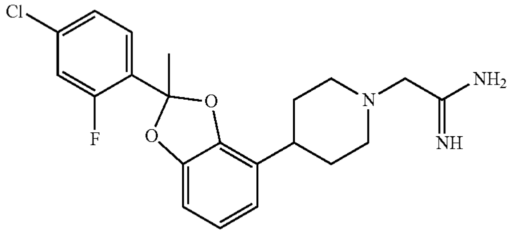 [SMILES: CC1(c2ccc(Cl)cc2F)Oc2cccc(C3CCN(CC(=N)N)CC3)c2O1]

To a solution of 4-(2-(4-chloro-2-fluorophenyl)-2-methylbenzo[d][1,3]dioxol-4-yl) piperidine (500 mg, 1.44 mmol) in DMF (7 mL) were added $K_2CO_3$ (596 mg, 4.32 mmol) and chloroacetamidine hydrochloride (223 mg, 1.73 mmol). The mixture was stirred at 80° C. for 7 hours. The reaction mixture was used directly in the next step without any purification. LC-MS: m/z 404.2 $(M+H)^+$.

Step B: 2-(4-(2-(4-chloro-2-fluorophenyl)-2-methylbenzo[d][1,3]dioxol-4-yl) piperidin-1-yl)-N-((1-ethyl-1H-imidazol-5-yl)methyl)acetimidamide

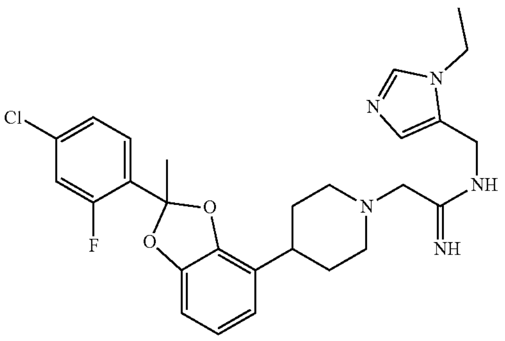 [SMILES: CCn1cncc1CNC(=N)CN1CCC(c2cccc3c2OC(C)(c2ccc(Cl)cc2F)O3)CC1]

To the reaction mixture of step A were added $K_2CO_3$ (596 mg, 4.32 mmol) and (1-ethyl-1H-imidazol-5-yl)methanamine (339 mg, 1.73 mmol, 2 HCl salt). The mixture was stirred at 80° C. for 12 hours. LCMS showed the reaction was almost completed. The reaction mixture was used directly in the next step without any purification. LC-MS: m/z 512.1 $(M+H)^+$.

Step C: 2-((4-(2-(4-chloro-2-fluorophenyl)-2-methylbenzo[d][1,3]dioxol-4-yl) piperidin-1-yl)methyl)-1-((1-ethyl-1H-imidazol-5-yl)methyl)-1H-imidazole-5-carbaldehyde

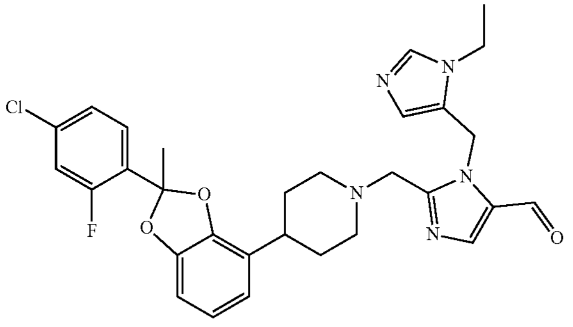 [SMILES: CCn1cncc1Cn1c(C=O)cnc1CN1CCC(c2cccc3c2OC(C)(c2ccc(Cl)cc2F)O3)CC1]

To the mixture of step B was added ((Z)-2-bromo-3-isopropoxyacrylaldehyde (417 mg, 2.16 mmol). The mixture was stirred at 50° C. for 8 hours. After cooled down to room temperature, the reaction mixture was diluted with water (50 mL) and extracted with EtOAc (3×40 mL). The organic layer was washed by brine, dried over $Na_2SO_4$, filtered and concentrated. The residue was purified by silica gel column chromatography (DCM/MeOH=10/1) to afford (3-bromo-2-(methoxymethoxy) phenyl)(4-chloro-2-fluorophenyl) methanol (152 mg, 19% over three steps) as a light yellow solid. $^1H$ NMR (400 MHz, $CDCl_3$) δ 9.73 (s, 1H), 7.77 (s, 1H), 7.45-7.57 (m, 2H), 7.09-7.16 (m, 2H), 6.76 (d, J=7.6 Hz, 1H), 6.65-6.72 (m, 3H), 5.95 (s, 2H), 3.96 (q, J=7.2 Hz, 2H), 3.64 (s, 2H), 2.78-2.90 (m, 2H), 2.62-2.73 (m, 1H), 2.22 (td, J=11.2, 3.2 Hz, 2H), 2.05 (s, 3H), 1.74-1.88 (m, 4H), 1.32 (t, J=7.2 Hz, 3H). LC-MS: m/z 564.2 $(M+H)^+$.

Compound 138 was then synthesized following the method described in Example 1 (step I) by using 2-((4-(2-(4-chloro-2-fluorophenyl)-2-methylbenzo[d][1,3]dioxol-4-yl)piperidin-1-yl)methyl)-1-((1-ethyl-1H-imidazol-5-yl) methyl)-1H-imidazole-5-carbaldehyde and ethyl 2-(diethoxyphosphoryl)propanoate. Compound 138b and Compound 138a were obtained via chiral separation of Compound 138.

(E)-3-(2-((4-(2-(4-chloro-2-fluorophenyl)-2-methylbenzo[d][1,3]dioxol-4-yl)piperidin-1-yl)methyl)-1-((1-ethyl-1H-imidazol-5-yl)methyl)-1H-imidazol-5-yl)-2-methylacrylic acid (Compound 138)

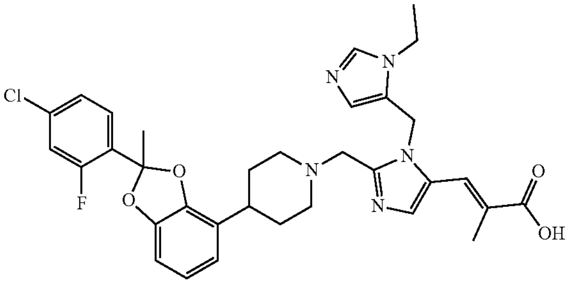 [SMILES: CCn1cncc1Cn1c(/C=C(\C)C(=O)O)cnc1CN1CCC(c2cccc3c2OC(C)(c2ccc(Cl)cc2F)O3)CC1]

$^1H$ NMR (400 MHz, $CD_3OD$) δ 7.74 (s, 1H), 7.55 (t, J=8.4 Hz, 1H), 7.45 (s, 1H), 7.33 (s, 1H), 7.27 (dd, J=10.8, 2.0 Hz, 1H), 7.20 (dd, J=8.4, 1.6 Hz, 1H), 6.76 (t, J=8.0 Hz, 1H), 6.67 (dd, J=7.6, 1.2 Hz, 1H), 6.62 (d, J=7.2 Hz, 1H), 6.40 (s, 1H), 5.54 (s, 2H), 4.13 (q, J=7.2 Hz, 2H), 3.64-3.77 (m, 2H), 2.87 (t, J=11.2 Hz, 2H), 2.60-2.51 (m, 1H), 2.09-2.26 (m, 5H), 2.01 (s, 3H), 1.72 (t, J=14.4 Hz, 2H), 1.48-1.59 (m, 2H), 1.42 (t, J=7.2 Hz, 3H). LC-MS: m/z 620.3 $(M+H)^+$.

(S,E)-3-(2-((4-(2-(4-chloro-2-fluorophenyl)-2-methylbenzo[d][1,3]dioxol-4-yl)piperidin-1-yl)methyl)-1-((1-ethyl-1H-imidazol-5-yl)methyl)-1H-imidazol-5-yl)-2-methylacrylic acid (Compound 138a)

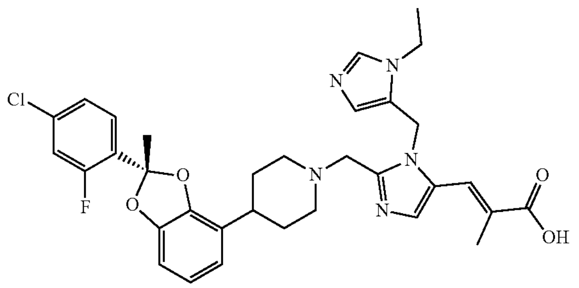 [SMILES: CCn1cncc1Cn1c(/C=C(\C)C(=O)O)cnc1CN1CCC(c2cccc3c2O[C@@](C)(c2ccc(Cl)cc2F)O3)CC1]

$^1$H NMR (400 MHz, $CDCl_3$) δ 7.66 (s, 1H), 7.47-7.52 (m, 2H), 7.28 (s, 1H), 7.04-7.15 (m, 2H), 6.91 (s, 1H), 6.76 (t, J=8.0 Hz, 1H), 6.70 (d, J=7.6 Hz, 1H), 6.64 (d, J=7.6 Hz, 1H). 5.41-5.59 (m, 2H), 3.93 (q, J=7.2 Hz, 2H), 3.69 (s, 2H), 2.92 (br. s, 2H), 2.59-2.74 (m, 1H), 2.25 (t, J=10.8 Hz, 2H), 2.09 (s, 3H), 2.04 (s, 3H), 1.62-1.88 (m, 4H), 1.26 (t, J=7.2 Hz, 3H). LC-MS: m/z 620.2 $(M+H)^+$.

(R,E)-3-(2-((4-(2-(4-chloro-2-fluorophenyl)-2-methylbenzo[d][1,3]dioxol-4-yl)piperidin-1-yl)methyl)-1-((1-ethyl-1H-imidazol-5-yl)methyl)-1H-imidazol-5-yl)-2-methylacrylic acid (Compound 138b)

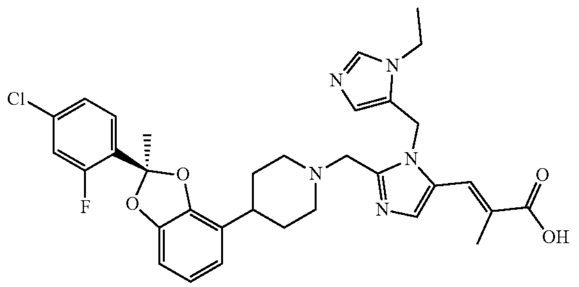 [SMILES: CCn1cncc1Cn1c(/C=C(\C)C(=O)O)cnc1CN1CCC(c2cccc3c2O[C@](C)(c2ccc(Cl)cc2F)O3)CC1]

$^1$H NMR (400 MHz, $CDCl_3$) δ 7.66 (s, 1H), 7.49 (t, J=8.0 Hz, 2H), 7.28 (s, 1H), 7.08-7.13 (m, 2H), 6.85 (s, 1H), 6.76 (t, J=7.6 Hz, 1H), 6.63 (d, J=7.6 Hz, 1H), 6.58 (d, J=7.6 Hz, 1H), 5.44-5.49 (m, 2H), 3.93 (q, J=7.2 Hz, 2H), 3.70 (s, 2H), 2.91 (br. s, 2H), 2.63-2.71 (m, 1H), 2.48 (t, J=11.2 Hz, 2H), 2.10 (s, 3H), 2.04 (s, 3H), 1.59-1.86 (m, 4H), 1.20 (t, J=7.6 Hz, 3H). LC-MS: m/z 620.2 $(M+H)^+$.

Compound 139b and Compound 139a were synthesized following the method described in Example 9 (step D to step F) starting from 2-((4-(2-(4-chloro-2-fluorophenyl)-2-methylbenzo[d][1,3]dioxol-4-yl)piperidin-1-yl)methyl)-1-((1-ethyl-1H-imidazol-5-yl)methyl)-1H-imidazole-5-carbaldehyde and methyl 2-(diethoxyphosphoryl)acetate.

(S,E)-3-(2-((4-(2-(4-chloro-2-fluorophenyl)-2-methylbenzo[d][1,3]dioxol-4-yl)piperidin-1-yl)methyl)-1-((1-ethyl-1H-imidazol-5-yl)methyl)-1H-imidazol-5-yl)acrylic acid (Compound 139a)

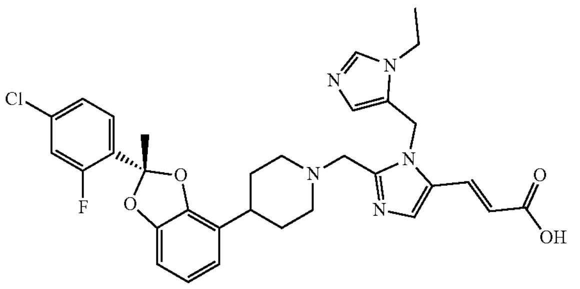 [SMILES: CCn1cncc1Cn1c(/C=C/C(=O)O)cnc1CN1CCC(c2cccc3c2O[C@@](C)(c2ccc(Cl)cc2F)O3)CC1]

$^1$H NMR (400 MHz, $CD_3OD$) δ 7.71 (s, 1H), 7.55 (t, J=8.0 Hz, 1H), 7.45 (s, 1H), 7.38 (d, J=16.0 Hz, 1H), 7.28 (dd, J=10.8, 2.0 Hz, 1H), 7.21 (dd, J=8.4, 2.0 Hz, 1H), 6.76 (t, J=8.0 Hz, 1H), 6.67 (d, J=8.0 Hz, 1H), 6.61 (d, J=7.6 Hz, 1H), 6.36-6.40 (m, 2H), 5.54 (s, 2H), 4.13 (q, J=7.2 Hz, 2H), 3.65 (s, 2H), 2.83 (t, J=12.0 Hz, 2H), 2.59-2.69 (m, 1H), 2.11 (t, J=12.0 Hz, 2H), 2.01 (s, 3H), 1.66-1.73 (m, 2H), 1.44-1.54 (m, 2H), 1.43 (t, J=7.2 Hz, 3H). LC-MS: m/z 606.2 $(M+H)^+$.

(R,E)-3-(2-((4-(2-(4-chloro-2-fluorophenyl)-2-methylbenzo[d][1,3]dioxol-4-yl)piperidin-1-yl)methyl)-1-((1-ethyl-1H-imidazol-5-yl)methyl)-1H-imidazol-5-yl)acrylic acid (Compound 139b)

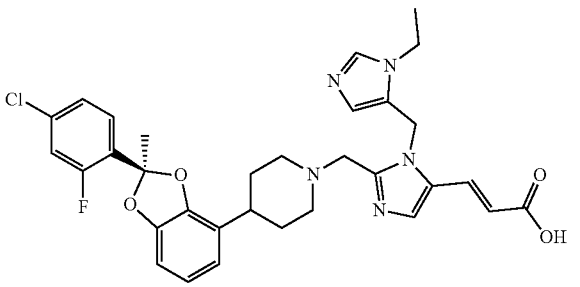 [SMILES: CCn1cncc1Cn1c(/C=C/C(=O)O)cnc1CN1CCC(c2cccc3c2O[C@](C)(c2ccc(Cl)cc2F)O3)CC1]

$^1$H NMR (400 MHz, $CD_3OD$) δ 7.71 (s, 1H), 7.55 (t, J=8.0 Hz, 1H), 7.45 (s, 1H), 7.38 (d, J=16.0 Hz, 1H), 7.28 (dd, J=10.8, 2.0 Hz, 1H), 7.21 (dd, J=8.4, 2.0 Hz, 1H), 6.76 (t, J=8.0 Hz, 1H), 6.67 (dd, J=8.0, 1.2 Hz, 1H), 6.61 (d, J=7.6 Hz, 1H), 6.36-6.40 (m, 2H), 5.54 (s, 2H), 4.13 (q, J=7.2 Hz, 2H), 3.65 (s, 2H), 2.83 (t, J=12.0 Hz, 2H), 2.59-2.63 (m, 1H), 2.11 (t, J=12.0 Hz, 2H), 2.01 (s, 3H), 1.65-1.73 (m, 2H), 1.45-1.54 (m, 2H), 1.43 (t, J=7.2 Hz, 3H) LC-MS: m/z 606.2 $(M+H)^+$.

(E)-3-(2-((4-(2-(4-chloro-2-fluorophenyl)-2-methylbenzo[d][1,3]dioxol-4-yl)piperidin-1-yl)methyl)-1-(((S)-tetrahydrofuran-2-yl)methyl)-1H-imidazol-5-yl)acrylic acid (Compound 140a) was synthesized following the method described in step I to step J in Example 1 starting from 2-((4-(2-(4-chloro-2-fluorophenyl)-2-methylbenzo[d][1,3]dioxol-4-yl)piperidin-1-yl)methyl)-1-(((S)-tetrahydrofuran-2-yl)methyl)-1H-imidazole-5-carbaldehyde which is obtained after two step conversion of 2-(4-(2-(4-chloro-2-fluorophenyl)-2-methylbenzo[d][1,3]dioxol-4-yl) piperidin- 1-yl)acetimidamide and (S)-(tetrahydrofuran-2-yl)methanamine analogous to the procedures in step B-C in Example 12.

(E)-3-(2-((4-(2-(4-chloro-2-fluorophenyl)-2-methylbenzo[d][1,3]dioxol-4-yl)piperidin-1-yl)methyl)-1-(((S)-tetrahydrofuran-2-yl)methyl)-1H-imidazol-5-yl)acrylic acid (Compound 140a)

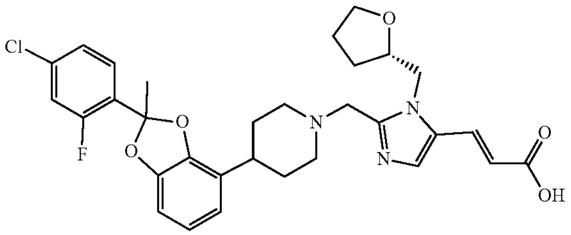 [SMILES: CC1(c2ccc(Cl)cc2F)Oc2cccc(C3CCN(Cc4ncc(/C=C/C(=O)O)n4C[C@@H]4CCCO4)CC3)c2O1]

$^1$H NMR (400 MHz, DMSO-$d_6$) δ 12.28 (br.s, 1H), 7.50-7.57 (m, 4H), 7.34 (d, J=8.4 Hz, 1H), 6.72-6.79 (m, 3H), 6.27 (d, J=16.0 Hz, 1H), 4.29 (d, J=14.4 Hz, 1H), 4.09-4.20 (m, 2H), 3.71-3.79 (m, 2H), 3.60-3.63 (m, 1H), 3.48 (dd, J=13.6, 2.4 Hz, 1H), 2.94-2.97 (m, 1H), 2.77-2.81 (m, 1H), 2.58-2.68 (m, 1H), 2.11-2.21 (m, 1H), 1.93-2.09 (m, 5H), 1.82-1.90 (m, 1H), 1.68-1.78 (m, 5H), 1.57-1.74 (m, 1H). LC-MS: m/z 582.2 (M+H)$^+$.

(E)-3-(2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)acrylic acid (Compound 141) was synthesized following the method described in step I to step J in Example 1 starting from 2-((4-(2-(4-chloro-2-fluorophenyl)-2-methylbenzo[d][1,3]dioxol-4-yl)piperidin-1-yl)methyl)-1-(2-methoxyethyl)-1H-imidazole-5-carbaldehyde which is obtained after two step conversion of 2-(4-(2-(4-chloro-2-fluorophenyl)-2-methylbenzo[d][1,3]dioxol-4-yl)piperidin-1-yl)acetimidamide and 2-methoxyethan-1-amine analogous to the procedures in step B-C in Example 12.

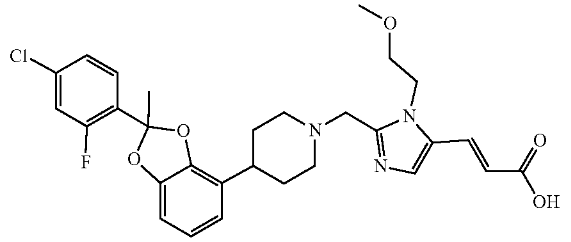 [SMILES: COCCn1c(/C=C/C(=O)O)cnc1CN1CCC(c2cccc3c2OC(C)(c2ccc(Cl)cc2F)O3)CC1]

$^1$H NMR (400 MHz, $CD_3OD$) δ 7.55-7.59 (m, 2H), 7.47 (s, 1H), 7.27 (dd, J=10.8, 2.0 Hz, 1H), 7.20 (dd, J=8.0, 2.0 Hz, 1H), 6.76-6.79 (m, 1H), 6.70 (d, J=8.0 Hz, 2H), 6.37 (d, J=15.6 Hz, 1H), 4.44 (t, J=4.8 Hz, 2H), 3.85 (d, J=4.8 Hz, 2H), 3.71 (s, 2H), 3.30 (s, 3H), 3.07-3.08 (m, 2H), 2.68-2.79 (m, 1H), 2.40 (t, J=11.6 Hz, 2H), 2.02 (s, 3H), 1.82-1.94 (m, 4H). LCMS: m/z 556.2 (M+H)$^+$.

3-(5-((4-(2-(4-chloro-2-fluorophenyl)-2-methylbenzo[d][1,3]dioxol-4-yl)piperidin-1-yl)methyl)-4-((1-ethyl-1H-imidazol-5-yl)methyl)-4H-1,2,4-triazol-3-yl)propanoic acid (Compound 144) was synthesized following similar route of Example 4 (step A to step B) starting from methyl (E)-3-(5-((4-(2-(4-chloro-2-fluorophenyl)-2-methyl benzo[d][1,3]dioxol-4-yl)piperidin-1-yl)methyl)-4-((1-ethyl-1H-imidazol-5-yl)methyl)-4H-1,2,4-triazol-3-yl)acrylate and platinum oxide.

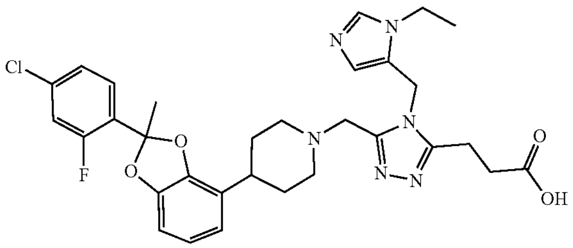 [SMILES: CCn1cncc1Cn1c(CCC(=O)O)nnc1CN1CCC(c2cccc3c2OC(C)(c2ccc(Cl)cc2F)O3)CC1]

$^1$H NMR (400 MHz, DMSO-$d_6$) δ 7.66 (s, 1H), 7.51-7.59 (m, 2H), 7.34 (dd, J=8.4, 2.0 Hz, 1H), 6.75-6.83 (m, 2H), 6.64 (dd, J=6.4, 2.8 Hz, 1H), 6.44 (s, 1H), 5.34 (s, 2H), 4.00 (q, J=7.2 Hz, 2H), 3.61 (s, 2H), 2.75-2.84 (m, 4H), 2.68 (t, J=7.2 Hz, 2H), 2.54-2.59 (m, 1H), 2.01-2.05 (m, 5H), 1.59-1.65 m, 2H), 1.37-1.45 (m, 2H), 1.24 (t, J=7.2 Hz, 3H). LC-MS: m/z 609.2 (M+H)$^+$.

3-(2-((4-(2-(4-chloro-2-fluorophenyl)-2-methylbenzo[d][1,3]dioxol-4-yl)piperidin-1-yl)methyl)-1-((1-ethyl-1H-imidazol-5-yl)methyl)-1H-imidazol-5-yl)propanoic acid (Compound 143) was synthesized following similar route of Example 4 (step A to step B) starting from ethyl (E)-3-(2-((4-(2-(4-chloro-2-fluorophenyl)-2-methyl benzo[d][1,3]dioxol-4-yl)piperidin-1-yl)methyl)-1-((1-ethyl-1H-imidazol-5-yl)methyl)-1H-imidazol-5-yl)acrylate and Platinum oxide.

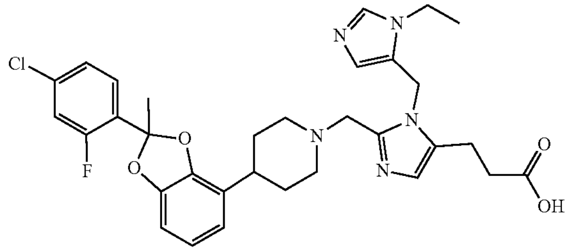 [SMILES: CCn1cncc1Cn1c(CCC(=O)O)cnc1CN1CCC(c2cccc3c2OC(C)(c2ccc(Cl)cc2F)O3)CC1]

$^1$H NMR (400 MHz, $CDCl_3$) δ 7.61 (s, 1H), 7.50 (t, J=8.4 Hz, 1H), 7.09-7.14 (m, 2H), 6.89 (s, 1H), 6.76 (t, J=8.0 Hz, 1H), 6.68 (dd, J=7.6, 1.2 Hz, 1H), 6.12-6.35 (m, 2H), 5.38 (s, 2H), 4.00 (q, J=7.2 Hz, 2H), 3.63 (s, 2H), 2.90 (br.s, 2H), 2.80 (t, J=6.8 Hz, 2H), 2.59-2.64 (m, 3H), 2.24 (t, J=12.0 Hz, 2H), 2.04 (s, 3H), 1.65-1.83 (m, 4H), 1.40 (t, J=7.2 Hz, 3H). LC-MS: m/z 608.2 (M+H)$^+$.

(E)-3-(2-((4-(6-((4-chloro-2-fluorobenzyl)oxy)pyridin-2-yl)piperidin-1-yl)methyl)-1-methyl-1H-imidazol-5-yl)-2-methylacrylic acid (Compound 110) was synthesized 10 following the method described in Example 1, using 2-((4-(6-((4-chloro-2-fluorobenzyl)oxy)pyridin-2-yl)piperidin-1-yl)methyl)-1-methyl-1H-imidazole-5-carbaldehyde and ethyl 2-(diethoxyphosphoryl)propanoate in step I.

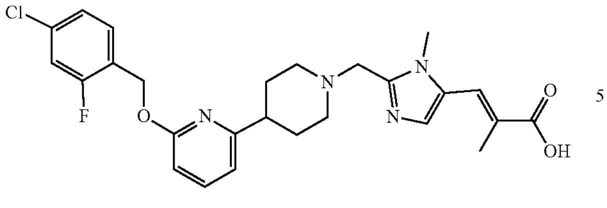

$^1$H NMR (400 MHz, $CD_3OD$) δ 7.54-7.59 (m, 2H), 7.48 (t, J=8.0 Hz, 1H), 7.28 (s, 1H), 7.16-7.21 (m, 2H), 6.82 (d, J=7.2 Hz, 1H), 6.63 (d, J=8.0 Hz, 1H), 5.40 (s, 2H), 3.78 (s, 5H), 3.04 (d, J=11.6 Hz, 2H), 2.61-2.67 (m, 1H), 2.30-2.36 (m, 2H), 2.11 (d, J=1.2 Hz, 3H), 1.81-1.92 (m, 4H). LC-MS: m/z 499.2 $(M+H)^+$.

(S,E)-3-(2-((4-(2-(4-chloro-2-fluorophenyl)-2-methylbenzo[d][1,3]dioxol-4-yl)piperidin-1-yl)methyl)-1-(2-(trifluoromethoxy)ethyl)-1H-imidazol-5-yl)acrylic acid (Compound 145) was synthesized following the method described in Example 1, using 2-(trifluoromethoxy)ethan-1-amine in step A and ethyl (S)-4-(2-(4-chloro-2-fluorophenyl)-2-methylbenzo[d][1,3]dioxol-4-yl)piperidine hydrochloride in step F.

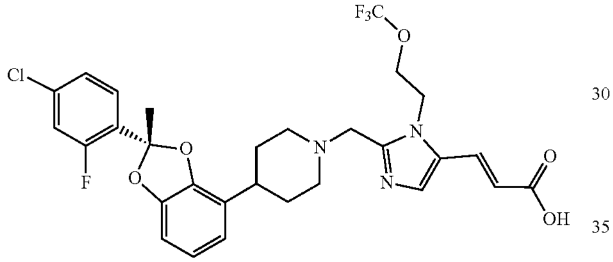

$^1$H NMR (400 MHz, DMSO-$d_6$) δ 12.28 (br. s, 1H), 7.52-7.59 (m, 3H), 7.49 (d, J=16.0 Hz, 1H), 7.33 (dd, J=8.4, 2.0 Hz, 1H), 6.77-6.81 (m, 2H), 6.65-6.72 (m, 1H), 6.32 (d, J=16.0 Hz, 1H), 4.46-4.60 (m, 4H), 3.62 (dd, J=22.0, 13.6 Hz, 2H), 2.81-2.95 (m, 2H), 2.57-2.72 (m, 1H), 2.03-2.17 (m, 2H), 2.00 (s, 3H), 1.65-1.78 (m, 4H). $^{19}$F NMR (377 MHz, DMSO-$d_6$): δ −59.28, −110.86. LC-MS: m/z 610.0 $(M+H)^+$.

(E)-3-(2-((4-(2-(4-chloro-2-fluorophenyl)-2-methylbenzo[d][1,3]dioxol-4-yl)piperidin-1-yl)methyl)-1-((2-(trifluoromethyl)pyridin-3-yl)methyl)-1H-imidazol-5-yl)acrylic acid (Compound 146) was synthesized following the route of Example 12, using (2-(trifluoromethyl)pyridin-3-yl)methanamine in step B.

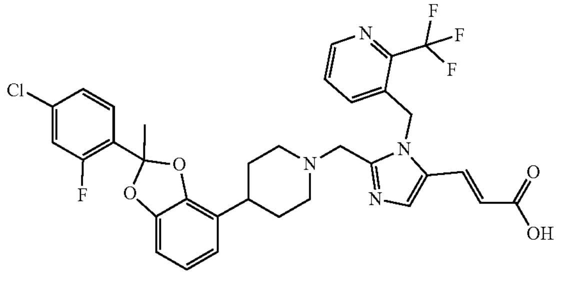 [SMILES: CC1(c2ccc(Cl)cc2F)Oc2cccc(C3CCN(Cc4ncc(/C=C/C(=O)O)n4Cc4cccnc4C(F)(F)F)CC3)c2O1]

$^1$H NMR (400 MHz, DMSO-$d_6$) δ 8.60 (d, J=4.0 Hz, 1H), 7.64-7.68 (m, 2H), 7.48-7.55 (m, 2H), 7.32 (d, J=8.4 Hz, 1H), 7.27 (d, J=16.0 Hz, 1H), 6.92 (d, J=7.6 Hz, 1H), 6.73-6.79 (m, 2H), 6.25-6.41 (m, 2H), 5.69 (s, 2H), 3.61 (dd, J=24.0, 14.0 Hz, 2H), 2.64 (dd, J=19.6, 11.2, 2H), 2.42-2.45 (m, 1H), 2.00 (s, 3H), 1.89-1.98 (m, 2H), 1.46 (dd, J=24.0, 12.0 Hz, 2H), 0.76-0.96 (m, 2H). LC-MS: m/z 656.8 $(M+H)^+$.

(E)-3-(2-((4-(2-(4-chloro-2-fluorophenyl)-2-methylbenzo[d][1,3]dioxol-4-yl)piperidin-1-yl)methyl)-1-((2-methylpyridin-3-yl)methyl)-1H-imidazol-5-yl)acrylic acid (Compound 147) was synthesized following the route of Example 12, using (2-methylpyridin-3-yl)methanamine in step B.

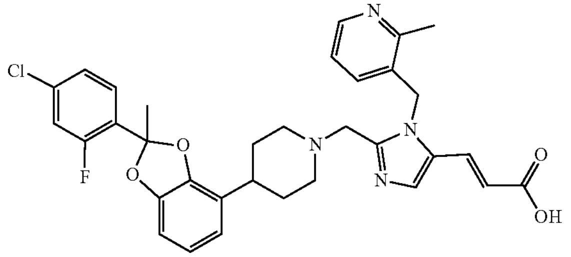 [SMILES: Cc1ncccc1Cn1c(/C=C/C(=O)O)cnc1CN1CCC(c2cccc3c2OC(C)(c2ccc(Cl)cc2F)O3)CC1]

$^1$H NMR (400 MHz, DMSO-$d_6$) δ 12.36 (br.s, 1H), 8.28 (d, J=4.0 Hz, 1H), 7.64 (s, 1H), 7.49-7.55 (m, 2H), 7.33 (d, J=8.4 Hz, 1H), 7.25 (d, J=16.0 Hz, 1H), 7.12 (dd, J=7.6, 5.2 Hz, 1H), 6.71-6.80 (m, 2H), 6.59 (d, J=7.6 Hz, 1H), 6.43 (d, J=6.8 Hz, 1H), 6.29 (d, J=16.0 Hz, 1H), 5.47 (s, 2H), 3.54-3.64 (m, 2H), 2.65-2.73 (m, 1H), 2.59 (s, 3H), 2.52-2.56 (m, 2H), 2.00 (s, 3H), 1.94-1.96 (m, 2H), 1.38-1.54 (m, 2H), 0.83-1.09 (m, 2H). LC-MS: m/z 602.9 $(M+H)^+$.

(E)-3-(2-((4-(2-(4-chloro-2-fluorophenyl)-2-methylbenzo[d][1,3]dioxol-4-yl)piperidin-1-yl)methyl)-1-((2-ethylpyridin-3-yl)methyl)-1H-imidazol-5-yl)acrylic acid (Compound 148) was synthesized following the route of Example 12, using (2-ethylpyridin-3-yl)methanamine in step B.

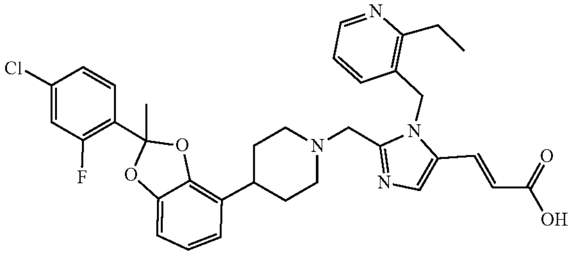 [SMILES: CCc1ncccc1Cn1c(/C=C/C(=O)O)cnc1CN1CCC(c2cccc3c2OC(C)(c2ccc(Cl)cc2F)O3)CC1]

$^1$H NMR (400 MHz, $CDCl_3$) δ 8.47 (d, J=4.0 Hz, 1H), 7.58 (s, 1H), 7.48 (t, J=8.0 Hz, 1H), 7.35 (d, J=16.0 Hz, 1H), 7.08-7.18 (m, 2H), 7.03-7.06 (m, 1H), 6.76 (t, J=7.6 Hz, 1H), 6.68 (d, J=7.6 Hz, 2H), 6.54 (d, J=7.6 Hz, 1H), 6.26 (d, J=16.0 Hz, 1H), 5.55 (s, 2H), 3.60 (s, 2H), 2.95 (q, J=7.6 Hz, 2H), 2.75-2.90 (m, 2H), 2.54-2.71 (m, 1H), 2.08-2.25 (m, 2H), 2.03 (s, 3H), 1.68-1.72 (m, 2H), 1.41-1.51 (m, 2H), 1.40 (t, J=7.2 Hz, 3H). LC-MS: m/z 617.0 $(M+H)^+$.

(E)-3-(2-((4-(2-(4-chloro-2-fluorophenyl)-2-methylbenzo[d][1,3]dioxol-4-yl)piperidin-1-yl)methyl)-1-(3-methoxybenzyl)-1H-imidazol-5-yl)acrylic acid (Compound 149) was synthesized following the route of Example 12, using (3-methoxyphenyl)methanamine in step B.

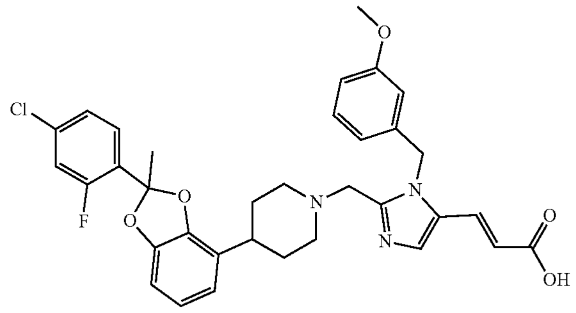 [SMILES: COc1cccc(Cn2c(/C=C/C(=O)O)cnc2CN2CCC(c3cccc4c3OC(C)(c3ccc(Cl)cc3F)O4)CC2)c1]

$^1$H NMR (400 MHz, DMSO-$d_6$) δ 12.30 (br.s, 1H), 7.60 (s, 1H), 7.54 (dt, J=16.8, 5.2 Hz, 2H), 7.29-7.37 (m, 2H), 7.24 (t, J=8.0 Hz, 1H), 6.80-6.85 (m, 1H), 6.74-6.78 (m, 2H), 6.64 (s, 1H), 6.53-6.61 (m, 2H), 6.26 (d, J=16.0 Hz, 1H), 5.44 (s, 2H), 3.69 (s, 3H), 3.53-3.62 (m, 2H), 2.82-2.85 (m, 2H), 2.54-2.60 (m, 1H), 2.06 (t, J=11.6 Hz, 2H), 2.00 (s, 3H), 1.59 (t, J=13.2 Hz, 2H), 1.28-1.46 (m, 2H). LC-MS: m/z 617.9 $(M+H)^+$.

(E)-3-(2-((4-(2-(4-chloro-2-fluorophenyl)-2-methylbenzo[d][1,3]dioxol-4-yl)piperidin-1-yl)methyl)-1-(3-chlorobenzyl)-1H-imidazol-5-yl)acrylic acid (Compound 150) was synthesized following the route of Example 12, using (3-chlorophenyl)methanamine in step B.

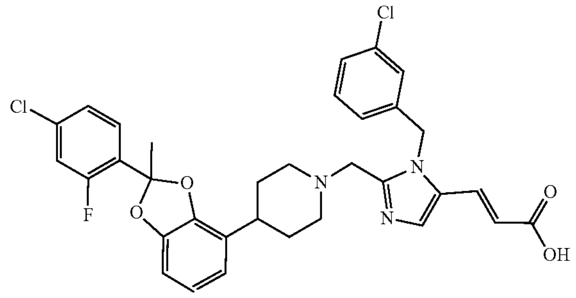 [SMILES: C=C/C(=C1/OC(C)(c2ccc(Cl)cc2F)O/C1=C/C)C1CCN(Cc2ncc(/C=C/C(=O)O)n2Cc2cccc(Cl)c2)CC1]

$^1$H NMR (400 MHz, DMSO-$d_6$) δ 12.25 (br.s, 1H), 7.61 (s, 1H), 7.49-7.56 (m, 2H), 7.26-7.39 (m, 4H), 7.15 (s, 1H), 7.01 (d, J=7.2 Hz, 1H), 6.73-6.80 (m, 2H), 6.55 (dd, J=6.4, 2.0 Hz, 1H), 6.27 (d, J=16.0 Hz, 1H), 5.48 (s, 2H), 3.60 (s, 2H), 2.75-2.91 (m, 2H), 2.54-2.63 (m, 1H), 2.06 (t, J=11.6 Hz, 2H), 2.00 (s, 3H), 1.59 (t, J=13.2 Hz, 2H), 1.20-1.39 (m, 2H). LC-MS: m/z 621.8 $(M+H)^+$.

(E)-3-(1-benzyl-2-((4-(2-(4-chloro-2-fluorophenyl)-2-methylbenzo[d][1,3]dioxol-4-yl)piperidin-1-yl)methyl)-1H-imidazol-5-yl)acrylic acid (Compound 151) was synthesized following the route of Example 12, using phenylmethanamine in step B.

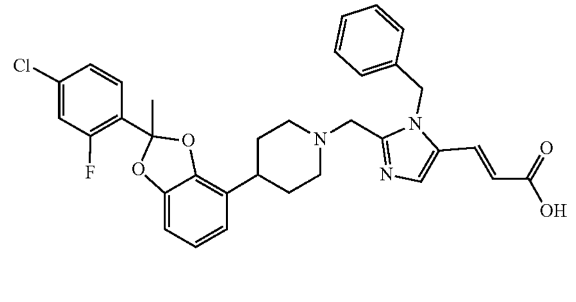 [SMILES: CC1(c2ccc(Cl)cc2F)Oc2cccc(C3CCN(Cc4ncc(/C=C/C(=O)O)n4Cc4ccccc4)CC3)c2O1]

$^1$H NMR (400 MHz, DMSO-$d_6$) δ 7.60 (s, 1H), 7.53 (t, J=8.8 Hz, 2H), 7.29-7.35 (m, 4H), 7.23 (t, J=7.2 Hz, 1H), 7.06 (d, J=7.6 Hz, 2H), 6.75-6.78 (m, 2H), 6.57 (dd, J=6.0, 2.8 Hz, 1H), 6.26 (d, J=15.6 Hz, 1H), 5.48 (s, 2H), 3.58 (s, 2H), 2.80-2.85 (m, 2H), 2.56-2.59 (m, 1H), 2.06 (t, J=11.2 Hz, 2H), 2.01 (s, 3H), 1.60 (t, J=13.2 Hz, 2H), 1.33-1.45 (m, 2H). LC-MS: m/z 587.8 $(M+H)^+$.

(E)-3-(2-((4-(2-(4-chloro-2-fluorophenyl)-2-methylbenzo[d][1,3]dioxol-4-yl)piperidin-1-yl)methyl)-1-((S)-1-phenylethyl)-1H-imidazol-5-yl)acrylic acid (Compound 152) was synthesized following the route of Example 12, using (S)-1-phenylethan-1-amine in step B.

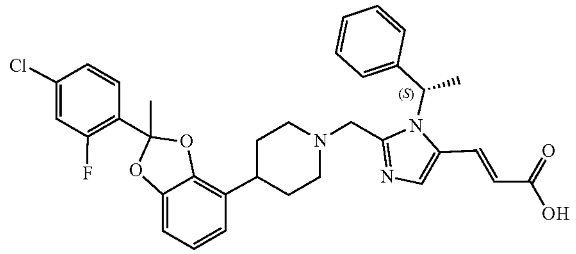

$^1$H NMR (400 MHz, $CDCl_3$) δ 7.45-7.52 (m, 1H), 7.44 (s, 1H), 7.35-7.38 (m, 2H), 7.29-7.31 (m, 1H), 7.21-7.25 (m, 3H), 7.07-7.14 (m, 2H), 6.73-6.77 (m, 1H), 6.68 (d, J=6.8 Hz, 1H), 6.62 (d, J=8.0 Hz, 1H), 6.08-6.15 (m, 2H), 3.78 (d, J=9.6 Hz, 1H), 3.69 (d, J=9.6 Hz, 1H), 2.86-2.98 (m, 2H), 2.65-2.73 (m, 1H), 2.27-2.30 (m, 2H), 2.03 (s, 3H), 1.93 (dd, J=6.8, 2.0 Hz, 3H), 1.73-1.87 (m, 4H). LC-MS: m/z 602.2 $(M+H)^+$.

(E)-3-(2-((4-(2-(4-chloro-2-fluorophenyl)-2-methylbenzo[d][1,3]dioxol-4-yl)piperidin-1-yl)methyl)-1-((R)-1-phenylethyl)-1H-imidazol-5-yl)acrylic acid (Compound 153) was synthesized following the route of Example 12, using (R)-1-phenylethan-1-amine in step B.

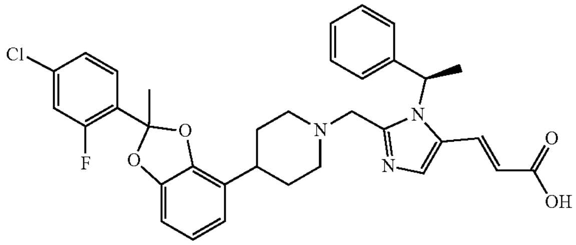 [SMILES: C[C@H](c1ccccc1)n1c(/C=C/C(=O)O)cnc1CN1CCC(c2cccc3c2OC(C)(c2ccc(Cl)cc2F)O3)CC1]

$^1$H NMR (400 MHz, $CD_3OD$) δ 7.51-7.55 (m, 1H), 7.44 (s, 1H), 7.35-7.40 (m, 2H), 7.26-7.30 (m, 4H), 7.15-7.25 (m, 2H), 6.74 (td, J=7.6, 1.2 Hz, 1H), 6.67 (d, J=7.6 Hz, 1H), 6.62 (d, J=8.0 Hz, 1H), 6.18-6.23 (m, 1H), 6.14 (d, J=16.0 Hz, 1H), 3.70-3.80 (m, 2H), 2.93-3.00 (m, 2H), 2.62-2.69 (m, 1H), 2.17-2.30 (m, 2H), 1.99 (s, 3H), 1.95 (dd, J=7.2, 2.4 Hz, 3H), 1.69-1.85 (m, 4H). LC-MS: m/z 602.1 $(M+H)^+$.

(E)-3-(2-((4-(2-(4-chloro-2-fluorophenyl)-2-methylbenzo[d][1,3]dioxol-4-yl)piperidin-1-yl)methyl)-1-(((R)-tetrahydrofuran-3-yl)methyl)-1H-imidazol-5-yl)acrylic acid (Compound 154) was synthesized following the route of Example 12, using (R)-(tetrahydrofuran-3-yl)methanamine in step B.

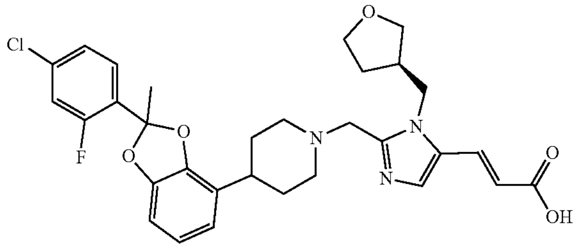 [SMILES: CC1(c2ccc(Cl)cc2F)Oc2cccc(C3CCN(Cc4ncc(/C=C/C(=O)O)n4C[C@H]4CCOC4)CC3)c2O1]

$^1$H NMR (400 MHz, DMSO-$d_6$) δ 12.32 (br.s, 1H), 7.50-7.58 (m, 3H), 7.48 (d, J=16.0 Hz, 1H), 7.34 (dd, J=8.4, 2.0 Hz, 1H), 6.76-6.82 (m, 2H), 6.67-6.74 (m, 1H), 6.33 (d, J=16.0 Hz, 1H), 4.18 (d, J=8.0 Hz, 2H), 3.79-3.87 (m, 1H), 3.51-3.67 (m, 4H), 3.44-3.49 (m, 1H), 2.91-2.93 (m, 2H), 2.59-2.74 (m, 2H), 2.07-2.18 (m, 2H), 2.01 (s, 3H), 1.84-1.93 (m, 1H), 1.63-1.77 (m, 5H). LC-MS: m/z 582.2 $(M+H)^+$.

(E)-3-(2-((4-((S)-2-(4-chloro-2-fluorophenyl)-2-methylbenzo[d][1,3]dioxol-4-yl)piperidin-1-yl)methyl)-1-(((R)-tetrahydrofuran-3-yl)methyl)-1H-imidazol-5-yl)acrylic acid (Compound 155) was synthesized following the route of Example 12, using (S)-4-(2-(4-chloro-2-fluorophenyl)-2-methylbenzo[d][1,3]dioxol-4-yl)piperidine hydrochloride in step A and (R)-(tetrahydrofuran-3-yl)methanamine in step B.

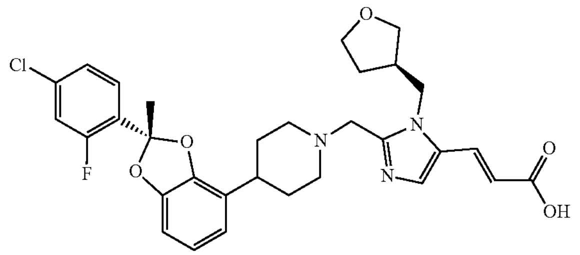 [SMILES: C[C@]1(c2ccc(Cl)cc2F)Oc2cccc(C3CCN(Cc4ncc(/C=C/C(=O)O)n4C[C@H]4CCOC4)CC3)c2O1]

$^1$H NMR (400 MHz, $CD_3OD$) δ 7.53-7.61 (m, 2H), 7.49 (s, 1H), 7.27 (dd, J=10.8, 2.0 Hz, 1H), 7.17-7.22 (m, 1H), 6.73-6.79 (m, 1H), 6.67-6.71 (m, 2H), 6.40 (d, J=16.0 Hz, 1H), 4.21-4.32 (m, 2H), 3.95-4.01 (m, 1H), 3.66-3.81 (m, 4H), 3.57 (dd, J=8.8, 4.8 Hz, 1H), 2.98-3.07 (m, 2H), 2.79-2.88 (m, 1H), 2.67-2.73 (m, 1H), 2.26-2.34 (m, 2H), 1.97-2.08 (m, 4H), 1.72-1.96 (m, 5H). LC-MS: m/z 582.1 $(M+H)^+$.

(E)-3-(2-((4-(2-(4-chloro-2-fluorophenyl)-2-methylbenzo[d][1,3]dioxol-4-yl)piperidin-1-yl)methyl)-1-(((S)-tetrahydrofuran-3-yl)methyl)-1H-imidazol-5-yl)acrylic acid (Compound 156) was synthesized following the route of Example 12, using (S)-(tetrahydrofuran-3-yl)methanamine in step B.

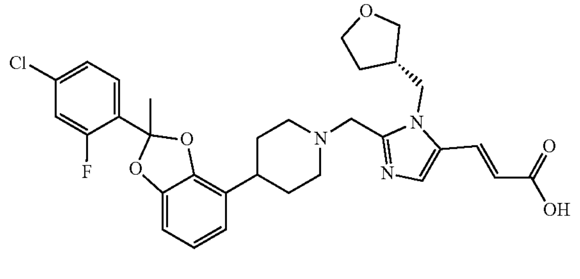 [SMILES: CC1(c2ccc(Cl)cc2F)Oc2cccc(C3CCN(Cc4ncc(/C=C/C(=O)O)n4C[C@@H]4CCOC4)CC3)c2O1]

$^1$H NMR (400 MHz, DMSO-$d_6$) δ 12.28 (br.s, 1H), 7.51-7.62 (m, 3H), 7.48 (d, J=16.0 Hz, 1H), 7.34 (dd, J=8.4, 2.0 Hz, 1H), 6.75-6.83 (m, 2H), 6.69-6.73 (m, 1H), 6.33 (d, J=16.0 Hz, 1H), 4.18 (d, J=8.0 Hz, 2H), 3.78-3.85 (m, 1H), 3.55-3.65 (m, 4H), 3.45-3.49 (m, 1H), 2.90-2.93 (m, 2H), 2.61-2.73 (m, 2H), 2.08-2.14 (m, 2H), 2.01 (s, 3H), 1.87-1.93 (m, 1H), 1.62-1.74 (m, 5H). LC-MS: m/z 582.2 $(M+H)^+$.

(E)-3-(2-((4-(2-(4-chloro-2-fluorophenyl)-2-methylbenzo[d][1,3]dioxol-4-yl)piperidin-1-yl)methyl)-1-((3-fluorooxetan-3-yl)methyl)-1H-imidazol-5-yl)acrylic acid (Compound 157) was synthesized following the route of Example 12, using (3-fluorooxetan-3-yl)methanamine in step B.

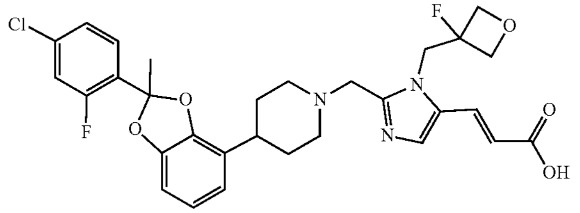 [SMILES: CC1(c2ccc(Cl)cc2F)Oc2cccc(C3CCN(Cc4ncc(/C=C/C(=O)O)n4CC4(F)COC4)CC3)c2O1]

$^1$H NMR (400 MHz, $CD_3OD$) δ 7.54-7.66 (m, 2H), 7.51 (s, 1H), 7.28 (dd, J=10.8, 2.0 Hz, 1H), 7.20 (dd, J=8.4, 2.4 Hz, 1H), 6.74-6.79 (m, 1H), 6.70 (dd, J=7.2, 3.6 Hz, 2H), 6.40 (d, J=16.0 Hz, 1H), 4.98 (d, J=21.6 Hz, 2H), 4.80 (d, J=3.2 Hz, 1H), 4.76 (dd, J=8.0, 3.2 Hz, 1H), 4.72 (d, J=8.0 Hz, 1H), 4.67 (d, J=8.0 Hz, 1H), 3.80 (s, 2H), 3.04 (d, J=11.2 Hz, 2H), 2.66-2.77 (m, 1H), 2.31 (t, J=11.2 Hz, 2H), 2.02 (s, 3H), 1.75-1.96 (m, 4H). LC-MS: m/z 586.0 $(M+H)^+$.

(E)-3-(2-((4-(2-(4-chloro-2-fluorophenyl)-2-methylbenzo[d][1,3]dioxol-4-yl)piperidin-1-yl)methyl)-1-(2-isopropoxyethyl)-1H-imidazol-5-yl)acrylic acid (Compound 158) was synthesized following the route of Example 12, using 2-isopropoxyethan-1-amine in step B.

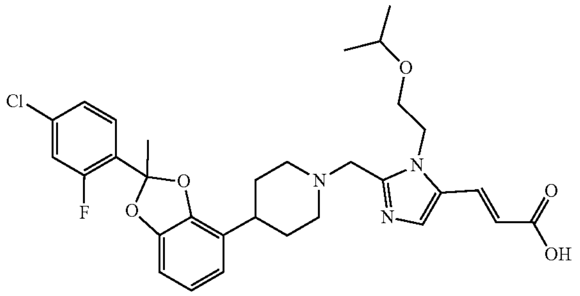 [SMILES: CC(C)OCCn1c(/C=C/C(=O)O)cnc1CN1CCC(c2cccc3c2OC(C)(c2ccc(Cl)cc2F)O3)CC1]

$^1$H NMR (400 MHz, DMSO-$d_6$) δ 12.28 (br.s, 1H), 7.51-7.59 (m, 3H), 7.49 (s, 1H), 7.34 (dd, J=8.4, 2.0 Hz, 1H), 6.75-6.81 (m, 2H), 6.69-6.73 (m, 1H), 6.27 (d, J=16.0 Hz, 1H), 4.27 (t, J=5.2 Hz, 2H), 3.67 (t, J=5.2 Hz, 2H), 3.60 (d, J=2.0 Hz, 2H), 3.41-3.47 (m, 1H), 2.87 (t, J=9.2 Hz, 2H), 2.57-2.69 (m, 1H), 2.06-2.12 (m, 2H), 2.01 (s, 3H), 1.64-1.74 (m, 4H), 0.98 (d, J=6.0 Hz, 6H). LC-MS: m/z 584.2 $(M+H)^+$.

(E)-3-(2-((4-(2-(4-chloro-2-fluorophenyl)-2-methylbenzo[d][1,3]dioxol-4-yl)piperidin-1-yl)methyl)-1-(2-methoxypropyl)-1H-imidazol-5-yl)acrylic acid (Compound 159) was synthesized following the route of Example 12, using 2-methoxypropan-1-aminium chloride in step B.

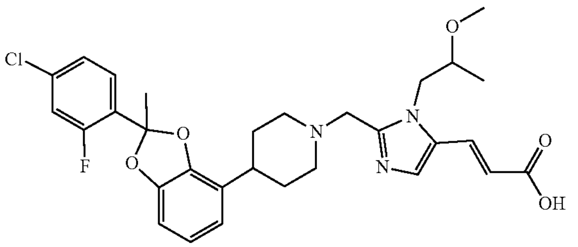 [SMILES: COC(C)Cn1c(/C=C/C(=O)O)cnc1CN1CCC(c2cccc3c2OC(C)(c2ccc(Cl)cc2F)O3)CC1]

$^1$H NMR (400 MHz, DMSO-$d_6$) δ 12.13 (br.s, 1H), 7.46-7.60 (m, 4H), 7.34 (dt, J=8.4, 2.4 Hz, 1H), 6.75-6.79 (m, 2H), 6.71-6.74 (m, 1H), 6.28 (d, J=16.0 Hz, 1H), 4.19 (dd, J=14.8, 3.2 Hz, 1H), 4.09 (dd, J=15.6, 9.6 Hz, 1H), 3.66-3.80 (m, 2H), 3.45 (d, J=13.6 Hz, 1H), 3.07 (d, J=9.6 Hz, 3H), 2.96 (d, J=9.2 Hz, 1H), 2.77-2.81 (m, 1H), 2.56-2.66 (m, 1H), 2.13-2.19 (m, 1H), 2.03-2.07 (m, 1H), 2.01 (s, 3H), 1.64-1.80 (m, 4H), 1.13 (d, J=6.0 Hz, 3H). LC-MS: m/z 570.2 $(M+H)^+$.

(E)-3-(2-((4-(2-(4-chloro-2-fluorophenyl)-2-methylbenzo[d][1,3]dioxol-4-yl)piperidin-1-yl)methyl)-1-(((S)-tetrahydrofuran-2-yl)methyl)-1H-imidazol-5-yl)acrylic acid (Compound 140a) was synthesized following the route of Example 12, using (S)-(tetrahydrofuran-2-yl)methanamine in step B.

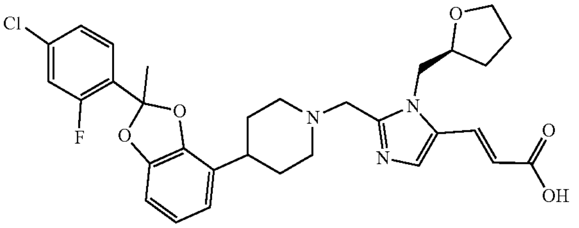 [SMILES: CC1(c2ccc(Cl)cc2F)Oc2cccc(C3CCN(Cc4ncc(/C=C/C(=O)O)n4C[C@@H]4CCCO4)CC3)c2O1]

$^1$H NMR (400 MHz, DMSO-$d_6$) δ 12.28 (br.s, 1H), 7.46-7.60 (m, 4H), 7.34 (d, J=8.4 Hz, 1H), 6.78-6.79 (m, 2H), 6.72-6.73 (m, 1H), 6.27 (d, J=16.0 Hz, 1H), 4.29 (d, J=14.4 Hz, 1H), 4.09-4.19 (m, 2H), 3.68-3.80 (m, 2H), 3.57-3.67 (m, 1H), 3.48 (dd, J=13.2, 2.4 Hz, 1H), 2.94-2.97 (m, 1H), 2.75-2.83 (m, 1H), 2.58-2.68 (m, 1H), 2.11-2.21 (m, 1H), 1.93-2.09 (m, 5H), 1.82-1.90 (m, 1H), 1.69-1.79 (m, 5H), 1.57-1.64 (m, 1H). LC-MS: m/z 582.2 $(M+H)^+$.

(E)-3-(2-((4-(2-(4-chloro-2-fluorophenyl)-2-methylbenzo[d][1,3]dioxol-4-yl)piperidin-1-yl)methyl)-1-(((R)-tetrahydrofuran-2-yl)methyl)-1H-imidazol-5-yl)acrylic acid (Compound 160) was synthesized following the route of Example 12, using (R)-(tetrahydrofuran-2-yl)methanamine in step B.

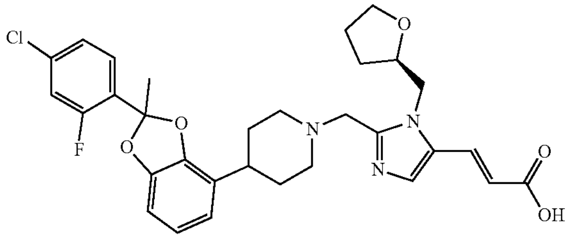 [SMILES: CC1(c2ccc(Cl)cc2F)Oc2cccc(C3CCN(Cc4ncc(/C=C/C(=O)O)n4C[C@H]4CCCO4)CC3)c2O1]

$^1$H NMR (400 MHz, DMSO-$d_6$) δ 12.26 (br.s, 1H), 7.48-7.62 (m, 4H), 7.34 (d, J=8.4 Hz, 1H), 6.76-6.83 (m, 2H), 6.67-6.74 (m, 1H), 6.30 (d, J=16.0 Hz, 1H), 4.31 (d, J=14.0 Hz, 1H), 4.14-4.24 (m, 1H), 4.03-4.13 (m, 1H), 3.77 (dd, J=14.8, 6.8 Hz, 2H), 3.52-3.68 (m, 2H), 2.95-3.14 (m, 1H), 2.79-2.94 (m, 1H), 2.59-2.67 (m, 1H), 2.08-2.29 (m, 1H), 1.90-2.05 (m, 5H), 1.68-1.89 (m, 6H), 1.55-1.65 (m, 1H). LC-MS: m/z 582.0 $(M+H)^+$.

(E)-3-(2-((4-(2-(4-chloro-2-fluorophenyl)-2-methylbenzo[d][1,3]dioxol-4-yl)piperidin-1-yl)methyl)-1-(2-(methylsulfonyl)ethyl)-1H-imidazol-5-yl)acrylic acid (Compound 161) was synthesized following the route of Example 12, using 2-(methylsulfonyl)ethan-1-amine in step B.

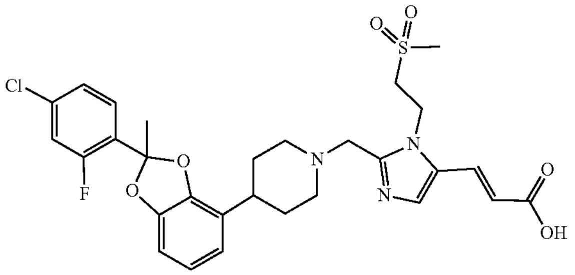 [SMILES: CC1(c2ccc(Cl)cc2F)Oc2cccc(C3CCN(Cc4ncc(/C=C/C(=O)O)n4CCS(C)(=O)=O)CC3)c2O1]

$^1$H NMR (400 MHz, DMSO-$d_6$) δ 7.82 (s, 1H), 7.65 (t, J=8.4 Hz, 1H), 7.48-7.59 (m, 2H), 7.34 (dd, J=8.4, 2.0 Hz, 1H), 6.81-6.87 (m, 2H), 6.73 (s, 1H), 6.49 (d, J=16.0 Hz, 1H), 4.74 (t, J=6.4 Hz, 2H), 4.55 (s, 2H), 3.61-3.71 (m, 4H), 3.30 (t, J=10.8 Hz, 2H), 3.08 (s, 3H), 2.97-2.99 (m, 1H), 2.13-2.15 (m, 2H), 1.91-2.08 (m, 5H). LC-MS: m/z 604.2 $(M+H)^+$.

(E)-3-(2-((4-(2-(4-chloro-2-fluorophenyl)-2-methylbenzo[d][1,3]dioxol-4-yl)piperidin-1-yl)methyl)-1-(cyclopropylmethyl)-1H-imidazol-5-yl)acrylic acid (Compound 162) was synthesized following the route of Example 12, using cyclopropylmethanamine in step B.

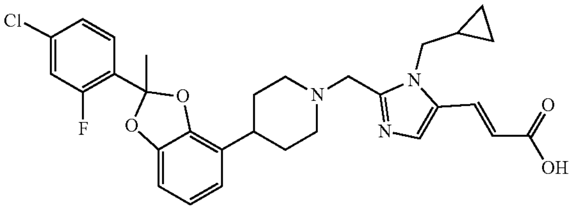 [SMILES: CC1(c2ccc(Cl)cc2F)Oc2cccc(C3CCN(Cc4ncc(/C=C/C(=O)O)n4CC4CC4)CC3)c2O1]

$^1$H NMR (400 MHz, $CD_3OD$) δ 7.53-7.62 (m, 2H), 7.49 (s, 1H), 7.27 (dd, J=10.8, 2.0 Hz, 1H), 7.20 (dd, J=8.4, 1.6 Hz, 1H), 6.72-6.79 (m, 1H), 6.65-6.72 (m, 2H), 6.40 (d, J=16.0 Hz, 1H), 4.16 (d, J=7.2 Hz, 2H), 3.77 (s, 2H), 3.03-3.06 (m, 2H), 2.68-2.73 (m, 1H), 2.32 (t, J=10.8 Hz, 2H), 2.01 (s, 3H), 1.77-1.96 (m, 4H), 1.25-1.29 (m, 1H), 0.56-0.64 (m, 2H), 0.43-0.54 (m, 2H). LC-MS: m/z 552.2 $(M+H)^+$.

(E)-3-(2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)acrylic acid 10 (Compound 141) was synthesized following the route of Example 12, using 2-methoxyethan-1-amine in step B.

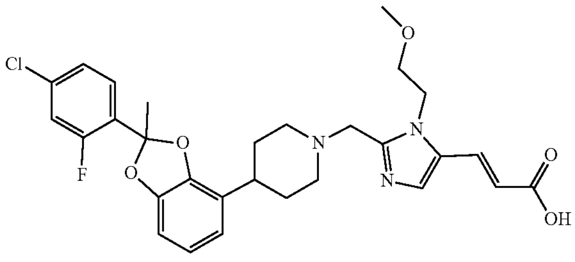 [SMILES: COCCn1c(/C=C/C(=O)O)cnc1CN1CCC(c2cccc3c2OC(C)(c2ccc(Cl)cc2F)O3)CC1]

$^1$H NMR (400 MHz, $CD_3OD$) δ 7.52-7.61 (m, 2H), 7.47 (s, 1H), 7.27 (d, J=10.8 Hz, 1H), 7.20 (d, J=8.4 Hz, 1H), 6.73-6.80 (m, 1H), 6.70 (d, J=8.0 Hz, 2H), 6.37 (d, J=16.0 Hz, 1H), 4.44 (t, J=4.8 Hz, 2H), 3.85 (t, J=4.8 Hz, 2H), 3.71 (s, 2H), 3.30 (s, 3H), 3.03-3.12 (m, 2H), 2.66-2.78 (m, 1H), 2.40 (t, J=11.6 Hz, 2H), 2.02 (s, 3H), 1.79-1.96 (m, 4H). LC-MS: m/z 556.2 $(M+H)^+$.

(E)-3-(2-((4-(2-(4-chloro-2-fluorophenyl)-2-methylbenzo [d][1,3]dioxol-4-yl)piperidin-1-yl)methyl)-1-((R)-tetrahydrofuran-3-yl)-1H-imidazol-5-yl)acrylic acid (Compound 163) was synthesized following the route of Example 12, using (R)-tetrahydrofuran-3-amine in step B.

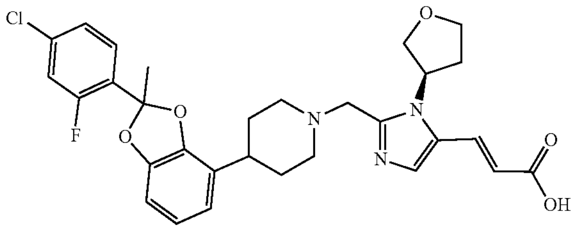 [SMILES: CC1(c2ccc(Cl)cc2F)Oc2cccc(C3CCN(Cc4ncc(/C=C/C(=O)O)n4[C@@H]4CCOC4)CC3)c2O1]

$^1$H NMR (400 MHz, DMSO-$d_6$) δ 12.20 (br.s, 1H), 7.75 (d, J=14.8 Hz, 1H), 7.50-7.67 (m, 3H), 7.35 (s, 1H), 6.66-6.89 (m, 3H), 6.29 (d, J=14.8 Hz, 1H), 5.40-5.52 (m, 1H), 4.18-4.24 (m, 1H), 3.85-4.02 (m, 2H), 3.60-3.80 (m, 3H), 2.75-2.88 (m, 2H), 2.56-2.70 (m, 3H), 1.94-2.10 (m, 5H), 1.65-1.77 (m, 4H). LC-MS: m/z 567.8 $(M+H)^+$.

(E)-3-(2-((4-(2-(4-chloro-2-fluorophenyl)-2-methylbenzo [d][1,3]dioxol-4-yl)piperidin-1-yl)methyl)-1-methyl-1H-imidazol-5-yl)acrylic acid (Compound 164) was synthesized following the route of Example 12, using methanamine hydrochloride in step B.

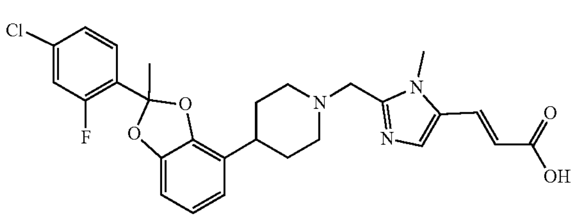 [SMILES: Cn1c(/C=C/C(=O)O)cnc1CN1CCC(c2cccc3c2OC(C)(c2ccc(Cl)cc2F)O3)CC1]

$^1$H NMR (400 MHz, DMSO-$d_6$) δ 12.29 (br.s, 1H), 7.52-7.59 (m, 2H), 7.49 (s, 1H), 7.46 (d, J=16.0 Hz, 1H), 7.34 (dd, J=8.4, 2.0 Hz, 1H), 6.68-6.81 (m, 3H), 6.29 (d, J=16.0 Hz, 1H), 3.72 (s, 3H), 3.60 (s, 2H), 2.88-2.90 (m, 2H), 2.60-2.67 (m, 1H), 2.07-2.17 (m, 2H), 2.02 (s, 3H), 1.65-1.71 (m, 4H). LC-MS: m/z 512.2 $(M+H)^+$.

Example 13

(E)-3-(2-((4-(2-(4-chloro-2-fluorophenyl)-2-methylbenzo[d][1,3]dioxol-4-yl)piperidin-1-yl)methyl)-1-((1,1-dioxidothietan-2-yl)methyl)-1H-imidazol-5-yl) acrylic acid (Compound 165)

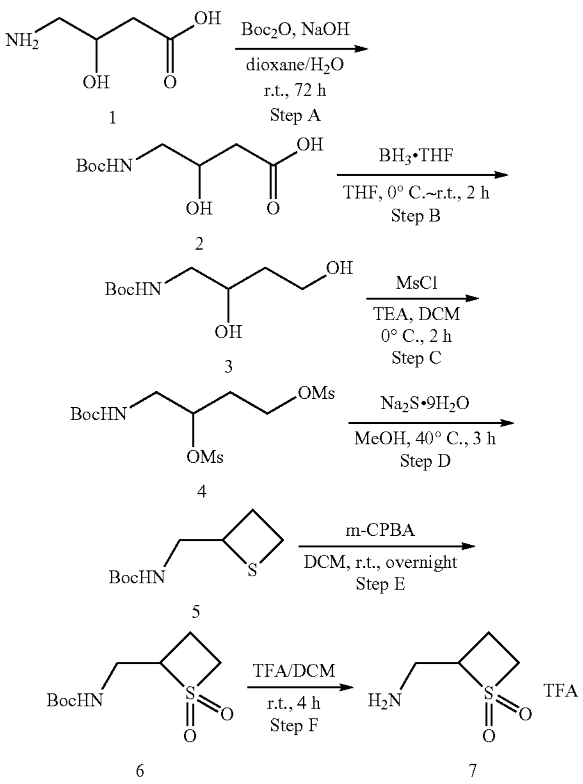

Step A: 4-((tert-butoxycarbonyl)amino)-3-hydroxybutanoic acid

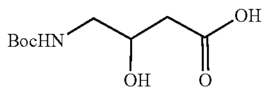 [SMILES: CC(C)(C)OC(=O)NCC(O)CC(=O)O]

To a solution of 4-amino-3-hydroxybutanoic acid (5.00 g, 42.0 mmol) in $H_2O$ (80 mL) were added NaOH (3.70 g, 92.4 mmol), $Boc_2O$ (12.0 g, 54.6 mmol), and 1,4-dioxane (12 mL). The reaction mixture was stirred at room temperature for 72 hours. Dioxane was evaporated and the pH was adjusted to 2-3 by 1 M HCl aqueous solution. The mixture was extracted with EtOAc (100 mL×3). The organic layers were washed with brine (100 mL), dried over $Na_2SO_4$, concentrated and purified by silica gel column (DCM/MeOH=40/1-20/1) to give 4-((tert-butoxycarbonyl)amino)-3-hydroxybutanoic acid as a colorless oil (9.00 g, 97% yield). $^1$H NMR (400 MHz, DMSO-$d_6$) δ 11.96 (br.s, 1H), 6.73 (t, J=5.6 Hz, 1H), 3.78-3.89 (m, 1H), 3.17 (s, 1H), 2.87-2.96 (m, 2H), 2.35 (dd, J=15.2, 4.4 Hz, 1H), 2.11 (dd, J=15.2, 8.8 Hz, 1H), 1.38 (s, 9H).

Step B: tert-butyl (2,4-dihydroxybutyl)carbamate

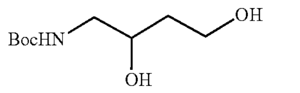 [SMILES: CC(C)(C)OC(=O)NCC(O)CCO]

To a solution of $BH_3$-THF (1 M in THF, 40 mL) was slowly added 4-((tert-butoxycarbonyl)amino)-3-hydroxybutanoic acid (3.20 g, 14.7 mmol) in THF (70 mL) at 0° C. The mixture was stirred at 0° C. for 2 hours. The reaction mixture was quenched with 10% AcOH in MeOH (60 mL). Then EtOAc (500 mL) was added and the reaction mixture was washed with 1 M HCl aqueous solution (100 mL) and 1 M $NaHCO_3$ aqueous solution (100 mL). The organic layer was dried over $Na_2SO_4$, concentrated and purified by silica gel column (DCM/MeOH=80/1-30/1) to give tert-butyl (2,4-dihydroxybutyl)carbamate as a colorless liquid (1.85 g, 61% yield). $^1$H NMR (400 MHz, DMSO-$d_6$) δ 6.61 (t, J=5.2 Hz, 1H), 4.50 (d, J=5.2 Hz, 1H), 4.32 (t, J=4.8 Hz, 1H), 3.51-3.59 (m, 1H), 3.41-3.50 (m, 2H), 2.81-2.97 (m, 2H), 1.46-1.59 (m, 1H), 1.39 (s, 9H), 1.30-1.35 (m, 1H). LC-MS: m/z 105.9 $(M-100)^+$.

Step C: 4-((tert-butoxycarbonyl)amino)butane-1,3-diyl dimethanesulfonate

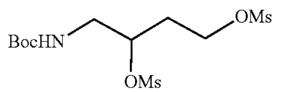 [SMILES: CC(C)(C)OC(=O)NCC(CCOS(C)(=O)=O)OS(C)(=O)=O]

To a mixture of tert-butyl (2,4-dihydroxybutyl)carbamate (1.85 g, 9.00 mmol) in DCM (40 mL) were added TEA (7.0 mL, 54.0 mmol) and MsCl (1.6 mL, 20.7 mmol) at 0° C. The reaction mixture was stirred at 0° C. for 2 hours. DCM (240 mL) was added and the reaction mixture was washed with 0.2 M HCl aqueous solution (120 mL), water (150 mL), 0.2 M $Na_2CO_3$ aqueous solution (120 mL) and brine (100 mL). The organic layer was dried over $Na_2SO_4$, concentrated to give 4-((tert-butoxycarbonyl)amino)butane-1,3-diyl dimethanesulfonate as a yellow oil (3.50 g, crude). $^1$H NMR (400 MHz, DMSO-$d_6$) δ 7.16 (t, J=6.0 Hz, 1H), 4.64-4.73 (m, 1H), 4.21-4.37 (m, 2H), 3.22-3.27 (m, 2H), 3.20 (s, 3H), 3.19 (s, 3H), 1.92-2.14 (m, 2H), 1.39 (s, 9H). LC-MS: m/z 261.9 $(M-100)^+$.

Step D: tert-butyl (thietan-2-ylmethyl)carbamate

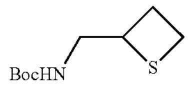

To a solution of 4-((tert-butoxycarbonyl)amino)butane-1,3-diyl dimethanesulfonate (1.00 g, 2.77 mmol) in MeOH (30 mL) was added $Na_2S \cdot 9H_2O$ (1.66 g, 6.93 mmol). The reaction mixture was stirred at 40° C. for 3 hours. Then methanol was partially removed in vacuum. Water (10 mL) was added and the reaction mixture was extracted with EtOAc (20 mL*3). The organic phases were combined, dried over anhydrous $Na_2SO_4$ and concentrated. The residue was purified by column (PE/EtOAC=80/1-20/1) to give tert-butyl (thietan-2-ylmethyl)carbamate as an colorless oil (210 mg, 37% yield).

$^1$H NMR (400 MHz, $CDCl_3$) δ 4.95 (s, 1H), 3.72-3.87 (m, 1H), 3.32-3.49 (m, 2H), 3.11-3.20 (m, 1H), 2.99-3.09 (m, 1H), 2.87-2.99 (m, 1H), 2.57-2.69 (m, 1H), 1.45 (s, 9H).

Step E: tert-butyl ((1,1-dioxidothietan-2-yl)methyl)carbamate

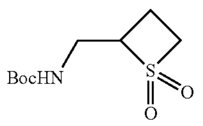 [SMILES: CC(C)(C)OC(=O)NCC1CCS1(=O)=O]

To a solution of tert-butyl (thietan-2-ylmethyl)carbamate (210 mg, 1.03 mmol) in DCM (5 mL) was added m-CPBA (85%, 627 mg, 3.09 mmol). The reaction mixture was stirred at room temperature overnight. Sat. aqueous $NaHCO_3$ solution (15 mL) and $Na_2Sa_2O_3$ solution (15 mL) were added. The reaction mixture was shortly stirred and extracted with DCM (30 mL*3). The extracts were dried over $Na_2SO_4$ and concentrated to give tert-butyl ((1,1-dioxidothietan-2-yl)methyl)carbamate as a white solid (250 mg crude). $^1$H NMR (400 MHz, $CDCl_3$) δ 5.12 (s, 1H), 4.46-4.65 (m, 1H), 3.91-4.12 (m, 2H), 3.53-3.75 (m, 2H), 2.19-2.32 (m, 1H), 1.81-1.94 (m, 1H), 1.45 (s, 9H). LC-MS: m/z 179.9 $(M-56+H)^+$.

Step F: 2-(aminomethyl)thietane 1,1-dioxide TFA Salt

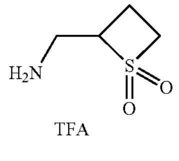

A solution of tert-butyl ((1,1-dioxidothietan-2-yl)methyl) carbamate (250 mg, 1.06 mmol) in TFA/DCM=2 mL/2 mL was stirred at room temperature for 4 hours. The reaction mixture was concentrated to give 2-(aminomethyl)thietane 1,1-dioxide TFA salt (crude, 180 mg). LC-MS: m/z 135.8 $(M+H-TFA)^+$.

(E)-3-(2-((4-(2-(4-chloro-2-fluorophenyl)-2-methylbenzo[d][1,3]dioxol-4-yl)piperidin-1-yl)methyl)-1-((1,1-dioxidothietan-2-yl)methyl)-1H-imidazol-5-yl) acrylic acid (Compound 165)

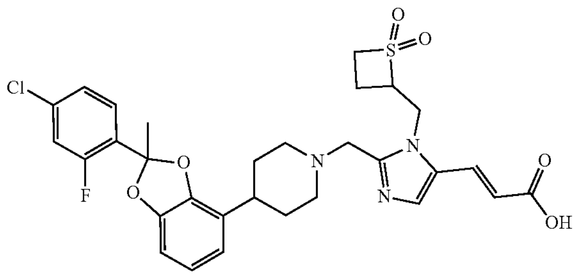 [SMILES: CC1(c2ccc(Cl)cc2F)Oc2cccc(C3CCN(Cc4ncc(/C=C/C(=O)O)n4CC4CCS4(=O)=O)CC3)c2O1]

(Compound 165) was then synthesized following the route of Example 12, using 2-(aminomethyl)thietane 1,1-dioxide TFA salt in step B.

$^1$H NMR (400 MHz, DMSO-$d_6$) δ 12.34 (br.s, 1H), 7.49-7.60 (m, 4H), 7.29-7.39 (m, 1H), 6.69-6.82 (m, 3H), 6.33 (d, J=16.0 Hz, 1H), 4.86-4.99 (m, 1H), 4.80 (dd, J=15.6, 7.6 Hz, 1H), 4.57 (dd, J=15.6, 6.0 Hz, 1H), 3.95-4.14 (m, 2H), 3.75 (dd, J=13.2, 4.0 Hz, 1H), 3.55 (dd, J=13.6, 2.8 Hz, 1H), 2.80-3.00 (m, 2H), 2.58-2.71 (m, 1H), 2.22-2.36 (m, 1H), 2.04-2.22 (m, 2H), 2.02 (s, 3H), 1.87-1.98 (m, 1H), 1.64-1.83 (m, 4H). LC-MS: m/z 615.8 $(M+H)^+$.

Example 14

(E)-3-(2-((4-(2-(4-chloro-2-fluorophenyl)-2-methylbenzo[d][1,3]dioxol-4-yl)piperidin-1-yl)methyl)-1-((1-methoxycyclobutyl)methyl)-1H-imidazol-5-yl) acrylic acid (Compound 166)

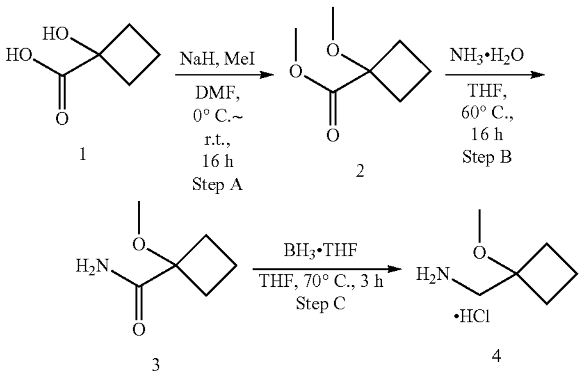

1
2
3
4

Step A: methyl 1-methoxycyclobutane-1-carboxylate

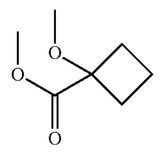

To a solution of 1-hydroxycyclobutane-1-carboxylic acid (1.00 g, 8.61 mmol) in DMF (25 mL) was added NaH (60% in oil, 344 mg, 34.4 mmol) at 0° C. The reaction mixture was stirred at room temperature for 2 hours, and then MeI (3.67 g, 25.8 mmol) was added. The reaction mixture was stirred at room temperature for 16 hours. The reaction mixture was quenched by saturated aqueous solution of $NH_4Cl$ (20 mL), and extracted with EtOAc (60*3 mL). The combined organic layer was washed with brine, dried over $Na_2SO_4$, filtered and concentrated to give methyl 1-methoxycyclobutane-1-carboxylate (1.50 g, crude) as a clear oil. $^1$H NMR (400 MHz, DMSO-$d_6$) δ 3.69 (s, 3H), 3.08 (s, 3H), 2.30-2.36 (m, 2H), 2.08-2.16 (m, 2H), 1.70-1.83 (m, 2H).

Step B: 1-methoxycyclobutane-1-carboxamide

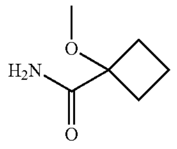

To a solution of methyl 1-methoxycyclobutane-1-carboxylate (750 mg, 4.31 mmol) in THF (3.0 mL) was added $NH_3 \cdot H_2O$ (25% in $H_2O$, 10.0 mL). The reaction mixture was sealed and stirred at 60° C. for 16 hours. The reaction mixture was cooled to room temperature, diluted with brine, and extracted with DCM (80*3 mL). The combined organic layer was washed with brine, dried over $Na_2SO_4$, filtered and concentrated to give 1-methoxycyclobutane-1-carboxamide (375 mg, 67% yield for two steps). LC-MS: m/z 130.22 $(M+H)^+$.

Step C: (1-methoxycyclobutyl)methanamine hydrochloride

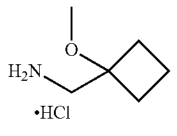

To a solution of 1-methoxycyclobutane-1-carboxamide (370 mg, 2.86 mmol) in THF (15 mL) was added $BH_3 \cdot THF$ (1M in THF, 8.6 mL, 8.60 mmol) under nitrogen. The reaction mixture was stirred at 70° C. for 3 hours, and then cooled to room temperature. The reaction mixture was quenched by MeOH, diluted with brine (40 mL), and extracted with EtOAc (80*3 mL). The combined organic layer was dried over $Na_2SO_4$, and filtered. The filtrate was diluted with 4M HCl in 1,4-dioxane (2 mL) and concentrated to give (1-methoxycyclobutyl)methanamine hydrochloride (crude, 135 mg, 31% yield). $^1$H NMR (400 MHz, DMSO-$d_6$) δ 8.02 (s, 3H), 3.12 (s, 3H), 3.02 (s, 2H), 2.07-2.16 (m, 2H), 1.92-1.98 (m, 2H), 1.53-1.69 (m, 2H).

(E)-3-(2-((4-(2-(4-chloro-2-fluorophenyl)-2-methylbenzo[d][1,3]dioxol-4-yl)piperidin-1-yl)methyl)-1-((1-methoxycyclobutyl)methyl)-1H-imidazol-5-yl) acrylic acid (Compound 166)

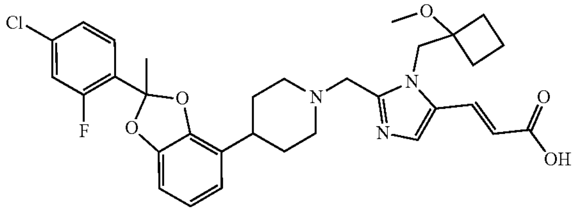 [SMILES: COC1(Cn2c(/C=C/C(=O)O)cnc2CN2CCC(c3cccc4c3OC(C)(c3ccc(Cl)cc3F)O4)CC2)CCC1]

Compound 166 was then synthesized following the similar route of Example 12, using (1-methoxycyclobutyl)methanamine hydrochloride in step B.

$^1$H NMR (400 MHz, DMSO-$d_6$) δ 12.18 (br.s, 1H), 7.47-7.64 (m, 4H), 7.34 (dd, J=8.4, 2.0 Hz, 1H), 6.76-6.80 (m, 2H), 6.70-6.76 (m, 1H), 6.27 (d, J=16.0 Hz, 1H), 4.49 (s, 2H), 3.67 (s, 2H), 3.17 (s, 3H), 2.82-2.88 (m, 2H), 2.59-2.64 (m, 1H), 2.08-2.21 (m, 4H), 2.01 (s, 3H), 1.63-1.80 (m, 8H). LC-MS: m/z 596.1 $(M+H)^+$.

Example 15

(E)-3-(2-((4-(2-(4-chloro-2-fluorophenyl)-2-methylbenzo[d][1,3]dioxol-4-yl)piperidin-1-yl)methyl)-1-((2,2-difluorocyclobutyl)methyl)-1H-imidazol-5-yl) acrylic acid (Compound 167)

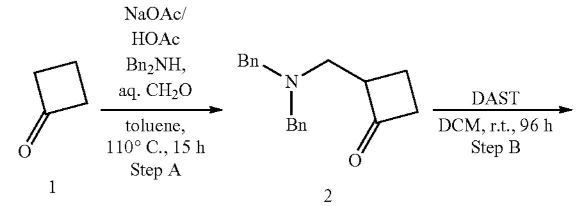

1 2

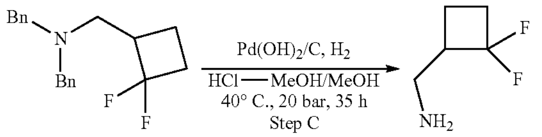

3 4

Step A Step B Step C

Step A: 2-((dibenzylamino)methyl)cyclobutan-1-one

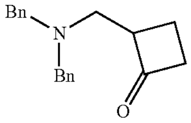 [SMILES: O=C1CCC1CN(Cc1ccccc1)Cc1ccccc1]

Cyclobutanone (10.0 g, 0.143 mol), 40% aqueous formaldehyde (10.5 g, 0.143 mol) and dibenzylamine (27.6 g, 0A43 mol) were added to toluene (10 mL). Then sodium acetate (2.30 g, 0.0280 mol) and acetic acid (1.70 g, 0.0280 mol) were added. The reaction mixture was stirred at 110° C. for 15 hours. And then the mixture was poured into saturated aqueous sodium bicarbonate solution (200 mL). The mixture was extracted with ethyl acetate (100 mL*3). The combined organic phases were washed with brine (150 mL), dried over anhydrous $Na_2SO_4$, concentrated and purified by flash chromatography (PE/EtOAC=10/1-3/1) to give 2-((dibenzylamino)methyl)cyclobutan-1-one as a yellow solid (16.7 g, 42% yield). LC MS: m/z 280.1 $(M+H)^+$.

Step B: N,N-dibenzyl-1-(2,2-difluorocyclobutyl)methanamine

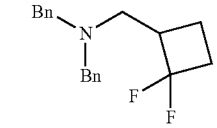 [SMILES: FC1(F)CCC1CN(Cc1ccccc1)Cc1ccccc1]

2-((dibenzylamino)methyl)cyclobutan-1-one (4.98 g, 17.8 mmol) was dissolved in DCM (60 mL) and cooled to 0° C. To the reaction mixture was added diethylaminosulfur trifluoride (DAST) (7.50 g, 42.8 mmol) in batches. After addition, the temperature was naturally raised to room temperature and stirred for another 96 hours. The reaction mixture was poured into saturated aqueous sodium bicarbonate (50 mL), and extracted with DCM (50 mL*3). The organic phases were washed with brine (80 mL), dried over anhydrous $Na_{22}SO_4$, concentrated and purified by flash chromatography (PE EtOAc=20/1-8/1) to give N,N-dibenzyl-1-(2,2-difluorocyclobutyl)methanamine as a light yellow oil (2.30 g, 43% yield). LC-MS: m/z 302.1 $(M+H)^+$.

Step C: (2,2-difluorocyclobutyl)methanamine

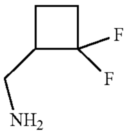

N,N-Dibenzyl-1-(2,2-difluorocyclobutyl)methanamine (1.50 g, 4.98 mmol) was dissolved in MeOH (25 mL) and then 4 N HCl in MeOH (5 mL) was added. After the addition of palladium hydroxide (10% on carbon, 1.00 g), the reaction mixture was stirred at 40° C. for 35 hours under 20 bar $H_2$. Then the mixture was filtered and concentrated to give crude (2,2-difluorocyclobutyl)methanamine as a dark brown oil (HCl salt, 603 mg, 78% yield). LC-MS: m/z 121.9 $(M+H)^+$.

(E)-3-(2-((4-(2-(4-chloro-2-fluorophenyl)-2-methylbenzo[d][1,3]dioxol-4-yl)piperidin-1-yl)methyl)-1-((2,2-difluorocyclobutyl)methyl)-1H-imidazol-5-yl) acrylic acid (Compound 167)

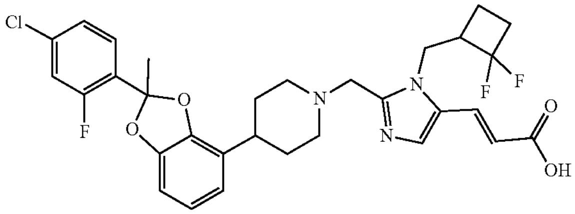 [SMILES: CC1(c2ccc(Cl)cc2F)Oc2cccc(C3CCN(Cc4ncc(/C=C/C(=O)O)n4CC4CCC4(F)F)CC3)c2O1]

Compound 167 was then synthesized following the similar route of Example 12, using 2-(2,2-difluorocyclobutyl) methanamine HCl salt in step B.

$^1$H NMR (400 MHz, $CD_3OD$) δ 7.54-7.61 (m, 2H), 7.46 (s, 1H), 7.25-7.29 (m, 1H), 7.19-7.22 (m, 1H), 6.74-6.80 (m, 1H), 6.66-6.71 (m, 2H), 6.38 (d, J=16.0 Hz, 1H), 4.60 (dd, J=15.2, 7.6 Hz, 1H), 4.34 (dd, J=15.2, 6.8 Hz, 1H), 3.81 (d, J=14.0 Hz, 1H), 3.69 (d, J=14.0 Hz, 1H), 3.33-3.44 (m, 1H), 2.93-3.07 (m, 2H), 2.64-2.75 (m, 1H), 2.39-2.54 (m, 2H), 2.19-2.35 (m, 2H), 2.02 (s, 3H), 1.64-1.98 (m, 6H). LC-MS: m/z 602.1 $(M+H)^+$.

Example 16

(E)-3-(2-((4-(2-(4-chloro-2-fluorophenyl)-2-methylbenzo[d][1,3]dioxol-4-yl)piperidin-1-yl)methyl)-1-(2-(difluoromethoxy)ethyl)-1H-imidazol-5-yl)acrylic acid (Compound 168)

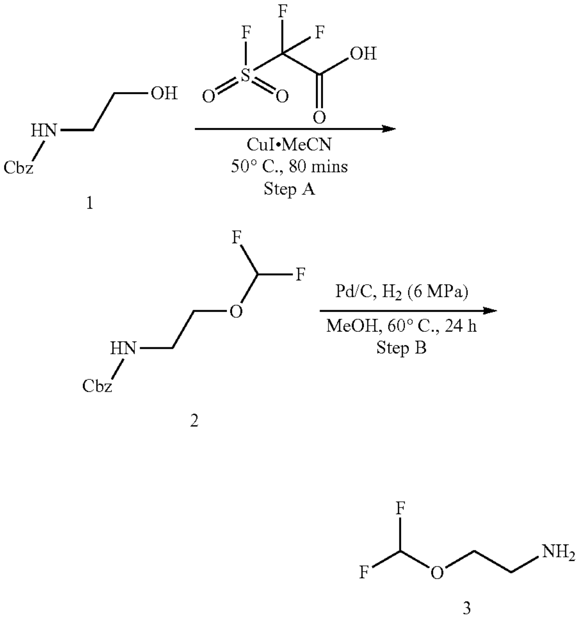

Step A: benzyl (2-(difluoromethoxy)ethyl)carbamate

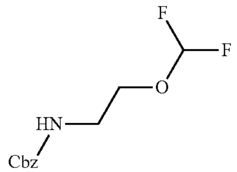 [SMILES: O=C(NCCOC(F)F)OCc1ccccc1]

Benzyl (2-hydroxyethyl)carbamate (9.00 g, 46.2 mmol) was dissolved in 90 mL ACN and CuI (1.75 g, 9.23 mmol) was added. The reaction mixture was heated to 50° C. and a solution of 2,2-difluoro-2-(fluorosulfonyl)acetic acid (10.6 g, 59.6 mmol) in 10 mL ACN was added dropwise over a period of 50 mins. The reaction mixture was heated for additional 30 mins at 50° C. Then ACN was evaporated in vacuo. The residue was suspended in EtOAc (50 mL) and the insoluble solid was filtered out. The filtrate was concentrated and purified by flash chromatography to give benzyl (2-(difluoromethoxy)ethyl)carbamate (7.10 g, 63% yield). $^1$H NMR (400 MHz, $CDCl_3$) δ 7.29-7.44 (m, 5H), 6.20 (t, J=74.4 Hz, 1H), 5.08-5.11 (m, 3H), 3.93 (t, J=4.8 Hz, 2H), 3.44-3.48 (m, 2H).

Step B: 2-(difluoromethoxy)ethan-1-amine

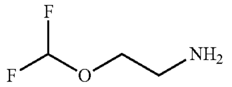

To a solution of Pd/C (10%, 300 mg) in MeOH (40 mL) was added benzyl (2-(difluoromethoxy)ethyl)carbamate (3.00 g, 12.2 mmol). The reaction mixture was stirred at 60° C. under $H_2$ (6 MPa) for 24 hours. The reaction mixture was filtered and washed with MeOH (10 mL*3). The filtrate was concentrated to give 2-(difluoromethoxy)ethan-1-amine as a yellow oil (2.00 g, crude), which was used in the next step without further purification. LC-MS: m/z 112.0 $(M+H)^+$.

(E)-3-(2-((4-(2-(4-chloro-2-fluorophenyl)-2-methylbenzo[d][1,3]dioxol-4-yl)piperidin-1-yl)methyl)-1-(2-(difluoromethoxy)ethyl)-1H-imidazol-5-yl)acrylic acid (Compound 168)

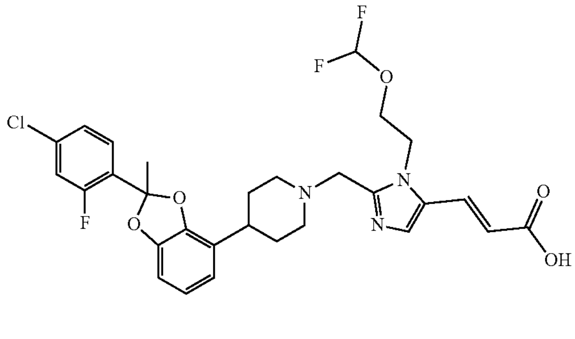 [SMILES: CC1(c2ccc(Cl)cc2F)Oc2cccc(C3CCN(Cc4ncc(/C=C/C(=O)O)n4CCOC(F)F)CC3)c2O1]

Compound 168 was then synthesized following the route of Example 12, using 2-(difluoromethoxy)ethan-1-amine in step B.

$^1$H NMR (400 MHz, DMSO-$d_6$) δ 12.34 (br.s, 1H), 7.51-7.59 (m, 3H), 7.48 (d, J=16.0 Hz, 1H), 7.33 (dd, J=8.4, 2.0 Hz, 1H), 6.78-6.79 (m, 2H), 6.69-6.72 (m, 1H), 6.62 (t, J=75.2 Hz, 1H), 6.31 (d, J=16.0 Hz, 1H), 4.45 (t, J=5.2 Hz, 2H), 4.18-4.21 (m, 2H), 3.62 (s, 2H), 2.87 (t, J=10.4 Hz, 2H), 2.60-2.68 (m, 1H), 2.07-2.11 (m, 2H), 2.01 (s, 3H), 1.64-1.74 (m, 4H). LC-MS: m/z 591.8 $(M+H)^+$.

Example 17

(E)-3-(2-((4-((S)-2-(4-chloro-2-fluorophenyl)-2-methylbenzo[d][1,3]dioxol-4-yl)piperidin-1-yl)methyl)-1-((S)-2-(difluoromethoxy)propyl)-1H-imidazol-5-yl)acrylic acid (Compound 169)

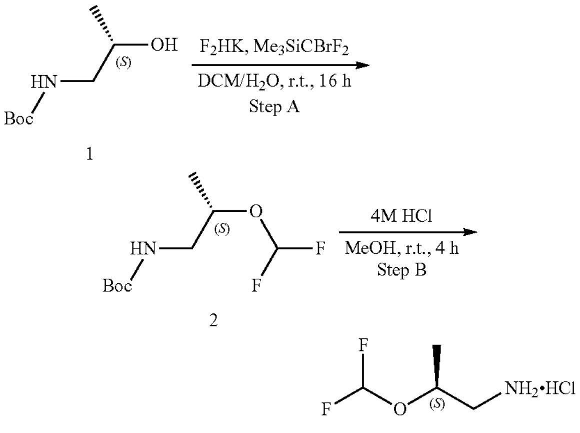

1

2

3

Step A: tert-butyl (S)-(2-(difluoromethoxy)propyl)carbamate

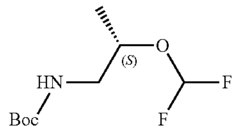

To a solution of tert-butyl (S)-(2-hydroxypropyl)carbamate (1.40 g, 8.00 mmol) in DCM (25 mL) and $H_2O$ (25 mL) were added (bromodifluoromethyl)trimethylsilane (8.12 g, 40.0 mmol) and $KHF_2$ (3.74 g, 48.0 mmol) at 0° C. The reaction mixture was stirred at room temperature for 16 hours. Then the reaction mixture was extracted with DCM (60 mL*3). The combined organic layer was washed with brine, dried over $Na_2SO_4$, filtered, concentrated and purified by silica gel column (0-20% EtOAc in PE) to give tert-butyl (S)-(2-(difluoromethoxy)propyl)carbamate (1.10 g, 61% yield) as a clear oil. LC-MS: m/z 226.1 $(M+H)^+$.

Step (S)-2-difluoromethoxy)propan-1-amine hydrochloride

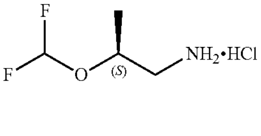

To a solution of tert-butyl (S)-(2-(difluoromethoxy)propyl)carbamate (1.10 g, 4.88 mmol) in MeOH (2.0 mL) and 1,4-dioxane (15.0 mL) was added 4M HCl in dioxane (5.0 mL). The reaction mixture was stirred at room temperature for 4 hours. Then the reaction mixture was concentrated to give (S)-2-(difluoromethoxy)propan-1-amine hydrochloride (500 mg, 64% yield). LC-MS: m/z 126.1 (M+H-HCl).

(E)-3-(2-((4-((S)-2-(4-chloro-2-fluorophenyl)-2-methylbenzo[d][1,3]dioxol-4-yl)piperidin-1-yl)methyl)-1-((S)-2-(difluoromethoxy)propyl)-1H-imidazol-5-yl)acrylic acid (Compound 169a)

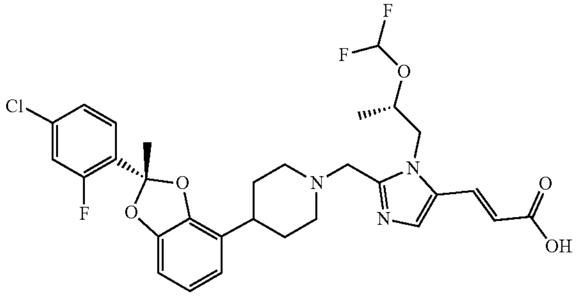 [SMILES: C[C@@H](Cn1c(/C=C/C(=O)O)cnc1CN1CCC(c2cccc3c2O[C@@](C)(c2ccc(Cl)cc2F)O3)CC1)OC(F)F]

Compound 169a was then synthesized following the route of Example 12, using (5)-4-(2-(4-chloro-2-fluorophenyl)-2-methylbenzo[d][1,3]dioxol-4-yl)piperidine hydrochloride in step A and (S)-2-(difluoromethoxy)propan-1-amine hydrochloride in step B.

$^1$H NMR (400 MHz, DMSO-$d_6$) δ 12.24 (br.s, 1H), 7.47-7.58 (m, 4H), 7.34 (dd, J=8.4, 2.0 Hz, 1H), 6.76-6.80 (m, 2H), 6.68-6.72 (m, 1H), 6.27-6.66 (m, 2H), 4.80-4.83 (m, 1H), 4.21-4.31 (m, 2H), 3.80 (d, J=13.6 Hz, 1H), 3.42 (d, J=13.6 Hz, 1H), 3.01 (d, J=10.8 Hz, 1H), 2.77 (d, J=11.6 Hz, 1H), 2.56-2.63 (m, 1H), 2.14-2.22 (m, 1H), 1.95-2.07 (m, 4H), 1.72-1.84 (m, 2H), 1.60-1.68 (m, 2H), 1.31 (d, J=6.0 Hz, 3H). LC-MS: m/z 606.1 $(M+H)^+$.

(E)-3-(2-((4-((S)-2-(4-chloro-2-fluorophenyl)-2-methylbenzo[d][1,3]dioxol-4-yl)piperidin-1-yl)methyl)-1-((R)-2-(difluoromethoxy)propyl)-1H-imidazol-5-yl)acrylic acid (Compound 169b) was synthesized following the route of Example 17, using tert-butyl (R)-(2-hydroxypropyl)carbamate in step A.

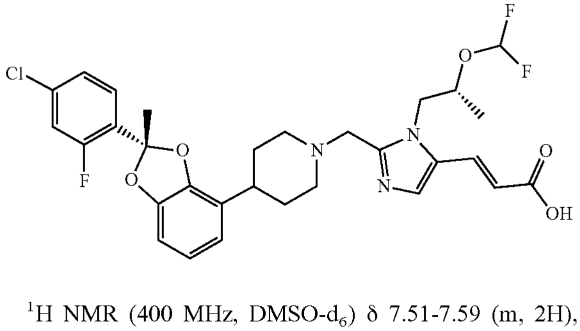

$^1$H NMR (400 MHz, DMSO-$d_6$) δ 7.51-7.59 (m, 2H), 7.46 (d, J=13.6 Hz, 2H), 7.32 (dd, J=8.4, 2.0 Hz, 1H), 6.76-6.81 (m, 2H), 6.68-6.74 (m, 1H), 6.24-6.67 (m, 2H), 4.68-4.88 (m, 1H), 4.13-4.36 (m, 2H), 3.78 (d, J=13.6 Hz, 1H), 3.44 (d, J=13.6 Hz, 1H), 2.99 (d, J=10.8 Hz, 1H), 2.81 (d, J=11.2 Hz, 1H), 2.52-2.55 (m, 1H), 2.12-2.24 (m, 1H), 2.03-2.09 (m, 1H), 2.01 (s, 3H), 1.60-1.80 (m, 4H), 1.30 (d, J=6.4 Hz, 3H). LC-MS: m/z 606.1 $(M+H)^+$.

Example 18

(E)-3-(2-((4-((S)-2-(4-chloro-2-fluorophenyl)-2-methylbenzo[d][1,3]dioxol-4-yl)piperidin-1-yl)methyl)-1-((R)-2-cyclopropoxypropyl)-1H-imidazol-5-yl)acrylic acid (Compound 170b)

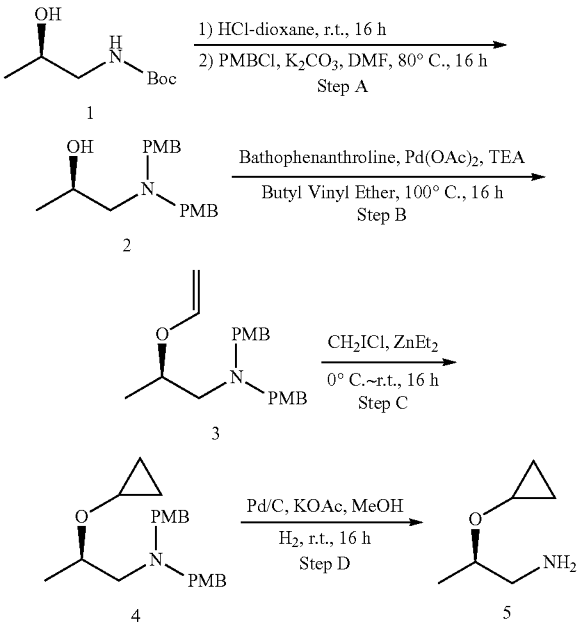

Step A: (R)-1-(bis(4-methoxybenzyl)amino)propan-2-ol

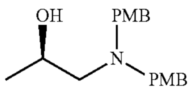

To a solution of tert-butyl (R)-(2-hydroxypropyl)carbamate (2.00 g, 11.4 mmol) in dioxane (15 mL) was added HCl-dioxane (4N, 15 mL). The resulting reaction mixture was stirred at room temperature for 16 hours. The reaction mixture was concentrated in vacuo and then the residue was dissolved in DMF (20 mL). To the solution were added PMBCl (3.95 g, 25.2 mmol) and $K_2CO_3$ (3.94 g, 28.6 mmol). The resulting reaction mixture was stirred at 80° C. for 16 hours. After that, the reaction mixture was diluted with water (50 mL) and extracted with EtOAc (70 mL*3). The combined organic layers were washed with water (100 mL) and brine (100 mL), dried over $Na_2SO_4$, filtered, concentrated and purified by silica gel chromatography (PE:EtOAc=10:1 to 5:1) to give (R)-1-(bis(4-methoxybenzyl)amino)propan-2-ol as a yellow oil (2.54 g, 71% yield). LC-MS: m/z 316.2 $(M+H)^+$.

Step B: (R)-N,N-bis(4-methoxybenzyl)-2-(vinyloxy)propan-1-amine

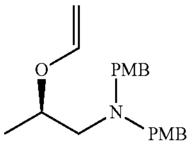

To a solution of (R)-1-(bis(4-methoxybenzyl)amino)propan-2-ol (2.54 g, 8.05 mmol) in butyl vinyl ether (12.1 g, 121 mmol) were added bathophenanthroline (134 mg, 0.403 mmol), $Pd(OAc)_2$ (91.0 mg, 0.403 mmol), and TEA (342 mg, 3.38 mmol). The reaction mixture was stirred at 100° C. for 16 hours. After cooled to room temperature, the reaction mixture was filtered. The filtrate was concentrated and purified by silica gel chromatography (PE:EtOAc=25:1/10:1) to give (R)-N,N-bis(4-methoxybenzyl)-2-(vinyloxy)propan-1-amine as a yellow oil (1.00 g, 36% yield). LC-MS: m/z 342.0 $(M+H)^+$.

Step C: (R)-2-cyclopropoxy-N,N-bis(4-methoxybenzyl)propan-1-amine

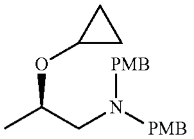

To a reaction mixture of (R)-N,N-bis(4-methoxybenzyl)-2-(vinyloxy)propan-1-amine (1.00 g, 2.93 mmol) in DCM (15 mL) were added $CH_2ICl$ (3.92 g, 14.6 mmol) and $Et_2Zn$ (1.80 g, 14.6 mmol) dropwise at 0° C. The reaction mixture was stirred at room temperature for 16 hours. The reaction solution was diluted with $NH_4Cl$ (80 mL) and then extracted with EtOAc (70 mL*3). The organic layers were washed with brine (100 mL), dried over $Na_2SO_4$, filtered, concentrated and purified by silica gel chromatography (PE: EtOAc=25:1/10:1) to give (R)-2-cyclopropoxy-N,N-bis(4-methoxybenzyl)propan-1-amine as a colorless oil (440 mg, 42% yield). LC-MS: m/z 356.2 $(M+H)^+$.

Step D: (R)-2-cyclopropoxypropan-1-amine

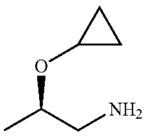

To a solution of (R)-2-cyclopropoxy-N,N-bis(4-methoxybenzyl)propan-1-amine (440 mg, 1.24 mmol) in MeOH (6 mL) were added Pd/C (10%, 60 mg) and KOAc (122 mg, 1.24 mmol). The reaction mixture was stirred at room temperature under $H_2$ for 16 hours. The reaction mixture was filtered and the filtrate was concentrated to give (R)-2-cyclopropoxypropan-1-amine as a gray oil (crude, 200 mg), which was used in the next step directly without further purification.

(E)-3-(2-((4-((S)-2-(4-chloro-2-fluorophenyl)-2-methylbenzo[d][1,3]dioxol-4-yl)piperidin-1-yl)methyl)-1-((R)-2-cyclopropoxypropyl)-1H-imidazol-5-yl)acrylic acid (Compound 170b)

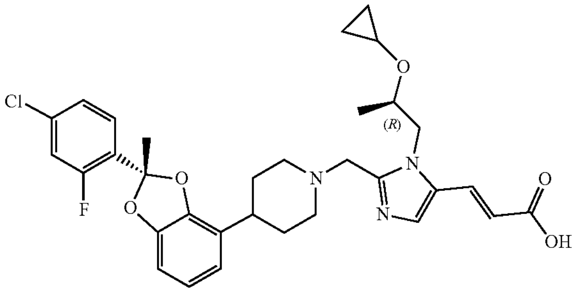

Compound 170b was then synthesized following the route of Example 12, using (S)-4-(2-(4-chloro-2-fluorophenyl)-2-methylbenzo[d][1,3]dioxol-4-yl)piperidine hydrochloride in step A and (R)-2-cyclopropoxypropan-1-amine in step B. $^{1}$H NMR (400 MHz, DMSO-$d_6$) δ 12.19 (br.s, 1H), 7.51-7.60 (m, 2H), 7.48 (d, J=15.2 Hz, 2H), 7.33 (dd, J=8.4, 2.0 Hz, 1H), 6.75-6.81 (m, 2H), 6.70-6.72 (m, 1H), 6.25 (d, J=16.0 Hz, 1H), 4.13 (d, J=12.8 Hz, 1H), 3.86-4.01 (m, 2H), 3.78 (d, J=13.6 Hz, 1H), 3.39 (d, J=13.6 Hz, 1H), 3.02-3.10 (m, 1H), 2.99 (d, J=10.8 Hz, 1H), 2.76 (d, J=11.2 Hz, 1H), 2.61-2.68 (m, 1H), 2.14-2.23 (m, 1H), 1.98-2.06 (m, 4H), 1.67-1.81 (m, 4H), 1.21 (d, J=6.0 Hz, 3H), 0.25-0.38 (m, 2H), 0.06-0.15 (m, 1H), −0.35-−0.25 (m, 1H). $^{19}$F NMR (377 MHz, DMSO-$d_6$): δ −110.44. LC-MS: m/z 596.2 (M+H)$^+$.

(E)-3-(2-((4-((S)-2-(4-chloro-2-fluorophenyl)-2-methylbenzo[d][1,3]dioxol-4-yl)piperidin-1-yl)methyl)-1-((S)-2-cyclopropoxypropyl)-1H-imidazol-5-yl)acrylic acid (Compound 170a) was synthesized following the route of Example 18, using tert-butyl (S)-(2-hydroxypropyl)carbamate in step A.

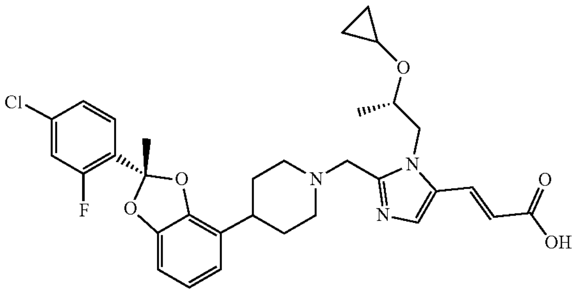 [SMILES: C[C@@H](Cn1c(/C=C/C(=O)O)cnc1CN1CCC(c2cccc3c2O[C@@](C)(c2ccc(Cl)cc2F)O3)CC1)OC1CC1]

$^{1}$H NMR (400 MHz, DMSO-$d_6$) δ 12.25 (br.s, 1H), 7.54-7.59 (m, 2H), 7.46-7.50 (m, 2H), 7.34 (dd, J=8.4, 2.0 Hz, 1H), 6.77-6.80 (m, 2H), 6.69-6.73 (m, 1H), 6.26 (d, J=16.0 Hz, 1H), 4.14 (d, J=12.4 Hz, 1H), 3.91-4.01 (m, 2H), 3.79 (d, J=13.6 Hz, 1H), 3.39 (d, J=13.6 Hz, 1H), 3.15-3.20 (m, 1H), 3.01 (d, J=10.8 Hz, 1H), 2.76 (d, J=11.2 Hz, 1H), 2.58-2.64 (m, 1H), 2.15-2.21 (m, 1H), 1.98-2.04 (m, 4H), 1.69-1.85 (m, 4H), 1.21 (d, J=5.6 Hz, 3H), 0.30-0.38 (m, 2H), 0.12-0.19 (m, 1H), −0.29-0.23 (m, 1H). $^{19}$F NMR (377 MHz, DMSO-$d_6$): δ −110.68. LC-MS: m/z 596.2 (M+H)$^+$.

Example 19

(E)-3-(2-((4-((S)-2-(4-chloro-2-fluorophenyl)-2-methylbenzo[d][1,3]dioxol-4-yl)piperidin-1-yl)methyl)-1-(((R)-5,5-dimethyltetrahydrofuran-3-yl)methyl)-1H-imidazol-5-yl)acrylic acid (Compound 171b) and (E)-3-(2-((4-((S)-2-(4-chloro-2-fluorophenyl)-2-methylbenzo[d][1,3]dioxol-4-yl)piperidin-1-yl)methyl)-1-(((S)-5,5-dimethyltetrahydrofuran-3-yl)methyl)-1H-imidazol-5-yl)acrylic acid (Compound 171a)

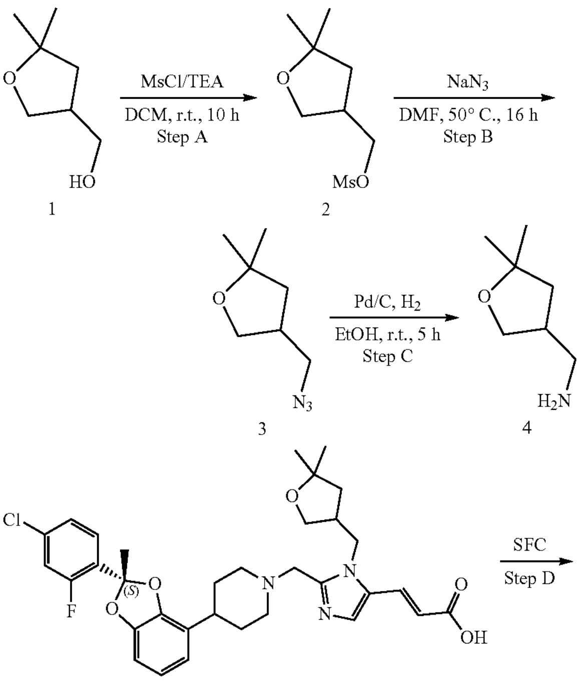

5

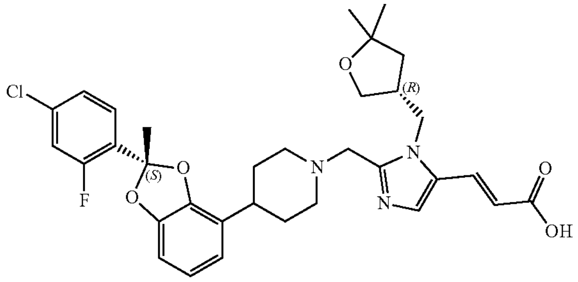

Compound 171b

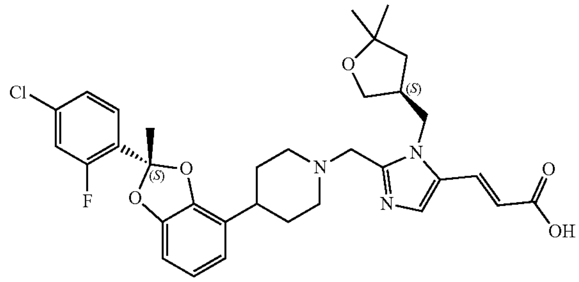

Compound 171a

Step A: (5,5-dimethyltetrahydrofuran-3-yl)methyl methanesulfonate

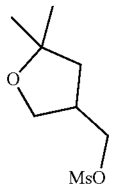

To a solution of (5,5-dimethyltetrahydrofuran-3-yl) methanol (3.58 g, 27.5 mmol) and TEA (4.17 g, 41.3 mmol) in DCM (120 mL) was added MsCl (4.73 g, 41.3 mmol) at 0° C. The resulting mixture was stirred at room temperature for 10 hours under $N_2$. Then the mixture was diluted with water (50 mL) and extracted with DCM (50 mL*3). The combined organic phase was washed with brine (50 mL), dried over anhydrous Nla2$SO_4$ and concentrated to give crude (5,5-dimethyltetrahydrofuran-3-yl)methyl methanesulfonate as a yellow oil (4.30 g, 75% yield). $^1$H NMR (400 MHz, $CD_3OD$) δ 4.14-4.26 (m, 2H), 3.97 (dd, J=9.2, 7.2 Hz, 1H), 3.63-3.68 (m, 1H), 3.07 (s, 3H), 2.75-2.84 (m, 1H), 1.99 (dd, J=12.4, 8.4 Hz, 1H), 1.53 (dd, J=12.4, 8.0 Hz, 1H), 1.29 (s, 3H), 1.22 (s, 3H).

Step B: 4-(azidomethyl)-2,2-dimethyltetrahydrofuran

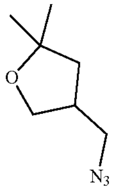

To a solution of (5,5-dimethyltetrahydrofuran-3-yl) methyl methanesulfonate (4.35 g, 20.9 mmol) in DMF (100 mL) was added $NaN_3$ (2.72 g, 41.8 mmol) at room temperature. The resulting mixture was stirred at 50° C. for 16 hours under $N_2$. Then the reaction mixture was diluted with water (40 mL) and extracted with EtOAc (50*3 mL). The combined organic phase was washed with brine (50 mL), dried over anhydrous $Na_2SO_4$ and concentrated to give crude 4-(azidomethyl)-2,2-dimethyltetrahydrofuran as a yellow oil (1.70 g, 32% yield). $^1$H NMR (400 MHz, $CDCl_3$) δ 3.98 (dd, J=9.2, 7.2 Hz, 1H), 3.58 (dd, J=9.2, 6.8 Hz, 1H), 3.26-3.39 (m, 2H), 2.57-2.64 (m, 1H), 1.96 (dd, J=12.4, 8.4 Hz, 1H), 1.44 (dd, J=12.4, 8.0 Hz, 1H), 1.30 (s, 3H), 1.22 (s, 3H).

Step C: (5,5-dimethyltetrahydrofuran-3-yl)methanamine

To a solution of 4-(azidomethyl)-2,2-dimethyltetrahydrofuran (1.70 g, 11.0 mmol) in EtOH (30 mL) was added Pd/C (10%, 100 g). The mixture was stirred at room temperature for 5 hours under $H_2$. Then the mixture was filtered and the filtrate was concentrated to give crude (5,5-dimethyltetrahydrofuran-3-yl)methanamine as a yellow oil (1.01 g, 78% yield). LC-MS: m/z 130.0 $(M+H)^+$.

Step D: (E-3-(2-((4-((S-2-(4-chloro-2-fluorophenyl)-2-methylbenzo[d][1,3]dioxol-4 yl)piperidin-1-yl) methyl)-1-(((R)-5,5-dimethyltetrahydrofuran-3-yl) methyl)-1H-imidazol-5-yl)acrylic acid (Compound 171b) and (E)-3-(2-((4-((S)-2-(4-chloro-2-fluorophenyl)-2-methylbenzo[d][1,3]dioxol-4-yl)piperidin-1-yl)methyl)-1-(((S)-5,5-dimethyltetrahydrofuran-3-yl)methyl)-1H-imidazol-5-yl)acrylic acid (Compound 171a)

Compound 171b

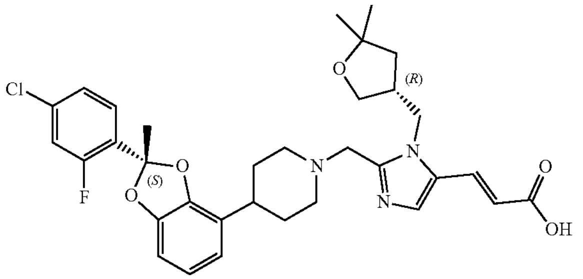

Compound 171a

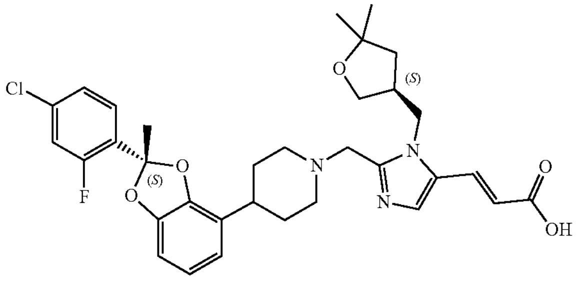

(E)-3-(2-((4-((S)-2-(4-chloro-2-fluorophenyl)-2-methylbenzo[d][1,3]dioxol-4-yl)piperidin-1-yl)methyl)-1-((5,5-dimethyltetrahydrofuran-3-yl)methyl)-1H-imidazol-5-yl) acrylic acid was then synthesized following the route of Example 12, using (S)-4-(2-(4-chloro-2-fluorophenyl)-2-methylbenzo[d][1,3]dioxol-4-yl)piperidine hydrochloride in step A and (5,5-dimethyltetrahydrofuran-3-yl)methanamine in step B. Then 230 mg of (E)-3-(2-((4-((S)-2-(4-chloro-2-fluorophenyl)-2-methylbenzo[d][1,3]dioxol-4-yl)piperidin-1-yl)methyl)-1-((5,5-dimethyltetrahydrofuran-3-yl)methyl)-1H-imidazol-5-yl)acrylic acid was purified via SFC to give (E)-3-(2-((4-((S)-2-(4-chloro-2-fluorophenyl)-2-methylbenzo[d][1,3]dioxol-4-yl)piperidin-1-yl)methyl)-1-(((R)-5,5-dimethyltetrahydrofuran-3-yl)methyl)-1H-imidazol-5-yl) acrylic acid (Compound 171b) and (E)-3-(2-((4-((S)-2-(4-chloro-2-fluorophenyl)-2-methylbenzo[d][1,3]dioxol-4-yl) piperidin-1-yl)methyl)-1-(((S)-5,5-dimethyltetrahydrofuran-3-yl)methyl)-1H-imidazol-5-yl) acrylic acid (Compound 171a).

Compound 171b: (103 mg, 45% yield). Retention time 2.924 minutes [Column: YMC Cellulose-SC (4.6*100 mm, 3 um); Mobile phase: $CO_2$/MeOH (0.2% Methanol Ammonia)=65/35, Flow rate: 3 mL/min; Temperature: 40° C.; Back pressure: 2000 psi]. $^1$H NMR (400 MHz, $CD_3OD$) δ 7.47-7.60 (m, 2H), 7.43 (s, 1H), 7.27 (dd, J=10.8, 2.0 Hz, 1H), 7.20 (dd, J=8.4, 2.0 Hz, 1H), 6.72-6.78 (m, 1H), 6.66-6.71 (m, 2H), 6.39 (d, J=16.0 Hz, 1H), 4.37 (dd, J=14.8, 8.4 Hz, 1H), 4.23 (dd, J=14.8, 6.8 Hz, 1H), 3.84 (dd, J=8.8, 6.8 Hz, 1H), 3.72 (q, J=13.6 Hz, 2H), 3.60 (dd, J=8.8, 6.8 Hz, 1H), 2.85-3.05 (m, 3H), 2.64-2.76 (m, 1H), 2.18-2.32 (m, 2H), 2.01 (s, 3H), 1.76-1.98 (m, 5H), 1.66 (dd, J=12.4, 8.0 Hz, 1H), 1.35 (s, 3H), 1.19 (s, 3H). LC-MS: m/z 610.2 $(M+H)^+$.

Compound 171a: (100 mg, 43% yield) Retention time 1.708 minutes (Analytical SFC condition identical to those used for Compound 171b). $^1H$ NMR (400 MHz, $CD_3OD$) δ 7.50-7.61 (m, 2H), 7.48 (s, 1H), 7.26 (dd, J=10.8, 2.0 Hz, 1H), 7.20 (dd, J=8.4, 2.0 Hz, 1H), 6.72-6.80 (m, 1H), 6.67-6.70 (m, 2H), 6.40 (d, J=16.0 Hz, 1H), 4.36 (dd, J=14.8, 8.4 Hz, 1H), 4.24 (dd, J=14.8, 6.8 Hz, 1H), 3.67-3.87 (m, 3H), 3.59 (dd, J=8.8, 6.8 Hz, 1H), 2.95-3.10 (m, 2H), 2.86-2.94 (m, 1H), 2.67-2.78 (m, 1H), 2.28-2.32 (m, 2H), 2.02 (s, 3H), 1.76-1.98 (m, 5H), 1.65 (dd, J=12.4, 8.0 Hz, 1H), 1.35 (s, 3H), 1.18 (s, 3H). LC-MS: m/z 610.2 $(M+H)^+$.

Example 20

(E)-3-(2-((4-((S)-2-(4-chloro-2-fluorophenyl)-2-methylbenzo[d][1,3]dioxol-4-yl)piperidin-1-yl) methyl)-1-((S)-2-methoxypropyl)-1H-imidazol-5-yl) acrylic acid (Compound 172a) and (E)-3-(2-((4-((S)-2-(4-chloro-2-fluorophenyl)-2-methylbenzo[d] [1,3]dioxol-4-yl)piperidin-1-yl)methyl)-1-((R)-2-methoxypropyl)-1H-imidazol-5-yl)acrylic acid (Compound 112b)

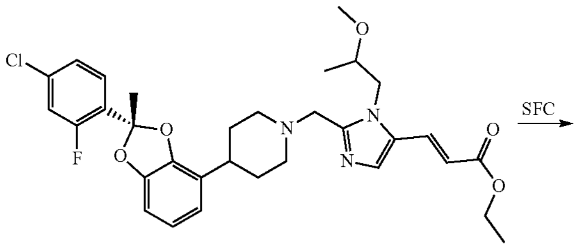

1

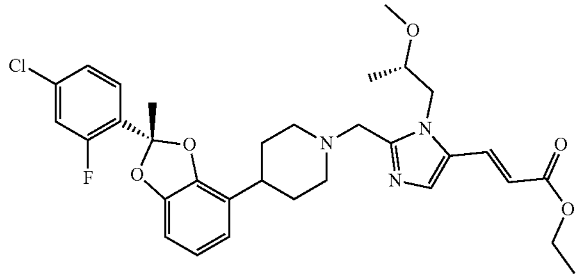

P1

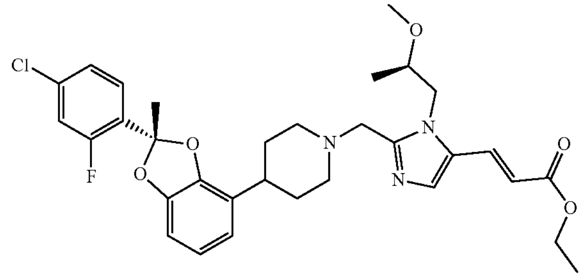

P2

Step A: ethyl (E)-3-(2-((4-((S)-2-(4-chloro-2-fluorophenyl)-2-methylbenzo[d][1,3]dioxol-4-yl)piperidin-1-yl)methyl)-1-((S)-2-methoxypropyl)-1H-imidazol-5-yl)acrylate and ethyl E)-3-(2-((4-((S)-2-(4-chloro-2-fluorophenyl)-2-methylbenzo[d][1,3]dioxol-4-yl) piperidin-1-yl)methyl)-1-((R)-2-methoxypropyl)-1H-imidazol-5-yl)acrylate Ethyl (E)-3-(2-((4-((S)-2-(4-chloro-2-fluorophenyl)-2-methylbenzo[d][1,3]dioxol-4-yl)piperidin-1-yl)methyl)-1-(2-methoxypropyl)-1H-imidazol-5-yl)acrylate (230 mg, synthesized following the route of Example 12, using (S)-4-(2-(4-chloro-2-fluorophenyl)-2-methylbenzo[d][1,3]dioxol-4-yl)piperidine hydrochloride in step A and 2-methoxypropan-1-aminium chloride in step B) was separated via SFC to give ethyl (E)-3-(2-((4-((S)-2-(4-chloro-2-fluorophenyl)-2-methylbenzo[d][1,3]dioxol-4-yl)piperidin-1-yl)methyl)-1-((S)-2-methoxypropyl)-1H-imidazol-5-yl) acrylate (P1) and ethyl (E)-3-(2-((4-((S)-2-(4-chloro-2-fluorophenyl)-2-methylbenzo[d][1,3]dioxol-4-yl)piperidin-1-yl)methyl)-1-((R)-2-methoxypropyl)-1H-imidazol-5-yl) acrylate (P2).

P1: 80.0 mg, 39% yield. LC-MS: m/z 598.2 $(M+H)^+$. Retention time 1.697 minute [Column: OD-3 4.6*100 mm 3 um; Mobile phase: MeOH [0.2% $NH_3$ (7M in MeOH)], Flow rate: 3 mL/min; Temperature: 40° C.; Back pressure: 2000 psi].

P2: 80.0 mg, 39% yield. LC-MS: m/z 598.2 $(M+H)^+$. Retention time 2.355 minute (Analytical SFC condition identical to those used for P1).

(E)-3-(2-((4-((S)-2-(4-chloro-2-fluorophenyl)-2-methylbenzo[d][1,3]dioxol-4-yl)piperidin-1-yl) methyl)-1-((S)-2-methoxypropyl)-1H-imidazol-5-yl) acrylic acid (Compound 172a) and (E)-3-(2-((4-((S)-2-(4-chloro-2-fluorophenyl)-2-methylbenzo[d] [1,3]dioxol-4-yl)piperidin-1-yl)methyl)-1-((R)-2-methoxypropyl)-1H-imidazol-5-yl)acrylic acid (Compound 172b)

Compound 172a

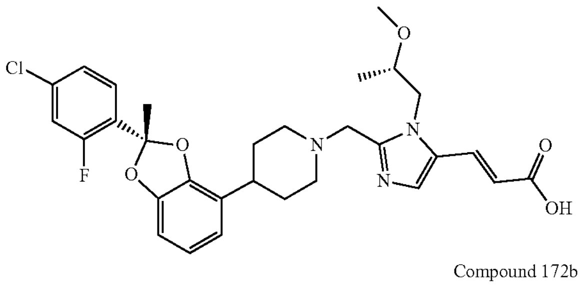

Compound 172b

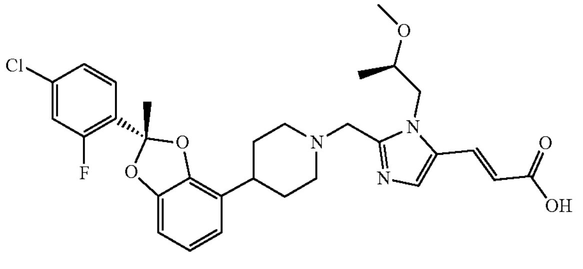

Compound 172a was synthesized following the step J of Example 1, using ethyl (E)-3-(2-((4-((S)-2-(4-chloro-2-fluorophenyl)-2-methylbenzo[d][1,3]dioxol-4-yl)piperidin-1-yl)methyl)-1-((S)-2-methoxypropyl)-1H-imidazol-5-yl) acrylate (P1) as starting material.

$^{1}$H NMR (400 MHz, DMSO-$d_6$) δ 12.28 (br.s, 1H), 7.50-7.56 (m, 4H), 7.34 (dd, J=8.4, 2.0 Hz, 1H), 6.76-6.83 (m, 2H), 6.67-6.76 (m, 1H), 6.28 (d, J=16.0 Hz, 1H), 4.19 (dd, J=14.8, 3.2 Hz, 1H), 4.09 (dd, J=14.8, 8.4 Hz, 1H), 3.74-3.78 (m, 2H), 3.45 (d, J=13.6 Hz, 1H), 3.09 (s, 3H), 2.96 (d, J=10.8 Hz, 1H), 2.79 (d, J=10.8 Hz, 1H), 2.59-2.63 (m, 1H), 2.12-2.18 (m, 1H), 2.05-2.08 (m, 1H), 2.01 (s, 3H), 1.60-1.85 (m, 4H), 1.13 (d, J=6.0 Hz, 3H). LC-MS: m/z 570.0 $(M+H)^+$.

Compound 172b was synthesized following the step J of Example 1, using ethyl (E)-3-(2-((4-((S)-2-(4-chloro-2-fluorophenyl)-2-methylbenzo[d][1,3]dioxol-4-yl)piperidin-1-yl)methyl)-1-((R)-2-methoxypropyl)-1H-imidazol-5-yl) acrylate (P2) as starting material.

$^{1}$H NMR (400 MHz, DMSO-$d_6$) δ 12.27 (br.s, 1H), 7.48-7.59 (m, 4H), 7.33 (dd, J=8.4, 2.0 Hz, 1H), 6.78 (dd, J=6.8, 6.0 Hz, 2H), 6.71-6.74 (m, 1H), 6.28 (d, J=16.0 Hz, 1H), 4.19 (dd, J=14.8, 3.2 Hz, 1H), 4.09 (dd, J=14.8, 8.4 Hz, 1H), 3.65-3.80 (m, 2H), 3.46 (d, J=13.6 Hz, 1H), 3.07 (s, 3H), 2.95 (d, J=11.2 Hz, 1H), 2.80 (d, J=11.2 Hz, 1H), 2.59-2.63 (m, 1H), 2.13-2.19 (m, 1H), 2.01-2.07 (m, 4H), 1.71-1.73 (m, 4H), 1.13 (d, J=6.0 Hz, 3H). LC-MS: m/z 570.1 $(M+H)^+$.

Example 21

(E)-3-(2-((4-((S)-2-(4-chloro-2-fluorophenyl)-2-methylbenzo[d][1,3]dioxol-4-yl)piperidin-1-yl)methyl)-1-(((S)-1,1-dioxidothietan-2-yl)methyl)-1H-imidazol-5-yl)acrylic acid (Compound 173a) and (E)-3-(2-((4-((S)-2-(4-chloro-2-fluorophenyl)-2-methylbenzo[d][1,3]dioxol-4-yl)piperidin-1-yl)methyl)-1-(((R)-1,1-dioxidothietan-2-yl)methyl)-1H-imidazol-5-yl)acrylic acid (Compound 173b)

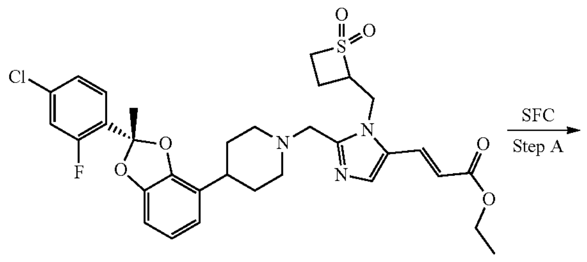

1

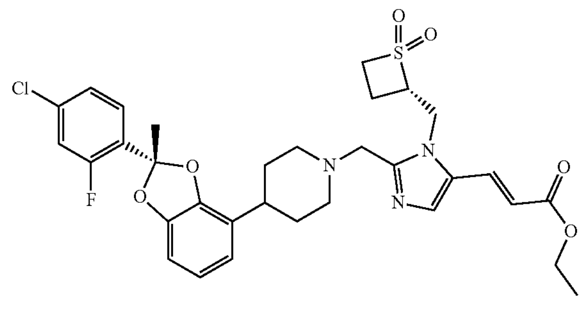

P1

-continued

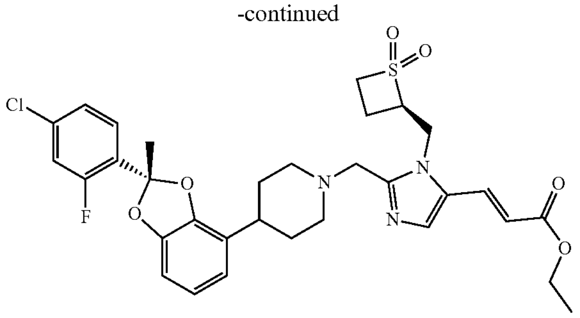

P2

Step A: ethyl (E)-3-(2-((4-((S)-2-(4-chloro-2-fluorophenyl)-2-methylbenzo[d][1,3]dioxol-4-yl)piperidin-1-yl)methyl)-1-(((S)-1,1-dioxidothietan-2-yl)methyl)-1H-imidazol-5-yl)acrylate and ethyl E)-3-(2-((4-((S)-2-(4-chloro-2-fluorophenyl)-2-methylbenzo[d][1,3]dioxol-4-yl)piperidin-1-yl)methyl)-1-(((R)-1,1-dioxidothietan-2-yl)methyl)-1H-imidazol-5-yl)acrylate

P1

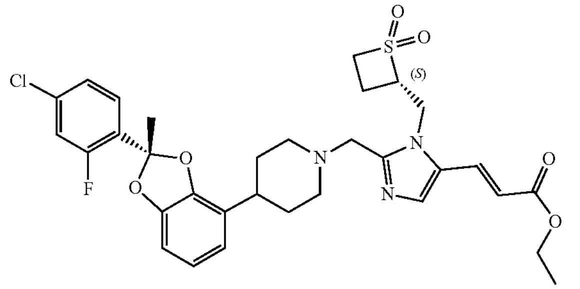

P2

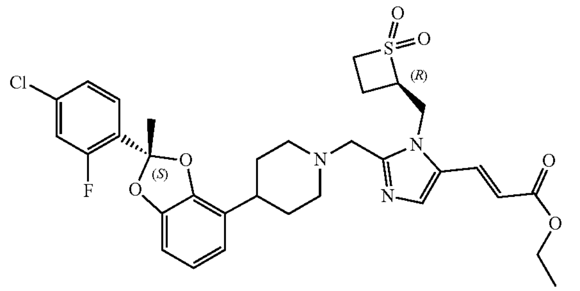

Ethyl (E)-3-(2-((4-((S)-2-(4-chloro-2-fluorophenyl)-2-methylbenzo[d][1,3]dioxol-4-yl)piperidin-1-yl)methyl)-1-((1,1-dioxidothietan-2-yl)methyl)-1H-imidazol-5-yl)acrylate (436 mg, synthesized following the route of Example 12, using (S)-4-(2-(4-chloro-2-fluorophenyl)-2-methylbenzo[d][1,3]dioxol-4-yl)piperidine hydrochloride in step A and 2-(aminomethyl)thietane 1,1-dioxide in step B) was separated via SFC to give ethyl (E)-3-(2-((4-((S)-2-(4-chloro-2-fluorophenyl)-2-methylbenzo[d][1,3]dioxol-4-yl)piperidin-1-yl)methyl)-1-(((S)-1,1-dioxidothietan-2-yl)methyl)-1H-imidazol-5-yl)acrylate (P1, the first eluting compound) and ethyl (E)-3-(2-((4-((S)-2-(4-chloro-2-fluorophenyl)-2-methylbenzo[d][1,3]dioxol-4-yl)piperidin-1-yl)methyl)-1-(((R)-1,1-dioxidothietan-2-yl)methyl)-1H-imidazol-5-yl)acrylate (P2, the second eluting compound).

P1: 125 mg, 29% yield. LC-MS: m/z 644.2 $(M+H)^+$. Retention time 2.137 minutes [Column: OZ-3 (4.6* 100 mm, 3 um); Mobile phase: MeOH [0.2% $NH_3$ (7M in MeOH)], Flow rate: 3 mL/min; Temperature: 40° C.; Back pressure: 2000 psi].

P2: 135 mg, 31% yield. LC-MS: m/z 644.2 $(M+H)^+$. Retention time 3.699 minutes (Analytical SFC condition identical to those used for P1).

(E)-3-(2-((4-((S)-2-(4-chloro-2-fluorophenyl)-2-methylbenzo[d][1,3]dioxol-4-yl)piperidin-1-yl)methyl)-1-(((S)-1,1-dioxidothietan-2-yl)methyl)-1H-imidazol-5-yl)acrylic acid (Compound 173a)) and (E)-3-(2-((4-((S)-2-(4-chloro-2-fluorophenyl)-2-methylbenzo[d][1,3]dioxol-4-yl)piperidin-1-yl)methyl)-1-(((R)-1,1-dioxidothietan-2-yl)methyl)-1H-imidazol-5-yl)acrylic acid (Compound 173b)

Compound 173a

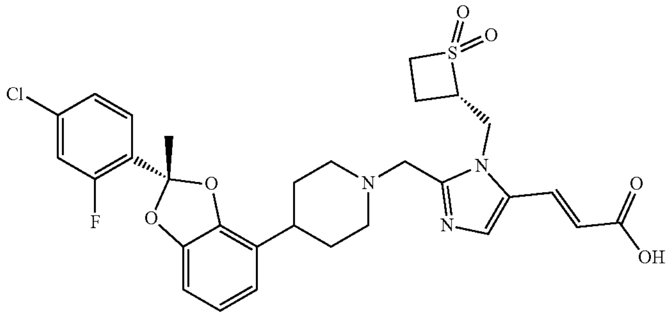

Compound 173b

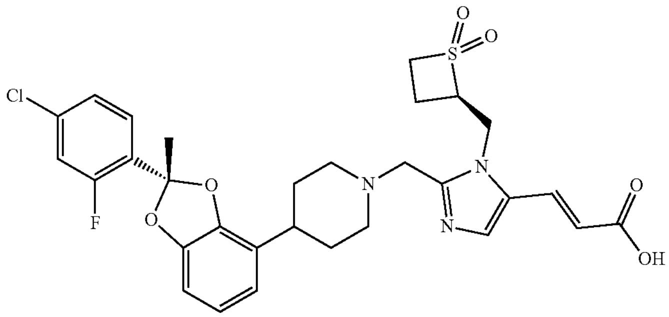

Compound 173a was synthesized following the step J of Example 1, using ethyl (E)-3-(2-((4-((S)-2-(4-chloro-2-fluorophenyl)-2-methylbenzo[d][1,3]dioxol-4-yl)piperidin-1-yl)methyl)-1-(((S)-1,1-dioxidothietan-2-yl)methyl)-1H-imidazol-5-yl)acrylate (P1) as starting material. ee value: 77.2%, $^1$H NMR (400 MHz, DMSO-$d_6$, 80° C.) δ 7.44-7.61 (m, 3H), 7.43 (s, 1H), 7.30 (dd, J=8.4, 2.0 Hz, 1H), 6.70-6.82 (m, 3H), 6.28 (d, J=15.6 Hz, 1H), 4.84-4.96 (m, 1H), 4.75-4.83 (m, 1H), 4.55 (dd, J=15.2, 6.0 Hz, 1H), 3.93-4.10 (m, 2H), 3.74 (d, J=13.6 Hz, 1H), 3.57 (d, J=13.6 Hz, 1H), 2.83-2.92 (m, 2H), 2.67-2.70 (m, 1H), 2.24-2.29 (m, 1H), 2.10-2.20 (m, 2H), 2.01 (s, 3H), 1.87-1.96 (m, 1H), 1.66-1.81 (m, 4H). $^{19}$F NMR (377 MHz, DMSO-$d_6$): δ −110.77, −110.80. LC-MS: m/z 616.0 $(M+H)^+$.

Compound 173b was synthesized following the step J of Example 1, using ethyl (E)-3-(2-((4-((S)-2-(4-chloro-2-fluorophenyl)-2-methylbenzo[d][1,3]dioxol-4-yl)piperidin-1-yl)methyl)-1-(((R)-1,1-dioxidothietan-2-yl)methyl)-1H-imidazol-5-yl)acrylate (P2) as starting material. ee value: 86.6%, $^1$H NMR (400 MHz, DMSO-$d_6$, 80° C.) δ 7.49-7.60 (m, 2H), 7.40-7.47 (m, 2H), 7.30 (dd, J=8.4, 1.6 Hz, 1H), 6.69-6.81 (m, 3H), 6.28 (d, J=16.0 Hz, 1H), 4.84-4.94 (m, 1H), 4.75-4.83 (m, 1H), 4.56 (dd, J=15.6, 6.0 Hz, 1H), 3.93-4.11 (m, 2H), 3.74 (d, J=13.6 Hz, 1H), 3.58 (d, J=13.6 Hz, 1H), 2.85-2.96 (m, 2H), 2.62-2.69 (m, 1H), 2.23-2.35 (m, 1H), 2.09-2.21 (m, 2H), 2.01 (s, 3H), 1.88-1.97 (m, 1H), 1.70-1.80 (m, 4H). $^{19}$F NMR (377 MHz, DMSO-$d_6$): δ −110.77, −110.80. LC-MS: m/z 616.0 $(M+H)^+$.

Example 22
(E)-3-(2-((4-(2-(4-chloro-2-fluorophenyl)-2-methylbenzo[d][1,3]dioxol-4-yl)piperidin-1-yl)methyl)-1-((1-(methylsulfonyl)azetidin-3-yl)methyl)-1H-imidazol-5-yl)acrylic acid (Compound 174)
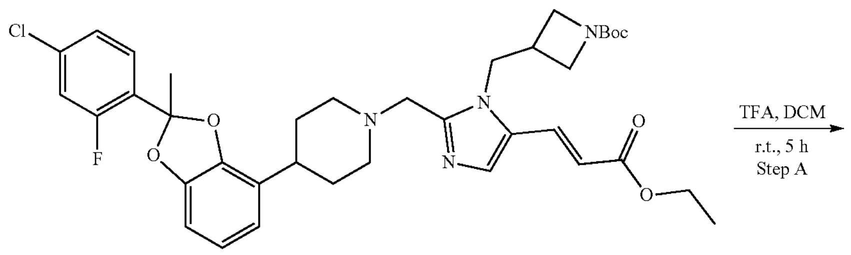
1
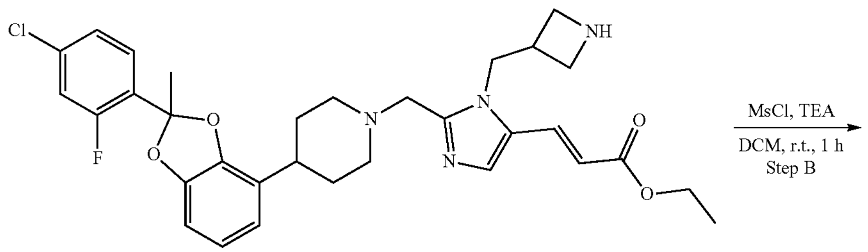
2
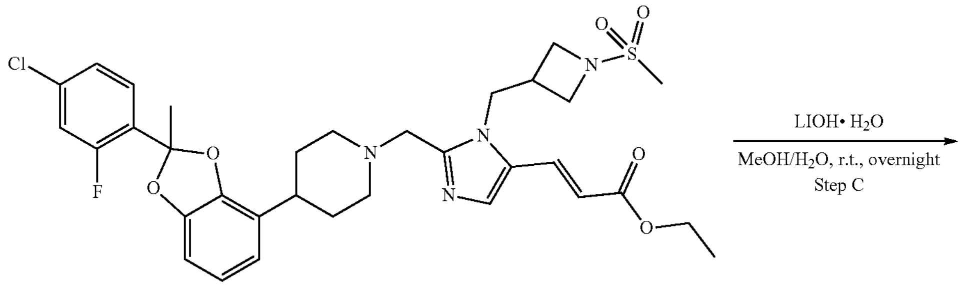
3
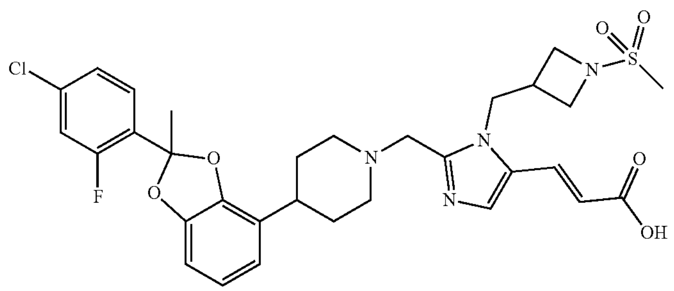
Compound 174

Step A: ethyl E)-3-(azetidin-3-ylmethyl)-2-((4-(2-(4-chloro-2-fluorophenyl)-2-methylbenzo[d][1,3]dioxol-4-yl)piperidin-1-yl)methyl)-1H-imidazol-5-yl)acrylate

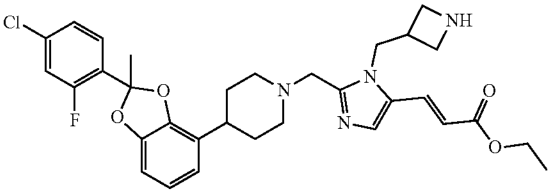 [SMILES: CCOC(=O)/C=C/c1cnc(CN2CCC(c3cccc4c3OC(C)(c3ccc(Cl)cc3F)O4)CC2)n1CC1CNC1]

To a mixture of tert-butyl (E)-3-((2-((4-(2-(4-chloro-2-fluorophenyl)-2-methylbenzo[d][1,3]dioxol-4-yl)piperidin-1-yl)methyl)-5-(3-ethoxy-3-oxoprop-1-en-1-yl)-1H-imidazol-1-yl)methyl)azetidine-1-carboxylate (80.0 mg, 0.115 mmol, prepared following the route of Example 12, using tert-butyl 3-(aminomethyl)azetidine-1-carboxylate in step B) in DCM (2 mL) was added TFA (0.2 mL). The reaction mixture was stirred at room temperature for 5 hours. Then the reaction mixture was concentrated in vacuo to give ethyl (E)-3-(1-(azetidin-3-ylmethyl)-2-((4-(2-(4-chloro-2-fluorophenyl)-2-methylbenzo[d][1,3]dioxol-4-yl)piperidin-1-yl)methyl)-1H-imidazol-5-yl)acrylate (crude, TFA salt, 72.0 mg, 88% yield). LC-MS: m/z 595.2 $(M+H)^+$.

Step B: ethyl E)-3-(2-((4-(2-(4-chloro-2-fluorophenyl)-2-methylbenzo[d][1,3]dioxol-4-yl)piperidin-1-yl)methyl)-1-((methylsulfonyl)azetidin-3-yl)methyl)-1H-imidazol-1-yl)acrylate

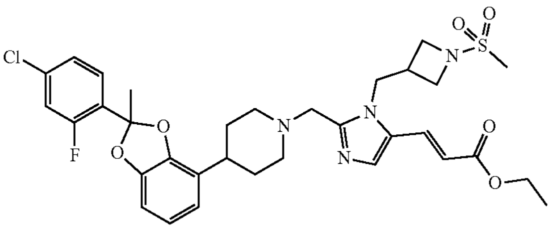 [SMILES: CCOC(=O)/C=C/c1cnc(CN2CCC(c3cccc4c3OC(C)(c3ccc(Cl)cc3F)O4)CC2)n1CC1CN(S(C)(=O)=O)C1]

To a mixture of ethyl (E)-3-(1-(azetidin-3-ylmethyl)-2-((4-(2-(4-chloro-2-fluorophenyl)-2-methylbenzo[d][1,3]dioxol-4-yl)piperidin-1-yl)methyl)-1H-imidazol-5-yl)acrylate (crude, TFA salt, 72.0 mg, 0.102 mmol) in DCM (2 mL) were added MsCl (0.0500 mL, 0.646 mmol) and TEA (0.200 mL, 1.44 mmol) at 0° C. The reaction mixture was stirred at room temperature for 1 hour. Then the reaction mixture was quenched with saturated sodium bicarbonate solution (10 mL) and extracted with EtOAc (10 mL*2). The organic layer was dried over $Na_2SO_4$, and concentrated in vacuo to give ethyl (E)-3-(2-((4-(2-(4-chloro-2-fluorophenyl)-2-methylbenzo[d][1,3]dioxol-4-yl)piperidin-1-yl)methyl)-1-((1-(methylsulfonyl)azetidin-3-yl)methyl)-1H-imidazol-5-yl) acrylate (80.0 mg, crude). LC-MS: m/z 673.2 $(M+H)^+$.

Step C: (E)-3-(2-((4-(2-(4-chloro-2-fluorophenyl)-2-methylbenzo[d][1,3]dioxol-4-yl)piperidin-1-yl)methyl)-1-((methylsulfonyl)azetidin-3-yl)methyl)-1H-imidazol-5-yl)acrylic acid (Compound 174)

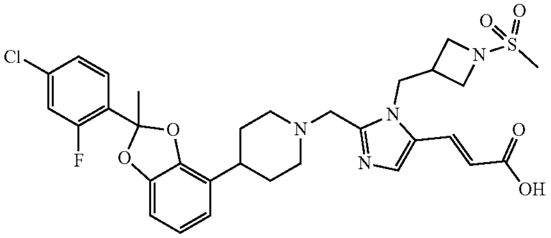 [SMILES: CC1(c2ccc(Cl)cc2F)Oc2cccc(C3CCN(Cc4ncc(/C=C/C(=O)O)n4CC4CN(S(C)(=O)=O)C4)CC3)c2O1]

To a solution of ethyl (E)-3-(2-((4-(2-(4-chloro-2-fluorophenyl)-2-methylbenzo[d][1,3]dioxol-4-yl)piperidin-1-yl)methyl)-1-((1-(methyl sulfonyl)azetidin-3-yl)methyl)-1H-imidazol-5-yl)acrylate (80.0 mg crude, 0.115 mmol) in MeOH (2 mL) and $H_2O$ (0.4 mL) was added LiOH (14.0 mg, 0.575 mmol). The mixture was stirred at room temperature overnight. Then the reaction mixture was adjusted to pH=5 with formic acid and concentrated. The residue was purified with Prep-HPLC (0.1% formic acid in water and acetonitrile) to give (E)-3-(2-((4-(2-(4-chloro-2-fluorophenyl)-2-methylbenzo[d][1,3]dioxol-4-yl)piperidin-1-yl)methyl)-1-((1-(methyl sulfonyl)azetidin-3-yl)methyl)-1H-imidazol-5-yl)acrylic acid as a white sold (25.8 mg, 39% yield over two steps). $^1$H NMR (400 MHz, DMSO-$d_6$) δ 7.47-7.58 (m, 4H), 7.34 (dd, J=8.4, 2.0 Hz, 1H), 6.75-6.78 (m, 3H), 6.34 (d, J=16.0 Hz, 1H), 4.46 (d, J=7.2 Hz, 2H), 3.87-3.92 (m, 2H), 3.79-3.83 (m, 2H), 3.60 (s, 2H), 2.93-2.98 (m, 6H), 2.63-2.68 (m, 1H), 2.08-2.12 (m, 2H), 2.02 (s, 3H), 1.70-1.77 (m, 4H). LC-MS: m/z 645.0 $(M+H)^+$.

Example 23

(E)-3-(2-((4-(2-(4-chloro-2-fluorophenyl)-2-methylbenzo[d][1,3]dioxol-4-yl)piperidin-1-yl)methyl)-1-(2-(N-methylacetamido)ethyl)-1H-imidazol-5-yl)acrylic acid (Compound 175)

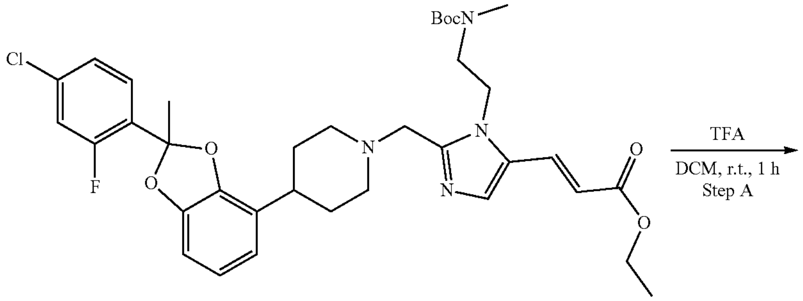

1

-continued

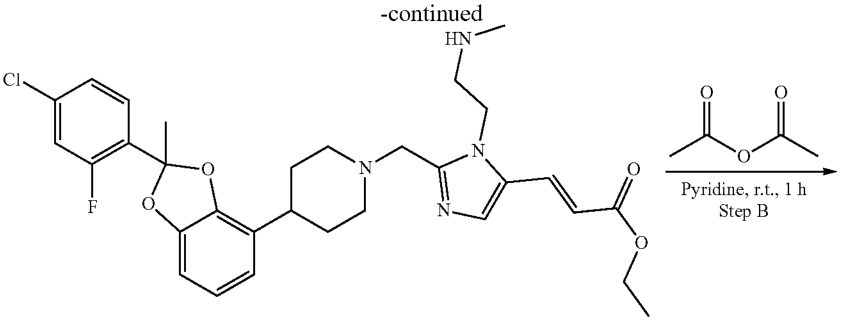

2

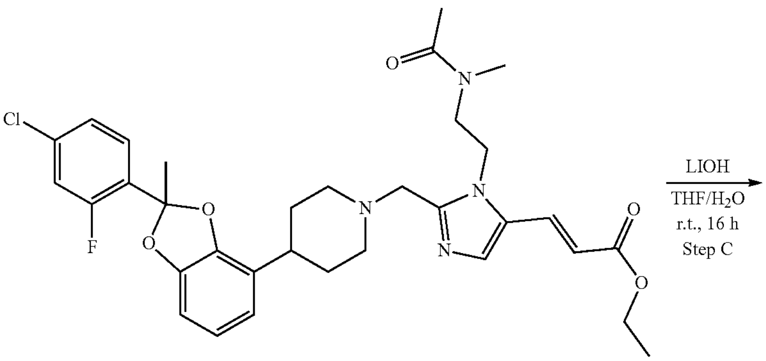

3

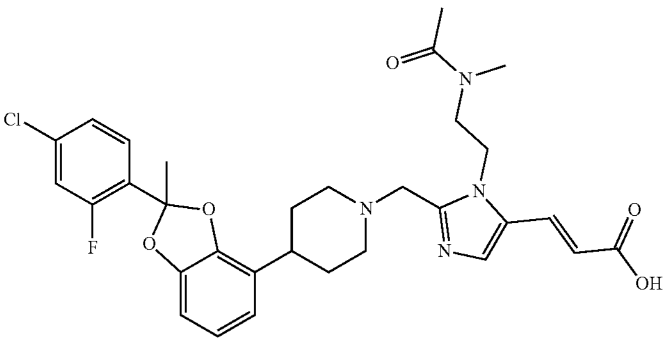

Compound 175

Step A: ethyl E)-3-(2-((4-(2-(4-chloro-2-fluorophenyl)-2-methylbenzo[d][1,3]dioxol-4-yl)piperidin-1-yl)methyl)-1-(2-(methylamino)ethyl)-1H-imidazol-5-yl)acrylate

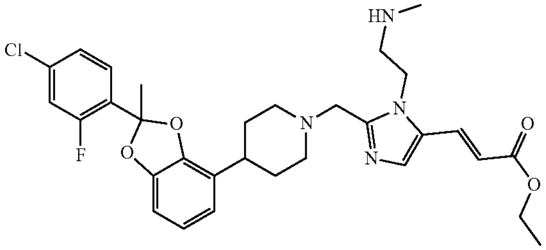 [SMILES: CCOC(=O)/C=C/c1cnc(CN2CCC(c3cccc4c3OC(C)(c3ccc(Cl)cc3F)O4)CC2)n1CCNC]

To a solution of ethyl (E)-3-(1-(2-((tert-butoxycarbonyl)(methyl)amino)ethyl)-2-((4-(2-(4-chloro-2-fluorophenyl)-2-methylbenzo[d][1,3]dioxol-4-yl)piperidin-1-yl)methyl)-1H-imidazol-5-yl)acrylate (560 mg, 0.0820 mmol, prepared following the route of Example 12, using tert-butyl (2-aminoethyl)(methyl)carbamate in step B) in DCM (0.8 mL) was added trifluoroacetic acid (0.2 mL, 2.69 mmol). The reaction mixture was stirred at room temperature for 1 hour. The reaction mixture was adjusted to pH=8 with $NaHCO_3$(aq.). Then the mixture was diluted with water (10 mL) and extracted with DCM (10 mL*3). The combined organic phase was washed with brine (20 mL), dried over anhydrous $Na_2SO_4$ and concentrated to give ethyl (E)-3-(2-((4-(2-(4-chloro-2-fluorophenyl)-2-methylbenzo[d][1,3]dioxol-4-yl)piperidin-1-yl)methyl)-1-(2-(methylamino)ethyl)-1H-imidazol-5-yl)acrylate as a yellow oil (40.0 mg, crude). LC-MS: m/z 583.1 $(M+H)^+$.

Step B: ethyl (E)-3-(2-((4-(2-(4-chloro-2-fluorophenyl)-2-methylbenzo[d][1,3]dioxol-4-yl)piperidin-1-yl)methyl)-1-(2-(N-methylacetamido)ethyl)-1H-imidazol-5-yl)acrylate

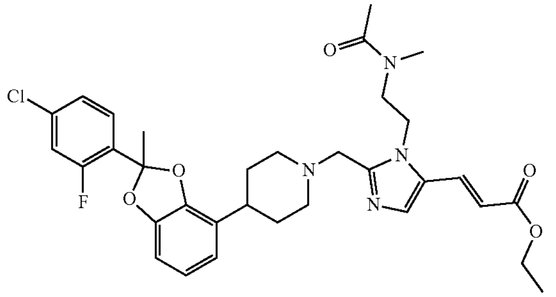 [SMILES: CCOC(=O)/C=C/c1cnc(CN2CCC(c3cccc4c3OC(C)(c3ccc(Cl)cc3F)O4)CC2)n1CCN(C)C(C)=O]

To a solution of ethyl (E)-3-(2-((4-(2-(4-chloro-2-fluorophenyl)-2-methylbenzo[d][1,3]dioxol-4-yl)piperidin-1-yl)methyl)-1-(2-(methylamino)ethyl)-1H-imidazol-5-yl)acrylate (40.0 mg, 0.0690 mmol, crude) in pyridine (0.2 mL) was added acetic anhydride (8.40 mg, 0.0820 mmol). The reaction mixture was stirred at room temperature for 1 hour. The reaction mixture was concentrated to give ethyl (E)-3-(2-((4-(2-(4-chloro-2-fluorophenyl)-2-methylbenzo[d][1,3]dioxol-4-yl)piperidin-1-yl)methyl)-1-(2-(N-methylacetamido)ethyl)-1H-imidazol-5-yl)acrylate as a yellow oil (40.0 mg, crude). LC-MS: m/z 625.2 $(M+H)^+$.

Step C: (E)-3-(2-((4-(2-(4-chloro-2-fluorophenyl)-2-methylbenzo[d][1,3]dioxol-4-yl)piperidin-1-yl)methyl)-1-(2-(N-methylacetamido)ethyl)-1H-imidazol-5-yl)acrylic acid (Compound 175)

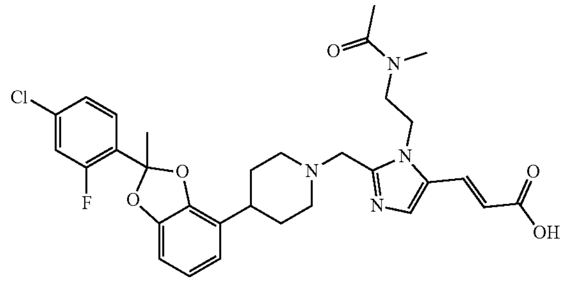 [SMILES: CC(=O)N(C)CCn1c(/C=C/C(=O)O)cnc1CN1CCC(c2cccc3c2OC(C)(c2ccc(Cl)cc2F)O3)CC1]

To a mixture of ethyl (E)-3-(2-((4-(2-(4-chloro-2-fluorophenyl)-2-methylbenzo[d][1,3]dioxol-4-yl)piperidin-1-yl)methyl)-1-(2-(N-methylacetamido)ethyl)-1H-imidazol-5-yl)acrylate (40.0 mg, 0.064 mmol) in THF (0.4 mL) was added $LiOH \cdot H_2O$ (5.0 mg, 0.128 mmol) in water (0.2 mL). The reaction mixture was stirred at room temperature for 3 hours. Then the reaction mixture was adjusted to pH=4 with formic acid and concentrated under 40° C. to remove THF. The residue was extracted with DCM (15 mL*2). The organic layer was dried over $Na_2SO_4$, and concentrated. The residue was purified with Prep-HPLC (0.1% formic acid in water and acetonitrile) to give (E)-3-(2-((4-(2-(4-chloro-2-fluorophenyl)-2-methylbenzo[d][1,3]dioxol-4-yl)piperidin-1-yl)methyl)-1-(2-(N-methylacetamido)ethyl)-1H-imidazol-5-yl)acrylic acid as a white solid (13.6 mg, 28% yield over three steps). $^1H$ NMR (400 MHz, DMSO-$d_6$, at 80° C.) δ 7.55 (t, J=8.4 Hz, 1H), 7.43 (d, J=10.8 Hz, 1H), 7.29 (d, J=8.4 Hz, 1H), 6.97-7.10 (m, 2H), 6.68-6.80 (m, 3H), 6.21 (d, J=16.0 Hz, 1H), 4.18-4.23 (m, 2H), 3.55-3.61 (m, 5H), 2.91 (s, 2H), 2.83 (s, 3H), 2.63-2.65 (m, 1H), 2.08-2.11 (m, 2H), 2.00 (s, 3H), 1.92-1.97 (m, 2H), 1.73-1.81 (m, 4H). LC-MS: m/z 597.0 $(M+H)^+$.

(E)-3-(2-((4-(2-(4-chloro-2-fluorophenyl)-2-methylbenzo[d][1,3]dioxol-4-yl)piperidin-1-yl)methyl)-1-(2-(N-methylmethyl sulfonamido)ethyl)-1H-imidazol-5-yl)acrylic acid (Compound 176) was synthesized following the similar route of Example 22, using ethyl (E)-3-(2-((4-(2-(4-chloro-2-fluorophenyl)-2-methylbenzo[d][1,3]dioxol-4-yl)piperidin-1-yl)methyl)-1-(2-(methylamino)ethyl)-1H-imidazol-5-yl)acrylate in step A.

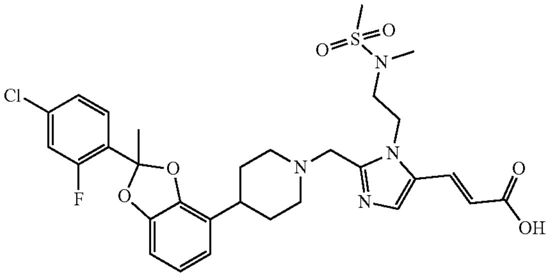 [SMILES: CN(CCn1c(/C=C/C(=O)O)cnc1CN1CCC(c2cccc3c2OC(C)(c2ccc(Cl)cc2F)O3)CC1)S(C)(=O)=O]

$^1H$ NMR (400 MHz, DMSO-$d_6$) δ 7.52-7.59 (m, 2H), 7.50 (s, 1H), 7.44 (d, J=16.0 Hz, 1H), 7.34 (dd, J=8.4, 1.6 Hz, 1H), 6.78 (d, J=4.4 Hz, 2H), 6.72-6.75 (m, 1H), 6.32 (d, J=16.0 Hz, 1H), 4.35 (t, J=6.4 Hz, 2H), 3.62 (s, 2H), 3.41 (d, J=6.8 Hz, 2H), 2.85-2.89 (m, 2H), 2.84 (s, 3H), 2.79 (s, 3H), 2.58-2.63 (m, 1H), 2.06-2.12 (m, 2H), 2.02 (s, 3H), 1.70-1.78 (m, 4H). LC-MS: m/z 633.1 $(M+H)^+$.

Example 24

(E)-3-(2-((4-(2-(4-chloro-2-fluorophenyl)-2-methylbenzo[d][1,3]dioxol-4-yl)piperidin-1-yl)methyl)-1-((3-hydroxycyclobutyl)methyl)-1H-imidazol-5-yl)acrylic acid (Compound 177)

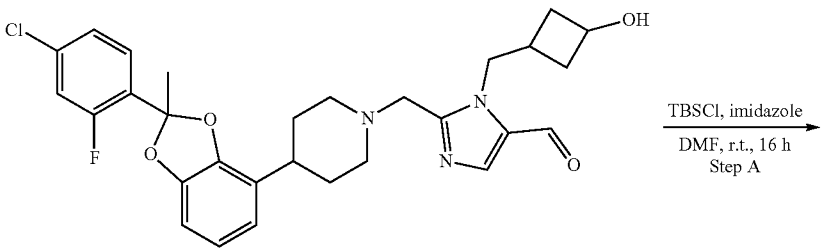

1

-continued

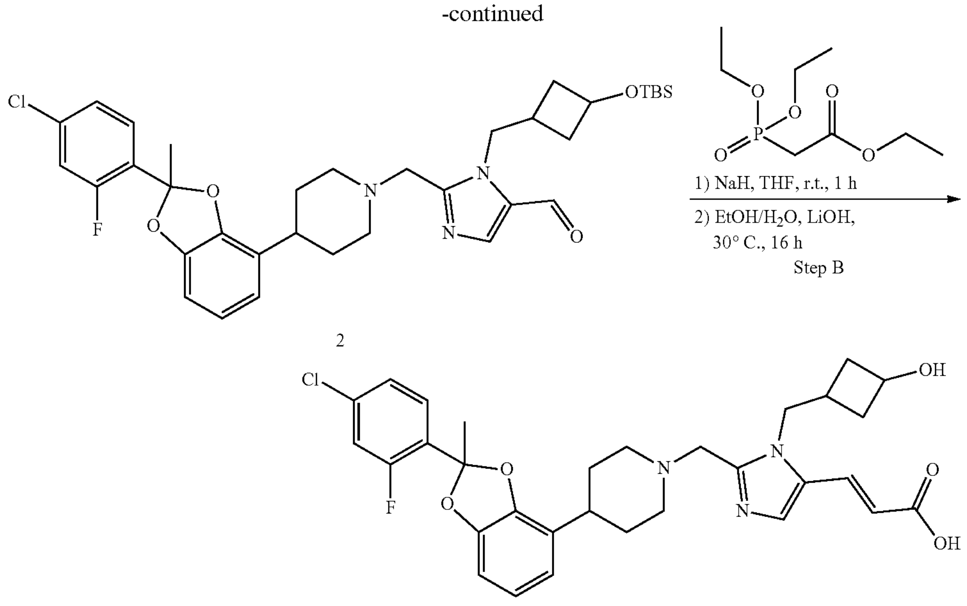

2

Compound 177

Step A: 1-((3-((tert-butyldimethylsilyl)oxy)cyclobutyl)methyl)-2-((4-(2-(4-chloro-2-fluorophenyl)-2-methylbenzo[d][1,3]dioxol-4-yl)piperidin-1-yl)methyl)-1H-imidazole-5-carbaldehyde

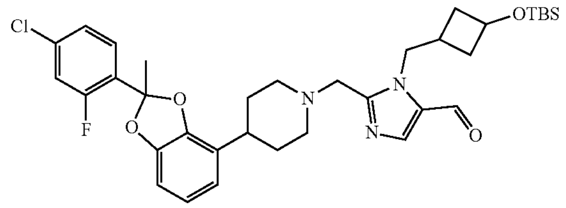 [SMILES: CC1(c2ccc(Cl)cc2F)Oc2cccc(C3CCN(Cc4ncc(C=O)n4CC4CC(O[Si](C)(C)C(C)(C)C)C4)CC3)c2O1]

To a solution of 2-((4-(2-(4-chloro-2-fluorophenyl)-2-methylbenzo[d][1,3]dioxol-4-yl)piperidin-1-yl)methyl)-1-((3-hydroxycyclobutyl)methyl)-1H-imidazole-5-carbaldehyde (70.0 mg, 0.130 mmol, synthesized following the route of example 1, step E and step F, using (3-hydroxycyclobutyl) methanaminium chloride) in DMF (4 mL) were added TBSCl (196 mg, 1.30 mmol) and imidazole (133 mg, 1.95 mmol). The resulting mixture was stirred at room temperature for 16 hours. The reaction mixture was diluted with water (30 mL) and extracted with EtOAc (30 mL*3). The organic layers were washed with brine (60 mL), dried over $Na_2SO_4$, filtered, concentrated and purified by silica gel chromatography (DCM:DCM/MeOH (10/1)=3:1) to give 1-((3-((tert-butyldimethylsilyl)oxy)cyclobutyl)methyl)-2-((4-(2-(4-chloro-2-fluorophenyl)-2-methylbenzo[d][1,3]dioxol-4-yl)piperidin-1-yl)methyl)-1H-imidazole-5-carbaldehyde as a yellow gum (70.0 mg, 82% yield). LC-MS: m/z 654.2 $(M+H)^+$ Step B: (E)-3-(2-((4-(2-(4-chloro-2-fluorophenyl)-2-methylbenzo[d][1,3]dioxol-4-yl)piperidin-1-yl)methyl)-1-((3-hydroxycyclobutyl)methyl)-1H-imidazol-5-yl)acrylic acid (Compound 177)

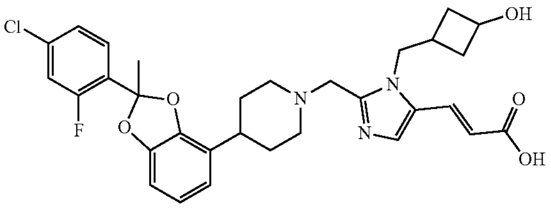 [SMILES: CC1(c2ccc(Cl)cc2F)Oc2cccc(C3CCN(Cc4ncc(/C=C/C(=O)O)n4CC4CC(O)C4)CC3)c2O1]

To a solution of 1-((3-((tert-butyldimethylsilyl)oxy)cyclobutyl)methyl)-2-((4-(2-(4-chloro-2-fluorophenyl)-2-methylbenzo[d][1,3]dioxol-4-yl)piperidin-1-yl)methyl)-1H-imidazole-5-carbaldehyde (70.0 mg, 0.110 mmol) in THF (5.5 mL) was added NaH (60% in oil, 9.00 mg, 0.210 mmol) at 0° C. and the reaction mixture was stirred at 0° C. for 30 minutes. A solution of ethyl 2-(diethoxyphosphoryl)acetate (48.0 mg, 0.0210 mmol) in THF (3 mL) was added into the mixture. The mixture was stirred at room temperature for 1 hour. To the resulting reaction mixture were added EtOH (4 mL), $H_2O$ (4 mL), and $LiOH{\cdot}H_2O$ (11.0 mg, 0.440 mmol). The reaction mixture was stirred at 30° C. for 16 hours. The reaction solution was adjusted to pH to 5-6 with 1 M formic acid aqueous solution. The mixture was extracted with EtOAc (10 mL*3). The organic phase was dried over $Na_2SO_4$, concentrated and purified with prep-HPLC (0.1% formic acid in water and acetonitrile) to give (E)-3-(2-((4-(2-(4-chloro-2-fluorophenyl)-2-methylbenzo[d][1,3]dioxol-4-yl)piperidin-1-yl)methyl)-1-((3-hydroxycyclobutyl)methyl)-1H-imidazol-5-yl)acrylic acid as a white solid (14.8 mg, 23% yield). $^1H$ NMR (400 MHz, $CD_3OD$) δ 7.51-7.60 (m, 2H), 7.49 (s, 1H), 7.28 (dd, J=10.8, 2.0 Hz, 1H), 7.21 (dd, J=8.4, 2.0 Hz, 1H), 6.74-6.80 (m, 1H), 6.66-6.73 (m, 2H), 6.37 (d, J=16.0 Hz, 1H), 4.30 (d, J=6.4 Hz, 2H), 3.92-4.08 (m, 1H), 3.78 (s, 2H), 3.02-3.08 (m, 2H), 2.68-2.77 (m, 1H), 2.30-2.43 (m, 4H), 2.11-2.25 (m, 1H), 2.03 (s, 3H), 1.78-1.97 (m, 4H), 1.69-1.72 (m, 2H). LC-MS: m/z 582.1 $(M+H)^+$.

Example 25

(E)-3-(2-((4-(2-(4-chloro-2-fluorophenyl)-2-methylbenzo[d][1,3]dioxol-4-yl)piperidin-1-yl)methyl)-1-(3-hydroxycyclobutyl)-1H-imidazol-5-yl)acrylic acid (Compound 178)

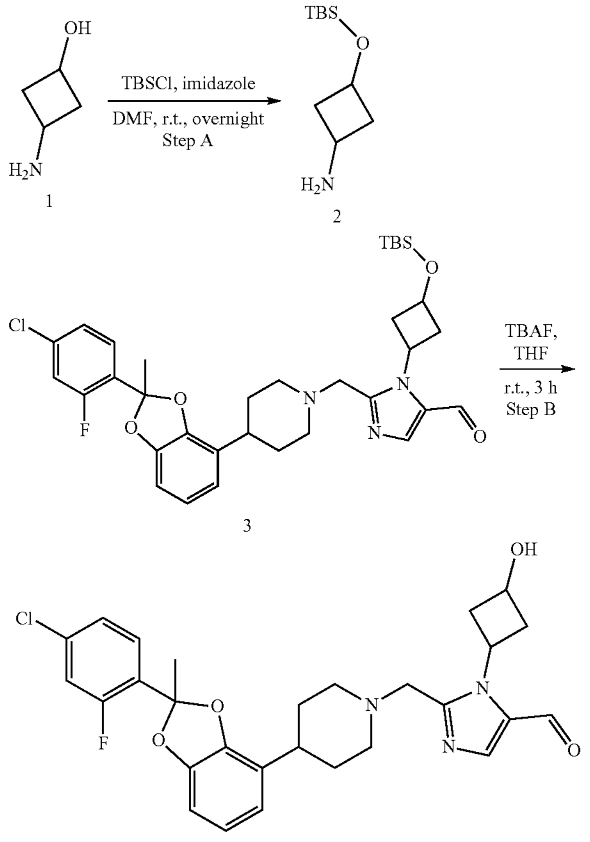

Step A: 3-((tert-butyldimethylsilyl)oxy)cyclobutanamine

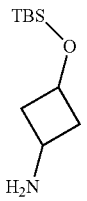

A solution of 3-aminocyclobutanol (400 mg, 4.60 mmol), TBSCl (695 mg, 4.60 mmol) and imidazole (469 mg, 6.90 mmol) at DMF (4 mL) was stirred at room temperature overnight. The reaction mixture was diluted with water (10 mL), and extracted with EtOAc (10 mL*3). The organic layers were washed with brine, dried over $Na_2SO_4$, and concentrated to give 3-((tert-butyldimethylsilyl)oxy)cyclobutanamine as an oil (800 mg, crude). $^1H$ NMR (400 MHz, $CDCl_3$) δ 3.85-3.96 (m, 1H), 2.95-3.06 (m, 1H), 2.58-2.71 (m, 2H), 1.75-1.87 (m, 2H), 0.84 (s, 9H), 0.00 (s, 6H). LC-MS: m/z 202.1 $(M+H)^+$.

Step B: 2-((4-(2-(4-chloro-2-fluorophenyl)-2-methylbenzo[d][1,3]dioxol-4-yl)piperidin-1-yl)methyl)-1-(3-hydroxycyclobutyl)-1H-imidazole-5-carbaldehyde

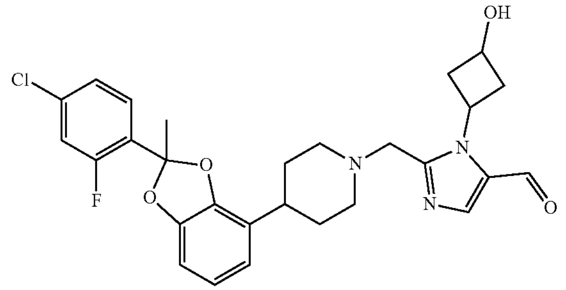 [SMILES: CC1(c2ccc(Cl)cc2F)Oc2cccc(C3CCN(Cc4ncc(C=O)n4C4CC(O)C4)CC3)c2O1]

To a solution of 1-(3-((tert-butyldimethylsilyl)oxy)cyclobutyl)-2-((4-(2-(4-chloro-2-fluorophenyl)-2-methylbenzo[d][1,3]dioxol-4-yl)piperidin-1-yl)methyl)-1H-imidazole-5-carbaldehyde (120 mg, 0.190 mmol, synthesized following the route of Example 12, step B and step C, using 3-((tert-butyldimethylsilyl)oxy)cyclobutanamine in step B) in THF (2 mL) was added TBAF in THF (1 M, 0.23 mL). The reaction mixture was stirred at room temperature for 3 hours. Then the reaction mixture was concentrated, and purified by Prep-HPLC (0.1% $NH_4HCO_3$ in water and acetonitrile) give 2-((4-(2-(4-chloro-2-fluorophenyl)-2-methylbenzo[d][1,3]dioxol-4-yl)piperidin-1-yl)methyl)-1-(3-hydroxycyclobutyl)-1H-imidazole-5-carbaldehyde as a white solid (4.00 mg, 4% yield). LC-MS: m/z 526.1 $(M+H)^+$.

(E)-3-(2-((4-(2-(4-chloro-2-fluorophenyl)-2-methylbenzo[d][1,3]dioxol-4-yl)piperidin-1-yl)methyl)-1-(3-hydroxycyclobutyl)-1H-imidazol-5-yl)acrylic acid (Compound 178)

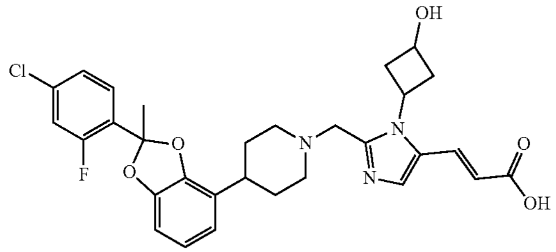 [SMILES: CC1(c2ccc(Cl)cc2F)Oc2cccc(C3CCN(Cc4ncc(/C=C/C(=O)O)n4C4CC(O)C4)CC3)c2O1]

Compound 178 was then syntheszied following the route of Example 1, using 2-((4-(2-(4-chloro-2-fluorophenyl)-2-methylbenzo[d][1,3]dioxol-4-yl)piperidin-1-yl)methyl)-1-(3-hydroxycyclobutyl)-1H-imidazole-5-carbaldehyde in step I.

$^1$H NMR (400 MHz, DMSO-$d_6$) δ 12.45 (br.s, 1H), 7.61 (d, J=15.6 Hz, 1H), 7.52-7.58 (m, 2H), 7.47 (s, 1H), 7.34 (dd, J=8.4, 1.6 Hz, 1H), 6.76-6.83 (m, 2H), 6.71-6.75 (m, 1H), 6.28 (d, J=15.6 Hz, 1H), 5.16-5.46 (m, 2H), 4.45 (t, J=7.2 Hz, 1H), 3.59 (s, 2H), 2.72-2.86 (m, 4H), 2.58-2.66 (m, 1H), 2.41-2.48 (m, 2H), 2.04-2.14 (m, 2H), 2.02 (s, 3H), 1.61-1.79 (m, 4H). LC-MS: m/z 568.2 $(M+H)^+$.

Example 26

(E)-3-(2-((4-(2-(4-chloro-2-fluorophenyl)-2-methylbenzo[d][1,3]dioxol-4-yl)piperazin-1-yl)methyl)-1-(((S)-oxetan-2-yl)methyl)-1H-imidazol-5-yl)acrylic acid (Compound 179)

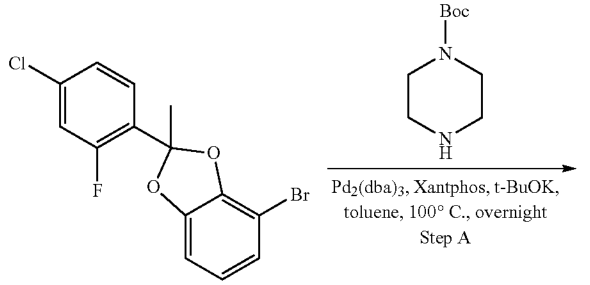

1

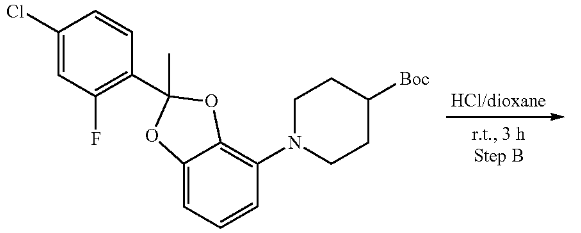

2

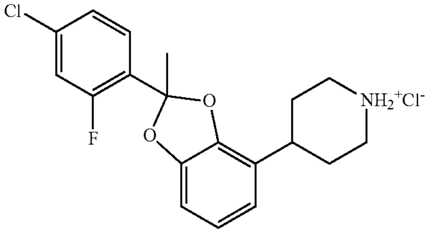

3

Step A: tert-butyl 4-(2-(4-chloro-2-fluorophenyl)-2-methylbenzo[d][1,3]dioxol-4-yl)piperazine-1-carboxylate

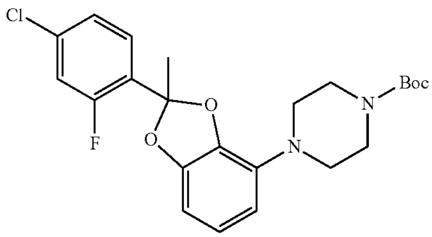 [SMILES: CC(C)(C)OC(=O)N1CCN(c2cccc3c2OC(C)(c2ccc(Cl)cc2F)O3)CC1]

To a solution of 4-bromo-2-(4-chloro-2-fluorophenyl)-2-methylbenzo[d][1,3]dioxole (100 mg, 0.290 mmol), and tert-butyl piperazine-1-carboxylate (54.2 mg, 0.290 mmol) in toluene (5 mL) were added t-BuOK (32.5 mg, 0.290 mmol), $Pd_2(dba)_3$ (13.3 mg, 0.150 mmol) and Xantphos (25.5 mg, 0.150 mmol). The reaction mixture was degassed and purged with $N_2$ for 3 times. Then the reaction mixture was stirred at 100° C. overnight under $N_2$ atmosphere. The reaction mixture was diluted with $H_2O$ (50 mL), and extracted with EtOAc (50 mL*3). The organic layer was dried over $Na_2SO_4$, concentrated in vacuo and purified by flash chromatography (DCM/MeOH=20/1) give tert-butyl 4-(2-(4-chloro-2-fluorophenyl)-2-methylbenzo[d][1,3]dioxol-4-yl)piperazine-1-carboxylate as a light yellow solid (28.0 mg, 22% yield). LC-MS: m/z 449.1 $(M+H)^+$, 393.1 $(M-56)^+$.

Step B: 1-(2-(4-chloro-2-fluorophenyl)-2-methylbenzo[d][1,3]dioxol-4-yl)piperazine

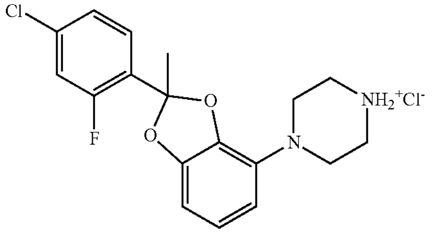

A solution of tert-butyl 4-(2-(4-chloro-2-fluorophenyl)-2-methylbenzo[d][1,3]dioxol-4-yl)piperazine-1-carboxylate (170 mg, 0.380 mmol) in 4 N HCl solution in dioxane (3 mL) was stirred at room temperature for 3 hours. The reaction mixture was concentrated in vacuo to give 1-(2-(4-chloro-2-fluorophenyl)-2-methylbenzo[d][1,3]dioxol-4-yl) piperazine HCl salt as a white solid (crude, 170 mg, over 100% yield). LC-MS: m/z 349.2 $(M+H)^+$.

(E)-3-(2-((4-(2-(4-chloro-2-fluorophenyl)-2-methylbenzo[d][1,3]dioxol-4-yl)piperazin-1-yl)methyl)-1-(((S)-oxetan-2-yl)methyl)-1H-imidazol-5-yl)acrylic acid (Compound 179)

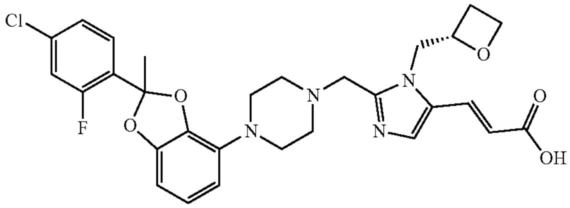 [SMILES: CC1(c2ccc(Cl)cc2F)Oc2cccc(N3CCN(Cc4ncc(/C=C/C(=O)O)n4C[C@@H]4CCO4)CC3)c2O1]

Compound 179 was then synthesized following the route of Example 1, using 1-(2-(4-chloro-2-fluorophenyl)-2-methylbenzo[d][1,3]dioxol-4-yl)piperazine HCl salt in step F.

$^1$H NMR (400 MHz, $CDCl_3$) δ 7.61 (d, J=15.6 Hz, 1H), 7.48-7.53 (m, 2H), 7.08-7.13 (m, 2H), 6.75 (t, J=8.0 Hz, 1H), 6.51 (d, J=8.0 Hz, 1H), 6.38 (d, J=8.4 Hz, 1H), 6.30 (d, J=16.0 Hz, 1H), 5.07-5.08 (m, 1H), 4.40-4.64 (m, 4H), 3.84 (s, 2H), 3.18-3.24 (m, 4H), 2.71 (br.m, 5H), 2.34-2.47 (m, 1H), 2.05 (s, 3H). LC-MS: m/z 569.0 $(M+H)^+$, (E)-3-(2-(((2 S)-4-(2-(4-chloro-2-fluorophenyl)-2-methylbenzo[d][1,3]dioxol-4-yl)-2-methylpiperazin-1-yl)methyl)-1-(((S)-oxetan-2-yl)methyl)-1H-imidazol-5-yl)acrylic acid (Compound 180) was synthesized following the route of Example 26, using tert-butyl (S)-2-methylpiperazine-1-carboxylate in step A.

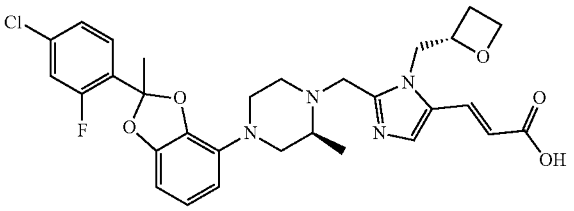 [SMILES: C[C@H]1CN(c2cccc3c2OC(C)(c2ccc(Cl)cc2F)O3)CCN1Cc1ncc(/C=C/C(=O)O)n1C[C@@H]1CCO1]

$^1$H NMR (400 MHz, DMSO-$d_6$) δ 7.42-7.61 (m, 4H), 7.32-7.36 (m, 1H), 6.74 (t, J=8.0 Hz, 1H), 6.54 (d, J=8.0 Hz, 1H), 6.37-6.45 (m, 1H), 6.29 (d, J=16.0 Hz, 1H), 4.98-5.04 (m, 1H), 4.39-4.57 (m, 3H), 4.22-4.28 (m, 1H), 4.08-4.16 (m, 1H), 3.32-3.42 (m, 3H), 2.73-2.85 (m, 1H), 2.63-2.67 (m, 4H), 2.30-2.33 (m, 2H), 2.01 (s, 3H), 1.07-1.13 (m, 3H). LC-MS: m/z 583.1 $(M+H)^+$.

Example 27

(E)-3-(2-((4-(2-(4-chloro-2-fluorophenyl)-2-methylbenzo[d][1,3]dioxol-4-yl)piperidin-1-yl)methyl)-1-(isoxazol-5-ylmethyl)-1H-imidazol-5-yl)acrylic acid (Compound 181) and (E)-3-(2-((4-(2-(4-chloro-2-fluorophenyl)-2-methylbenzo[d][1,3]dioxol-4-yl)piperidin-1-yl)methyl)-1-(isoxazol-5-ylmethyl)-1H-imidazol-4-yl)acrylic acid (Compound 182)

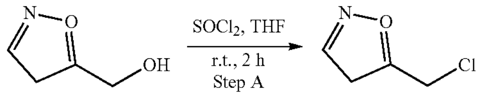

1 2

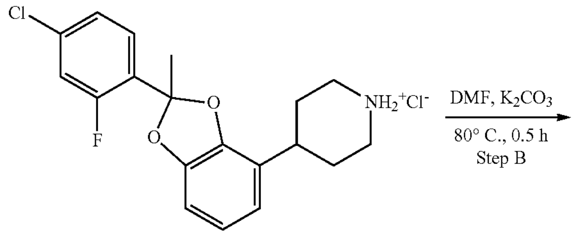

3

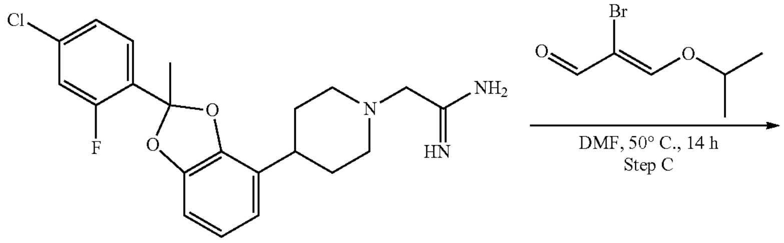

4

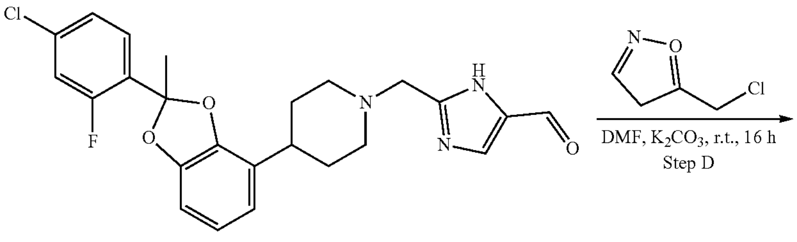

5

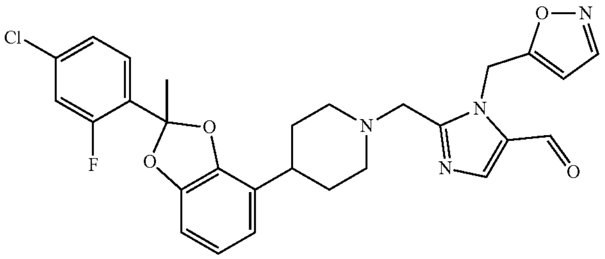

6

-continued

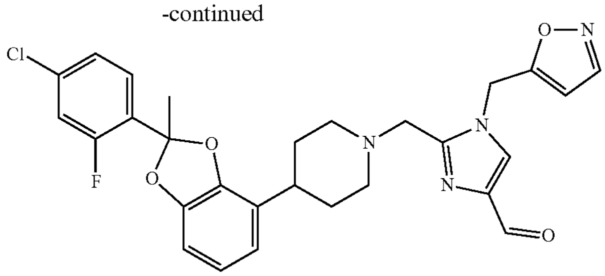

7

Step A: 5-(chloromethyl)isoxazole

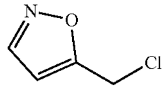

To a solution of isoxazol-5-ylmethanol (60.0 mg, 0.606 mmol) in THF (2 mL) was added thionyl chloride (144 mg, 1.21 mmol) at room temperature. The reaction mixture was stirred at room temperature for 2 hours. The solvent and thionyl chloride were removed in vacuo to give 5-(chloromethyl)isoxazole (71.0 mg, crude), which was used in the next step without further purification.

Step B: 2-(4-(2-(4-chloro-2-fluorophenyl)-2-methylbenzo[d][1,3]dioxol-4-yl)piperidin-1-yl)acetimidamide

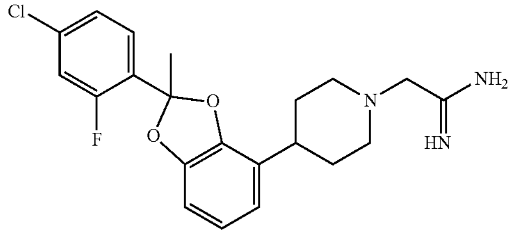 [SMILES: CC1(c2ccc(Cl)cc2F)Oc2cccc(C3CCN(CC(=N)N)CC3)c2O1]

To a solution of 4-(2-(4-chloro-2-fluorophenyl)-2-methylbenzo[d][1,3]dioxol-4-yl)piperidin-1-ium chloride (1.00 g, 2.60 mmol) and 2-chloroacetamidine hydrochloride (400 mg, 3.10 mmol) in DMF (10 mL) was added $K_2CO_3$ (1.08 g, 7.81 mmol). The resulting mixture was stirred at 80° C. for 0.5 hour. The resulted mixture was used in next step directly. LC-MS: m/z 403.8 $(M+H)^+$.

Step C: 2-((4-(2-(4-chloro-2-fluorophenyl)-2-methylbenzo[d][1,3]dioxol-4-yl)piperidin-1-yl)methyl)-1H-imidazole-5-carbaldehyde

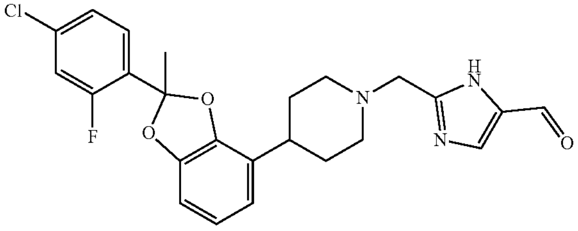 [SMILES: CC1(c2ccc(Cl)cc2F)Oc2cccc(C3CCN(Cc4ncc(C=O)[nH]4)CC3)c2O1]

The above mixture was cooled to room temperature, and then freshly prepared (Z)-2-bromo-3-isopropoxy-prop-2-enal (652 mg, 3.38 mmol) was added. The reaction mixture was stirred at 50° C. for 14 hours. The reaction mixture was diluted with water (20 mL) and extracted with EtOAc (30 mL*3). The combined organic phase was dried over anhydrous $Na_2SO_4$, filtered and concentrated. The residue was purified by flash chromatography (DCM/MeOH=20/1) to give 2-((4-(2-(4-chloro-2-fluorophenyl)-2-methylbenzo[d][1,3]dioxol-4-yl)piperidin-1-yl)methyl)-1H-imidazole-5-carbaldehyde (720 mg, 60% yield) as a yellow solid. LC-MS: m/z 456.1 $(M+H)^+$.

Step D: 2-((4-(2-(4-chloro-2-fluorophenyl)-2-methylbenzo[d][1,3]dioxol-4-yl)piperidin-1-yl)methyl)-1-(isoxazol-5-ylmethyl)-1H-imidazole-5-carbaldehyde and 2-((4-(2-(4-chloro-2-fluorophenyl)-2-methylbenzo[d][1,3]dioxol-4-yl)piperidin-1-yl)methyl)-1-(isoxazol-5-ylmethyl)-1H-imidazole-4-carbaldehyde

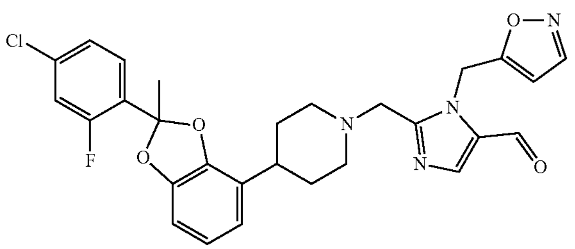

-continued

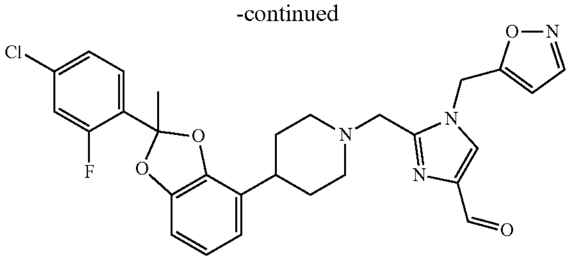

To a solution of 2-((4-(2-(4-chloro-2-fluorophenyl)-2-methylbenzo[d][1,3]dioxol-4-yl)piperidin-1-yl)methyl)-1H-imidazole-5-carbaldehyde (190 mg, 0.417 mmol) in DMF (2 mL) were added $K_2CO_3$ (130 mg, 0.927 mmol) and 5-(chloromethyl)isoxazole (crude, 71.0 mg, 0.606 mmol). The reaction mixture was stirred at room temperature for 16 hours. Then the reaction mixture was diluted with water (10 mL) and extracted with EtOAc (10 mL*3). The combined organic phase was washed with brine (10 mL), dried over anhydrous $Na_2SO_4$ and concentrated. The residue was purified by prep-HPLC (0.1% $NH_4HCO_3$ in water and acetonitrile) to give 2-((4-(2-(4-chloro-2-fluorophenyl)-2-methylbenzo[d][1,3]dioxol-4-yl)piperidin-1-yl)methyl)-1-(isoxazol-5-ylmethyl)-1H-imidazole-5-carbaldehyde (6) as a white solid (33.0 mg, 15% yield) and 2-((4-(2-(4-chloro-2-fluorophenyl)-2-methylbenzo[d][1,3]dioxol-4-yl)piperidin-1-yl)methyl)-1-(isoxazol-5-ylmethyl)-1H-imidazole-4-carbaldehyde (7) as a white solid (44.0 mg, 20% yield).

(6) $^1$H NMR (400 MHz, $CDCl_3$) δ 9.72 (s, 1H), 8.19 (d, J=0.8 Hz, 1H), 7.74 (s, 1H), 7.46-7.56 (m, 1H), 7.08-7.16 (m, 2H), 6.63-6.83 (m, 3H), 6.24 (s, 1H), 6.06 (s, 2H), 3.86 (s, 2H), 2.88-3.01 (m, 2H), 2.63-2.77 (m, 1H), 2.28 (t, J=12.0 Hz, 2H), 2.05 (s, 3H), 1.70-1.88 (m, 4H);

(7) $^1$H NMR (400 MHz, $CDCl_3$) δ 9.85 (s, 1H), 8.24 (d, J=1.2 Hz, 1H), 7.70 (s, 1H), 7.50 (t, J=8.4 Hz, 1H), 7.10-7.15 (m, 2H), 6.62-6.81 (m, 3H), 6.19 (s, 1H), 5.66 (s, 2H), 3.74 (s, 2H), 2.82-3.00 (m, 2H), 2.69 (t, J=12.0 Hz, 1H), 2.25 (t, J=10.8 Hz, 2H), 2.05 (s, 3H), 1.67-1.89 (m, 4H).

(E)-3-(2-((4-(2-(4-chloro-2-fluorophenyl)-2-methylbenzo[d][1,3]dioxol-4-yl)piperidin-1-yl)methyl)-1-(isoxazol-5-ylmethyl)-1H-imidazol-5-yl)acrylic acid (Compound 181)

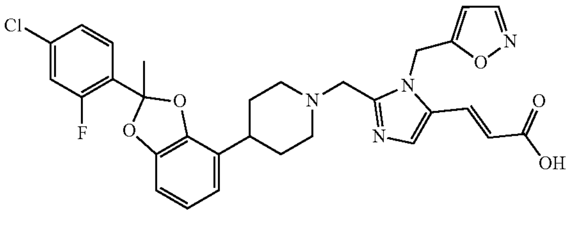 [SMILES: CC1(c2ccc(Cl)cc2F)Oc2cccc(C3CCN(Cc4ncc(/C=C/C(=O)O)n4Cc4ccno4)CC3)c2O1]

Compound 181 was then synthesized following the route of Example 1, using 2-((4-(2-(4-chloro-2-fluorophenyl)-2-methylbenzo[d][1,3]dioxol-4-yl)piperidin-1-yl)methyl)-1-(isoxazol-5-ylmethyl)-1H-imidazole-5-carbaldehyde in step I.

$^1$H NMR (400 MHz, DMSO-$d_6$) δ 12.30 (br.s, 1H), 7.51-7.61 (m, 4H), 7.44 (d, J=15.6 Hz, 1H), 7.33 (dd, J=8.4, 2.0 Hz, 1H), 6.77-6.81 (m, 2H), 6.72-6.76 (m, 2H), 6.36 (d, J=16.0 Hz, 1H), 4.97 (s, 2H), 3.87 (s, 2H), 2.87-3.15 (m, 3H), 2.70-2.81 (m, 1H), 2.03 (s, 3H), 1.99-2.01 (m, 1H), 1.71-1.82 (m, 4H). LC-MS: m/z 579.2 (M+H)$^+$.

(E)-3-(2-((4-(2-(4-chloro-2-fluorophenyl)-2-methylbenzo[d][1,3]dioxol-4-yl)piperidin-1-yl)methyl)-1-(isoxazol-5-ylmethyl)-1H-imidazol-4-yl)acrylic acid (Compound 182)

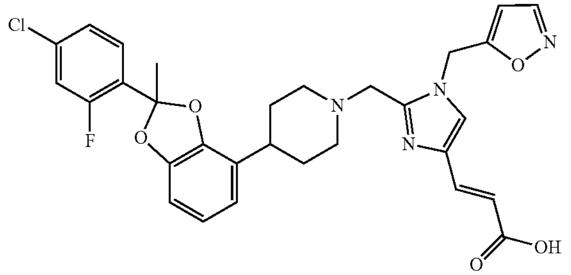 [SMILES: CC1(c2ccc(Cl)cc2F)Oc2cccc(C3CCN(Cc4nc(/C=C/C(=O)O)cn4Cc4ccno4)CC3)c2O1]

Compound 182 was then synthesized following the route of Example 1, using 2-((4-(2-(4-chloro-2-fluorophenyl)-2-methylbenzo[d][1,3]dioxol-4-yl)piperidin-1-yl)methyl)-1-(isoxazol-5-ylmethyl)-1H-imidazole-4-carbaldehyde in step I.

$^1$H NMR (400 MHz, DMSO-$d_6$) δ 12.07 (br.s, 1H), 7.52-7.62 (m, 4H), 7.42 (d, J=15.2 Hz, 1H), 7.33 (dd, J=8.4, 2.0 Hz, 1H), 6.80 (d, J=5.2 Hz, 2H), 6.72-6.77 (m, 2H), 6.28 (d, J=15.6 Hz, 1H), 4.85 (s, 2H), 3.88 (s, 2H), 2.97-3.15 (m, 3H), 2.72-2.80 (m, 1H), 1.98-2.05 (m, 4H), 1.71-1.85 (m, 4H). LC-MS: m/z 579.2 (M+H)$^+$.

(E)-3-(2-((4-(2-(4-chloro-2-fluorophenyl)-2-methylbenzo[d][1,3]dioxol-4-yl)piperidin-1-yl)methyl)-1-(oxazol-2-ylmethyl)-1H-imidazol-5-yl)acrylic acid (Compound 183) was synthesized following the route of Example 27, using 2-(chloromethyl)oxazole in step D.

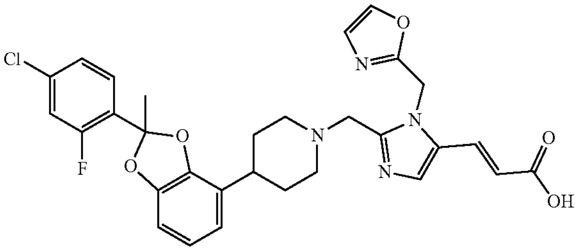 [SMILES: CC1(c2ccc(Cl)cc2F)Oc2cccc(C3CCN(Cc4ncc(/C=C/C(=O)O)n4Cc4ncco4)CC3)c2O1]

$^1$H NMR (400 MHz, DMSO-$d_6$) δ 8.09 (d, J=0.4 Hz, 1H), 7.52-7.56 (m, 3H), 7.46 (d, J=15.6 Hz, 1H), 7.34 (dd, J=8.4, 1.6 Hz, 1H), 7.18 (d, J=0.4 Hz, 1H), 6.75-6.81 (m, 2H), 6.63 (dd, J=6.8, 2.0 Hz, 1H), 6.32 (d, J=15.6 Hz, 1H), 5.65 (s, 2H), 3.64 (s, 2H), 2.77 (t, J=9.6 Hz, 2H), 2.55-2.59 (m, 1H), 1.99-2.05 (m, 5H), 1.60 (t, J=13.6 Hz, 2H), 1.27-1.42 (m, 2H). LC-MS: m/z 579.2 (M+H)$^+$.

(E)-3-(2-((4-(2-(4-chloro-2-fluorophenyl)-2-methylbenzo[d][1,3]dioxol-4-yl)piperidin-1-yl)methyl)-1-((4-ethyloxazol-5-yl)methyl)-1H-imidazol-5-yl)acrylic acid (Compound 184) was synthesized following the route of Example 27, using (4-ethyloxazol-5-yl)methanol in step A.

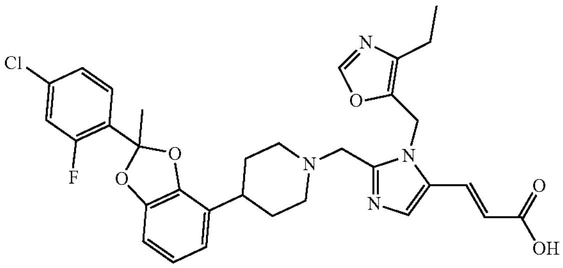 [SMILES: CCc1ncoc1Cn1c(/C=C/C(=O)O)cnc1CN1CCC(c2cccc3c2OC(C)(c2ccc(Cl)cc2F)O3)CC1]

$^1$HNMR (400 MHz, DMSO-$d_6$) δ 12.29 (br.s, 1H), 8.20 (s, 1H), 7.46-7.61 (m, 4H), 7.34 (dd, J=8.4, 2.0 Hz, 1H), 6.76-6.81 (m, 2H), 6.68-6.74 (m, 1H), 6.29 (d, J=16.0 Hz, 1H), 5.63 (s, 2H), 3.67 (s, 2H), 2.82-2.90 (m, 2H), 2.55-2.59 (m, 3H), 2.10 (t, J=10.8 Hz, 2H), 2.02 (s, 3H), 1.56-1.76 (m, 4H), 1.14 (t, J=7.2 Hz, 3H). LC-MS: m/z 606.8 (M+H)$^+$.

(E)-3-(2-((4-(2-(4-chloro-2-fluorophenyl)-2-methylbenzo[d][1,3]dioxol-4-yl)piperidin-1-yl)methyl)-1-(2-hydroxybutyl)-1H-imidazol-5-yl)acrylic acid (Compound 185) was synthesized following the route of Example 27, using 1-bromobutan-2-ol in step D.

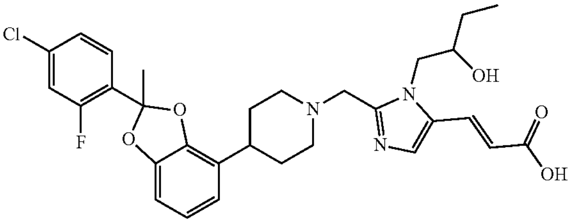 [SMILES: CCC(O)Cn1c(/C=C/C(=O)O)cnc1CN1CCC(c2cccc3c2OC(C)(c2ccc(Cl)cc2F)O3)CC1]

$^1$H NMR (400 MHz, DMSO-$d_6$) δ 7.44-7.66 (m, 3H), 7.34 (d, J=8.4 Hz, 1H), 6.58-6.88 (m, 4H), 6.29 (d, J=16.0 Hz, 1H), 5.34-4.92 (m, 1H), 4.12-4.32 (m, 1H), 3.78-4.05 (m, 1H), 3.51-3.77 (m, 3H), 2.89-2.93 (m, 2H), 2.61-2.67 (m, 1H), 2.04-2.18 (m, 2H), 2.01 (s, 3H), 1.64-1.77 (m, 4H), 1.33-1.62 (m, 2H), 0.88-1.33 (m, 3H). LC-MS: m/z 570.1 (M+H)$^+$.

(R,E)-3-(2-((4-(2-(4-chlorophenyl)-2,3-dihydrobenzo[b][1,4]dioxin-5-yl)piperidin-1-yl)methyl)-1-(oxazol-2-ylmethyl)-1H-imidazol-5-yl)acrylic acid (Compound 186a) was synthesized following the route of Example 27, using (R)-2-((4-(2-(4-chlorophenyl)-2,3-dihydrobenzo[b][1,4]dioxin-5-yl)piperidin-1-yl)methyl)-1H-imidazole-5-carbaldehyde and 2-(chloromethyl)oxazole in step D.

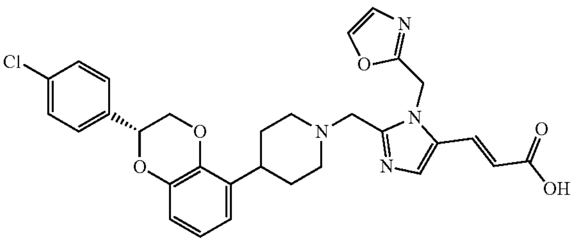 [SMILES: O=C(O)/C=C/c1cnc(CN2CCC(c3cccc4c3OC[C@@H](c3ccc(Cl)cc3)O4)CC2)n1Cc1ncco1]

$^1$H NMR (400 MHz, DMSO-$d_6$) δ 8.13 (d, J=0.4 Hz, 1H), 7.51 (s, 1H), 7.45-7.50 (m, 4H), 7.43 (d, J=16.0 Hz, 1H), 7.20 (d, J=0.4 Hz, 1H), 6.78-6.86 (m, 2H), 6.66 (dd, J=6.8, 2.0 Hz, 1H), 6.32 (d, J=16.0 Hz, 1H), 5.64 (s, 2H), 5.22 (dd, J=8.4, 2.4 Hz, 1H), 4.47 (dd, J=11.2, 2.0 Hz, 1H), 4.02 (dd, J=10.8, 8.4 Hz, 1H), 3.63 (s, 2H), 2.67-2.80 (m, 3H), 1.99 (t, J=8.8 Hz, 2H), 1.55 (dd, J=23.2, 12.4 Hz, 2H), 1.16-1.34 (m, 2H). LC-MS: m/z 561.2 (M+H)$^+$.

(R,E)-3-(2-((4-(2-(4-chlorophenyl)-2,3-dihydrobenzo[b][1,4]dioxin-5-yl)piperidin-1-yl)methyl)-1-(isoxazol-5-ylmethyl)-1H-imidazol-5-yl)acrylic acid (Compound 187a) was synthesized following the route of Example 27, using (R)-2-((4-(2-(4-chlorophenyl)-2,3-dihydrobenzo[b][1,4]dioxin-5-yl)piperidin-1-yl)methyl)-1H-imidazole-5-carbaldehyde and 5-(chloromethyl)isoxazole in step D.

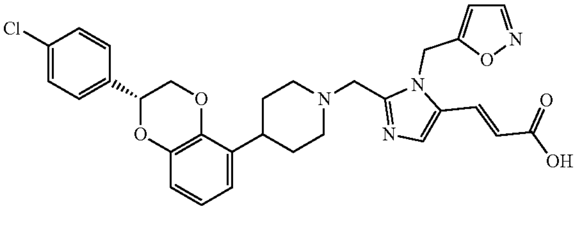 [SMILES: O=C(O)/C=C/c1cnc(CN2CCC(c3cccc4c3OC[C@@H](c3ccc(Cl)cc3)O4)CC2)n1Cc1ccno1]

$^1$H NMR (400 MHz, DMSO-$d_6$) δ 12.36 (br.s, 1H), 7.55 (s, 1H), 7.47-7.53 (m, 5H), 7.42 (d, J=15.6 Hz, 1H), 6.76-6.86 (m, 4H), 6.33 (d, J=15.6 Hz, 1H), 5.26 (dd, J=8.0, 2.0 Hz, 1H), 4.86 (s, 2H), 4.51 (dd, J=11.6, 2.4 Hz, 1H), 4.06 (dd, J=11.6, 8.4 Hz, 1H), 3.83 (s, 2H), 2.87-3.08 (m, 3H), 2.35-2.45 (m, 2H), 1.58-1.80 (m, 4H). LC-MS: m/z 561.2 (M+H)$^+$.

Example 28

(E)-3-(2-((4-(2-(4-chloro-2-fluorophenyl)-2-methylbenzo[d][1,3]dioxol-4-yl)piperidin-1-yl)methyl)-1-((4-ethylthiazol-5-yl)methyl)-1H-imidazol-5-yl)acrylic acid (Compound 188)

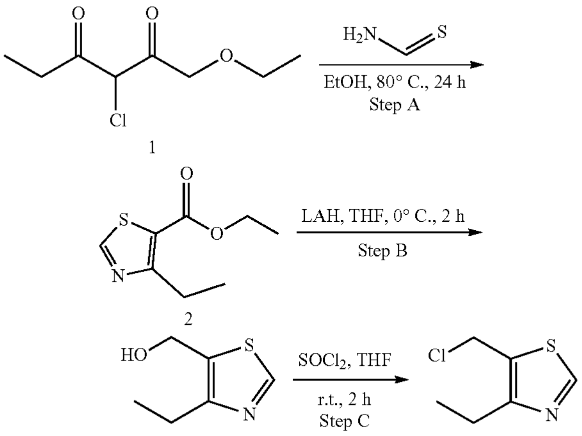

1 2 3 4

Step A: ethyl 4-ethylthiazole-5-carboxylate

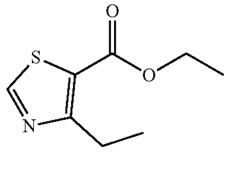

To a stirred solution of 3-chloro-1-ethoxyhexane-2,4-dione (1.00 g, 5.60 mmol) in EtOH (10 mL) under $N_2$ was added thioformamide (3.30 g, 55.6 mmol) at room temperature. The reaction mixture was heated at 80° C. for 24 hours. Then the solvent was removed in vacuo and the residue was purified by silica gel column chromatography (10% EtOAc/PE) to give ethyl 4-ethylthiazole-5-carboxylate as a yellow solid (715 mg, 69% yield). LC-MS: m/z 186.0 $(M+H)^+$.

Step B: (4-ethylthiazol-5-yl)methanol

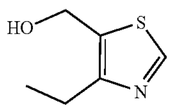

To a stirred solution of ethyl 4-ethylthiazole-5-carboxylate (350 mg, 1.89 mmol) in THF (3 mL) under $N_2$ was added lithium aluminium hydride (1 M in THF, 2.8 mL, 2.80 mmol) at 0° C. The reaction mixture was stirred at 0° C. for 2 hours. Then the reaction mixture was quenched with water (0.1 mL), 10% NaOH aqueous solution (0.1 mL) and water (0.3 mL), filtered through celite and washed with DCM (10 mL). The filtrate was washed with brine (5 mL), dried over $Na_2SO_4$, concentrated in vacuo and purified by column chromatography (DCM/MeOH=20/1) to give (4-ethylthiazol-5-yl)methanol as a yellow solid (180 mg, 66% yield). LC-MS: m/z 144.2 $(M+H)^+$.

Step C: 5-(chloromethyl)-4-ethylthiazole

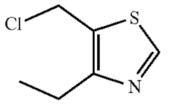

To a solution of (4-ethylthiazol-5-yl)methanol (40.0 mg, 0.278 mmol) in THF (2 mL) was added thionyl chloride (66.0 mg, 0.555 mmol) at room temperature. The reaction mixture was stirred at room temperature for 2 hours. The solvent and thionyl chloride was removed in vacuo to give 5-(chloromethyl)-4-ethylthiazole as a light yellow solid (45.0 mg, crude), which was used in next step without further purification.

(E)-3-(2-((4-(2-(4-chloro-2-fluorophenyl)-2-methylbenzo[d][1,3]dioxol-4-yl)piperidin-1-yl)methyl)-1-((4-ethylthiazol-5-yl)methyl)-1H-imidazol-5-yl) acrylic acid (Compound 188)

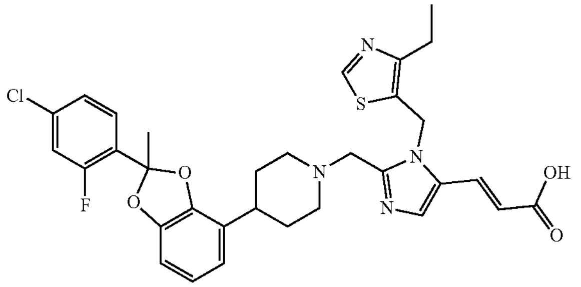 [SMILES: CCc1ncsc1Cn1c(/C=C/C(=O)O)cnc1CN1CCC(c2cccc3c2OC(C)(c2ccc(Cl)cc2F)O3)CC1]

Compound 188 was then synthesized following the route of Example 27, using 5-(chloromethyl)-4-ethylthiazole in step D.

$^1H$ NMR (400 MHz, DMSO-$d_6$) δ 12.11 (br.s, 1H), 8.84 (s, 1H), 7.50-7.60 (m, 3H), 7.29-7.40 (m, 2H), 6.73-6.82 (m, 2H), 6.59-6.69 (m, 1H), 6.28 (d, J=15.6 Hz, 1H), 5.66 (s, 2H), 3.63 (s, 2H), 2.85 (q, J=7.6 Hz, 4H), 2.54-2.59 (m, 1H), 1.98-2.10 (m, 5H), 1.48-1.69 (m, 4H), 1.27 (t, J=7.6 Hz, 3H). LC-MS: m/z 622.8 $(M+H)^+$.

(E)-3-(2-((4-(2-(4-chloro-2-fluorophenyl)-2-methylbenzo[d][1,3]dioxol-4-yl)piperidin-1-yl)methyl)-1-((4-methylthiazol-5-yl)methyl)-1H-imidazol-5-yl)acrylic acid (Compound 189) was synthesized following the route of Example 28, using ethyl 4-methylthiazole-5-carboxylate in step B.

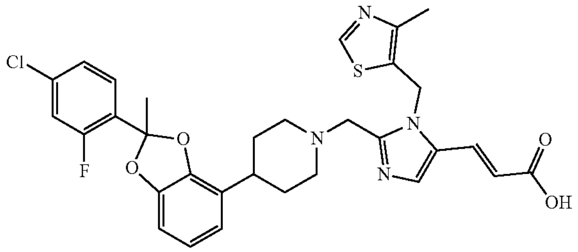 [SMILES: Cc1ncsc1Cn1c(/C=C/C(=O)O)cnc1CN1CCC(c2cccc3c2OC(C)(c2ccc(Cl)cc2F)O3)CC1]

$^1H$ NMR (400 MHz, DMSO-$d_6$) δ 12.27 (br.s, 1H), 8.84 (s, 1H), 7.52-7.56 (m, 3H), 7.31-7.41 (m, 2H), 6.74-6.82 (m, 2H), 6.62-6.69 (m, 1H), 6.28 (d, J=16.0 Hz, 1H), 5.63 (s, 2H), 3.63 (s, 2H), 2.85 (t, J=10.8 Hz, 2H), 2.55-2.62 (m, 1H), 2.49 (s, 3H), 2.04-2.09 (m, 2H), 2.02 (s, 3H), 1.48-1.69 (m, 4H). LC-MS: m/z 609.0 $(M+H)^+$.

Example 29

(E)-3-(2-((4-(2-(4-chloro-2-fluorophenyl)-2-methylbenzo[d][1,3]dioxol-4-yl)piperidin-1-yl)methyl)-1-((4-methyloxazol-5-yl)methyl)-1H-imidazol-5-yl) acrylic acid (Compound 190)

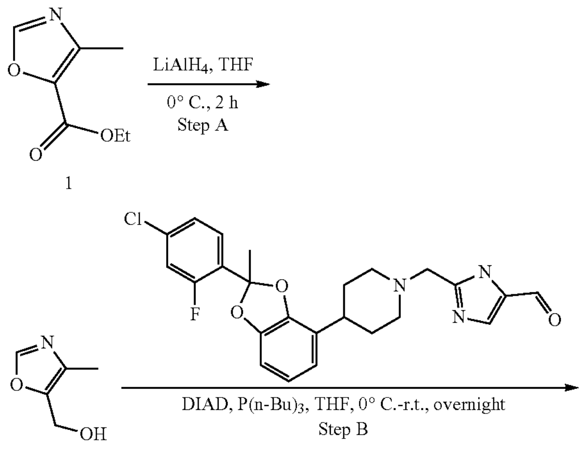

1

2

-continued

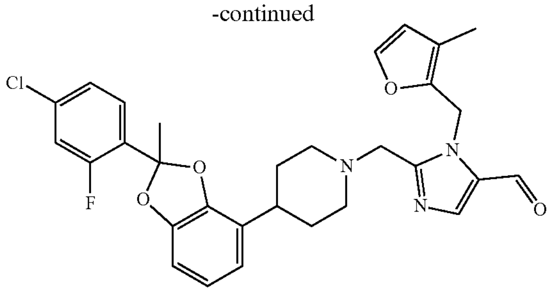

4

Step A: (4-methyloxazol-5-yl)methanol

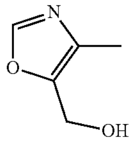

To a stirred solution of ethyl 4-methyloxazole-5-carboxylate (780 mg, 5.03 mmol) in THF (10 mL) under $N_2$ was added lithium aluminium hydride (1M in THF, 7.54 mL, 7.54 mmol) at 0° C. The mixture was stirred at 0° C. for 2 hours. The reaction mixture was quenched with saturated (0.3 mL), 10% NaOH solution (0.3 mL) and water (0.9 mL), filtered through celite and washed with DCM (15 mL). The filtrate was concentrated in vacuo and purified by column chromatography (DCM/MeOH=20/1) to give (4-methyloxazol-5-yl)methanol as a yellow solid (300 mg, 53% yield). LC-MS: m/z 114.2 $(M+H)^+$.

Step B: 2-((4-(2-(4-chloro-2-fluorophenyl)-2-methylbenzo[d][1,3]dioxol-4-yl)piperidin-1-yl)methyl)-1-((4-methyloxazol-5-yl)methyl)-1H-imidazole-5-carbaldehyde

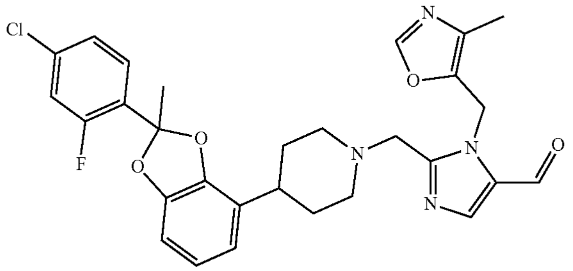 [SMILES: Cc1ncoc1Cn1c(C=O)cnc1CN1CCC(c2cccc3c2OC(C)(c2ccc(Cl)cc2F)O3)CC1]

To a solution of 2-((4-(2-(4-chloro-2-fluorophenyl)-2-methylbenzo[d][1,3]dioxol-4-yl)piperidin-1-yl)methyl)-1H-imidazole-5-carbaldehyde (80.0 mg, 0.175 mmol) in THF (1 mL), (4-methyloxazol-5-yl)methanol (24.0 mg, 0.212 mmol) and $P(n\text{-}Bu)_3$ (71.0 mg, 0.350 mmol) were added. The resulting mixture was stirred at 0° C. for 10 mins and DIAD (53.0 mg, 0.263 mmol) was added. The reaction mixture was stirred at room temperature overnight. The solvents were distilled off under reduced pressure and the residue was purified by perp-TLC to give 2-((4-(2-(4-chloro-2-fluorophenyl)-2-methylbenzo[d][1,3]dioxol-4-yl)piperidin-1-yl)methyl)-1-((4-methyloxazol-5-yl)methyl)-1H-imidazole-5-carbaldehyde as a yellow solid (45.0 mg, 47% yield). LC-MS: m/z 551.2 $(M+H)^+$.

(E)-3-(2-((4-(2-(4-chloro-2-fluorophenyl)-2-methylbenzo[d][1,3]dioxol-4-yl)piperidin-1-yl)methyl)-1-((4-methyloxazol-5-yl)methyl)-1H-imidazol-5-yl)acrylic acid (Compound 190)

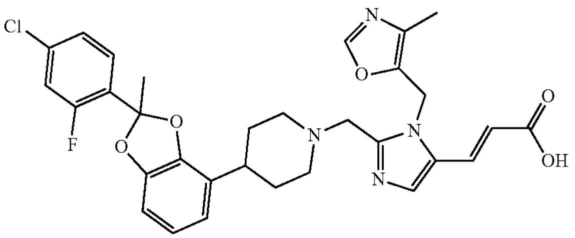 [SMILES: Cc1ncoc1Cn1c(/C=C/C(=O)O)cnc1CN1CCC(c2cccc3c2OC(C)(c2ccc(Cl)cc2F)O3)CC1]

Compound 190 was then synthesized following the route of Example 1, using 2-((4-(2-(4-chloro-2-fluorophenyl)-2-methylbenzo[d][1,3]dioxol-4-yl)piperidin-1-yl)methyl)-1-((4-methyloxazol-5-yl)methyl)-1H-imidazole-5-carbaldehyde in step I.

$^1$H NMR (400 MHz, DMSO-$d_6$) δ 12.08 (br.s, 1H), 8.19 (s, 1H), 7.47-7.58 (m, 4H), 7.34 (dd, J=8.4, 1.6 Hz, 1H), 6.76-6.80 (m, 2H), 6.68-6.74 (m, 1H), 6.29 (d, J=16.0 Hz, 1H), 5.61 (s, 2H), 3.66 (s, 2H), 2.80-2.91 (m, 2H), 2.62-2.68 (m, 1H), 2.16 (s, 3H), 2.06-2.13 (m, 2H), 2.02 (s, 3H), 1.59-1.73 (m, 4H). LC-MS: m/z 593.2 $(M+H)^+$.

(E)-3-(2-((4-(2-(4-chloro-2-fluorophenyl)-2-methylbenzo[d][1,3]dioxol-4-yl)piperidin-1-yl)methyl)-1-(2-cyclopropylethyl)-1H-imidazol-5-yl)acrylic acid (Compound 191) was synthesized following the route of Example 29, using 2-cyclopropylethan-1-ol in step B.

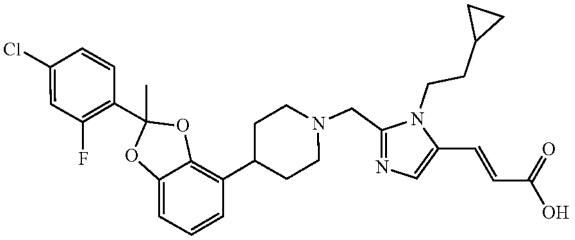 [SMILES: CC1(c2ccc(Cl)cc2F)Oc2cccc(C3CCN(Cc4ncc(/C=C/C(=O)O)n4CCC4CC4)CC3)c2O1]

$^1$H NMR (400 MHz, DMSO-$d_6$) δ 7.53-7.57 (m, 2H), 7.47 (s, 1H), 7.43 (d, J=15.6 Hz, 1H), 7.34 (dd, J=8.4, 2.0 Hz, 1H), 6.78 (d, J=4.8 Hz, 2H), 6.69-6.72 (m, 1H), 6.28 (d, J=15.6 Hz, 1H), 4.20 (t, J=7.2 Hz, 2H), 3.60 (s, 2H), 2.85-2.87 (m, 2H), 2.60-2.62 (m, 1H), 2.06-2.11 (m, 2H), 2.02 (s, 3H), 1.57-1.72 (m, 6H), 0.69-0.73 (m, 1H), 0.39 (d, J=6.4 Hz, 2H), −0.01-0.05 (m, 2H). LC-MS: m/z 565.9 $(M+H)^+$.

(E)-3-(2-((4-(2-(4-chloro-2-fluorophenyl)-2-methylbenzo[d][1,3]dioxol-4-yl)piperidin-1-yl)methyl)-1-((1-cyanocyclopropyl)methyl)-1H-imidazol-5-yl)acrylic acid (Compound 192) was synthesized following the route of Example 29, using 1-(hydroxymethyl)cyclopropane-1-carbonitrile in step B.

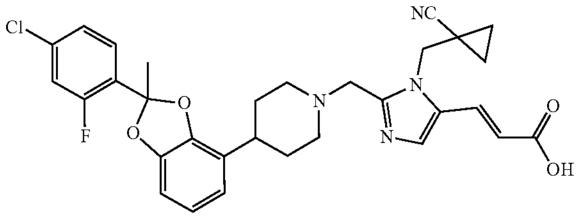 [SMILES: CC1(c2ccc(Cl)cc2F)Oc2cccc(C3CCN(Cc4ncc(/C=C/C(=O)O)n4CC4(C#N)CC4)CC3)c2O1]

$^1$HNMR (400 MHz, DMSO-$d_6$) δ 7.54-7.58 (m, 2H), 7.42-7.47 (m, 2H), 7.33 (dd, J=8.4, 1.2 Hz, 1H), 6.78-6.79 (m, 2H), 6.72-6.76 (m, 1H), 6.35 (d, J=15.6 Hz, 1H), 4.50 (s, 2H), 3.68 (s, 2H), 2.89-2.92 (m, 2H), 2.59-2.67 (m, 1H), 2.08-2.11 (m, 2H), 2.02 (s, 3H), 1.71-1.73 (m, 4H), 1.30-1.40 (m, 2H), 1.22-1.30 (m, 2H). LC-MS: m/z 576.8 $(M+H)^+$.

(E)-3-(1-(but-2-yn-1-yl)-2-((4-(2-(4-chloro-2-fluorophenyl)-2-methylbenzo[d][1,3]dioxol-4-yl)piperidin-1-yl)methyl)-1H-imidazol-5-yl)acrylic acid (Compound 193) was synthesized following the route of Example 29, using but-2-yn-1-ol in step B.

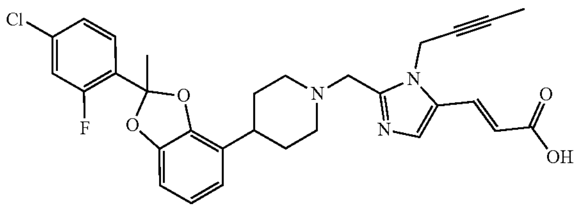 [SMILES: CC#CCn1c(/C=C/C(=O)O)cnc1CN1CCC(c2cccc3c2OC(C)(c2ccc(Cl)cc2F)O3)CC1]

$^1$HNMR (400 MHz, DMSO-$d_6$) δ 12.31 (br.s, 1H), 7.47-7.63 (m, 4H), 7.34 (dd, J=8.4, 2.0 Hz, 1H), 6.77-6.83 (m, 2H), 6.68-6.75 (m, 1H), 6.35 (d, J=16.0 Hz, 1H), 5.08 (d, J=3.2 Hz, 2H), 3.66 (s, 2H), 2.88 (s, 2H), 2.59-2.70 (m, 1H), 2.07-2.25 (m, 2H), 2.02 (s, 3H), 1.77-1.78 (m, 7H). LC-MS: m/z 550.0 $(M+H)^+$.

(E)-3-(2-((4-(2-(4-chloro-2-fluorophenyl)-2-methylbenzo[d][1,3]dioxol-4-yl)piperidin-1-yl)methyl)-1-(oxetan-3-ylmethyl)-1H-imidazol-5-yl)acrylic acid (Compound 194) was synthesized following the route of Example 29, using oxetan-3-ylmethanol in step B.

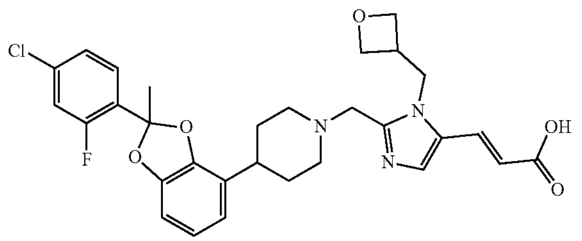 [SMILES: CC1(c2ccc(Cl)cc2F)Oc2cccc(C3CCN(Cc4ncc(/C=C/C(=O)O)n4CC4COC4)CC3)c2O1]

$^1$H NMR (400 MHz, DMSO-$d_6$) δ 12.42 (br.s, 1H), 7.45-7.59 (m, 4H), 7.34 (dd, J=8.4, 1.6 Hz, 1H), 6.77-6.81 (m, 2H), 6.70-6.76 (m, 1H), 6.31 (d, J=16.0 Hz, 1H), 4.57-4.63 (m, 2H), 4.44-4.52 (m, 4H), 3.59 (s, 2H), 3.34-3.43 (m, 1H), 2.91 (d, J=11.2 Hz, 2H), 2.57-2.64 (m, 1H), 2.05-2.15 (m, 2H), 2.01 (s, 3H), 1.67-1.79 (m, 4H). LC-MS: m/z 567.9 $(M+H)^+$.

(E)-3-(2-((4-(2-(4-chloro-2-fluorophenyl)-2-methylbenzo[d][1,3]dioxol-4-yl)piperidin-1-yl)methyl)-1-(3-methoxypropyl)-1H-imidazol-5-yl)acrylic acid (Compound 195) was synthesized following the route of Example 29, using 3-methoxypropan-1-ol in step B.

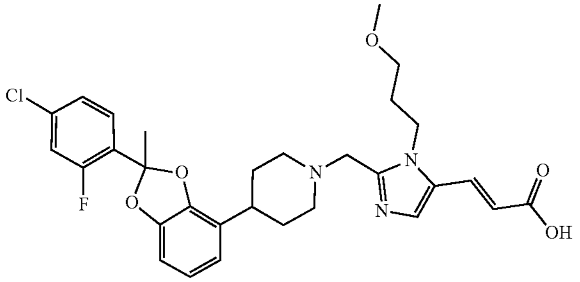 [SMILES: COCCCn1c(/C=C/C(=O)O)cnc1CN1CCC(c2cccc3c2OC(C)(c2ccc(Cl)cc2F)O3)CC1]

$^1$H NMR (400 MHz, DMSO-$d_6$) δ 12.42 (br.s, 1H), 7.52-7.59 (m, 2H), 7.48 (s, 1H), 7.41 (d, J=16.0 Hz, 1H), 7.34 (dd, J=8.4, 2.0 Hz, 1H), 6.75-6.80 (m, 2H), 6.67-6.74 (m, 1H), 6.31 (d, J=16.0 Hz, 1H), 4.18 (t, J=7.2 Hz, 2H), 3.58 (s, 2H), 3.32 (t, J=5.6 Hz, 2H), 2.86-2.89 (m, 2H), 2.56-2.64 (m, 1H), 2.05-2.16 (m, 2H), 2.02 (s, 3H), 1.89-1.97 (m, 2H), 1.62-1.77 (m, 4H). LC-MS: m/z 569.9 $(M+H)^+$.

(E)-3-(2-((4-(2-(4-chloro-2-fluorophenyl)-2-methylbenzo[d][1,3]dioxol-4-yl)piperidin-1-yl)methyl)-1-((1-methoxycyclopropyl)methyl)-1H-imidazol-5-yl)acrylic acid (Compound 196) was synthesized following the route of Example 29, using (1-methoxycyclopropyl)methanol in step B.

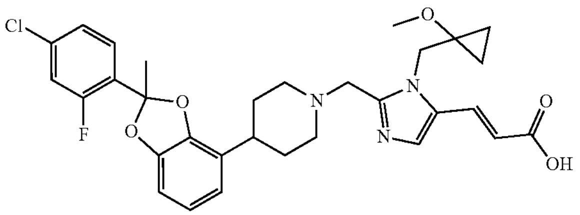 [SMILES: COC1(Cn2c(/C=C/C(=O)O)cnc2CN2CCC(c3cccc4c3OC(C)(c3ccc(Cl)cc3F)O4)CC2)CC1]

$^1$HNMR (400 MHz, DMSO-$d_6$) δ 7.44-7.68 (m, 4H), 7.34 (d, J=8.4 Hz, 1H), 6.66-6.89 (m, 3H), 6.30 (d, J=16.0 Hz, 1H), 4.51 (s, 2H), 3.62 (s, 2H), 3.14 (s, 3H), 2.85-2.94 (m, 2H), 2.60-2.67 (m, 1H), 2.04-2.16 (m, 2H), 2.02 (s, 3H), 1.62-1.82 (m, 4H), 0.59-0.89 (m, 4H). LC-MS: m/z 581.8 $(M+H)^+$.

(E)-3-(2-((4-(2-(4-chloro-2-fluorophenyl)-2-methylbenzo[d][1,3]dioxol-4-yl)piperidin-1-yl)methyl)-1-(2-ethoxyethyl)-1H-imidazol-5-yl)acrylic acid (Compound 197) was synthesized following the route of Example 29, using 2-ethoxyethan-1-ol in step B.

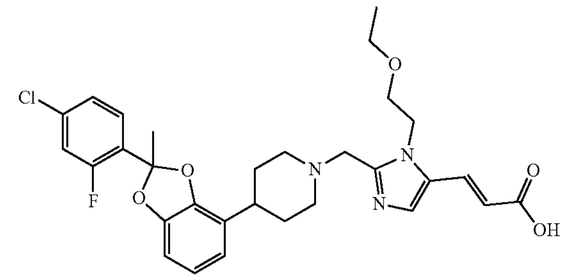 [SMILES: CCOCCn1c(/C=C/C(=O)O)cnc1CN1CCC(c2cccc3c2OC(C)(c2ccc(Cl)cc2F)O3)CC1]

$^1$H NMR (400 MHz, DMSO-$d_6$) δ 12.17 (br.s, 1H), 7.46-7.61 (m, 4H), 7.34 (dd, J=8.4, 2.0 Hz, 1H), 6.76-6.81

(m, 2H), 6.70-6.75 (m, 1H), 6.27 (d, J=16.0 Hz, 1H), 4.31 (t, J=5.2 Hz, 2H), 3.67 (t, J=5.2 Hz, 2H), 3.61 (s, 2H), 2.86 (dd, J=11.2, 3.6 Hz, 2H), 2.66-2.70 (m, 1H), 2.59-2.65 (m, 2H), 2.05-2.15 (m, 2H), 2.01 (s, 3H), 1.63-1.78 (m, 4H), 1.03 (t, J=6.8 Hz, 3H). LC-MS: m/z 569.9 $(M+H)^+$.

(S,E)-3-(2-((4-(2-(4-chloro-2-fluorophenyl)-2-methylbenzo[d][1,3]dioxol-4-yl)piperidin-1-yl)methyl)-1-(2-(2,2,2-trifluoroethoxy)ethyl)-1H-imidazol-5-yl)acrylic acid (Compound 198a) was synthesized following the route of Example 29, using (S)-2-((4-(2-(4-chloro-2-fluorophenyl)-2-methylbenzo[d][1,3]dioxol-4-yl)piperidin-1-yl)methyl)-1H-imidazole-5-carbaldehyde and 2-(2,2,2-trifluoroethoxy)ethan-1-ol in step B.

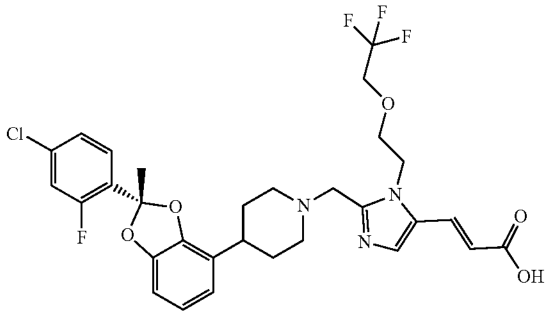 [SMILES: C[C@]1(c2ccc(Cl)cc2F)Oc2cccc(C3CCN(Cc4ncc(/C=C/C(=O)O)n4CCOCC(F)(F)F)CC3)c2O1]

$^1$H NMR (400 MHz, DMSO-$d_6$) δ 7.52-7.60 (m, 2H), 7.48 (d, J=14.8 Hz, 2H), 7.34 (dd, J=8.4, 1.6 Hz, 1H), 6.76-6.81 (m, 2H), 6.68-6.75 (m, 1H), 6.29 (d, J=16.0 Hz, 1H), 4.41 (t, J=5.2 Hz, 2H), 4.02 (q, J=9.2 Hz, 2H), 3.90 (t, J=5.2 Hz, 2H), 3.61 (s, 2H), 2.81-2.95 (m, 2H), 2.60-2.71 (m, 1H), 2.05-2.18 (m, 2H), 2.02 (s, 3H), 1.57-1.82 (m, 4H). LC-MS: m/z 624.0 $(M+H)^+$.

(R,E)-3-(2-((4-(2-(4-chlorophenyl)-2,3-dihydrobenzo[b][1,4]dioxin-5-yl)piperidin-1-yl)methyl)-1-((4-methyloxazol-5-yl)methyl)-1H-imidazol-5-yl)acrylic acid (Compound 199a) was synthesized following the route of Example 29, using (R)-2-((4-(2-(4-chlorophenyl)-2,3-dihydrobenzo[b][1,4]dioxin-5-yl)piperidin-1-yl)methyl)-1H-imidazole-5-carbaldehyde in step B.

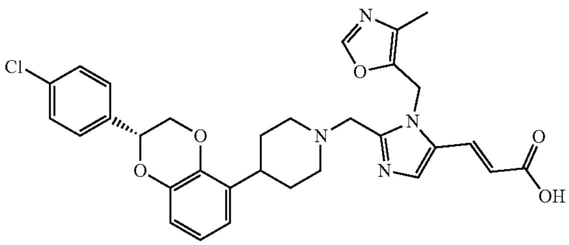 [SMILES: Cc1ncoc1Cn1c(/C=C/C(=O)O)cnc1CN1CCC(c2cccc3c2OC[C@@H](c2ccc(Cl)cc2)O3)CC1]

$^1$H NMR (400 MHz, DMSO-$d_6$) δ 8.20 (s, 1H), 7.47-7.52 (m, 4H), 7.25-7.38 (m, 2H), 6.79-6.85 (m, 2H), 6.76 (dd, J=6.4, 2.8 Hz, 1H), 6.24 (d, J=16.0 Hz, 1H), 5.55 (s, 2H), 5.24 (dd, J=8.0, 2.4 Hz, 1H), 4.49 (dd, J=11.6, 2.4 Hz, 1H), 4.04 (dd, J=11.6, 8.4 Hz, 1H), 3.63 (s, 2H), 2.78-2.89 (m, 3H), 2.14 (s, 3H), 2.02-2.10 (m, 2H), 1.47-1.71 (m, 4H). LC-MS: m/z 575.2 $(M+H)^+$.

Example 30

(E)-3-(2-((4-(2-(4-chloro-2-fluorophenyl)-2-methylbenzo[d][1,3]dioxol-4-yl)piperidin-1-yl)methyl)-1-(2-(2-oxooxazolidin-3-yl)ethyl)-1H-imidazol-5-yl)acrylic acid (Compound 200)

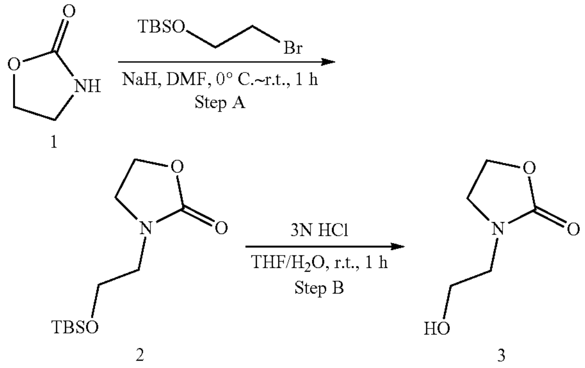

Step A: 3-(2-((tert-butyldimethyl silyl)oxy)ethyl)oxazolidin-2-one

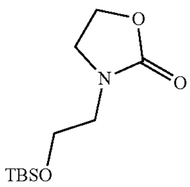 [SMILES: CC(C)(C)[Si](C)(C)OCCN1CCOC1=O]

Oxazolidin-2-one (1.00 g, 11.5 mmol) was added to a mixture of NaH (60% in mineral oil) in DMF (10 mL) at 0° C., and then the mixture was stirred for 20 mins. (2-Bromoethoxy)(tert-butyl)dimethylsilane (4.04 g, 16.1 mmol) was added dropwise while ice-cooling, and then the reaction mixture was stirred for 1 hour at room temperature. The mixture was diluted with water (30 mL) and extracted with EtOAc (30 mL*3). The organic layers were dried over $Na_2SO_4$, concentrated and purified by silica column (eluted with PE/EtOAc=50/1-2/1) to give 3-(2-((tert-butyldimethylsilyl)oxy)ethyl)oxazolidin-2-one as a colorless oil. (285 mg, 10% yield). $^1$H NMR (400 MHz, $CDCl_3$) δ 4.25 (dd, J=8.8, 7.2 Hz, 2H), 3.72 (t, J=5.2 Hz, 2H), 3.65 (dd, J=8.8, 7.2 Hz, 2H), 3.31 (t, J=5.2 Hz, 2H), 0.83 (s, 9H), 0.00 (s, 6H). LC-MS: m/z 246.1 $(M+H)^+$.

Step B: 3-(2-hydroxyethyl)oxazolidin-2-one

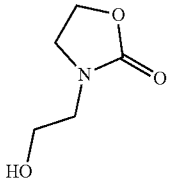

To a solution of 3-(2-((tert-butyldimethylsilyl)oxy)ethyl) oxazolidin-2-one (285 mg, 1.16 mmol) in THF (6 mL) was added 3N HCl (aq. 2 mL) and the mixture was stirred at room temperature for 1 hour. THF was removed in vacuo and the residue was extracted with EtOAc (5 mL*3). The aqueous phase was neutralized by 1N NaOH (aq., 6 mL) and concentrated. The residue was suspended in EtOAc (10 mL), and filtered. The filtrate was concentrated to give 3-(2-hydroxyethyl)oxazolidin-2-one as a colorless oil (40 mg, 26% yield, crude). $^1H$ NMR (400 MHz, $CDCl_3$) δ 4.37 (dd, J=8.8, 7.2 Hz, 2H), 3.84 (t, J=5.2 Hz, 2H), 3.71 (dd, J=8.8, 7.2 Hz, 2H), 3.43 (t, J=5.2 Hz, 2H), 2.08 (s, 1H).

(E)-3-(2-((4-(2-(4-chloro-2-fluorophenyl)-2-methyl-benzo[d][1,3]dioxol-4-yl)piperidin-1-yl)methyl)-1-(2-(2-oxooxazolidin-3-yl)ethyl)-1H-imidazol-5-yl) acrylic acid (Compound 200)

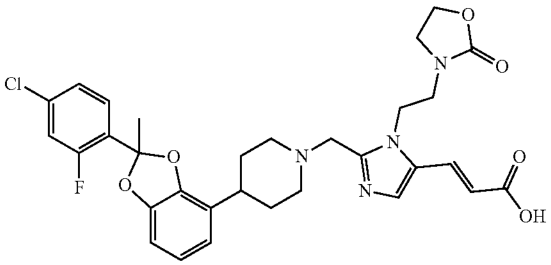 [SMILES: CC1(c2ccc(Cl)cc2F)Oc2cccc(C3CCN(Cc4ncc(/C=C/C(=O)O)n4CCN4CCOC4=O)CC3)c2O1]

Compound 200 was then synthesized following the route of Example 29, using 3-(2-hydroxyethyl)oxazolidin-2-one in step B.

$^1H$ NMR (400 MHz, DMSO-$d_6$) δ 12.35 (br.s, 1H), 7.49-7.59 (m, 3H), 7.44 (d, J=16.0 Hz, 1H), 7.33 (dd, J=8.4, 2.0 Hz, 1H), 6.76-6.80 (m, 2H), 6.70-6.76 (m, 1H), 6.33 (d, J=16.0 Hz, 1H), 4.30 (t, J=6.0 Hz, 2H), 4.18 (td, J=8.0, 3.2 Hz, 2H), 3.54-3.64 (m, 4H), 3.51 (t, J=8.0 Hz, 2H), 2.85-2.97 (m, 2H), 2.57-2.65 (m, 1H), 2.04-2.16 (m, 2H), 2.01 (s, 3H), 1.64-1.82 (m, 4H). LC-MS: m/z 611.2 $(M+H)^+$.

Example 31

(E)-3-(2-((4-(2-(4-chloro-2-fluorophenyl)-2-methyl-benzo[d][1,3]dioxol-4-yl)piperidin-1-yl)methyl)-1-(2-cyclopropoxyethyl)-1H-imidazol-5-yl)acrylic acid (Compound 201)

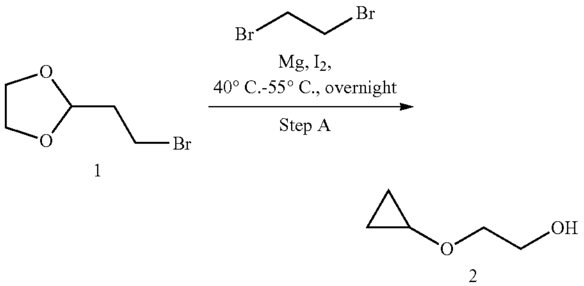

1

2

Step A: 2-cyclopropoxyethan-1-ol

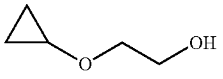

A mixture of Mg (2.69 g, 110 mmol) and $I_2$ (28.0 mg, 0.110 mmol) in THF (14 mL) was degassed and refilled with $N_2$ for three times. Then a solution of 1,2-dibromoethane (10.4 g, 55.2 mmol) in THF (40 mL) was added at 40° C.-55° C. dropwise. The resulting mixture was stirred at 40° C.-55° C. for 20 minutes. A solution of 2-(2-bromoethyl)-1,3-dioxolane (2.00 g, 11.0 mmol) was added and the mixture was stirred at 40° C.-55° C. for 16 hours. The mixture was quenched with sat. aq. $NH_4Cl$ (60 mL) slowly at 0° C. The mixture was filtered and THF was removed under vacuum. The aqueous solution was extracted with DCM/i-PrOH (10/1, 70 mL*3). The organic layers were dried over $Na_2SO_4$, concentrated and purified by silica gel chromatography (PE:EtOAc=5:1 to 2:1) to give 2-cyclopropoxyethan-1-ol as a colorless oil (140 mg, 13% yield). $^1H$NMR (400 MHz, $CDCl_3$) δ 3.62-3.68 (m, 2H), 3.52-3.57 (m, 2H), 3.24-3.28 (m, 1H), 2.06 (s, OH), 0.48-0.57 (m, 2H), 0.38-0.45 (m, 2H).

(E)-3-(2-((4-(2-(4-chloro-2-fluorophenyl)-2-methyl-benzo[d][1,3]dioxol-4-yl)piperidin-1-yl)methyl)-1-(2-cyclopropoxyethyl)-1H-imidazol-5-yl)acrylic acid (Compound 201)

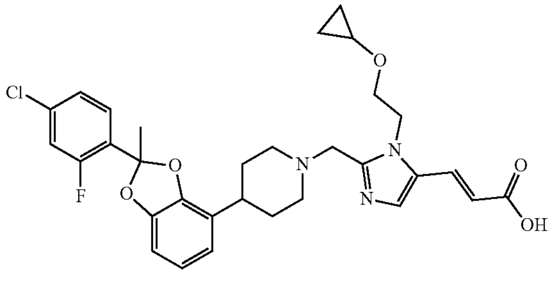 [SMILES: CC1(c2ccc(Cl)cc2F)Oc2cccc(C3CCN(Cc4ncc(/C=C/C(=O)O)n4CCOC4CC4)CC3)c2O1]

Compound 201 was synthesized following the route of Example 29, using 2-cyclopropoxyethan-1-olin step B.

$^1H$NMR (400 MHz, $CD_3OD$) δ 7.55-7.64 (m, 2H), 7.49 (s, 1H), 7.27 (dd, J=10.8, 2.0 Hz, 1H), 7.20 (dd, J=8.4, 2.0 Hz, 1H), 6.78 (dd, J=8.4, 6.8 Hz, 1H), 6.70 (d, J=7.2 Hz, 2H), 6.37 (d, J=16.0 Hz, 1H), 4.40 (t, J=5.2 Hz, 2H), 3.78-3.87 (m, 4H), 3.23-3.27 (m, 1H), 3.04-3.13 (m, 2H), 2.68-2.79 (m, 1H), 2.40 (t, J=10.8 Hz, 2H), 2.02 (s, 3H), 1.78-1.96 (m, 4H), 0.32-0.43 (m, 4H). LC-MS: m/z 581.9 $(M+H)^+$.

Example 32

(E)-3-(2-((4-(2-(4-chloro-2-fluorophenyl)-2-methylbenzo[d][1,3]dioxol-4-yl)piperidin-1-yl)methyl)-1-((2-methyloxazol-5-yl)methyl)-1H-imidazol-5-yl) acrylic acid (Compound 202)

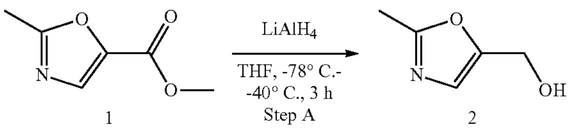

Step A: (2-methyloxazol-5-yl)methanol

To a solution of methyl 2-methyloxazole-5-carboxylate (1.00 g, 7.09 mmol) in THF (30 mL) which was cooled to −78° C. was added a 1.0 M solution of $LiAlH_4$ in THF (7.09 mL, 7.09 mmol) and the solution was slowly warmed to −40° C. and stirred for 3 hours. Water (0.5 mL) was slowly added, followed by 15% aqueous NaOH (0.5 mL) and water (0.5 mL) and the mixture was stirred for another 1 hour. The reaction mixture was filtered and the filtrate was concentrated to give (2-methyloxazol-5-yl)methanol as a light yellow oil (150 mg, 19% yield). LC-MS: m/z 114.0 $(M+H)^+$.

(E)-3-(2-((4-(2-(4-chloro-2-fluorophenyl)-2-methylbenzo[d][1,3]dioxol-4-yl)piperidin-1-yl)methyl)-1-((2-methyloxazol-5-yl)methyl)-1H-imidazol-5-yl) acrylic acid (Compound 202)

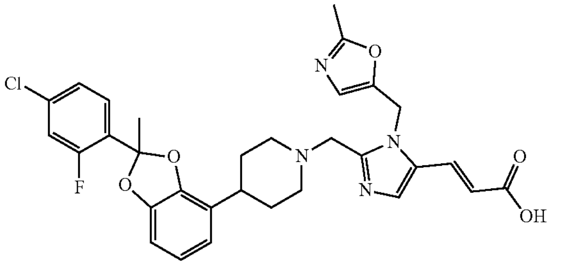 [SMILES: Cc1ncc(Cn2c(/C=C/C(=O)O)cnc2CN2CCC(c3cccc4c3OC(C)(c3ccc(Cl)cc3F)O4)CC2)o1]

Compound 202 was then synthesized following the route of Example 29, using (2-methyloxazol-5-yl)methanol in step B.

$^1$H NMR (400 MHz, $CDCl_3$) δ 7.60 (d, J=15.6 Hz, 1H), 7.48-7.52 (m, 2H), 7.30 (s, 1H), 7.09-7.14 (m, 2H), 6.71 (t, J=7.6 Hz, 1H), 6.69 (d, J=7.2 Hz, 1H), 6.65 (d, J=7.6 Hz, 1H), 6.29 (d, J=15.6 Hz, 1H), 5.38 (s, 2H), 3.85 (s, 2H), 2.98-3.06 (m, 2H), 2.69-2.74 (m, 1H), 2.40 (s, 3H), 2.26-2.39 (m, 2H), 2.04 (s, 3H), 1.76-1.88 (m, 4H). LC-MS: m/z 592.8 $(M+H)^+$.

Example 33

(E)-3-(2-((4-(2-(4-chloro-2-fluorophenyl)-2-methylbenzo[d][1,3]dioxol-4-yl)piperidin-1-yl)methyl)-1-((3-ethylisoxazol-4-yl)methyl)-1H-imidazol-5-yl) acrylic acid (Compound 203)

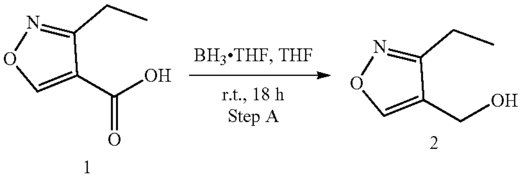

Step A: (3-ethylisoxazol-4-yl)methanol

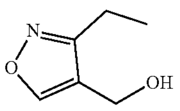

To a solution of 3-ethylisoxazole-4-carboxylic acid (423 mg, 3.00 mmol) in THF (12 mL) was added $BH_3$·THF (12.0 mL, 12.0 mmol, 1 mol/L) at room temperature. The resulting mixture was stirred at room temperature for 18 hours under $N_2$. The mixture was quenched with methanol (36 mL) and concentrated in vacuo. The residue was purified by flash chromatography (DCM/MeOH=20/1) to give (3-ethylisoxazol-4-yl)methanol as a clear oil (160 mg, 38% yield). $^1$H NMR (400 MHz, DMSO-$d_6$) δ 8.63 (s, 1H), 5.07 (t, J=4.8 Hz, 1H), 4.35 (d, J=4.4 Hz, 2H), 2.65 (q, J=7.6 Hz, 2H), 1.20 (t, J=7.6 Hz, 3H).

(E)-3-(2-((4-(2-(4-chloro-2-fluorophenyl)-2-methylbenzo[d][1,3]dioxol-4-yl)piperidin-1-yl)methyl)-1-((3-ethylisoxazol-4-yl)methyl)-1H-imidazol-5-yl) acrylic acid (Compound 203)

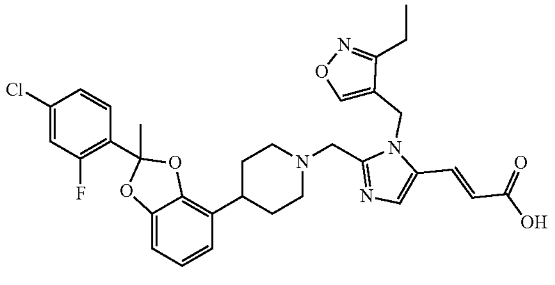 [SMILES: CCc1nocc1Cn1c(/C=C/C(=O)O)cnc1CN1CCC(c2cccc3c2OC(C)(c2ccc(Cl)cc2F)O3)CC1]

Compound 203 was then synthesized following the route of Example 29, using (3-ethylisoxazol-4-yl)methanol in step B.

$^1$H NMR (400 MHz, DMSO-$d_6$) δ 8.23 (s, 1H), 7.52-7.56 (m, 3H), 7.32-7.36 (m, 2H), 6.75-6.78 (m, 2H), 6.62 (dd, J=6.4, 3.2 Hz, 1H), 6.28 (d, J=15.6 Hz, 1H), 5.29 (s, 2H), 3.62 (s, 2H), 2.76-2.82 (m, 2H), 2.65-2.70 (m, 2H), 2.56-2.58 (m, 1H), 1.98-2.04 (m, 5H), 1.55-1.64 (m, 2H), 1.27-1.42 (m, 2H), 1.20 (t, J=7.6 Hz, 3H). LC-MS: m/z 607.2 $(M+H)^+$.

(E)-3-(2-((4-(2-(4-chloro-2-fluorophenyl)-2-methylbenzo[d][1,3]dioxol-4-yl)piperidin-1-yl)methyl)-1-((3-methylisoxazol-4-yl)methyl)-1H-imidazol-5-yl)acrylic acid (Compound 204) was synthesized following the route of Example 33, using 3-methylisoxazole-4-carboxylic acid in step A.

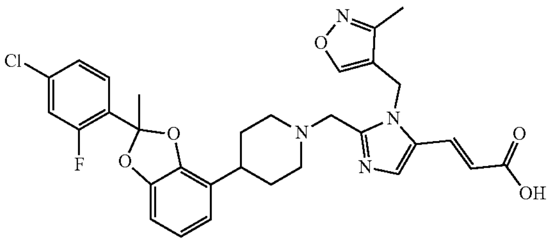 [SMILES: Cc1nocc1Cn1c(/C=C/C(=O)O)cnc1CN1CCC(c2cccc3c2OC(C)(c2ccc(Cl)cc2F)O3)CC1]

$^1$HNMR (400 MHz, $CD_3OD$) δ 8.22 (s, 1H), 7.44-7.59 (m, 3H), 7.16-7.31 (m, 2H), 6.76 (t, J=7.6 Hz, 1H), 6.66 (ddd, J=14.4, 8.0, 1.2 Hz, 2H), 6.37 (d, J=16.0 Hz, 1H), 5.35 (s, 2H), 3.75 (s, 2H), 2.93 (t, J=11.2 Hz, 2H), 2.65 (tt, J=12.0, 3.6 Hz, 1H), 2.30 (s, 3H), 2.22 (tt, J=12.0, 3.2 Hz, 2H), 2.02 (s, 3H), 1.53-1.80 (m, 4H). LC-MS: m/z 593.0 $(M+H)^+$.

Example 34

(R,E)-3-(2-((4-(2-(4-chlorophenyl)-2,3-dihydrobenzo[b][1,4]dioxin-5-yl)piperidin-1-yl)methyl)-1-(oxazol-5-ylmethyl)-1H-imidazol-5-yl)acrylic acid (Compound 205a)

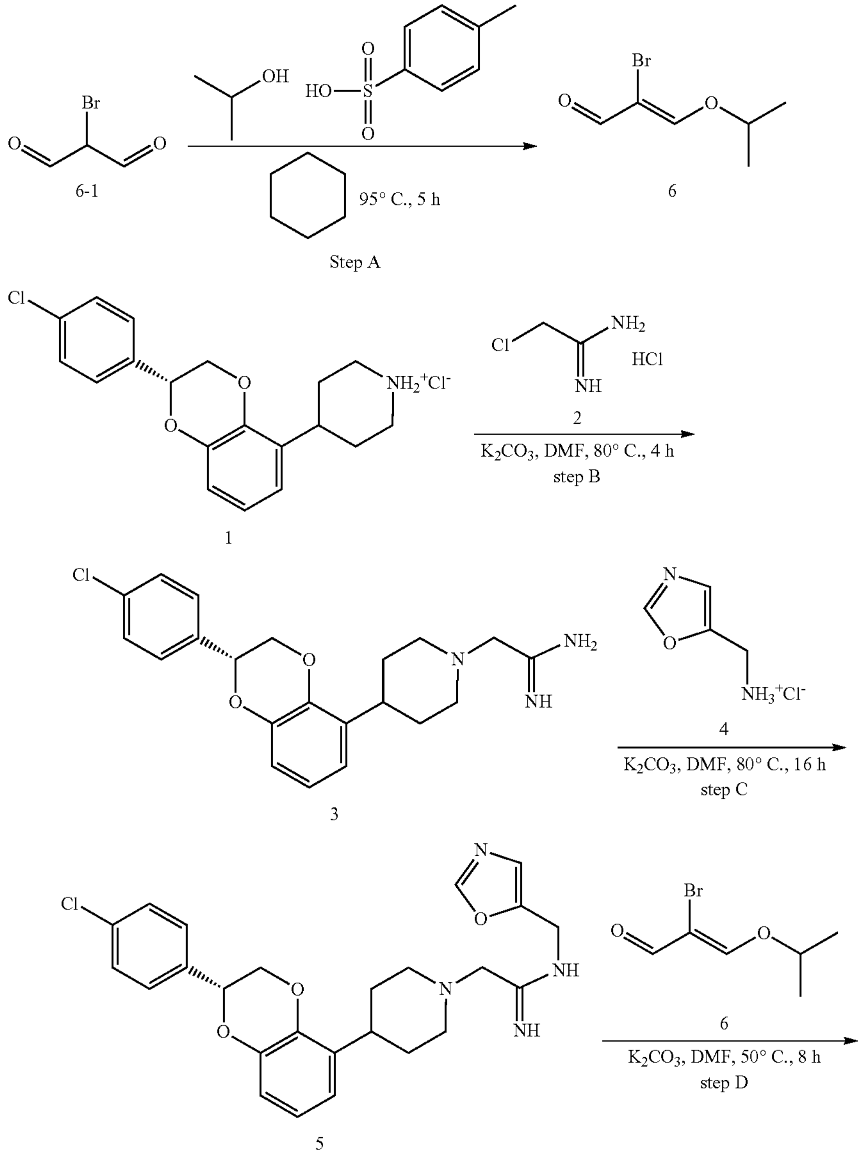

-continued

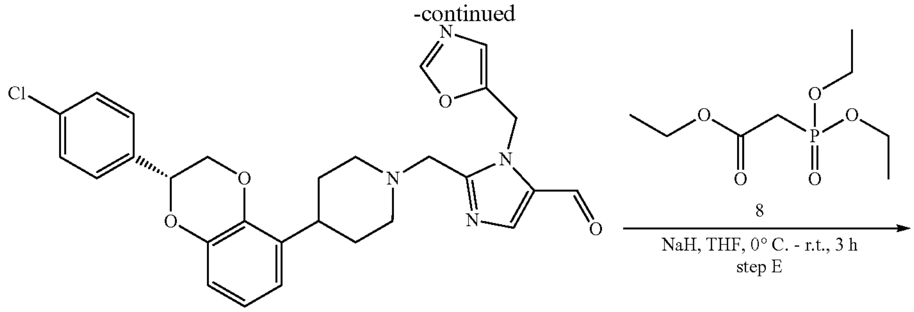

7

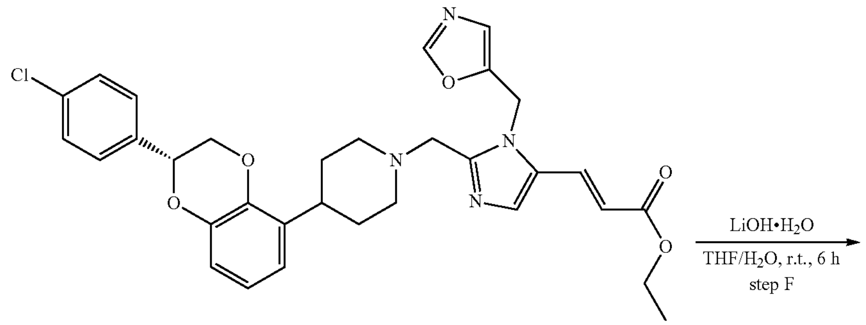

9

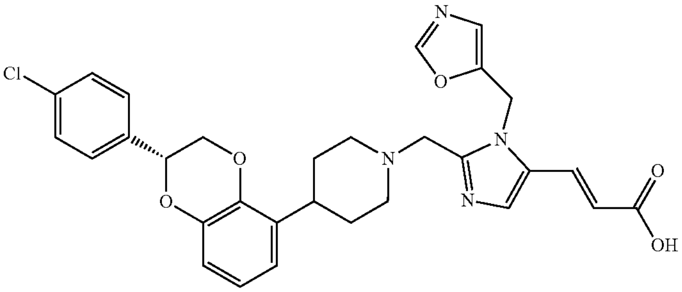

Compound 205a

Step A: (Z)-2-bromo-3-isopropoxyacrylaldehyde

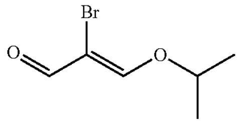

To a mixture of 2-bromomalonaldehyde (300 mg, 1.99 mmol) in cyclohexane (4 mL) were added 4-methylbenzenesulfonic acid (6.80 mg, 0.0400 mmol) and propan-2-ol (0.7 mL). The reaction mixture was stirred at 95° C.; for 5 hours. The mixture was quenched with saturated $NaHCO_3$ aqueous solution, and extracted with EtOAc (50 mL*3). The organic layers were washed with brine (20 mL), dried over $Na_2SO_4$ and concentrated to give (Z)-2-bromo-3-isopropoxyacrylaldehyde (240 mg, crude), which was used in next step without further purification.

Step B: (R)-2-(4-(2-(4-chlorophenyl)-2,3-dihydrobenzo[b][1,4]dioxin-5-yl)piperidin-1-yl)acetimidamide

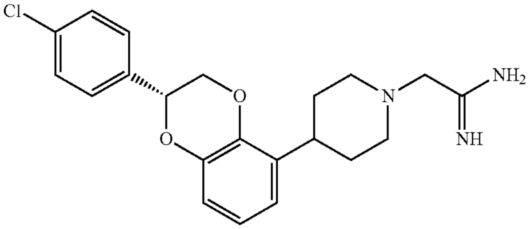 [SMILES: N=C(N)CN1CCC(c2cccc3c2OC[C@@H](c2ccc(Cl)cc2)O3)CC1]

To a mixture of (R)-4-(2-(4-chlorophenyl)-2,3-dihydrobenzo[b][1,4]dioxin-5-yl)piperidine hydrochloride (500 mg, 1.37 mmol) in DMF (8 mL) were added $K_2CO_3$ (755 mg, 5.46 mmol) and 2-chloroacetimidamide (194 mg, 1.50 mmol). The mixture was stirred at 80° C. for 4 hours. LCMS showed the reaction was complete. The mixture was used in next step directly. LC-MS: m/z 386.2 $(M+H)^+$.

Step C: (R)-2-(4-(2-(4-chlorophenyl)-2,3-dihydrobenzo[b][1,4]dioxin-5-yl)piperidin-1-yl)-N-(oxazol-5-ylmethyl)acetimidamide

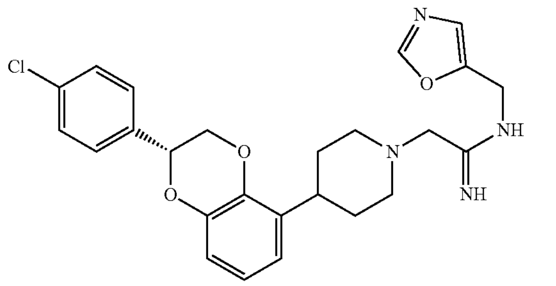 [SMILES: N=C(CN1CCC(c2cccc3c2OC[C@@H](c2ccc(Cl)cc2)O3)CC1)NCc1cnco1]

To the mixture of step A were added oxazol-5-ylmethanaminium chloride (202 mg, 1.50 mmol) and $K_2CO_3$ (565 mg, 4.09 mmol). The mixture was stirred at 80° C. for 16 hours and then at 100° C. for another 8 hours. The reaction mixture was used in next step directly. LC-MS: m/z 467.2 $(M+H)^+$.

Step D: (R)-2-((4-(2-(4-chlorophenyl)-2,3-dihydrobenzo[b][1,4]dioxin-5-yl)piperidin-1-yl)methyl)-1-(oxazol-5-ylmethyl)-1H-imidazole-5-carbaldehyde

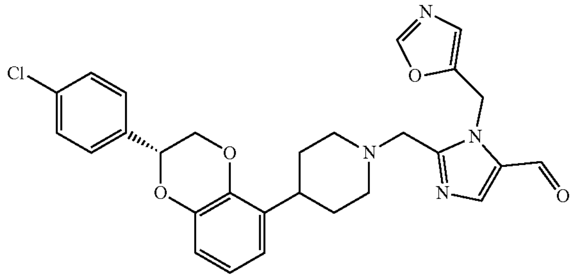 [SMILES: O=Cc1cnc(CN2CCC(c3cccc4c3OC[C@@H](c3ccc(Cl)cc3)O4)CC2)n1Cc1cnco1]

To the mixture of step B was added (Z)-2-bromo-3-isopropoxyacrylaldehyde (342 mg, 1.77 mmol). The mixture was stirred at 50° C. for 8 hours. The mixture was diluted with water (25 mL), and extracted with EtOAc (50 mL*3). The organic layers were washed with brine (25 mL), dried over anhydrous $Na_2SO_4$, concentrated and purified by flash column chromatography (eluting with McOH/DCM) to give (R)-2-((4-(2-(4-chlorophenyl)-2,3-dihydrobenzo[b][1,4]dioxin-5-yl)piperidin-1-yl)methyl)-1-(oxazol-5-ylmethyl)-1H-imidazole-5-carbaldehyde as a yellow oil (70.0 mg, 10% yield over three steps). LC-MS: m/z 519.2 $(M+H)^+$.

Step E: ethyl R,E)-3-(2-((4-(2-(4-chlorophenyl)-2,3-dihydrobenzo[b][1,4]dioxin-5-yl)piperidin-1-yl)methyl)-1-(oxazol-5-ylmethyl)-1H-imidazol-5-yl)acrylate

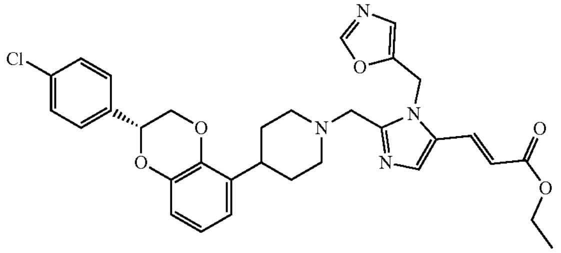 [SMILES: CCOC(=O)/C=C/c1cnc(CN2CCC(c3cccc4c3OC[C@@H](c3ccc(Cl)cc3)O4)CC2)n1Cc1cnco1]

To a solution of (R)-2-((4-(2-(4-chlorophenyl)-2,3-dihydrobenzo[b][1,4]dioxin-5-yl)piperidin-1-yl)methyl)-1-(oxazol-5-ylmethyl)-1H-imidazole-5-carbaldehyde (70.0 mg, 0.135 mmol) in anhydrous THF (3 mL) were added ethyl 2-(diethoxyphosphoryl)acetate (36.0 mg, 0.162 mmol) and NaH (60% in oil, 7.00 mg) at 0° C. under $N_2$. The reaction mixture was stirred at room temperature for 2.5 hours. The reaction mixture was quenched with saturated ammonium chloride aqueous solution (10 mL), extracted with EtOAc (20 mL*3). The organic layer was washed with brine (20 mL), dried over $Na_2SO_4$, concentrated and purified by flash column chromatography (eluting with MeOH/DCM) to give ethyl (R,E)-3-(2-((4-(2-(4-chlorophenyl)-2,3-dihydrobenzo[b][1,4]dioxin-5-yl)piperidin-1-yl)methyl)-1-(oxazol-5-ylmethyl)-1H-imidazol-5-yl)acrylate as a light yellow gel (41.0 mg, 52% yield). LC-MS: m/z 589.2 $(M+H)^+$.

Step F: (R,E)-3-(2-((4-(2-(4-chlorophenyl)-2,3-dihydrobenzo[b][1,4]dioxin-5-yl)piperidin-1-yl)methyl)-1-(oxazol-5-ylmethyl)-1H-imidazol-5-yl)acrylic acid (Compound 205a)

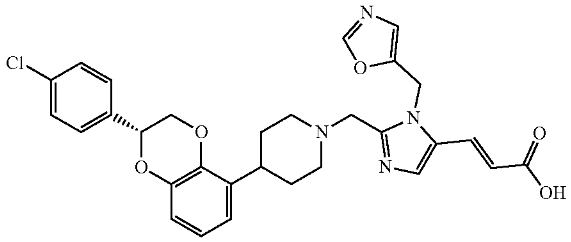 [SMILES: O=C(O)/C=C/c1cnc(CN2CCC(c3cccc4c3OC[C@@H](c3ccc(Cl)cc3)O4)CC2)n1Cc1cnco1]

To a solution of ethyl (R,E)-3-(2-((4-(2-(4-chlorophenyl)-2,3-dihydrobenzo[b][1,4]dioxin-5-yl)piperidin-1-yl)methyl)-1-(oxazol-5-ylmethyl)-1H-imidazol-5-yl)acrylate (41.0 mg, 0.07 mmol) in THF (1.5 mL) and water (1.5 mL) was added $LiOH \cdot H_2O$ (12.0 mg, 0.28 mmol). The mixture was stirred at room temperature for 6 hours. 1M HCl aqueous solution was added to adjust pH to 5-6. The mixture was filtered, and the filtrate was purified by prep-HPLC (0.1% formic acid in water and acetonitrile) to give (R,E)-3-(2-((4-(2-(4-chlorophenyl)-2,3-dihydrobenzo[b][1,4]dioxin-5-yl)piperidin-1-yl)methyl)-1-(oxazol-5-ylmethyl)-1H-imidazol-5-yl)acrylic acid as a white solid (20.0 mg, 51% yield). $^1H$ NMR (400 MHz, DMSO-$d_6$) δ 12.36 (br.s, 1H), 8.36 (s, 1H), 7.55 (t, J=8.0 Hz, 2H), 7.48-7.52 (m, 4H), 7.07 (s, 1H), 6.77-6.88 (m, 2H), 6.73 (dd, J=6.4, 2.8 Hz, 1H), 6.33 (d, J=16.0 Hz, 1H), 5.63 (s, 2H), 5.24 (dd, J=8.4, 2.4 Hz, 1H), 4.49 (dd, J=11.4, 2.4 Hz, 1H), 4.04 (dd, J=11.4, 8.4 Hz, 1H), 3.06-3.64 (m, 2H), 2.76-2.89 (m, 3H), 2.02-2.11 (m, 2H), 1.32-1.77 (m, 4H). LC-MS: m/z 561.2 $(M+H)^+$.

(R,E)-3-(2-((4-(2-(4-chlorophenyl)-2,3-dihydrobenzo[b][1,4]dioxin-5-yl)piperidin-1-yl)methyl)-1-((1-methyl-1H-imidazol-5-yl)methyl)-1H-imidazol-5-yl)acrylic acid (Compound 206a) was synthesized following the route of Example 34, using (1-methyl-1H-imidazol-5-yl)methanamine in step C.

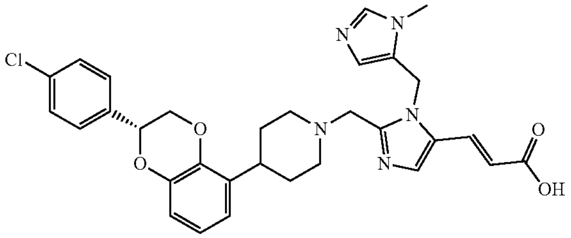 [SMILES: Cn1cncc1Cn1c(/C=C/C(=O)O)cnc1CN1CCC(c2cccc3c2OC[C@@H](c2ccc(Cl)cc2)O3)CC1]

$^1$H NMR (400 MHz, DMSO-$d_6$) (HCl salt) δ 14.47 (br.s, 1H), 10.91 (br.s, 1H), 9.15 (s, 1H), 7.92 (s, 1H), 7.48-7.53 (m, 4H), 7.46 (d, J=16.0 Hz, 1H), 7.01 (s, 1H), 6.85-6.90 (m, 2H), 6.71-6.78 (m, 1H), 6.50 (d, J=16.0 Hz, 1H), 5.84 (s, 2H), 5.28 (dd, J=8.0, 2.4 Hz, 1H), 4.42-4.56 (m, 3H), 4.10 (dd, J=11.2, 8.0 Hz, 1H), 3.94 (s, 3H), 3.61-3.64 (m, 2H), 3.20-3.32 (m, 2H), 3.07-3.18 (m, 1H), 1.98-2.11 (m, 2H), 1.82-1.96 (m, 2H). LC-MS: m/z 574.2 $(M+H)^+$.

(R,E)-3-(2-((4-(2-(4-chlorophenyl)-2,3-dihydrobenzo[b][1,4]dioxin-5-yl)piperidin-1-yl)methyl)-1-((1-ethyl-1H-imidazol-5-yl)methyl)-1H-imidazol-5-yl)acrylic acid (Compound 207a) was synthesized following the route of Example 34, using (1-ethyl-1H-imidazol-5-yl)methanamine in step C.

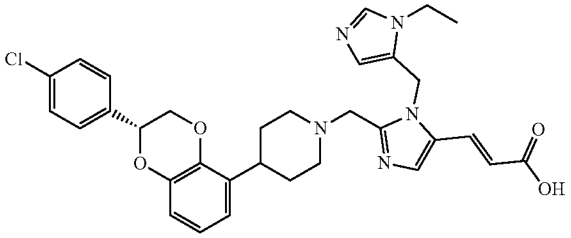 [SMILES: CCn1cncc1Cn1c(/C=C/C(=O)O)cnc1CN1CCC(c2cccc3c2OC[C@@H](c2ccc(Cl)cc2)O3)CC1]

$^1$H NMR (400 MHz, DMSO-$d_6$) δ 12.24 (br.s, 1H), 7.68 (s, 1H), 7.59 (s, 1H), 7.44-7.53 (m, 4H), 7.40 (d, J=16.0 Hz, 1H), 6.75-6.87 (m, 2H), 6.64 (dd, J=7.2, 2.0 Hz, 1H), 6.31 (d, J=16.0 Hz, 1H), 6.18 (s, 1H), 5.48 (s, 2H), 5.23 (dd, J=8.4, 2.0 Hz, 1H), 4.46 (dd, J=11.2, 2.4 Hz, 1H), 3.95-4.13 (m, 3H), 3.60 (s, 2H), 2.73-2.76 (m, 3H), 1.98 (t, J=10.8 Hz, 2H), 1.55 (dd, J=22.8, 11.6 Hz, 2H), 1.32 (t, J=7.2 Hz, 3H), 1.11-1.26 (m, 2H). LC-MS: m/z 588.2 $(M+H)^+$.

(R,E)-3-(2-((4-(2-(4-chlorophenyl)-2,3-dihydrobenzo[b][1,4]dioxin-5-yl)piperidin-1-yl)methyl)-1-((1-ethyl-1H-imidazol-5-yl)methyl)-1H-imidazol-5-yl)-2-methylacrylic acid (Compound 208a) was synthesized following the route of Example 34, using (1-ethyl-1H-imidazol-5-yl)methanamine in step C and methyl 2-(diethoxyphosphoryl)propanoate in step E.

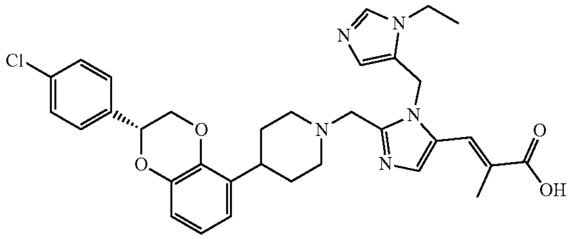 [SMILES: CCn1cncc1Cn1c(/C=C(\C)C(=O)O)cnc1CN1CCC(c2cccc3c2OC[C@@H](c2ccc(Cl)cc2)O3)CC1]

$^1$H NMR (400 MHz, DMSO-$d_6$) δ 12.78 (br.s, 1H), 7.66 (s, 1H), 7.46-7.51 (m, 4H), 7.40 (s, 1H), 7.30 (s, 1H), 6.76-6.86 (m, 2H), 6.65 (dd, J=7.2, 2.0 Hz, 1H), 6.20 (s, 1H), 5.44 (s, 2H), 5.23 (dd, J=8.4, 2.0 Hz, 1H), 4.47 (dd, J=11.2, 2.0 Hz, 1H), 3.98-4.13 (m, 3H), 3.62 (s, 2H), 2.75-2.78 (m, 3H), 1.92-2.07 (m, 5H), 1.56 (dd, J=23.2, 12.4 Hz, 2H), 1.31 (t, J=7.2 Hz, 3H), 1.23-13.0 (m, 2H). LC-MS: m/z 602.2 $(M+H)^+$.

(R,E)-3-(2-((4-(2-(4-chlorophenyl)-2,3-dihydrobenzo[b][1,4]dioxin-5-yl)piperidin-1-yl)methyl)-1-(pyridin-3-ylmethyl)-1H-imidazol-5-yl)acrylic acid (Compound 209a) was synthesized following the route of Example 34, using pyridin-3-ylmethanamine in step C.

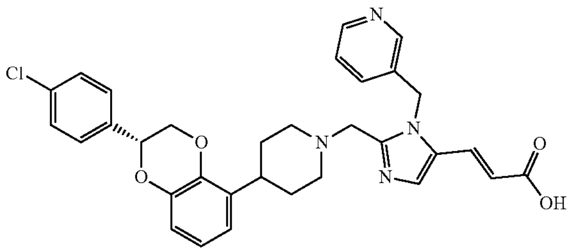 [SMILES: O=C(O)/C=C/c1cnc(CN2CCC(c3cccc4c3OC[C@@H](c3ccc(Cl)cc3)O4)CC2)n1Cc1cccnc1]

$^1$H NMR (400 MHz, DMSO-$d_6$) δ 8.49 (t, J=3.2 Hz, 1H), 8.35 (s, 1H), 7.59 (s, 1H), 7.45-7.52 (m, 4H), 7.38 (dd, J=3.2, 1.6 Hz, 2H), 7.31 (d, J=16.0 Hz, 1H), 6.77-6.82 (m, 2H), 6.54 (dd, J=7.2, 2.4 Hz, 1H), 6.28 (d, J=16.0 Hz, 1H), 5.52 (s, 2H), 5.22 (dd, J=8.4, 2.4 Hz, 1H), 4.45 (dd, J=11.2, 2.4 Hz, 1H), 4.01 (dd, J=11.2, 8.4 Hz, 1H), 3.60 (s, 2H), 2.66-2.82 (m, 3H), 2.00 (t, J=10.8 Hz, 2H), 1.51 (dd, J=23.6, 12.0 Hz, 2H), 1.02-1.20 (m, 2H). LC-MS: m/z 571.2 $(M+H)^+$.

(R,E)-3-(1-benzyl-2-((4-(2-(4-chlorophenyl)-2,3-dihydrobenzo[b][1,4]dioxin-5-yl)piperidin-1-yl)methyl)-1H-imidazol-5-yl)acrylic acid (Compound 210a) was synthesized following the route of Example 34, using phenylmethanamine in step C.

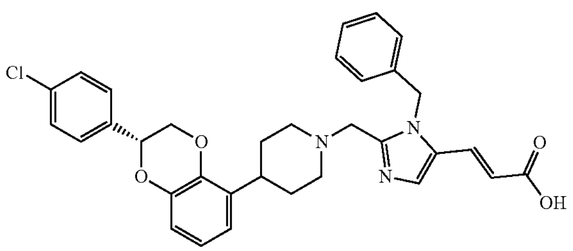 [SMILES: O=C(O)/C=C/c1cnc(CN2CCC(c3cccc4c3OC[C@@H](c3ccc(Cl)cc3)O4)CC2)n1Cc1ccccc1]

$^1$H NMR (400 MHz, DMSO-$d_6$) δ 12.27 (br.s, 1H), 7.59 (s, 1H), 7.45-7.53 (m, 4H), 7.25-7.37 (m, 4H), 7.04 (d, J=7.2 Hz, 2H), 6.78-6.83 (m, 2H), 6.58 (dd, J=6.8, 2.8 Hz, 1H), 6.26 (d, J=16.0 Hz, 1H), 5.48 (s, 2H), 5.22 (dd, J=8.0, 2.0 Hz, 1H), 4.45 (dd, J=11.2, 2.4 Hz, 1H), 4.01 (dd, J=11.2, 8.4 Hz, 1H), 3.57 (s, 2H), 2.72-2.82 (m, 3H), 2.03 (t, J=10.8 Hz, 2H), 1.54 (dd, J=28.4, 12.0 Hz, 2H), 1.22-1.31 (m, 2H). LC-MS: m/z 570.2 $(M+H)^+$.

(E)-3-(2-((4-(6-((4-chloro-2-fluorobenzyl)oxy)pyridin-2-yl)piperidin-1-yl)methyl)-1-(cyclobutylmethyl)-1H-imidazol-5-yl)acrylic acid (Compound 211) was synthesized following the route of Example 34, using 2-((4-chloro-2-fluorobenzyl)oxy)-6-(piperidin-4-yl)pyridine in step B and Cyclobutylmethanamine in step C.

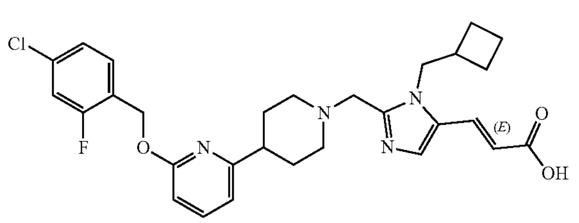 [SMILES: O=C(O)/C=C/c1cnc(CN2CCC(c3cccc(OCc4ccc(Cl)cc4F)n3)CC2)n1CC1CCC1]

$^1$H NMR (400 MHz, $CD_3OD$) δ 7.71 (s, 1H), 7.64 (dd, J 8.0, 7.2 Hz, 1H), 7.60 (d, J=16.0 Hz, 1H), 7.50 (t, J=8.0 Hz, 1H), 7.18-7.26 (m, 2H), 6.90 (d, J=7.2 Hz, 1H), 6.72 (d, J=8.0 Hz, 1H), 6.46 (d, J=16.0 Hz, 1H), 5.42 (s, 2H), 4.52 (s, 2H), 4.24 (d, J=7.2 Hz, 2H), 3.63-3.77 (m, 2H), 3.18-3.29 (m, 2H), 2.92-3.05 (m, 1H), 2.60-2.73 (m, 1H), 2.11-2.23 (m, 4H), 1.98-2.06 (m, 2H), 1.86-1.95 (m, 2H), 1.76-1.85 (m, 2H). LC-MS: m/z 539.3 $(M+H)^+$.

(E)-3-(2-((4-(6-((4-chloro-2-fluorobenzyl)oxy)pyridin-2-yl)piperidin-1-yl)methyl)-1-(2-(methylsulfonyl)ethyl)-1H-imidazol-5-yl)acrylic acid (Compound 212) was synthesized following the route of Example 34, using 2-((4-chloro-2-fluorobenzyl)oxy)-6-(piperidin-4-yl)pyridine in step B and 2-methylsulfonylethanamine in step C.

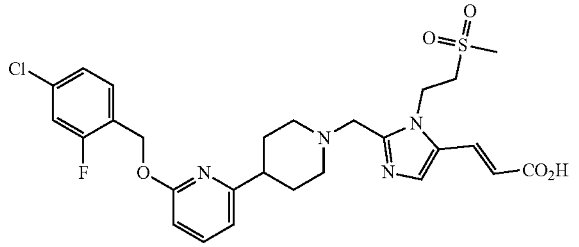 [SMILES: CS(=O)(=O)CCn1c(/C=C/C(=O)O)cnc1CN1CCC(c2cccc(OCc3ccc(Cl)cc3F)n2)CC1]

$^1$H NMR (400 MHz, $CD_3OD$) δ 7.48-7.62 (m, 4H), 7.17-7.28 (m, 2H), 6.85 (d, J=7.6 Hz, 1H), 6.64 (d, J=8.4 Hz, 1H), 6.45 (d, J=16.0 Hz, 1H), 5.42 (s, 2H), 4.77 (t, J=7.2 Hz, 2H), 3.85 (s, 2H), 3.80 (t, J=7.2 Hz, 2H), 3.02-3.11 (m, 5H), 2.69 (dd, J=10.4, 5.2 Hz, 1H), 2.30-2.41 (m, 2H), 1.86-1.96 (m, 4H). LC-MS: m/z 577.3 $(M+H)^+$.

(E)-3-(2-((4-(6-((4-chloro-2-fluorobenzyl)oxy)pyridin-2-yl)piperidin-1-yl)methyl)-1-((tetrahydrofuran-2-yl)methyl)-1H-imidazol-5-yl)acrylic acid (Compound 213) was synthesized following the route of Example 34, using 2-((4-chloro-2-fluorobenzyl)oxy)-6-(piperidin-4-yl)pyridine in step B and (tetrahydrofuran-2-yl)methanamine in step C.

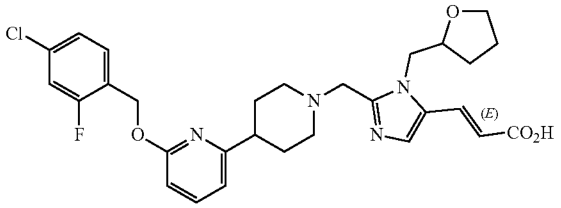 [SMILES: O=C(O)/C=C/c1cnc(CN2CCC(c3cccc(OCc4ccc(Cl)cc4F)n3)CC2)n1CC1CCCO1]

$^1$H NMR (400 MHz, $CD_3OD$) δ 7.48-7.64 (m, 3H), 7.46 (s, 1H), 7.15-7.26 (m, 2H), 6.84 (d, J=7.2 Hz, 1H), 6.65 (d, J=8.0 Hz, 1H), 6.38 (d, J=16.0 Hz, 1H), 5.41 (s, 2H), 4.37-4.45 (m, 1H), 4.26-4.34 (m, 1H), 4.15-4.24 (m, 1H), 3.71-4.04 (m, 4H), 3.02-3.26 (m, 2H), 2.62-2.79 (m, 1H), 2.37-2.57 (m, 2H), 2.11-2.23 (m, 1H), 1.83-1.99 (m, 6H), 1.62-1.75 (m, 1H). LC-MS: m/z 555.2 $(M+H)^+$.

(E)-3-(2-((4-(6-((4-chloro-2-fluorobenzyl)oxy)pyridin-2-yl)piperidin-1-yl)methyl)-1-((1-ethyl-1H-imidazol-5-yl)methyl)-1H-imidazol-5-yl)acrylic acid (Compound 214) was synthesized following the route of Example 34, using 2-((4-chloro-2-fluorobenzyl)oxy)-6-(piperidin-4-yl)pyridine in step B and (1-ethyl-1H-imidazol-5-yl)methanamine in step C.

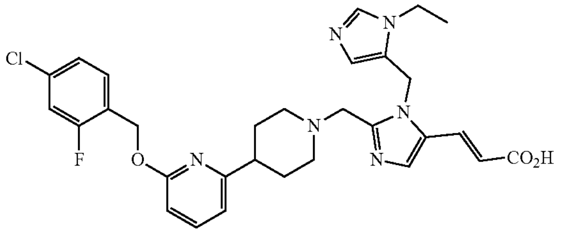 [SMILES: CCn1cncc1Cn1c(/C=C/C(=O)O)cnc1CN1CCC(c2cccc(OCc3ccc(Cl)cc3F)n2)CC1]

$^1$H NMR (400 MHz, $CD_3OD$) δ 7.84 (s, 1H), 7.55-7.58 (m, 2H), 7.48 (dd, J=16.4, 9.2 Hz, 2H), 7.17-7.25 (m, 2H), 6.76 (d, J=7.2 Hz, 1H), 6.63 (d, J=8.0 Hz, 1H), 6.46 (s, 1H), 6.36 (d, J=16.0 Hz, 1H), 5.58 (s, 2H), 5.39 (s, 2H), 4.14 (q, J=7.2 Hz, 2H), 3.75 (s, 2H), 2.92 (d, J=10.8 Hz, 2H), 2.53-2.68 (m, 1H), 2.23 (t, J=11.6 Hz, 2H), 1.79 (d, J=11.6 Hz, 2H), 1.54-1.66 (m, 2H), 1.44 (t, J=7.2 Hz, 3H). LC-MS: m/z 579.2 $(M+H)^+$.

(S,Z)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)-2-fluoroacrylic acid (Compound 215a) was synthesized following the route of Example 34, using 2-((4-chloro-2-fluorobenzyl)oxy)-6-(piperidin-4-yl)pyridine in step B, (S)-oxetan-2-ylmethanamine methanesulfonate in step C and ethyl 2-diethoxyphosphoryl-2-fluoro-acetate in step E.

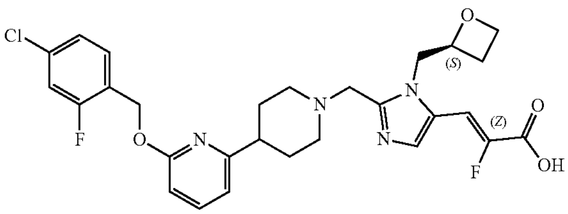

$^1$H NMR (400 MHz, $CD_3OD$) δ 7.57-7.66 (m, 2H), 7.48 (t, J 8.0 Hz, 1H), 7.17-7.24 (m, 2H), 6.85 (d, J=7.2 Hz, 1H), 6.66 (d, J=8.0 Hz, 1H), 6.39 (d, J 20.8 Hz, 1H), 5.41 (s, 2H), 5.06-5.14 (m, 1H), 4.62-4.71 (m, 1H), 4.35-4.59 (m, 3H), 4.16 (s, 2H), 3.33-3.41 (m, 2H), 2.70-2.88 (m, 4H), 2.45-2.59 (m, 1H), 1.87-2.07 (m, 4H). LC-MS: m/z 559.1 $(M+H)^+$.

Example 35

(S,E)-2-((2-((4-(6-((4-chloro-2-fluorobenzyl)oxy)pyridin-2-yl)piperidin-1-yl)methyl)-1-(oxetan-2-ylmethyl)-1H-imidazol-5-yl)methylene)-4-methoxybutanoic acid (Compound 216a)

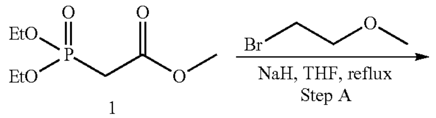

1

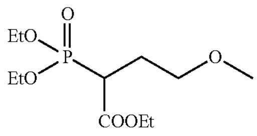

2

Step A: ethyl 2-diethoxyphosphoryl-4-methoxy-butanoate

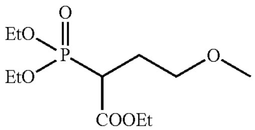 [SMILES: CCOC(=O)C(CCOC)P(=O)(OCC)OCC]

To a solution of ethyl 2-diethoxyphosphorylacetate (2.10 g, 9.37 mmol, 1.86 mL) in THF (20 mL) was added NaH (375 mg, 9.37 mmol, 60% purity) portionwise at 0° C. After stirring for 0.5 hour, 1-bromo-2-methoxy-ethane (1.30 g, 9.37 mmol, 880 uL) was added. The reaction mixture was stirred at 25° C. for 3 hours. The reaction mixture was concentrated under reduced pressure to remove the solvent. The residue was diluted with $H_2O$ (50 mL) and extracted with EtOAc (30 mL*3). The combined organic layers were washed with brine (50 mL), dried over anhydrous $Na_2SO_4$, filtered and concentrated under reduced pressure to give a residue. The residue was purified by prep-HPLC (Column: Xtimate C18 150*40 mm*10 um; eluent: 10% to 40% (v/v) water (10 mM $NH_4HCO$)-ACN; Gradient Time: 10 min; Flow Rate: 90 mL/min) to give ethyl 2-diethoxyphosphoryl-4-methoxy-butanoate (1 g, 3.54 mmol, 37.8% yield) as a colorless oil. LC-MS: m/z 283.1 $(M+H)^+$. $^1H$ NMR (400 MHz, $CDCl_3$) δ 4.08-4.25 (m, 6H), 3.32-3.49 (m, 2H), 3.29 (s, 3H), 3.07-3.19 (m, 1H), 2.04-2.32 (m, 2H), 1.25-1.36 (m, 9H).

(SE)-2-((2-((4-(6-((4-chloro-2-fluorobenzyl)oxy)pyridin-2-yl)piperidin-1-yl)methyl)-1-(oxetan-2-ylmethyl)-1H-imidazol-5-yl)methylene)-4-methoxybutanoic acid (Compound 216a)

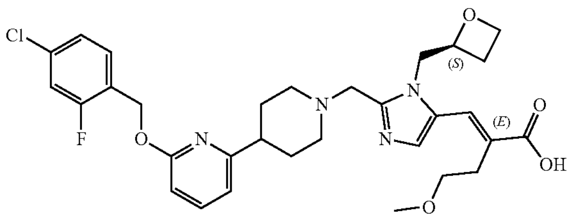

Compound 216a was then synthesized following the route of Example 34, using 2-((4-chloro-2-fluorobenzyl)oxy)-6-(piperidin-4-yl)pyridine in step B, (S)-oxetan-2-ylmethanamine methanesulfonate in step C and ethyl 2-diethoxyphosphoryl-4-methoxy-butanoate in step E.

$^1H$ NMR (400 MHz, $CD_3OD$) δ 7.59 (d, J=8.0 Hz, 1H), 7.56 (s, 1H), 7.48 (t, J 8.0 Hz, 1H), 7.43 (s, 1H), 7.20 (t, J=9.6 Hz, 2H), 6.84 (d, J=7.2 Hz, 1H), 6.61-6.74 (m, 1H), 5.41 (s, 2H), 5.03-5.16 (m, 1H), 4.59-4.71 (m, 2H), 4.42-4.53 (m, 2H), 3.89-4.07 (m, 2H), 3.58 (t, J=6.8 Hz, 2H), 3.34 (s, 3H), 3.04-3.24 (m, 2H), 2.82-2.88 (m, 2H), 2.70-2.79 (m, 2H), 2.43-2.57 (m, 3H), 1.72-2.08 (m, 4H). LC-MS: m/z 599.4 $(M+H)^+$.

Example 36

(S,E)-3-(2-((4-(6-((5-chloropyridin-2-yl)methoxy)pyridin-2-yl)piperidin-1-yl)methyl)-1-(oxetan-2-ylmethyl)-1H-imidazol-5-yl)-2-methylacrylic acid (Compound 217a)

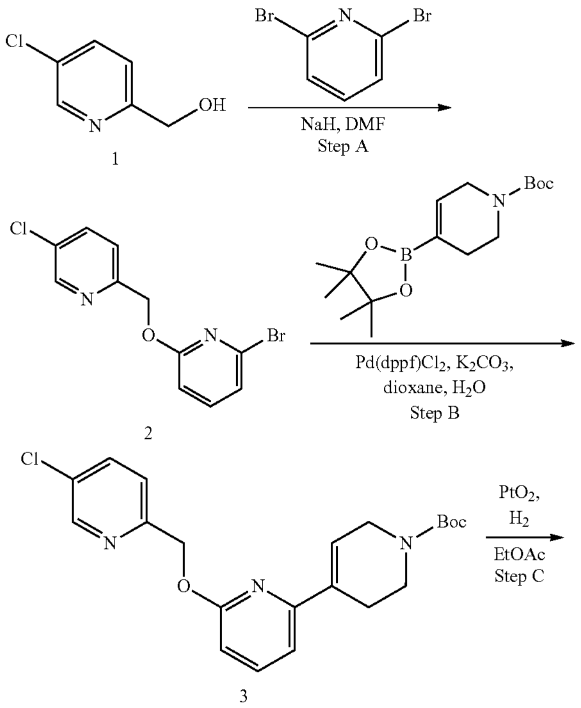

-continued

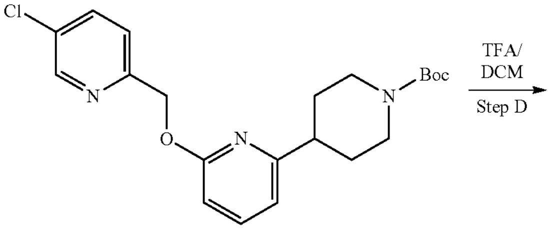

4

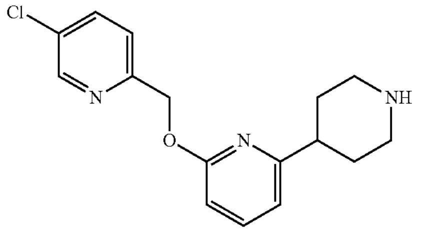

6

Step A: 2-(((6-bromopyridin-2-yl)oxy)methyl)-5-chloropyridine

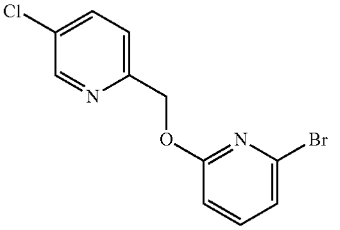 [SMILES: Clc1ccc(COc2cccc(Br)n2)nc1]

To a solution of (5-chloro-2-pyridyl)methanol (1.00 g, 6.97 mmol) in THF (10 mL) was added dropwise NaH (334 mg, 8.36 mmol, 60% purity) at 0° C. After addition, the mixture was stirred at this temperature for 1 hour, and then 2,6-dibromopyridine (1.65 g, 6.97 mmol) was added at 25° C. The resulting mixture was stirred at 25° C. for 4 hours. The mixture was poured into ice-water and stirred for 10 minutes. The aqueous phase was extracted with EtOAc (20 mL*3). The combined organic phase was washed with brine (30 mL), dried over anhydrous $Na_2SO_4$, filtered and concentrated in vacuum to give a residue. The residue was purified by column chromatography ($SiO_2$, Petroleum ether/Ethyl acetate=15/1 to 10/1) to give 2-(((6-bromopyridin-2-yl)oxy)methyl)-5-chloropyridine (810 mg, 38.8% yield) as a white solid. LC-MS: m/z 301.0 $(M+H)^+$.

Step B: tert-butyl 6-((5-chloropyridin-2-yl)methoxy)-3',6'-dihydro-[2,4'-bipyridine]-1'(2'H)-carboxylate

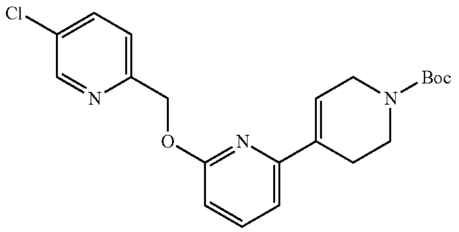

A mixture of 2-(((6-bromopyridin-2-yl)oxy)methyl)-5-chloropyridine (810 mg, 2.70 mmol), tert-butyl 4-(4,4,5,5-tetramethyl-1,3,2-dioxaborolan-2-yl)-3,6-dihydro-2H-pyridine-1-carboxylate (1.00 g, 3.24 mmol), $K_2CO_3$ (747 mg, 5.41 mmol) and Pd(dppf)$Cl_2$ (198 mg, 270 umol) in $H_2O$ (3 mL) and dioxane (10 mL) was degassed and purged with $N_2$ for 3 times, and then the mixture was stirred at 80° C. for 12 hours under $N_2$ atmosphere. Then the reaction mixture was concentrated under reduced pressure to remove solvent. The residue was diluted with $H_2O$ (30 mL) and extracted with EtOAc (30 mL*3). The combined organic layers were washed with brine (40 mL), dried over anhydrous $Na_2SO_4$, filtered and concentrated under reduced pressure to give a residue. The residue was purified by column chromatography ($SiO_2$, Petroleum ether/Ethyl acetate=20/1 to 10/1) to give tert-butyl 6-((5-chloropyridin-2-yl)methoxy)-3',6'-dihydro-[2,4'-bipyridine]-1'(2'H)-carboxylate (850 mg, 78.2% yield) as a colorless oil. LC-MS: m/z 402.0 $(M+H)^+$.

Step C: tert-butyl 4-(6-((5-chloropyridin-2-yl)methoxy)pyridin-2-yl)piperidine-1-carboxylate

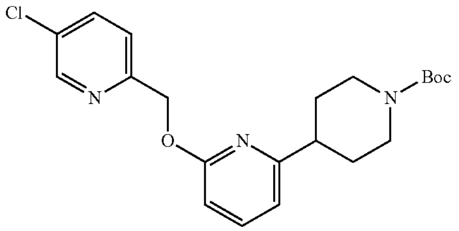 [SMILES: CC(C)(C)OC(=O)N1CCC(c2cccc(OCc3ccc(Cl)cn3)n2)CC1]

To a solution of tert-butyl 6-((5-chloropyridin-2-yl)methoxy)-3',6'-dihydro-[2,4'-25 bipyridine]-1'(2'H)-carboxylate (850 mg, 2.12 mmol) in EtOAc (15 mL) was added $PtO_2$ (20%, 200 mg) under $N_2$ atmosphere. The suspension was degassed under vacuum and purged with $H_2$ several times. The mixture was stirred under $H_2$ (15 psi) at 25° C. for 2 hours. The reaction mixture was filtered and the filter was concentrated to give a residue. The residue was purified by flash silica gel chromatography (ISCO®; 20 g SepaFlash® Silica Flash Column, Eluent of 0-20% Ethyl acetate/Petroleum ether gradient @ 80 mL/min) to give tert-butyl 4-(6-((5-chloropyridin-2-yl)methoxy)pyridin-2-yl)piperidine-1-carboxylate (260 mg, 30.4% yield) as a colorless oil. LC-MS: m/z 404.1 $(M+H)^+$.

Step D: 5-chloro-2-(((6-(piperidin-4-yl)pyridin-2-yl)oxy)methyl)pyridine TFA salt

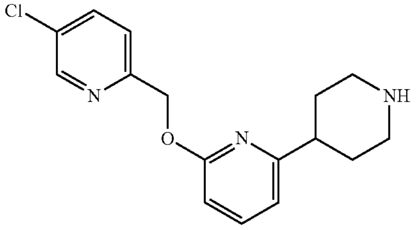 [SMILES: Clc1ccc(COc2cccc(C3CCNCC3)n2)nc1]

To a solution of tert-butyl 4-(6-((5-chloropyridin-2-yl)methoxy)pyridin-2-yl)piperidine-1-carboxylate (1.33 g, 3.29 mmol) in DCM (10 mL) was added TFA (3.75 g, 32.93 mmol, 2.44 mL) dropwise at 0° C. The reaction mixture was stirred at 25° C. for 4 hours. The reaction mixture was concentrated to give 5-chloro-2-(((6-(piperidin-4-yl)pyridin-2-yl)oxy)methyl)pyridine TFA salt (crude, 300 mg). LC-MS: m/z 304.1 $(M+H)^+$.

(S,E)-3-(2-((4-(6-((5-chloropyridin-2-yl)methoxy)pyridin-2-yl)piperidin-1-yl)methyl)-1-(oxetan-2-ylmethyl)-1H-imidazol-5-yl)-2-methylacrylic acid (Compound 217a)

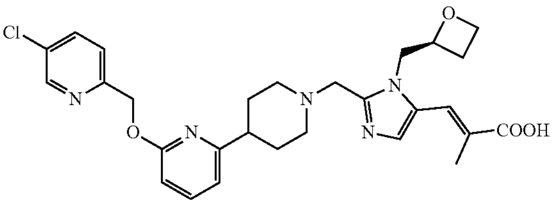 [SMILES: C/C(=C\c1cnc(CN2CCC(c3cccc(OCc4ccc(Cl)cn4)n3)CC2)n1C[C@@H]1CCO1)C(=O)O]

Compound 217a was then synthesized following the route of Example 12, using 5-chloro-2-(((6-(piperidin-4-yl)pyridin-2-yl)oxy)methyl)pyridine TFA salt in step A and (S)-oxetan-2-ylmethanamine methanesulfonate in step B.

$^1$H NMR (400 MHz, $CD_3OD$) δ 8.52 (d, J=2.0 Hz, 1H), 7.83 (dd, J=8.4, 2.4 Hz, 1H), 7.61 (t, J 7.8 Hz, 1H), 7.55 (s, 1H), 7.49 (d, J 8.4 Hz, 1H), 7.29 (s, 1H), 6.84 (d, J=7.2 Hz, 1H), 6.73 (d, J=8.4 Hz, 1H), 5.46 (s, 2H), 5.04-5.18 (m, 1H), 4.60-4.72 (m, 2H), 4.42-4.54 (m, 2H), 3.82-4.04 (m, 2H), 2.98-3.18 (m, 2H), 2.74-2.84 (m, 1H), 2.59-2.70 (m, 1H), 2.37-2.55 (m, 3H), 2.10 (s, 3H), 1.74-1.88 (m, 4H). LC-MS: m/z 538.2 $(M+H)^+$.

(SE)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)-2-methylacrylic acid (Compound 218a) was synthesized following the route of Example 12, using 2-((4-chloro-2-fluorobenzyl)oxy)-6-(piperidin-4-yl)pyri dine in step A and (S)-oxetan-2-ylmethanamine methanesulfonate in step B.

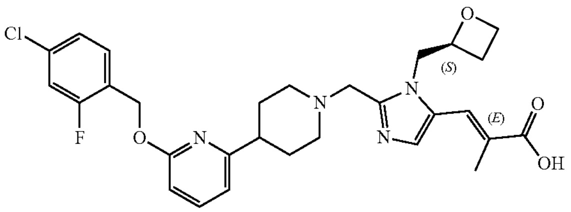

$^1$H NMR (400 MHz, $CD_3OD$) δ 7.44-7.65 (m, 3H), 7.30 (s, 1H), 7.20 (t, J=9.2 Hz, 2H), 6.84 (d, J=7.2 Hz, 1H), 6.65 (d, J=8.0 Hz, 1H), 5.42 (s, 2H), 5.09-4.97 (m, 1H), 4.44-4.52 (m, 2H), 3.93-3.99 (m, 2H), 3.07-3.21 (m, 1H), 2.39-2.91 (m, 8H), 2.11 (s, 3H), 1.84-1.95 (m, 4H). LC-MS: m/z 555.1 $(M+H)^+$.

(E)-3-(2-((4-(6-((4-chloro-2-fluorobenzyl)oxy)pyridin-2-yl)piperidin-1-yl)methyl)-1-((1-ethyl-1H-imidazol-5-yl)methyl)-1H-imidazol-5-yl)-2-methylacrylic acid (Compound 219) was synthesized following the route of Example 12, using 2-((4-chloro-2-fluorobenzyl)oxy)-6-(piperidin-4-yl)pyridine in step A.

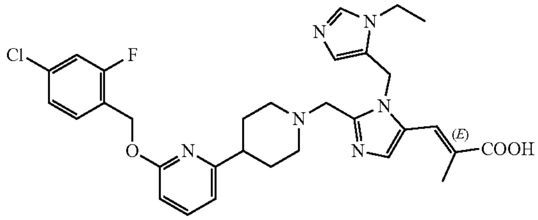

$^1$H NMR (400 MHz, $CD_3OD$) δ 7.71 (s, 1H), 7.52-7.59 (m, 1H), 7.44-7.51 (m, 2H), 7.32-7.34 (m, 1H), 7.17-7.23 (m, 2H), 6.76 (d, J=7.6 Hz, 1H), 6.62 (d, J=8.0 Hz, 1H), 6.39 (s, 1H), 5.57 (s, 2H), 5.38 (s, 2H), 4.12 (q, J=7.2 Hz, 2H), 3.71 (s, 2H), 2.85-2.92 (m, 2H), 2.51-2.65 (m, 1H), 2.12-2.22 (m, 2H), 2.09 (s, 3H), 1.72-1.83 (m, 2H), 1.50-1.64 (m, 2H), 1.41 (t, J=7.2 Hz, 3H). LC-MS: m/z 593.1 $(M+H)^+$.

(E)-3-(2-((4-(6-((5-chloropyridin-2-yl)methoxy)pyridin-2-yl)piperidin-1-yl)methyl)-1-((1-ethyl-1H-imidazol-5-yl)methyl)-1H-imidazol-5-yl)-2-methylacrylic acid (Compound 220) was synthesized following the route of Example 12, using 5-chloro-2-(((6-(piperidin-4-yl)pyridin-2-yl)oxy)methyl)pyridine in step A.

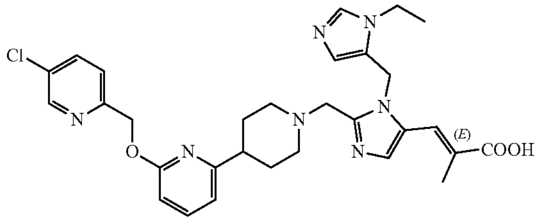

$^1$H NMR (400 MHz, $CD_3OD$) δ 8.47-8.57 (m, 1H), 7.76-7.86 (m, 2H), 7.58 (t, J=7.2 Hz, 1H), 7.49 (d, J=8.4 Hz, 1H), 7.43 (s, 1H), 7.30 (s, 1H), 6.76 (d, J=7.2 Hz, 1H), 6.69 (d, J=8.4 Hz, 1H), 6.39 (s, 1H), 5.54 (s, 2H), 5.45 (s, 2H), 4.13 (q, J=7.2 Hz, 2H), 3.70 (s, 2H), 2.80-2.90 (m, 2H), 2.44-2.59 (m, 1H), 2.15 (t, J=10.4 Hz, 2H), 2.11 (s, 3H), 1.65-1.77 (m, 2H), 1.44-1.58 (m, 2H), 1.40 (t, J=7.2 Hz, 3H). LC-MS: m/z 576.3 $(M+H)^+$.

Example 37
(Z)-3-(2-((4-(6-((4-chloro-2-fluorobenzyl)oxy)pyridin-2-yl)piperidin-1-yl)methyl)-1-(2-methoxyethyl)-1H-imidazol-5-yl)-3-fluoroacrylic acid (Compound 221)
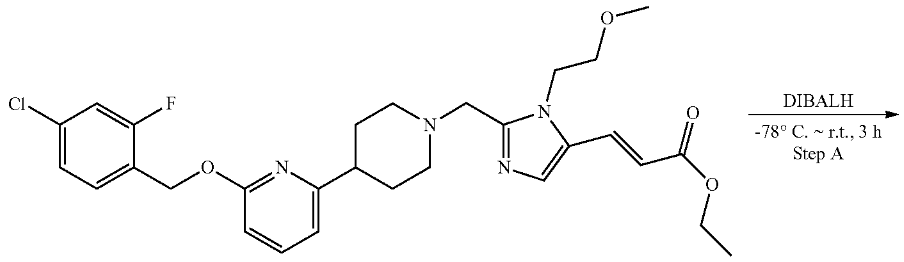
1
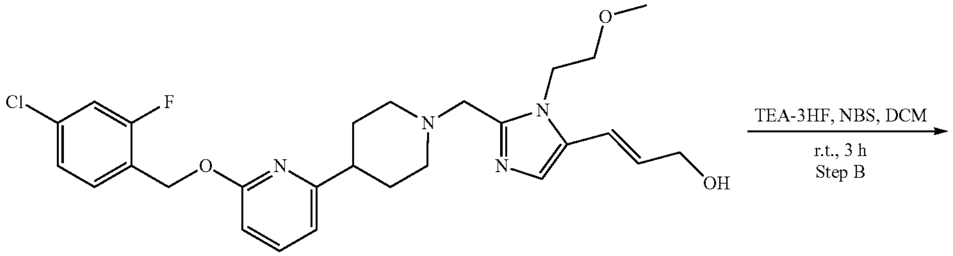
2
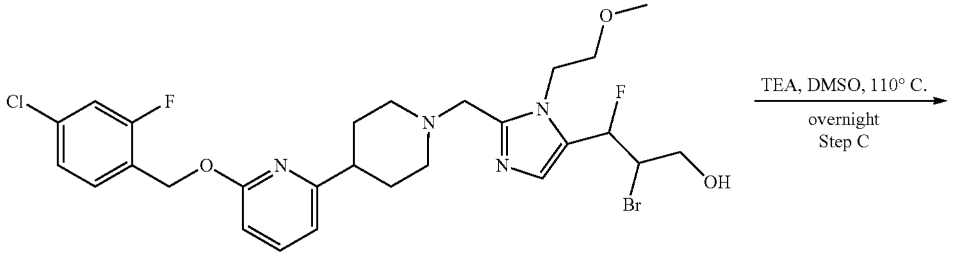
3
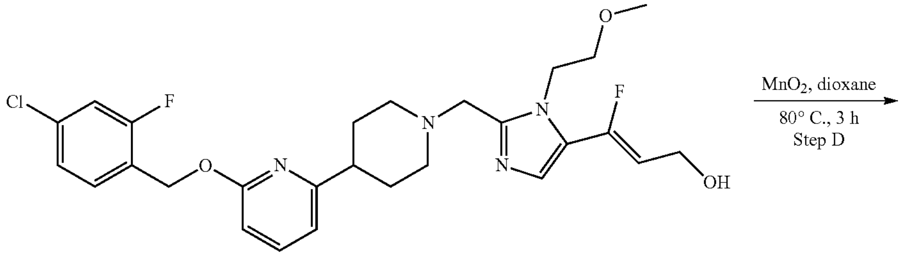
4
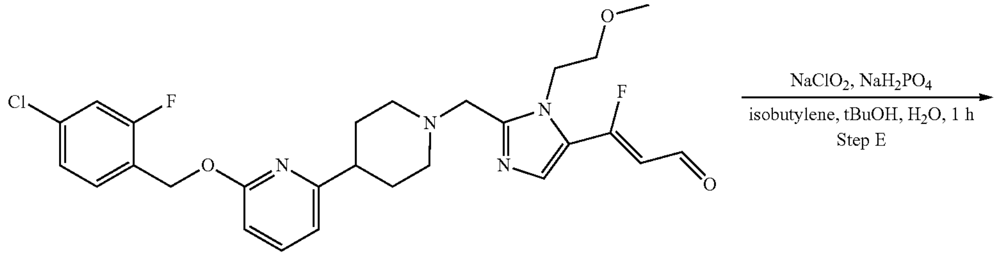
5

-continued

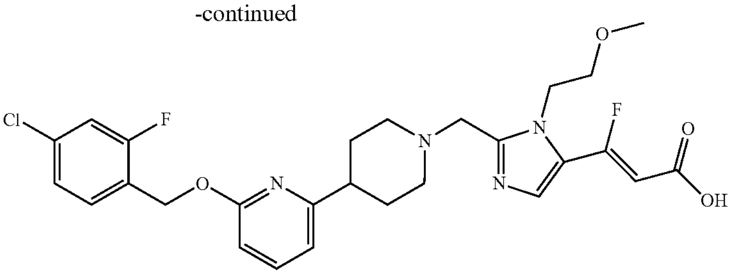

Compound 221

Step A: (E)-3-(2-((4-(6-((4-chloro-2-fluorobenzyl)oxy)pyridin-2-yl)piperidin-1-yl)methyl)-1-(2-methoxyethyl)-1H-imidazol-5-yl)prop-2-en-1-ol

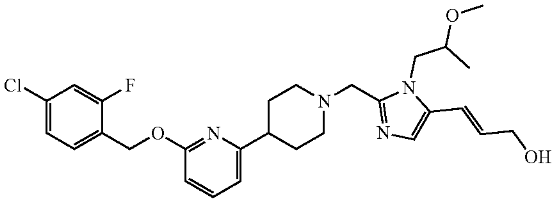 [SMILES: COC(C)Cn1c(/C=C/CO)cnc1CN1CCC(c2cccc(OCc3ccc(Cl)cc3F)n2)CC1]

To a reaction mixture of ethyl (E)-3-(2-((4-(6-((4-chloro-2-fluorobenzyl)oxy)pyridin-2-yl)piperidin-1-yl)methyl)-1-(2-methoxyethyl)-1H-imidazol-5-yl)acrylate (885 mg, 1.59 mmol, synthesized following the route of Example 34 using 4-(6-((4-chloro-2-fluorobenzyl)oxy)pyridin-2-yl)piperidin-1-ium chloride in step B and 2-methoxyethanamine in step C) in THF (20 mL) was added DIBAL-H (11 mL, 1 M in hexane) at −78° C. under $N_2$. The reaction mixture was stirred at room temperature for 3 hours under $N_2$. Then the reaction mixture was quenched with saturated potassium sodium tartrate aqueous solution and filtered. THF was removed and aqueous layer was extracted with DCM (10 mL*3). The organic phase was dried over $Na_2SO_4$, concentrated and purified by flash column chromatography (silica gel, eluting with MeOH/DCM) to give (E)-3-(2-((4-(6-((4-chloro-2-fluorobenzyl)oxy)pyridin-2-yl)piperidin-1-yl)methyl)-1-(2-methoxyethyl)-1H-imidazol-5-yl)prop-2-en-1-ol as a light yellow oil (223 mg, 62% yield). LC-MS: m/z 515.2 $(M+H)^+$.

Step B: 2-bromo-3-(2-((4-(6-((4-chloro-2-fluorobenzyl)oxy)pyridin-2-yl)piperidin-1-yl)methyl)-1-(2-methoxyethyl)-1H-imidazol-5-yl)-3-fluoropropan-1-ol

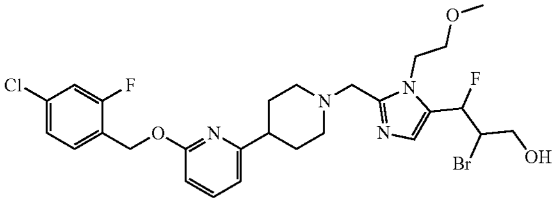 [SMILES: COCCn1c(C(F)C(Br)CO)cnc1CN1CCC(c2cccc(OCc3ccc(Cl)cc3F)n2)CC1]

To a reaction mixture of (E)-3-(2-((4-(6-((4-chloro-2-fluorobenzyl)oxy)pyridin-2-yl)piperidin-1-yl)methyl)-1-(2-methoxyethyl)-1H-imidazol-5-yl)prop-2-en-1-ol (335 mg, 0.650 mmol) in DCM (6 mL) was added TEA3HF (157 mg, 0.976 mmol). After stirred at room temperature for 10 minutes, NBS (127 mg, 0.715 mmol) was added. The reaction mixture was stirred for 3 hours at room temperature, and then dry DMSO was added. The DCM was evaporated in vacuo and the remained residue was used in the next step directly. LC-MS: m/z 613.2/615.2 $(M+H)^+$.

Step C: (Z)-3-(2-((4-(6-((4-chloro-2-fluorobenzyl)oxy)pyridin-2-yl)piperidin-1-yl)methyl)-1-(2-methoxyethyl)-1H-imidazol-5-yl)-3-fluoroprop-2-en-1-ol

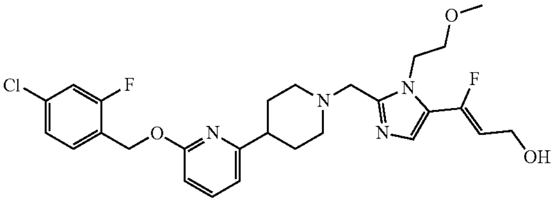 [SMILES: COCCn1c(/C(F)=C/CO)cnc1CN1CCC(c2cccc(OCc3ccc(Cl)cc3F)n2)CC1]

To the reaction mixture of step B was added TEA (1 mL). The reaction mixture was stirred at 110° C. overnight under $N_2$. The reaction mixture was quenched with saturated ammonium chloride aqueous solution, and extracted with EtOAc (30 mL*3). The organic layers was washed with brine (10 mL), dried over $Na_2SO_4$, concentrated and purified by flash column chromatography (silica gel, eluting with MeOH/DCM) to give (Z)-3-(2-((4-(6-((4-chloro-2-fluorobenzyl)oxy)pyridin-2-yl)piperidin-1-yl)methyl)-1-(2-methoxyethyl)-1H-imidazol-5-yl)-3-fluoroprop-2-en-1-ol as a yellow oil (78.0 mg, 22% yield over two steps). LC-MS: m/z 533.2 $(M+H)^+$.

Step D: (Z)-3-(2-((4-(6-((4-chloro-2-fluorobenzyl)oxy)pyridin-2-yl)piperidin-1-yl)methyl)-1-(2-methoxyethyl)-1H-imidazol-5-yl)-3-fluoroacrylaldehyde

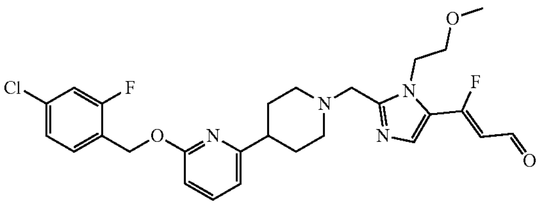 [SMILES: COCCn1c(/C(F)=C/C=O)cnc1CN1CCC(c2cccc(OCc3ccc(Cl)cc3F)n2)CC1]

To a reaction mixture of (Z)-3-(2-((4-(6-((4-chloro-2-fluorobenzyl)oxy)pyridin-2-yl)piperidin-1-yl)methyl)-1-(2-methoxyethyl)-1H-imidazol-5-yl)-3-fluoroprop-2-en-1-ol (78.0 mg, 0.146 mmol) in dioxane (2.5 mL) was added $MnO_2$ (127 mg, 1.46 mmol). The reaction mixture was stirred at 80° C. for 3 hours. Then the reaction mixture was filtered, the filtrate was concentrated and purified by flash column chromatography (silica gel, eluting with MeOH/DCM) to give (Z)-3-(2-((4-(6-((4-chloro-2-fluorobenzyl)oxy)pyridin-2-yl)piperidin-1-yl)methyl)-1-(2-methoxyethyl)-1H-imidazol-5-yl)-3-fluoroacrylaldehyde as a light yellow oil (27.0 mg, 35% yield). LC-MS: m/z 531.2 $(M+H)^+$.

Step E: (Z)-3-(2-((4-(6-((4-chloro-2-fluorobenzyl)oxy)pyridin-2-yl)piperidin-1-yl)methyl)-1-(2-methoxyethyl)-1H-imidazol-5-yl)-3-fluoroacrylic acid (Compound

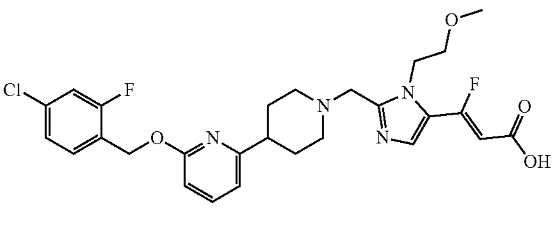 [SMILES: COCCn1c(/C(F)=C/C(=O)O)cnc1CN1CCC(c2cccc(OCc3ccc(Cl)cc3F)n2)CC1]

To a reaction mixture of (Z)-3-(2-((4-(6-((4-chloro-2-fluorobenzyl)oxy)pyridin-2-yl)piperidin-1-yl)methyl)-1-(2-methoxyethyl)-1H-imidazol-5-yl)-3-fluoroacrylaldehyde (27.0 mg, 0.0510 mmol) and isobutylene (29.0 mg, 0.407 mmol) in t-Butanol (2 mL) was added a solution of $NaClO_2$ (37.0 mg, 0.407 mmol) and $NaH_2PO_4$ (49.0 mg, 0.407 mmol) in water (0.9 mL) dropwise. The reaction mixture was stirred at room temperature for 1 hour. The reaction mixture was quenched with 10% HCl aqueous solution (1 mL) and brine (2 mL), and then extracted with EtOAc (10 mL*3). The organic layer was washed with saturated sodium bicarbonate aqueous solution (10 mL) and brine (10 mL), dried over $Na_2SO_4$, concentrated and purified by Prep-HPLC (0.1% formic acid in water and acetonitrile) to give (Z)-3-(2-((4-(6-((4-chloro-2-fluorobenzyl)oxy)pyridin-2-yl)piperidin-1-yl)methyl)-1-(2-methoxyethyl)-1H-imidazol-5-yl)-3-fluoroacrylic acid as a white solid (1.2 mg, 4% yield). $^1H$ NMR (400 MHz, DMSO-$d_6$) δ 7.63 (t, J=8.0 Hz, 1H), 7.55 (t, J=8.0 Hz, 1H), 7.45 (d, J=10.0 Hz, 1H), 7.29 (d, J=6.4 Hz, 2H), 6.86 (d, J=7.2 Hz, 1H), 6.67 (d, J=8.0 Hz, 1H), 5.72 (d, J=36.8 Hz, 1H), 5.36 (s, 2H), 4.35 (s, 2H), 3.60-3.70 (m, 4H), 3.23 (s, 3H), 2.85 (d, J=10.8 Hz, 2H), 2.56-2.64 (m, 1H), 2.11 (t, J=11.2 Hz, 2H), 1.60-1.86 (m, 4H). LC-MS: m/z 547.2 $(M+H)^+$.

Example 38

(R,E)-3-(2-((4-(2-(4-chlorophenyl)-2,3-dihydrobenzo[b][1,4]dioxin-5-yl)piperidin-1-yl)methyl)-1-(oxazol-2-ylmethyl)-1H-imidazol-4-yl)acrylic acid (Compound 222a)

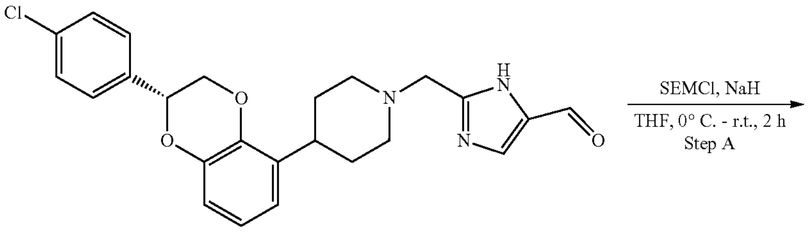

1

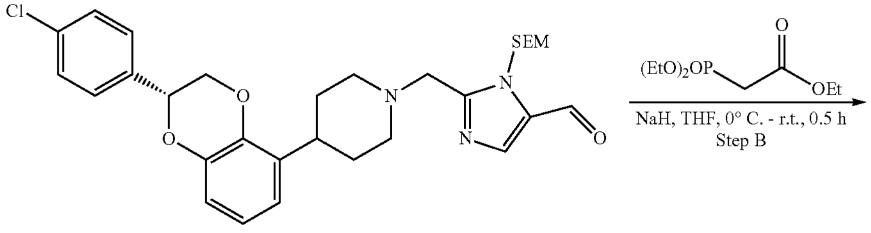

2

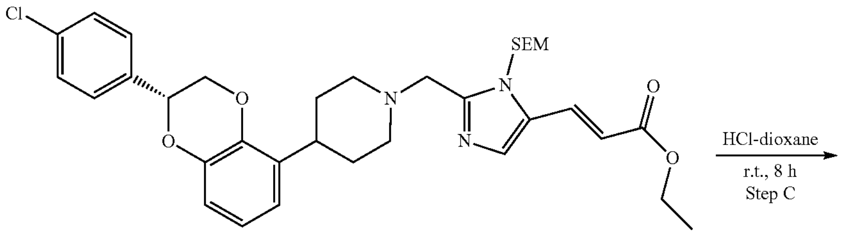

3

-continued

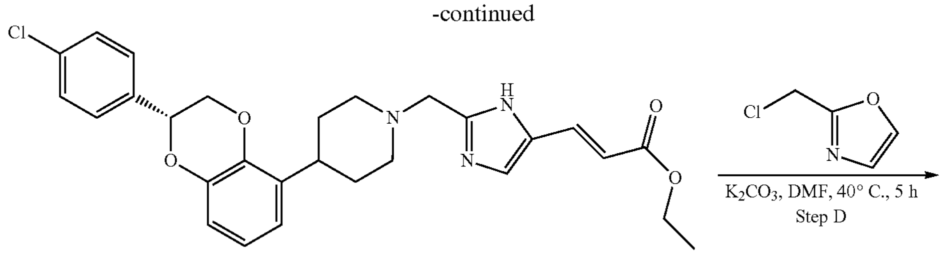

4

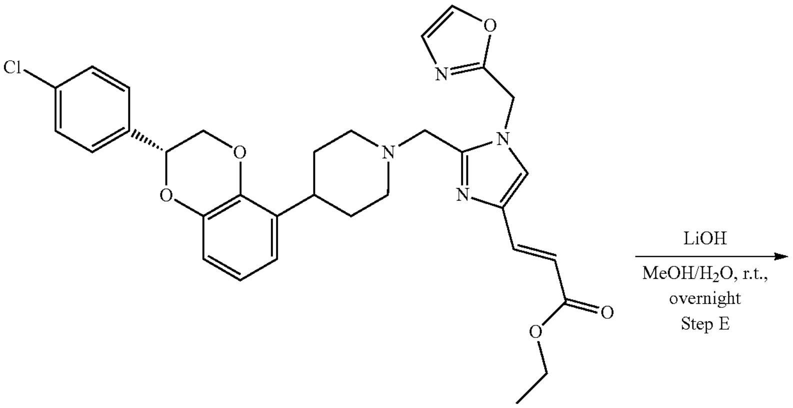

5

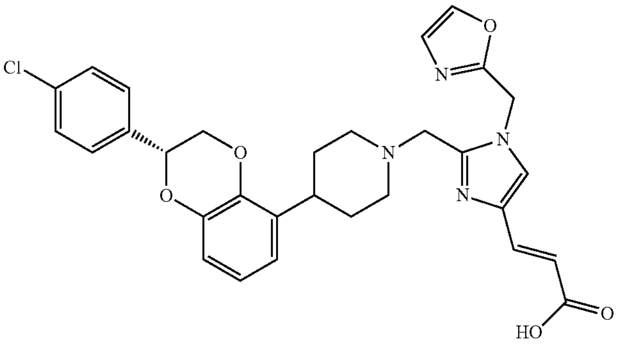

Compound 222a

Step A: (R)-2-((4-(2-(4-chlorophenyl)-2,3-dihydrobenzo[b][1,4]dioxin-5-yl)piperidin-1-yl)methyl)-1-((2-(trimethyl silyl)ethoxy)methyl)-1H-imidazole-5-carbaldehyde

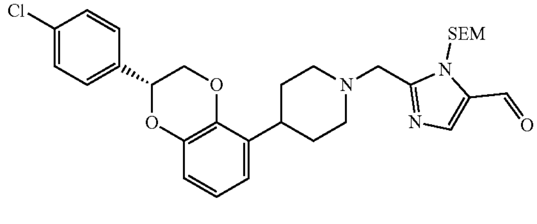 [SMILES: C[Si](C)(C)CCOCn1c(C=O)cnc1CN1CCC(c2cccc3c2OC[C@@H](c2ccc(Cl)cc2)O3)CC1]

To a solution of (R)-2-((4-(2-(4-chlorophenyl)-2,3-dihydrobenzo[b][1,4]dioxin-5-yl)piperidin-1-yl)methyl)-1H-imidazole-5-carbaldehyde (100 mg, 0.230 mmol) in THF (2 mL) was added NaH (60% in oil, 18.3 mg, 0.460 mmol) at 0° C. The mixture was stirred at room temperature for 0.5 hour, and (2-(chloromethoxy)ethyl)trimethylsilane (76.3 mg, 0.460 mmol) was added. The reaction mixture was stirred at room temperature for 2 hours. The reaction solution was quenched with sat. $NH_4Cl$ aq. solution (2 mL) and extracted with EtOAc (5 mL*3). The organic layers were washed with brine (5 mL), dried over $Na_2SO_4$, concentrated to give (R)-2-((4-(2-(4-chlorophenyl)-2,3-dihydrobenzo[b][1,4]dioxin-5-yl)piperidin-1-yl)methyl)-1-((2-(trimethylsilyl)ethoxy)methyl)-1H-imidazole-5-carbaldehyde as an oil (crude, 140 mg). LC-MS: m/z 568.3 $(M+H)^+$.

Step B: ethyl (R,E)-3-(2-((4-(2-(4-chlorophenyl)-2,3-dihydrobenzo[b][1,4]dioxin-5-yl)piperidin-1-yl)methyl)-1-((2-(trimethylsilyl)ethoxy)methyl)-1H-imidazol-5-yl)acrylate

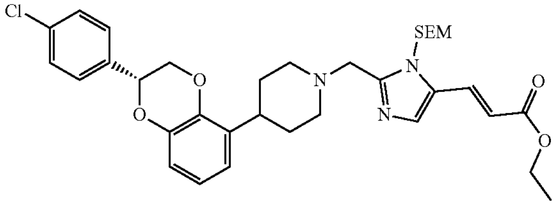 [SMILES: CCOC(=O)/C=C/c1cnc(CN2CCC(c3cccc4c3OC[C@@H](c3ccc(Cl)cc3)O4)CC2)n1COCC[Si](C)(C)C]

To a solution of (R)-2-((4-(2-(4-chlorophenyl)-2,3-dihydrobenzo[b][1,4]dioxin-5-yl)piperidin-1-yl)methyl)-1-((2-(trimethyl silyl)ethoxy)methyl)-1H-imidazole-5-carbaldehyde (crude, 140 mg, 0.250 mmol) in THF (2 mL) was added NaH (60% in oil, 20.0 mg, 0.500 mmol) at 0° C. The reaction mixture was stirred at room temperature for 0.5 hour, and ethyl 2-(diethoxyphosphoryl)acetate (82.9 mg, 0.370 mmol) was added. The reaction mixture was stirred at room temperature for 0.5 hour. Then the reaction mixture was quenched with sat. $NH_4Cl$ aq. solution (2 mL) and extracted with EtOAc (5 mL*3). The organic layers were washed with brine (5 mL), dried over $Na_2SO_4$, concentrated and purified by prep-HPLC (0.1% formic acid in water and acetonitrile) to give ethyl (RE)-3-(2-((4-(2-(4-chlorophenyl)-2,3-dihydrobenzo[b][1,4]dioxin-5-yl)piperidin-1-yl)methyl)-1-((2-(trimethylsilyl)ethoxy)methyl)-1H-imidazol-5-yl)acrylate as a white solid (100 mg, 63% yield over two steps). LC-MS: m/z 638.3 $(M+H)^+$.

Step C: ethyl (R,E)-3-(2-((4-(2-(4-chlorophenyl)-2,3-dihydrobenzo[b][1,4]dioxin-5-yl)piperidin-1-yl)methyl)-1H-imidazol-5-yl)acrylate

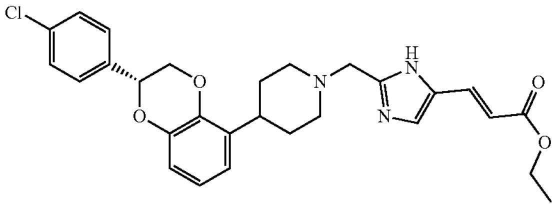 [SMILES: CCOC(=O)/C=C/c1cnc(CN2CCC(c3cccc4c3OC[C@@H](c3ccc(Cl)cc3)O4)CC2)[nH]1]

A solution of ethyl (RE)-3-(2-((4-(2-(4-chlorophenyl)-2,3-dihydrobenzo[b][1,4]dioxin-5-yl)piperidin-1-yl)methyl)-1-((2-(trimethylsilyl)ethoxy)methyl)-1H-imidazol-5-yl)acrylate (100 mg, 0.160 mmol) in HCl-dioxane solution (2 mL, 4 mol/L) was stirred at room temperature for 8 hours. The reaction mixture was concentrated in vacuo to give ethyl (R,E)-3-(2-((4-(2-(4-chlorophenyl)-2,3-dihydrobenzo[b][1,4]dioxin-5-yl)piperidin-1-yl)methyl)-1H-imidazol-5-yl)acrylate as a white solid (crude, HCl salt, 130 mg, over 100% yield). LC-MS: m/z 508.2 $(M+H)^+$.

Step D: ethyl (R,E)-3-(2-((4-(2-(4-chlorophenyl)-2,3-dihydrobenzo[b][1,4]dioxin-5-yl)piperidin-1-yl)methyl)-1-(oxazol-2-ylmethyl)-1H-imidazol-5-yl)acrylate

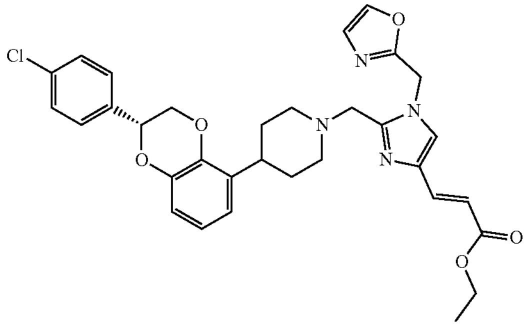 [SMILES: CCOC(=O)/C=C/c1cn(Cc2ncco2)c(CN2CCC(c3cccc4c3OC[C@@H](c3ccc(Cl)cc3)O4)CC2)n1]

A mixture of ethyl (RE)-3-(2-((4-(2-(4-chlorophenyl)-2,3-dihydrobenzo[b][1,4]dioxin-5-yl)piperidin-1-yl)methyl)-1H-imidazol-5-yl)acrylate (80.0 mg, 0.150 mmol, HCl salt), 2-(chloromethyl)oxazole (18.8 mg, 0.160 mmol), and $K_2CO_3$ (60.8 mg, 0.440 mmol) in DMF (2 mL) was stirred at 40° C. for 5 hours under $N_2$ atmosphere. The reaction mixture was diluted with $H_2O$ (10 mL) and extracted with EtOAc (10 mL*3). The organic layers were washed with brine (10 mL), dried over $Na_2SO_4$, and concentrated in vacuo to give ethyl (R,E)-3-(2-((4-(2-(4-chlorophenyl)-2,3-dihydrobenzo[b][1,4]dioxin-5-yl)piperidin-1-yl)methyl)-1-(oxazol-2-ylmethyl)-1H-imidazol-5-yl)acrylate (crude, 88.4 mg), which was used in next step directly. LC-MS: m/z 589.2 $(M+H)^+$.

Step E: (R,E)-3-(2-((4-(2-(4-chlorophenyl)-2,3-dihydrobenzo[b][1,4]dioxin-5-yl)piperidin-1-yl)methyl)-1-(oxazol-2-ylmethyl)-1H-imidazol-4-yl)acrylic acid (Compound 222a)

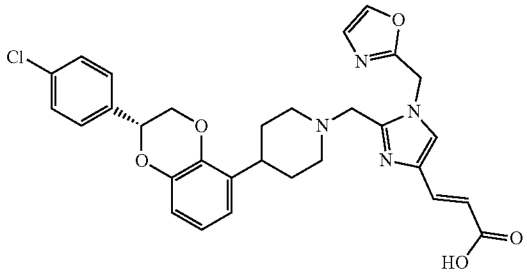 [SMILES: O=C(O)/C=C/c1cn(Cc2ncco2)c(CN2CCC(c3cccc4c3OC[C@@H](c3ccc(Cl)cc3)O4)CC2)n1]

A solution of ethyl (RE)-3-(2-((4-(2-(4-chlorophenyl)-2,3-dihydrobenzo[b][1,4]dioxin-5-yl)piperidin-1-yl)methyl)-1-(oxazol-2-ylmethyl)-1H-imidazol-5-yl)acrylate (crude, 88.4 mg, 0.150 mmol), LiOH (18.0 mg, 0.750 mmol) in McOH/$H_2O$ (2 mL/0.5 mL) was stirred at room temperature overnight. The mixture was adjusted to pH=5-6, and purified by prep-HPLC (0.1% formic acid in water and acetonitrile) to give (RE)-3-(2-((4-(2-(4-chlorophenyl)-2,3-dihydrobenzo[b][1,4]dioxin-5-yl)piperidin-1-yl)methyl)-1-(oxazol-2-ylmethyl)-1H-imidazol-4-yl)acrylic acid (10.0 mg, 12% yield over two steps). $^1H$ NMR (400 MHz, DMSO-$d_6$) δ 12.20 (br.s, 1H), 8.14 (d, J=0.4 Hz, 1H), 7.68 (s, 1H), 7.47-7.53 (m, 4H), 7.42 (d, J=15.6 Hz, 1H), 7.23 (d, J=0.4 Hz, 1H), 6.80-6.86 (m, 2H), 6.70 (dd, J=7.2, 2.0 Hz, 1H), 6.26 (d, J=15.6 Hz, 1H), 5.54 (s, 2H), 5.24 (dd, J=8.4, 2.4 Hz, 1H), 4.48 (dd, J=11.6, 2.4 Hz, 1H), 4.03 (dd, J=11.6, 8.4 Hz, 1H), 3.59 (s, 2H), 2.76-2.78 (m, 3H), 2.02 (t, J=10.8 Hz, 2H), 1.54-1.63 (m, 2H), 1.29-1.36 (m, 2H). LC-MS: m/z 561.2 $(M+H)^+$.

Example 39

(Z)-3-(2-((4-(6-((4-chloro-2-fluorobenzyl)oxy)pyridin-2-yl)piperidin-1-yl)methyl)-1-methyl-1H-imidazol-5-yl)acrylic acid (Compound 109)

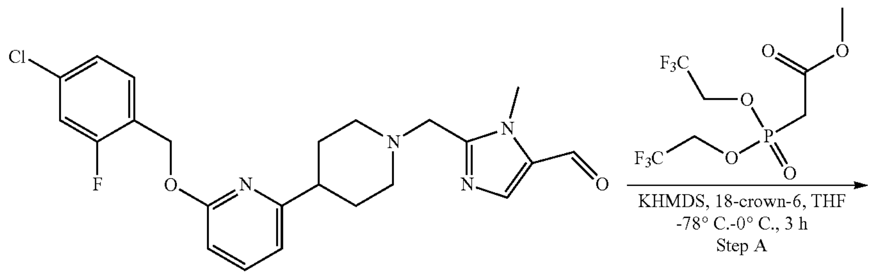

1

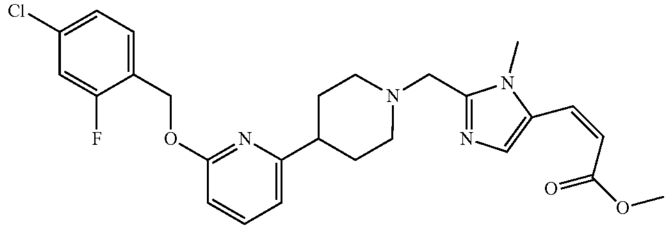

2

Step A: (Z)-methyl 3-(2-((4-(6-((4-chloro-2-fluorobenzyl)oxy)pyridin-2-yl)piperidin-1-yl)methyl)-1-methyl-1H-imidazol-5-yl)acrylate

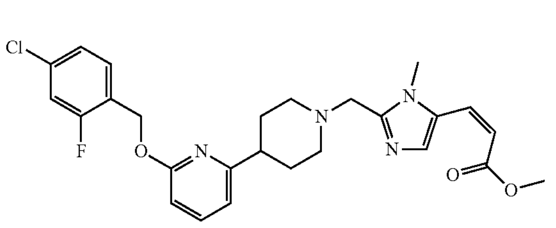 [SMILES: COC(=O)/C=C\c1cnc(CN2CCC(c3cccc(OCc4ccc(Cl)cc4F)n3)CC2)n1C]

To a solution of 2-((4-(6-((4-chloro-2-fluorobenzyl)oxy)pyridin-2-yl)piperidin-1-yl)methyl)-1-methyl-1H-imidazole-5-carbaldehyde (200 mg, 0.450 mmol) in THF (5 mL) were added 18-crown-6 ether (299 mg, 1.13 mmol) and KHMDS (1.0 M in THF, 0.68 mL, 0.680 mmol) dropwise at −78° C. under $N_2$ over 10 mins. The resulting mixture was stirred at −78° C. for 0.5 hour. Then a solution of ethyl 2-(bis(2,2,2-trifluoroethoxy)phosphoryl)acetate (200 mg, 0.450 mmol) in THF (2 mL) was added dropwise. The resulting mixture was stirred at −78° C. for another 3 hours. The reaction mixture was quenched with sat. aq. $NH_4Cl$ solution (5 mL) and extracted with EtOAc (10 mL*3). The combined organic layers were washed by brine (10 mL), dried over $Na_2SO_4$, filtered and concentrated. The residue was purified by silica gel chromatography column (DCM/MeOH=100/1 to 25/1) to give (Z)-methyl 3-(2-((4-(6-((4-chloro-2-fluorobenzyl)oxy)pyridin-2-yl)piperidin-1-yl)methyl)-1-methyl-1H-imidazol-5-yl)acrylate as a yellow solid (100 mg, 43% yield). LC-MS: m/z 499.1 $(M+H)^+$.

(Z)-3-(2-((4-(6-((4-chloro-2-fluorobenzyl)oxy)pyridin-2-yl)piperidin-1-yl)methyl)-1-methyl-1H-imidazol-5-yl)acrylic acid (Compound 109)

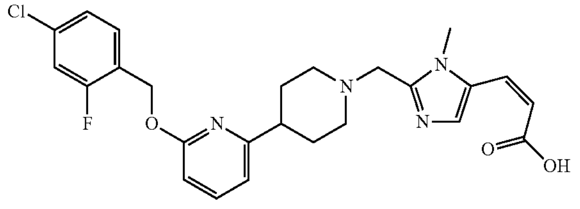 [SMILES: Cn1c(/C=C\C(=O)O)cnc1CN1CCC(c2cccc(OCc3ccc(Cl)cc3F)n2)CC1]

(Compound 109) was then synthesized following the route of Example 1, using (Z)-methyl 3-(2-((4-(6-((4-chloro-2-fluorobenzyl)oxy)pyridin-2-yl)piperidin-1-yl)methyl)-1-methyl-1H-imidazol-5-yl)acrylate in step J.

$^1H$ NMR (400 MHz, DMSO-$d_6$) δ 8.02 (s, 1H), 7.62 (t, J=8.0 Hz, 1H), 7.56 (t, J=8.0 Hz, 1H), 7.45 (dd, J=10.0, 2.0 Hz, 1H), 7.29 (dd, J=8.0, 2.0 Hz, 1H), 6.81-6.99 (m, 2H), 6.66 (d, J=8.0 Hz, 1H), 5.75 (d, J=12.8 Hz, 1H), 5.36 (s, 2H), 3.68 (s, 3H), 3.60 (s, 2H), 2.87 (d, J=11.2 Hz, 2H), 2.53-2.60 (m, 1H), 2.10 (t, J=11.6 Hz, 2H), 1.60-1.80 (m, 4H). LC-MS: m/z 485.1 $(M+H)^+$.

Example 40

(E)-3-(5-((4-(6-((4-chloro-2-fluorobenzyl)oxy)pyridin-2-yl)piperidin-1-yl)methyl)-4-(2-methoxyethyl)-4H-1,2,4-triazol-3-yl)acrylic acid (Compound 223)

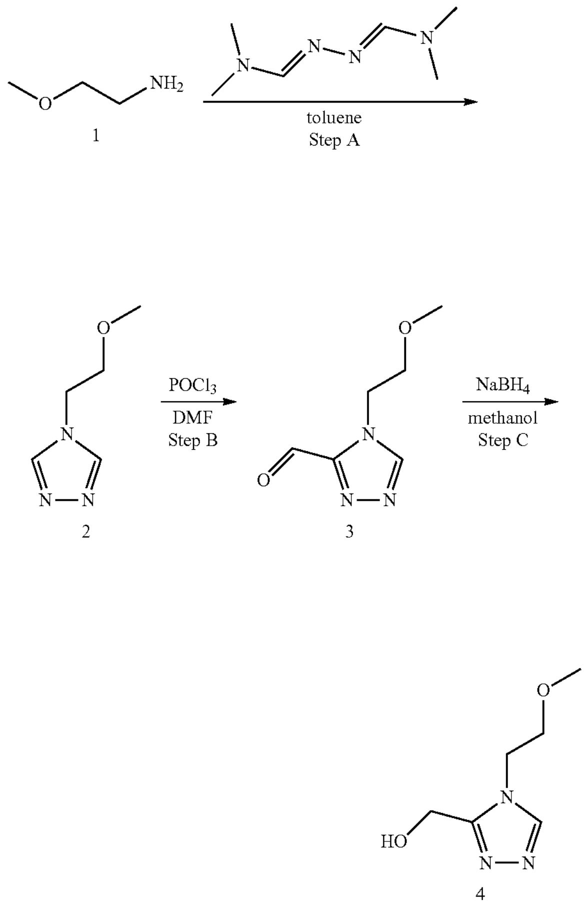

Step A: 4-(2-methoxyethyl)-4H-1,2,4-triazole

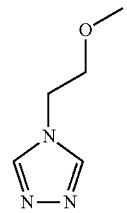

The mixture of 2-methoxyethanamine (2.12 g, 28.2 mmol, 2.45 mL) and N-[(E)-dimethylaminomethyleneamino]-N,N-dimethyl-formamidine (4.00 g, 28.1 mmol) in toluene (40 mL) was stirred at 120° C. for 16 hours. The reaction mixture was concentrated under vacuum to give 4-(2-methoxyethyl)-4H-1,2,4-triazole (3.90 g, crude) as a light-yellow oil. $^1$H NMR (400 MHz, $CDCl_3$) δ 8.21 (s, 2H), 4.16 (t, J=4.8 Hz, 2H), 3.62 (t, J 4.8 Hz, 2H), 3.33 (s, 3H).

Step B: 4-(2-methoxyethyl)-4H-1,2,4-triazole-3-carbaldehyde

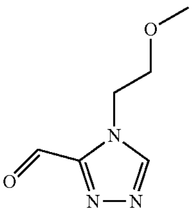

$POCl_3$ (23.5 g, 153 mmol, 14.3 mL) was added dropwise to DMF (45 mL) at 0° C. After stirring at 0° C. for 2 hours, a solution of 4-(2-methoxyethyl)-4H-1,2,4-triazole (3.9 g, 28.1 mmol) in DMF (45 mL) was added dropwise at 0° C. The reaction mixture was stirred at 25° C. for 16 hours. The reaction mixture was poured into saturated $NaHCO_3$ aqueous solution (300 mL) until pH reached to 7-8. The reaction mixture was extracted with n-BuOH (250 mL*3), the combined organic phase was washed with $H_2O$ (200 mL*3), dried over anhydrous $Na_2SO_4$, filtered and evaporated to give crude 4-(2-methoxyethyl)-4H-1,2,4-triazole-3-carbaldehyde (2.58 g, 59.1% yield over two steps) as a brown oil. $^1$H NMR (400 MHz, $CDCl_3$) δ 10.12 (s, 1H), 8.38 (s, 1H), 4.54 (t, J=4.8 Hz, 2H), 3.62 (t, J 4.8 Hz, 2H), 3.30 (s, 3H).

Step C: (4-(2-methoxyethyl)-4H-1,2,4-triazol-3-yl)methanol

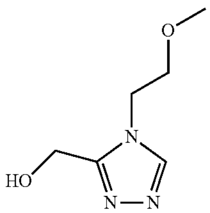

To the mixture of 4-(2-methoxyethyl)-4H-1,2,4-triazole-3-carbaldehyde (2.58 g, 16.6 mmol) in MeOH (40 mL) was added $NaBH_4$ (692 mg, 18.3 mmol) in portions at 0° C. The mixture was stirred at 0° C. for 0.5 hour. The reaction mixture was quenched with $H_2O$ (10 mL). Methanol was removed under vacuum. The reaction mixture was extracted with n-BuOH (30 mL*3). The organic layer was dried over $Na_2SO_4$, filtered and concentrated under vacuum to give (4-(2-methoxyethyl)-4H-1,2,4-triazol-3-yl)methanol (2.14 g, 81.9% yield) as a light yellow oil which was used for next step directly.

(E)-3-(5-((4-(6-((4-chloro-2-fluorobenzyl)oxy)pyridin-2-yl)piperidin-1-yl)methyl)-4-(2-methoxyethyl)-4H-1,2,4-triazol-3-yl)acrylic acid (Compound 223)

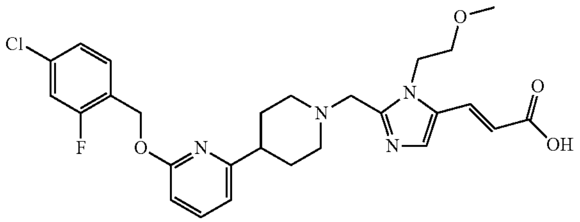 [SMILES: COCCn1c(/C=C/C(=O)O)cnc1CN1CCC(c2cccc(OCc3ccc(Cl)cc3F)n2)CC1]

Compound 223 was then synthesized following the route of Example 8, using (4-(2-methoxyethyl)-4H-1,2,4-triazol-3-yl)methanol in step A.

$^1$H NMR (400 MHz, $CD_3OD$) δ 7.48 (t, J=8.0 Hz, 1H), 7.38-7.43 (m, 2H), 7.07-7.12 (m, 2H), 6.83 (d, J=8.0 Hz, 1H), 6.72 (d, J=4.0 Hz, 1H), 6.53 (d, J=4.0 Hz, 1H), 5.30 (s, 2H), 4.38 (t, J 4.8 Hz, 2H), 3.75 (s, 2H), 3.65 (t, J=4.8 Hz, 2H), 3.22 (s, 3H), 2.89-2.92 (m, 2H), 2.55-2.57 (m, 1H), 2.20-2.25 (m, 2H), 1.73-1.78 (m, 4H). LC-MS: m/z 530.2 $(M+H)^+$.

(E)-3-(5-((4-(6-((4-chloro-2-fluorobenzyl)oxy)pyridin-2-yl)piperidin-1-yl)methyl)-4-(2-methoxyethyl)-4H-1,2,4-triazol-3-yl)-2-methylacrylic acid (Compound 224) was synthesized following the route of Example 8, using (4-(2-methoxyethyl)-4H-1,2,4-triazol-3-yl)methanol in step A and 2-methylpropanedioic acid in step D.

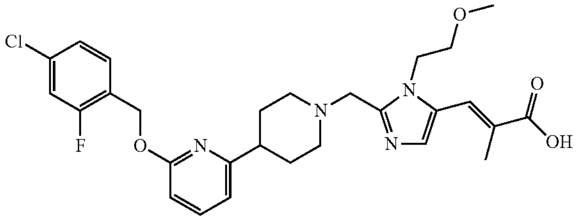 [SMILES: COCCn1c(/C=C(\C)C(=O)O)cnc1CN1CCC(c2cccc(OCc3ccc(Cl)cc3F)n2)CC1]

$^1$H NMR (400 MHz, $CD_3OD$) δ 7.47 (t, J=8.0 Hz, 1H), 7.38 (t, J=8.0 Hz, 1H), 7.26 (s, 1H), 7.07-7.12 (m, 2H), 6.71 (d, J=7.2 Hz, 1H), 6.53 (d, J=8.4 Hz, 1H), 5.30 (s, 2H), 4.33 (t, J=5.2 Hz, 2H), 3.76 (s, 2H), 3.62 (t, J=5.2 Hz, 2H), 3.20 (s, 3H), 2.89-2.95 (m, 2H), 2.51-2.60 (m, 1H), 2.20-2.24 (m, 5H), 1.73-1.77 (m, 4H). LC-MS: m/z 544.2 $(M+H)^+$.

Example 41

(S,E)-3-(5-((4-(6-((4-chloro-2-fluorobenzyl)oxy)pyridin-2-yl)piperidin-1-yl)methyl)-4-(oxetan-2-ylmethyl)-4H-1,2,4-triazol-3-yl)acrylic acid (Compound 225a)

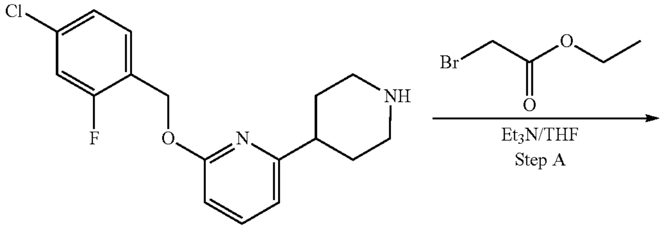

1

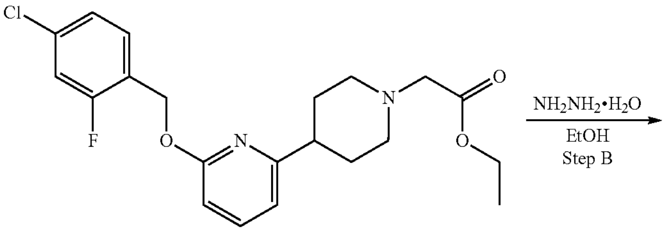

2

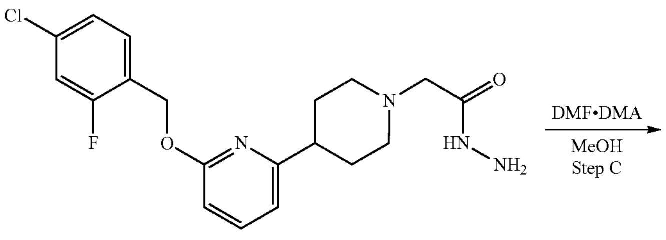

3

-continued
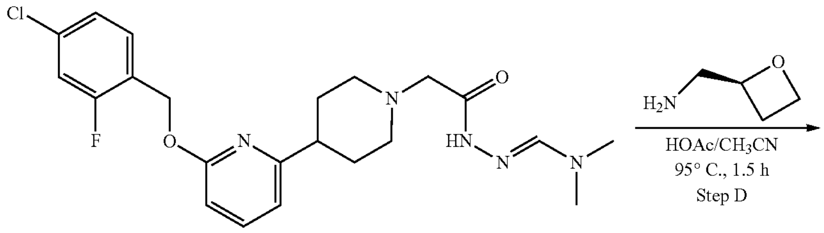
4
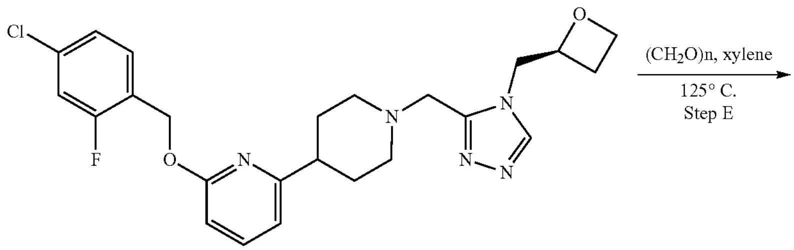
4
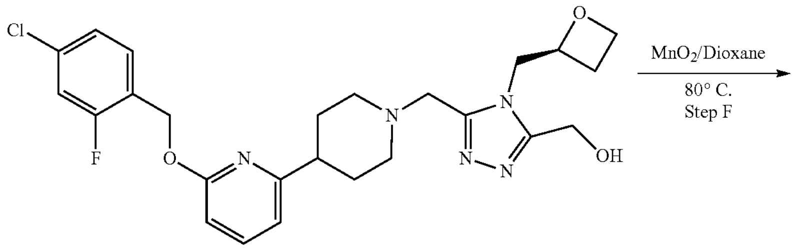
6
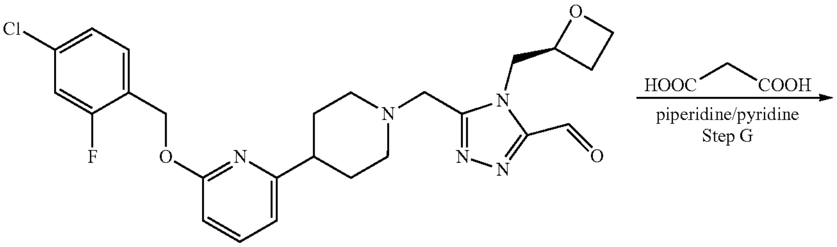
7
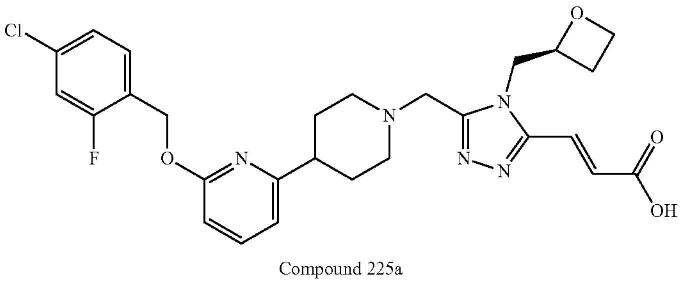
Compound 225a Step A: ethyl 2-(4-(6-((4-chloro-2-fluorobenzyl) oxy)pyridin-2-yl)piperidin-1-yl)acetate

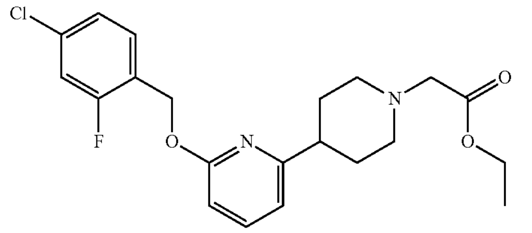

To a mixture of 2-((4-chloro-2-fluorobenzyl)oxy)-6-(piperidin-4-yl)pyridine (1.45 g, 4.52 mmol) in THF (20 mL) were added TEA (686.09 mg, 6.78 mmol, 943.72 uL) and ethyl 2-bromoacetate (830 mg, 4.97 mmol, 550 uL) at 0° C. The reaction mixture was stirred at 75° C. for 0.5 hour. The reaction mixture was quenched with sat. $NaHCO_3$ (10 mL), extracted with EtOAc (20 mL*3). The organic layer was dried and concentrated under vacuum. The residue was purified by flash silica gel chromatography (ISCO®; 40 g SepaFlash® Silica Flash Column, Eluent of 0-15% Ethyl acetate/Petroleum ether gradient @ 40 mL/min) to give ethyl 2-(4-(6-((4-chloro-2-fluorobenzyl)oxy)pyridin-2-yl)piperidin-1-yl)acetate (1.23 g, 66.9% yield) as a light yellow oil which was used directly for next step.

Step B: 2-(4-(6-((4-chloro-2-fluorobenzyl)oxy)pyridin-2-yl)piperidin-1-yl)acetohydrazide

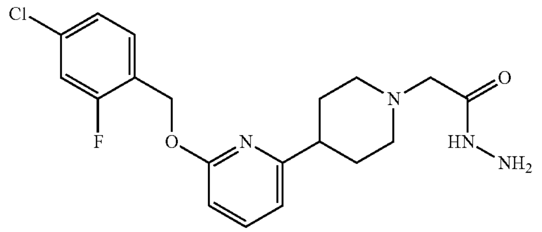 [SMILES: NNC(=O)CN1CCC(c2cccc(OCc3ccc(Cl)cc3F)n2)CC1]

To a mixture of ethyl 2-(4-(6-((4-chloro-2-fluorobenzyl)oxy)pyridin-2-yl)piperidin-1-yl)acetate (1.23 g, 3.02 mmol,) in EtOH (15 mL) was added hydrazine monohydrate (605 mg, 12.1 mmol, 588 uL). The reaction mixture was stirred at 90° C. for 20 hours. The reaction mixture was cooled to ambient temperature and to the mixture was added $H_2O$ (10 mL). The mixture was extracted with EtOAc (20 mL*3). The organic layer was dried over anhydrous $Na_2SO_4$, filtered and concentrated under vacuum to give 2-(4-(6-((4-chloro-2-fluorobenzyl)oxy)pyridin-2-yl)piperidin-1-yl)acetohydrazide (1.16 g, 97.7% yield) as a light yellow oil, which was used for next step directly.

Step C: (E)-N'-2-(4-(6-((4-chloro-2-fluorobenzyl) oxy)pyridin-2-yl)piperidin-1-yl)acetyl)-N,N-dimethylformohydrazonamide

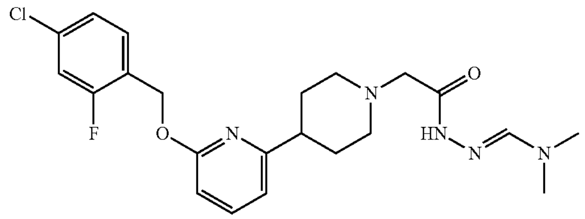 [SMILES: CN(C)/C=N/NC(=O)CN1CCC(c2cccc(OCc3ccc(Cl)cc3F)n2)CC1]

To a solution of 2-(4-(6-((4-chloro-2-fluorobenzyl)oxy) pyridin-2-yl)piperidin-1-yl)acetohydrazide (1.16 g, 2.95 mmol) in MeOH (8 mL) was added DMF-DMA (352 mg, 2.95 mmol). The mixture was stirred at 80° C. for 1 hour. The mixture was concentrated under vacuum to give (E)-N'-(2-(4-(6-((4-chloro-2-fluorobenzyl)oxy)pyridin-2-yl)piperidin-1-yl)acetyl)-N,N-dimethylformohydrazonamide (1.29 g, crude) which was used directly for the next step without further purification. LC-MS: m/z 448.2 $(M+H)^+$.

Step D: (S)-2-((4-chloro-2-fluorobenzyl)oxy)-6-(1-((4-(oxetan-2-ylmethyl)-4H-1,2,4-triazol-3-yl) methyl)piperidin-4-yl)pyridine

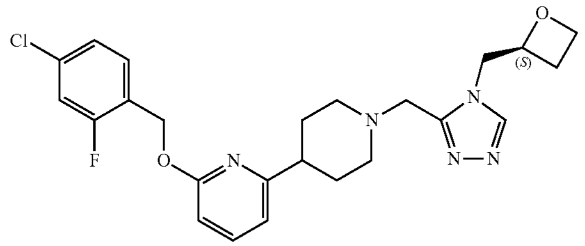

To a mixture of [(2S)-oxetan-2-yl]methanamine (491 mg, 2.68 mmol, MsOH salt) and (E)-N'-(2-(4-(6-((4-chloro-2-fluorobenzyl)oxy)pyridin-2-yl)piperidin-1-yl)acetyl)-N,N-dimethylformohydrazonamide (1.00 g, 2.23 mmol) in $CH_3CN$ (10 mL) was added HOAc (2.63 g, 43.7 mmol). The mixture was stirred at 95° C. for 1.5 hours under $N_2$. To the mixture was added 1 N NaOH (~5 mL) until pH=7. The mixture was diluted with water (40 mL), extracted with EtOAc (30 mL*3). The combined organic layer was dried over anhydrous $Na_2SO_4$, filtered and concentrated under vacuum. The residue was purified by flash silica gel chromatography (ISCO®; g SepaFlash® Silica Flash Column, Eluent of 0-10% methanol (0.025% $NH_3$ in methanol (7 N)/DCM gradient @ mL/min) to give (S)-2-((4-chloro-2-fluorobenzyl)oxy)-6-(1-((4-(oxetan-2-ylmethyl)-4H-1,2,4-triazol-3-yl)methyl)piperidin-4-yl)pyridine (960 mg, 91.1% yield) as a light yellow oil. LC-MS: m/z 472.2 $(M+H)^+$.

Step E: (S)-(5-((4-(@(4-chloro-2-fluorobenzyl)oxy)pyridin-2-yl)piperidin-1-yl)methyl)-4-(oxetan-2-ylmethyl)-4H-1,2,4-triazol-3-yl)methanol

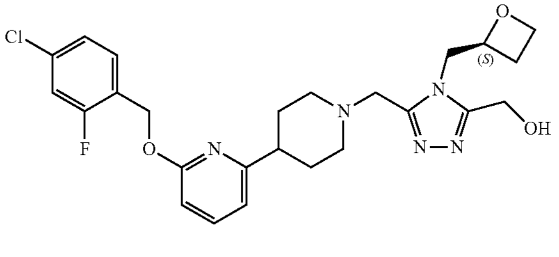

To a mixture of (S)-2-((4-chloro-2-fluorobenzyl)oxy)-6-(1-((4-(oxetan-2-ylmethyl)-4H-1,2,4-triazol-3-yl)methyl)piperidin-4-yl)pyridine (300 mg, 636 umol) in xylene (5 mL) was added paraformaldehyde (381 mg, 12.7 mmol). The mixture was stirred at 125° C. for 16 hours. The solvent was removed under vacuum. The residue was mixed with water (10 mL), extracted with EtOAc (20 mL*3). The organic layer was dried over anhydrous $Na_2SO_4$ and concentrated under vacuum to give a residue. The residue was purified by flash silica gel chromatography (ISCO®; 4 g SepaFlash® Silica Flash Column, Eluent of 0-10% methanol (0.025 $NH_3$ in methanol, 7 N)/DCM gradient @ 40 mL/min) to give (S)-(5-((4-(6-((4-chloro-2-fluorobenzyl)oxy)pyridin-2-yl)piperidin-1-yl)methyl)-4-(oxetan-2-ylmethyl)-4H-1,2,4-triazol-3-yl)methanol (230 mg, 403 umol, 63.5% yield) as a light yellow oil. LC-MS: m/z 502.3 $(M+H)^+$.

Step F: (S)-5-((4-(@(4-chloro-2-fluorobenzyl)oxy)pyridin-2-yl)piperidin-1-yl)methyl)-4-(oxetan-2-ylmethyl)-4H-1,2,4-triazole-3-carbaldehyde

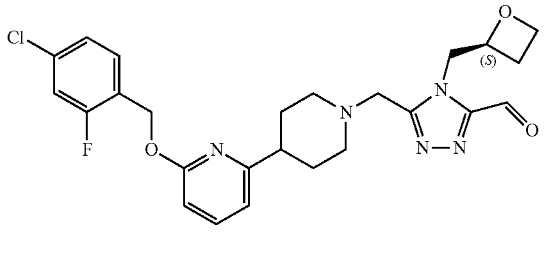

To a mixture of (S)-(5-((4-(6-((4-chloro-2-fluorobenzyl)oxy)pyridin-2-yl)piperidin-1-yl)methyl)-4-(oxetan-2-ylmethyl)-4H-1,2,4-triazol-3-yl)methanol (220 mg, 438 umol) in dioxane (6 mL) was added $MnO_2$ (381 mg, 4.38 mmol). The mixture was stirred at 80° C. for 3 hours. The mixture was filtered through a celite and washed with DCM (10 mL*4). The resulting filtrate was concentrated under vacuum to give (S)-5-((4-(6-((4-chloro-2-fluorobenzyl)oxy)pyridin-2-yl)piperidin-1-yl)methyl)-4-(oxetan-2-ylmethyl)-4H-1,2,4-triazole-3-carbaldehyde (0.23 g, crude) as a pink oil.

Step G: (S,E)-3-(5-((4-(6-((4-chloro-2-fluorobenzyl)oxy)pyridin-2-yl)piperidin-1-yl)methyl)-4-(oxetan-2-ylmethyl)-4H-1,2,4-triazol-3-yl)acrylic acid (Compound 225a)

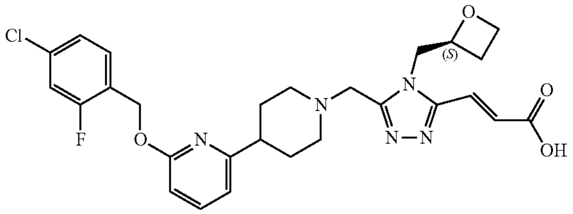

To a mixture of (S)-5-((4-(6-((4-chloro-2-fluorobenzyl)oxy)pyridin-2-yl)piperidin-1-yl)methyl)-4-(oxetan-2-ylmethyl)-4H-1,2,4-triazole-3-carbaldehyde (140 mg, 280 umol) in pyridine (3 mL) were added piperidine (19.1 mg, 224 umol) and malonicacid (29.1 mg, 280 umol). The mixture was stirred at 80° C. for 2 hours. The mixture was purified by Prep-HPLC (column: Phenomenex Gemini-NX C18 75*30 mm*3 um; mobile phase: [water (10 mM $NH_4HCO_3$)-ACN]; B %: 8%-48%, 14 min) to give (S,E)-3-(5-((4-(6-((4-chloro-2-fluorobenzyl)oxy)pyridin-2-yl)piperidin-1-yl)methyl)-4-(oxetan-2-ylmethyl)-4H-1,2,4-triazol-3-yl)acrylic acid (30.10 mg, 55.15 umol, 19.7% yield, 99.3% purity) as a white solid. $^1H$ NMR (400 MHz, $CD_3OD$) δ 7.39-7.50 (m, 3H), 7.09-7.12 (m, 2H), 6.85 (d, J 8.0 Hz, 1H), 6.72 (d, J=3.6 Hz, 1H), 6.53 (d, J=8.0 Hz, 1H), 5.31 (s, 2H), 5.06-5.07 (m, 1H), 4.52-4.58 (m, 2H), 4.39-4.45 (m, 2H), 3.81 (dd, J=35.2, 14.0 Hz, 2H), 2.56-3.01 (m, 4H), 2.26-2.38 (m, 3H), 1.70-1.79 (m, 4H). LC-MS: m/z 542.2 $(M+H)^+$.

(S,E)-3-(5-((4-(6-((4-chloro-2-fluorobenzyl)oxy)pyridin-2-yl)piperidin-1-yl)methyl)-4-(oxetan-2-ylmethyl)-4H-1,2,4-triazol-3-yl)-2-methylacrylic acid (Compound 226a) was synthesized following the route of Example 41, using 2-methylpropanedioic acid in step G.

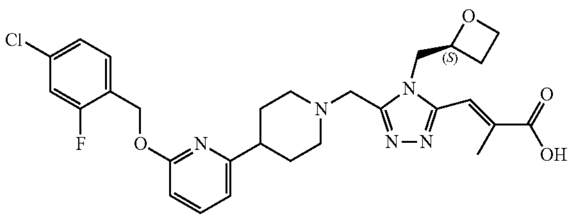

$^1H$ NMR (400 MHz, $CD_3OD$) δ 7.50 (t, J=7.2 Hz, 1H), 7.34-7.46 (m, 2H), 7.08-7.13 (m, 2H), 6.73 (d, J=7.6 Hz, 1H), 6.54 (d, J=8.0 Hz, 1H), 5.31 (s, 2H), 5.02-5.04 (m, 1H), 4.52-4.58 (m, 2H), 4.37-4.41 (m, 2H), 3.84 (dd, J=34.4, 14.0 Hz, 2H), 2.57-2.99 (m, 4H), 2.22-2.37 (m, 5H), 1.77-2.10 (m, 5H). LC-MS: m/z 556.2 $(M+H)^+$.

Example 42

(E)-3-(5-((4-(6-((4-chloro-2-fluorobenzyl)oxy)pyridin-2-yl)piperidin-1-yl)methyl)-4-(2-(methyl sulfonyl)ethyl)-4H-1,2,4-triazol-3-yl)-2-methylacrylic acid (Compound 227)

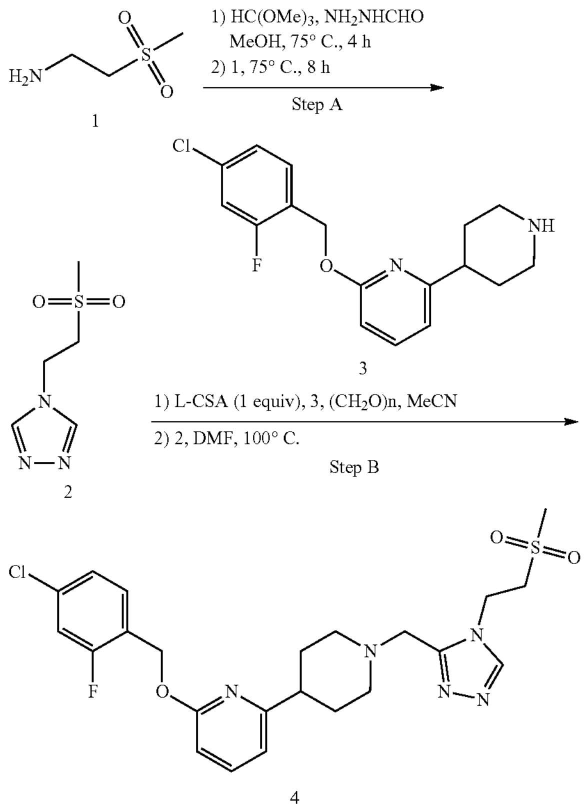

Step A: 4-(2-(methylsulfonyl)ethyl)-4H-1,2,4-triazole

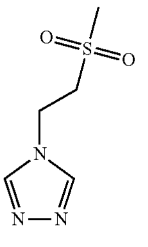

A mixture of formohydrazide (2.34 g, 38.97 mmol) and trimethoxymethane (4.14 g, 39.0 mmol, 4.27 mL) in MeOH (50 mL) was stirred at 75° C. for 4 hours. After cooling down, 2-methylsulfonylethanamine (2.40 g, 19.5 mmol) was added, the resulting mixture was stirred at 75° C. for 8 hours. After cooling to 25° C., the precipitate was filtered, washed with MeOH (5 mL) and collected to give 4-(2-methylsulfonylethyl)-1,2,4-triazole (2.67 g, 78.2% yield) as a white solid. $^1$H NMR (400 MHz, DMSO-$d_6$) δ 8.55 (s, 2H), 4.50 (t, J=4.8 Hz, 2H), 3.72 (t, J=4.8 Hz, 2H), 2.98 (s, 3H).

Step B: 2-((4-chloro-2-fluorobenzyl)oxy)-6-(1-((4-(2-(methyl sulfonyl)ethyl)-4H-1,2,4-triazol-3-yl)methyl)piperidin-4-yl)pyridine

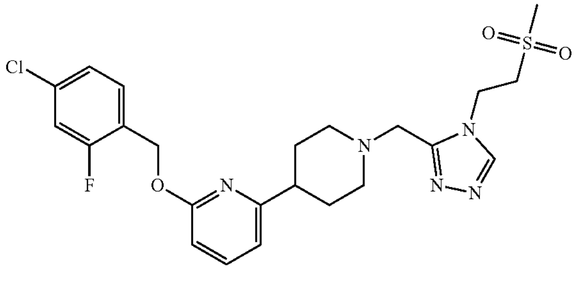 [SMILES: CS(=O)(=O)CCn1cnnc1CN1CCC(c2cccc(OCc3ccc(Cl)cc3F)n2)CC1]

To a solution of 2-((4-chloro-2-fluorobenzyl)oxy)-6-(piperidin-4-yl)pyridine (500 mg, 1.56 mmol) and formaldehyde (56.16 mg, 1.87 mmol) in MeCN (5 mL) was added L-CSA (362 mg, 1.56 mmol) and anhydrous $Na_2SO_4$ (443 mg, 3.12 mmol), the mixture was stirred at 30° C. for 1 hour. The solvent was removed under reduced pressure to give a residue, the residue was suspended in DMF (4 mL), and 4-(2-methylsulfonylethyl)-1,2,4-triazole (273 mg, 1.56 mmol) was added, the mixture was stirred at 100° C. for 35 hours. Then the reaction mixture was poured into water (100 mL) and extracted with EtOAc (50 mL×3), the combined organic phase was dried over anhydrous $Na_2SO_4$, filtered and evaporated to give the crude 2-((4-chloro-2-fluorobenzyl)oxy)-6-(1-((4-(2-(methyl sulfonyl)ethyl)-4H-1,2,4-triazol-3-yl)methyl)piperidin-4-yl)pyridine (640 mg, 80.8% yield) as a brown oil, which was used directly for the next step without further purification. LC-MS: m/z 508.0 $(M+H)^+$.

(E)-3-(5-((4-(6-((4-chloro-2-fluorobenzyl)oxy)pyridin-2-yl)piperidin-1-yl)methyl)-4-(2-(methyl sulfonyl)ethyl)-4H-1,2,4-triazol-3-yl)-2-methylacrylic acid (Compound 227)

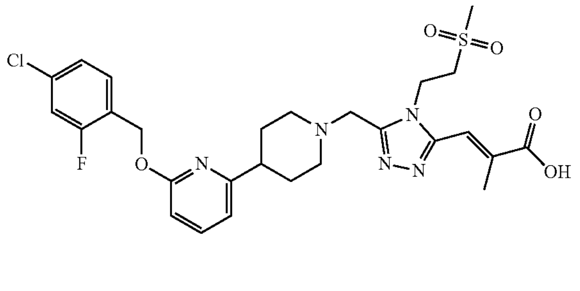 [SMILES: C/C(=C\c1nnc(CN2CCC(c3cccc(OCc4ccc(Cl)cc4F)n3)CC2)n1CCS(C)(=O)=O)C(=O)O]

Compound 227 was then synthesized following the route of Example 41, using 2-((4-chloro-2-fluorobenzyl)oxy)-6-(1-((4-(2-(methyl sulfonyl)ethyl)-4H-1,2,4-triazol-3-yl)methyl)piperidin-4-yl)pyridine in step E and 2-methylpropanedioic acid in step G.

$^1$H NMR (400 MHz, $CD_3OD$) δ 7.44-7.62 (m, 2H), 7.07-7.30 (m, 3H), 6.82 (d, J=6.4 Hz, 1H), 6.61 (d, J=8.0 Hz, 1H), 5.39 (s, 2H), 4.67-4.76 (m, 2H), 3.77-3.91 (m, 4H), 3.07 (s, 3H), 3.00 (d, J=11.6 Hz, 2H), 2.54-2.71 (m, 1H), 2.32 (s, 3H), 2.18-2.28 (m, 2H), 1.79-1.91 (m, 4H). LC-MS: m/z 592.4 $(M+H)^+$.

Example 43
(E)-3-(5-((4-(6-((4-chloro-2-fluorobenzyl)oxy)pyridin-2-yl)piperidin-1-yl)methyl)-4-((1-ethyl-1H-imidazol-5-yl)methyl)-4H-1,2,4-triazol-3-yl)acrylic acid (Compound 228)
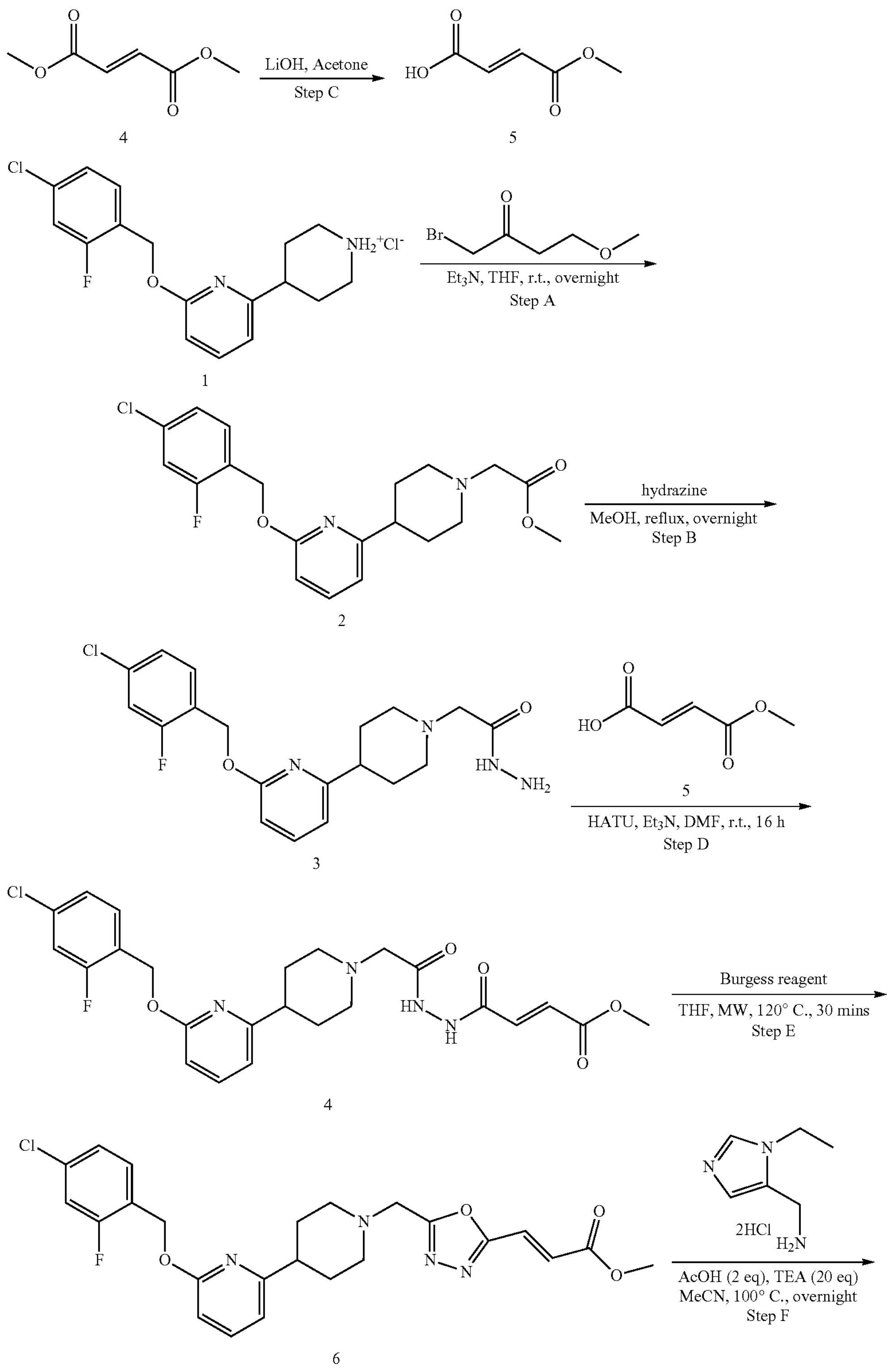
4
5
1
2
3
5
4
6

-continued

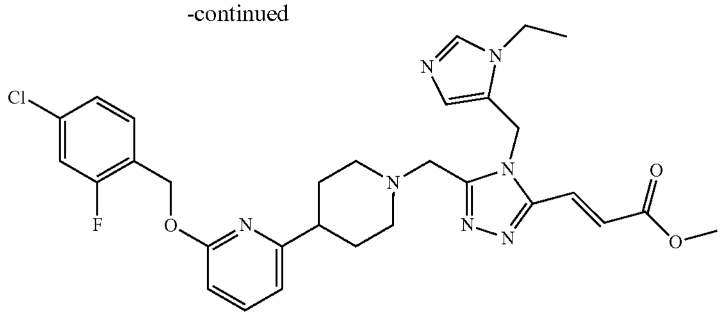

7

Step A: methyl 2-(4-(6-((4-chloro-2-fluorobenzyl)oxy)pyridin-2-yl)piperidin-1-yl)acetate

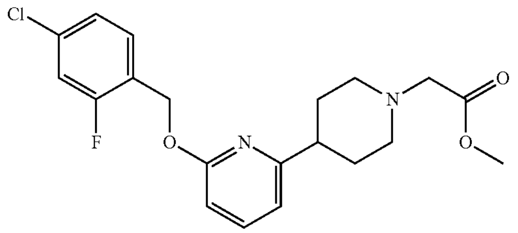 [SMILES: COC(=O)CN1CCC(c2cccc(OCc3ccc(Cl)cc3F)n2)CC1]

To a mixture of 4-(6-((4-chloro-2-fluorobenzyl)oxy)pyridin-2-yl)piperidin-1-ium chloride (1.00 g, 3.10 mmol) in THF (12 mL) were added methyl 2-bromoacetate (711 mg, 4.65 mmol) and TEA (939 mg, 9.30 mmol). The mixture was stirred at room temperature overnight. The reaction mixture was diluted with water (30 mL), and extracted with DCM (30 mL*3). The organic layer was washed with brine, dried over anhydrous $Na_2SO_4$, and concentrated. The residue was purified by silica gel column (PE/EA=10/1) to give methyl 2-(4-(6-((4-chloro-2-fluorobenzyl)oxy)pyridin-2-yl)piperidin-1-yl)acetate as a colorless oil (776 mg, 65% yield). $^1$H NMR (400 MHz, $CDCl_3$) δ 7.50 (dd, J=8.0, 7.6 Hz, 1H), 7.44 (t, J=8.4 Hz, 1H), 7.08-7.14 (m, 2H), 6.74 (d, J=7.6 Hz, 1H), 6.60 (d, J=8.0 Hz, 1H), 5.41 (s, 2H), 3.74 (s, 3H), 3.29 (s, 2H), 3.07 (d, J=11.2 Hz, 2H), 2.57-2.62 (m, 1H), 2.33 (t, J=10.4 Hz, 2H), 1.88-2.01 (m, 4H). LC-MS: m/z 393.2 $(M+H)^+$.

Step B: 2-(4-(6-((4-chloro-2-fluorobenzyl)oxy)pyridin-2-yl)piperidin-1-yl)acetohydrazide

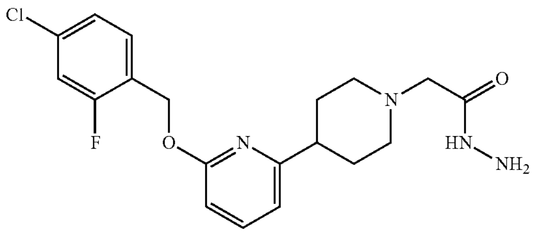 [SMILES: NNC(=O)CN1CCC(c2cccc(OCc3ccc(Cl)cc3F)n2)CC1]

To a solution of methyl 2-(4-(6-((4-chloro-2-fluorobenzyl)oxy)pyridin-2-yl)piperidin-1-yl)acetate (776 mg, 2.00 mmol) in MeOH (10 mL) was added hydrazine (80%, 300 mg, 6.00 mmol). The mixture was stirred at 80° C. overnight. MeOH was evaporated and the residue was purified by silica gel column (DCM/MeOH=30/1) to give 2-(4-(6-((4-chloro-2-fluorobenzyl)oxy)pyridin-2-yl)piperidin-1-yl)acetohydrazide as a colorless oil (750 mg, 97% yield). $^1$H NMR (400 MHz, DMSO-$d_6$) δ 8.86 (s, 1H), 7.63 (dd, J=8.4, 7.6 Hz, 1H), 7.58 (t, J=8.4 Hz, 1H), 7.47 (dd, J=10.0, 2.0 Hz, 1H), 7.31 (dd, J=8.4, 1.6 Hz, 1H), 6.87 (d, J=7.2 Hz, 1H), 6.67 (d, J=7.6 Hz, 1H), 5.38 (s, 2H), 4.23 (s, 2H), 2.93 (s, 2H), 2.89 (d, J=11.2 Hz, 2H), 2.53-2.58 (m, 1H), 2.11-2.20 (m, 2H), 1.72-1.84 (m, 4H). LC-MS: m/z 393.2 $(M+H)^+$.

Step C: (E)-4-methoxy-4-oxobut-2-enoic acid

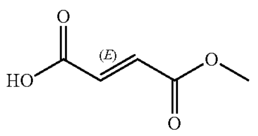

$LiOH \cdot H_2O$ (1 M, 13.9 mL) was added dropwisely to the mixture of dimethyl fumarate (2.00 g, 13.9 mmol) in acetone (80 mL) within 20 minutes. After addition, the reaction mixture was stirred at 25° C. for 1 hour. To the mixture was added 2N HCl (~150 mL) until pH=2-3. The mixture was extracted with EtOAc (150 mL*3). The organic layer was dried over $Na_2SO_4$, filtered and concentrated under vacuum to give (E)-4-methoxy-4-oxobut-2-enoic acid (1.80 g, 13.8 mmol, 99.7% yield) as a white solid. $^1$H NMR (400 MHz, $CDCl_3$) δ 6.84-6.96 (m, 2H), 3.81 (s, 3H).

Step D: methyl(E)-4-(2-(2-(4-(6-((4-chloro-2-fluorobenzyl)oxy)pyridin-2-yl)piperidin-1-yl)acetyl)hydrazinyl)-4-oxobut-2-enoate

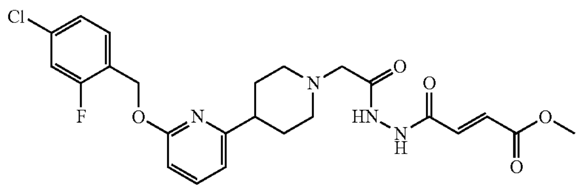 [SMILES: COC(=O)/C=C/C(=O)NNC(=O)CN1CCC(c2cccc(OCc3ccc(Cl)cc3F)n2)CC1]

To a mixture of 2-(4-(6-((4-chloro-2-fluorobenzyl)oxy)pyridin-2-yl)piperidin-1-yl)acetohydrazide (750 mg, 1.91 mmol) in DMF (8 mL) were added (E)-4-methoxy-4-oxobut-2-enoic acid (273 mg, 2.10 mmol), HATU (798 mg, 2.10 mmol), and TEA (579 mg, 5.73 mmol). The mixture was stirred at room temperature overnight. The reaction mixture was diluted with water (20 mL), extracted with EtOAc (20 mL*3). The organic layer was washed with water (20 mL), brine (20 mL), dried over anhydrous $Na_2SO_4$ and concentrated. The crude was suspended in PE/EA (10:1, 20 mL) and filtered. The filter cake was dried in vacuo to give methyl (E)-4-(2-(2-(4-(6-((4-chloro-2-fluorobenzyl)oxy) pyridin-2-yl)piperidin-1-yl)acetyl)hydrazinyl)-4-oxobut-2-enoate as a white solid (495 mg, 51% yield). $^1$H NMR (400 MHz, DMSO-$d_6$) δ 10.61 (s, 1H), 9.95 (s, 1H), 7.64 (dd, J=8.0, 7.2 Hz, 1H), 7.58 (t, J=8.4 Hz, 1H), 7.47 (dd, J=10.0, 2.0 Hz, 1H), 7.31 (dd, J=8.4, 1.6 Hz, 1H), 7.06 (d, J=15.6 Hz, 1H), 6.88 (d, J=7.2 Hz, 1H), 6.68 (d, J=15.6 Hz, 1H), 6.67 (d, J=8.0 Hz, 1H), 5.38 (s, 2H), 3.74 (s, 3H), 3.08 (s, 2H), 3.00 (d, J=11.2 Hz, 2H), 2.52-2.60 (m, 1H), 2.17-2.24 (m, 2H), 1.74-1.85 (m, 4H). LC-MS: m/z 505.2 $(M+H)^+$.

Step E: methyl E)-3-(5-((4-(6-((4-chloro-2-fluorobenzyl)oxy)pyridin-2-yl)piperidin-1-yl)methyl)-1,3,4-oxadiazol-2-yl)acrylate

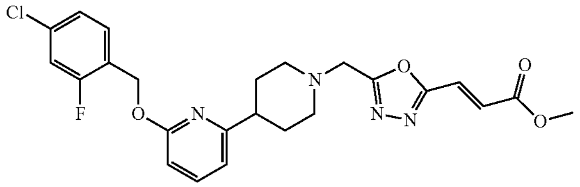 [SMILES: COC(=O)/C=C/c1nnc(CN2CCC(c3cccc(OCc4ccc(Cl)cc4F)n3)CC2)o1]

To a mixture of methyl (E)-4-(2-(2-(4-(6-((4-chloro-2-fluorobenzyl)oxy)pyridin-2-yl)piperidin-1-yl)acetyl)hydrazinyl)-4-oxobut-2-enoate (1.00 g, 1.98 mmol) in THF (10 mL) was added Burgess reagent (1.43 g, 6.00 mmol). The reaction mixture was stirred at 120° C. for 30 mins under microwave irradiation. The reaction mixture was quenched with water (20 mL), and extracted with DCM (20 mL*3). The combined organic layer was dried over anhydrous $Na_2SO_4$ and concentrated under vacuum. The residue was purified by flash silica gel chromatography (DCM/MeOH=40/1) to give methyl (E)-3-(5-((4-(6-((4-chloro-2-fluorobenzyl)oxy)pyridin-2-yl)piperidin-1-yl)methyl)-1,3,4-oxadiazol-2-yl)acrylate as a white solid (860 mg, 89% yield). $^1$H NMR (400 MHz, $CDCl_3$) δ 7.56 (d, J=16.0 Hz, 1H), 7.49 (dd, J=8.4, 7.2 Hz, 1H), 7.43 (t, J=8.0 Hz, 1H), 7.08-7.12 (m, 2H), 6.86 (d, J=16.0 Hz, 1H), 6.73 (d, J=7.2 Hz, 1H), 6.60 (d, J=8.0 Hz, 1H), 5.40 (s, 2H), 3.91 (s, 2H), 3.85 (s, 3H), 3.07 (d, J=11.6 Hz, 2H), 2.54-2.62 (m, 1H), 2.28-2.39 (m, 2H), 1.85-1.97 (m, 4H). LC-MS: m/z 487.2 $(M+H)^+$ Step F: methyl (E)-3-(5-((4-(6-((4-chloro-2-fluorobenzyl)oxy)pyridin-2-yl)piperidin-1-yl)methyl)-4-((1-ethyl-1H-imidazol-5-yl)methyl)-4H-1,2,4-triazol-3-yl)acrylate

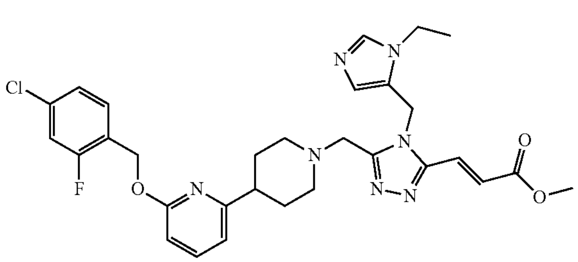 [SMILES: CCn1cncc1Cn1c(/C=C/C(=O)OC)nnc1CN1CCC(c2cccc(OCc3ccc(Cl)cc3F)n2)CC1]

A solution of methyl (E)-3-(5-((4-(6-((4-chloro-2-fluorobenzyl)oxy)pyridin-2-yl)piperidin-1-yl)methyl)-1,3,4-oxadiazol-2-yl)acrylate (50.0 mg, 0.103 mmol), AcOH (15.0 mg, 0.250 mmol), ((1-ethyl-1H-imidazol-5-yl)methyl) amine dihydrochloride (203 mg, 1.025 mmol) and TEA (204 mg, 2.02 mmol) in ACN (2 mL) was stirred at 100° C. for 24 hours. The reaction mixture was concentrated and purified by flash chromatography to give methyl (E)-3-(5-((4-(6-((4-chloro-2-fluorobenzyl)oxy)pyridin-2-yl)piperidin-1-yl)methyl)-4-((1-ethyl-1H-imidazol-5-yl)methyl)-4H-1,2,4-triazol-3-yl)acrylate (30.0 mg, 49% yield). LC-MS: m/z 94.3 $(M+H)^+$.

(E)-3-(5-((4-(6-((4-chloro-2-fluorobenzyl)oxy)pyridin-2-yl)piperidin-1-yl)methyl)-4-((1-ethyl-1H-imidazol-5-yl)methyl)-4H-1,2,4-triazol-3-yl)acrylic acid (Compound 228)

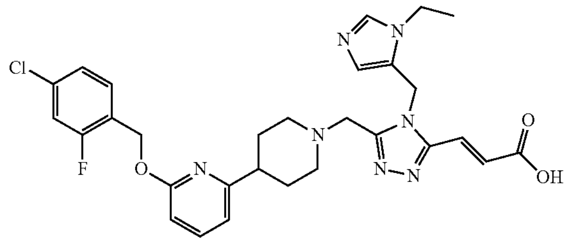 [SMILES: CCn1cncc1Cn1c(/C=C/C(=O)O)nnc1CN1CCC(c2cccc(OCc3ccc(Cl)cc3F)n2)CC1]

Compound 228 was then synthesized following step J of Example 1, using methyl (E)-3-(5-((4-(6-((4-chloro-2-fluorobenzyl)oxy)pyridin-2-yl)piperidin-1-yl)methyl)-4-((1-ethyl-1H-imidazol-5-yl)methyl)-4H-1,2,4-triazol-3-yl)acrylate as starting material. $^1$H NMR (400 MHz, DMSO-$d_6$) 7.62 (t, J=8.4 Hz, 2H), 7.56 (t, J=8.4 Hz, 1H), 7.47 (dd, J=10.0, 2.0 Hz, 1H), 7.37 (d, J=15.6 Hz, 1H), 7.31 (dd, J=8.4, 2.0 Hz, 1H), 6.78 (s, 1H), 6.77 (d, J=15.6 Hz, 1H), 6.66 (d, J=8.4 Hz, 1H), 6.29 (s, 1H), 5.55 (s, 2H), 5.36 (s, 2H), 4.01 (q, J=7.2 Hz, 2H), 3.70 (s, 2H), 2.76-2.79 (m, 2H), 2.55-2.58 (m, 1H), 2.03-2.08 (m, 2H), 1.67-1.70 (m, 2H), 1.34-1.49 (m, 2H), 1.26 (t, J=7.2 Hz, 3H). LC-MS: m/z 580.2 $(M+H)^+$.

(E)-3-(5-((4-(6-((4-chloro-2-fluorobenzyl)oxy)pyridin-2-yl)piperidin-1-yl)methyl)-4-(cyclobutylmethyl)-4H-1,2,4-triazol-3-yl)acrylic acid (Compound 229) was synthesized following similar route of Example 43, using cyclobutylmethanamine in step F.

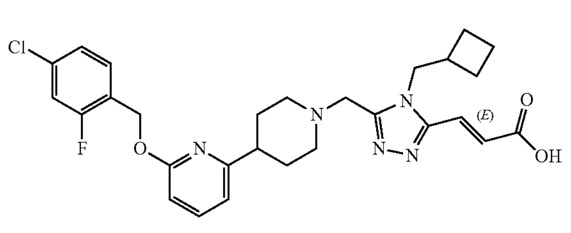 [SMILES: O=C(O)/C=C/c1nnc(CN2CCC(c3cccc(OCc4ccc(Cl)cc4F)n3)CC2)n1CC1CCC1]

$^1$H NMR (400 MHz, $CD_3OD$) δ 7.50-7.62 (m, 3H), 7.20-7.24 (m, 2H), 6.94 (d, J=16.0 Hz, 1H), 6.84 (d, J=7.6 Hz, 1H), 6.66 (d, J=8.4 Hz, 1H), 5.43 (s, 2H), 4.32-4.37 (m, 2H), 3.85 (s, 2H), 3.03-3.06 (m, 2H), 2.68-2.85 (m, 2H), 2.32-2.36 (m, 2H), 2.04-2.08 (m, 2H), 1.91-1.93 (m, 8H). LC-MS: m/z 540.4 $(M+H)^+$.

(E)-3-(5-((4-(6-((4-chloro-2-fluorobenzyl)oxy)pyridin-2-yl)piperidin-1-yl)methyl)-4-(2,2-difluoroethyl)-4H-1,2,4-triazol-3-yl)acrylic acid (Compound 230) was synthesized following similar route of Example 43, using 2,2-difluoroethanamine in step F.

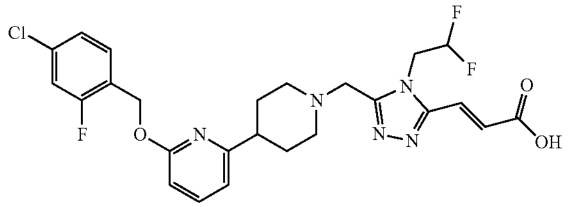 [SMILES: O=C(O)/C=C/c1nnc(CN2CCC(c3cccc(OCc4ccc(Cl)cc4F)n3)CC2)n1CC(F)F]

$^1$H NMR (400 MHz, $CD_3OD$) δ 7.57 (t, J=7.6 Hz, 1H), 7.44-7.53 (m, 2H), 7.16-7.26 (m, 2H), 6.99 (d, J=16.0 Hz, 1H), 6.84 (d, J=7.2 Hz, 1H), 6.65 (d, J=8.4 Hz, 1H), 6.41 (t, J=3.2 Hz, 1H), 5.42 (s, 2H), 4.76-4.54 (m, 2H), 3.88 (s, 2H), 2.99 (d, J=11.2 Hz, 2H), 2.59-2.71 (m, 1H), 2.23-2.37 (m, 2H), 1.79-1.91 (m, 4H). LC-MS: m/z 536.3 $(M+H)^+$.

(E)-3-(5-((4-(6-((4-chloro-2-fluorobenzyl)oxy)pyridin-2-yl)piperidin-1-yl)methyl)-4-((tetrahydrofuran-2-yl)methyl)-4H-1,2,4-triazol-3-yl)acrylic acid (Compound 231) was synthesized following similar route of Example 43, using (tetrahydrofuran-2-yl)methanamine in step F.

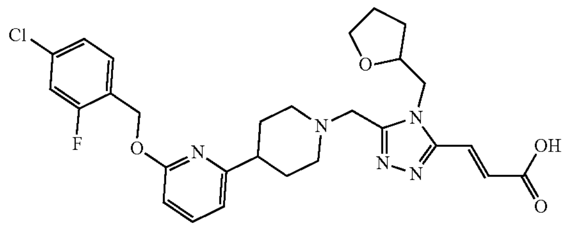 [SMILES: O=C(O)/C=C/c1nnc(CN2CCC(c3cccc(OCc4ccc(Cl)cc4F)n3)CC2)n1CC1CCCO1]

$^1$H NMR (400 MHz, DMSO-$d_6$) δ 12.74 (br.s, 1H), 7.63 (dd, J=8.0, 7.2 Hz, 1H), 7.52-7.57 (m, 2H), 7.46 (dd, J=10.0, 2.0 Hz, 1H), 7.29 (dd, J=8.0, 2.0 Hz, 1H), 6.86 (d, J=7.2 Hz, 1H), 6.73 (d, J=15.6 Hz, 1H), 6.67 (d, J=8.4 Hz, 1H), 5.36 (s, 2H), 4.35 (dd, J=14.8, 2.4 Hz, 1H), 4.20-4.26 (m, 1H), 4.10-4.18 (m, 1H), 3.81 (d, J=13.6 Hz, 1H), 3.76 (dd, J=14.8, 7.2 Hz, 1H), 3.58-3.66 (m, 2H), 2.96 (d, J=10.8 Hz, 1H), 2.78 (d, J=11.2 Hz, 1H), 2.56-2.60 (m, 1H), 2.21 (t, J=10.4 Hz, 1H), 2.10 (t, J=10.8 Hz, 1H), 1.97-2.05 (m, 1H), 1.69-1.91 (m, 5H), 1.55-1.67 (m, 2H). LC-MS: m/z 556.2 $(M+H)^+$.

(E)-3-(5-((4-(6-((4-chloro-2-fluorobenzyl)oxy)pyridin-2-yl)piperidin-1-yl)methyl)-4-((tetrahydrofuran-3-yl)methyl)-4H-1,2,4-triazol-3-yl)acrylic acid (Compound 232) was synthesized following similar route of Example 43, using tetrahydrofuran-3-ylmethanamine in step F.

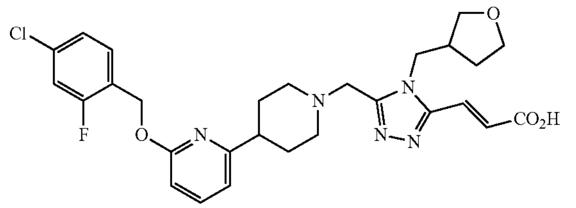 [SMILES: O=C(O)/C=C/c1nnc(CN2CCC(c3cccc(OCc4ccc(Cl)cc4F)n3)CC2)n1CC1CCOC1]

$^1$H NMR (400 MHz, $CD_3OD$) δ 7.47 (t, J=7.6 Hz, 1H), 7.33-7.42 (m, 2H), 7.05-7.14 (m, 2H), 6.87 (d, J=15.6 Hz, 1H), 6.71 (d, J=7.2 Hz, 1H), 6.52 (d, J 8.4 Hz, 1H), 5.40 (s, 2H), 4.12-4.27 (m, 2H), 3.84-3.92 (m, 1H), 3.59-3.79 (m, 4H), 3.45-3.53 (m, 1H), 2.86-2.97 (m, 2H), 2.74-2.84 (m, 1H), 2.49-2.61 (m, 1H), 2.14-2.27 (m, 2H), 1.88-1.99 (m, 1H), 1.61-1.82 (m, 5H). LC-MS: m/z 556.4 $(M+H)^+$.

(E)-3-[5-[[4-[6-[(4-chloro-2-fluoro-phenyl)methoxy]-2-pyridyl]-1-piperidyl]methyl]-4-(tetrahydropyran-4-ylmethyl)-1,2,4-triazol-3-yl]prop-2-enoic acid (Compound 233) was synthesized following similar route of Example 43, using tetrahydropyran-4-ylmethanamine in step F.

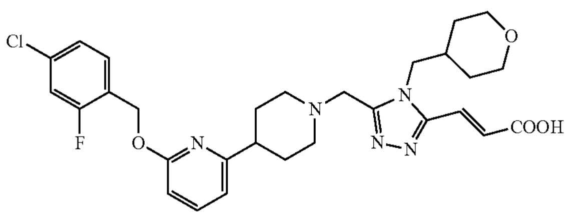 [SMILES: O=C(O)/C=C/c1nnc(CN2CCC(c3cccc(OCc4ccc(Cl)cc4F)n3)CC2)n1CC1CCOCC1]

$^1$H NMR (400 MHz, $CD_3OD$) δ 7.58 (dd, J=7.2, 8.0 Hz, 1H), 7.48 (t, J=8.0 Hz, 1H), 7.37 (d, J=15.6 Hz, 1H), 7.13-7.25 (m, 2H), 6.97 (d, J=15.6 Hz, 1H), 6.82 (d, J=7.2 Hz, 1H), 6.63 (d, J=8.0 Hz, 1H), 5.40 (s, 2H), 4.17 (d, J=7.6 Hz, 2H), 3.87-4.01 (m, 2H), 3.79 (s, 2H), 3.33-3.48 (m, 2H), 2.91-3.09 (m, 2H), 2.56-2.70 (m, 1H), 2.18-2.41 (m, 3H), 1.74-1.98 (m, 4H), 1.35-1.60 (m, 4H). LC-MS: m/z 570.4 $(M+H)^+$.

(R,E)-3-(5-((4-(2-(4-chlorophenyl)-2,3-dihydrobenzo[b][1,4]dioxin-5-yl)piperidin-1-yl)methyl)-4-((1-ethyl-1H-imidazol-5-yl)methyl)-4H-1,2,4-triazol-3-yl)acrylic acid (Compound 234a) was synthesized following similar route of Example 43, using (R)-4-(2-(4-chlorophenyl)-2,3-dihydrobenzo[b][1,4]dioxin-5-yl)piperidine hydrochloride in step A and ((1-ethyl-1H-imidazol-5-yl)methyl)amine in step F.

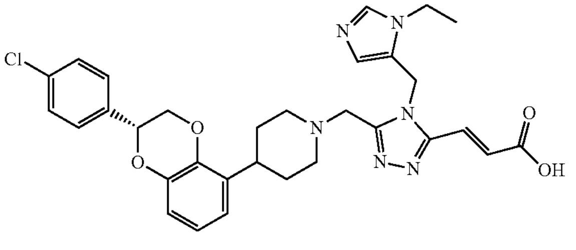 [SMILES: CCn1cncc1Cn1c(/C=C/C(=O)O)nnc1CN1CCC(c2cccc3c2OC[C@@H](c2ccc(Cl)cc2)O3)CC1]

$^1$HNMR (400 MHz, DMSO-$d_6$) 7.70 (s, 1H), 7.46-7.53 (m, 4H), 7.28 (d, J=15.6 Hz, 1H), 6.73-6.87 (m, 3H), 6.64 (dd, J=7.2, 2.0 Hz, 1H), 6.25 (s, 1H), 5.51 (s, 2H), 5.23 (dd, J=8.4, 2.0 Hz, 1H), 4.47 (dd, J=11.2, 2.4 Hz, 1H), 4.00-4.06 (m, 3H), 3.69 (s, 2H), 2.72-2.80 (m, 3H), 2.00-2.05 (m, 2H), 1.51-1.60 (m, 2H), 1.29 (t, J=7.2 Hz, 3H), 1.18-1.23 (m, 2H). LC-MS: m/z 589.2 $(M+H)^+$.

Example 44

3-(5-((4-(6-((4-chloro-2-fluorobenzyl)oxy)pyridin-2-yl)piperidin-1-yl)methyl)-4-(2-methoxyethyl)-4H-1,2,4-triazol-3-yl)but-2-enoic acid (Compound 235)

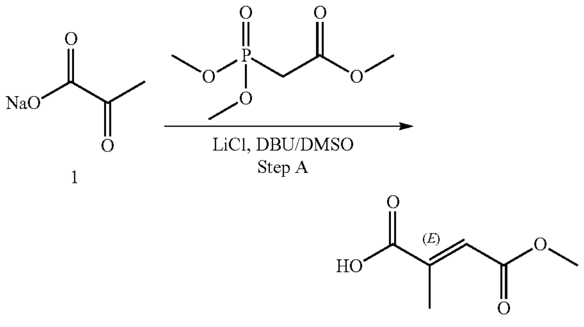

1

2

Step A: (E)-4-methoxy-2-methyl-4-oxobut-2-enoic acid

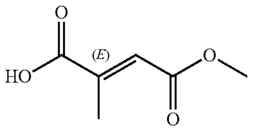

To a mixture of methyl 2-dimethoxyphosphorylacetate (3.00 g, 16.5 mmol, 2.4 mL) in DMSO (45 mL) were added DBU (3.76 g, 24.7 mmol, 3.7 mL) and LiCl (1.19 g, 28.0 mmol). The mixture was stirred at 25° C. for 15 minutes under nitrogen. Then sodium 2-oxopropanoate (1.81 g, 16.5 mmol) was added in portions to the mixture. The reaction mixture was stirred at 100° C. for 16 hours under $N_2$. The reaction mixture was quenched with 1 N HCl (~20 mL). The mixture was extracted with EtOAc (30 mL*3). The organic layer was washed with $H_2O$ (20 mL*3), dried over $Na_2SO_4$, filtered and concentrated under vacuum. The residue was purified by flash silica gel chromatography (ISCO®; 40 g SepaFlash® Silica Flash Column, Eluent of 10-40% Ethyl acetate/Petroleum ether gradient @ 40 mL/min) to give E and Z mixture of two isomers (1.6 g), which was further recrystallized from pentane to give the desired (E)-4-methoxy-2-methyl-4-oxobut-2-enoic acid (600 mg, 25.3% yield) as a white solid. $^1$H NMR (400 MHz, $CDCl_3$) δ 6.89 (s, 1H), 3.78 (s, 3H), 2.30 (s, 3H).

3-(5-((4-(6-((4-chloro-2-fluorobenzyl)oxy)pyridin-2-yl)piperidin-1-yl)methyl)-4-(2-methoxyethyl)-4H-1,2,4-triazol-3-yl)but-2-enoic acid (Compound 235))

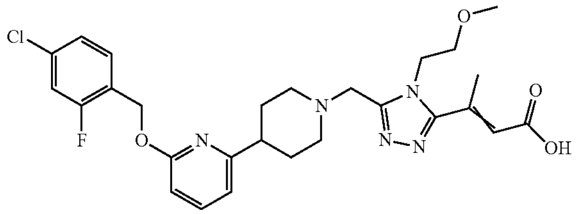 [SMILES: COCCn1c(CN2CCC(c3cccc(OCc4ccc(Cl)cc4F)n3)CC2)nnc1C(C)=CC(=O)O]

Compound 235 was then synthesized following the route of Example 43, using (E)-4-methoxy-2-methyl-4-oxobut-2-enoic acid in step D and 2-methoxyethanamine in step F.

$^1$H NMR (400 MHz, $CD_3OD$) δ 7.47 (J=8.0 Hz, 1H), 7.37-7.41 (m, 1H), 7.07-7.12 (m, 2H), 6.72 (d, J=7.2 Hz, 1H), 6.53 (d, J=8.0 Hz, 1H), 6.14-6.24 (m, 1H), 5.61-5.65 (m, 1H), 5.30 (s, 2H), 4.34-4.43 (m, 1H), 4.26-4.30 (m, 1H), 3.52-3.81 (m, 4H), 3.21 (s, 3H), 2.92-2.95 (m, 2H), 2.56-2.57 (m, 1H), 2.12-2.34 (m, 4H), 1.77-1.79 (m, 4H). LC-MS: m/z 544.4 $(M+H)^+$.

3-(5-((4-(6-((4-chloro-2-fluorobenzyl)oxy)pyridin-2-yl)piperidin-1-yl)methyl)-4-(cyclobutylmethyl)-4H-1,2,4-triazol-3-yl)but-2-enoic acid (Compound 236) was synthesized following similar route of Example 44, using (E)-4-methoxy-2-methyl-4-oxobut-2-enoic acid in step D and cyclobutylmethanamine in step F.

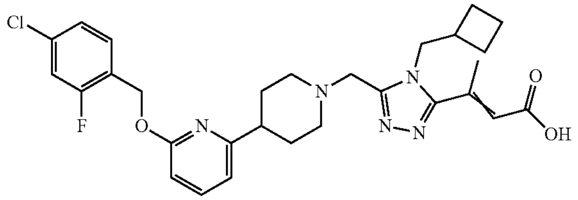 [SMILES: CC(=CC(=O)O)c1nnc(CN2CCC(c3cccc(OCc4ccc(Cl)cc4F)n3)CC2)n1CC1CCC1]

$^1$H NMR (400 MHz, $CD_3OD$) δ 7.47 (t, J=8.0 Hz, 1H), 7.36-7.41 (m, 1H), 7.07-7.11 (m, 2H), 6.72 (d, J=7.2 Hz, 1H), 6.53 (d, J=8.4 Hz, 1H), 5.51-6.24 (m, 1H), 5.31 (s, 2H), 4.00-4.26 (m, 2H), 3.66-3.71 (m, 2H), 2.55-2.91 (m, 4H), 2.33 (s, 2H), 1.91-2.19 (m, 5H), 1.72-1.79 (m, 8H). LC-MS: m/z 554.4 $(M+H)^+$.

Example 45

(E)-3-(6-((4-(6-((4-chloro-2-fluorobenzyl)oxy)pyridin-2-yl)piperidin-1-yl)methyl)-5-methylpyridin-3-yl)acrylic acid (Compound 120) was synthesized following the method described in Example 3, using (5-bromo-3-methylpicolinaldehyde in step A.

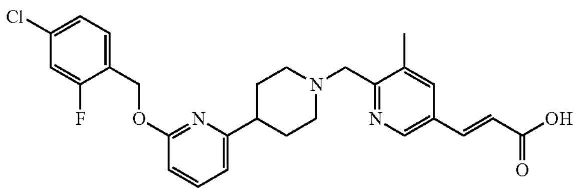 [SMILES: Cc1cc(/C=C/C(=O)O)cnc1CN1CCC(c2cccc(OCc3ccc(Cl)cc3F)n2)CC1]

$^1$H NMR (400 MHz, $CD_3OD$) δ 8.71 (d, J=1.6 Hz, 1H), 8.10 (t, J=8.0 Hz, 1H), 8.05 (s, 1H), 7.70 (d, J=16.0 Hz, 1H), 7.60 (t, J=8.4 Hz, 1H), 7.20-7.35 (m, 4H), 6.68 (d, J=16.0 Hz, 1H), 5.55 (s, 2H), 4.66 (s, 2H), 3.76-3.89 (m, 2H), 3.41-3.49 (m, 2H), 3.18-3.27 (m, 1H), 3.43 (s, 3H), 2.23-2.39 (m, 4H). LC-MS: m/z 496.4 $(M+H)^+$.
Example 46
(E)-3-(6-((4-(6-((4-chloro-2-fluorobenzyl)oxy)pyridin-2-yl)piperidin-1-yl)methyl)-5-((tetrahydrofuran-2-yl)methyl)pyridin-3-yl)acrylic acid (Compound 128)
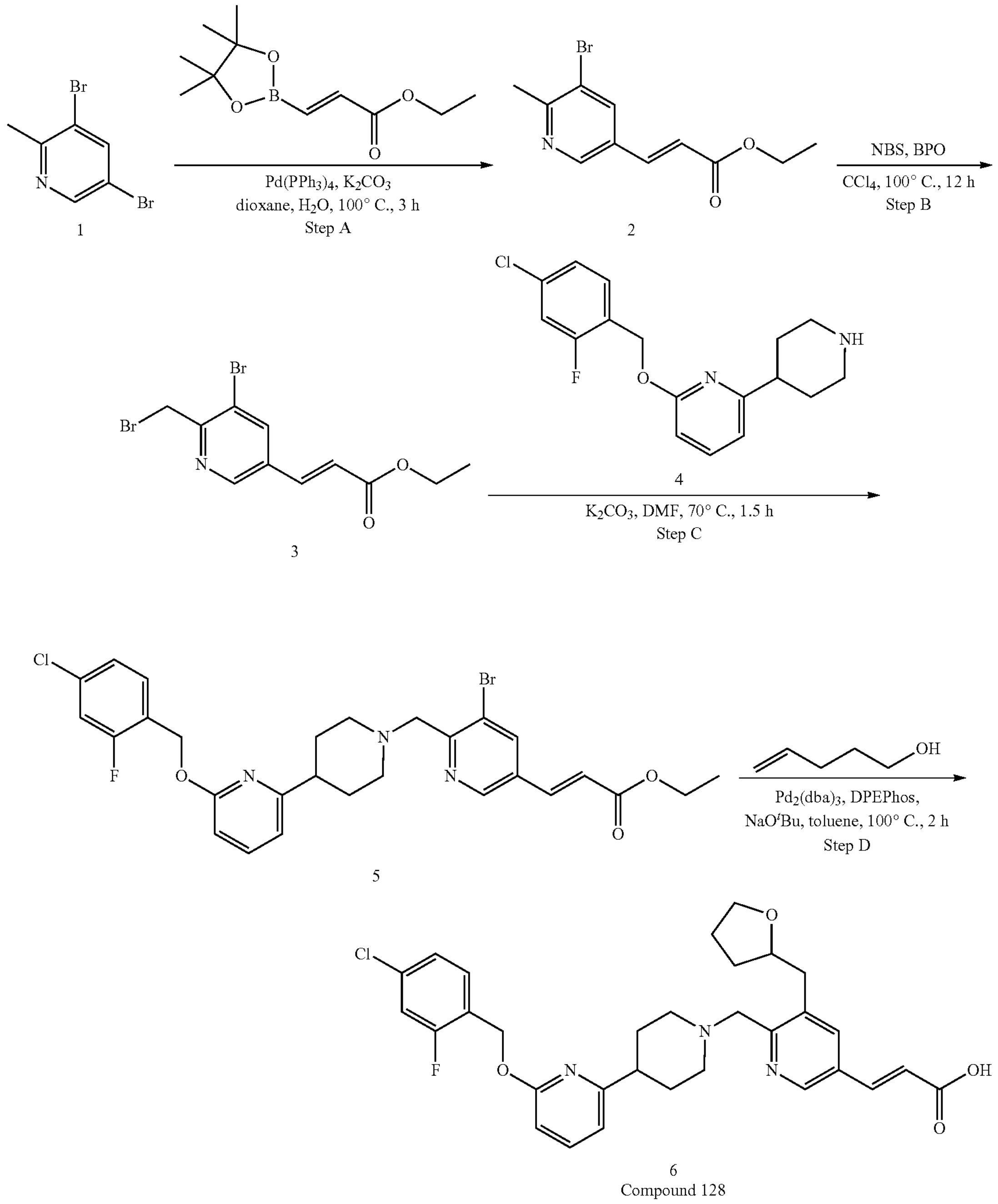

Step A: (E)-ethyl 3-(5-bromo-6-methylpyridin-3-yl) acrylate

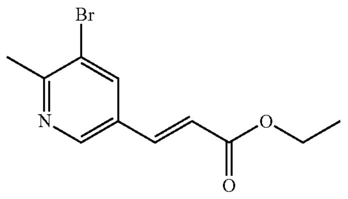

A mixture of 3,5-dibromo-2-methylpyridine (2.50 g, 10.0 mmol), (E)-ethyl 3-(4,4,5,5-tetramethyl-1,3,2-dioxaborolan-2-yl)acrylate (2.50 g, 11.0 mmol), $Pd(PPh_3)_4$ (1.10 g, 1.00 mmol) and $K_2CO_3$ (4.10 g, 30.0 mmol) in dioxane/$H_2O$ (20/5 mL) was stirred at 100° C. for 3 hours under $N_2$ atmosphere. The reaction mixture was diluted with water (50 mL) and extracted with ethyl ether (50 mL*3). The combined organic phase was washed with brine (30 mL), dried over anhydrous $Na_2SO_4$ and concentrated in vacuo. The residue was purified by chromatography on silica gel (PE/EtOAc=100/1) to give (E)-ethyl 3-(5-bromo-6-methylpyridin-3-yl)acrylate as a white solid (750 mg, 29% yield). LC-MS: m/z 270.1, 272.1 $(M+H)^+$.

Step B: (E)-ethyl 3-(5-bromo-6-(bromomethyl)pyridin-3-yl)acrylate

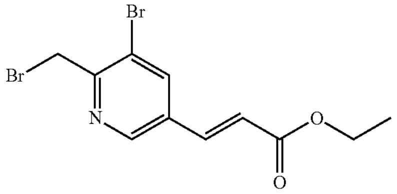 [SMILES: CCOC(=O)/C=C/c1cnc(CBr)c(Br)c1]

A mixture of (E)-ethyl 3-(5-bromo-6-methylpyridin-3-yl) acrylate (430 mg, 1.60 mmol), NBS (313 mg, 1.76 mmol) and benzoyl peroxide (27.0 mg, 0.100 mmol) in $CCl_4$ (20 mL) was stirred at 100° C. for 12 hours under $N_2$ atmosphere. The reaction mixture was diluted with water (30 mL) and extracted with DCM (30 mL*3). The combined organic phase was washed with brine (20 mL), dried over anhydrous $Na_2SO_4$ and concentrated in vacuo. The residue was purified by chromatography on silica gel (PE/EtOAc=10/1) to give (E)-ethyl 3-(5-bromo-6-(bromomethyl)pyridin-3-yl)acrylate as a white solid (150 mg, 27% yield). LC-MS: m/z 348.9 $(M+H)^+$.

Step C: (E)-ethyl 3-(5-bromo-6-((4-(6-((4-chloro-2-fluorobenzyl)oxy)pyridin-2-yl)piperidin-1-yl)methyl)pyridin-3-yl)acrylate

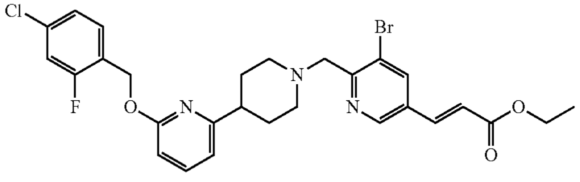 [SMILES: CCOC(=O)/C=C/c1cnc(CN2CCC(c3cccc(OCc4ccc(Cl)cc4F)n3)CC2)c(Br)c1]

A mixture of (E)-ethyl 3-(5-bromo-6-(bromomethyl)pyridin-3-yl)acrylate (150 mg, 0.500 mmol), 2-((4-chloro-2-fluorobenzyl)oxy)-6-(piperidin-4-yl)pyridine (160 mg, 0.500 mmol) and $K_2CO_3$ (140 mg, 1.00 mmol) in DMF (5 mL) was stirred at 70° C. for 1.5 hours. The reaction mixture was diluted with water (30 mL) and extracted with ethyl ether (30 mL*3). The combined organic phase was washed with brine (20 mL), dried over anhydrous $Na_2SO_4$ and concentrated in vacuo. The residue was purified by chromatography on silica gel (PE/EtOAc=5/1) to give (E)-ethyl 3-(5-bromo-6-((4-(6-((4-chloro-2-fluorobenzyl)oxy)pyridin-2-yl)piperidin-1-yl)methyl)pyridin-3-yl)acrylate as a colorless oil (140 mg, 47% yield). LC-MS: m/z 588.1 $(M+H)^+$.

Step D: (E)-3-(6-((4-(6-((4-chloro-2-fluorobenzyl)oxy)pyridin-2-yl)piperidin-1-yl)methyl)-5-((tetrahydrofuran-2-yl)methyl)pyridin-3-yl)acrylic acid (Compound 128)

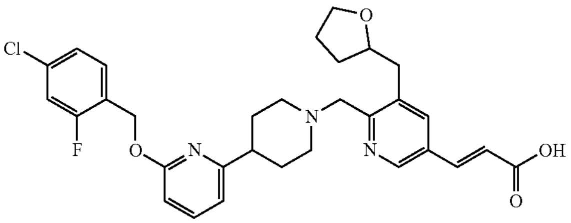 [SMILES: O=C(O)/C=C/c1cnc(CN2CCC(c3cccc(OCc4ccc(Cl)cc4F)n3)CC2)c(CC2CCCO2)c1]

A mixture of (E)-ethyl 3-(5-bromo-6-((4-(6-((4-chloro-2-fluorobenzyl)oxy)pyridin-2-yl)piperidin-1-yl)methyl)pyridin-3-yl)acrylate (240 mg, 0.480 mmol), pent-4-en-1-ol (42.0 mg, 0.240 mmol), Pd2(dba)$_3$ (22.0 mg, 0.0200 mmol), DPEPhos (26.0 mg, 0.0400 mmol) and $^t$BuONa (102 mg, 1.05 mmol) in dry toluene (2 mL) was stirred at 100° C. under $N_2$ for 2 hours. The reaction mixture was acidified with HCOOH to pH=5-6, diluted with water (10 mL) and extracted with ethyl ether (10 mL*3). The combined organic phase was washed with brine (10 mL), dried over anhydrous $Na_2SO_4$ and concentrated in vacuo. The residue was purified by reverse phase chromatography ($CH_3CN/H_2O$) to give (E)-3-(6-((4-(6-((4-chloro-2-fluorobenzyl)oxy)pyridin-2-yl)piperidin-1-yl)methyl)-5-((tetrahydrofuran-2-yl)methyl)pyridin-3-yl)acrylic acid as a white solid (12.0 mg, 4% yield). $^1$H NMR (400 MHz, $CD_3OD$) δ 8.63 (d, J=2.0 Hz, 1H), 7.96 (d, J=2.0 Hz, 1H), 7.64 (dd, J=8.0, 7.2 Hz, 1H), 7.50 (t, J=8.0 Hz, 1H), 7.42 (d, J=16.0 Hz, 1H), 7.20-7.25 (m, 2H), 6.90 (d, J=7.2 Hz, 1H), 6.71 (d, J=8.0 Hz, 1H), 6.64 (d, J=16.0 Hz, 1H), 5.45 (s, 2H), 4.44-4.53 (m, 2H), 4.06-4.12 (m, 1H), 3.89 (dd, J=14.8, 6.8 Hz, 1H), 3.70 (dd, J=14.0, 7.2 Hz, 1H), 3.53-3.59 (m, 2H), 3.10-3.16 (m, 2H), 2.87-3.05 (m, 3H), 2.09-2.24 (m, 5H), 1.88-1.95 (m, 2H), 1.62-1.71 (m, 1H). LC-MS: m/z 566.2 $(M+H)^+$.

Example 47

3-(2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)propanoic acid (Compound 237) was synthesized following similar route of Example 4 starting from (E)-3-(2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)acrylic acid and platinum oxide.

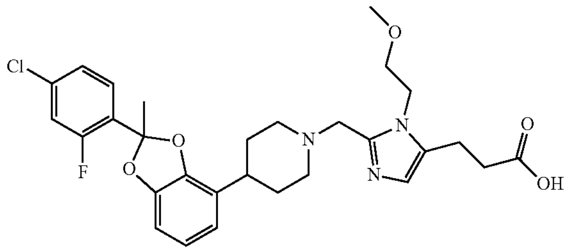 [SMILES: COCCn1c(CCC(=O)O)cnc1CN1CCC(c2cccc3c2OC(C)(c2ccc(Cl)cc2F)O3)CC1]

$^{1}$H NMR (400 MHz, DMSO-$d_6$) δ 7.49-7.61 (m, 2H), 7.34 (dd, J=8.4, 2.0 Hz, 1H), 6.79 (dd, J=6.4, 2.4 Hz, 2H), 6.69-6.75 (m, 1H), 6.52 (s, 1H), 4.15 (t, J=5.6 Hz, 2H), 3.65 (t, J=5.6 Hz, 2H), 3.51 (s, 2H), 3.22 (s, 3H), 2.86-2.89 (m, 2H), 2.77 (t, J=7.6 Hz, 2H), 2.54-2.69 (m, 3H), 1.97-2.12 (m, 5H), 1.69-1.72 (m, 4H). LC-MS: m/z 558.2 $(M+H)^+$.

3-(2-((4-(2-(4-chloro-2-fluorophenyl)-2-methylbenzo[d][1,3]dioxol-4-yl)piperidin-1-yl)methyl)-1-(2-(difluoromethoxy)ethyl)-1H-imidazol-5-yl)propanoic acid (Compound 238) was synthesized following similar route of Example 4 starting from ethyl (E)-3-(2-((4-(2-(4-chloro-2-fluorophenyl)-2-methylbenzo[d][1,3]dioxol-4-yl)piperidin-1-yl)methyl)-1-(2-(difluoromethoxy)ethyl)-1H-imidazol-5-yl)acrylate and platinum oxide.

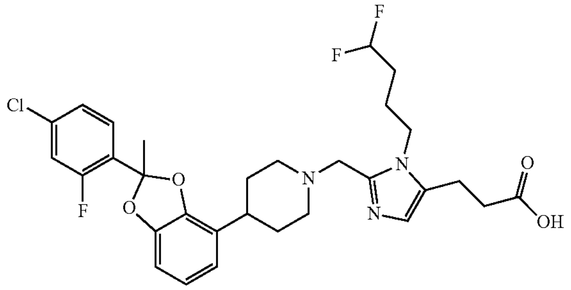 [SMILES: CC1(c2ccc(Cl)cc2F)Oc2cccc(C3CCN(Cc4ncc(CCC(=O)O)n4CCCC(F)F)CC3)c2O1]

$^{1}$HNMR (400 MHz, DMSO-$d_6$) δ 12.27 (br.s, 1H), 7.53-7.57 (m, 2H), 7.34 (dd, J=8.4, 2.0 Hz, 1H), 6.77-6.78 (m, 2H), 6.69-6.72 (m, 1H), 6.64 (t, J=75.6 Hz, 1H), 6.54 (s, 1H), 4.14-4.32 (m, 4H), 3.52 (dd, J=15.6, 13.2 Hz, 2H), 2.84-2.89 (m, 2H), 2.77 (t, J=7.2 Hz, 2H), 2.61-2.67 (m, 1H), 2.57 (t, J=7.6 Hz, 2H), 2.03-2.07 (m, 2H), 2.01 (s, 3H), 1.61-1.77 (m, 4H). $^{19}$F NMR (377 MHz, DMSO-$d_6$): δ −83.17, −110.82. LC-MS: m/z 593.8 $(M+H)^+$.

3-(2-((4-(2-(4-chloro-2-fluorophenyl)-2-methylbenzo[d][1,3]dioxol-4-yl)piperidin-1-yl)methyl)-1-(((S)-oxetan-2-yl)methyl)-1H-imidazol-5-yl)propanoic acid (Compound 239) was synthesized following similar route of Example 4 starting from methyl (E)-3-(2-((4-(2-(4-chloro-2-fluorophenyl)-2-methylbenzo[d][1,3]dioxol-4-yl)piperidin-1-yl) methyl)-1-(((S)-oxetan-2-yl)methyl)-1H-imidazol-5-yl) acrylate and platinum oxide.

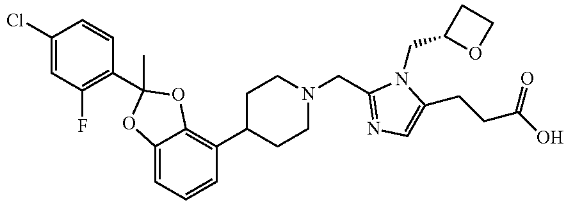 [SMILES: CC1(c2ccc(Cl)cc2F)Oc2cccc(C3CCN(Cc4ncc(CCC(=O)O)n4C[C@@H]4CCO4)CC3)c2O1]

$^{1}$H NMR (400 MHz, DMSO-$d_6$) δ 12.34 (br.s, 1H), 7.54-7.59 (m, 2H), 7.35 (d, J=8.4 Hz, 1H), 6.72-6.79 (m, 3H), 6.53 (s, 1H), 4.94-5.01 (m, 1H), 4.34-4.52 (m, 3H), 4.20 (d, J=14.8 Hz, 1H), 3.65 (dd, J=13.2, 4.4 Hz, 1H), 3.41 (dd, J=13.2, 2.0 Hz, 1H), 2.94 (d, J=8.8 Hz, 1H), 2.78-2.82 (m, 3H), 2.61-2.69 (m, 2H), 2.54-2.58 (m, 2H), 2.37-2.42 (m, 1H), 2.08-2.15 (m, 1H), 1.93-2.11 (m, 4H), 1.65-1.78 (m, 4H). LC-MS: m/z 570.0 $(M+H)^+$.

3-(2-((4-(2-(4-chloro-2-fluorophenyl)-2-methylbenzo[d][1,3]dioxol-4-yl)piperidin-1-yl)methyl)-1-((1,1-dioxidothietan-2-yl)methyl)-1H-imidazol-5-yl)propanoic acid (Compound 240) was synthesized following similar route of Example 4 starting from ethyl (E)-3-(2-((4-(2-(4-chloro-2-fluorophenyl)-2-methylbenzo[d][1,3]dioxol-4-yl)piperidin-1-yl)methyl)-1-((1,1-dioxidothietan-2-yl)methyl)-1H-imidazol-5-yl)acrylate and platinum oxide.

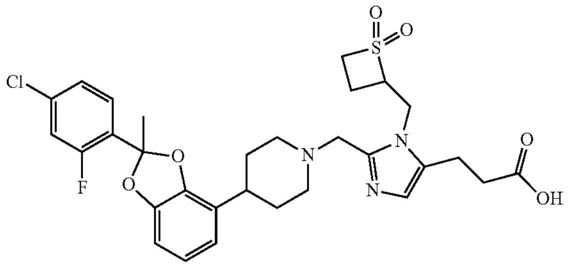 [SMILES: CC1(c2ccc(Cl)cc2F)Oc2cccc(C3CCN(Cc4ncc(CCC(=O)O)n4CC4CCS4(=O)=O)CC3)c2O1]

$^{1}$H NMR (400 MHz, DMSO-$d_6$) δ 12.36 (br.s, 1H), 7.51-7.60 (m, 2H), 7.32-7.38 (m, 1H), 6.72-6.82 (m, 3H), 6.56 (s, 1H), 4.95-5.08 (m, 1H), 4.61 (dd, J=15.6, 7.2 Hz, 1H), 4.35 (dd, J=15.6, 5.6 Hz, 1H), 3.93-4.13 (m, 2H), 3.67 (dd, J=13.6, 5.2 Hz, 1H), 3.44 (dd, J=13.2, 3.2 Hz, 1H), 2.99-2.90 (m, 1H), 2.72-2.89 (m, 3H), 2.55-2.65 (m, 3H), 2.25-2.32 (m, 1H), 2.06-2.16 (m, 1H), 1.99-2.05 (m, 4H), 1.87-1.97 (m, 1H), 1.62-1.81 (m, 4H). $^{19}$F NMR (377 MHz, DMSO-$d_6$): δ −110.77, −110.80. LC-MS: m/z 617.8 $(M+H)^+$.

3-(2-((4-(2-(4-chloro-2-fluorophenyl)-2-methylbenzo[d][1,3]dioxol-4-yl)piperidin-1-yl)methyl)-1-((4-methyloxazol-5-yl)methyl)-1H-imidazol-5-yl)propanoic acid (Compound 241) was synthesized following similar route of Example 4 starting from ethyl (E)-3-(2-((4-(2-(4-chloro-2-fluorophenyl)-2-methylbenzo[d][1,3]dioxol-4-yl)piperidin-1-yl)methyl)-1-((4-methyloxazol-5-yl)methyl)-1H-imidazol-5-yl)acrylate and platinum oxide.

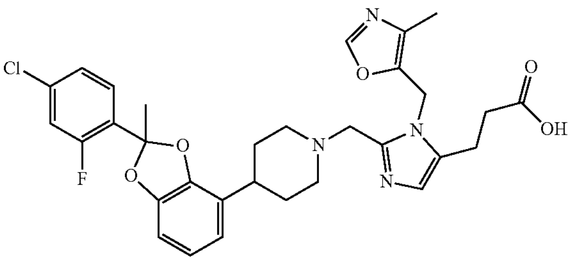 [SMILES: Cc1ncoc1Cn1c(CCC(=O)O)cnc1CN1CCC(c2cccc3c2OC(C)(c2ccc(Cl)cc2F)O3)CC1]

$^{1}$HNMR (400 MHz, DMSO-$d_6$) δ 8.20 (s, 1H), 7.52-7.60 (m, 2H), 7.34 (dd, J=8.4, 2.0 Hz, 1H), 6.76-6.81 (m, 2H), 6.69-6.74 (m, 1H), 6.55 (s, 1H), 5.40 (s, 2H), 3.55 (s, 2H), 2.84 (t, J=9.6 Hz, 2H), 2.75 (t, J=7.6 Hz, 2H), 2.57-2.70 (m, 2H), 2.46-2.48 (m, 1H), 2.12 (s, 3H), 2.01-2.08 (m, 5H), 1.57-1.72 (m, 4H). LC-MS: m/z 595.1 $(M+H)^+$.

3-(1-benzyl-2-((4-(2-(4-chloro-2-fluorophenyl)-2-methylbenzo[d][1,3]dioxol-4-yl)piperidin-1-yl)methyl)-1H-imidazol-5-yl)propanoic acid (Compound 242) was synthesized following similar route of Example 4 starting from ethyl (E)-3-(1-benzyl-2-((4-(2-(4-chloro-2-fluorophenyl)-2-methylbenzo[d][1,3]dioxol-4-yl)piperidin-1-yl)methyl)-1H-imidazol-5-yl)acrylate and platinum oxide.

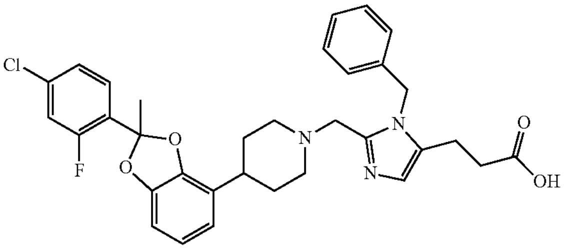 [SMILES: CC1(c2ccc(Cl)cc2F)Oc2cccc(C3CCN(Cc4ncc(CCC(=O)O)n4Cc4ccccc4)CC3)c2O1]

$^1$H NMR (400 MHz, DMSO-$d_6$) δ 12.23 (br.s, 1H), 7.51-7.57 (m, 2H), 7.29-7.37 (m, 3H), 7.21-7.25 (m, 1H), 7.06 (d, J=7.2 Hz, 2H), 6.74-6.80 (m, 2H), 6.57-6.63 (m, 2H), 5.28 (s, 2H), 3.46 (s, 2H), 2.81-2.83 (m, 2H), 2.57-2.62 (m, 3H), 2.42-2.46 (m, 2H), 1.96-2.06 (m, 5H), 1.61 (t, J=12.4 Hz, 2H), 1.32-1.53 (m, 2H). LC-MS: m/z 589.9 $(M+H)^+$.

3-(2-((4-(2-(4-chloro-2-fluorophenyl)-2-methylbenzo[d][1,3]dioxol-4-yl)piperidin-1-yl)methyl)-1-(3-methoxybenzyl)-1H-imidazol-5-yl)propanoic acid (Compound 243) was synthesized following similar route of Example 4 starting from ethyl (E)-3-(2-((4-(2-(4-chloro-2-fluorophenyl)-2-methylbenzo[d][1,3]dioxol-4-yl)piperidin-1-yl)methyl)-1-(3-methoxybenzyl)-1H-imidazol-5-yl)acrylate and platinum oxide.

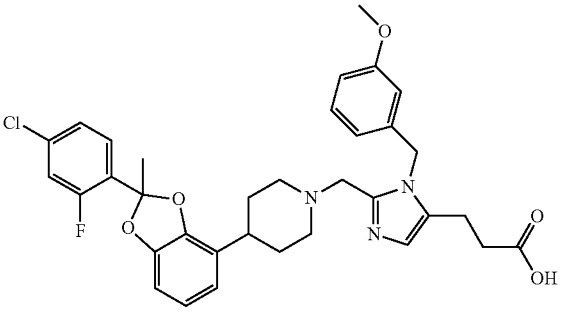 [SMILES: COc1cccc(Cn2c(CCC(=O)O)cnc2CN2CCC(c3cccc4c3OC(C)(c3ccc(Cl)cc3F)O4)CC2)c1]

$^1$H NMR (400 MHz, DMSO-$d_6$) δ 12.22 (br.s, 1H), 7.51-7.56 (m, 2H), 7.33 (dd, J=8.4, 2.0 Hz, 1H), 7.24 (t, J=8.0 Hz, 1H), 6.73-6.85 (m, 3H), 6.54-6.68 (m, 4H), 5.26 (s, 2H), 3.69 (s, 3H), 3.46-3.53 (m, 2H), 2.80-2.89 (m, 2H), 2.55-2.64 (m, 3H), 2.46-2.49 (m, 2H), 2.03-2.08 (m, 2H), 2.01 (s, 3H), 1.62 (t, J=12.4 Hz, 2H), 1.33-1.52 (m, 2H). LC-MS: m/z 619.8 $(M+H)^+$.

3-(2-((4-(6-((4-chloro-2-fluorobenzyl)oxy)pyridin-2-yl)piperidin-1-yl)methyl)-1-((1-ethyl-1H-imidazol-5-yl)methyl)-1H-imidazol-5-yl)propanoic acid (Compound 244) was synthesized following similar route of Example 4 starting from methyl (E)-3-(2-((4-(6-((4-chloro-2-fluorobenzyl)oxy)pyridin-2-yl)piperidin-1-yl)methyl)-1-((1-ethyl-1H-imidazol-5-yl)methyl)-1H-imidazol-5-yl)acrylate and platinum oxide.

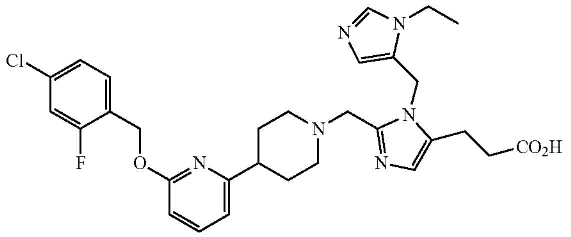 [SMILES: CCn1cncc1Cn1c(CCC(=O)O)cnc1CN1CCC(c2cccc(OCc3ccc(Cl)cc3F)n2)CC1]

$^1$H NMR (400 MHz, $CD_3OD$) δ 7.78 (s, 1H), 7.57 (dd, J=8.0, 7.2 Hz, 1H), 7.49 (t, J=8.0 Hz, 1H), 7.17-7.24 (m, 2H), 6.88 (s, 1H), 6.77 (d, J=7.2 Hz, 1H), 6.63 (d, J=8.0 Hz, 1H), 6.45 (s, 1H), 5.47 (s, 2H), 5.39 (s, 2H), 4.12 (q, J=7.2 Hz, 2H), 3.68 (s, 2H), 2.92 (d, J=11.2 Hz, 2H), 2.83 (t, J=7.2 Hz, 2H), 2.54-2.64 (m, 3H), 2.22 (t, J=10.8 Hz, 2H), 1.80 (d, J=11.2 Hz, 2H), 1.62-1.68 (m, 2H), 1.42 (t, J=7.2 Hz, 3H). LC-MS: m/z 581.2 $(M+H)^+$.

(R)-3-(2-((4-(2-(4-chlorophenyl)-2,3-dihydrobenzo[b][1,4]dioxin-5-yl)piperidin-1-yl)methyl)-1-((1-ethyl-1H-imidazol-5-yl)methyl)-1H-imidazol-5-yl)propanoic acid (Compound 245) was synthesized following similar route of Example 4 starting from (R,E)-3-(2-((4-(2-(4-chlorophenyl)-2,3-dihydrobenzo[b][1,4]dioxin-5-yl)piperidin-1-yl)methyl)-1-((1-ethyl-1H-imidazol-5-yl)methyl)-1H-imidazol-5-yl)acrylic acid and platinum oxide.

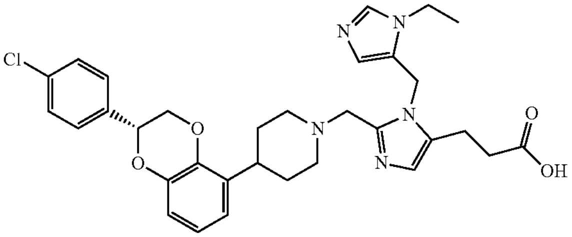 [SMILES: CCn1cncc1Cn1c(CCC(=O)O)cnc1CN1CCC(c2cccc3c2OC[C@@H](c2ccc(Cl)cc2)O3)CC1]

$^1$H NMR (400 MHz, DMSO-$d_6$) δ 7.65 (s, 1H), 7.44-7.53 (m, 4H), 6.78-6.86 (m, 2H), 6.67 (dd, J=6.8, 2.0 Hz, 1H), 6.60 (s, 1H), 6.26 (s, 1H), 5.28 (s, 2H), 5.23 (dd, J=8.4, 2.0 Hz, 1H), 4.47 (dd, J=11.6, 2.0 Hz, 1H), 3.96-4.07 (m, 3H), 3.47 (s, 2H), 2.75-2.78 (m, 3H), 2.68 (t, J=7.2 Hz, 2H), 2.47-2.49 (m, 2H), 1.95 (t, J=10.8 Hz, 2H), 1.57 (dd, J=23.6, 11.8 Hz, 2H), 1.23-1.35 (m, 5H). LC-MS: m/z 590.2 $(M+H)^+$.

(R)-3-(5-((4-(2-(4-chlorophenyl)-2,3-dihydrobenzo[b][1,4]dioxin-5-yl)piperidin-1-yl)methyl)-4-((1-ethyl-1H-imidazol-5-yl)methyl)-4H-1,2,4-triazol-3-yl)propanoic acid (Compound 246) was synthesized following similar route of Example 4 starting from methyl (R,E)-3-(5-((4-(2-(4-chlorophenyl)-2,3-dihydrobenzo[b][1,4]dioxin-5-yl)piperidin-1-yl)methyl)-4-((1-ethyl-1H-imidazol-5-yl)methyl)-4H-1,2,4-triazol-3-yl)acrylate and platinum oxide.

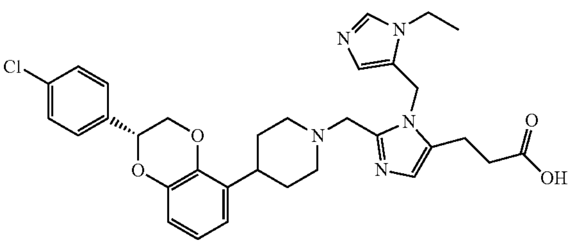 [SMILES: CCn1cncc1Cn1c(CCC(=O)O)cnc1CN1CCC(c2cccc3c2OC[C@@H](c2ccc(Cl)cc2)O3)CC1]

$^1$HNMR (400 MHz, DMSO-$d_6$) δ 12.23 (br.s, 1H), 7.69 (s, 1H), 7.47-7.53 (m, 4H), 6.76-6.87 (m, 2H), 6.67 (dd, J=6.8, 2.4 Hz, 1H), 6.42 (s, 1H), 5.33 (s, 2H), 5.23 (dd, J=8.0, 2.4 Hz, 1H), 4.47 (dd, J=11.2, 2.4 Hz, 1H), 3.97-4.07 (m, 3H), 3.59 (s, 2H), 2.83 (t, J=7.2 Hz, 2H), 2.66-2.80 (m, 5H), 2.00 (t, J=11.6 Hz, 2H), 1.58 (dd, J=15.6, 12.4 Hz, 2H), 1.21-1.33 (m, 5H). LC-MS: m/z 591.2 $(M+H)^+$.
Example 48
3-(5-((4-(6-((4-chloro-2-fluorobenzyl)oxy)pyridin-2-yl)piperidin-1-yl)methyl)-6-oxo-1,6-dihydropyridin-2-yl)propanoic acid (Compound 121) and 3-(5-((4-(6-((4-chloro-2-fluorobenzyl)oxy)pyridin-2-yl)piperidin-1-yl)methyl)-6-methoxypyridin-2-yl)propanoic acid (Compound 124)
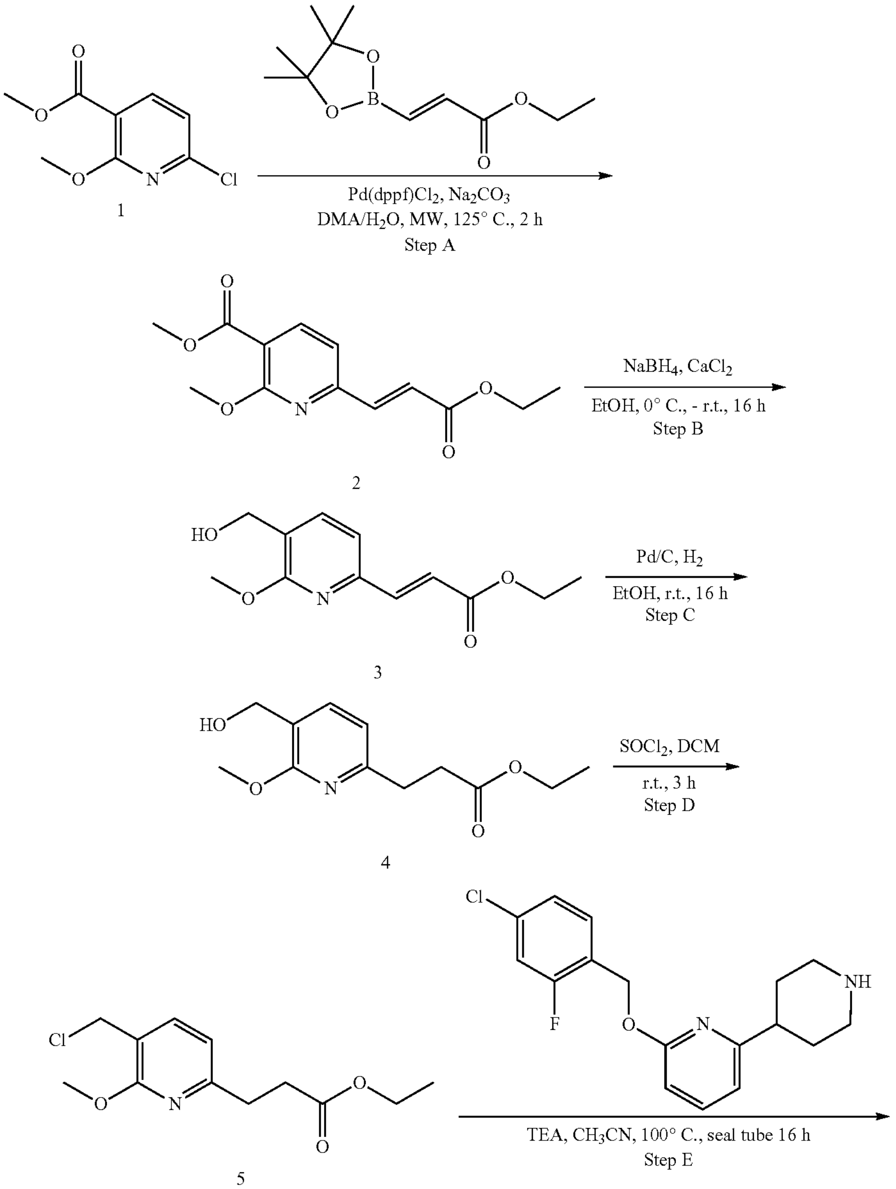
1
2
3
4
5

-continued

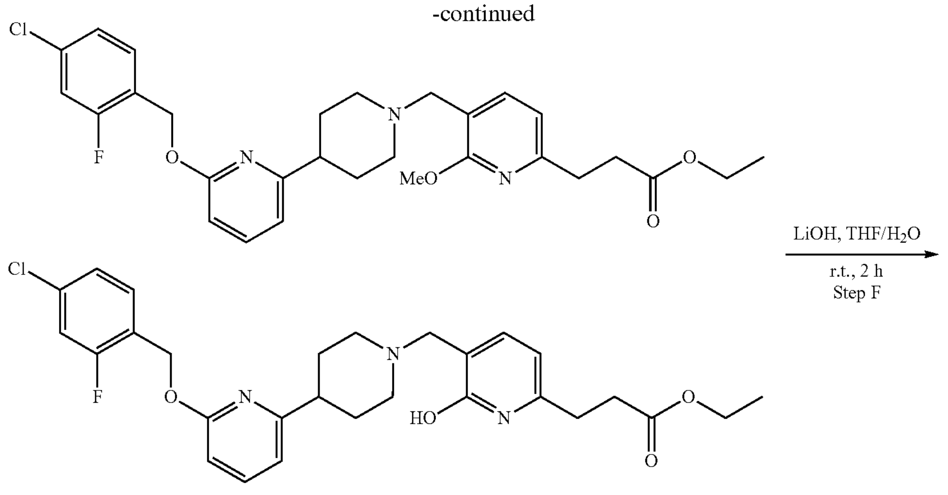

6 and 6'

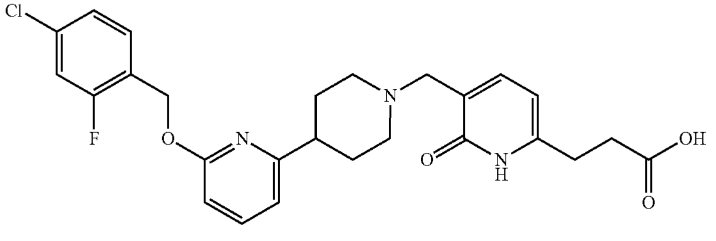

Compound 121

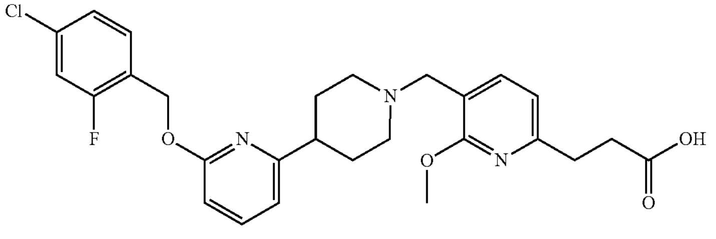

Compound 124

Step A: methyl (E)-6-(3-ethoxy-3-oxoprop-1-en-1-yl)-2-methoxynicotinate

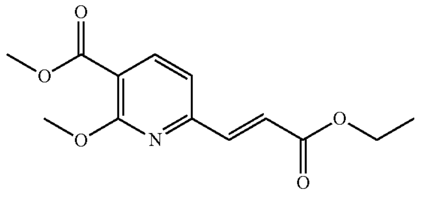 [SMILES: CCOC(=O)/C=C/c1ccc(C(=O)OC)c(OC)n1]

To a solution of methyl 6-chloro-2-methoxynicotinate (1.10 g, 5.46 mmol) in DMA (13 mL) and water (1.3 mL) were added ethyl (E)-3-(4,4,5,5-tetramethyl-1,3,2-dioxaborolan-2-yl)acrylate (1.48 g, 6.55 mmol), Pd(dppf)$Cl_2$ (445 mg, 0.546 mmol), $Na_2CO_3$ (1.16 g, 10.9 mmol). The resulting mixture was degassed and refilled with $N_2$ for three times and stirred at 125° C. under microwave irradiation for 2 hours. The mixture was diluted with water (40 mL), and extracted with EtOAc (30 mL*3). The organic layers were washed with brine (60 ml), dried over $Na_2SO_4$, filtered, concentrated and purified by silica gel chromatography (PE:EtOAc=10:1) to give methyl (E)-6-(3-ethoxy-3-oxoprop-1-en-1-yl)-2-methoxynicotinate as a white solid (900 mg, 62% yield). LC-MS: m/z 266.2 $(M+H)^+$.

Step B: ethyl E)-3-(5-(hydroxymethyl)-6-methoxy-pyridin-2-yl)acrylate

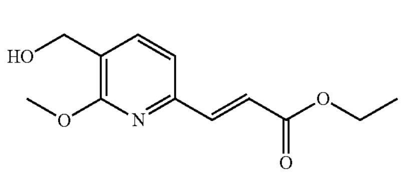 [SMILES: CCOC(=O)/C=C/c1ccc(CO)c(OC)n1]

To a solution of methyl (E)-6-(3-ethoxy-3-oxoprop-1-en-1-yl)-2-methoxynicotinate (800 mg, 3.02 mmol) in THF (24 mL) and EtOH (24 mL) were added $CaCl_2$) (483 mg, 12.1 mmol) and $NaBH_4$ (838 mg, 7.55 mmol) at 0° C. The mixture was stirred at room temperature for 16 hours. The reaction mixture was quenched by MeOH (40 mL) and concentrated. The crude was dissolved with EtOAc (60 mL) and washed with water (50 mL) and brine (50 mL). The organic layers was dried over $Na_2SO_4$, filtered and concentrated to give a crude product, which was purified by silica gel chromatography (PE/EtOAc=1/3) to give ethyl (E)-3-(5-(hydroxymethyl)-6-methoxypyridin-2-yl)acrylate as a colorless oil (312 mg, 44% yield). LC-MS: m/z 238.2 $(M+H)^+$.

Step C: ethyl 3-(5-(hydroxymethyl)-6-methoxypyridin-2-yl)propanoate

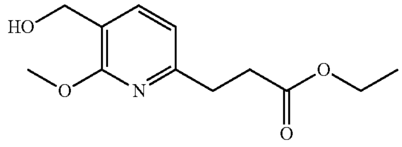 [SMILES: CCOC(=O)CCc1ccc(CO)c(OC)n1]

To a solution of ethyl (E)-3-(5-(hydroxymethyl)-6-methoxypyridin-2-yl)acrylate (470 mg, 1.98 mmol) in EtOH (8 mL) was added Pd/C (10%, 50.0 mg) and the mixture was stirred under $H_2$ at room temperature for 16 hours. The reaction solution was filtered and the filtrate was concentrated to give ethyl 3-(5-(hydroxymethyl)-6-methoxypyridin-2-yl)propanoate as a gum (475 mg, crude), which was used in next step without further purification. LC-MS: m/z 240.2 $(M+H)^+$.

Step D: ethyl chloromethyl)-6-methoxypyridin-2-yl)propanoate

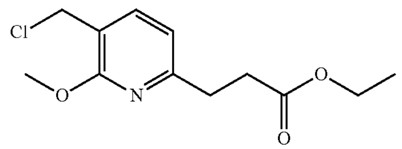 [SMILES: CCOC(=O)CCc1ccc(CCl)c(OC)n1]

To a solution of ethyl 3-(5-(hydroxymethyl)-6-methoxypyridin-2-yl)propanoate (475 mg, 1.98 mmol, crude) in DCM (9 ml) was added $SOCl_2$ (472 mg, 3.97 mmol). The reaction mixture was stirred at room temperature for 3 hours. The reaction solution was concentrated to give ethyl 3-(5-(chloromethyl)-6-methoxypyridin-2-yl)propanoate as a yellow solid (522 mg, crude). LC-MS: m/z 258.2 $(M+H)^+$.

Step E: ethyl 3-(5-((4-(6-((4-chloro-2-fluorobenzyl)oxy)pyridin-2-yl)piperidin-1-yl)methyl)-6-methoxypyridin-2-yl)propanoate and ethyl 3-(5-((4-(6-((4-chloro-2-fluorobenzyl)oxy)pyridin-2-yl)piperidin-1-yl)methyl)-6-hydroxypyridin-2-yl)propanoate

6

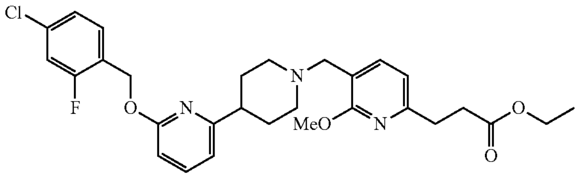

and

-continued

6'

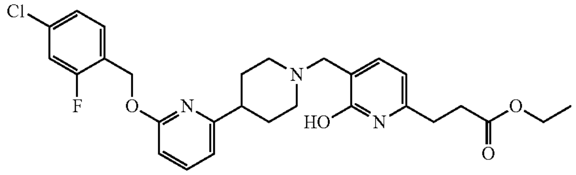

To a solution of ethyl 3-(5-(chloromethyl)-6-methoxypyridin-2-yl)propanoate (320 mg, 1.24 mmol, crude) in $CH_3CN$ (12 mL) were added 2-((4-chloro-2-fluorobenzyl)oxy)-6-(piperidin-4-yl)pyridine (357 mg, 1.11 mmol) and TEA (376 mg, 3.72 mmol). Then the reaction mixture was stirred in sealed tube at 100° C. for 16 hours. The reaction solution was concentrated and purified by flash silica gel chromatography (DCM/MeOH=40/1 to 20/1) to give ethyl 3-(5-((4-(6-((4-chloro-2-fluorobenzyl)oxy)pyridin-2-yl)piperidin-1-yl)methyl)-6-methoxypyridin-2-yl)propanoate (compound 6, 180 mg, 27% yield over three steps) and 3-(5-((4-(6-((4-chloro-2-fluorobenzyl)oxy)pyridin-2-yl)piperidin-1-yl)methyl)-6-hydroxypyridin-2-yl)propanoate as a yellow solid (compound 6', 430 mg, 66% yield over three steps). LC-MS: m/z 542.2 $(M+H)^+$ (compound 6); LC-MS: m/z 528.2 (M+H)+(compound 6').

Step F: 3-(5-((4-(6-((4-chloro-2-fluorobenzyl)oxy)pyridin-2-yl)piperidin-1-yl)methyl)-6-oxo-1,6-dihydropyridin-2-yl)propanoic acid (Compound 121) and 3-(5-((4-(6-((4-chloro-2-fluorobenzyl)oxy)pyridin-2-yl)piperidin-1-yl)methyl)-6-methoxypyridin-2-yl)propanoic acid (Compound 124)

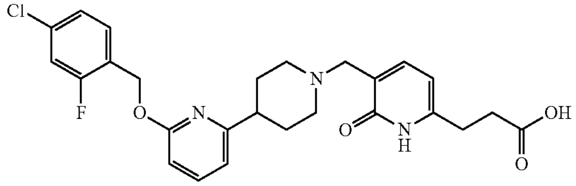 [SMILES: O=C(O)CCc1ccc(CN2CCC(c3cccc(OCc4ccc(Cl)cc4F)n3)CC2)c(=O)[nH]1]

To a solution of ethyl 3-(5-((4-(6-((4-chloro-2-fluorobenzyl)oxy)pyridin-2-yl)piperidin-1-yl)methyl)-6-hydroxypyridin-2-yl)propanoate (100 mg, 0.190 mmol) in THF (2 mL) and $H_2O$ (2 mL) was added $LiOH \cdot H_2O$ (32.0 mg, 0.760 mmol). The reaction mixture was stirred at room temperature for 2 hours. The reaction solution was concentrated and dissolved with $CH_3CN$ (2.5 mL). The mixture was adjusted to pH=5~6 with 1 M HCl aqueous solution, and purified with prep-HPLC (0.1% formic acid in water and acetonitrile) to give 3-(5-((4-(6-((4-chloro-2-fluorobenzyl)oxy)pyridin-2-yl)piperidin-1-yl)methyl)-6-oxo-1,6-dihydropyridin-2-yl)propanoic acid as a white solid (16.3 mg, 17% yield). $^1H$ NMR (400 MHz, $CD_3OD$) δ 8.07 (t, J=8.0 Hz, 1H), 7.80 (d, J=7.2 Hz, 1H), 7.58 (t, J=8.0 Hz, 1H), 7.25-7.32 (m, 2H), 7.19 (d, J=8.4 Hz, 2H), 6.34 (t, J=7.2 Hz, 1H), 5.52 (s, 2H), 4.22 (s, 2H), 3.66 (d, J=12.4 Hz, 2H), 3.23 (td, J=12.4, 2.0 Hz, 2H), 3.07-3.16 (m, 1H), 2.86-2.95 (m, 2H), 2.68-2.77 (m, 2H), 2.07-2.26 (m, 4H). LC-MS: m/z 500.2 $(M+H)^+$.

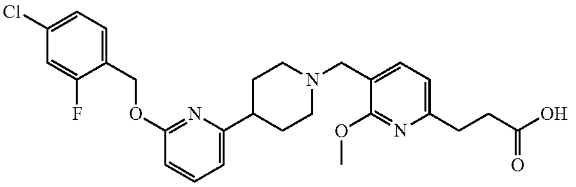 [SMILES: COc1nc(CCC(=O)O)ccc1CN1CCC(c2cccc(OCc3ccc(Cl)cc3F)n2)CC1]

3-(5-((4-(6-((4-Chloro-2-fluorobenzyl)oxy)pyridin-2-yl)piperidin-1-yl)methyl)-6-methoxypyridin-2-yl)propanoic acid (Compound 124) was synthesized using same method as Compound 121, from ethyl 3-(5-((4-(6-((4-chloro-2-fluorobenzyl)oxy)pyridin-2-yl)piperidin-1-yl)methyl)-6-methoxypyridin-2-yl)propanoate. $^1$H NMR (400 MHz, DMSO-$d_6$) δ 12.05 (br.s, 1H), 7.61-7.69 (m, 2H), 7.58 (t, J=8.4 Hz, 1H), 7.47 (dd, J=10.0, 2.0 Hz, 1H), 7.31 (dd, J=8.4, 2.0 Hz, 1H), 6.88 (dd, J=7.2, 4.0 Hz, 2H), 6.68 (d, J=8.0 Hz, 1H), 5.37 (s, 2H), 3.87 (s, 3H), 3.62 (s, 2H), 2.97-3.06 (m, 2H), 2.91 (t, J=7.2 Hz, 2H), 2.65 (t, J=7.2 Hz, 3H), 2.27-2.39 (m, 2H), 1.78-1.86 (m, 4H). LC-MS: m/z 514.2 $(M+H)^+$.

Example 49

3-(2-((4-(2-(4-chloro-2-fluorophenyl)-2-methyl-benzo[d][1,3]dioxol-4-yl)piperidin-1-yl)methyl)-1-methyl-1H-imidazol-5-yl)cyclopentane-1-carboxylic acid (Compound 247)

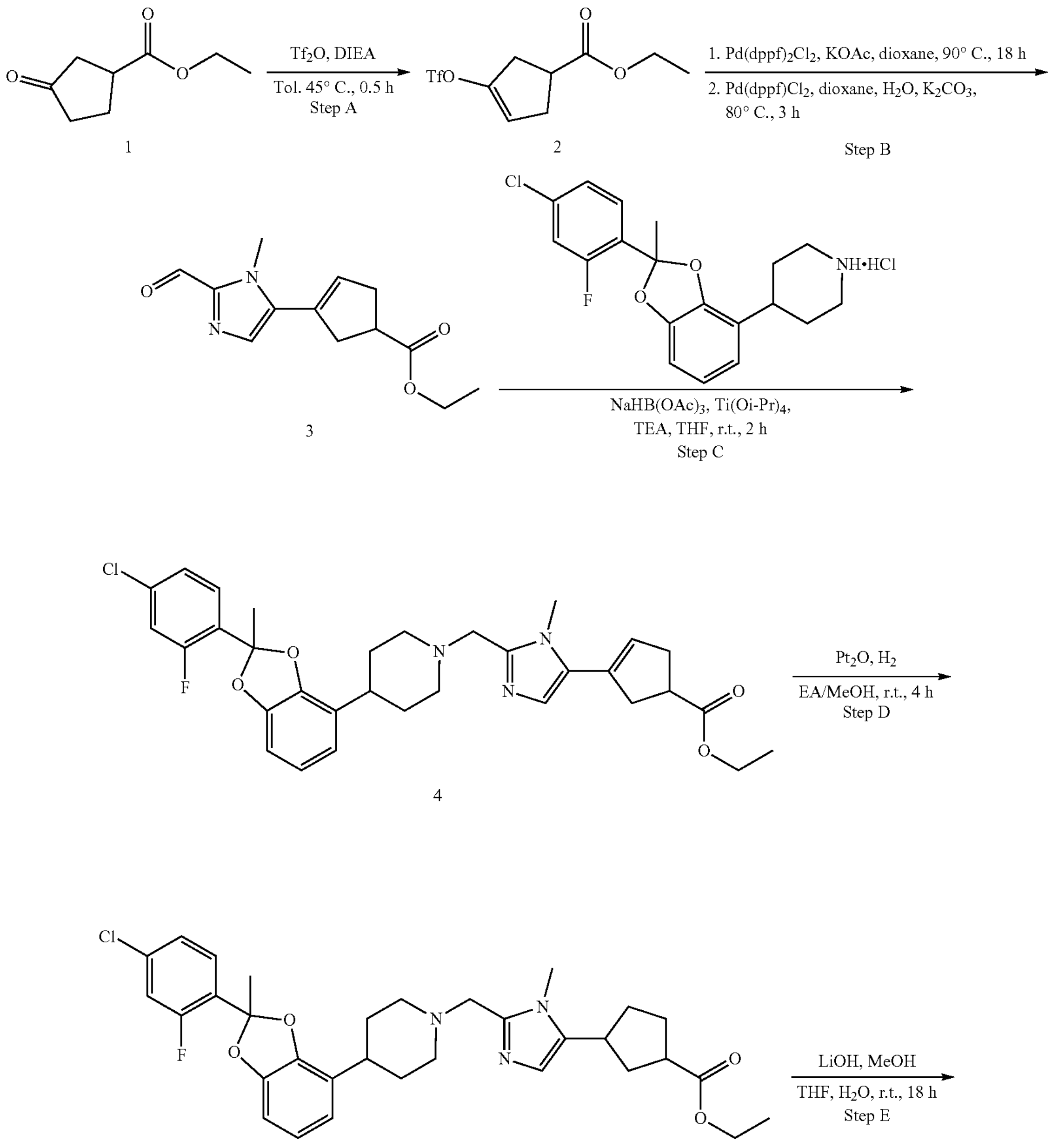

1

2

3

4

5

-continued

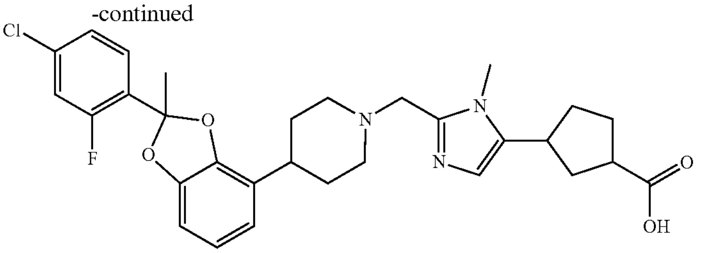

Compound 247

Step A: ethyl 3-(((trifluoromethyl)sulfonyl)oxy) cyclopent-3-ene-1-carboxylate

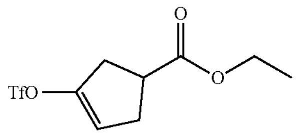 [SMILES: CCOC(=O)C1CC=C(OS(=O)(=O)C(F)(F)F)C1]

A solution of ethyl 3-oxocyclopentane-1-carboxylate (500 mg, 3.18 mmol), and DIEA (1.05 mL, 6.37 mmol) in toluene (10 mL) was heated to 45° C. Then $Tf_2O$ (1.07 mL, 6.37 mmol) was added dropwise. The reaction mixture was stirred at 45° C. for another 0.5 hour. The reaction mixture was diluted with saturated $Na_2CO_3$ aqueous solution (20 mL) and extracted with EtOAc (20 mL*3). The combined organic phase was dried over $Na_2SO_4$ and filtered. The filtrate was concentrated and purified by flash column chromatography (PE/EtOAc=20/1) to give ethyl 3-(((trifluoromethyl)sulfonyl)oxy)cyclopent-3-ene-1-carboxylate as a yellow oil (746 mg, 81% yield). The product was a mixture of two olefin isomers. $^1H$ NMR (400 MHz, $CDCl_3$) δ 5.71 (dd, J=4.0, 2.0 Hz, 0.5H), 5.57-5.61 (m, 0.5H), 4.13-4.23 (m, 2H), 3.56-3.65 (m, 0.5H), 3.21-3.52 (m, 0.5H), 2.92-3.02 (m, 0.5H), 2.76-2.88 (m, 0.5H), 2.57-2.76 (m, 2H), 2.25-2.40 (m, 1H), 1.24-1.51 (m, 3H).

Step B: ethyl 3-(2-formyl-1-methyl-1H-imidazol-5-yl)cyclopent-3-ene-1-carboxylate

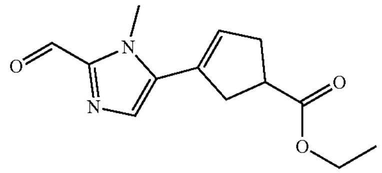 [SMILES: CCOC(=O)C1CC=C(c2cnc(C=O)n2C)C1]

A reaction mixture of ethyl 3-(((trifluoromethyl)sulfonyl)oxy)cyclopent-3-ene-1-carboxylate (500 mg, 1.73 mmol, reaction mixture of two isomers), $(BPin)_2$ (571 mg, 2.25 mmol), $Pd(dppf)_2Cl_2$ (126 mg, 0.173 mmol), and KOAc (508 mg, 5.19 mmol) in anhydrous 1,4-dioxane (3 mL) was stirred at 90° C. for 18 hours under $N_2$. To the reaction mixture were added 5-bromo-1-methyl-1H-imidazole-2-carbaldehyde (250 mg, 1.33 mmol), $Pd(dppf)_2Cl_2$ (108 mg, 0.133 mmol), $K_2CO_3$ (550 mg, 3.99 mmol) and $H_2O$ (1.5 mL). The resulting reaction mixture was stirred at 80° C. for 3 hours. Then the reaction mixture was diluted with $H_2O$ (20 mL) and extracted with EtOAc (20 mL*3). The combined organic phase was dried over $Na_2SO_4$ and filtered. The filtrate was concentrated and purified by flash column chromatography (PE/EtOAc=2/1) to give ethyl 3-(2-formyl-1-methyl-1H-imidazol-5-yl)cyclopent-3-ene-1-carboxylate as a yellow oil (233 mg, 70% yield). The product was a mixture of two isomers. LC-MS: m/z 249.0 $(M+H)^+$.

Step C: ethyl 3-(2-((4-(2-(4-chloro-2-fluorophenyl)-2-methylbenzo[d][1,3]dioxol-4-yl)piperidin-1-yl) methyl)-1-methyl-1H-imidazol-5-yl)cyclopent-3-ene-1-carboxylate

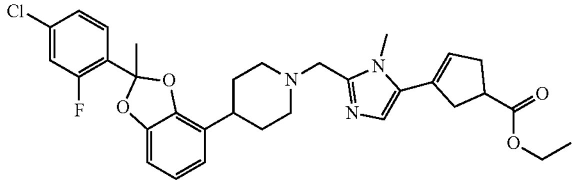 [SMILES: CCOC(=O)C1CC=C(c2cnc(CN3CCC(c4cccc5c4OC(C)(c4ccc(Cl)cc4F)O5)CC3)n2C)C1]

A reaction mixture of ethyl 3-(2-formyl-1-methyl-1H-imidazol-5-yl)cyclopent-3-ene-1-carboxylate (40.0 mg, 0.161 mmol, reaction mixture of two isomers), 4-(2-(4-chloro-2-fluorophenyl)-2-methylbenzo[d][1,3]dioxol-4-yl) piperidine hydrochloride (61.7 mg, 0.133 mmol), $Ti(Oi\text{-}Pr)_4$ (91.4 mg, 0.322 mmol), and TEA (48.8 mg, 0.483 mmol) in anhydrous THF (2 mL) was stirred at room temperature for 1 hour. Then $NaBH(OAc)_3$ (102 mg, 0.483 mmol) was added. The resulting reaction mixture was stirred at room temperature for another 1 hour. The reaction mixture was filtered. The filtrate was diluted with saturated $NaHCO_3$ aqueous solution (5 mL) and extracted with EtOAc (10 mL*3). The combined organic phase was dried over $Na_2SO_4$ and filtered. The filtrate was concentrated and purified by flash column chromatography (DCM/MeOH=40/1) to give ethyl 3-(2-((4-(2-(4-chloro-2-fluorophenyl)-2-methylbenzo [d][1,3]dioxol-4-yl)piperidin-1-yl)methyl)-1-methyl-1H-imidazol-5-yl)cyclopent-3-ene-1-carboxylate as a yellow oil (92.8 mg, 99% yield). The product was a reaction mixture of two isomers. LC-MS: m/z 580.2 $(M+H)^+$.

Step D: ethyl 3-(2-((4-(2-(4-chloro-2-fluorophenyl)-2-methylbenzo[d][1,3]dioxol-4-yl)piperidin-1-yl)methyl)-1-methyl-1H-imidazol-5-yl)cyclopentane-1-carboxylate

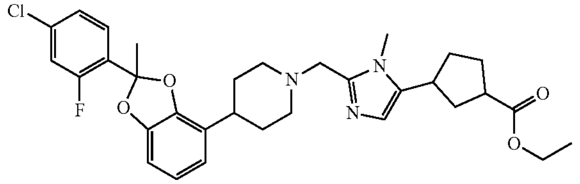 [SMILES: CCOC(=O)C1CCC(c2cnc(CN3CCC(c4cccc5c4OC(C)(c4ccc(Cl)cc4F)O5)CC3)n2C)C1]

To a solution of ethyl 3-(2-((4-(2-(4-chloro-2-fluorophenyl)-2-methylbenzo[d][1,3]dioxol-4-yl)piperidin-1-yl)methyl)-1-methyl-1H-imidazol-5-yl)cyclopent-3-ene-1-carboxylate (50.0 mg, 0.0862 mmol, mixture of two isomers) in EtOAc/MeOH (2 mL/2 mL) was added $PtO_2$ (10.0 mg). The resulting reaction mixture was stirred at room temperature for 4 hours under $H_2$. The reaction mixture was filtered. The filtrate was concentrated and purified by prep-HPLC (0.1% $NH_4HCO_3$ in water and acetonitrile) to give ethyl 3-(2-((4-(2-(4-chloro-2-fluorophenyl)-2-methylbenzo[d][1,3]dioxol-4-yl)piperidin-1-yl)methyl)-1-methyl-1H-imidazol-5-yl)cyclopentane-1-carboxylate as a white solid (21.0 mg, 42% yield). LC-MS: m/z 582.2 $(M+H)^+$.

Step E: 3-(2-((4-(2-(4-chloro-2-fluorophenyl)-2-methylbenzo[d][1,3]dioxol-4-yl)piperidin-1-yl)methyl)-1-methyl-1H-imidazol-5-yl)cyclopentane-1-carboxylic acid (Compound 247)

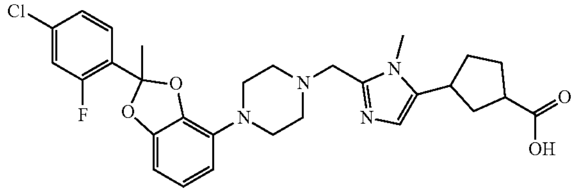 [SMILES: Cn1c(C2CCC(C(=O)O)C2)cnc1CN1CCN(c2cccc3c2OC(C)(c2ccc(Cl)cc2F)O3)CC1]

To a reaction mixture of ethyl 3-(2-((4-(2-(4-chloro-2-fluorophenyl)-2-methylbenzo[d][1,3]dioxol-4-yl)piperidin-1-yl)methyl)-1-methyl-1H-imidazol-5-yl)cyclopentane-1-carboxylate (21.0 mg, 0.0360 mmol) in THF/MeOH/$H_2O$ (1 mL/1 mL/1 mL) was added LiOH (4.30 mg, 0.180 mmol). The resulting reaction mixture was stirred at room temperature for 18 hours. THF and MeOH were removed in vacuum. The aqueous mixture was acidified to pH=3-4 with formic acid and purified by prep-HPLC (0.1% formic acid in water and acetonitrile) to give 3-(2-((4-(2-(4-chloro-2-fluorophenyl)-2-methylbenzo[d][1,3]dioxol-4-yl)piperidin-1-yl)methyl)-1-methyl-1H-imidazol-5-yl)cyclopentane-1-carboxylic acid as a white solid (10.0 mg, 50% yield). $^1H$ NMR (400 MHz, DMSO-$d_6$) δ 7.52-7.62 (m, 2H), 7.34 (d, J=8.0 Hz, 1H), 6.70-6.83 (m, 4H), 3.68 (s, 2H), 3.61 (s, 3H), 3.04-3.17 (m, 2H), 2.92-3.03 (m, 2H), 2.81-2.90 (m, 1H), 2.63-2.72 (m, 1H), 2.19-2.35 (m, 3H), 2.00-2.09 (m, 4H), 1.87-1.96 (m, 2H), 1.70-1.80 (m, 4H), 1.54-1.63 (m, 1H). LC-MS: m/z 554.2 $(M+H)^+$.

Example 50

2-((6-((4-(6-((4-chloro-2-fluorobenzyl)oxy)pyridin-2-yl)piperidin-1-yl)methyl)pyridin-3-yl)oxy)acetic acid (Compound 119)

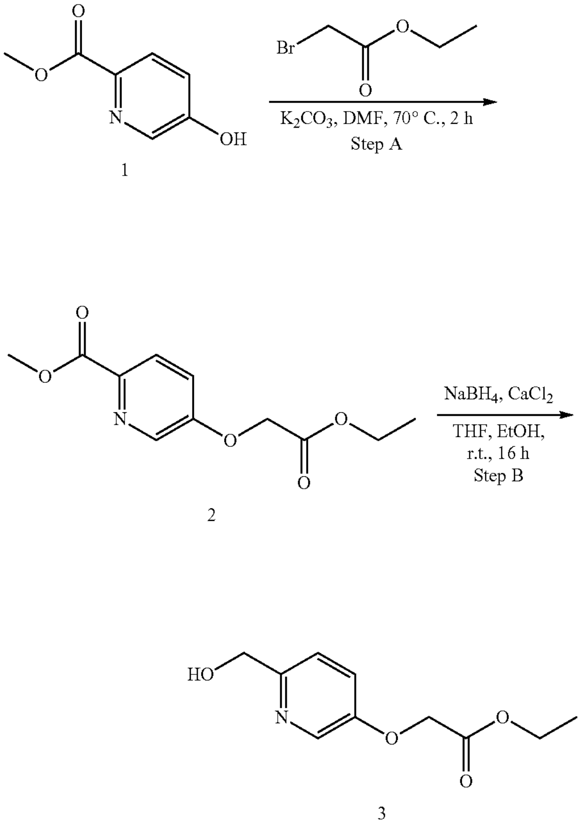

Step A: methyl 5-(2-ethoxy-2-oxoethoxy)picolinate

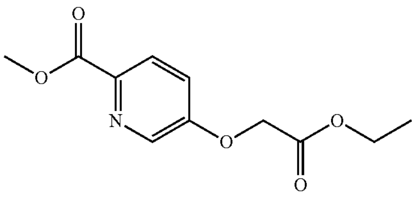 [SMILES: CCOC(=O)COc1ccc(C(=O)OC)nc1]

To a mixture of methyl 5-hydroxypicolinate (400 mg, 2.61 mmol) in DMF (12 mL) was added $K_2CO_3$ (722 mg, 5.22 mmol). The reaction mixture was stirred for 20 mins, then ethyl 2-bromoacetate (654 mg, 3.92 mmol) was added. The reaction mixture was stirred at 70° C.; for 2 hours. Then the reaction mixture was diluted with water (25 mL) and extracted with EtOAc (30 mL*3). The organic layers were washed with brine (20 mL), dried over $Na_2SO_4$, and concentrated to give methyl 5-(2-ethoxy-2-oxoethoxy)picolinate as a white solid (620 mg, crude). LC-MS: m/z 240.2 $(M+H)^+$.

Step B: ethyl 2-((6-(hydroxymethyl)pyridin-3-yl)oxy)acetate

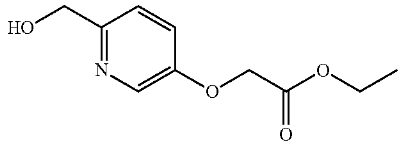

To a solution of methyl 5-(2-ethoxy-2-oxoethoxy)picolinate (620 mg, 2.59 mmol) in THF (7 mL) and EtOH (7 mL) were added $CaCl_2$) (1.15 g, 10.4 mmol) and $NaBH_4$ (245 mg, 6.48 mmol) at 0° C. The reaction mixture was stirred at room temperature for 16 hours. Then the reaction mixture was quenched by saturated ammonium chloride aqueous solution (15 mL) and extracted with DCM (20 mL*3). The organic layers were washed with brine (15 mL), dried over $Na_2SO_4$, concentrated and purified by flash column chromatography (eluting with McOH/DCM) to give ethyl 2-((6-(hydroxymethyl)pyridin-3-yl)oxy)acetate as a brown oil (300 mg, 55% yield over 2 steps). LC-MS: m/z 212.2 $(M+H)^+$.

2-((6-((4-(6-((4-chloro-2-fluorobenzyl)oxy)pyridin-2-yl)piperidin-1-yl)methyl)pyridin-3-yl)oxy)acetic acid (Compound 119)

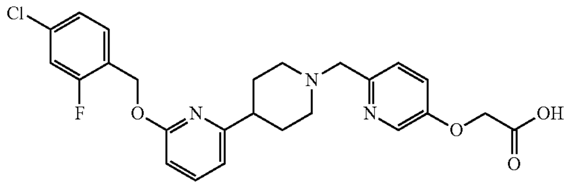 [SMILES: O=C(O)COc1ccc(CN2CCC(c3cccc(OCc4ccc(Cl)cc4F)n3)CC2)nc1]

Compound 119 was then synthesized following the route of Example 3 (from step B to step D), using ethyl 2-((6-(hydroxymethyl)pyridin-3-yl)oxy)acetate in step B.

$^1$H NMR (400 MHz, DMSO-$d_6$) δ 10.54 (br.s, 1H), 8.39 (d, J=2.8 Hz, 1H), 7.59-7.75 (m, 3H), 7.45-7.55 (m, 2H), 7.33 (dd, J=8.4, 1.6 Hz, 1H), 6.90 (d, J=6.8 Hz, 1H), 6.73 (d, J=8.0 Hz, 1H), 5.38 (s, 2H), 4.85 (s, 2H), 4.21-4.25 (m, 2H), 3.41-3.55 (m, 2H), 3.08-3.22 (m, 2H), 2.83-2.96 (m, 1H), 1.98-2.19 (m, 4H). LC-MS: m/z 486.2 $(M+H)^+$.

2-((6-((4-(6-((4-chloro-2-fluorobenzyl)oxy)pyridin-2-yl)piperidin-1-yl)methyl)pyridin-3-yl)oxy)propanoic acid (Compound 125) was synthesized following the route of Example 50, using ethyl 2-bromopropanoate in step A.

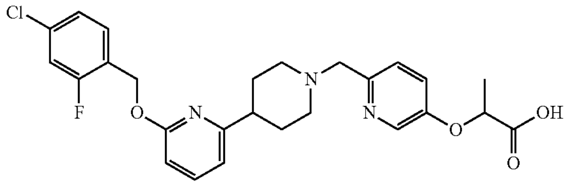 [SMILES: CC(Oc1ccc(CN2CCC(c3cccc(OCc4ccc(Cl)cc4F)n3)CC2)nc1)C(=O)O]

$^1$H NMR (400 MHz, $CD_3OD$) δ 8.30-8.34 (m, 1H), 7.63 (t, J=7.6 Hz, 1H), 7.49 (t, J=8.0 Hz, 1H), 7.43 (dd, J=8.4, 3.2 Hz, 1H), 7.32 (dd, J=8.4, 2.8 Hz, 1H), 7.19-7.25 (m, 2H), 6.89 (d, J=7.2 Hz, 1H), 6.71 (d, J=8.4 Hz, 1H), 5.43 (s, 2H), 4.69 (q, J=6.8 Hz, 1H), 4.35 (s, 2H), 3.59 (d, J=12.0 Hz, 2H), 3.09-3.26 (m, 2H), 2.87-3.06 (m, 1H), 2.05-2.23 (m, 4H), 1.60 (d, J=6.8 Hz, 3H). LC-MS: m/z 500.2 $(M+H)^+$.

2-((6-((4-(6-((4-chloro-2-fluorobenzyl)oxy)pyridin-2-yl)piperidin-1-yl)methyl)pyridin-3-yl)oxy)-2-methylpropanoic acid (Compound 122) was synthesized following the route of Example 50, using ethyl 2-bromo-2-methylpropanoate in step A.

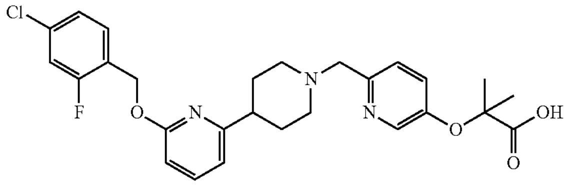 [SMILES: CC(C)(Oc1ccc(CN2CCC(c3cccc(OCc4ccc(Cl)cc4F)n3)CC2)nc1)C(=O)O]

$^1$H NMR (400 MHz, $CD_3OD$) δ 8.45 (d, J=2.8 Hz, 1H), 8.12 (t, J=8.0 Hz, 1H), 7.78 (d, J=8.4 Hz, 1H), 7.54-7.67 (m, 2H), 7.23-7.31 (m, 4H), 5.53 (s, 2H), 4.57 (s, 2H), 3.69 (d, J=12.0 Hz, 2H), 3.34-3.41 (m, 2H), 3.12-3.22 (m, 1H), 2.23 (s, 4H), 1.69 (s, 6H). LC-MS: m/z 514.2 $(M+H)^+$.

Example 51

2-((6-((4-(6-((4-chloro-2-fluorobenzyl)oxy)pyridin-2-yl)piperidin-1-yl)methyl)pyridin-3-yl)amino)propanoic acid (Compound 130)

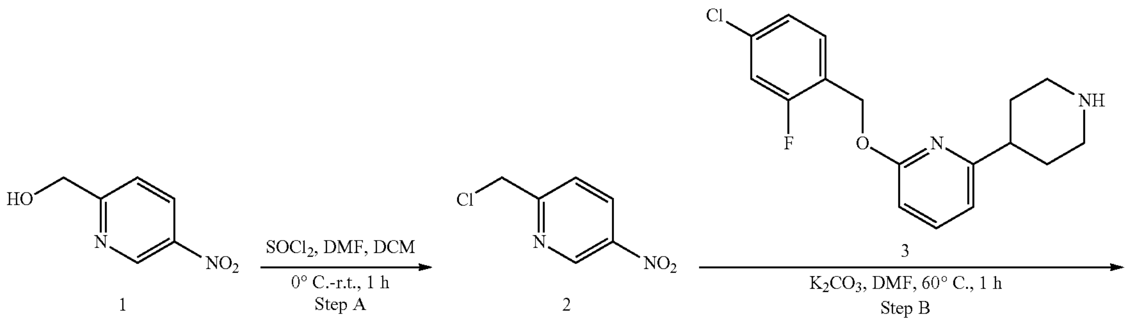

1 2 3

-continued

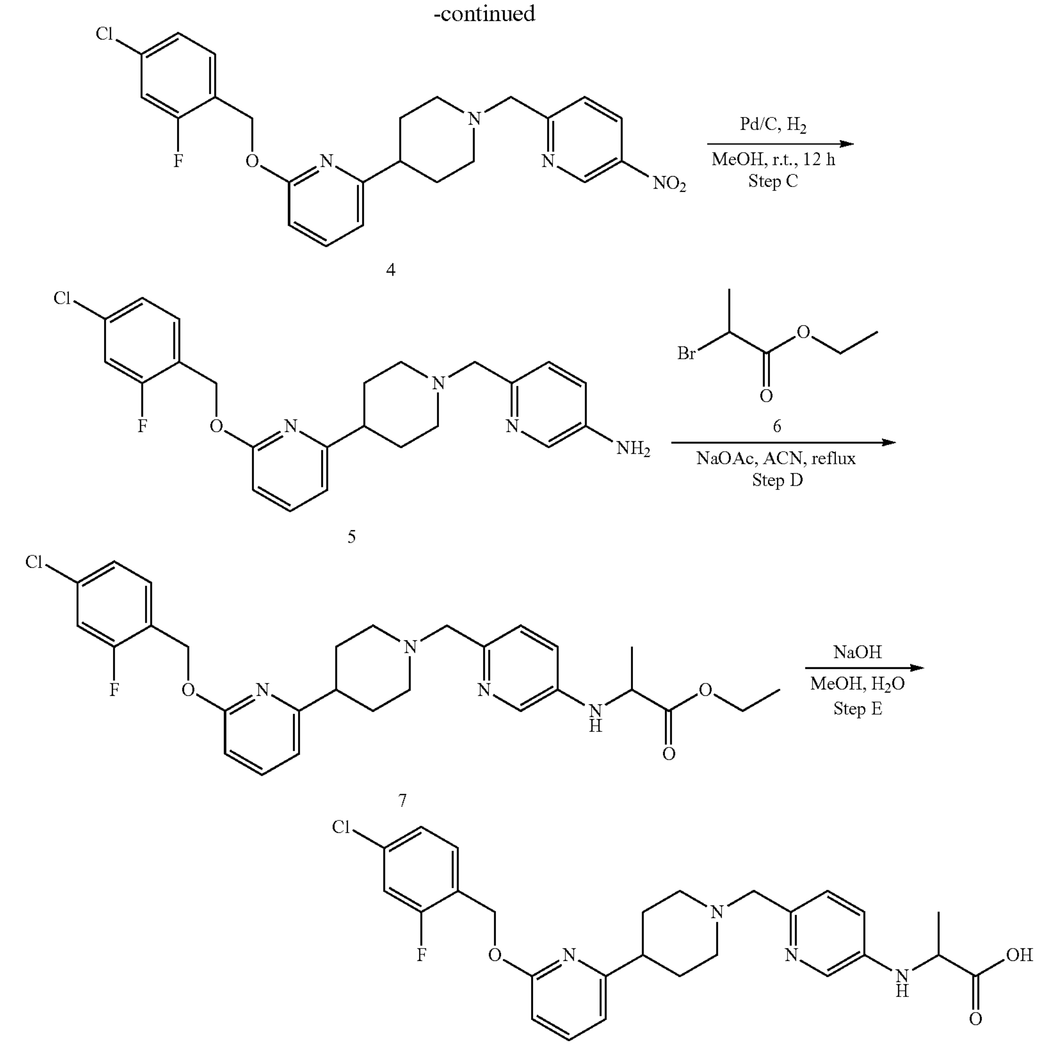

Compound 130

Step A: 2-(chloromethyl)-5-nitropyridine

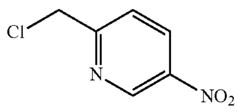 [SMILES: O=[N+]([O-])c1ccc(CCl)nc1]

To a mixture of (5-nitropyridin-2-yl)methanol (450 mg, 3.00 mmol) and DMF (0.1 mL) in DCM (15 mL) was added dropwise $SOCl_2$ (720 mg, 6.00 mmol) at 0° C. under $N_2$ atmosphere. Then the reaction mixture was stirred at room temperature for 1 hour. The reaction mixture was quenched with water (50 mL) and extracted with DCM (50 mL*3). The combined organic phase was washed with brine (30 mL), dried over anhydrous $Na_2SO_4$ and concentrated in vacuo. The residue was purified by silica gel chromatography (PE/EtOAc=30/1) to give 2-(chloromethyl)-5-nitropyridine as a yellow oil (270 mg, 52% yield). LC-MS: m/z 173.1 $(M+H)^+$.

Step B: 2-(4-(6-((4-chloro-2-fluorobenzyl)oxy)pyridin-2-yl)piperidin-1-yl)methyl)-5-nitropyridine

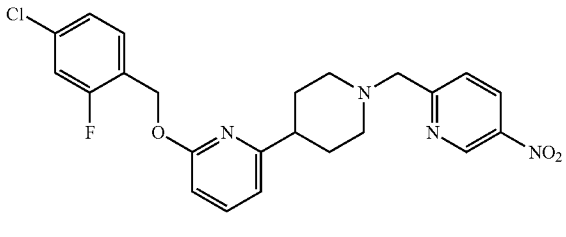 [SMILES: O=[N+]([O-])c1ccc(CN2CCC(c3cccc(OCc4ccc(Cl)cc4F)n3)CC2)nc1]

A mixture of 2-(chloromethyl)-5-nitropyridine (172 mg, 1.00 mmol), 2-((4-chloro-2-fluorobenzyl)oxy)-6-(piperidin-4-yl)pyridine (320 mg, 1.00 mmol) and $K_2CO_3$ (276 mg, 2.00 mmol) in DMF (5 mL) was stirred at 60° C. for 1 hour. The reaction mixture was diluted with water (50 mL) and extracted with DCM (50 mL*3). The combined organic phase was washed with brine (30 mL), dried over anhydrous $Na_2SO_4$ and concentrated in vacuo. The residue was purified by silica gel chromatography (PE/EtOAc=10/1) to give 2-((4-(6-((4-chloro-2-fluorobenzyl)oxy)pyridin-2-yl)piperidin-1-yl)methyl)-5-nitropyridine as a yellow oil (270 mg, 59% yield). LC-MS: m/z 457.1 $(M+H)^+$.

Step C: 6-((4-(6-((4-chloro-2-fluorobenzyl)oxy)pyridin-2-yl)piperidin-1-yl)methyl)pyridin-3-amine

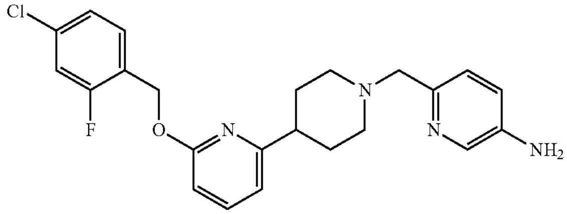

A mixture of 2-((4-(6-((4-chloro-2-fluorobenzyl)oxy)pyridin-2-yl)piperidin-1-yl)methyl)-5-nitropyridine (245 mg, 0.500 mmol) and Pd/C (10%, 25 mg) in MeOH (10 mL) was stirred at room temperature under $H_2$ atmosphere for 12 hours. The reaction mixture was filtered through celite and concentrated. The residue was purified by silica gel chromatography (DCM/MeOH=10/1) to give 6-((4-(6-((4-chloro-2-fluorobenzyl)oxy)pyridin-2-yl)piperidin-1-yl)methyl)pyridin-3-amine as a colorless oil (180 mg, 84% yield). LC-MS: m/z 427.1 $(M+H)^+$.

Step D: ethyl 2-((6-((4-(6-((4-chloro-2-fluorobenzyl)oxy)pyridin-2-yl)piperidin-1-yl)methyl)pyridin-3-yl)amino)propanoate

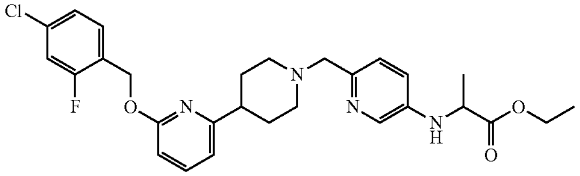 [SMILES: CCOC(=O)C(C)Nc1ccc(CN2CCC(c3cccc(OCc4ccc(Cl)cc4F)n3)CC2)nc1]

A mixture of 6-((4-(6-((4-chloro-2-fluorobenzyl)oxy)pyridin-2-yl)piperidin-1-yl)methyl)pyridin-3-amine (170 mg, 0.400 mmol), ethyl 2-bromopropanoate (145 mg, 0.800 mmol) and NaOAc (98.0 mg, 1.20 mmol) in $CH_3CN$ (4 mL) was refluxed for 24 hours under $N_2$ atmosphere. The reaction mixture was concentrated and residue was purified by silica gel chromatography (DCM/MeOH=10/1) to give ethyl 2-((6-((4-(6-((4-chloro-2-fluorobenzyl)oxy)pyridin-2-yl)piperidin-1-yl)methyl)pyridin-3-yl)amino)propanoate as a colorless oil (60.0 mg, 28% yield). LC-MS: m/z 527.1 $(M+H)^+$.

Step E: 2-((6-((4-(6-((4-chloro-2-fluorobenzyl)oxy)pyridin-2-yl)piperidin-1-yl)methyl)pyridin-3-yl)amino)propanoic acid

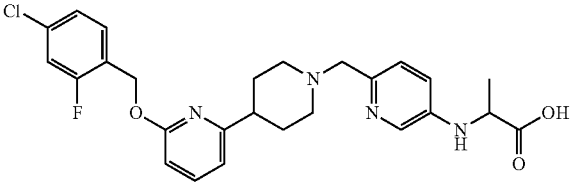 [SMILES: CC(Nc1ccc(CN2CCC(c3cccc(OCc4ccc(Cl)cc4F)n3)CC2)nc1)C(=O)O]

A mixture of ethyl 2-((6-((4-(6-((4-chloro-2-fluorobenzyl)oxy)pyridin-2-yl)piperidin-1-yl)methyl)pyridin-3-yl)amino)propanoate (60.0 mg, 0.110 mmol) and NaOH (44.0 mg, 1.10 mmol) in McOH/$H_2O$ (3 mL/0.3 mL) was stirred at 30° C. for 2 hours. The reaction mixture was acidified with HCOOH to pH=5-7, diluted with water (10 mL) and extracted with EtOAc (10 mL*3). The combined organic phase was washed with brine (10 mL), dried over anhydrous $Na_2SO_4$ and concentrated in vacuo. The residue was purified by reverse phase chromatography ($CH_3CN/H_2O$) to give 2-((6-((4-(6-((4-chloro-2-fluorobenzyl)oxy)pyridin-2-yl)piperidin-1-yl)methyl)pyridin-3-yl)amino)propanoic acid as a white solid (25.0 mg, 45% yield). $^1H$ NMR (400 MHz, $CD_3OD$) δ 8.18 (d, J=2.4 Hz, 1H), 7.47-7.60 (m, 4H), 7.17-7.22 (m, 2H), 6.82 (d, J=7.2 Hz, 1H), 6.63 (d, J=8.0 Hz, 1H), 5.85 (q, J=7.2 Hz, 1H), 5.40 (s, 2H), 3.85 (d, J=14.4 Hz, 1H), 3.69 (d, J=14.0 Hz, 1H), 3.00 (d, J=12.0 Hz, 1H), 2.88 (d, J=11.2 Hz, 1H), 2.59-2.67 (m, 1H), 2.23-2.34 (m, 2H), 1.77-1.90 (m, 7H). LC-MS: m/z 499.1 $(M+H)^+$.

Example 52

2-{2-[(4-{6-[(4-chloro-2-fluorophenyl)methoxy]pyridin-2-yl}piperidin-1-yl)methyl]-1-{[(2S)-oxetan-2-yl]methyl}-1H-imidazol-5-yl}cyclopropane-1-carboxylic acid (Compound 114a)

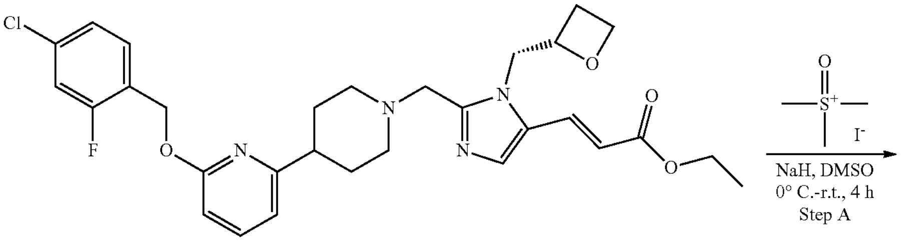

1

-continued

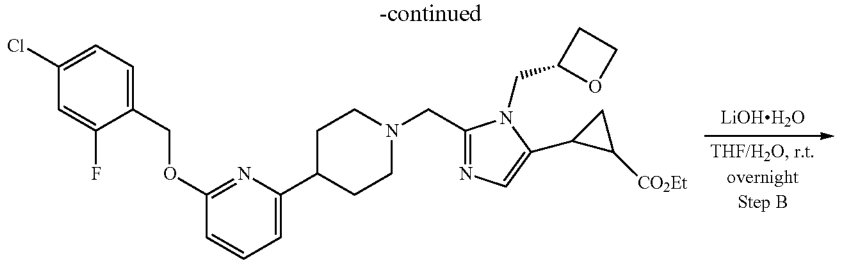

2

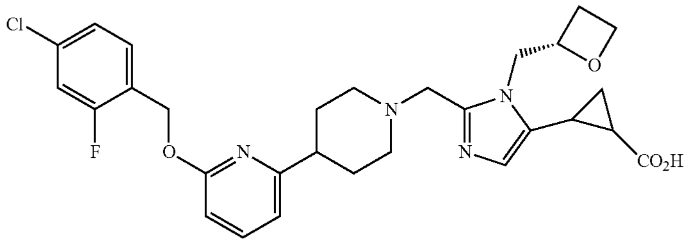

Compound 114a

Step A: ethyl 2-(2-((4-(6-((4-chloro-2-fluorobenzyl)oxy)pyridin-2-yl)piperidin-1-yl)methyl)-1-(((S)-oxetan-2-yl)methyl)-1H-imidazol-5-yl)cyclopropane-1-carboxylate

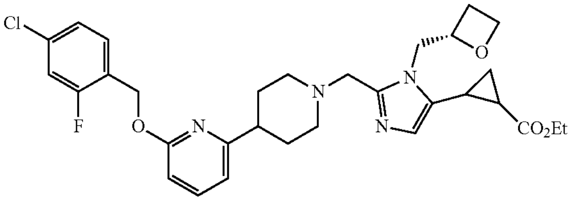 [SMILES: CCOC(=O)C1CC1c1cnc(CN2CCC(c3cccc(OCc4ccc(Cl)cc4F)n3)CC2)n1C[C@@H]1CCO1]

To a suspension of sodium hydride (60% in oil, 6.40 mg, 0.160 mmol) in dry DMSO (2 mL) was added trimethylsulfoxonium iodide (41.0 mg, 0.186 mmol) at 0° C., and then the mixture was stirred at room temperature for 1 hour. To the reaction mixture was added a solution of methyl (S,E)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)acrylate (70.0 mg, 0.123 mmol) in dry DMSO (1 mL) at 0° C., and the mixture was stirred at room temperature for 4 hours. The reaction mixture was quenched with water (5 mL), and the mixture was extracted with EtOAc (5 mL*3). The extract was washed with brine (5 mL), dried over anhydrous $Na_2SO_4$, and concentrated. The residue was purified by silica gel column chromatography (DCM/MeOH=20/1) to give ethyl 2-(2-((4-(6-((4-chloro-2-fluorobenzyl)oxy)pyridin-2-yl)piperidin-1-yl)methyl)-1-(((S)-oxetan-2-yl)methyl)-1H-imidazol-5-yl)cyclopropane-1-carboxylate (40.0 mg, 56% yield). LC-MS: m/z 583.4 $(M+H)^+$.

Step B: 2-(2-((4-(6-((4-chloro-2-fluorobenzyl)oxy)pyridin-2-yl)piperidin-1-yl)methyl)-1-(((S)-oxetan-2-yl)methyl)-1H-imidazol-5-yl)cyclopropane-1-carboxylic acid (Compound 114a)

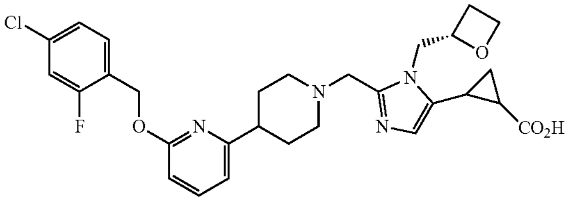 [SMILES: O=C(O)C1CC1c1cnc(CN2CCC(c3cccc(OCc4ccc(Cl)cc4F)n3)CC2)n1C[C@@H]1CCO1]

To a solution of ethyl 2-(2-((4-(6-((4-chloro-2-fluorobenzyl)oxy)pyridin-2-yl)piperidin-1-yl)methyl)-1-(((S)-oxetan-2-yl)methyl)-1H-imidazol-5-yl)cyclopropane-1-carboxylate (80.0 mg, 0.137 mmol) in $THF/H_2O$ (5 mL/1 mL) was added $LiOH{\cdot}H_2O$ (28.8 mg, 0.686 mmol). The resulting mixture was stirred at room temperature for 2 hours. Then the reaction mixture was adjusted to pH=5-6 with HCOOH. The mixture was diluted with EtOAc (20 mL), and washed with water (10 mL), brine (10 mL), dried over $Na_2SO_4$, concentrated and purified by Prep-HPLC (0.1% formic acid in water and acetonitrile) to give 2-(2-((4-(6-((4-chloro-2-fluorobenzyl)oxy)pyridin-2-yl)piperidin-1-yl)methyl)-1-(((S)-oxetan-2-yl)methyl)-1H-imidazol-5-yl)cyclopropane-1-carboxylic acid as a white solid (34.0 mg, 45% yield).

$^1H$ NMR (400 MHz, DMSO-$d_6$) δ 12.35 (br.s, 1H), 7.63 (t, J=7.6 Hz, 1H), 7.56 (t, J=8.0 Hz, 1H), 7.46 (dd, J=10.0, 2.0 Hz, 1H), 7.30 (d, J=8.0 Hz, 1H), 6.87 (d, J=7.2 Hz, 1H), 6.67 (d, J=8.0 Hz, 1H), 6.53 (s, 1H), 5.38 (s, 2H), 4.97-5.12 (m, 1H), 4.45-4.50 (m, 3H), 4.21-4.35 (m, 1H), 3.65 (dd, J=17.2, 13.6 Hz, 1H), 3.39-3.45 (m, 1H), 2.88-2.92 (m, 1H), 2.74-2.79 (m, 1H), 2.65-2.72 (m, 1H), 2.53-2.59 (m, 1H), 2.32-2.44 (m, 2H), 2.07-2.13 (m, 1H), 1.97-2.04 (m, 1H), 1.65-1.83 (m, 4H), 1.53-1.65 (m, 1H), 1.18-1.39 (m, 2H). LC-MS: m/z 555.2 $(M+H)^+$.

2-(2-((4-(6-((4-chloro-2-fluorobenzyl)oxy)pyridin-2-yl)piperidin-1-yl)methyl)-1-(2-methoxyethyl)-1H-imidazol-5-yl)cyclopropanecarboxylic acid (Compound 103) was synthesized following the route of Example 52, using ethyl (E)-3-(2-((4-(6-((4-chloro-2-fluorobenzyl)oxy)pyridin-2-yl)piperidin-1-yl)methyl)-1-(2-methoxyethyl)-1H-imidazol-5-yl)acrylate in step A.

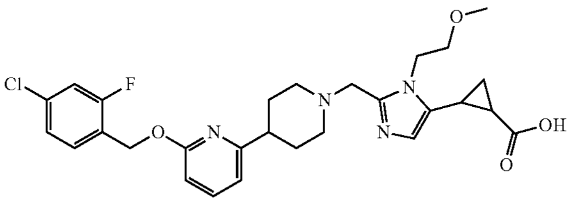 [SMILES: COCCn1c(C2CC2C(=O)O)cnc1CN1CCC(c2cccc(OCc3ccc(Cl)cc3F)n2)CC1]

$^1$H NMR (400 MHz, DMSO-$d_6$) δ 7.62 (t, J=8.0 Hz, 1H), 7.55 (t, J=8.0 Hz, 1H), 7.45 (dd, J=10.0, 1.6 Hz, 1H), 7.29 (dd, J=8.4, 1.6 Hz, 1H), 6.86 (d, J=7.6 Hz, 1H), 6.67 (d, J=8.0 Hz, 1H), 6.52 (s, 1H), 5.36 (s, 2H), 4.20-4.24 (m, 2H), 3.69 (t, J=5.2 Hz, 2H), 3.51 (dd, J=22.0, 13.2 Hz, 2H), 3.23 (s, 3H), 2.80-2.86 (m, 2H), 2.51-2.60 (m, 1H), 2.20-2.29 (m, 1H), 2.02-2.06 (m, 2H), 1.57-1.79 (m, 5H), 1.23-1.34 (m, 2H). LC-MS: m/z 543.2 $(M+H)^+$.

2-(2-((4-(6-((4-chloro-2-fluorobenzyl)oxy)pyridin-2-yl)piperidin-1-yl)methyl)-1-methyl-1H-imidazol-5-yl)cyclopropanecarboxylic acid (Compound 108) was synthesized following the method described in Example 52, using ethyl (E)-3-(2-((4-(6-((4-chloro-2-fluorobenzyl)oxy)pyridin-2-yl)piperidin-1-yl)methyl)-1-methyl-1H-imidazol-5-yl)acrylate in step A.

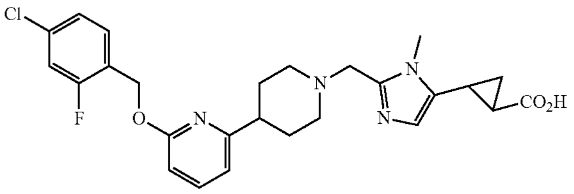 [SMILES: Cn1c(C2CC2C(=O)O)cnc1CN1CCC(c2cccc(OCc3ccc(Cl)cc3F)n2)CC1]

$^1$H NMR (400 MHz, D20) δ 7.66 (t, J=8.0 Hz, 1H), 7.40 (t, J=8.0 Hz, 1H), 7.19 (d, J=10.0 Hz, 1H), 7.16 (d, J=8.4 Hz, 1H), 7.00 (s, 1H), 6.89 (d, J=7.2 Hz, 1H), 6.72 (d, J=8.4 Hz, 1H), 5.29 (s, 2H), 4.42 (s, 2H), 3.75 (s, 3H), 3.49 (d, J=12.0 Hz, 2H), 3.10 (t, J=12.0 Hz, 2H), 2.85-2.92 (m, 1H), 2.15-2.25 (m, 1H), 1.93-2.02 (m, 4H), 1.63-1.75 (m, 1H), 1.39-1.52 (m, 1H), 1.23-1.29 (m, 1H). LC-MS: m/z 499.4 $(M+H)^+$.

2-(2-((4-((R)-2-(4-chlorophenyl)-2,3-dihydrobenzo[b][1,4]dioxin-5-yl)piperidin-1-yl)methyl)-1-(((S)-oxetan-2-yl)methyl)-1H-imidazol-5-yl)cyclopropane-1-carboxylic acid (Compound 248) was synthesized following the method described in Example 52, using methyl (E)-3-(2-((4-((R)-2-(4-chlorophenyl)-2,3-dihydrobenzo [b][1,4]dioxin-5-yl)piperidin-1-yl)methyl)-1-(((S)-oxetan-2-yl)methyl)-1H-imidazol-5-yl)acrylate in step A.

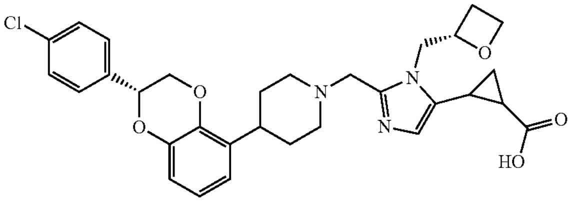 [SMILES: O=C(O)C1CC1c1cnc(CN2CCC(c3cccc4c3OC[C@@H](c3ccc(Cl)cc3)O4)CC2)n1C[C@@H]1CCO1]

$^1$H NMR (400 MHz, $CD_3OD$) δ 7.43 (dd, J=14.8, 8.4 Hz, 4H), 6.73-6.87 (m, 4H), 5.12-5.23 (m, 2H), 4.55-4.74 (m, 3H), 4.36-4.48 (m, 2H), 3.95-4.10 (m, 3H), 3.26-3.30 (m, 2H), 3.01-3.07 (m, 1H), 2.74-2.86 (m, 1H), 2.61-2.66 (m, 2H), 2.50-2.57 (m, 1H), 2.24-2.33 (m, 1H), 1.84-1.96 (m, 4H), 1.74-1.77 (m, 0.6H), 1.62-1.66 (m, 0.6H), 1.45-1.49 (m, 1H), 1.27-1.31 (m, 0.4H), 1.19-1.23 (m, 0.4H). LC-MS: m/z 564.2 $(M+H)^+$.

2-(6-((4-(6-((4-chloro-2-fluorobenzyl)oxy)pyridin-2-yl)piperidin-1-yl)methyl)pyridin-3-yl)cyclopropane-1-carboxylic acid (Compound 126) was synthesized following the method described in Example 52, using ethyl (E)-3-(6-((4-(6-((4-chloro-2-fluorobenzyl)oxy)pyridin-2-yl)piperidin-1-yl)methyl)pyridin-3-yl)acrylate in step A.

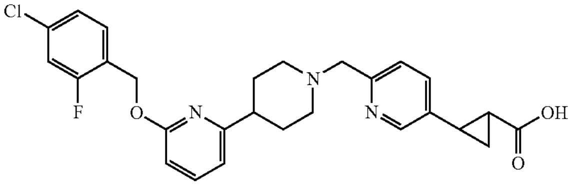 [SMILES: O=C(O)C1CC1c1ccc(CN2CCC(c3cccc(OCc4ccc(Cl)cc4F)n3)CC2)nc1]

$^1$H NMR (400 MHz, $CD_3OD$) δ 8.91 (s, 1H), 8.35-8.39 (m, 2H), 8.28-8.30 (m, 1H), 7.65 (t, J=8.0 Hz, 1H), 7.52 (d, J=8.8 Hz, 1H), 7.42 (d, J=7.6 Hz, 1H), 7.30-7.35 (m, 2H), 5.59 (s, 2H), 4.82 (s, 2H), 3.74 (d, J=12.0 Hz, 2H), 3.51 (t, J=9.6 Hz, 2H), 3.31-3.34 (m, 1H), 2.76-2.81 (m, 1H), 2.26-2.35 (m, 5H), 1.73-1.78 (m, 1H), 1.63-1.68 (m, 1H). LC-MS: m/z 496.2 $(M+H)^+$.

Example 53

2-((4-(6-((4-chloro-2-fluorobenzyl)oxy)pyridin-2-yl)piperidin-1-yl)methyl)-1-methyl-1H-imidazole-5-carboxylic acid (Compound 101)

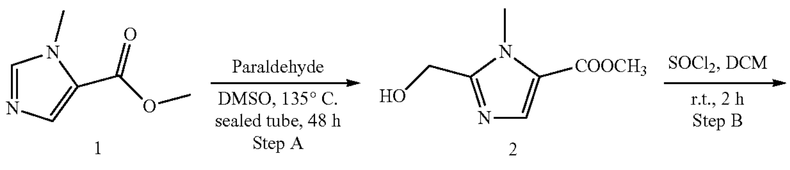

-continued

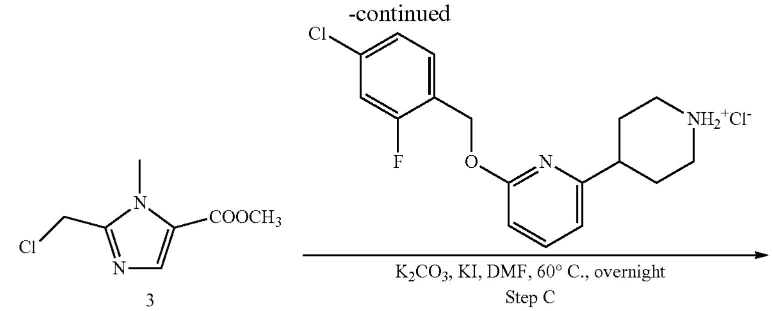

3

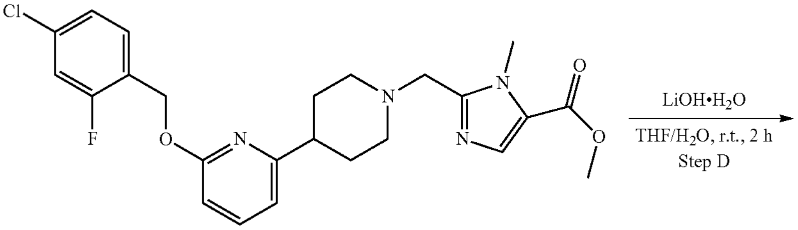

4

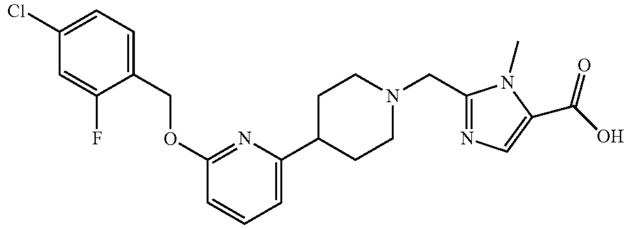

Compound 101

Step A: methyl 2-(hydroxymethyl)-1-methyl-1H-imidazole-5-carboxylate

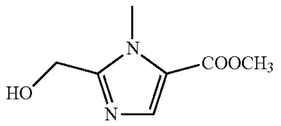

To a sealed tube were added methyl 1-methyl-1H-imidazole-5-carboxylate (1.00 g, 7.10 mmol), paraformaldehyde (2.20 g, 49.0 mmol) and DMSO (7 mL). The mixture was stirred at 135° C. for 48 hours. The mixture was filtered and the filtrate was concentrated. The residue was purified by flash column chromatography (eluting with EtOAc/PE) to give methyl 2-(hydroxymethyl)-1-methyl-1H-imidazole-5-carboxylate as a white solid (700 mg, 57% yield). LC-MS: m/z 171.1 $(M+H)^+$.

Step B: methyl 2-(chloromethyl)-1-methyl-1H-imidazole-5-carboxylate

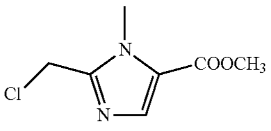

To a solution of methyl 2-(hydroxymethyl)-1-methyl-1H-imidazole-5-carboxylate (180 mg, 1.05 mmol) in DCM (5 mL) was added $SOCl_2$ (4 mL) at 0° C. The mixture was stirred at room temperature for 2 hours. The mixture was concentrated to give methyl 2-(chloromethyl)-1-methyl-1H-imidazole-5-carboxylate as oil (217 mg, crude), which was used for next step directly.

Step C: methyl 2-((4-(6-((4-chloro-2-fluorobenzyl)oxy)pyridin-2-yl)piperidin-1-yl)methyl)-1-methyl-1H-imidazole-5-carboxylate

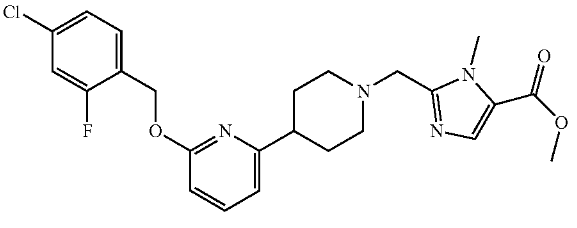 [SMILES: COC(=O)c1cnc(CN2CCC(c3cccc(OCc4ccc(Cl)cc4F)n3)CC2)n1C]

To a mixture of methyl 2-(chloromethyl)-1-methyl-1H-imidazole-5-carboxylate (217 mg, 1.15 mmol, crude) and $K_2CO_3$ (318 mg, 2.30 mmol) in DMF (2 mL) were added KI (38.0 mg, 0.230 mmol) and 4-(6-((4-chloro-2-fluorobenzyl)oxy)pyridin-2-yl)piperidin-1-ium chloride (375 mg, 1.05 mmol). The mixture was stirred at 60° C. overnight. The mixture was diluted with water (5 mL), and extracted with EtOAc (10 mL*3). The organic layer was washed with water (10 mL), brine (10 mL), dried over anhydrous $Na_2SO_4$, filtered and concentrated. The residue was purified by flash column chromatography (eluting with McOH/DCM) to give methyl 2-((4-(6-((4-chloro-2-fluorobenzyl)oxy)pyridin-2-yl)piperidin-1-yl)methyl)-1-methyl-1H-imidazole-5-carboxylate as a white solid (300 mg, 60% yield over two steps). LC-MS: m/z 472.9 $(M+H)^+$.

Step D: 2-(4-(6-((4-chloro-2-fluorobenzyl)oxy)pyridin-2-yl)piperidin-1-yl)methyl)-1-methyl-1H-imidazole-5-carboxylic acid

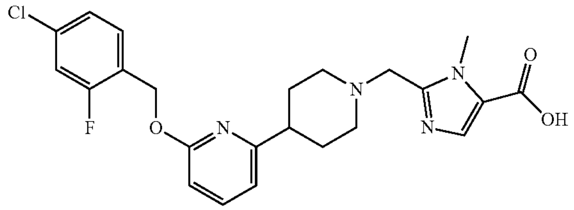 [SMILES: Cn1c(C(=O)O)cnc1CN1CCC(c2cccc(OCc3ccc(Cl)cc3F)n2)CC1]

To a solution of methyl 2-((4-(6-((4-chloro-2-fluorobenzyl)oxy)pyridin-2-yl)piperidin-1-yl)methyl)-1-methyl-1H-imidazole-5-carboxylate (300 mg, 0.630 mmol) in THF/$H_2O$=2:1 (4 mL) was added $LiOH{\cdot}H_2O$ (53.0 mg, 1.26 mmol). The resulting mixture was stirred at room temperature for 2 hours. 1N HCl aqueous solution was used to adjust pH to 5. The mixture was concentrated and purified by prep-HPLC (0.1% formic acid in water and acetonitrile) to give 2-((4-(6-((4-chloro-2-fluorobenzyl)oxy)pyridin-2-yl) piperidin-1-yl)methyl)-1-methyl-1H-imidazole-5-carboxylic acid as a white solid (200 mg, 96% yield). $^1H$ NMR (400 MHz, DMSO-$d_6$) δ 11.24 (br.s, 1H), 7.87 (s, 1H), 7.60-7.74 (m, 2H), 7.47 (dd, J=10.0, 2.0 Hz, 1H), 7.33 (dd, J=8.4, 2.0 Hz, 1H), 6.90 (d, J=6.8 Hz, 1H), 6.73 (d, J=8.0 Hz, 1H), 5.39 (s, 2H), 4.58 (s, 2H), 4.02 (s, 3H), 3.61-3.78 (m, 2H), 3.18-3.38 (m, 2H), 2.82-2.99 (m, 1H), 2.12-2.29 (m, 2H), 1.96-2.10 (m, 2H). LC-MS: m/z 459.2 $(M+H)^+$.

Example 54

2-((4-chloro-2-fluorobenzyl)oxy)-6-(1-((1-methyl-5-(2H-tetrazol-5-yl)-1H-imidazol-2-yl)methyl)piperidin-4-yl)pyridine (Compound 105)

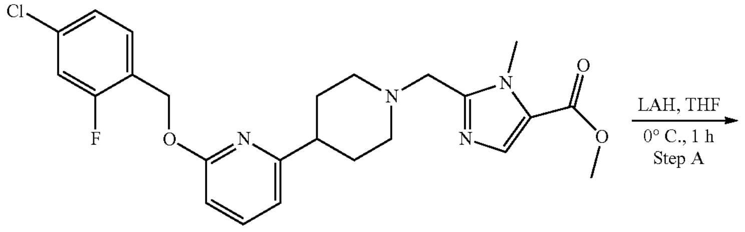

1

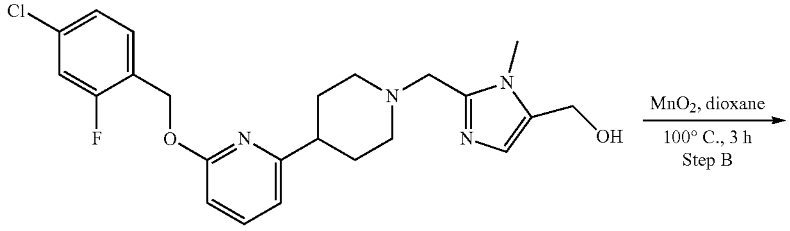

2

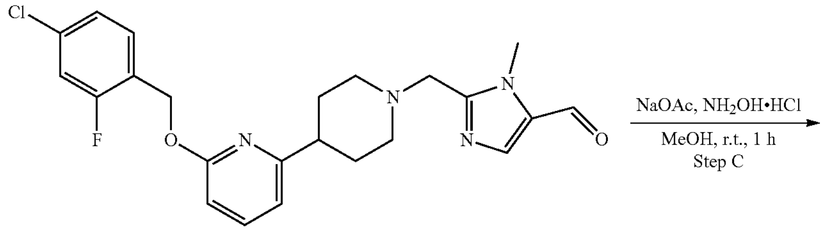

3

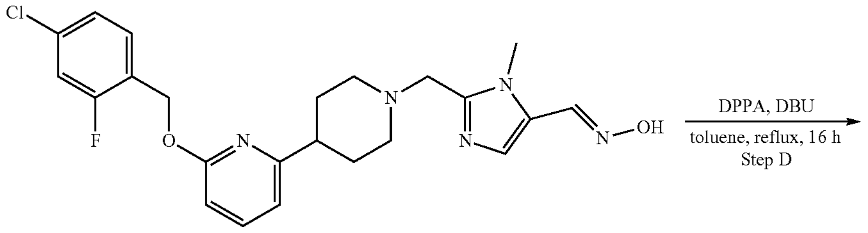

4

-continued

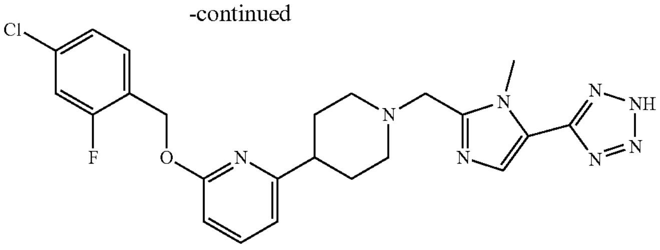

Compound 105

Step A: (2-((4-(6-((4-chloro-2-fluorobenzyl)oxy) pyridin-2-yl)piperidin-1-yl)methyl)-1-methyl-1H-imidazol-S-yl)methanol

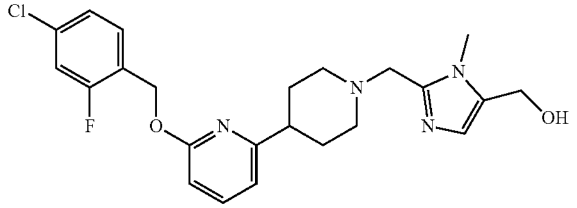 [SMILES: Cn1c(CO)cnc1CN1CCC(c2cccc(OCc3ccc(Cl)cc3F)n2)CC1]

To a mixture of methyl 2-((4-(6-((4-chloro-2-fluorobenzyl)oxy)pyridin-2-yl)piperidin-1-yl)methyl)-1-methyl-1H-imidazole-5-carboxylate (400 mg, 0.846 mmol) in THF (8 mL) was added lithium aluminum hydride (1M in THF, 1.69 mL, 1.69 mmol) at 0° C. The reaction mixture was stirred at 0° C. for 1 hour under $N_2$. Then the reaction mixture was quenched with $Na_2SO_4 \cdot 10H_2O$ and filtered. The filtrate was concentrated to give (2-((4-(6-((4-chloro-2-fluorobenzyl)oxy)pyridin-2-yl)piperidin-1-yl)methyl)-1-methyl-1H-imidazol-5-yl)methanol as a colorless oil (385 mg, crude). LC-MS: m/z 445.2 $(M+H)^+$.

Step B: 2-(4-(6-((4-chloro-2-fluorobenzyl)oxy)pyridin-2-yl)piperidin-1-yl)methyl)-1-methyl-1H-imidazole-5-carbaldehyde

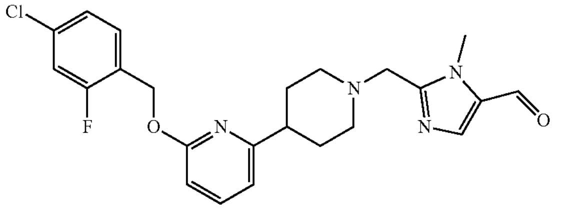 [SMILES: Cn1c(C=O)cnc1CN1CCC(c2cccc(OCc3ccc(Cl)cc3F)n2)CC1]

To a mixture of (2-((4-(6-((4-chloro-2-fluorobenzyl)oxy) pyridin-2-yl)piperidin-1-yl)methyl)-1-methyl-1H-imidazol-5-yl)methanol (385 mg, 0.865 mmol) in dioxane (8 mL) was added $MnO_2$ (376 mg, 4.33 mmol). The reaction mixture was stirred at 100° C. for 3 hours. Then the reaction mixture was filtered. The filtrate was concentrated and purified by flash column chromatography (silica gel, eluting with MeOH/DCM) to give 2-((4-(6-((4-chloro-2-fluorobenzyl)oxy)pyridin-2-yl)piperidin-1-yl)methyl)-1-methyl-1H-imidazole-5-carbaldehyde as a light yellow oil (195 mg, 51% yield over two steps). LC-MS: m/z 443.2 $(M+H)^+$.

Step C: (E)-2-((4-(6-((4-chloro-2-fluorobenzyl)oxy) pyridin-2-yl)piperidin-1-yl)methyl)-1-methyl-1H-imidazole-5-carbaldehyde oxime

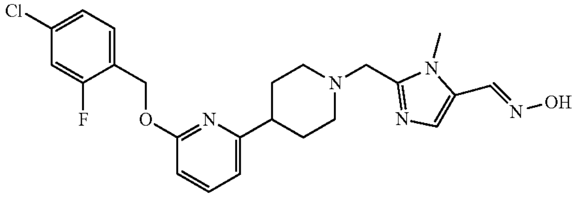 [SMILES: Cn1c(/C=N/O)cnc1CN1CCC(c2cccc(OCc3ccc(Cl)cc3F)n2)CC1]

To a mixture of 2-((4-(6-((4-chloro-2-fluorobenzyl)oxy) pyridin-2-yl)piperidin-1-yl)methyl)-1-methyl-1H-imidazole-5-carbaldehyde (175 mg, 0.395 mmol) in MeOH (5 mL) was added NaOAc (48.6 mg, 0.593 mmol) and $NH_2OH \cdot HCl$ (30.2 mg, 0.435 mmol). The reaction mixture was stirred at room temperature for 1 hour. Then the reaction mixture was concentrated and purified by flash column chromatography (silica gel, eluting with MeOH/DCM) to give (E)-2-((4-(6-((4-chloro-2-fluorobenzyl)oxy)pyridin-2-yl)piperidin-1-yl)methyl)-1-methyl-1H-imidazole-5-carbaldehyde oxime as a little yellow solid (163 mg, 90% yield). LC-MS: m/z 458.4 $(M+H)^+$.

Step D: 2-((4-chloro-2-fluorobenzyl)oxy)-6-(1-((1-methyl-5-(2H-tetrazol-5-yl)-1H-imidazol-2-yl) methyl)piperidin-4-yl)pyridine

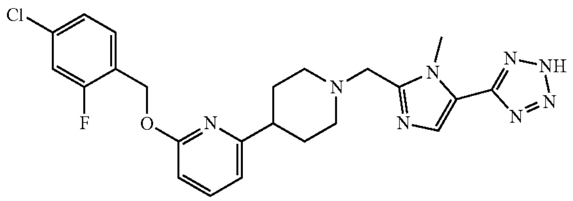 [SMILES: Cn1c(-c2nn[nH]n2)cnc1CN1CCC(c2cccc(OCc3ccc(Cl)cc3F)n2)CC1]

To a mixture of (E)-2-((4-(6-((4-chloro-2-fluorobenzyl) oxy)pyridin-2-yl)piperidin-1-yl)methyl)-1-methyl-1H-imidazole-5-carbaldehyde oxime (163 mg, 0.356 mmol) in toluene (6 mL) were added DPPA (150 mg, 0.534 mmol) and DBU (163 mg, 1.07 mmol). The reaction mixture was stirred at 115° C. for 24 hours. The mixture was cooled to room temperature and saturated sodium bicarbonate aqueous solution (2.5 mL) was added. After stirred for 5 mins, the reaction mixture was diluted with EtOAc (15 mL) and acidified to pH=2 with 1 M HCl aqueous solution. The reaction mixture was extracted with EtOAc (20 mL*9). The combined organic layer was washed with brine (15 mL), dried over $Na_2SO_4$, concentrated in vacuo and purified by Prep-HPLC (0.1% formic acid in water and acetonitrile) to give 2-((4-chloro-2-fluorobenzyl)oxy)-6-(1-((1-methyl-5-(2H-tetrazol-5-yl)-1H-imidazol-2-yl)methyl)piperidin-4-yl)pyridine as a white solid (163 mg, 90% yield). $^1H$ NMR (400 MHz, $CD_3OD$) δ 8.28 (s, 1H), 8.00 (t, J=8.0 Hz, 1H), 7.56-7.62 (m, 1H), 7.23-7.33 (m, 2H), 7.16 (d, J=7.2 Hz, 1H), 7.10 (d, J=8.4 Hz, 1H), 5.51 (s, 2H), 4.92 (s, 2H), 4.36 (s, 3H), 3.85 (d, J=11.6 Hz, 2H), 3.51 (t, J=11.2 Hz, 2H), 3.14-3.20 (m, 1H), 2.19-2.44 (m, 4H). LC-MS: m/z 483.1 $(M+H)^+$.

Example 55

((S)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)-1,2,4-oxadiazol-5(4H)-one (Compound 249a)

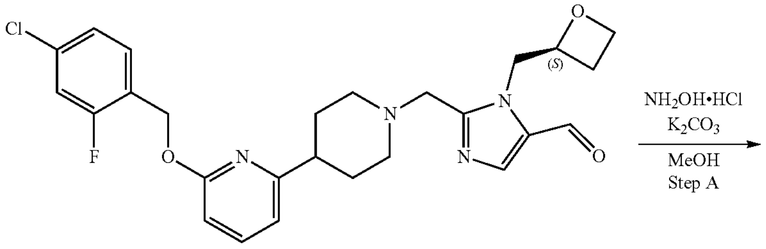

1

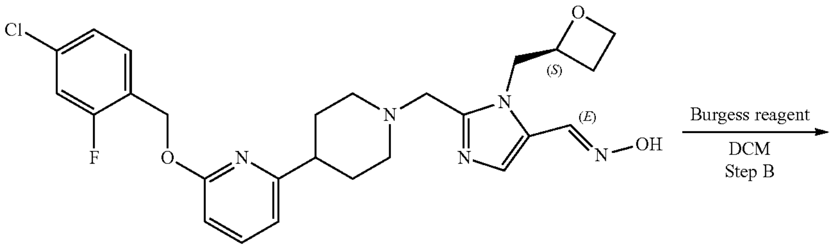

2

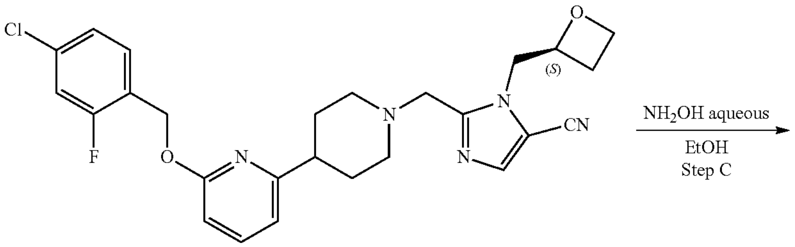

3

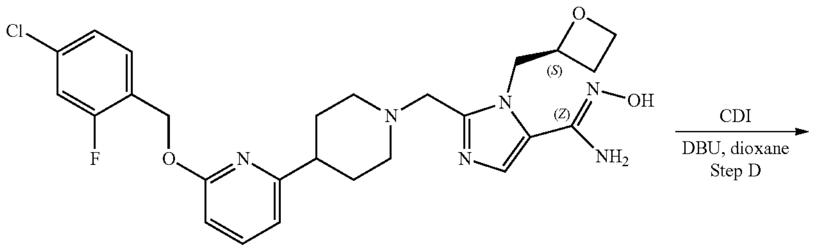

4

-continued

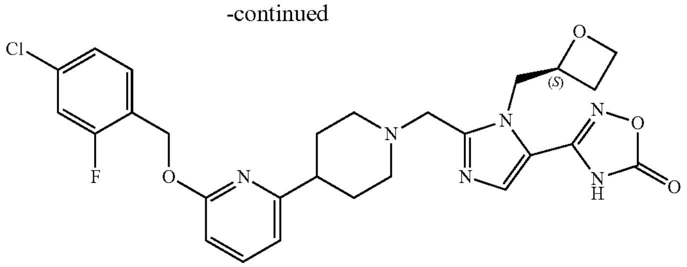

Compound 249a

Step A: (S,E)-2-((4-(6-((4-chloro-2-fluorobenzyl)oxy)pyridin-2-yl)piperidin-1-yl)methyl)-1-(oxetan-2-ylmethyl)-1H-imidazole-5-carbaldehyde oxime

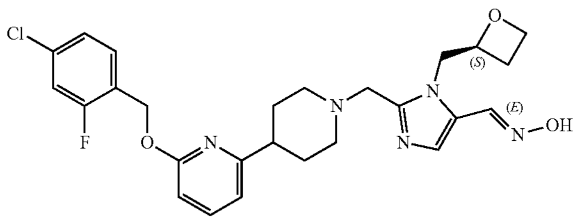

A mixture of (S)-2-((4-(6-((4-chloro-2-fluorobenzyl)oxy)pyridin-2-yl)piperidin-1-yl)methyl)-1-(oxetan-2-ylmethyl)-1H-imidazole-5-carbaldehyde (100 mg, 200 umol), $K_2CO_3$ (27.7 mg, 200 umol), $NH_2OH{\cdot}HCl$ (16.7 mg, 240 umol) in MeOH (5 mL) was degassed and purged with $N_2$ for 3 times, and then the mixture was stirred at 25° C. for 2 hours under $N_2$ atmosphere. The reaction mixture was diluted with water (20 mL) and extracted with EtOAc (30 mL*3). The combined organic layers were dried over anhydrous $Na_2SO_4$, filtered and concentrated under reduced pressure to give the crude (SE)-2-((4-(6-((4-chloro-2-fluorobenzyl)oxy)pyridin-2-yl)piperidin-1-yl)methyl)-1-(oxetan-2-ylmethyl)-1H-imidazole-5-carbaldehyde oxime (97.0 mg, 89.5% yield) as a white solid. LC-MS: m/z 514.3 $(M+H)^+$.

Step B: (S)-2-((4-(6-((4-chloro-2-fluorobenzyl)oxy)pyridin-2-yl)piperidin-1-yl)methyl)-1-(oxetan-2-ylmethyl)-1H-imidazole-5-carbonitrile

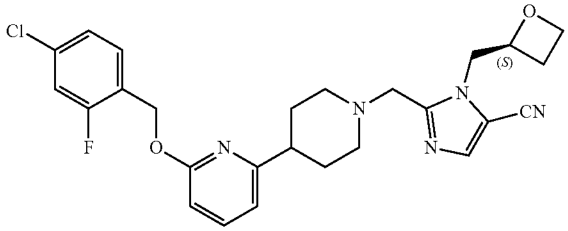

To a solution of (SE)-2-((4-(6-((4-chloro-2-fluorobenzyl)oxy)pyridin-2-yl)piperidin-1-yl)methyl)-1-(oxetan-2-ylmethyl)-1H-imidazole-5-carbaldehyde oxime in DCM (5 mL) was added (Methoxycarbonylsulfamoyl)triethylammonium hydroxide (Burgess reagent, 157 mg, 661 umol) in three equal portions and degassed and purged with $N_2$ for 3 times, and then the mixture was stirred at 25° C. for 3 hours under $N_2$ atmosphere. The reaction mixture was diluted with water (20 mL) and extracted with EtOAc (30 mL*3). The combined organic layers were dried over anhydrous $Na_2SO_4$, filtered and concentrated under reduced pressure to give the crude (S)-2-((4-(6-((4-chloro-2-fluorobenzyl)oxy)pyridin-2-yl)piperidin-1-yl)methyl)-1-(oxetan-2-ylmethyl)-1H-imidazole-5-carbonitrile (80.0 mg, 85.5% yield) as a yellow oil. LC-MS: m/z 496.2 $(M+H)^+$.

Step C: (S,Z)-2-((4-(6-((4-chloro-2-fluorobenzyl)oxy)pyridin-2-yl)piperidin-1-yl)methyl)-N-hydroxy-1-(oxetan-2-ylmethyl)-1H-imidazole-5-carboximidamide

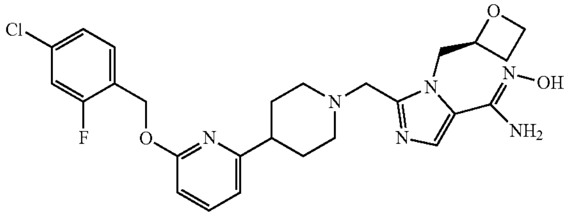 [SMILES: N/C(=N\O)c1cnc(CN2CCC(c3cccc(OCc4ccc(Cl)cc4F)n3)CC2)n1C[C@@H]1CCO1]

To a solution of (S)-2-((4-(6-((4-chloro-2-fluorobenzyl)oxy)pyridin-2-yl)piperidin-1-yl)methyl)-1-(oxetan-2-ylmethyl)-1H-imidazole-5-carbonitrile (80.0 mg, 161 umol) in EtOH (2 mL) was added hydroxylamine aqueous (85.1 mg, 1.29 mmol, 50% purity). The resulting mixture was stirred at 25° C. for 2 hours. The reaction mixture was diluted with water (30 mL), then extracted with EtOAc (30 mL*3). The combined organic layers were dried over $Na_2SO_4$, filtered and concentrated under reduced pressure to give the crude (S,Z)-2-((4-(6-((4-chloro-2-fluorobenzyl)oxy)pyridin-2-yl)piperidin-1-yl)methyl)-N-hydroxy-1-(oxetan-2-ylmethyl)-1H-imidazole-5-carboximidamide (70 mg, 82.0% yield) as a yellow oil. LC-MS: m/z 529.1 $(M+H)^+$.

Step D: (S)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)-1,2,4-oxadiazol-5(4H)-one (Compound 249a)

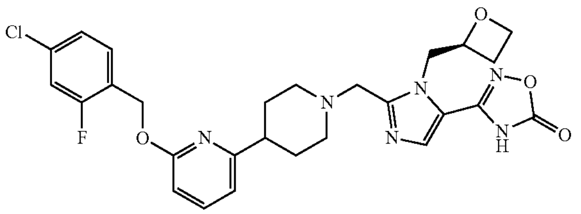 [SMILES: O=c1[nH]c(-c2cnc(CN3CCC(c4cccc(OCc5ccc(Cl)cc5F)n4)CC3)n2C[C@@H]2CCO2)no1]

A mixture of (S,Z)-2-((4-(6-((4-chloro-2-fluorobenzyl)oxy)pyridin-2-yl)piperidin-1-yl)methyl)-N-hydroxy-1-(oxetan-2-ylmethyl)-1H-imidazole-5-carboximidamide (70.0 mg, 132 umol), CDI (32.2 mg, 198 umol), DBU (22.2 mg, 146 umol, 21.9 uL) in dioxane (3 mL) was degassed and purged with $N_2$ for 3 times, and then the reaction mixture was stirred at 25° C. for 3 hours under $N_2$ atmosphere. The reaction mixture was diluted with water (20 mL), extracted with EtOAc (30 mL*3). The combined organic layers were dried over anhydrous $Na_2SO_4$, filtered and concentrated under reduced pressure to give a residue. The residue was purified by prep-HPLC (Column: Phenomenex Gemini-NX C18 75*30 mm*3 um; Eluent: 7% to 47% water (0.04% $NH_3 \cdot H_2O$+10 mM $NH_4HCO_3$)-ACN) to give(S)-3-(2-((4-(6-((4-chloro-2-fluorobenzyl)oxy)pyridin-2-yl)piperidin-1-yl)methyl)-1-(oxetan-2-ylmethyl)-1H-imidazol-5-yl)-1,2,4-oxadiazol-5(4H)-one (7.91 mg, 10.43% yield) as a white solid.

$^1$H NMR (400 MHz, $CD_3OD$) δ 7.61 (t, J=8.0 Hz, 1H), 7.45-7.55 (m, 2H), 7.16-7.25 (m, 2H), 6.86 (d, J=7.2 Hz, 1H), 6.67 (d, J=8.0 Hz, 1H), 5.42 (s, 2H), 5.16-5.24 (m, 1H), 4.63-4.72 (m, 2H), 4.45-4.53 (m, 1H), 4.24 (s, 2H), 3.39 (d, J=9.2 Hz, 2H), 2.66-2.90 (m, 5H), 2.44-2.55 (m, 1H), 1.92-2.06 (m, 4H). LC-MS: m/z 555.3 $(M+H)^+$.

Example 56

5-(2-((4-(6-((4-chloro-2-fluorobenzyl)oxy)pyridin-2-yl)piperidin-1-yl)methyl)-1-methyl-1H-imidazol-5-yl)isoxazol-3 (2H)-one (Compound 250)

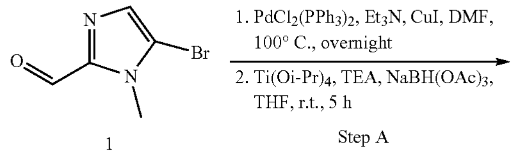

1

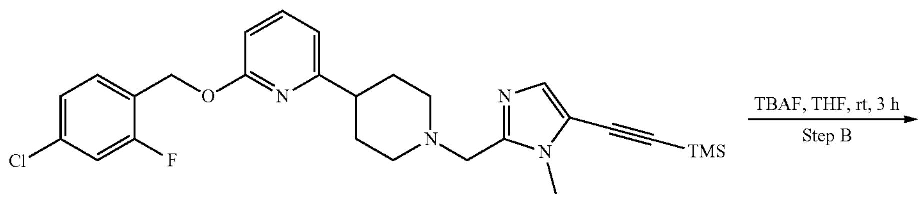

2

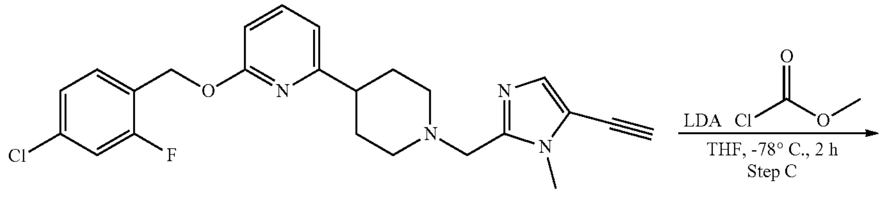

3

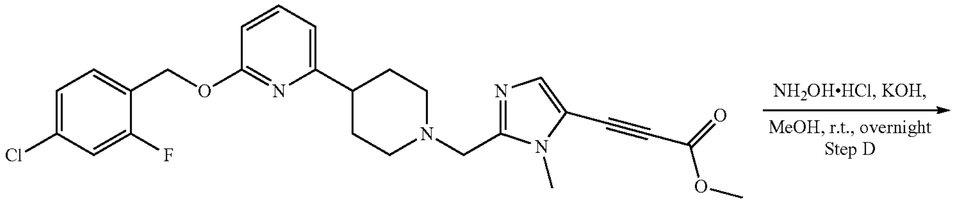

4

-continued

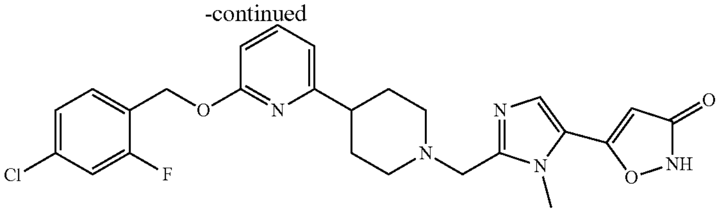

Compound 250

Step A: 2-((4-chloro-2-fluorobenzyl)oxy)-6-(1-((1-methyl-5-((trimethylsilyl)ethynyl)-1H-imidazol-2-yl)methyl)piperidin-4-yl)pyridine

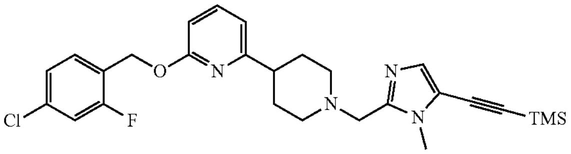 [SMILES: Cn1c(C#C[Si](C)(C)C)cnc1CN1CCC(c2cccc(OCc3ccc(Cl)cc3F)n2)CC1]

A reaction mixture of 5-bromo-1-methyl-1H-imidazole-2-carbaldehyde (950 mg, 5.03 mmol), $Pd(PPh_3)_2Cl_2$ (353 mg, 0.500 mmol), and CuI (192 mg, 1.00 mmol) in DMF (10 mL) was degassed and purged with $N_2$ for 3 times. To the reaction mixture were added ethynyltrimethylsilane (1.48 g, 15.1 mmol), and $Et_3N$ (2.55 g, 25.2 mmol). The reaction mixture was stirred at 100° C. overnight. The reaction mixture was cooled down. 2-((4-chloro-2-fluorobenzyl)oxy)-6-(piperidin-4-yl)pyridine (1.80 g, 5.03 mmol), $Ti(O^iPr)_4$ (2.87 g, 10.1 mmol), TEA (1.53 g, 15.1 mmol), and THF (5 mL) were added. After stirred at room temperature for 4 hours under $N_2$ atmosphere, $NaBH(OAc)_3$ (3.20 g, 15.1 mmol) was added. The reaction mixture was stirred at room temperature for another 1 hour under $N_2$ atmosphere. The reaction mixture was diluted with aqueous $NaHCO_3$ solution (20 mL) and extracted with DCM (20 mL*3). The organic layer was washed with brine, dried over $Na_2SO_4$, concentrated and purified by prep-HPLC (0.1% $NH_4HCO_3$ in water and acetonitrile) to give 2-((4-chloro-2-fluorobenzyl)oxy)-6-(1-((1-methyl-5-((trimethylsilyl)ethynyl)-1H-imidazol-2-yl)methyl)piperidin-4-yl)pyridine as a white solid (420 mg, 16% yield). LC-MS: m/z 511.2 $(M+H)^+$.

Step B: 2-((4-chloro-2-fluorobenzyl)oxy)-6-(1-((5-ethynyl-1-methyl-1H-imidazol-2-yl)methyl)piperidin-4-yl)pyridine

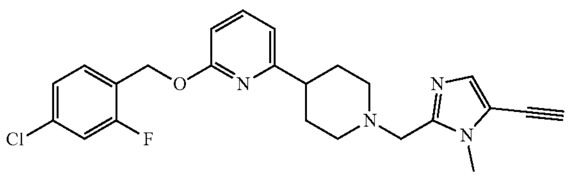 [SMILES: C#Cc1cnc(CN2CCC(c3cccc(OCc4ccc(Cl)cc4F)n3)CC2)n1C]

To a solution of 2-((4-chloro-2-fluorobenzyl)oxy)-6-(1-((1-methyl-5-((trimethylsilyl)ethynyl)-1H-imidazol-2-yl)methyl)piperidin-4-yl)pyridine (420 mg, 0.820 mmol) in THF (5 mL) was added 1 M TBAF in THF (1.0 mL). The reaction mixture was stirred at room temperature for 3 hours. Then the reaction mixture was concentrated and purified by prep-TLC (DCM:MeOH=20:1) to give 2-((4-chloro-2-fluorobenzyl)oxy)-6-(1-((5-ethynyl-1-methyl-1H-imidazol-2-yl)methyl)piperidin-4-yl)pyridine as a white solid (320 mg, 89% yield). LC-MS: m/z 439.0 $(M+H)^+$.

Step C: methyl 3-(2-((4-(6-((4-chloro-2-fluorobenzyl)oxy)pyridin-2-yl)piperidin-1-yl)methyl)-1-methyl-1H-imidazol-5-yl)propiolate

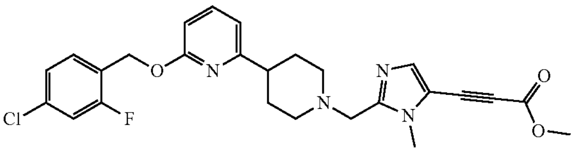 [SMILES: COC(=O)C#Cc1cnc(CN2CCC(c3cccc(OCc4ccc(Cl)cc4F)n3)CC2)n1C]

To a solution of 2-((4-chloro-2-fluorobenzyl)oxy)-6-(1-((5-ethynyl-1-methyl-1H-imidazol-2-yl)methyl)piperidin-4-yl)pyridine (150 mg, 0.228 mmol) in THF (2 mL) was added 2 M LDA in THF (0.170 mL, 0.340 mmol). The reaction mixture was stirred at −78° C. for 1 hour under $N_2$ atmosphere. To the reaction mixture was added methyl carbonochloridate (25.8 mg, 0.273 mmol). The reaction mixture was stirred at −78° C. for 1 hour under $N_2$ atmosphere. The reaction mixture was quenched with $H_2O$ (10 mL) and extracted with EtOAc (20 mL*3). The organic layer was dried over $Na_2SO_4$, concentrated in vacuo and purified by flash column chromatography (DCM/MeOH=30/1) to give methyl 3-(2-((4-(6-((4-chloro-2-fluorobenzyl)oxy)pyridin-2-yl)piperidin-1-yl)methyl)-1-methyl-1H-imidazol-5-yl)propiolate as a white solid (50.0 mg, 44% yield). LC-MS: m/z 497.0 $(M+H)^+$.

Step D: 5-(2-((4-(6-((4-chloro-2-fluorobenzyl)oxy)pyridin-2-yl)piperidin-1-yl)methyl)-1-methyl-1H-imidazol-5-yl)isoxazol-3(2H)-one (Compound 250)

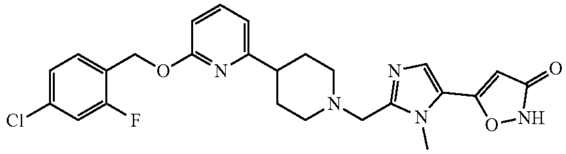 [SMILES: Cn1c(-c2cc(=O)[nH]o2)cnc1CN1CCC(c2cccc(OCc3ccc(Cl)cc3F)n2)CC1]

To a solution of methyl 3-(2-((4-(6-((4-chloro-2-fluorobenzyl)oxy)pyridin-2-yl)piperidin-1-yl)methyl)-1-methyl-1H-imidazol-5-yl)propiolate (50.0 mg, 0.100 mmol), and $NH_2OH{\cdot}HCl$ (21.0 mg, 0.301 mmol) in MeOH (1 mL) was added KOH (28.2 mg, 0.503 mmol). The reaction was stirred at room temperature overnight under $N_2$ atmosphere. The reaction mixture was acidified to pH=1 with HCl (conc.) at 0° C. The resulting reaction mixture was extracted with EtOAc (20 mL*3). The organic layer was dried over $Na_2SO_4$, concentrated in vacuo and purified by prep-TLC to give 5-(2-((4-(6-((4-chloro-2-fluorobenzyl)oxy)pyridin-2-yl)piperidin-1-yl)methyl)-1-methyl-1H-imidazol-5-yl)isoxazol-3(2H)-one as a white solid (8.80 mg, 15% yield). $^1$H NMR (400 MHz, DMSO-$d_6$) δ 7.62 (t, J=8.0 Hz, 1H), 7.56 (t, J=8.0 Hz, 1H), 7.45 (dd, J=10.0, 2.0 Hz, 1H), 7.25-7.33 (m, 2H), 6.86 (d, J=7.2 Hz, 1H), 6.66 (d, J=8.4 Hz, 1H), 6.23 (s, 1H), 5.36 (s, 2H), 3.80 (s, 3H), 3.63

(s, 2H), 2.88 (d, J=11.2 Hz, 2H), 2.54-2.67 (m, 1H), 2.07-2.14 (m, 2H), 1.64-1.79 (m, 4H). $^{19}$F NMR (377 MHz, DMSO-$d_6$): δ −115.15. LC-MS: m/z 498.0 $(M+H)^+$.

Example 57

3-((2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)methyl)-1,2,4-oxadiazol-5(4H)-one (Compound 251)

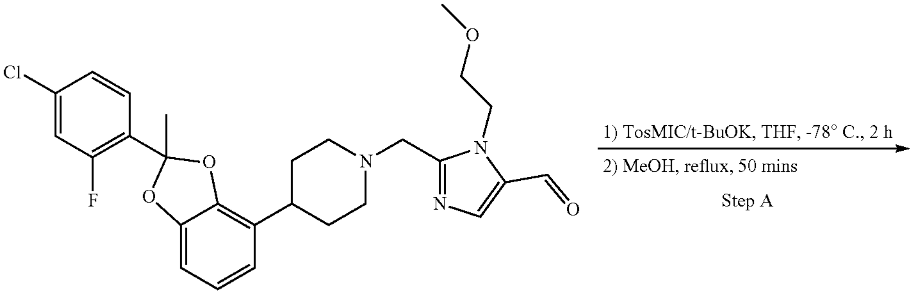

1

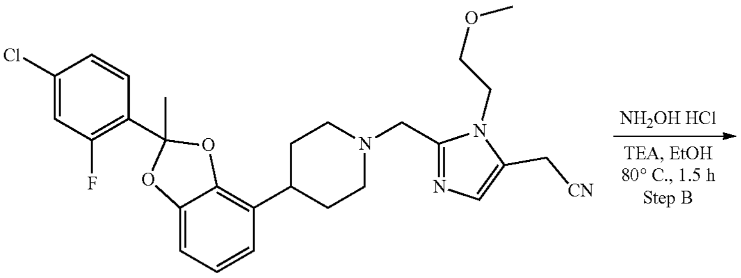

2

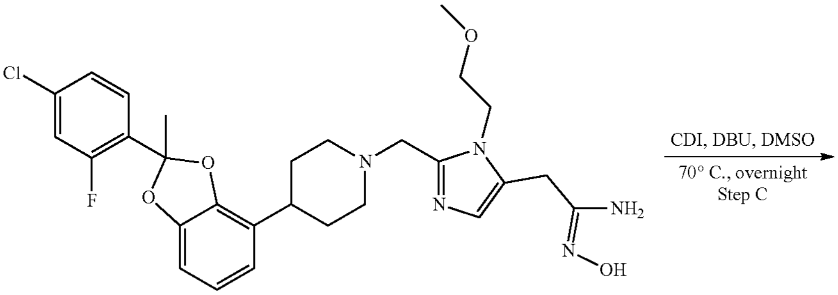

3

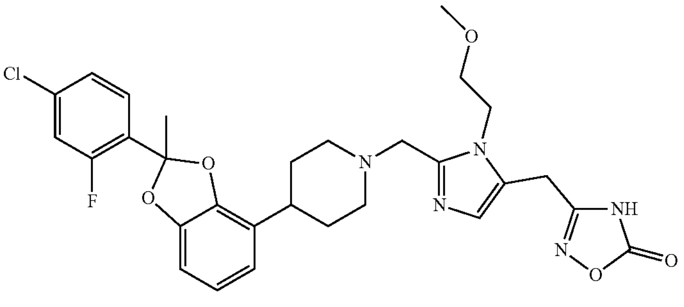

Compound 251

Step A: 2-(2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)acetonitrile

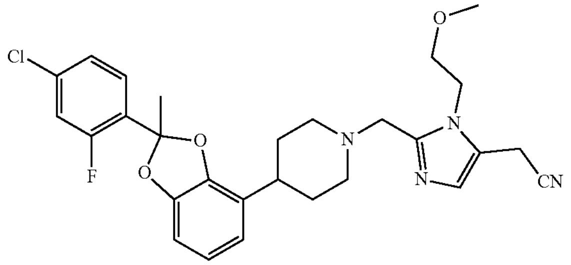 [SMILES: COCCn1c(CC#N)cnc1CN1CCC(c2cccc3c2OC(C)(c2ccc(Cl)cc2F)O3)CC1]

To a suspension of t-BuOK (123 mg, 1.10 mmol) in THF (3 mL) was added a solution of TosMIC (105 mg, 0.500 mmol) in THF (2 mL) at −78° C. The reaction mixture was stirred at −78° C. for 30 mins, then a solution of 2-((4-(2-(4-chloro-2-fluorophenyl)-2-methylbenzo[d][1,3]dioxol-4-yl)piperidin-1-yl)methyl)-1-(2-methoxyethyl)-1H-imidazole-5-carbaldehyde (250 mg, 0.500 mmol) in THF (1 mL) was added dropwise. The reaction mixture was stirred at −78° C. for another 2 hours. Methanol (8 mL) was added and the reaction mixture was heated at reflux for 50 mins. THF was removed under vacuum to give a crude product, which was purified by flash column chromatography (DCM/MeOH=20/1-10/1) to give 2-(2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)acetonitrile as a yellow oil (147 mg, 58% yield). LC-MS: m/z 525.2 $(M+H)^+$.

Step B: (Z)-2-(2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)-N'-hydroxyacetimidamide

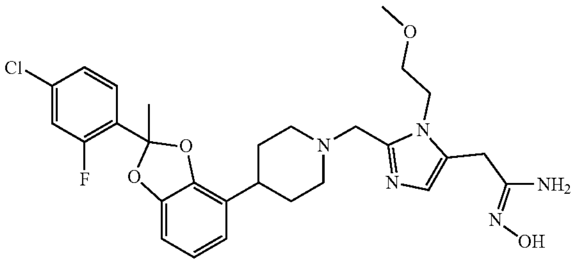 [SMILES: COCCn1c(C/C(N)=N/O)cnc1CN1CCC(c2cccc3c2OC(C)(c2ccc(Cl)cc2F)O3)CC1]

To a solution of 2-(2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)acetonitrile (150 mg, 0.300 mmol) in EtOH (2 mL) were added $NH_2OH \cdot HCl$ (80.0 mg, 1.10 mmol) and TEA (0.1 mL, 0.600 mmol). The reaction mixture was stirred at 80° C. for 1.5 hours. Then the reaction mixture was concentrated and purified by flash column chromatography (DCM/MeOH=20/1-10/1) to give (Z)-2-(2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)-N'-hydroxyacetimidamide as a faint yellow solid (140 mg, 88% yield). LC-MS: m/z 558.1 $(M+H)^+$.

Step C: 3-((2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)methyl)-1,2,4-oxadiazol-5(4H)-one (Compound 251)

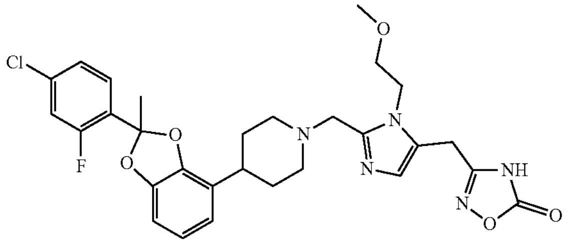 [SMILES: COCCn1c(Cc2noc(=O)[nH]2)cnc1CN1CCC(c2cccc3c2OC(C)(c2ccc(Cl)cc2F)O3)CC1]

To a solution of (Z)-2-(2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)-N'-hydroxyacetimidamide (180 mg, 0.300 mmol) in DMSO (2 mL) were added CDI (420 mg, 2.60 mmol) and DBU (492 mg, 3.20 mmol). The reaction mixture was stirred at 70° C. overnight. Then the reaction mixture was diluted with water (5 mL) and extracted with EtOAc (10 mL*3). The combined organic phase was washed with brine (10 mL), dried over anhydrous $Na_2SO_4$ and concentrated. The residue was purified by prep-HPLC (0.1% $NH_4HCO_3$ in water and acetonitrile) to give 3-((2-((4-(2-(4-chloro-2-fluorophenyl)-2-methylbenzo[d][1,3]dioxol-4-yl)piperidin-1-yl)methyl)-1-(2-methoxyethyl)-1H-imidazol-5-yl)methyl)-1,2,4-oxadiazol-5(4H)-one as a white solid (30.5 mg, 16% yield). $^1H$ NMR (400 MHz, $CD_3OD$) δ 7.57 (t, J=8.4 Hz, 1H), 7.28 (dd, J=10.8, 2.0 Hz, 1H), 7.21 (ddd, J=8.4, 2.0, 0.8 Hz, 1H), 6.96 (s, 1H), 6.75-6.81 (m, 1H), 6.68-6.73 (m, 2H), 4.36 (t, J=5.2 Hz, 2H), 3.97 (s, 2H), 3.85 (s, 2H), 3.70 (t, J=5.2 Hz, 2H), 3.31 (s, 3H), 3.06-3.16 (m, 2H), 2.68-2.80 (m, 1H), 2.36-2.47 (m, 2H), 2.02 (s, 3H), 1.76-1.97 (m, 4H). LC-MS: m/z 584.1 $(M+H)^+$.

Example 58

6-((4-(6-((4-chloro-2-fluorobenzyl)oxy)pyridin-2-yl) piperidin-1-yl)methyl)-5-methylnicotinic acid (Compound 129)

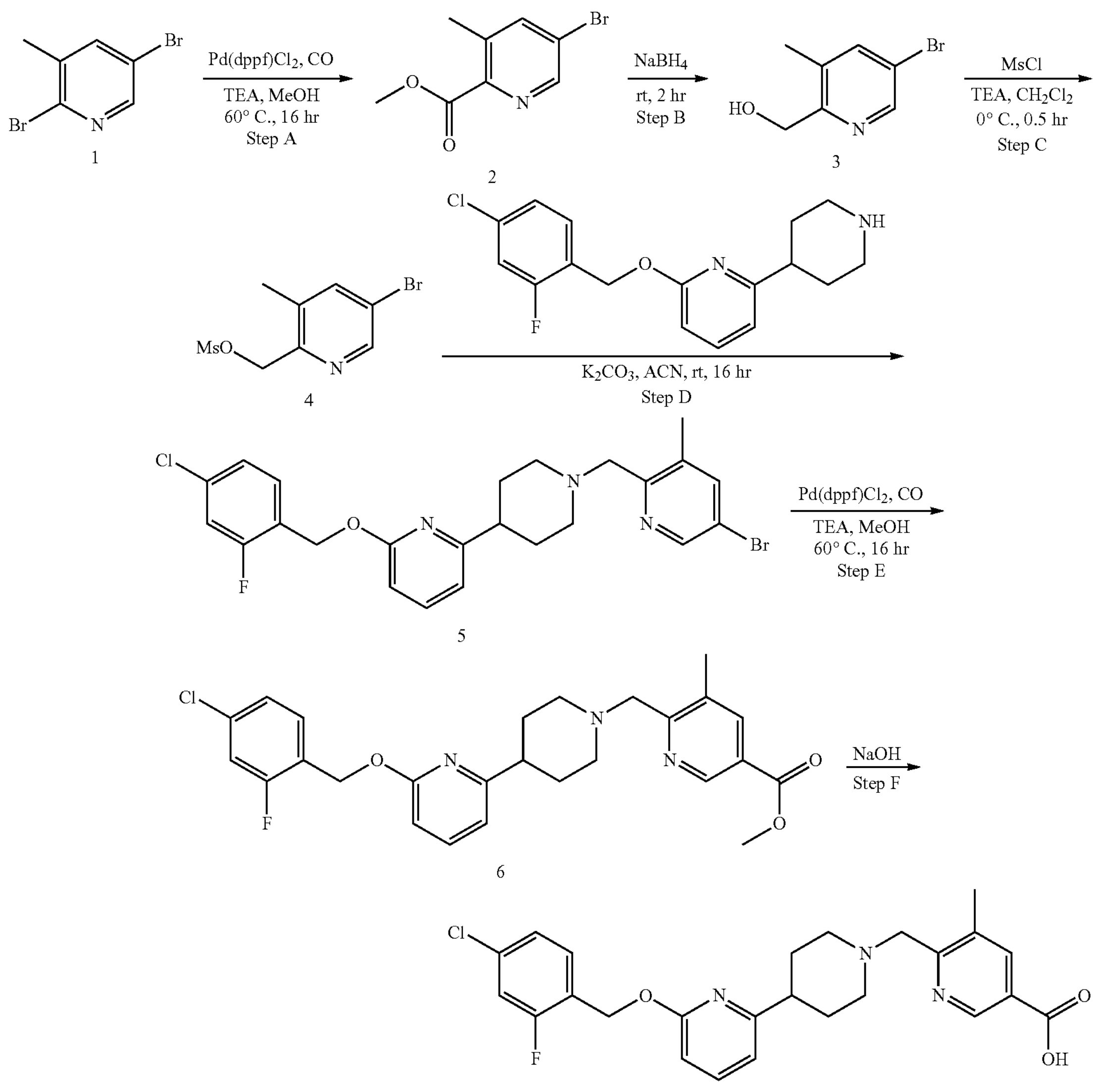

Compound 129

Step A: methyl 5-bromo-3-methylpicolinate

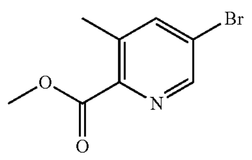

The mixture of 2,5-dibromo-3-methylpyridine (2.5 g, 10.0 mmol), Pd(dppf)$Cl_2$ (816 mg, 1.0 mmol), TEA (2.1 g, 20.06 mmol) in MeOH (100 mL) was degassed and refilled with CO for three times and then stirred at 60° C. under CO gas for 16 hours. The mixture was filtered and the filtrate was concentrated in vacuo, the residue was purified by silica gel chromatography (PE:EtOAc=10:1) to give methyl 5-bromo-3-methylpicolinate as a white solid (900 mg, 35.9% yield). LC-MS: m/z 228.2 $(M+H)^+$.

Step B: (5-bromo-3-methylpyridin-2-yl)methanol

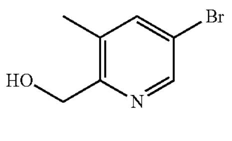

To a solution of methyl 5-bromo-3-methylpicolinate (3.0 g, 13.1 mmol) in MeOH (30 mL) was added $NaBH_4$ (1.5 g, 39.3 mmol) at room temperature. The mixture was stirred at room temperature for 2 hours. The reaction mixture was quenched by water (100 mL) and concentrated. The crude was extracted with EtOAc (50 mL*2) The organic layer was washed with brine (100 mL*2), dried over anhydrous $Na_2SO_4$, filtered and concentrated. The residue was purified by flash column chromatography (PE:EtOAc=5:1) to give (5-bromo-3-methylpyridin-2-yl)methanol as a white solid (2.5 g, 93% yield). LC-MS: m/z 202.2 $(M+H)^+$.

Step C: (5-bromo-3-methylpyridin-2-yl)methyl methanesulfonate

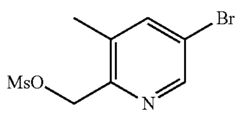

To a solution of (5-bromo-3-methylpyridin-2-yl)methanol (2.0 g, 50 mmol) in DCM (30 mL) was added TEA (2.1 g, 20 mmol) and MsCl (2.3 g, 20 mmol) at 0° C. The reaction mixture was stirred at 0° C. for 1 hour. The mixture was diluted with water (5 mL), and extracted with EtOAc (50 mL*2). The organic layer was washed with brine (100 mL*2), dried over anhydrous $Na_2SO_4$, filtered and concentrated. The residue was purified by flash column chromatography (PE:EtOAc=5:1) to give (5-bromo-3-methylpyridin-2-yl)methyl methanesulfonate as a red oil (2.1 g, 75% yield). LC-MS: m/z 280.3 $(M+H)^+$.

Step D: 5-bromo-2-((4-(6-((4-chloro-2-fluorobenzyl)oxy)pyridin-2-yl)piperidin-1-yl)methyl)-3-methylpyridine

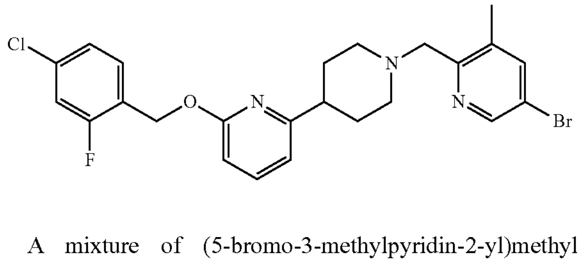

A mixture of (5-bromo-3-methylpyridin-2-yl)methyl methanesulfonate (1.7 g, 6.1 mmol), 2-((4-chloro-2-fluorobenzyl)oxy)-6-(piperidin-4-yl)pyridine (2.7 g, 6.1 mmol) and $K_2CO_3$ (3.4 g, 24.4 mmol) in ACN (50 mL) was stirred at room temperature for 16 hour. The mixture was filtered and the filtrate was concentrated in vacuo, the residue was purified by silica gel chromatography (PE:EtOAc=5:1) to give 5-bromo-2-((4-(6-((4-chloro-2-fluorobenzyl)oxy)pyridin-2-yl)piperidin-1-yl)methyl)-3-methylpyridine as a white solid (2.1 g, 68.2% yield). LC-MS: m/z 504.1 $(M+H)^+$.

Step E: methyl 6-((4-(6-((4-chloro-2-fluorobenzyl)oxy)pyridin-2-yl)piperidin-1-yl)methyl)-5-methylnicotinate

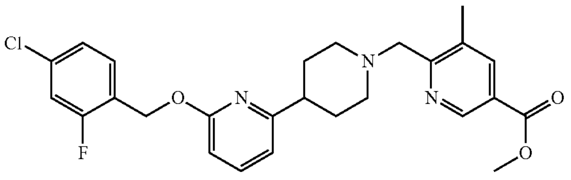 [SMILES: COC(=O)c1cnc(CN2CCC(c3cccc(OCc4ccc(Cl)cc4F)n3)CC2)c(C)c1]

The mixture of 5-bromo-2-((4-(6-((4-chloro-2-fluorobenzyl)oxy)pyridin-2-yl)piperidin-1-yl)methyl)-3-methylpyridine (300 mg, 0.6 mmol), $Pd(dppf)Cl_2$ (50 mg, 0.06 mmol), TEA (130 mg, 1.2 mmol) in MeOH (10 mL) was degassed and refilled with CO for three times and then stirred at 60° C. under CO gas for 16 hours. The mixture was filtered and the filtrate was concentrated in vacuo, the residue was purified by silica gel chromatography (PE:EtOAc=3:1) to give methyl 6-((4-(6-((4-chloro-2-fluorobenzyl)oxy)pyridin-2-yl)piperidin-1-yl)methyl)-5-methylnicotinate as a colorless oil (90 mg, 31% yield). LC-MS: m/z 484.2 $(M+H)^+$.

Step F: 6-(4-(6-((4-chloro-2-fluorobenzyl)oxy)pyridin-2-yl)piperidin-1-yl)methyl)-5-methylnicotinic acid (Compound 129)

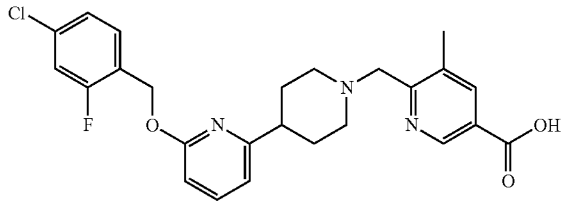 [SMILES: Cc1cc(C(=O)O)cnc1CN1CCC(c2cccc(OCc3ccc(Cl)cc3F)n2)CC1]

To a solution of methyl 6-((4-(6-((4-chloro-2-fluorobenzyl)oxy)pyridin-2-yl)piperidin-1-yl)methyl)-5-methylnicotinate (90.0 mg, 0.186 mmol) in McOH/THF (1 mL/1 mL) was added NaOH (1 N in water, 0.37 mL, 0.373 mmol), the reaction mixture was stirred at room temperature for 4 hours. The reaction mixture was acidified with HCl (0.5 N in water) to pH=4~5, diluted with water (10 mL) and extracted with EtOAc (10 mL*3). The combined organic phase was concentrated in vacuo. The residue was purified by prep-HPLC (0.1% $NH_4HCO_3$ in water and acetonitrile) to give 6-((4-(6-((4-chloro-2-fluorobenzyl)oxy)pyridin-2-yl)piperidin-1-yl)methyl)-5-methylnicotinic acid as a white solid (58.0 mg, 66.3% yield).

$^1H$ NMR (400 MHz, DMSO-$d_6$) 8.81 (d, J=1.6 Hz, 1H), 8.05 (d, J=1.2 Hz, 1H), 7.62 (t, J=8.0 Hz, 1H), 7.56 (t, J=8.0 Hz, 1H), 7.44 (dd, J=10.4, 2.0 Hz, 1H), 7.28 (dd, J=8.0, 1.6 Hz, 1H), 6.86 (d, J=7.2 Hz, 1H), 6.67 (d, J=10.0 Hz, 1H), 5.36 (s, 2H), 3.71 (s, 2H), 2.89 (d, J=7.2 Hz, 2H), 2.56-2.62 (m, 1H), 2.48 (s, 3H), 2.22 (t, J=10.8 Hz, 2H), 1.64-1.78 (m, 4H). LC-MS: m/z 470.1 $(M+H)^+$.

Example 59

2-((4-(6-((4-chloro-2-fluorobenzyl)oxy)pyridin-2-yl)piperidin-1-yl)methyl)-5-(2H-tetrazol-5-yl)pyridine (Compound 127)

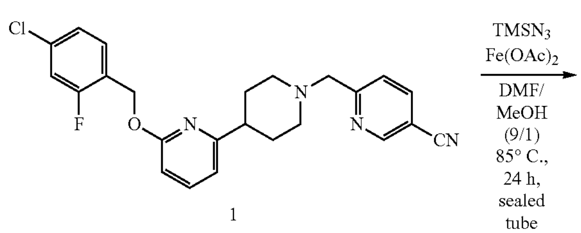

1

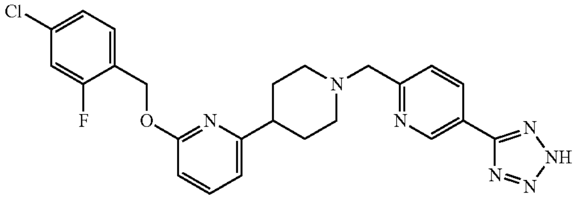

Compound 127

Step A: 2-(4-(6-((4-chloro-2-fluorobenzyl)oxy)pyridin-2-yl)piperidin-1-yl)methyl)-5-(2H-tetrazol-5-yl)pyridine

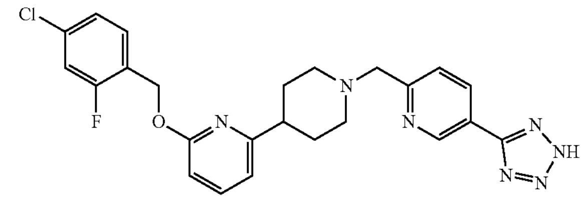 [SMILES: Fc1cc(Cl)ccc1COc1cccc(C2CCN(Cc3ccc(-c4nn[nH]n4)cn3)CC2)n1]

A sealed tube was charged with 6-((4-(6-((4-chloro-2-fluorobenzyl)oxy)pyridin-2-yl)piperidin-1-yl)methyl)nicotinonitrile (165 mg, 0.378 mmol, synthesized following step D of Example 3, using 6-(chloromethyl)nicotinonitrile as starting material), $TMSN_3$ (52.0 mg, 0.453 mmol), $Fe(OAc)_2$ (16.5 mg, 0.0380 mmol), DMF (4.5 mL) and MeOH (0.5 mL). The reaction mixture was stirred at 85° C. for 24 hours. The reaction mixture was filtered. The filtrate was concentrated and purified by Prep-HPLC (0.1% formic acid in water and acetonitrile) to give 2-((4-(6-((4-chloro-2-fluorobenzyl)oxy)pyridin-2-yl)piperidin-1-yl)methyl)-5-(2H-tetrazol-5-yl)pyridine as a brown solid (11.9 mg, 7% yield). $^1H$ NMR (400 MHz, DMSO-$d_6$) δ 10.71 (s, 1H), 9.41 (d, J=1.6 Hz, 1H), 8.62 (dd, J=8.0, 2.0 Hz, 1H), 7.94 (d, J=8.0 Hz, 1H), 7.61-7.73 (m, 2H), 7.48 (dd, J=10.0, 2.0 Hz, 1H), 7.33 (dd, J=8.0, 1.6 Hz, 1H), 6.90 (d, J=6.8 Hz, 1H), 6.74 (d, J=8.0 Hz, 1H), 5.39 (s, 2H), 4.60 (s, 2H), 3.54-3.64 (m, 2H), 3.16-3.29 (m, 2H), 2.86-2.97 (m, 1H), 2.00-2.25 (m, 4H). LC-MS: m/z 480.2 $(M+H)^+$.

Example 60

3-(6-((4-(2-(4-chloro-2-fluorophenyl)-2-methylbenzo[d][1,3]dioxol-4-yl)piperidin-1-yl)methyl)-5-methylpyridin-3-yl)-1,2,4-oxadiazol-5(4H)-one (Compound 252)

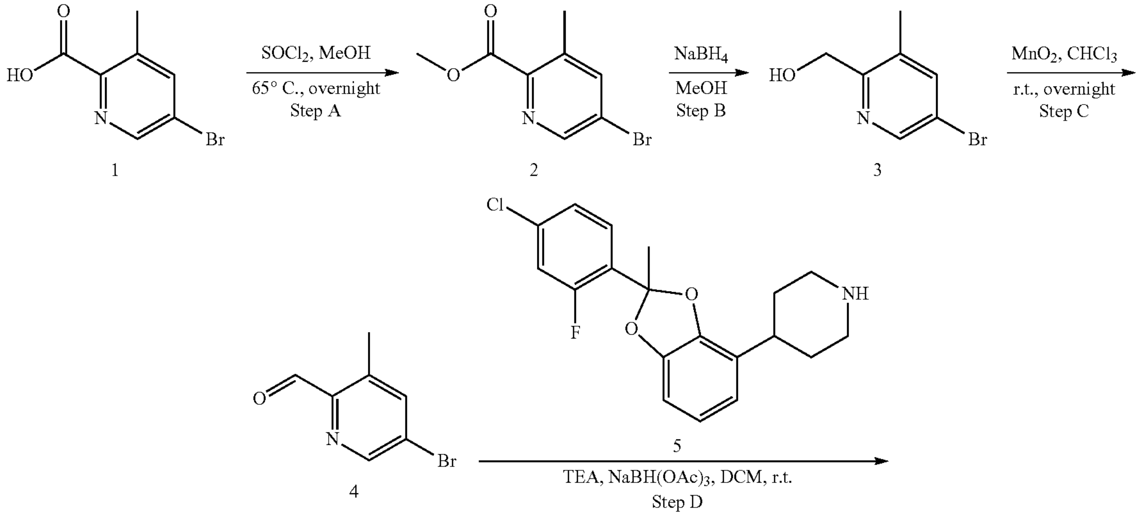

1 2 3 5 4

-continued

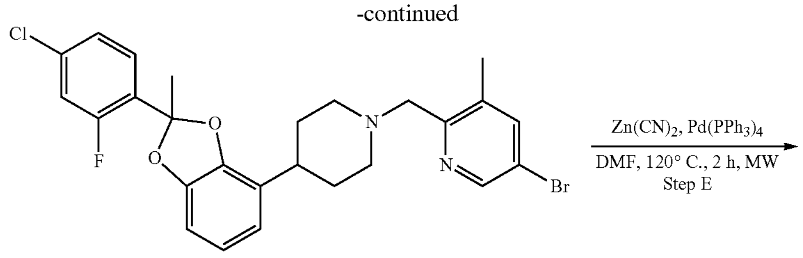

6

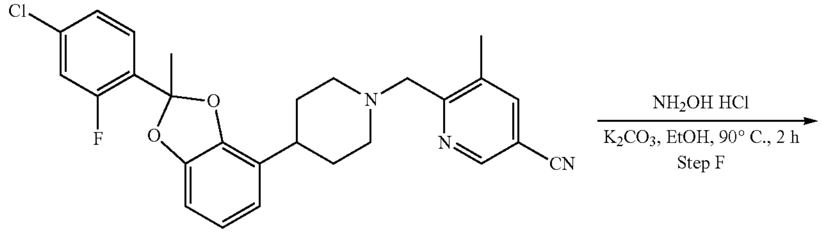

7

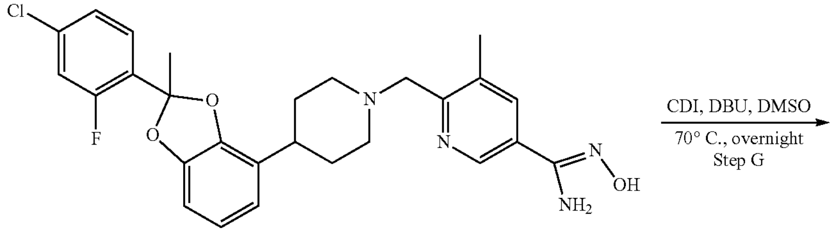

8

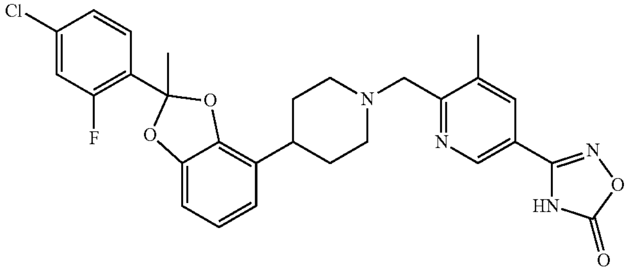

Compound 252

Step A: methyl 5-bromo-3-methylpicolinate

To a solution of 5-bromo-3-methylpicolinic acid (3.00 g, 13.9 mmol) in MeOH (20 mL) was added $SOCl_2$ (2.48 g, 20.8 mmol). The mixture was stirred at 65° C. overnight. The mixture was concentrated. Aq. $K_2CO_3$ solution (1M, 20 mL) was added and the mixture was stirred for 10 mins. The mixture was extracted with EA (20 mL*3). The organic layers were washed with brine, dried over $Na_2SO_4$, concentrated to give methyl 5-bromo-3-methylpicolinate as a white solid (2.79 g, 87% yield).

MS Calcd.: 229.0; MS Found: 230.0 $[M+H]^+$.

Step B: (5-bromo-3-methylpyridin-2-yl)methanol

To a solution of methyl 5-bromo-3-methylpicolinate (200 mg) in MeOH (2 mL) was added $NaBH_4$ (165 mg, 4.35 mmol). The mixture was heated to reflux for 4 h. The mixture was concentrated and purification by Prep-TLC to give (5-bromo-3-methylpyridin-2-yl)methanol as a white solid (95.0 mg, 54% yield).

MS Calcd.: 201.0; MS Found: 202.0 $[M+H]^+$.

Step C: 5-bromo-3-methylpicolinaldehyde

A mixture of (5-bromo-3-methylpyridin-2-yl)methanol (1.29 g, 6.39 mmol) and $MnO_2$ (5.56 g, 63.9 mmol) in $CHCl_3$ (10 mL) was stirred at room temperature overnight. The mixture was filtered and purification by silica gel column to give 5-bromo-3-methylpicolinaldehyde as a white solid (970 mg, 76% yield).

$^1$H NMR (400 MHz, $CDCl_3$) δ 10.13 (d, J=0.4 Hz, 1H), 8.70 (d, J=2.0 Hz, 1H), 7.77-7.82 (m, 1H), 2.65 (s, 3H).

Step D: 5-bromo-2-((4-(2-(4-chloro-2-fluorophenyl)-2-methylbenzo[d][1,3]dioxol-4-yl)piperidin-1-yl)methyl)-3-methylpyridine A mixture of 5-bromo-3-methylpicolinaldehyde (500 mg, 2.50 mmol), 4-(2-(4-chloro-2-fluorophenyl)-2-methylbenzo [d][1,3]dioxol-4-yl)piperidine (1.13 g, 3.25 mmol) and TEA (506 mg, 5.00 mmol) in DCM (3 mL) was stirred at room temperature for 1 h. To the mixture was added $NaBH(OAc)_3$ (954 mg, 4.50 mmol), and then the reaction mixture was stirred at room temperature for another 1 h. The mixture was diluted with water (5 mL) and extracted with DCM (5 mL*3). The organic layers were concentrated and purification by silica gel column to give 5-bromo-2-((4-(2-(4-chloro-2-fluorophenyl)-2-methylbenzo[d][1,3]dioxol-4-yl)piperidin-1-yl)methyl)-3-methylpyridine (1.03 g, 77% yield) as an oil.

MS Calcd.: 530.1; MS Found: 531.1 $[M+H]^+$.

Step E: 6-((4-(2-(4-chloro-2-fluorophenyl)-2-methylbenzo[d][1,3]dioxol-4-yl)piperidin-1-yl)methyl)-5-methylnicotinonitrile A mixture of 5-bromo-2-((4-(2-(4-chloro-2-fluorophenyl)-2-methylbenzo[d][1,3]dioxol-4-yl)piperidin-1-yl)methyl)-3-methylpyridine (80.0 mg, 0.150 mmol), $Zn(CN)_2$ (53.0 mg, 0.450 mmol) and $Pd(PPh_3)_4$ (17.0 mg, 0.0150 mmol) in DMF (2 mL) was heated for 2 h at 120° C. under microwave irradiation. The mixture was diluted with water (5 mL) and extracted with EA (5 mL*3). The organic layer was dried over $Na_2SO_4$ and concentrated. The residue was purified with Prep-TLC to give 6-((4-(2-(4-chloro-2-fluorophenyl)-2-methylbenzo [d][1,3]dioxol-4-yl)piperidin-1-yl)methyl)-5-methylnicotinonitrile (22.0 mg, 31% yield) as an oil.

MS Calcd.: 477.2; MS Found: 478.3 $[M+H]^+$.

Step F: 6-((4-(2-(4-chloro-2-fluorophenyl)-2-methylbenzo[d][1,3]dioxol-4-yl)piperidin-1-yl)methyl)-N'-hydroxy-5-methylnicotinimidamide A mixture of 6-((4-(2-(4-chloro-2-fluorophenyl)-2-methylbenzo[d][1,3]dioxol-4-yl)piperidin-1-yl)methyl)-5-methylnicotinonitrile (22.0 mg, 0.0460 mmol), hydroxylamine hydrochloride (16.0 mg, 0.230 mmol) and $K_2CO_3$ (35.0 mg, 0.253 mmol) in EtOH (3 mL) was stirred at 90° C. for 2h. To the mixture was added water, and the mixture was stirred until a fine grained precipitate formed. After filtration, the filter cake was dried to give 6-((4-(2-(4-chloro-2-fluorophenyl)-2-methylbenzo[d][1,3]dioxol-4-yl)piperidin-1-yl)methyl)-N'-hydroxy-5-methylnicotinimidamide (23.0 mg crude), which was used in next step without purification.

MS Calcd.: 510.2; MS Found: 511.2 $[M+H]^+$.

Step G: 3-(6-((4-(2-(4-chloro-2-fluorophenyl)-2-methylbenzo[d][1,3]dioxol-4-yl)piperidin-1-yl)methyl)-5-methylpyridin-3-yl)-1,2,4-oxadiazol-5(4H)-one A solution of 6-((4-(2-(4-chloro-2-fluorophenyl)-2-methylbenzo[d][1,3]dioxol-4-yl)piperidin-1-yl)methyl)-N'-hydroxy-5-methylnicotinimidamide (32.0 mg), CDI (41.0 mg, 0.252 mmol) and DBU (48.0 mg, 0.315 mmol) in DMSO (2 mL) was stirred at 70° C. overnight. The mixture was adjusted to pH=4 with formic acid and then water (5 mL) was added. The suspension was filtered and the filter cake was purification by Prep-HPLC to give 3-(6-((4-(2-(4-chloro-2-fluorophenyl)-2-methylbenzo [d][1,3]dioxol-4-yl)piperidin-1-yl)methyl)-5-methylpyridin-3-yl)-1,2,4-oxadiazol-5(4H)-one (Compound 252) (5.80 mg, 17% yield) as a white solid.

MS Calcd.: 536.2; MS Found: 537.2 $[M+H]^+$.

$^1$H NMR (400 MHz, $CDCl_3$) δ 8.56 (s, 1H), 7.92 (d, J=1.2 Hz, 1H), 7.50 (t, J=8.4 Hz, 1H), 7.05-7.14 (m, 2H), 6.67-6.80 (m, 4H), 4.15 (s, 2H), 3.83-4.00 (m, 2H), 2.92 (t, J=12.0 Hz, 3H), 2.40 (s, 3H), 2.28-2.41 (m, 2H), 1.95-2.10 (m, 5H). $^{19}$F-NMR (377 MHz): −111.18.

Example 61

2-({4-[2-(4-chloro-2-fluorophenyl)-2-methyl-2H-1,3-benzodioxol-4-yl]piperidin-1-yl}methyl)-3-methyl-5-(1H-1,2,3,4-tetrazol-5-yl)pyridine (Compound 253)

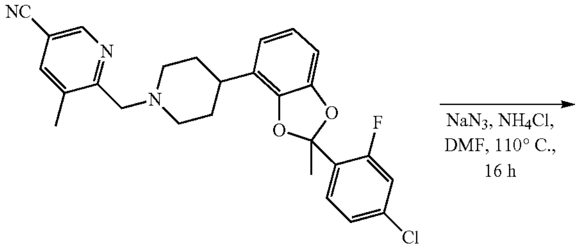

1

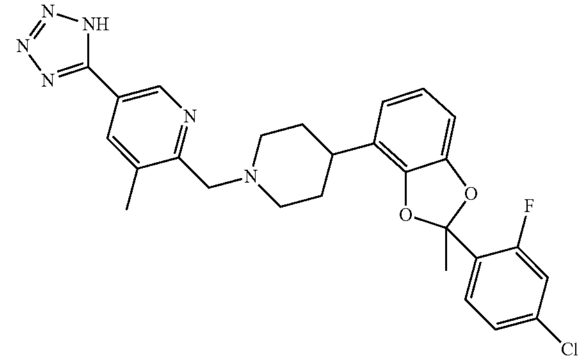

Compound 253

A mixture of 6-((4-(2-(4-chloro-2-fluorophenyl)-2-methylbenzo[d][1,3]dioxol-4-yl)piperidin-1-yl)methyl)-5-methylnicotinonitrile (25 mg, 0.0524 mmol), $NaN_3$ (5 mg, 0.0786 mmol) and $NH_4Cl$ (4 mg, 0.0786 mmol) in DMF (0.5 ml) was stirred at 110° C. for 16 hours. The reaction mixture was filtered and the residue was purified by prep-HPLC directly to give 2-({4-[2-(4-chloro-2-fluorophenyl)-2-methyl-2H-1,3-benzodioxol-4-yl]piperidin-1-yl}methyl)-3-methyl-5-(1H-1,2,3,4-tetrazol-5-yl)pyridine (Compound 253) (10.3 mg, yield: 37.8%) as white solid.

MS Calcd.: 520.2; MS Found: 521.1 $[M+H]^+$.

$^1$H NMR (400 MHz, MeOD) δ 9.11 (d, J=1.2 Hz, 1H), 8.26 (s, 1H), 7.62 (t, J=8.4 Hz, 1H), 7.30 (dd, $J_1$=2.0 Hz, $J_2$=11.2 Hz, 1H), 7.23 (dd, J=1.6 Hz, $J_2$=8.4 Hz, 1H), 6.90-6.75 (m, 3H), 4.51 (s, 2H), 3.78-3.65 (m, 2H), 3.40-3.15 (m, 2H), 3.15-3.00 (m, 1H), 2.44 (s, 3H), 2.37-2.20 (m, 2H), 2.15-2.06 (m, 2H), 2.06 (s, 3H). $^{19}$F-NMR (377 MHz): −112.23.

Example 62
5-[6-({4-[2-(4-chloro-2-fluorophenyl)-2-methyl-2H-1,3-benzodioxol-4-yl]piperidin-1-yl}methyl)-5-methylpyridin-3-yl]-2,3-dihydro-1,3,4-oxadiazol-2-one (Compound 254)
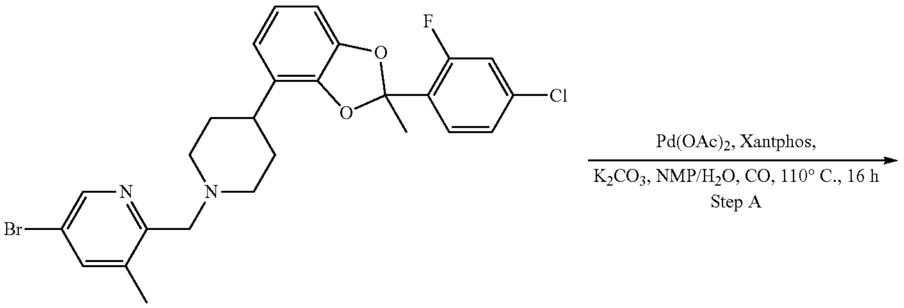
1
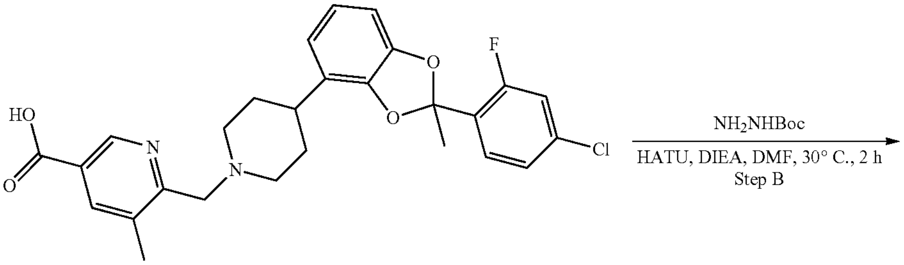
2
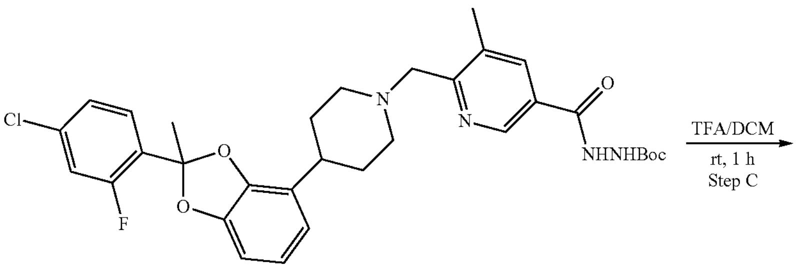
3
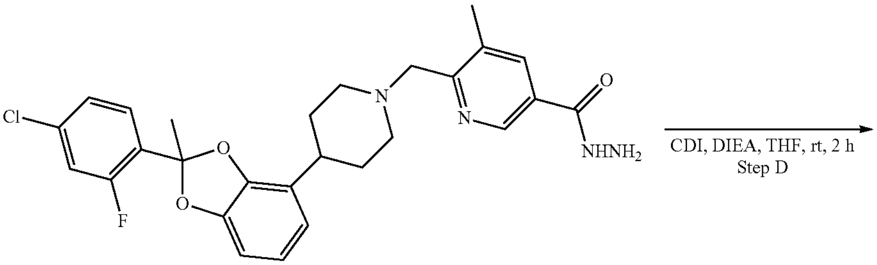
4

-continued

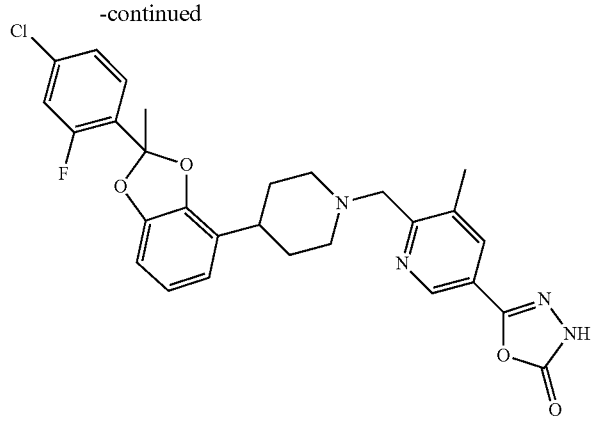

Compound 254

Step A: 6-((4-(2-(4-chloro-2-fluorophenyl)-2-methylbenzo[d][1,3]dioxol-4-yl)piperidin-1-yl)methyl)-5-methylnicotinic acid A mixture of 5-bromo-2-((4-(2-(4-chloro-2-fluorophenyl)-2-methylbenzo[d][1,3]dioxol-4-yl)piperidin-1-yl) methyl)-3-methylpyridine (980 mg, 1.85 mmol), Xantphos (428 mg, 0.74 mmol), $Pd(OAc)_2$ (83 mg, 0.37 mmol) and $K_2CO_3$ (511 mg, 3.7 mmol) in NMP/$H_2O$ (15 mL/5 mL) was stirred at 110° C. under CO for 16 hours. The mixture was filtered and the residue was purified by silica gel column chromatography to furnish 6-((4-(2-(4-chloro-2-fluorophenyl)-2-methylbenzo[d][1,3]dioxol-4-yl)piperidin-1-yl) methyl)-5-methylnicotinic acid (580 mg, yield: 63.2%) as yellow solid.

Step B: tert-butyl 2-(6-((4-(2-(4-chloro-2-fluorophenyl)-2-methylbenzo[d][1,3]dioxol-4-yl)piperidin-1-yl)methyl)-5-methylnicotinoyl)-114-diazane-1-carboxylate A mixture of 6-((4-(2-(4-chloro-2-fluorophenyl)-2-methylbenzo[d][1,3]dioxol-4-yl)piperidin-1-yl)methyl)-5-methylnicotinic acid (300 mg, 0.605 mmol), $NH_2NHBoc$ (160 mg, 1.21 mmol), HATU (345 mg, 0.907 mmol), and DIEA (0.3 mL, 3.7 mmol) in DMF (5 mL) was stirred at 30° C. for 2 hours. The mixture was filtered and the residue was purified by silica gel column chromatography to furnish tert-butyl 2-(6-((4-(2-(4-chloro-2-fluorophenyl)-2-methylbenzo [d][1,3]dioxol-4-yl)piperidin-1-yl)methyl)-5-methylnicotinoyl)-114-diazane-1-carboxylate (120 mg, yield: 32.5%) as white solid.

MS Calcd.: 610.2; MS Found: 611.1 $[M+H]^+$.

Step C: 6-((4-(2-(4-chloro-2-fluorophenyl)-2-methylbenzo[d][1,3]dioxol-4-yl)piperidin-1-yl)methyl)-5-methylnicotinohydrazide A mixture of tert-butyl 2-(6-((4-(2-(4-chloro-2-fluorophenyl)-2-methylbenzo[d][1,3]dioxol-4-yl)piperidin-1-yl) methyl)-5-methylnicotinoyl)-114-diazane-1-carboxylate (120 mg, 0.20 mmol) and TFA (1 mL) in DCM (2 mL) was stirred at room temperature for 1 hour. The mixture was filtered to furnish 6-((4-(2-(4-chloro-2-fluorophenyl)-2-methylbenzo [d][1,3]dioxol-4-yl)piperidin-1-yl)methyl)-5-methylnicotinohydrazide (120 mg, crude product) as white solid.

MS Calcd.: 510.2; MS Found: 511.0 $[M+H]^+$.

Step D: 5-[6-({4-[2-(4-chloro-2-fluorophenyl)-2-methyl-2H-1,3-benzodioxol-4-yl]piperidin-1-yl}methyl)-5-methylpyridin-3-yl]-2,3-dihydro-1,3,4-oxadiazol-2-one (Compound 254)

A mixture of 6-((4-(2-(4-chloro-2-fluorophenyl)-2-methylbenzo[d][1,3]dioxol-4-yl)piperidin-1-yl)methyl)-5-methylnicotinohydrazide (120 mg), CDI (93 mg, 0.58 mmol) and DIEA (122 mg, 0.95 mmol) in THF (5 mL) was stirred at room temperature for 2 hours. The reaction mixture was the mixture was poured into cold water (50 mL) and extracted with EtOAc (2×50 mL), the combined organic layer was washed with brine, dried over sodium sulfate, filtered and concentrated under reduced pressure, the residue was purified by prep-HPLC to give 5-[6-({4-[2-(4-chloro-2-fluorophenyl)-2-methyl-2H-1,3-benzodioxol-4-yl]piperidin-1-yl}methyl)-5-methylpyridin-3-yl]-2,3-dihydro-1,3,4-oxadiazol-2-one (Compound 254) (19.8 mg, yield: 19.2%) as white solid.

MS Calcd.: 536.2; MS Found: 537.1 $[M+H]^+$.

$^1H$ NMR (400 MHz, MeOD) 8.76 (s, 1H), 8.02 (s, 1H), 7.58 (t, J=8.4 Hz, 1H), 7.27 (dd, $J_1$=2.0 Hz, $J_2$=11.2 Hz, 1H), 7.20 (dd, $J_1$=1.6 Hz, $J_2$=8.4 Hz, 1H), 6.80-6.65 (m, 3H), 3.80 (s, 2H), 3.06 (d, J=8.0 Hz, 2H), 2.80-2.68 (m, 1H), 2.52 (s, 3H), 2.36 (t, J=11.6 Hz, 2H), 2.02 (s, 3H), 1.98-1.75 (m, 4H).

$^{19}F$-NMR (377 MHz): −112.30.

Example 63

2-({4-[2-(4-chloro-2-fluorophenyl)-2-methyl-2H-1,3-benzodioxol-4-yl]piperidin-1-yl}methyl)-3-methyl-5-[5-(trifluoromethyl)-4H-1,2,4-triazol-3-yl]pyridine (Compound 255)

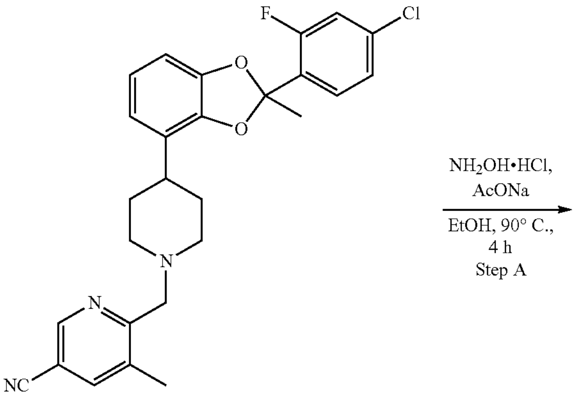

1

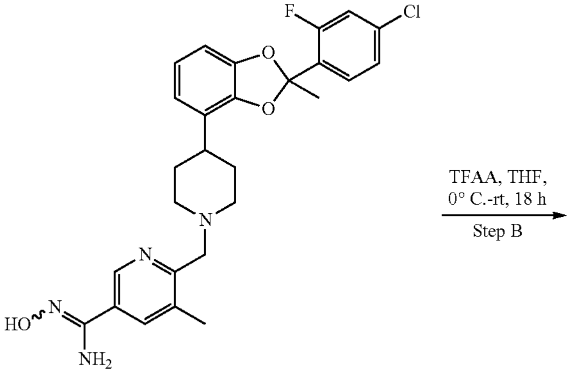

2

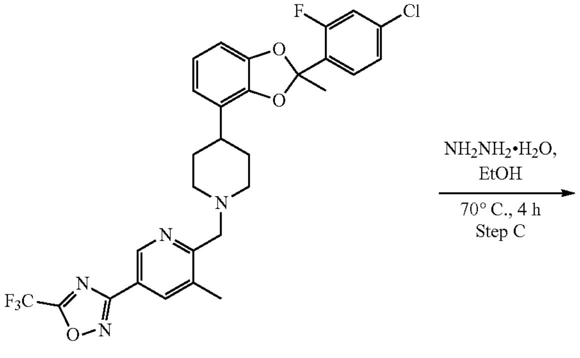

3

-continued

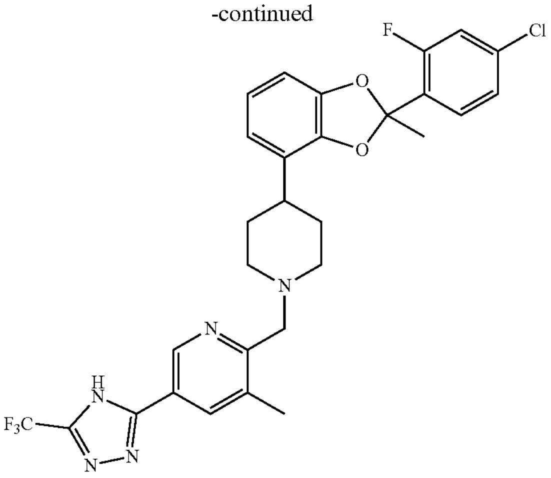

Compound 255

Step A: 6-((4-(2-(4-chloro-2-fluorophenyl)-2-methylbenzo[d][1,3]dioxol-4-yl)piperidin-1-yl)methyl)-N'-hydroxy-5-methylpicotinimidamide A mixture of hydroxylamine hydrochloride (117 mg, 1.676 mmol), AcONa (165 mg, 2.016 mmol) and 6-((4-(2-(4-chloro-2-fluorophenyl)-2-methylbenzo[d][1,3]dioxol-4-yl)piperidin-1-yl)methyl)-5-methylnicotinonitrile (80 mg, 0.168 mmol) in EtOH (3.0 ml) was stirred at 90° C. for 4 hrs in a sealed tube. Upon cooling down, the reaction mixture was diluted with $H_2O$ (50 mL) and extracted with EA (15 mL×3). The combined organic layers were dried over anhydrous $Na_2SO_4$ and concentrated under vacuum to furnish 6-((4-(2-(4-chloro-2-fluorophenyl)-2-methylbenzo[d][1,3]dioxol-4-yl)piperidin-1-yl)methyl)-N'-hydroxy-5-methylnicotinimidamide (85 mg, crude) as crude yellow solid. MS Calcd.: 510.2; MS Found: 511.1 $[M+H]^+$.

Step B: 2-(4-[2-({4-chloro-2-fluorophenyl)-2-methyl-2H-1,3-benzodioxol-4-yl]piperidin-1-yl}methyl)-3-methyl-5-[5-(trifluoromethyl)-1,2,4-oxadiazol-3-yl]pyridine To a stirred solution of 6-((4-(2-(4-chloro-2-fluorophenyl)-2-methylbenzo[d][1,3]dioxol-4-yl)piperidin-1-yl)methyl)-N'-hydroxy-5-methylnicotinimidamide (50 mg) in THF (4.0 mL) was added TFAA (122 mg, 0.588 mmol) at 0° C. The reaction mixture was stirred at room temperature for 18 h. The mixture was quenched by addition of saturated $NaHCO_3$ (50 mL) and extracted with EA (15 mL×3). The combined organic layers were dried over anhydrous $Na_2SO_4$, concentrated under vacuum. The residue was purified by Prep-HPLC to furnish 2-({4-[2-(4-chloro-2-fluorophenyl)-2-methyl-2H-1,3-benzodioxol-4-yl]piperidin-1-yl}methyl)-3-methyl-5-[5-(trifluoromethyl)-1,2,4-oxadiazol-3-yl]pyridine (7.18 mg, 12.4%) as a white solid. MS Calcd.: 588.2; MS Found: 589.2 $[M+H]^+$.

$^1H$ NMR (400 MHz, $CD_3OD$) δ 9.03 (d, J=1.6 Hz, 1H), 8.30 (d, J=1.2 Hz, 1H), 7.58 (t, J=8.0 Hz, 1H), 7.27 (dd, J=10.8, 2.0 Hz, 1H), 7.20 (dd, J=8.8, 1.6 Hz, 1H), 6.80-6.73 (m, 1H), 6.73-6.66 (m, 2H), 3.79 (s, 2H), 3.07-2.99 (m, 2H), 2.77-2.68 (m, 1H), 2.57 (s, 3H), 2.36-2.28 (m, 2H), 2.02 (s, 3H), 1.96-1.84 (m, 2H), 1.84-1.72 (m, 2H). $^{19}F$-NMR (377 MHz): −δ 7.29, −112.31.

Step C: 2-({4-[2-(4-chloro-2-fluorophenyl)-2-methyl-2H-1,3-benzodioxol-4-yl]piperidin-1-yl}methyl)-3-methyl-5-[5-(trifluoromethyl)-4H-1,2,4-triazol-3-yl]pyridine (Compound 255)

A mixture of 2-({4-[2-(4-chloro-2-fluorophenyl)-2-methyl-2H-1,3-benzodioxol-4-yl]piperidin-1-yl}methyl)-3-methyl-5-[5-(trifluoromethyl)-1,2,4-oxadiazol-3-yl]pyridine (5.0 mg, 0.0085 mmol) and $N_2H_4H_2O$ (0.05 mL) in EtOH (1.0 mL) was stirred at 70° C. for 4 h. Upon cooling down, the reaction mixture was directly purified by Prep-HPLC to furnish 2-({4-[2-(4-chloro-2-fluorophenyl)-2-methyl-2H-1,3-benzodioxol-4-yl]piperidin-1-yl}methyl)-3-methyl-5-[5-(trifluoromethyl)-4H-1,2,4-triazol-3-yl]pyridine (Compound 255) (1.57 mg, yield: 31.4%) as a white solid.

MS Calcd.: 587.2; MS Found: 588.0 $[M+H]^+$.

$^1H$ NMR (400 MHz, MeOD) δ 9.00 (s, 1H), 8.17 (s, 1H), 7.52 (t, J=8.4 Hz, 1H), 7.18 (dd, J=10.8, 1.5 Hz, 1H), 7.13 (dd, J=8.4, 1.5 Hz, 1H), 6.78-6.65 (m, 3H), 4.50-4.30 (m, 4H), 3.59-3.50 (m, 2H), 3.00-2.85 (m, 1H), 2.37 (s, 3H), 2.20-2.05 (m, 2H), 1.96 (s, 3H), 2.03-1.90 (m, 2H). $^{19}F$-NMR (377 MHz): −δ5.37, −112.26.

Example 64

2-({4-[2-(4-chloro-2-fluorophenyl)-2-methyl-2H-1,3-benzodioxol-4-yl]piperidin-1-yl}methyl)-3-(2-methoxyethyl)-5-(1H-1,2,3,4-tetrazol-5-yl)pyridine (Compound 256)

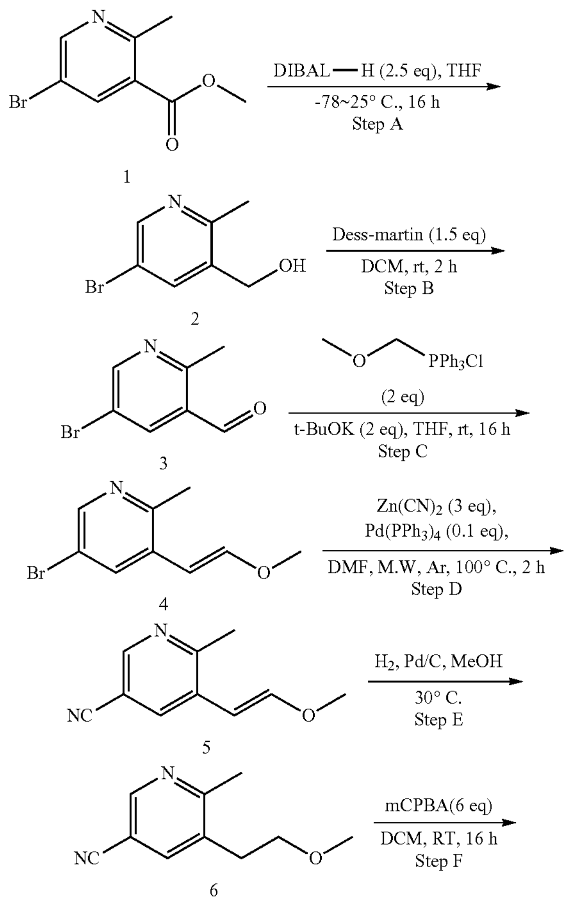

-continued

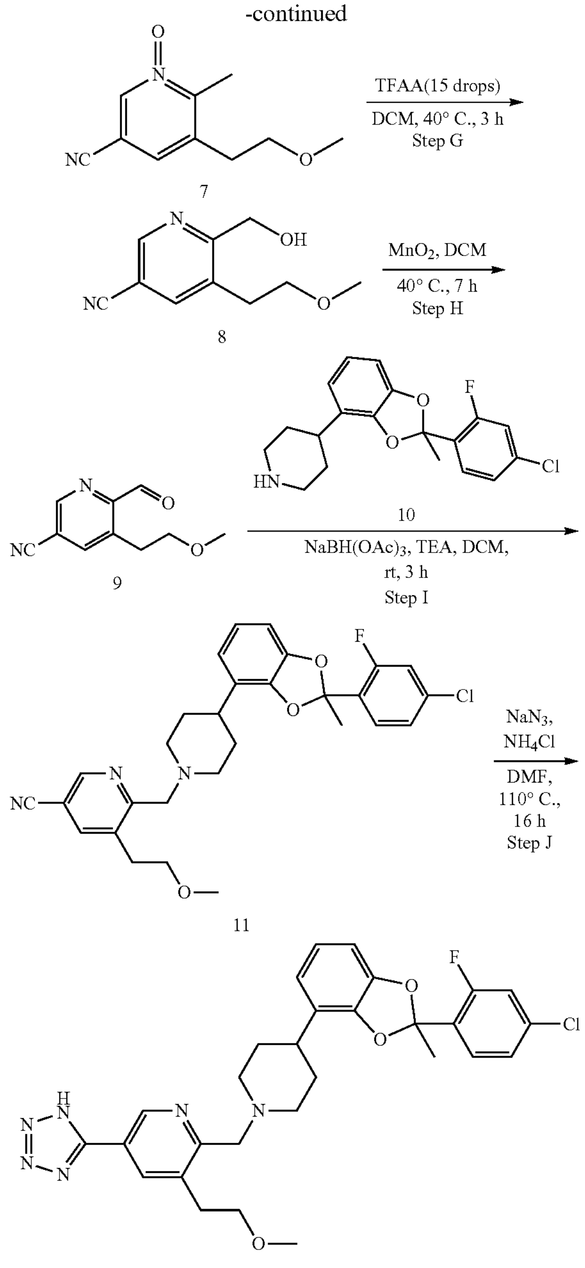

Compound 256

Step A: (5-bromo-2-methylpyridin-3-yl)methanol

To a solution of methyl 5-bromo-2-methylnicotinate (2.0 g, 8.69 mmol) in THF (30 mL) was dropwise added DIBAL-H (1.0 M, 21.74 mL, 21.74 mmol) at −78° C. under $N_2$. After 0.5 h, the mixture was stirred at 25° C. for 16 hours. After the reaction was completed, the reaction was quenched with water (0.9 mL). aq NaOH (15%, 0.9 mL) and $H_2O$ (0.9 mL) were added sequentially. The mixture was dried over $Na_2SO_4$, filtered. The filtrate was washed with brine, dried over sodium sulfate, concentrated to give (5-bromo-2-methylpyridin-3-yl)methanol (1.4 g, crude) as yellow solid.

MS Calcd.: 201.0; MS Found: 201.9 $[M+H]^+$.

Step B: 5-bromo-2-methylnicotinaldehyde

To a solution of (5-bromo-2-methylpyridin-3-yl)methanol (1.4 g) in DCM (24 mL) was added Dess-Martin reagent (4.39 g, 10.34 mmol) in batches. The reaction was stirred at RT for 2 hours. After the reaction was completed, the reaction was filtered, the filtrate was washed with aq $NaHCO_3$ (50 mL) and brine, dried over sodium sulfate, concentrated in vacuum. The residue was purified by column chromatography (PE:EA=5/1) to give 5-bromo-2-methylnicotinaldehyde (926 mg, 67% yield) as a yellow solid.

MS Calcd.: 199.0; MS Found: 200.0 $[M+H]^+$.

Step C: (E)-5-bromo-3-(2-methoxyvinyl)-2-methylpyridine

To a solution of (methoxymethyl)triphenylphosphonium chloride (3.16 g, 9.22 mmol) in THF (20 mL) was added t-BuOK (1.03 g, 9.22 mmol) at room temperature. The mixture was stirred at RT for 0.5 hour. A solution of 5-bromo-2-methylnicotinaldehyde (926 mg, 4.61 mmol) in THF (10 mL) was added, the mixture was stirred at RT for 16 hours. After the reaction was completed, the reaction was diluted with $H_2O$, extracted with EA, The combined organic layer was washed with brine, dried over sodium sulfate, concentrated in vacuum. The residue was purified by column chromatography (PE:EA=5/1) to give (E)-5-bromo-3-(2-methoxyvinyl)-2-methylpyridine (820 mg, 78% yield) as yellow solid.

MS Calcd.: 227.0; MS Found: 228.0 $[M+H]^+$.

Step D:
(E)-5-(2-methoxyvinyl)-6-methylnicotinonitrile

A mixture of (E)-5-bromo-3-(2-methoxyvinyl)-2-methylpyridine (820 mg, 3.6 mmol), $Zn(CN)_2$ (1.27 g, 10.79 mmol) and $Pd(PPh_3)_4$ (416 mg, 0.36 mmol) in DMF (10 mL) was stirred at 100° C. under Ar in microwave reactor for 2 hours. After the reaction was completed, the reaction was filtered, the filtrate was diluted with ethyl acetate, washed with brine, dried over sodium sulfate, concentrated in vacuum. The residue was purified by column chromatography to give (E)-5-(2-methoxyvinyl)-6-methylnicotinonitrile (580 mg, 92.6% yield) as yellow solid.

MS Calcd.: 174.1; MS Found: 175.1 $[M+H]^+$.

Step E: 5-(2-methoxyethyl)-6-methylnicotinonitrile

To a solution of (E)-5-(2-methoxyvinyl)-6-methylnicotinonitrile (100 mg, 0.57 mmol) in MeOH (10 mL) was added Pd/C (100 mg) the mixture was stirred at 30° C. under $H_2$ for 70 minutes. 3 batches were run separately and after the reaction was completed, the reaction mixture were combined, was filtered, the filtrate was concentrated. The residue was purified by column chromatography (PE:EA=2:1) to give 5-(2-methoxyethyl)-6-methylnicotinonitrile (110 mg, 36.5% yield) as white solid.

MS Calcd.: 176.1. MS Found: 177.1 $[M+H]^+$.

Step F:
5-cyano-3-(2-methoxyethyl)-2-methylpyridine 1-oxide

To a solution of 5-(2-methoxyethyl)-6-methylnicotinonitrile (50 mg, 0.28 mmol) in DCM (6 mL) was added m-CPBA (294 mg, 1.7 mmol) at 0° C. The mixture was stirred at RT under $N_2$ for 16 hours. After the reaction was completed, the mixture was diluted with DCM, washed with aq $Na_2SO_3$, aq $NaHCO_3$ and brine, dried over $Na_2SO_4$ and concentrated to give 5-cyano-3-(2-methoxyethyl)-2-methylpyridine 1-oxide (75 mg, crude) as a white solid.

MS Calcd.: 192.1; MS Found: 193.1 $[M+H]^+$.

Step G: 6-(hydroxymethyl)-5-(2-methoxyethyl)nicotinonitrile

To a solution of 5-cyano-3-(2-methoxyethyl)-2-methylpyridine 1-oxide (75 mg crude, 0.028 mmol) in DCM (6 mL) was added TFAA (15 drops) at 0° C., the mixture was stirred at 40° C. for 3 hours. The mixture was diluted with DCM, washed with aq $NaHCO_3$ and brine, dried over $Na_2SO_4$, concentrated under vacuum. The residue was purified by prep-TLC (PE:EA=1:1) to give 6-(hydroxymethyl)-5-(2-methoxyethyl)nicotinonitrile (43 mg, yield: 80%) as colorless oil.

MS Calcd.: 192.1; MS Found: 193.1 $[M+H]^+$.

Step H: 6-formyl-5-(2-methoxyethyl)nicotinonitrile

To a solution of 6-(hydroxymethyl)-5-(2-methoxyethyl) nicotinonitrile (43 mg, 0.22 mmol) in DCM (5 mL) was added $MnO_2$ (57 mg, 0.67 mmol), the mixture was stirred at 40° C. for 3 hour. Another portion of $MnO_2$ (57 mg, 0.67 mmol) was added, the mixture was stirred at 40° C. for an additional 4 hours. The mixture diluted with DCM, washed with water and brine, dried over $Na_2SO_4$, concentrated under vacuum. The residue was purified by prep-TLC (DCM:MeOH=30:1) to give 6-formyl-5-(2-methoxyethyl) nicotinonitrile (21 mg, yield: 50%) as yellow oil.

MS Calcd.: 190.1; MS Found: 191.0 $[M+H]^+$.

Step I: 6-((4-(2-(4-chloro-2-fluorophenyl)-2-methylbenzo[d][1,3]dioxol-4-yl)piperidin-1-yl)methyl)-5-(2-methoxyethyl)nicotinonitrile To a solution of 4-(2-(4-chloro-2-fluorophenyl)-2-methylbenzo[d][1,3]dioxol-4-yl)piperidine (77 mg, 0.22 mmol) in DCM (4 mL) was added TEA (111 mg, 1.1 mmol). After 15 min, 6-formyl-5-(2-methoxyethyl)nicotinonitrile (42 mg, 0.22 mmol) was added at 0° C., Then, the $NaBH(OAc)_3$ (187 mg, 0.88 mmol) in batches was added to the above mixture at ice-bath. After stirring for 10 min, the mixture was warmed to rt and stirred for 3 hours. The water and EtOAc were added to the mixture and separated. The organic phase was washed by NaCl aq, dried over $Na_2SO_4$, the organic solvent was filtered, the filtrate was concentrated to be purified by pre-TLC to give 6-((4-(2-(4-chloro-2-fluorophenyl)-2-methylbenzo[d][1,3]dioxol-4-yl)piperidin-1-yl) methyl)-5-(2-methoxyethyl)nicotinonitrile (58 mg) as a yellow oil.

MS Calcd.: 521.2; MS Found: 522.1 $[M+H]^+$.

Step J: 2-({4-[2-(4-chloro-2-fluorophenyl)-2-methyl-2H-1,3-benzodioxol-4-yl]piperidin-1-yl}methyl)-3-(2-methoxyethyl)-5-(1H-1,2,3,4-tetrazol-5-yl)pyridine (Compound 256)

A mixture of 6-((4-(2-(4-chloro-2-fluorophenyl)-2-methylbenzo[d][1,3]dioxol-4-yl)piperidin-1-yl)methyl)-5-(2-methoxyethyl)nicotinonitrile (58 mg, 0.11 mmol), NaN3 (11 mg, 0.17 mmol) and $NH_4Cl$ (9 mg, 0.17 mmol) in DMF (3 mL) was stirred at 110° C. under Ar for 16 hours. The mixture was filtered, the filtrate was purified by prep-HPLC (0.1% $NH_4HCO_3$) to give 2-({4-[2-(4-chloro-2-fluorophenyl)-2-methyl-2H-1,3-benzodioxol-4-yl]piperidin-1-yl}methyl)-3-(2-methoxyethyl)-5-(1H-1,2,3,4-tetrazol-5-yl) pyridine (Compound 256) (9.98 mg, 16.1% yield) as white solid.

MS Calcd.: 564.2; MS Found: 565.1 $[M+H]^+$.

$^1$H-NMR (400 MHz, MeOD) δ 9.15 (d, J=1.6 Hz, 1H), 8.35 (d, J=2.0 Hz, 1H), 7.62 (t, J=8.4 Hz, 1H), 7.31 (dd, $J_1$=1.6 Hz, $J_2$=10.8 Hz, 1H), 7.22 (dd, $J_1$=2.0 Hz, $J_2$=8.4 Hz, 1H), 6.88-6.80 (m, 1H), 6.80-6.77 (m, 2H), 4.70-4.45 (m, 2H), 3.80-3.52 (m, 5H), 3.34 (s, 3H), 3.10-3.00 (m, 4H), 2.35-2.15 (m, 2H), 2.15-2.06 (m, 5H). $^{19}$F-NMR (377 MHz): −112.22.

Example 65

2-({4-[2-(4-chloro-2-fluorophenyl)-2-methyl-2H-1,3-benzodioxol-4-yl]piperidin-1-yl}methyl)-5-[5-(difluoromethyl)-4H-1,2,4-triazol-3-yl]-3-methylpyridine (Compound 257)

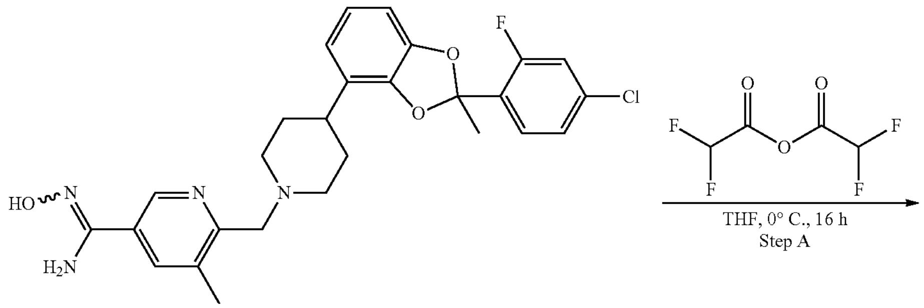

1

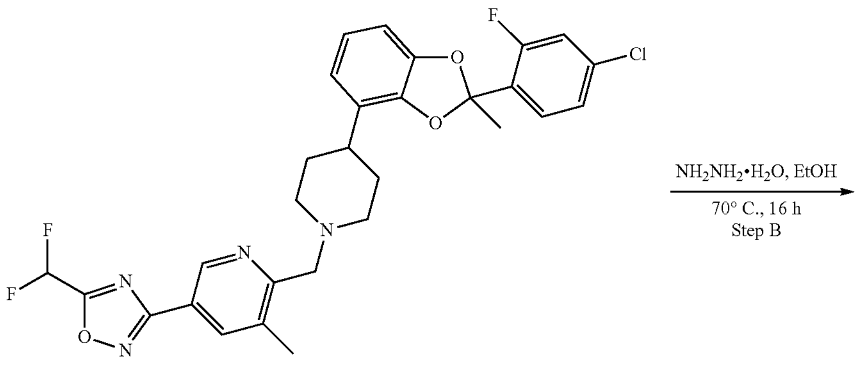

2

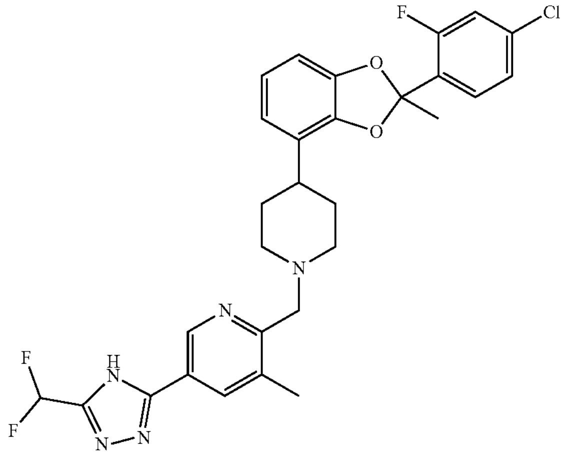

Compound 257

Step A: 3-(6-((4-(2-(4-chloro-2-fluorophenyl)-2-methylbenzo[d][1,3]dioxol-4-yl)piperidin-1-yl)methyl)-5-methylpyridin-3-yl)-5-(difluoromethyl)-1,2,4-oxadiazole To a solution of 6-((4-(2-(4-chloro-2-fluorophenyl)-2-methylbenzo[d][1,3]dioxol-4-yl)piperidin-1-yl)methyl)-N'-hydroxy-5-methylnicotinimidamide (22 mg) in THF (1 mL) was added 2,2-difluoroacetic anhydride (38 mg, 0.216 mmol) in THF (0.5 mL) dropwisely at 0° C. The mixture was stirred at room temperature for 16 hours. The reaction mixture was concentrated under reduced pressure. The residue was purified by silica gel column chromatography to furnish 3-(6-((4-(2-(4-chloro-2-fluorophenyl)-2-methylbenzo [d][1,3]dioxol-4-yl)piperidin-1-yl)methyl)-5-methylpyridin-3-yl)-5-(difluoromethyl)-1,2,4-oxadiazole (15 mg, yield: 61.0%) as white solid.

MS Calcd.: 570.2; MS Found: 571.1 $[M+H]^+$.

Step B: 2-({4-[2-(4-chloro-2-fluorophenyl)-2-methyl-2H-1,3-benzodioxol-4-yl]piperidin-1-yl}methyl)-5-[5-(difluoromethyl)-4H-1,2,4-triazol-3-yl]-3-methylpyridine (Compound 257)

A mixture of 3-(6-((4-(2-(4-chloro-2-fluorophenyl)-2-methylbenzo [d][1,3]dioxol-4-yl)piperidin-1-yl)methyl)-5-methylpyridin-3-yl)-5-(difluoromethyl)-1,2,4-oxadiazole (15 mg, 0.0263 mmol), and $NH_2NH_2 \cdot H_2O$ (0.1 mL) in EtOH (1 mL) was stirred at 70° C. for 16 hours. The reaction mixture was purified by prep-HPLC to give 2-({4-[2-(4-chloro-2-fluorophenyl)-2-methyl-2H-1,3-benzodioxol-4-yl]piperidin-1-yl}methyl)-5-[5-(difluoromethyl)-4H-1,2,4-triazol-3-yl]-3-methylpyridine (Compound 257) (1.7 mg, yield: 11.3%) as white solid.

MS Calcd.: 569.2; MS Found: 570.3 $[M+H]^+$.

$^1$H NMR (400 MHz, MeOD) 8.92 (d, J=2.0 Hz, 1H), 8.14 (d, J=1.2 Hz, 1H), 7.51 (t, J=8.0 Hz, 1H), 7.19 (dd, J=1.6 Hz/J=10.8 Hz, 1H), 7.12 (dd, J=2.0 Hz, J=8.4 Hz, 1H), 6.91-6.60 (m, 4H), 3.96 (s, 2H), 3.26-3.22 (m, 2H), 2.82-2.70 (m, 1H), 2.67-2.50 (m, 2H), 2.42 (s, 3H), 2.02-1.88 (m, 2H), 1.91 (s, 3H), 1.88-1.78 (m, 2H).

$^{19}$F-NMR (377 MHz): −112.29, −116.88, −116.91.

Example 66

1-{[2-({4-[(2 S)-2-(4-chloro-2-fluorophenyl)-2-methyl-2H-1,3-benzodioxol-4-yl]piperidin-1-yl}methyl)-5-[5-(trifluoromethyl)-4H-1,2,4-triazol-3-yl]pyridin-3-yl]methyl}cyclopropane-1-carbonitrile (Compound 258)

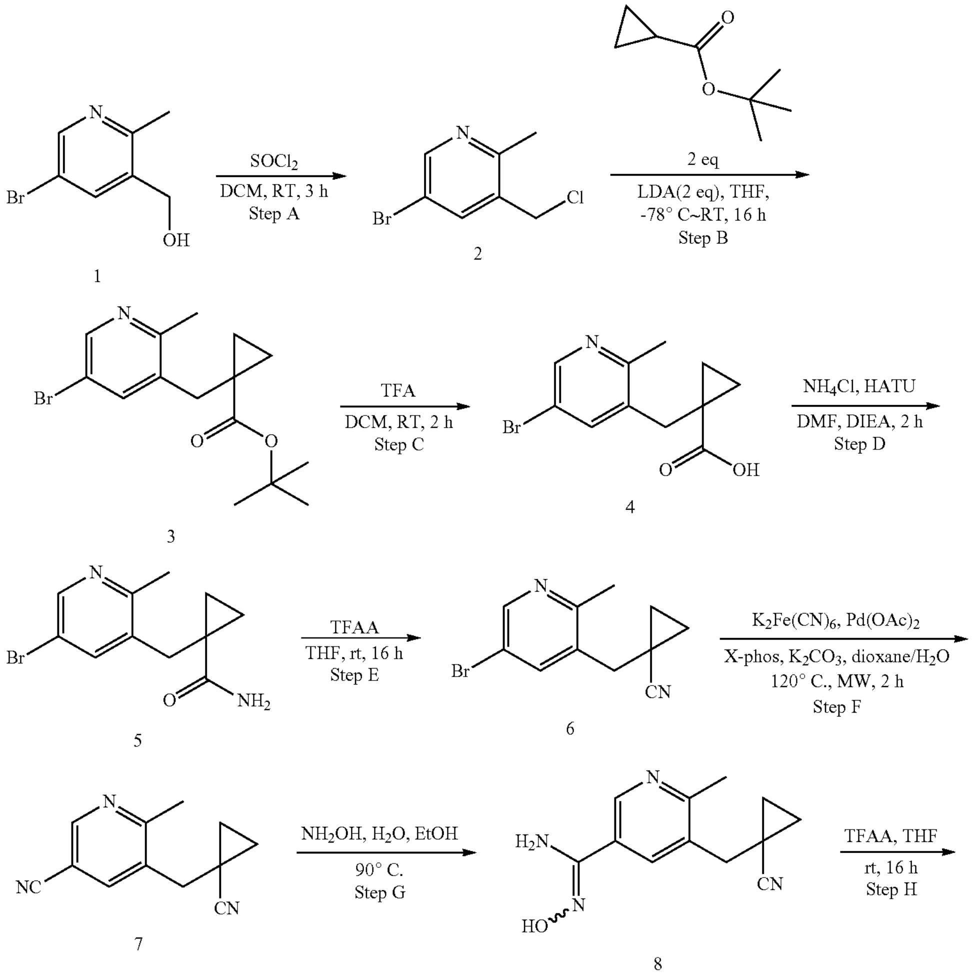

1 2 3 4 5 6 7 8

-continued

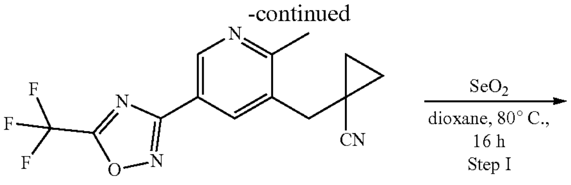

9

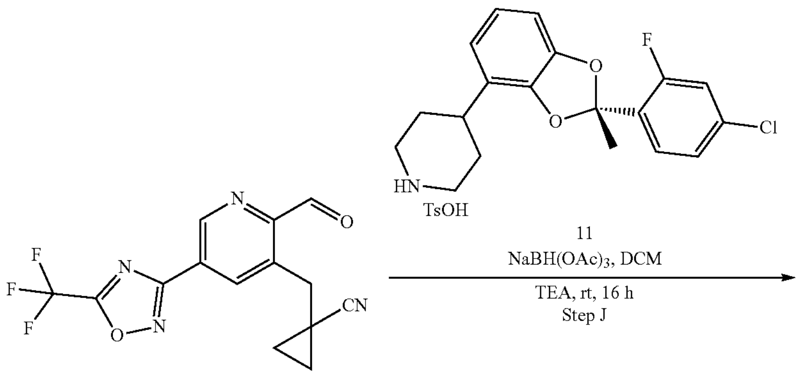

10

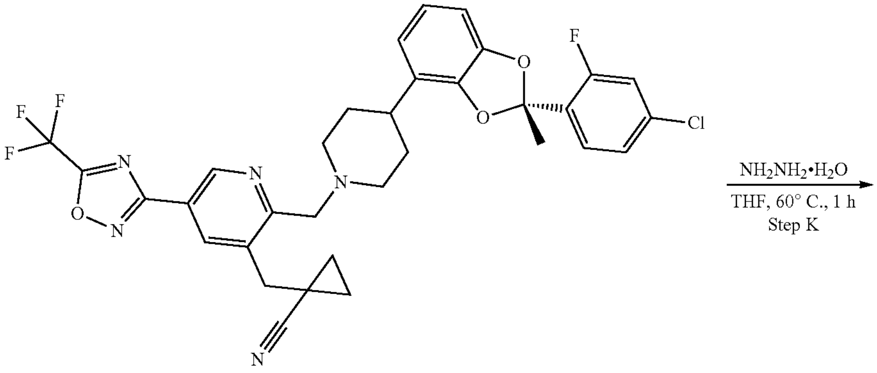

12

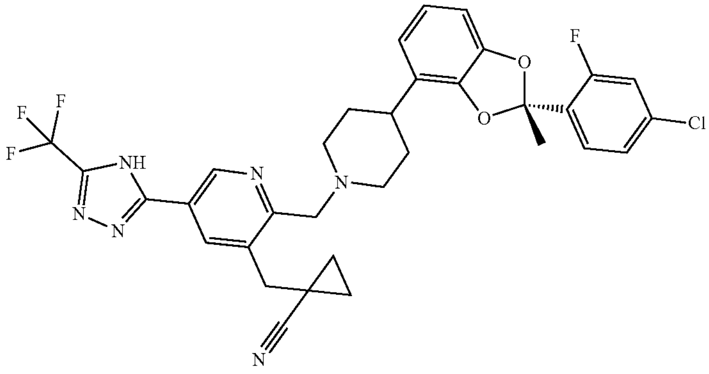

Compound 258

Step A: 5-bromo-3-(chloromethyl)-2-methylpyridine

To a solution of (5-bromo-2-methylpyridin-3-yl)methanol (5.5 g, 27.11 mmol) in DCM (55 mL) was dropwise added $SOCl_2$ (4.8 g, 40.6 mmol) at 0° C., the reaction was stirred at rt for 3 hours. After the reaction was completed, the reaction was quenched with aq $NaHCO_3$, extracted with DCM. The organic layer was combined and washed with brine, dried over sodium sulfate, filtered and concentrated to give 5-bromo-3-(chloromethyl)-2-methylpyridine (5.5 g, 91.8% yield) as yellow solid.

MS Calcd.: 219.0; MS Found: 221.9 $[M+H]^+$.

Step B: tert-butyl 1-((5-bromo-2-methylpyridin-3-yl)methyl)cyclopropane-1-carboxylate To a solution of tert-butyl cyclopropanecarboxylate (642 mg, 4.52 mmol) in THF (15 mL) was added LDA (2.26 mL, 4.52 mmol, 2N) dropwisely under Ar at −78° C. The mixture was stirred at −78° C. for 1 hour. Then 5-bromo-3-(chloromethyl)-2-methylpyridine (500 mg, 2.26 mmol) in THF (2 mL) was added dropwise, the reaction temperature was raised stirred from −78° C. to rt slowly and stirred at rt for 16 h. After the reaction was completed, the reaction was diluted with EA, washed with aq $NH_4Cl$ and brine, dried over sodium sulfate, concentrated in vacuum. The residue was purified by column chromatography (PE/EA=7/1) to give tert-butyl 1-((5-bromo-2-methylpyridin-3-yl)methyl) cyclopropane-1-carboxylate (339 mg, 46% yield) as yellow oil.

MS Calcd.: 325.1; MS Found: 328.1 $[M+H]^+$.

Step C: 1-((5-bromo-2-methylpyridin-3-yl)methyl) cyclopropane-1-carboxylic acid

To a solution of tert-butyl 1-((5-bromo-2-methylpyridin-3-yl)methyl)cyclopropane-1-carboxylate (339 mg, 1.04 mmol) in DCM (6 mL) was added TFA (3 mL). The reaction was stirred at RT for 2 hours. After the reaction was completed, the reaction was concentrated to give crude 1-((5-bromo-2-methylpyridin-3-yl)methyl)cyclopropane-1-carboxylic acid (660 mg, crude) as a yellow oil.

MS Calcd.: 269.0; MS Found: 270.0 $[M+H]^+$.

Step D: 1-((5-bromo-2-methylpyridin-3-yl)methyl) cyclopropane-1-carboxamide

A mixture of 1-((5-bromo-2-methylpyridin-3-yl)methyl) cyclopropane-1-carboxylic acid (560 mg) and DIEA (8 mL) in DMF (5 mL) was stirred at rt for 10 min, $NH_4C_1$ (1.11 g, 20.7 mmol) was added, then HATU (1.57 g, 4.14 mmol) was added, the mixture was stirred at room temperature for 2 hrs. After the reaction was completed, the reaction was diluted with EA, washed with aq $NaHCO_3$ and brine, dried over sodium sulfate, concentrated in vacuum. The residue was purified by column chromatography (PE/EA=2/1~DCM/MeOH=50/1) to give 1-((5-bromo-2-methylpyridin-3-yl) methyl)cyclopropane-1-carboxamide (310 mg, 56% yield) as a yellow oil.

MS Calcd.: 268.0; MS Found: 269.0 $[M+H]^+$.

Step E: 1-((5-bromo-2-methylpyridin-3-yl)methyl) cyclopropane-1-carbonitrile

To a solution of 1-((5-bromo-2-methylpyridin-3-yl) methyl)cyclopropane-1-carboxamide (310 mg, 1.15 mmol) in THF (6 mL) was added TFAA (2.42 g, 11.5 mmol) dropwisely at 0° C., the mixture was stirred at rt for 16 hours. After the reaction was completed, the reaction was diluted with EA, washed with aq $NaHCO_3$ and brine, dried over sodium sulfate, concentrated in vacuum. The residue was purified by column chromatography (PE/EA=3/1) to give 1-((5-bromo-2-methylpyridin-3-yl)methyl)cyclopropane-1-carbonitrile (160 mg, 55.4% yield) as a yellow oil.

MS Calcd.: 250.0; MS Found: 251.0 $[M+H]^+$.

Step F: 5-((1-cyanocyclopropyl)methyl)-6-methylnicotinonitrile

A mixture of 1-((5-bromo-2-methylpyridin-3-yl)methyl) cyclopropane-1-carbonitrile (200 mg, 0.79 mmol), $K_2Fe(CN)_6$ (167 mg, 0.39 mmol), $Pd(OAc)_2$ (18 mg, 0.079 mmol), X-phos (75 mg, 0.16 mmol) and $K_2CO_3$ (327 mg, 2.37 mmol) in dioxane/$H_2O$ (3 mL/0.6 mL) was stirred at 120° C. under Ar in microwave reactor for 2 hours. Upon cooling down, the reaction was concentrated under vacuum. The residue was purified by prep-TLC (PE/EA=4/1, 1/1, twice) to give 5-((1-cyanocyclopropyl)methyl)-6-methylnicotinonitrile (46 mg, 29% yield) as a white solid.

MS Calcd.: 197.1; MS Found: 198.1 $[M+H]^+$.

Step G: 5-((1-cyanocyclopropyl)methyl)-N'-hydroxy-6-methylnicotinimidamide

To a solution of 5-((1-cyanocyclopropyl)methyl)-6-methylnicotinonitrile (46 mg, 0.23 mmol) in EtOH (4 mL) was added $NH_2OH/H_2O$ (18 mg, 0.28 mmol) in EtOH (1 mL) dropwisely. The mixture was stirred at 90° C. for 1 hour. Another portion of $NH_2OH/H_2O$ (16 mg, 0.24 mmol) in EtOH (1 mL) was added dropwise, the mixture was stirred at 90° C. for an additional 1 hour. The mixture was concentrated to give 5-((1-cyanocyclopropyl)methyl)-N'-hydroxy-6-methylnicotinimidamide (53 mg, crude) as a yellow oil.

MS Calcd.: 230.1; MS Found: 231.1 $[M+H]^+$.

Step H: 1-((2-methyl-5-(5-(trifluoromethyl)-1,2,4-oxadiazol-3-yl)pyridin-3-yl)methyl)cyclopropane-1-carbonitrile To a solution of 5-((1-cyanocyclopropyl)methyl)-N'-hydroxy-6-methylnicotinimidamide (53 mg, crude) in THF (5 mL) was dropwise added TFAA (290 mg, 1.38 mmol) in THF (1 mL) at 0° C., the mixture was stirred at rt for 16 hours. the reaction was diluted with EA, washed with aq $NaHCO_3$ and brine, dried over sodium sulfate, concentrated in vacuum. The residue was purified by prep-TLC (PE/EA=2/1) give 1-((2-methyl-5-(5-(trifluoromethyl)-1,2,4-oxadiazol-3-yl)pyridin-3-yl)methyl)cyclopropane-1-carbonitrile (26 mg, yield: 36.7%) as a yellow oil.

MS Calcd.: 308.1; MS Found: 309.1 $[M+H]^+$.

Step I: 1-((2-formyl-5-(5trifluoromethyl)-1,2,4-oxadiazol-3-yl)pyridin-3-yl)methyl)cyclopropane-1-carbonitrile A mixture of 1-((2-methyl-5-(5-(trifluoromethyl)-1,2,4-oxadiazol-3-yl)pyridin-3-yl)methyl)cyclopropane-1-carbonitrile (21 mg, 0.068 mmol) and SeO2 (75 mg, 0.68 mmol) in dioxane (2.5 mL) was stirred at 80° C. for 16 hours. the reaction was concentrated in vacuum, purified by pre-TLC (PE/EA=2/1) to give 1-((2-formyl-5-(5-(trifluoromethyl)-1,2,4-oxadiazol-3-yl)pyridin-3-yl)methyl)cyclopropane-1-carbonitrile (15 mg, yield: 68.5%) as a yellow oil.

MS Calcd.: 322.1; MS Found: 323.1 $[M+H]^+$.

Step J: (S)-1-((2-((4-(2-(4-chloro-2-fluorophenyl)-2-methylbenzo[d][1,3]dioxol-4-yl)piperidin-1-yl) methyl)-5-(5-(trifluoromethyl)-1,2,4-oxadiazol-3-yl) pyridin-3-yl)methyl)cyclopropane-1-carbonitrile A mixture of (S)-4-(2-(4-chloro-2-fluorophenyl)-2-methylbenzo[d][1,3]dioxol-4-yl)piperidine 4-methylbenzenesulfonate (24 mg, 0.046 mmol) and TEA (23 mg, 0.23 mmol) in DCM (2 mL) was stirred at rt for 15 min. 1-((2-formyl-5-(5-(trifluoromethyl)-1,2,4-oxadiazol-3-yl) pyridin-3-yl)methyl)cyclopropane-1-carbonitrile (15 mg, 0.046 mmol) in DCM (4 mL) was added, $NaBH(OAc)_3$ (39 mg, 0.184 mmol) was added, the mixture was stirred at rt for 16 hrs. The reaction was diluted with DCM, washed with $H_2O$ and brine, dried over sodium sulfate, concentrated in vacuum. The residue was purified by prep-TLC (PE/EA=1/

1) to give (S)-1-((2-((4-(2-(4-chloro-2-fluorophenyl)-2-methylbenzo[d][1,3]dioxol-4-yl)piperidin-1-yl)methyl)-5-(5-(trifluoromethyl)-1,2,4-oxadiazol-3-yl)pyridin-3-yl)methyl)cyclopropane-1-carbonitrile (12 mg, yield: 40%) as a colorless oil.

MS Calcd.: 653.2; MS Found: 654.2 $[M+H]^+$.

Step K: 1-{[2-({4-[(2S)-2-(4-chloro-2-fluorophenyl)-2-methyl-2H-1,3-benzodioxol-4-yl]piperidin-1-yl}methyl)-5-[5-(trifluoromethyl)-4H-1,2,4-triazol-3-yl]pyridin-3-yl]methyl}cyclopropane-1-carbonitrile (Compound 258)

A mixture of (S)-1-((2-((4-(2-(4-chloro-2-fluorophenyl)-2-methylbenzo[d][1,3]dioxol-4-yl)piperidin-1-yl)methyl)-5-(5-(trifluoromethyl)-1,2,4-oxadiazol-3-yl)pyridin-3-yl)methyl)cyclopropane-1-carbonitrile (12 mg, 0.018 mmol) and $NH_2NH_2 \cdot H_2O$ (0.3 mL) in EtOH (2 mL) was stirred at 60° C. for 1 hour. The mixture was filtered, the filtrate was purified by prep-HPLC (0.1% $NH_3H_2O$) to give 1-{[2-({4-[(2S)-2-(4-chloro-2-fluorophenyl)-2-methyl-2H-1,3-benzodioxol-4-yl]piperidin-1-yl}methyl)-5-[5-(trifluoromethyl)-4H-1,2,4-triazol-3-yl]pyridin-3-yl]methyl}cyclopropane-1-carbonitrile (Compound 258) (3.34 mg, 27.3%) as a white solid.

MS Calcd.: 652.2; MS Found: 653.2 $[M+H]^+$.

$^1$H NMR (400 MHz, MeOD) δ 9.20 (d, J=1.6 Hz, 1H), 8.51 (d, J=1.6 Hz, 1H), 7.61 (t, J=8.0 Hz, 1H), 7.30 (dd, $J_1$=2.0 Hz, $J_2$=11.2 Hz, 1H), 7.23 (dd, $J_1$=1.2 Hz, $J_2$=8.0 Hz, 1H), 6.84-6.80 (m, 1H), 6.80-6.72 (m, 2H), 4.50-4.38 (m, 2H), 3.60-3.40 (m, 3H), 3.11 (s, 2H), 3.10-2.90 (m, 2H), 2.28-2.10 (m, 2H), 2.10-1.97 (m, 5H), 1.44-1.40 (m, 2H), 1.32-1.25 (m, 2H).

$^{19}$F-NMR (377 MHz): −65.09, −112.26.

Example 67

2-({4-[(2 S)-2-(4-chloro-2-fluorophenyl)-2-methyl-2H-1,3-benzodioxol-4-yl]piperidin-1-yl}methyl)-3-(2-methoxyethyl)-5-[5-(trifluoromethyl)-4H-1,2,4-triazol-3-yl]pyridine (Compound 259)

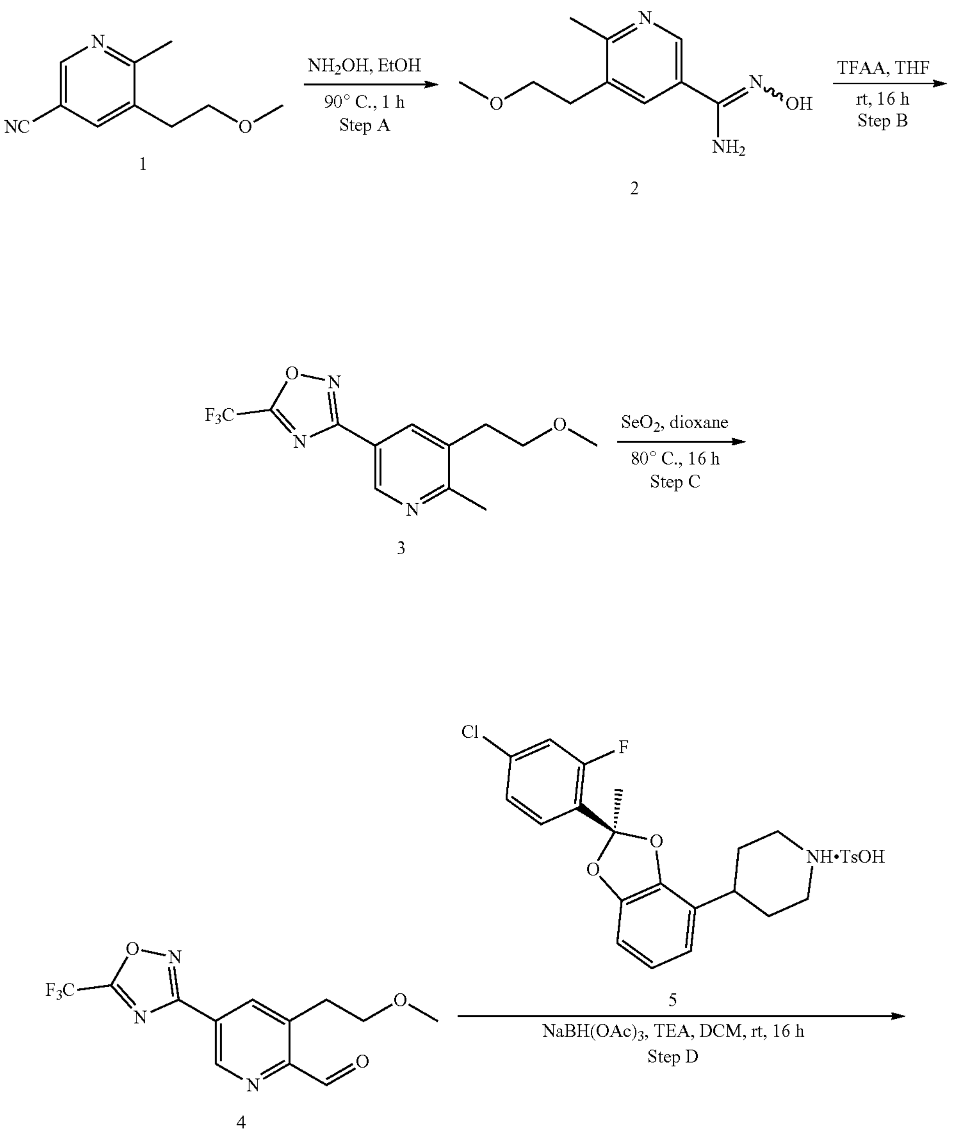

1

2

3

4

5

-continued

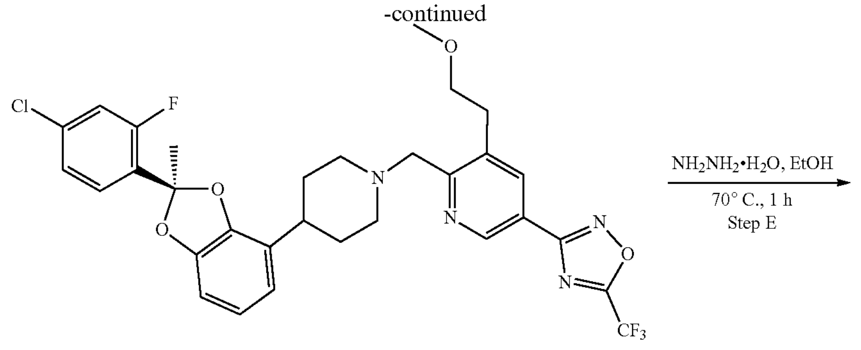

6

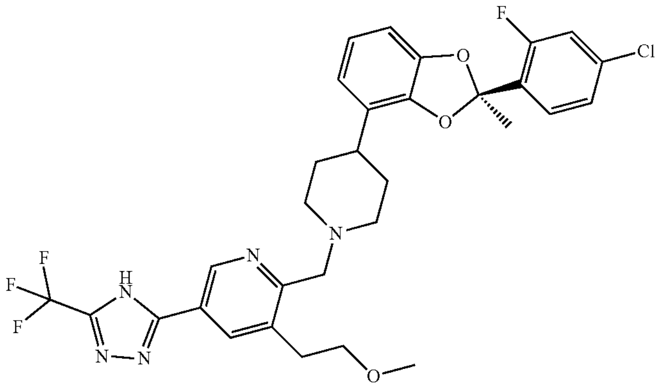

Compound 259

Step A: N'-hydroxy-5-(2-methoxyethyl)-6-methylnicotinimidamide

A mixture of 5-(2-methoxyethyl)-6-methylnicotinonitrile (140 mg), $NH_2OH$ aqueous solution (630 mg, 9.54 mmol) and EtOH (3 mL) in a microwave vial was stirred at 90° C. for 1 hour. The mixture was poured into cold water (10 mL) and extracted with EtOAc (2×10 mL), the combined organic layer was washed with brine, dried over sodium sulfate, filtered and concentrated under reduced pressure. The residue was without purified to furnish N'-hydroxy-5-(2-methoxyethyl)-6-methylnicotinimidamide (160 mg, crude) as colorless oil.

MS Calcd.: 209.1; MS Found: 210.1 $[M+H]^+$.

Step B: 3-(5-(2-methoxyethyl)-6-methylpyridin-3-yl)-5-(trifluoromethyl)-1,2,4-oxadiazole To a solution of N'-hydroxy-5-(2-methoxyethyl)-6-methylnicotinimidamide (160 mg) in THF (10 mL) was added TFAA (803.8 mg, 3.83 mmol) at 0° C. and stirred at 0° C. for 30 mins, then the reaction mixture was stirred at room temperature for 16 h. The mixture was adjusted pH=7 with $NaHCO_3$(aq), poured into cold water (10 mL) and extracted with EtOAc (2×20 mL), the combined organic layer was washed with brine, dried over sodium sulfate, filtered and concentrated under reduced pressure to yield 3-(5-(2-methoxyethyl)-6-methylpyridin-3-yl)-5-(trifluoromethyl)-1,2,4-oxadiazole (200 mg, yield: 91.0%) as colorless oil as a crude product, which was directly used in next steps without further purifications.

MS Calcd.: 287.1; MS Found: 288.0 $[M+H]^+$.

Step C: 3-(2-methoxyethyl)-5-(5trifluoromethyl)-1,2,4-oxadiazol-3-yl)picolinaldehyde A mixture of 3-(5-(2-methoxyethyl)-6-methylpyridin-3-yl)-5-(trifluoromethyl)-1,2,4-oxadiazole (100 mg) and $SeO_2$ (116 mg, 1.05 mmol) in dioxane (2 mL) was stirred at 80° C. for 16 hours in a microwave vial. The mixture was filtered and concentrated under reduced pressure to yield 3-(2-methoxyethyl)-5-(5-(trifluoromethyl)-1,2,4-oxadiazol-3-yl) picolinaldehyde (100 mg, crude) as yellow oil as a crude product, which was directly used in next steps without further purifications.

MS Calcd.: 301.1; MS Found: 302.0 $[M+H]^+$.

Step D: (R)-3-(6-((4-(2-(4-chloro-2-fluorophenyl)-2-methylbenzo[d][1,3]dioxol-4-yl) piperidin-1-yl) methyl)-5-(2-methoxyethyl)pyridin-3-yl)-5-(trifluoromethyl)-1,2,4-oxadiazole A mixture of (R)-4-(2-(4-chloro-2-fluorophenyl)-2-methylbenzo[d][1,3]dioxol-4-yl)piperidine 4-methylbenzenesulfonate (51.8 mg) and TEA (50.4 mg, 0.50 mmol) in DCM (5 mL) was stirred at room temperature for 20 mins. 3-(2-methoxyethyl)-5-(5-(trifluoromethyl)-1,2,4-oxadiazol-3-yl)picolinaldehyde (30 mg) and $NaBH(OAc)_3$ (84.5 mg, 0.40 mmol) was added and the reaction mixture was stirred at room temperature for 16 hours. The mixture was poured into cold water (10 mL) and extracted with DCM (2×10 mL), the combined organic layer was washed with brine, dried over sodium sulfate, filtered and concentrated under reduced pressure. The residue was purified by prep-TLC to furnish (R)-3-(6-((4-(2-(4-chloro-2-fluorophenyl)-2-methylbenzo[d][1,3]dioxol-4-yl)piperidin-1-yl)methyl)-5-(2-methoxyethyl)pyridin-3-yl)-5-(trifluoromethyl)-1,2,4-oxadiazole (30 mg, yield: 47.6%) as yellow solid.

MS Calcd.: 632.2; MS Found: 633.3 $[M+H]^+$.

Step E: 2-({4-[(2S)-2-(4-chloro-2-fluorophenyl)-2-methyl-2H-1,3-benzodioxol-4-yl]piperidin-1-yl}methyl)-3-(2-methoxyethyl)-5-[5-trifluoromethyl)-4H-1,2,4-triazol-3-yl]pyridine (Compound 259)

A mixture of (R)-3-(6-((4-(2-(4-chloro-2-fluorophenyl)-2-methylbenzo [d][1,3]dioxol-4-yl) piperidin-1-yl)methyl)-5-(2-methoxyethyl)pyridin-3-yl)-5-(trifluoromethyl)-1,2,4-oxadiazole (20 mg, 0.03 mmol) and $NH_2NH_2 \cdot H_2O$ (0.2 mL) in EtOH (1 mL) was stirred at 70° C. for 1 hour. The reaction mixture was purified by prep-HPLC to give 2-({4-[(2S)-2-(4-chloro-2-fluorophenyl)-2-methyl-2H-1,3-benzodioxol-4-yl]piperidin-1-yl}methyl)-3-(2-methoxyethyl)-5-[5-(trifluoromethyl)-4H-1,2,4-triazol-3-yl]pyridine (Compound 259) (9.34 mg, yield: 46.5%) as white solid.

MS Calcd.: 631.2; MS Found: 632.2 $[M+H]^+$.

$^1H$ NMR (400 MHz, MeOD): 9.12 (d, J=2.0 Hz, 1H), 8.33 (d, J=1.6 Hz, 1H), 7.61 (t J=8.4 Hz, 1H), 7.35-7.20 (m, 2H), 6.89-6.73 (m, 3H), 4.57-4.45 (m, 2H), 3.73 (t J=6.0 Hz, 2H), 3.65-3.52 (m, 2H), 3.34 (s, 3H), 3.20-3.09 (m, 2H), 3.08-2.98 (m, 3H), 2.30-2.14 (m, 2H), 2.10-2.00 (m, 5H).

$^{19}F$-NMR (377 MHz): −65.17, −112.23

Example 68

3-fluoro-4-[(2S)-4-(1-{[3-(2-methoxyethyl)-5-[5-(trifluoromethyl)-4H-1,2,4-triazol-3-yl]pyridin-2-yl]methyl}piperidin-4-yl)-2-methyl-2H-1,3-benzodioxol-2-yl]benzonitrile (Compound 260)

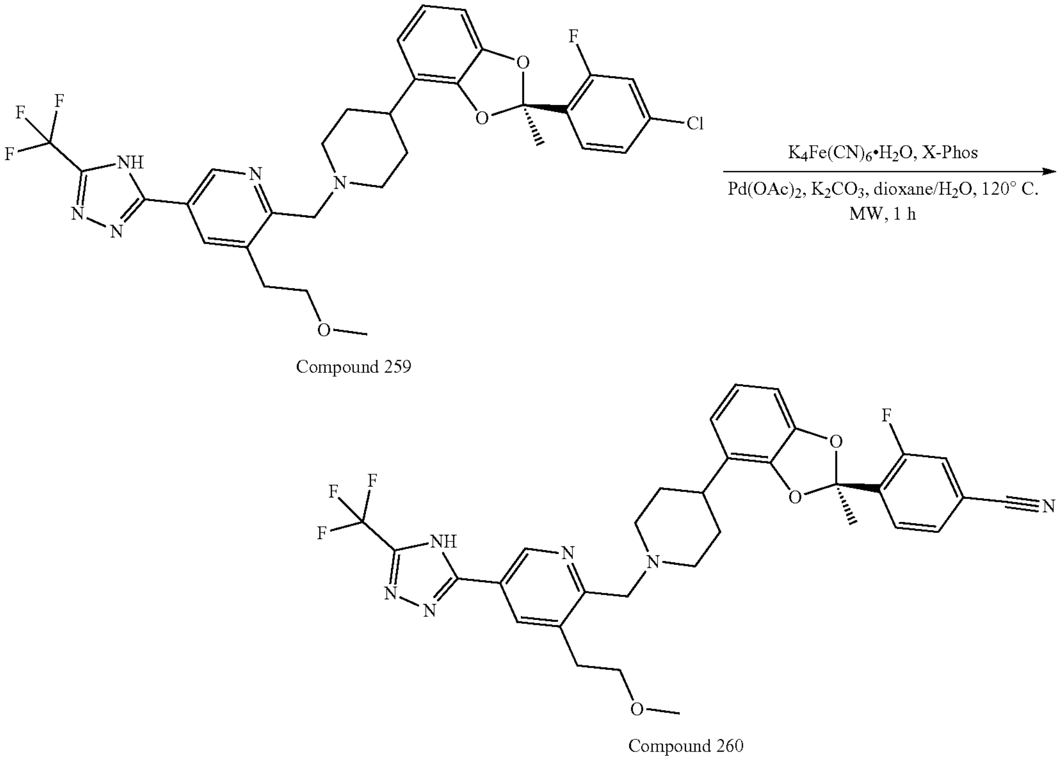

Compound 259

Compound 260

A mixture of (R)-2-((4-(2-(4-chloro-2-fluorophenyl)-2-methylbenzo[d][1,3]dioxol-4-yl)piperidin-1-yl)methyl)-3-(2-methoxyethyl)-5-(5-(trifluoromethyl)-4H-1,2,4-triazol-3-yl)pyridine (Compound 259, 20 mg, 0.03 mmol), $K_4Fe(CN)_6 \cdot H_2O$ (13.3 mg, 0.03 mmol), $K_2CO_3$ (13.1 mg, 0.095 mmol), X-phos (3 mg, 0.006 mmol) and $Pd(OAc)_2$ (1 mg, 0.003 mmol) in dioxane (1 mL) and $H_2O$ (0.2 ml) was stirred in M.W. at 120° C. for 1 hour under $N_2$. The reaction mixture was purified by prep-HPLC to give 3-fluoro-4-[(2S)-4-(1-{[3-(2-methoxyethyl)-5-[5-(trifluoromethyl)-4H-1,2,4-triazol-3-yl]pyridin-2-yl]methyl}piperidin-4-yl)-2-methyl-2H-1,3-benzodioxol-2-yl]benzonitrile (Compound 260) (1.01 mg, yield: 5.1%) as white solid.

MS Calcd.: 622.2; MS Found: 623.2 $[M+H]^+$.

$^1H$ NMR (400 MHz, MeOD): 9.13 (s, 1H), 8.34 (s, 1H), 7.82 (t, J=7.4 Hz, 1H), 7.67 (d, J=10.4 Hz, 1H), 7.60 (d, J=8.0 Hz, 1H), 6.90-6.78 (m, 3H), 4.60-4.50 (m, 4H), 3.74 (t, J=6.0 Hz, 2H), 3.65-3.52 (m, 2H), 3.35 (s, 3H), 3.20-3.10 (m, 1H), 3.05 (t, J=6.0 Hz, 2H), 2.30-2.15 (m, 2H), 2.09 (s, 3H), 2.10-2.00 (m, 2H).

$^{19}F$-NMR (377 MHz): −65.37, −65.38, −111.95.

Example 69

2-({4-[2-(4-chlorophenyl)-2-methyl-2H-1,3-benzodioxol-4-yl]piperidin-1-yl}methyl)-3-(2-methoxyethyl)-5-[5-(trifluoromethyl)-4H-1,2,4-triazol-3-yl] pyridine (Compound 261)

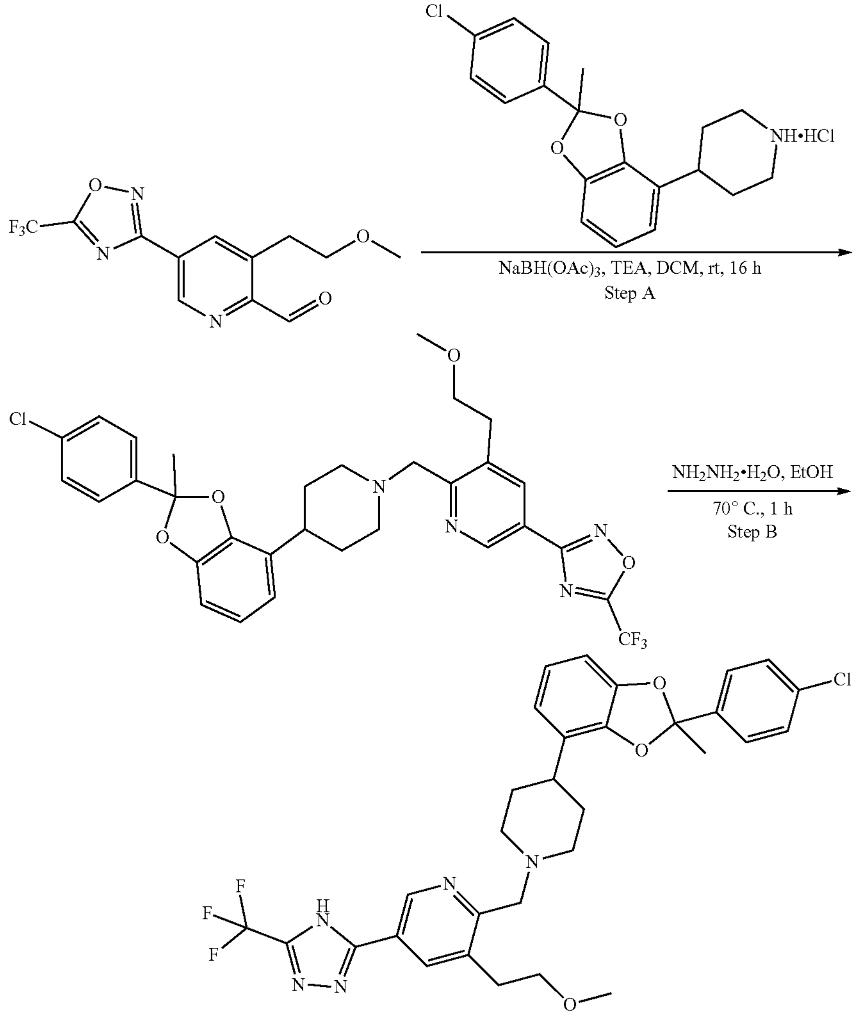

Compound 261

Step A: The synthesis of 3-(6-((4-(2-(4-chlorophenyl)-2-methylbenzo[d][1,3]dioxol-4-yl)piperidin-1-yl) methyl)-5-(2-methoxyethyl)pyridin-3-yl)-5-(trifluoromethyl)-1,2,4-oxadiazole A mixture of 4-(2-(4-chlorophenyl)-2-methylbenzo[d][1,3]dioxol-4-yl)piperidine hydrochloride (54.8 mg, 0.17 mmol) and TEA (83.9 mg, 0.83 mmol) in DCM (10 mL) was stirred at room temperature for 20 mins. 3-(2-methoxyethyl)-5-(5-(trifluoromethyl)-1,2,4-oxadiazol-3-yl) picolinaldehyde (50 mg, 0.17 mmol) and $NaBH(OAc)_3$ (140.9 mg, 0.66 mmol) were added and the reaction mixture was stirred at room temperature for 16 hours. The mixture was poured into cold water (10 mL) and extracted with DCM (2×10 mL), the combined organic layer was washed with brine, dried over sodium sulfate, filtered and concentrated under reduced pressure. The residue was purified by prep-TLC to furnish 3-(6-((4-(2-(4-chlorophenyl)-2-methylbenzo[d][1,3] dioxol-4-yl)piperidin-1-yl)methyl)-5-(2-15 methoxyethyl) pyridin-3-yl)-5-(trifluoromethyl)-1,2,4-oxadiazole (60 mg, yield: 58.8%) as a white solid.

MS Calcd.: 614.2; MS Found: 615.1 $[M+H]^+$.

Step B: 2-({4-[2-(4-chlorophenyl)-2-methyl-2H-1,3-benzodioxol-4-yl]piperidin-1-yl}methyl)-3-(2-methoxyethyl)-5-[5-(trifluoromethyl)-4H-1,2,4-triazol-3-yl]pyridine (Compound 261)

A mixture of 3-(6-((4-(2-(4-chlorophenyl)-2-methylbenzo [d][1,3]dioxol-4-yl)piperidin-1-yl)methyl)-5-(2-methoxyethyl)pyridin-3-yl)-5-(trifluoromethyl)-1,2,4-oxadiazole (30 mg, 0.05 mmol) and $NH_2NH_2{\cdot}H_2O$ (0.3 mL) in EtOH (1 mL) was stirred at 70° C. for 1 hour. The reaction mixture was purified by prep-HPLC (0.1% of NH3·H2O in $CH_3CN$) to give 2-({4-[2-(4-chlorophenyl)-2-methyl-2H-1,3-benzodioxol-4-yl]piperidin-1-yl}methyl)-3-(2-methoxyethyl)-5-[5-(trifluoromethyl)-4H-1,2,4-triazol-3-yl]pyridine (11.36 mg, yield: 37.9%) as a white solid.

MS Calcd.: 613.2; MS Found: 614.2 $[M+H]^+$.

$^1H$ NMR (400 MHz, MeOD): 9.17 (s, 1H), 8.37 (s, 1H), 7.62 (d, J=8.4 Hz, 2H), 7.41 (d, J1=8.8 Hz, 2H), 6.90-6.75 (m, 3H), 4.73 (s, 2H), 3.81-3.70 (m, 4H), 3.40-3.25 (m, 5H), 3.05-3.00 (m, 3H), 2.40-2.13 (m, 2H), 2.20-2.10 (m, 2H), 1.98 (s, 3H)

$^{19}F$-NMR (377 MHz): −66.70.

Example 70

2-({4-[2-(5-chloropyridin-2-yl)-2-methyl-2H-1,3-benzodioxol-4-yl]piperidin-1-yl}methyl)-3-methyl-5-[5-(trifluoromethyl)-4H-1,2,4-triazol-3-yl]pyridine (Compound 264)

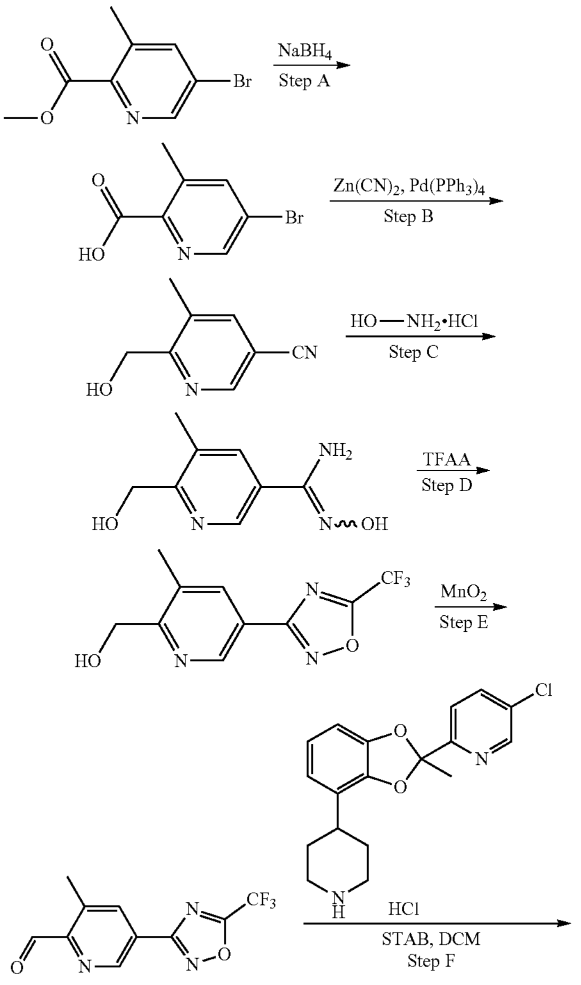

-continued

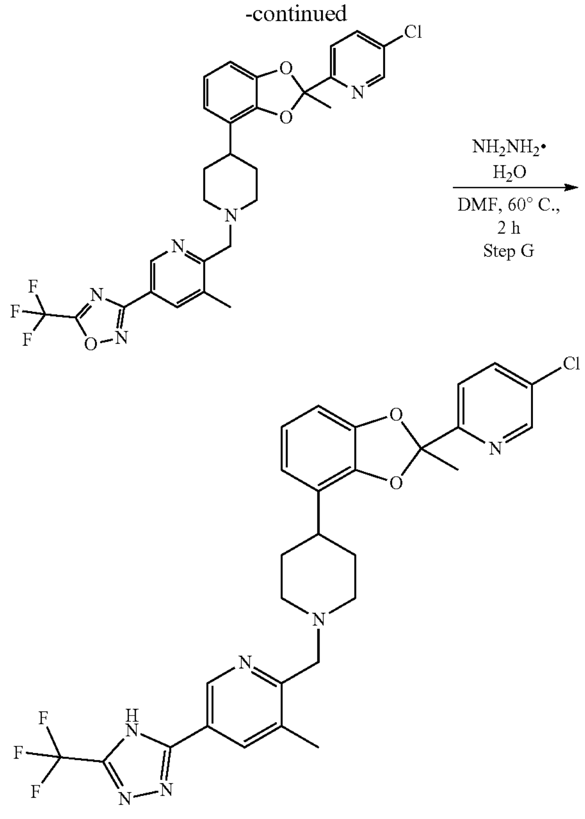

Compound 264

Step A: (5-bromo-3-methylpyridin-2-yl)methanol

To a solution of methyl 5-bromo-3-methylpicolinate (5 g, 21.74 mmol) in MeOH (50 mL) was added $NaBH_4$ (8.27 g, 217.39 mmol) at 0° C. The reaction was stirred at 90° C. for 2 hours. After the reaction was completed, the reaction was quenched with water (50 mL) and extracted with ethyl acetate (100 mL×3). The organic layer was combined and washed with brine (50 mL×2), dried over sodium sulfate, filtered and concentrated in vacuum. The residue was purified by column chromatography on silica gel (PE:EA=3:1) to give (5-bromo-3-methylpyridin-2-yl)methanol (3.4 g, 77% yield) as yellow oil.

MS Calcd.: 201.0; MS Found: 202.1 $[M+H]^+$.

Step: 6-(hydroxymethyl)-5-methylnicotinonitrile

A mixture of (5-bromo-3-methylpyridin-2-yl)methanol (3 g, 14.9 mmol), $Zn(CN)_2$ (3.48 g, 29.7 mmol) and $Pd(PPh3)_4$ (1.7 g, 1.49 mmol) in dry DMF (30 mL) was stirred at 140° C. for 4 h under $N_2$. After the reaction was completed, the reaction was quenched with water (100 mL) and extracted with ethyl acetate (100 mL×3). The organic layer was combined and washed with brine (100 mL×2), dried over sodium sulfate, filtered and concentrated in vacuum. The residue was purified by column chromatography on silica gel (PE:EA=1:1) to give 6-(hydroxymethyl)-5-methylnicotinonitrile (1.2 g, 54% yield) as a yellow solid.

MS Calcd.: 148.1; MS Found: 149.1 $[M+H]^+$.

Step C: N'-hydroxy-6-(hydroxymethyl)-5-methylnicotinimidamide

To a solution of 6-(hydroxymethyl)-5-methylnicotinonitrile (1 g, 6.8 mmol), $K_2CO_3$ (5.6 g, 40.8 mmol) and DIEA (5.23 g, 40.8 mmol) in EtOH (5 mL) was added hydroxylamine hydrochloride (2.33 g, 33.8 mmol) at room temperature. The reaction was stirred at 80° C. for 3 hours. After the reaction was completed, the reaction was filtered and concentrated under reduced pressure to give crude product. The residue was purified by column chromatography on silica gel (PE:EA=5:1) to give N'-hydroxy-6-(hydroxymethyl)-5-methylnicotinimidamide (1.8 g, impurity) as yellow solid.

MS Calcd.: 181.1; MS Found: 182.1 $[M+H]^+$.

Step D: (3-methyl trifluoromethyl)-1,2,4-oxadiazol-3-yl)pyridin-2-yl)methanol

To a solution of N'-hydroxy-6-(hydroxymethyl)-5-methylnicotinimidamide (1.8 g, 9.9 mmol) in THF (20 mL) was added TFAA (2.33 g, 33.8 mmol) at 0° C. The reaction was stirred at room temperature for 2 hours. After the reaction was completed, the reaction was quenched with water (50 mL) and extracted with ethyl acetate (100 mL×3). The organic layer was combined and washed with brine (50 mL×2), dried over sodium sulfate, filtered and concentrated in vacuum. The residue was purified by column chromatography on silica gel (PE:EA=4: 1) to give (3-methyl-5-(5-(trifluoromethyl)-1,2,4-oxadiazol-3-yl)pyridin-2-yl)methanol (1.15 g, 45% yield) as colorless oil.

MS Calcd.: 259.1; MS Found: 260.0 $[M+H]^+$.

Step E: 3-methyl-5-(5-(trifluoromethyl)-1,2,4-oxadiazol-3-yl)picolinaldehyde

To a solution of (3-methyl-5-(5-(trifluoromethyl)-1,2,4-oxadiazol-3-yl)pyridin-2-yl)methanol (1.1 g, 4.2 mmol) in DCM (20 mL) added $MnO_2$ (7.36 g, 84.6 mmol) at room temperature. The reaction was stirred at room temperature for 2 hours. After the reaction was completed, the reaction was filtered and concentrated under reduced pressure to give crude product. The residue was purified by column chromatography on silica gel (PE:EA=5: 1) to give 3-methyl-5-(5-(trifluoromethyl)-1,2,4-oxadiazol-3-yl)picolinaldehyde (680 mg, 62% yield) as a yellow solid.

MS Calcd.: 257.0; MS Found: 258.1 $[M+H]^+$.

Step F: 3-(6-((4-(2-(5-chloropyridin-2-yl)-2-methylbenzo[d][1,3]dioxol-4-yl)piperidin-1-yl)methyl)-5-methylpyridin-3-yl)-5-(trifluoromethyl)-1,2,4-oxadiazole To a solution of 3-methyl-5-(5-(trifluoromethyl)-1,2,4-oxadiazol-3-yl)picolinaldehyde (100 mg, 0.39 mmol) and 5-chloro-2-(2-methyl-4-(piperidin-4-yl)benzo[d][1,3]dioxol-2-yl)pyridine HCl salt (142 mg, 0.39 mmol) in DCM (3 mL) was added NaOAc (32 mg, 0.39 mmol) and NaBH $(OAc)_3$. The reaction was stirred at room temperature for 16 hours. After the reaction was completed, the reaction was quenched with water (20 mL) and extracted with ethyl acetate (50 mL×3). The organic layer was combined and washed with brine (50 mL×2), dried over sodium sulfate, filtered and concentrated in vacuum to give 3-(6-((4-(2-(5-chloropyridin-2-yl)-2-methylbenzo [d][1,3]dioxol-4-yl)piperidin-1-yl)methyl)-5-methylpyridin-3-yl)-5-(trifluoromethyl)-1,2,4-oxadiazole (150 mg, crude) as yellow oil.

MS Calcd.: 571.2; MS Found: 572.2 $[M+H]^+$.

Step G: 2-({4-[2-(5-chloropyridin-2-yl)-2-methyl-2H-1,3-benzodioxol-4-yl]piperidin-1-yl}methyl)-3-methyl-5-[5-(trifluoromethyl)-4H-1,2,4-triazol-3-yl]pyridine (Compound 264)

To a solution of 3-(6-((4-(2-(5-chloropyridin-2-yl)-2-methylbenzo[d][1,3]dioxol-4-yl)piperidin-1-yl)methyl)-5-methylpyridin-3-yl)-5-(trifluoromethyl)-1,2,4-oxadiazole (150 mg) in DMF (2 mL) was added $NH_2NH_2 \cdot H_2O$ (65 mg, 1.31 mmol). The reaction was stirred at 60° C. for 2 hour. After the reaction was completed, the reaction was filtered and purified by Prep-HPLC to give 2-({4-[2-(5-chloropyridin-2-yl)-2-methyl-2H-1,3-benzodioxol-4-yl]piperidin-1-yl}methyl)-3-methyl-5-[5-(trifluoromethyl)-4H-1,2,4-triazol-3-yl]pyridine (77.6 mg, 52% yield) as a white solid.

MS Calcd.: 570.2; MS Found: 571.7 $[M+H]^+$.

$^1$H NMR (400 MHz, DMSO-$d_6$): δ 8.99 (d, J=1.6 Hz, 1H), 8.72 (d, J=2.4 Hz, 1H), 8.20 (d, J=1.6 Hz, 1H), 8.01 (dd, J=8.4, J=2.4 Hz, 1H), 7.62 (d, J=8.4 Hz, 1H), 6.73-6.85 (m, 3H), 3.94 (s, 2H), 3.08-3.16 (m, 2H), 2.70-2.80 (m, 1H), 2.48-2.55 (m, 2H), 2.46 (s, 3H), 2.02 (s, 3H), 1.74-1.90 (m, 4H).

$^{19}$F-NMR (377 MHz): −62.80.

Example 71

2-({4-[2-(2,4-difluorophenyl)-2-methyl-2H-1,3-benzodioxol-4-yl]piperidin-1-yl}methyl)-3-methyl-5-[5-(trifluoromethyl)-4H-1,2,4-triazol-3-yl]pyridine (Compound 262)

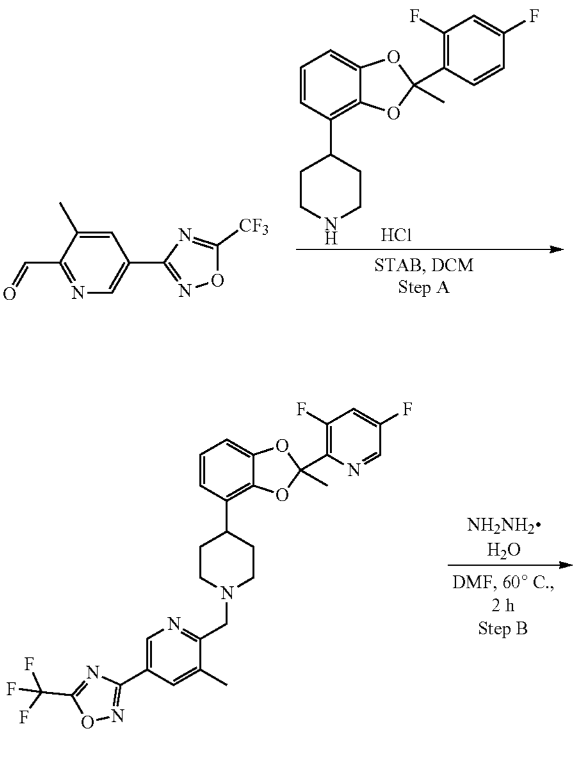

-continued

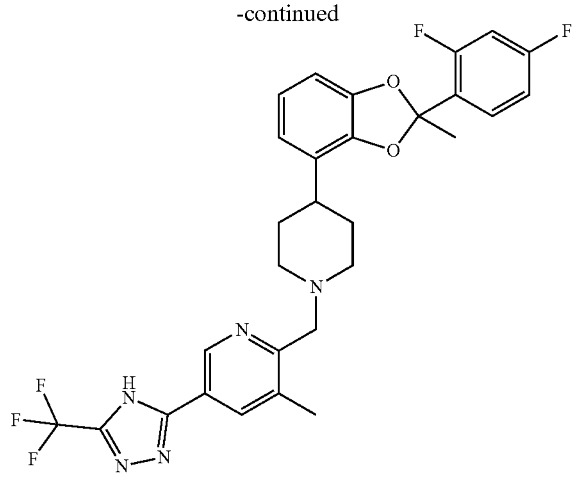

Compound 262

Step A: 3-(6-((4-(2-(2,4-difluorophenyl)-2-methylbenzo[d][1,3]dioxol-4-yl)piperidin-1-yl)methyl)-5-methylpyridin-3-yl)-5-(trifluoromethyl)-1,2,4-oxadiazole To a solution of 3-methyl-5-(5-(trifluoromethyl)-1,2,4-oxadiazol-3-yl)picolinaldehyde (100 mg, 0.39 mmol) and 4-(2-(2,4-difluorophenyl)-2-methylbenzo[d][1,3]dioxol-4-yl)piperidine HCl salt (143 mg, 0.39 mmol) in DCM (3 mL) was added $NaBH(OAc)_3$ (165 mg, 0.78 mmol). The reaction was stirred at room temperature for 16 hours. After the reaction was completed, the reaction was quenched with water (20 mL) and extracted with ethyl acetate (50 mL×3). The organic layer was combined and washed with brine (50 mL×2), dried over sodium sulfate, filtered and concentrated in vacuum to give crude product 3-(6-((4-(2-(2,4-difluorophenyl)-2-methylbenzo [d][1,3]dioxol-4-yl)piperidin-1-yl)methyl)-5-methylpyridin-3-yl)-5-(trifluoromethyl)-1,2,4-oxadiazole (200 mg, crude) as yellow oil.

MS Calcd.: 572.2; MS Found: 573.6 $[M+H]^+$.

Step B: 2-({4-[2-(2,4-difluorophenyl)-2-methyl-2H-1,3-benzodioxol-4-yl]piperidin-1-yl}methyl)-3-methyl-5-[5-(trifluoromethyl)-4H-1,2,4-triazol-3-yl]pyridine (Compound 262)

To a solution of 3-(6-((4-(2-(2,4-difluorophenyl)-2-methylbenzo[d][1,3]dioxol-4-yl)piperidin-1-yl)methyl)-5-methylpyridin-3-yl)-5-(trifluoromethyl)-1,2,4-oxadiazole (200 mg) in DMF (2 mL) was added $NH_2NH_2 \cdot H_2O$ (87 mg, 1.75 mmol). The reaction was stirred at 60° C. for 2 hour. After the reaction was completed, the reaction was filtered and purified by Prep-HPLC to give 2-({4-[2-(2,4-difluorophenyl)-2-methyl-2H-1,3-benzodioxol-4-yl]piperidin-1-yl}methyl)-3-methyl-5-[5-(trifluoromethyl)-4H-1,2,4-triazol-3-yl]pyridine (77.61 mg, 39% yield) as a white solid.

MS Calcd.: 571.2; MS Found: 572.7 $[M+H]^+$.

$^1H$ NMR (400 MHz, DMSO-$d_6$): δ 9.12 (d, J=1.2 Hz, 1H), 8.33 (d, J=1.6 Hz, 1H), 7.65-7.72 (m, 1H), 7.31-7.40 (m, 1H), 7.10-7.17 (m, 1H), 6.83-6.91 (m, 2H), 6.78-6.83 (m, 1H), 4.64 (s, 2H), 3.59-3.70 (m, 2H), 3.24-3.38 (m, 2H), 2.99-3.10 (m, 1H), 2.44 (s, 3H), 2.12-2.28 (m, 2H), 2.05 (s, 3H), 1.94-2.10 (m, 2H).

$^{19}F$-NMR (377 MHz): −63.81, −108.06, −108.09, −108.75, −108.78.

Example 72

2-({4-[2-(4-fluorophenyl)-2-methyl-2H-1,3-benzodioxol-4-yl]piperidin-1-yl}methyl)-3-methyl-5-[5-(trifluoromethyl)-4H-1,2,4-triazol-3-yl]pyridine (Compound 263)

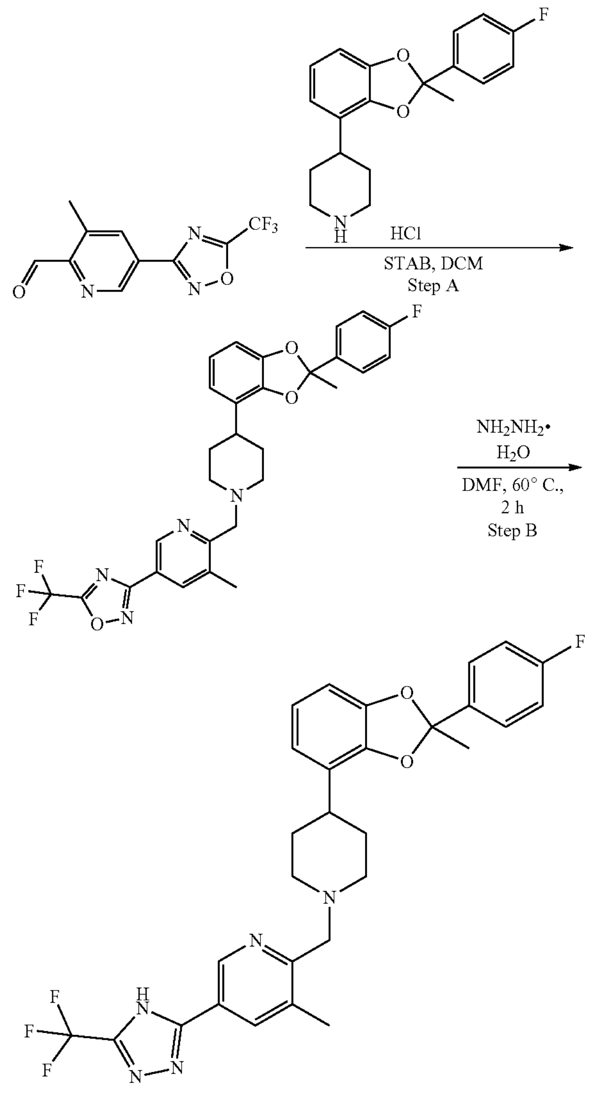

Compound 263

Step A: 3-(6-((4-(2-(4-fluorophenyl)-2-methylbenzo[d][1,3]dioxol-4-yl)piperidin-1-yl)methyl)-5-methylpyridin-3-yl)-5-trifluoromethyl)-1,2,4-oxadiazole To a solution of 3-methyl-5-(5-(trifluoromethyl)-1,2,4-oxadiazol-3-yl)picolinaldehyde (150 mg, 0.58 mmol) and 4-(2-(4-fluorophenyl)-2-methylbenzo[d][1,3]dioxol-4-yl)piperidine HCl salt (200 mg, 0.58 mmol) in DCM (3 mL) was added NaOAc (48 mg, 0.58 mmol) and $NaBH(OAc)_3$ (247 mg, 1.16 mmol). The reaction was stirred at room temperature for 16 hours. After the reaction was completed, the reaction was quenched with water (20 mL) and extracted with ethyl acetate (50 mL×3). The organic layer was combined and washed with brine (50 mL×2), dried over sodium sulfate, filtered and concentrated in vacuum to give crude product. The residue was purified by column chromatography on silica gel (PE:EA=4:1) to give 3-(6-((4-(2-(4-fluorophenyl)-2-methylbenzo [d][1,3]dioxol-4-yl)piperidin-1-yl)methyl)-5-methylpyridin-3-yl)-5-(trifluoromethyl)-1,2,4-oxadiazole (150 mg, 46% yield) as yellow oil.

MS Calcd.: 554.2; MS Found: 555.2 [M+H]$^+$.

Step B: 2-({4-[2-(4-fluorophenyl)-2-methyl-2H-1,3-benzodioxol-4-yl]piperidin-1-yl}methyl)-3-methyl-5-[5-(trifluoromethyl)-4H-1,2,4-triazol-3-yl]pyridine (Compound 263)

To a solution of 3-(6-((4-(2-(4-fluorophenyl)-2-methylbenzo[d][1,3]dioxol-4-yl)piperidin-1-yl)methyl)-5-methylpyridin-3-yl)-5-(trifluoromethyl)-1,2,4-oxadiazole (150 mg, 0.27 mmol) in DMF (2 mL) was added $NH_2NH_2 \cdot H_2O$ (68 mg, 1.35 mmol). The reaction was stirred at 60° C. for 2 hour. After the reaction was completed, the reaction was filtered and purified by Prep-HPLC to give 2-({4-[2-(4-fluorophenyl)-2-methyl-2H-1,3-benzodioxol-4-yl]piperidin-1-yl}methyl)-3-methyl-5-[5-(trifluoromethyl)-4H-1,2,4-triazol-3-yl]pyridine (106.09 mg, 71% yield) as a white solid.

MS Calcd.: 553.2; MS Found: 554.6 [M+H]$^+$.

$^1$H NMR (400 MHz, DMSO-$d_6$): δ 8.97 (d, J=1.6 Hz, 1H), 8.19 (d, J=1.6 Hz, 1H), 7.58-7.63 (m, 2H), 7.20-7.28 (m, 2H), 6.70-6.80 (m, 3H), 3.92 (s, 2H), 3.05-3.15 (m, 2H), 2.68-2.80 (m, 1H), 2.50-2.58 (m, 2H), 2.46 (s, 3H), 1.96 (s, 3H), 1.73-1.89 (m, 4H).

$^{19}$F-NMR (377 MHz): −62.86, −112.83.

Example 73

2-({4-[2-(4-chlorophenyl)-2-methyl-2H-1,3-benzodioxol-4-yl]piperidin-1-yl}methyl)-3-methyl-5-[5-(trifluoromethyl)-4H-1,2,4-triazol-3-yl]pyridine (Compound 265)

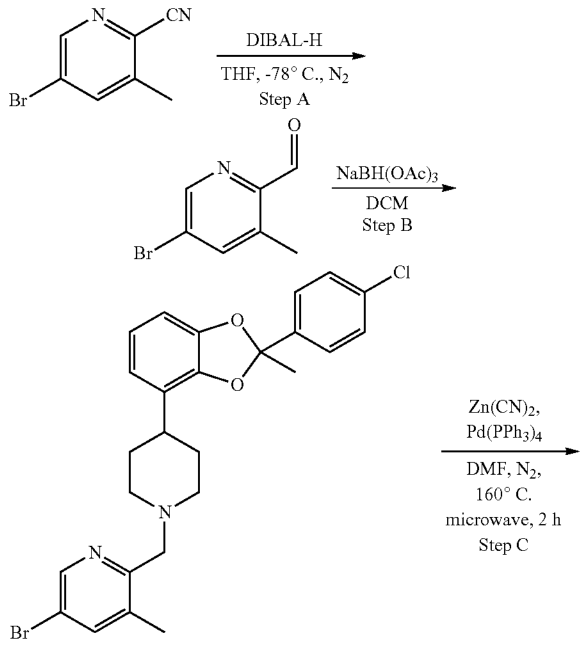

-continued

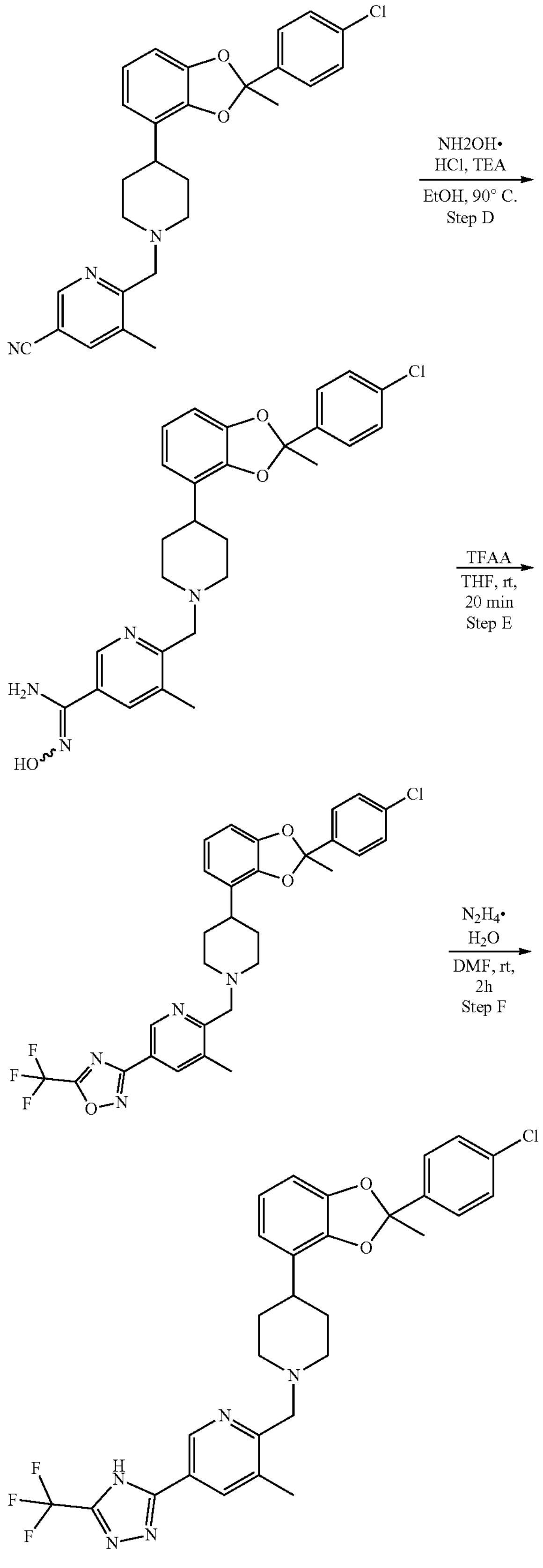

Compound 265

Step A: 5-bromo-3-methylpicolinaldehyde

To a solution of 5-bromo-3-methylpicolinonitrile (2 g, 10.2 mmol) in THF (30 mL) was added DIBAL-H (1 M, 30.6 mL, 30.6 mmol) and stirred at −78° C. for 3 hours under $N_2$. After the reaction was completed, the reaction mixture was quenched with MeOH (10 mL) and filtrated. The filtrate was diluted with ethyl acetate (100 mL). The organic layer was washed with brine (10 mL), dried over sodium sulfate, filtered and concentrated in vacuum. The residue was purified by column chromatography on silica gel (PE/EA=10/1) to give 5-bromo-3-methylpicolinaldehyde (350 mg, 15.3%) as a white solid.

MS Calcd.: 199.0; MS Found: 200.0 $[M+H]^+$.

Step B: 5-bromo-2-((4-(2-(4-chlorophenyl)-2-methylbenzo[d][1,3]dioxol-4-yl)piperidin-1-yl)methyl)-3-methylpyridine To a solution of 5-bromo-3-methylpicolinaldehyde (305 mg, 1.55 mmol), 4-(2-(4-chlorophenyl)-2-methylbenzo [d][1,3]dioxol-4-yl)piperidine (497 mg, 1.55 mmol) in DCM (5 mL) was added $NaBH(OAc)_3$ (567 mg, 3.10 mmol) and at room temperature. The reaction was stirred at room temperature for 16 hours under $N_2$. After the reaction was completed, the reaction was quenched with water (10 mL) and extracted with ethyl acetate (30 mL×3). The organic layer was combined and washed with brine (10 mL), dried over sodium sulfate, filtered and concentrated in vacuum. The residue was purified by column chromatography on silica gel (PE/EA=7/1) to give 5-bromo-2-((4-(2-(4-chlorophenyl)-2-methylbenzo [d][1,3]dioxol-4-yl)piperidin-1-yl)methyl)-3-methylpyridine (261 mg, 33.3% yield) as a colorless oil.

MS Calcd.: 512.1; MS Found: 513.1 $[M+H]^+$.

Step C: 6-((4-(2-(4-chlorophenyl)-2-methylbenzo[d][1,3]dioxol-4-yl)piperidin-1-yl)methyl)-5-methylnicotinonitrile A mixture of 5-bromo-2-((4-(2-(4-chlorophenyl)-2-methylbenzo[d][1,3]dioxol-4-yl)piperidin-1-yl)methyl)-3-methylpyridine (211 mg, 0.412 mmol), $Zn(CN)_2$ (141 mg, 1.24 mmol), $Pd(PPh3)_4$ (48 mg, 0.0412 mmol) in DMF (3 mL) was stirred at 160° C. for 2 hours in MW under $N_2$. After the reaction was completed, the reaction was quenched with water (10 mL) and extracted with ethyl acetate (30 mL×3). The organic layer was combined and washed with brine (10 mL), dried over sodium sulfate, filtered and concentrated in vacuum. The residue was purified by column chromatography on silica gel (DCM/MeOH=10/1) to give 6-((4-(2-(4-chlorophenyl)-2-methylbenzo[d][1,3]dioxol-4-yl)piperidin-1-yl)methyl)-5-methylnicotinonitrile (60 mg, 31.7% yield) as colorless oil.

MS Calcd.: 459.2; MS Found: 460.2 $[M+H]^+$.

Step D: 6-((4-(2-(4-chlorophenyl)-2-methylbenzo[d][1,3]dioxol-4-yl)piperidin-1-yl)methyl)-N'-hydroxy-5-methylnicotinimidamide To a solution of 6-((4-(2-(4-chlorophenyl)-2-methylbenzo [d][1,3]dioxol-4-yl)piperidin-1-yl)methyl)-5-methylnicotinonitrile (40 mg, 0.09 mmol) in EtOH (5 mL) was added $NH_2OH·HCl$ (7 mg, 0.10 mmol) and TEA (26 mg, 0.26 mmol) at room temperature. The mixture was stirred at 90° C. for 16 hours. After the reaction was completed, the reaction was quenched with water (10 mL) and extracted with ethyl acetate (20 mL×3). The organic layer was combined and washed with brine (10 mL×5), dried over sodium sulfate, filtered and concentrated in vacuum. The residue was purified by column chromatography on silica gel (MeOH/DCM=10/1) to give the 6-((4-(2-(4-chlorophenyl)-2-methylbenzo [d][1,3]dioxol-4-yl)piperidin-1-yl)methyl)-N'-hydroxy-5-methylnicotinimidamide (40 mg, 93.3% yield) as a colorless oil.

MS Calcd.: 492.2; MS Found: 493.2 $[M+H]^+$.

Step E: 3-(6-((4-(2-(4-chlorophenyl)-2-methylbenzo[d][1,3]dioxol-4-yl)piperidin-1-yl)methyl)-5-methylpyridin-3-yl)-5-(trifluoromethyl)-1,2,4-oxadiazole To a solution of 6-((4-(2-(4-chlorophenyl)-2-methylbenzo [d][1,3]dioxol-4-yl)piperidin-1-yl)methyl)-N'-hydroxy-5-methylnicotinimidamide (40 mg, 0.0813 mmol) in THF (2 mL) was added TFAA (0.05 mL) at room temperature. The reaction was stirred at room temperature for 20 min. After the reaction was completed, the reaction was concentrated in vacuum to give 3-(6-((4-(2-(4-chlorophenyl)-2-methylbenzo [d][1,3]dioxol-4-yl)piperidin-1-yl)methyl)-5-methylpyridin-3-yl)-5-(trifluoromethyl)-1,2,4-oxadiazole (crude, 46 mg) as a white solid.

MS Calcd.: 570.2; MS Found: 571.1 $[M+H]^+$.

Step F: 2-({4-[2-(4-chlorophenyl)-2-methyl-2H-1,3-benzodioxol-4-yl]piperidin-1-yl}methyl)-3-methyl-5-[5-(trifluoromethyl)-4H-1,2,4-triazol-3-yl]pyridine (Compound 265))

To a solution of 3-(6-((4-(2-(4-chlorophenyl)-2-methylbenzo[d][1,3]dioxol-4-yl)piperidin-1-yl)methyl)-5-methylpyridin-3-yl)-5-(trifluoromethyl)-1,2,4-oxadiazole (crude, 46 mg, 0.08 mmol) in DMF (1 mL) was added $N_2H_4·H_2O$ (8 mg, 0.16 mmol) at room temperature. The reaction was stirred at room temperature for 2 hours. After the reaction was completed, the reaction was purified by Prep-HPLC to give 2-({4-[2-(4-chlorophenyl)-2-methyl-2H-1,3-benzodioxol-4-yl]piperidin-1-yl}methyl)-3-methyl-5-[5-(trifluoromethyl)-4H-1,2,4-triazol-3-yl]pyridine (2 mg, 4.4% yield) as a white solid.

MS Calcd.: 569.2; MS Found: 570.7 $[M+H]^+$.

$^1H$ NMR (400 MHz, DMSO-$d_6$): δ 8.95 (s, 1H), 8.17 (s, 1H), 7.59 (d, J=7.6 Hz, 2H), 7.49 (d, J=7.6 Hz, 2H), 6.69-6.84 (m, 3H), 3.78 (s, 2H), 2.93-3.05 (m, 2H), 2.60-2.75 (m, 1H), 2.48 (s, 3H), 2.25-2.40 (m, 2H), 1.97 (s, 3H), 1.66-1.82 (m, 4H).

$^{19}F$-NMR (377 MHz): −62.56.

Example 74
2-{[2-({4-[2-(4-chloro-2-fluorophenyl)-2-methyl-2H-1,3-benzodioxol-4-yl]piperidin-1-yl}methyl)-5-[5-(trifluoromethyl)-4H-1,2,4-triazol-3-yl]pyridin-3-yl]methyl}-1λ[6]-thiolane-1,1-dione (Compound 266)
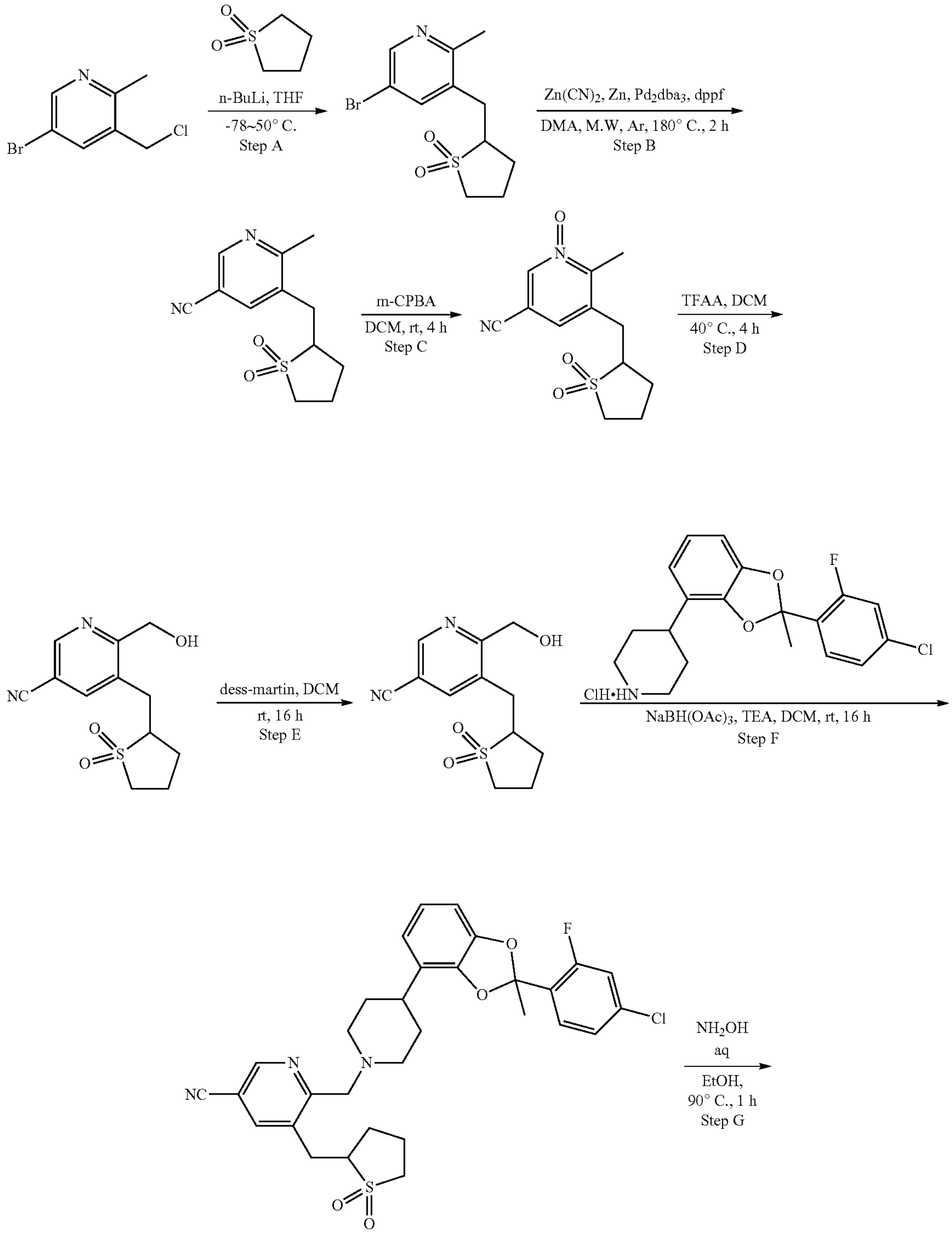

-continued

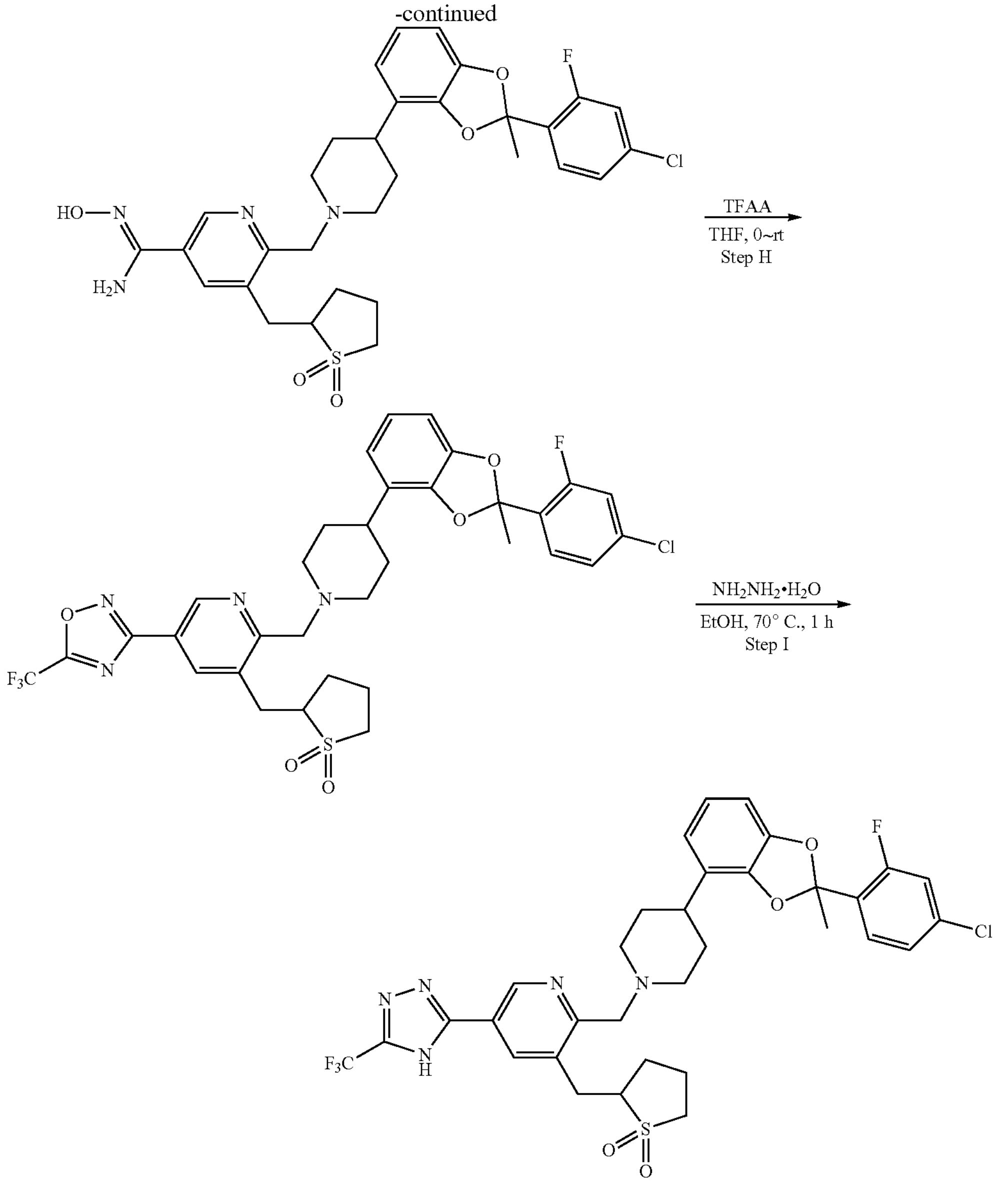

Compound 266

Step A: 2-((5-bromo-2-methylpyridin-3-yl)methyl) tetrahydrothiophene 1,1-dioxide To a solution of tetrahydrothiophene 1,1-dioxide (1.1 g, 9.13 mmol) in THF (12 mL) was added dropwise n-BuLi (3.6 mL, 9.13 mmol) at −78° C. under Ar. The mixture was stirred at −78° C. for 15 min. 5-bromo-3-(chloromethyl)-2-methylpyridine (400 mg, 1.83 mmol) in THF (15 mL) was added dropwisely and stirred at −50° C. for 1 h. The mixture was poured into water (12 mL) and filtered. The filtrate was purified by flash column chromatography (reversed phase) to obtain 2-((5-bromo-2-methylpyridin-3-yl)methyl)tetrahydrothiophene 1,1-dioxide (230 mg, yield: 41.6%) as yellow oil.

MS Calcd: 303.0; MS Found: 304.1 $[M+H]^+$.

Step B: 5-(1,1-dioxidotetrahydrothiophen-2-yl) methyl)-6-methylnicotinonitrile

A mixture of 2-((5-bromo-2-methylpyridin-3-yl)methyl) tetrahydrothiophene 1,1-dioxide (230 mg, 0.76 mmol), $Zn(CN)_2$ (444 mg, 3.79 mmol), Zn (12 mg, 0.19 mmol), $Pd_2(dba)_3$ (28 mg, 0.03 mmol) and dppf (33 mg, 0.06 mmol) in DMA (2 mL) was stirred at 180° C. under Ar with M.W for 2 h. The mixture was filtered and the filtrate was purified by flash column chromatography (reversed phase) to obtain 5-((1,1-dioxidotetrahydrothiophen-2-yl)methyl)-6-methylnicotinonitrile (125 mg, yield: 65.8%) as yellow solid.

MS Calcd: 250.1; MS Found: 251.1 $[M+H]^+$.

Step C: 5-cyano-3-((1,1-dioxidotetrahydrothiophen-2-yl)methyl)-2-methylpyridine 1-oxide To a solution of 5-((1,1-dioxidotetrahydrothiophen-2-yl) methyl)-6-methylnicotinonitrile (25 mg, 0.1 mmol) in DCM (5 mL) was added m-CPBA (104 mg, 0.6 mmol) at 0° C. The mixture was stirred at rt for 4 h. The mixture was filtered and the filtrate was purified by flash column chromatography (reversed phase) to obtain 5-cyano-3-((1,1-dioxidotetrahydrothiophen-2-yl)methyl)-2-methylpyridine 1-oxide (15 mg, yield: 56.4%) as white solid.

MS Calcd: 266.1; MS Found: 267.1 $[M+H]^+$.

Step D: 5-((1,1-dioxidotetrahydrothiophen-2-yl) methyl)-6-(hydroxymethyl)nicotinonitrile To a solution of 5-cyano-3-((1,1-dioxidotetrahydrothiophen-2-yl)methyl)-2-methylpyridine 1-oxide (45 mg, 0.17 mmol) in DCM (5 mL) was added TFAA (20 drops) dropwisely at 0° C. The mixture was stirred at 40° C. for 4 h. The mixture was poured into water (30 mL) and extracted with DCM (2×30 mL), the combined organic layer was washed with brine, dried over sodium sulfate, filtered and the residue was concentrated to obtain 5-((1,1-dioxidotetrahydrothiophen-2-yl)methyl)-6-(hydroxymethyl)nicotinonitrile (50 mg, crude) as yellow oil.

MS Calcd: 266.1; MS Found: 267.0 $[M+H]^+$.

Step E: 5-(1,1-dioxidotetrahydrothiophen-2-yl) methyl)-6-formylnicotinonitrile

A mixture of 5-((1,1-dioxidotetrahydrothiophen-2-yl) methyl)-6-(hydroxymethyl)nicotinonitrile (50 mg) and Dess-Martin reagent (96 mg, 0.23 mmol) in DCM (5 mL) was stirred at rt for 16 h. The mixture was poured into sodium bicarbonate solution (30 mL) and extracted with DCM (2×30 mL), the combined organic layer was washed with brine, dried over sodium sulfate, filtered and the residue was concentrated. The residue was purified by column chromatography on silica gel to obtain 5-((1,1-dioxidotetrahydrothiophen-2-yl)methyl)-6-formylnicotinonitrile (15 mg, yield: 30%) as yellow solid.

MS Calcd: 264.1; MS Found: 265.2 $[M+H]^+$

Step F: 6-((4-(2-(4-chloro-2-fluorophenyl)-2-methylbenzo[d][1,3]dioxol-4-yl)piperidin-1-yl)methyl)-5-((1,1-dioxidotetrahydrothiophen-2-yl)methyl)nicotinonitrile A mixture of 4-(2-(4-chloro-2-fluorophenyl)-2-methylbenzo[d][1,3]dioxol-4-yl)piperidine hydrochloride (22 mg, 0.057 mmol) and TEA (17 mg, 0.17 mmol) in DCM (3 mL) was stirred at rt for 15 min. The mixture was added 5-((1,1-dioxidotetrahydrothiophen-2-yl)methyl)-6-formylnicotinonitrile (15 mg, 0.057 mmol). The mixture was added $NaBH(OAc)_3$ (48 mg, 0.23 mmol) at 0° C. and stirred at rt for 16 h. The mixture was poured into water (30 mL) and extracted with DCM (2×30 mL), the combined organic layer was washed with brine, dried over sodium sulfate, filtered and the residue was concentrated. The residue was purified by column chromatography on silica gel to obtain 6-((4-(2-(4-chloro-2-fluorophenyl)-2-methylbenzo[d][1,3]dioxol-4-yl)piperidin-1-yl)methyl)-5-((1,1-dioxidotetrahydrothiophen-2-yl)methyl)nicotinonitrile (10 mg, yield: 29.6%) as yellow solid.

MS Calcd: 595.2; MS Found: 596.2 $[M+H]^+$

Step G: 6-((4-(2-(4-chloro-2-fluorophenyl)-2-methylbenzo[d][1,3]dioxol-4-yl)piperidin-1-yl)methyl)-5-((1,1-dioxidotetrahydrothiophen-2-yl)methyl)-N'-hydroxynicotinimidamide A mixture of 6-((4-(2-(4-chloro-2-fluorophenyl)-2-methylbenzo[d][1,3]dioxol-4-yl)piperidin-1-yl)methyl)-5-((1,1-dioxidotetrahydrothiophen-2-yl)methyl)nicotinonitrile (10 mg, 0.017 mmol) and $NH_2OH$ aq (11 mg, 0.17 mmol) in EtOH (2 mL) was stirred at 90° C. for 1 h. The mixture was concentrated to obtain 6-((4-(2-(4-chloro-2-fluorophenyl)-2-methylbenzo[d][1,3]dioxol-4-yl)piperidin-1-yl)methyl)-5-((1,1-dioxidotetrahydrothiophen-2-yl)methyl)-N'-hydroxynicotinimidamide (10 mg, crude) as white solid.

MS Calcd: 628.2; MS Found: 629.2 $[M+H]^+$

Step H: 2-((2-((4-(2-(4-chloro-2-fluorophenyl)-2-methylbenzo[d][1,3]dioxol-4-yl)piperidin-1-yl) methyl)-5-(5-(trifluoromethyl)-1,2,4-oxadiazol-3-yl) pyridin-3-yl)methyl)tetrahydrothiophene 1,1-dioxide To a solution of 6-((4-(2-(4-chloro-2-fluorophenyl)-2-methylbenzo[d][1,3]dioxol-4-yl)piperidin-1-yl)methyl)-5-((1,1-dioxidotetrahydrothiophen-2-yl)methyl)-N'-hydroxynicotinimidamide (10 mg) in THF (2 mL) was added dropwise TFAA (17 mg, 0.08 mmol) at 0° C. The mixture was stirred at rt for 16 h. The mixture was purified by flash column chromatography (reversed phase) to obtain 2-((2-((4-(2-(4-chloro-2-fluorophenyl)-2-methylbenzo[d][1,3]dioxol-4-yl)piperidin-1-yl)methyl)-5-(5-(trifluoromethyl)-1,2,4-oxadiazol-3-yl)pyridin-3-yl)methyl)tetrahydrothiophene 1,1-dioxide (10 mg, yield: >99%) as white solid.

MS Calcd: 706.2; MS Found: 707.1 $[M+H]^+$

Step I: 2-{[2-({4-[2-(4-chloro-2-fluorophenyl)-2-methyl-2H-1,3-benzodioxol-4-yl]piperidin-1-yl}methyl)-5-[5-(trifluoromethyl)-4H-1,2,4-triazol-3-yl]pyridin-3-yl]methyl}-1$\lambda^6$-thiolane-1,1-dione (Compound 266)

A mixture of 2-((2-((4-(2-(4-chloro-2-fluorophenyl)-2-methylbenzo [d][1,3]dioxol-4-yl)piperidin-1-yl)methyl)-5-(5-(trifluoromethyl)-1,2,4-oxadiazol-3-yl)pyridin-3-yl) methyl)tetrahydrothiophene 1,1-dioxide (10 mg) and $NH_2NH_2 \cdot H_2O$ (1 drop) in EtOH (0.5 mL) was stirred at 70° C. for 1 h. The mixture was purified by prep-HPLC to obtain 2-{[2-({4-[2-(4-chloro-2-fluorophenyl)-2-methyl-2H-1,3-benzodioxol-4-yl]piperidin-1-yl}methyl)-5-[5-(trifluoromethyl)-4H-1,2,4-triazol-3-yl]pyridin-3-yl]methyl}-1$\lambda^6$-thiolane-1,1-dione (1.0 mg, yield: 10.0%) as white solid.

MS Calcd: 705.2; MS Found: 706.2 $[M+H]^+$ $^1$H NMR (400 MHz, MeOD) 9.04 (s, 1H), 8.37 (s, 1H), 7.65-7.56 (m, 1H), 7.28 (d, J=10.8 Hz, 1H), 7.21 (d, J=8.4 Hz, 1H), 6.82-6.68 (m, 3H), 5.36-5.32 (m, 1H), 4.57 (s, 2H), 3.63-3.50 (m, 1H), 3.50-3.45 (m, 1H), 3.20-2.95 (m, 4H), 2.90-2.70 (m, 1H), 2.40-2.15 (m, 2H), 2.12-1.80 (m, 7H), 2.05 (s, 3H), 1.65-1.55 (m, 1H).

$^{19}$F-NMR (377 MHz): −64.91, −112.21.

Example 75
2-({4-[2-(4-chloro-2-fluorophenyl)-2-methyl-2H-1,3-benzodioxol-4-yl]piperidin-1-yl}methyl)-3-(2-methanesulfonylethyl)-5-[5-(trifluoromethyl)-4H-1,2,4-triazol-3-yl]pyridine (Compound 267)
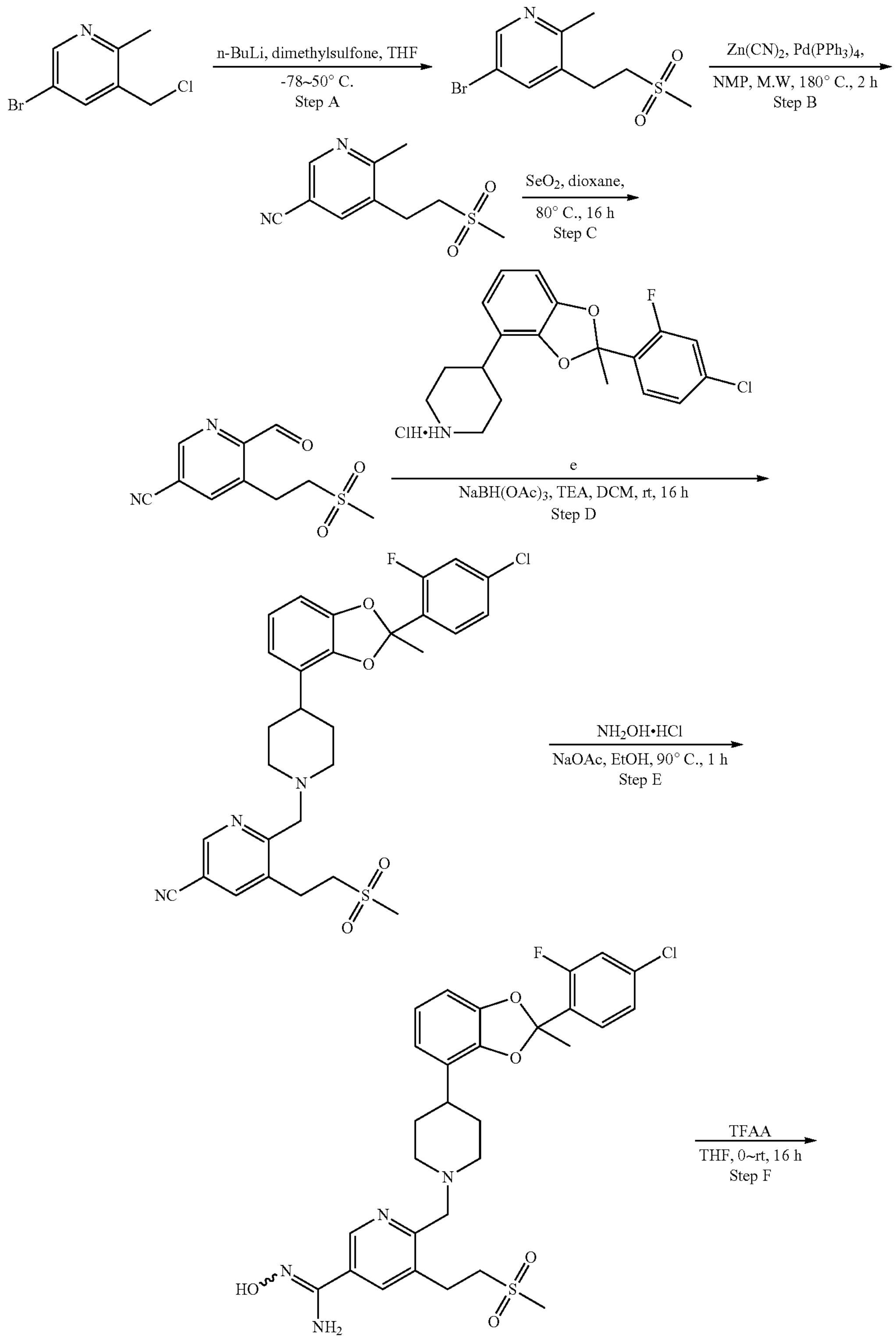

-continued

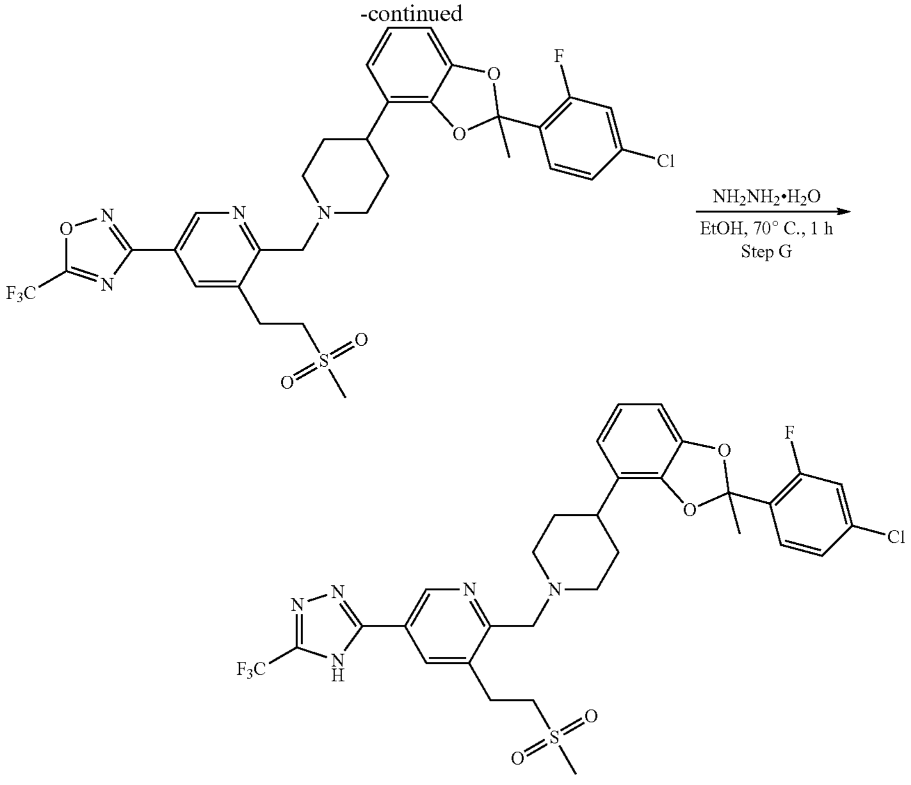

Compound 267

Step A: 5-bromo-2-methyl-3-(2-(methyl sulfonyl)ethyl)pyridine

To a solution of dimethyl sulfone (429 mg, 6.85 mmol) in THF (8 mL) was added dropwise n-BuLi (2.7 mL, 6.85 mmol) at −78° C. under Ar. The mixture was stirred at 78° C. for 15 min. 5-bromo-3-(chloromethyl)-2-methylpyridine (300 mg, 1.37 mmol) in THF (10 mL) was added dropwisely and stirred at −50° C. for 1 h. The mixture was poured into water (12 mL) and filtered. The filtrate was purified by flash column chromatography (reversed phase) to obtain 5-bromo-2-methyl-3-(2-(methylsulfonyl)ethyl)pyridine (300 mg, yield: 79.1%) as a yellow oil.

MS Calcd: 277.0; MS Found: 278.0 $[M+H]^+$.

Step B: 6-methyl-5-(2-(methylsulfonyl)ethyl)nicotinonitrile

A mixture of 5-bromo-2-methyl-3-(2-(methylsulfonyl)ethyl)pyridine (100 mg, 0.361 mmol), $Zn(CN)_2$ (127 mg, 1.083 mmol) and $Pd(PPh_3)_4$ (42 mg, 0.0361 mmol) in NMP (2 mL) was stirred at 180° C. under Ar with M.W for 2 h. The mixture was filtered and the filtrate was purified by flash column chromatography (reversed phase) to obtain 6-methyl-5-(2-(methylsulfonyl)ethyl)nicotinonitrile (50 mg, yield: 51.5%) as yellow oil.

MS Calcd: 224.1; MS Found: 225.1 $[M+H]^+$.

Step C: 6-formyl-5-(2-(methylsulfonyl)ethyl)nicotinonitrile

A mixture of 6-methyl-5-(2-(methylsulfonyl)ethyl)nicotinonitrile (170 mg, 0.76 mmol) and $SeO_2$ (253 mg, 2.28 mmol) in 1,4-dioxane (10 mL) was stirred at 80° C. for 16 h. The mixture was filtered and the filtrate was concentrated to dryness to obtain 6-formyl-5-(2-(methylsulfonyl)ethyl)nicotinonitrile (50 mg, yield: 51.5%) as yellow solid.

MS Calcd: 238.0; MS Found: 239.1 $[M+H]^+$.

Step D: 6-((4-(2-(4-chloro-2-fluorophenyl)-2-methylbenzo[d][1,3]dioxol-4-yl)piperidin-1-yl)methyl)-5-(2-(methyl sulfonyl)ethyl)nicotinonitrile A mixture of 4-(2-(4-chloro-2-fluorophenyl)-2-methylbenzo[d][1,3]dioxol-4-yl)piperidine hydrochloride (90 mg, 0.235 mmol) and TEA (190 mg, 8.0 mmol) in DCM (5 mL) was stirred at rt for 15 min. 6-formyl-5-(2-(methylsulfonyl)ethyl)nicotinonitrile (56 mg, 0.235 mmol) was added. $NaBH(OAc)_3$ (199 mg, 0.94 mmol) was added at 0° C. and the mixture was stirred at rt for 16 h. The mixture was poured into water (50 mL) and extracted with DCM (2×50 mL), the combined organic layers were washed with brine, dried over sodium sulfate, filtered and the residue was concentrated. The residue was purified by column chromatography on silica gel to obtain 6-((4-(2-(4-chloro-2-fluorophenyl)-2-methylbenzo[d][1,3]dioxol-4-yl)piperidin-1-yl)methyl)-5-(2-(methylsulfonyl)ethyl)nicotinonitrile (44 mg, yield: 32.9%) as white solid.

MS Calcd: 569.2; MS Found: 570.2 $[M+H]^+$.

Step E: 6-((4-(2-(4-chloro-2-fluorophenyl)-2-methylbenzo[d][1,3]dioxol-4-yl)piperidin-1-yl)methyl)-N'-hydroxy-5-(2-(methylsulfonyl)ethyl)nicotinimidamide A mixture of 6-((4-(2-(4-chloro-2-fluorophenyl)-2-methylbenzo[d][1,3]dioxol-4-yl)piperidin-1-yl)methyl)-5-(2-

(methylsulfonyl)ethyl)nicotinonitrile (44 mg, 0.077 mmol), $NH_2OH{\cdot}HCl$ (54 mg, 0.77 mmol) and NaOAc (76 mg, 0.924 mmol) in EtOH (5 mL) was stirred at 90° C. for 1 h. The mixture was poured into water (30 mL) and extracted with DCM (2×30 mL), the combined organic layer was washed with brine, dried over sodium sulfate, filtered and the residue was concentrated to obtain 6-((4-(2-(4-chloro-2-fluorophenyl)-2-methylbenzo[d][1,3]dioxol-4-yl)piperidin-1-yl)methyl)-N'-hydroxy-5-(2-(methylsulfonyl)ethyl)nicotinimidamide (25 mg, yield: 53.8%) as white solid.

MS Calcd: 602.2; MS Found: 603.2 $[M+H]^+$.

Step F: 3-(6-((4-(2-(4-chloro-2-fluorophenyl)-2-methylbenzo[d][1,3]dioxol-4-yl)piperidin-1-yl)methyl)-5-(2-(methylsulfonyl)ethyl)pyridin-3-yl)-5-(trifluoromethyl)-1,2,4-oxadiazole To a solution of 6-((4-(2-(4-chloro-2-fluorophenyl)-2-methylbenzo[d][1,3]dioxol-4-yl)piperidin-1-yl)methyl)-N'-hydroxy-5-(2-(methylsulfonyl)ethyl)nicotinimidamide (25 mg) in THF (2 mL) was added dropwise TFAA (44 mg, 0.208 mmol) at 0° C. The mixture was stirred at rt for 16 h. The mixture was purified by prep-HPLC to obtain 3-(6-((4-(2-(4-chloro-2-fluorophenyl)-2-methylbenzo[d][1,3]dioxol-4-yl)piperidin-1-yl)methyl)-5-(2-(methylsulfonyl)ethyl)pyridin-3-yl)-5-(trifluoromethyl)-1,2,4-oxadiazole (20 mg, yield: 70.9%) as white solid.

MS Calcd: 680.2; MS Found: 681.2 $[M+H]^+$

Step G: 2-({4-[2-(4-chloro-2-fluorophenyl)-2-methyl-2H-1,3-benzodioxol-4-yl]piperidin-1-yl}methyl)-3-(2-methanesulfonylethyl)-5-[5-(trifluoromethyl)-4H-1,2,4-triazol-3-yl]pyridine (Compound 267)

A mixture of 3-(6-((4-(2-(4-chloro-2-fluorophenyl)-2-methylbenzo[d][1,3]dioxol-4-yl)piperidin-1-yl)methyl)-5-(2-(methylsulfonyl)ethyl)pyridin-3-yl)-5-(trifluoromethyl)-1,2,4-oxadiazole (20 mg, 0.029 mmol) and $NH_2NH_2{\cdot}H_2O$ (0.2 mL) in EtOH (0.5 mL) was stirred at 70° C. for 1 h. The mixture was purified by prep-HPLC (0.1% of $NH_4HCO_3$ aq in $CH_3CN$) to obtain 2-({4-[2-(4-chloro-2-fluorophenyl)-2-methyl-2H-1,3-benzodioxol-4-yl]piperidin-1-yl}methyl)-3-(2-methanesulfonylethyl)-5-[5-(trifluoromethyl)-4H-1,2,4-triazol-3-yl]pyridine (4.1 mg, yield: 20.5%) as white solid.

MS Calcd: 679.2; MS Found: 680.2 $[M+H]^+$ $^1H$ NMR (400 MHz, MeOD) 8.98 (s, 1H), 8.26 (s, 1H), 7.50 (t, J=8.4 Hz, 1H), 7.18 (dd, J=2.0 Hz, J=12.0 Hz, 1H), 7.12 (dd, J=2.0 Hz, J=8.0 Hz, 1H), 6.73-6.60 (m, 3H), 4.08 (s, 2H), 3.60-3.54 (m, 2H), 3.28-3.20 (m, 4H), 2.95 (s, 3H), 2.85-2.70 (m, 1H), 2.70-2.54 (m, 2H), 2.06-1.88 (m, 2H), 1.94 (s, 3H), 1.87-1.75 (m, 2H).

$^{19}F$-NMR (377 MHz): −65.15, −112.25.

Example 76

3-[6-({4-[2-(4-chloro-2-fluorophenyl)-2-methyl-2H-1,3-benzodioxol-4-yl]piperidin-1-yl}methyl)-5-(2-methoxyethyl)pyridin-3-yl]-4,5-dihydro-1,2,4-oxadiazol-5-one (Compound 268)

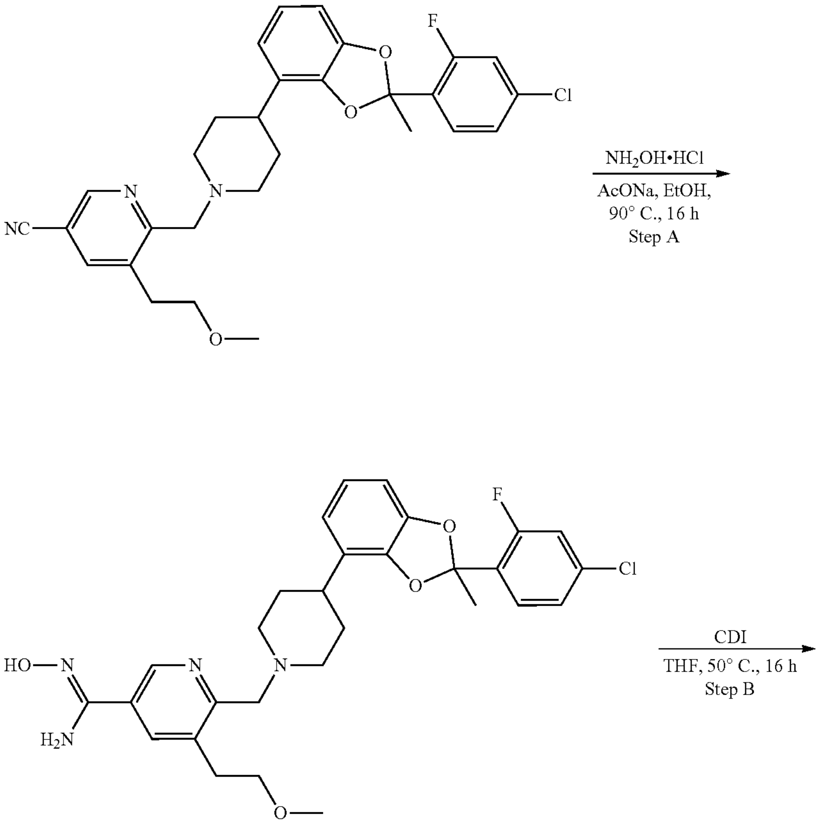

-continued

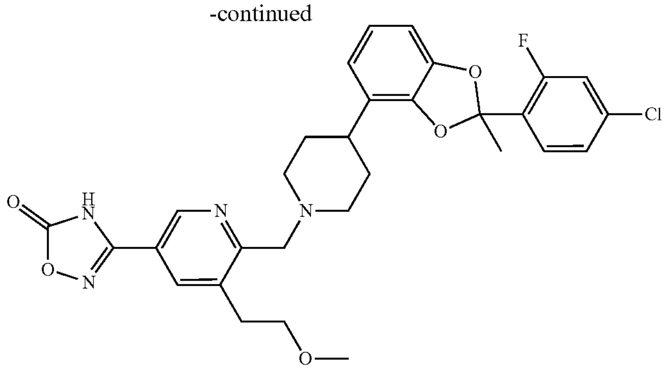

Compound 268

Step A: 6-((4-(2-(4-chloro-2-fluorophenyl)-2-methylbenzo[d][1,3]dioxol-4-yl)piperidin-1-yl)methyl)-N'-hydroxy-5-(2-methoxyethyl)nicotinimidamide A mixture of 6-((4-(2-(4-chloro-2-fluorophenyl)-2-methylbenzo[d][1,3]dioxol-4-yl)piperidin-1-yl)methyl)-5-(2-methoxyethyl)nicotinonitrile (28 mg, 0.054 mmol), hydroxylamine hydrochloride (37 mg, 0.54 mmol) and NaOAc (53 mg, 0.65 mmol) in EtOH (4 mL) was stirred at 90° C. under Ar for 16 hours. After the reaction was completed, the reaction was filtered, the filtrate was concentrated, purified by prep-TLC (DCM/MeOH=10/1) to give 6-((4-(2-(4-chloro-2-fluorophenyl)-2-methylbenzo[d][1,3]dioxol-4-yl)piperidin-1-yl)methyl)-N'-hydroxy-5-(2-methoxyethyl)nicotinimidamide (17 mg, 56.8% yield) as a yellow oil.

MS Calcd.: 554.2; MS Found: 555.3 $[M+H]^+$.

Step B: 3-[6-({4-[2-(4-chloro-2-fluorophenyl)-2-methyl-2H-1,3-benzodioxol-4-yl]piperidin-1-yl}methyl)-5-(2-methoxyethyl)pyridin-3-yl]-4,5-dihydro-1,2,4-oxadiazol-5-one (Compound 268)

To a solution of 6-((4-(2-(4-chloro-2-fluorophenyl)-2-methylbenzo[d][1,3]dioxol-4-yl)piperidin-1-yl)methyl)-N'-hydroxy-5-(2-methoxyethyl)nicotinimidamide (17 mg, 0.031 mmol) in THF (3 mL) was added CDI (25 mg, 0.153 mmol). The reaction was stirred at 50° C. for 16 hours. After the reaction was completed, the reaction was filtered, the filtrate was purified by prep-HPLC (0.1% $NH_4HCO_3$) to give 3-[6-({4-[2-(4-chloro-2-fluorophenyl)-2-methyl-2H-1,3-benzodioxol-4-yl]piperidin-1-yl}methyl)-5-(2-methoxyethyl)pyridin-3-yl]-4,5-dihydro-1,2,4-oxadiazol-5-one (2.94 mg, 16.3% yield) as a white solid.

MS Calcd.: 580.2; MS Found: 581.3 $[M+H]^+$.

$^1$H-NMR (400 MHz, MeOD) δ 8.92 (s, 1H), 8.15 (s, 1H), 7.61 (t, J=8.4 Hz, 1H), 7.30 (d, J=10.8 Hz, 1H), 7.22 (d, J=8.0 Hz, 1H), 6.85-6.80 (m, 1H), 6.80-6.72 (m, 2H), 4.46 (s, 2H), 3.70 (t, J=6.0 Hz, 2H), 3.60-3.48 (m, 2H), 3.33 (s, 3H), 3.20-2.95 (m, 5H), 2.30-2.10 (m, 2H), 2.10-1.98 (m, 5H).

$^{19}$F-NMR (377 MHz): −112.24.

Example 77

2-({4-[(2 S)-2-(4-chloro-2-fluorophenyl)-2-methyl-2H-1,3-benzodioxol-4-yl]piperidin-1-yl}methyl)-3-(oxolan-3-yl)-5-[5-(trifluoromethyl)-4H-1,2,4-triazol-3-yl]pyridine (Compound 282)

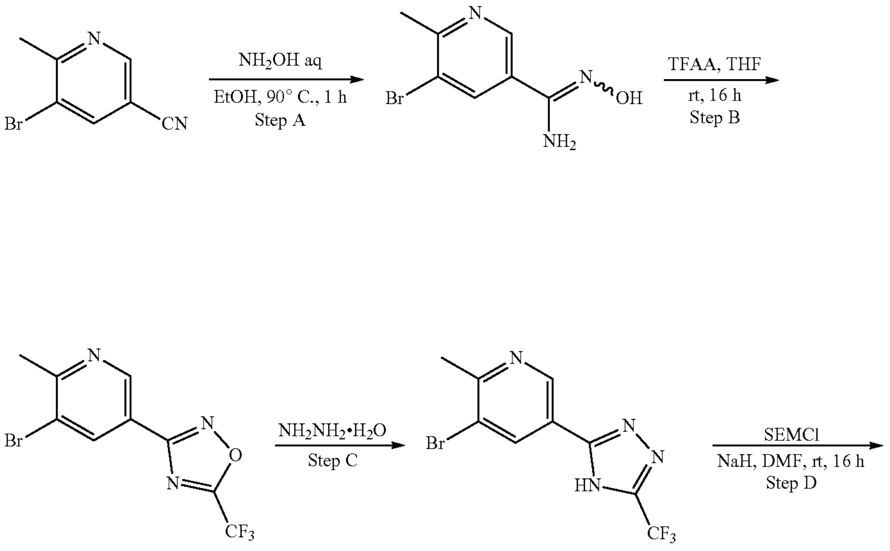

-continued

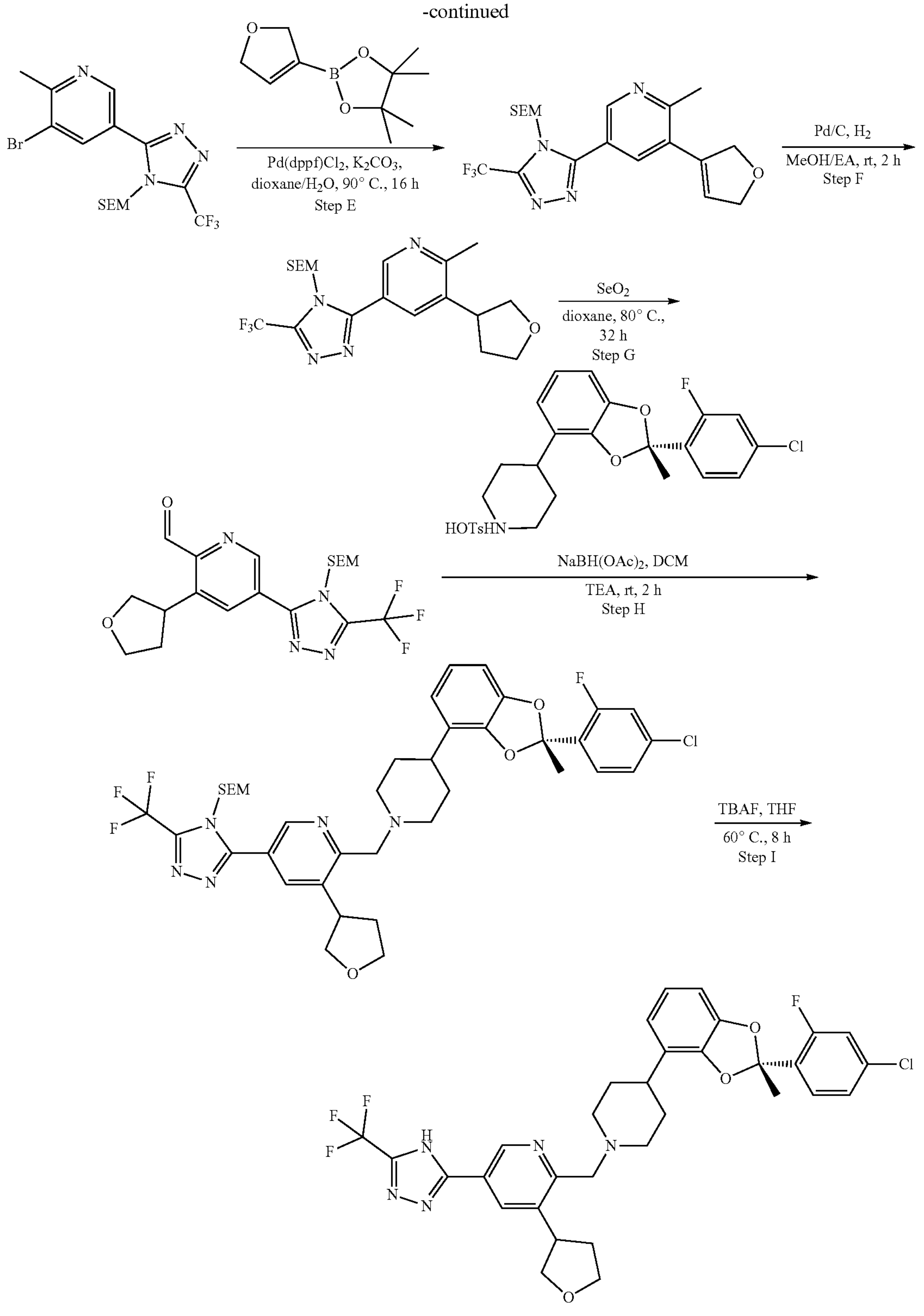

Compound 282

Step A:
5-bromo-N'-hydroxy-6-methylnicotinimidamide

To a solution of 5-bromo-6-methylnicotinonitrile (310 mg, 1.58 mmol) in EtOH (10 mL) was added $NH_2OH$ (1.05 g, 15.8 mmol), the mixture was stirred at 90° C. for 1 h. The solvent and excess $NH_2OH$ were removed under reduced pressure to furnish 5-bromo-N'-hydroxy-6-methylnicotinimidamide (360 mg, yield: 99.40%) as a yellow solid.

MS Calcd.: 229.0; MS Found: 230.0 $[M+H]^+$.

Step B: 3-(2,5-dihydrofuran-3-yl)-2-methyl trifluoromethyl)-4-((2-(trimethylsilyl) ethoxy)methyl)-4H-1,2,4-triazol-3-yl)pyridine To a solution of bromo-N'-hydroxy-6-methylnicotinimidamide (360 mg) in THF (10 mL) was added TFAA (1.70 g, 7.85 mmol) at 0° C. After 10 mins, the mixture was warmed to rt and stirred for 16 hours. The solvent was removed under reduced pressure, the residue was dissolved with EA, washed with $NaHCO_3$ aq and NaCl aq, dried over $Na_2SO_4$, and concentrated to furnish 3-(5-bromo-6-methylpyridin-3-yl)-5-(trifluoromethyl)-1,2,4-oxadiazole (425 mg, crude) as a yellow solid.

MS Calcd.: 307.0; MS Found: 308.0 [M+H]+

Step C: 3-bromo-2-methyl-5-(5-(trifluoromethyl)-4H-1,2,4-triazol-3-yl)pyridine

To a solution of 3-(5-bromo-6-methylpyridin-3-yl)-5-(trifluoromethyl)-1,2,4-oxadiazole (425 mg) in EtOH (10 mL) was added $NH_2NH_2{\cdot}H_2O$ (5.0 mL), the mixture was stirred at 70° C. for 1 h. The mixture was concentrated and to furnish 3-bromo-2-methyl-5-(5-(trifluoromethyl)-4H-1,2,4-triazol-3-yl)pyridine (372 mg) as a yellow solid.

MS Calcd.: 306.0; MS Found: 306.9 [M+H]+

Step D: 3-bromo-2-methyl trifluoromethyl)-4-((2-(trimethylsilyl)ethoxy)methyl)-4H-1,2,4-triazol-3-yl) pyridine To a solution of 3-bromo-2-methyl-5-(5-(trifluoromethyl)-4H-1,2,4-triazol-3-yl)pyridine (342 mg) in DMF (7 mL) was added NaH (89 mg, 60% w/w, 2.23 mmol) in portions at 0° C. under Ar. After 1 hour, SEMCl (221 mg, 1.33 mmol) was dropwise added at 0° C., the mixture was warmed tort and stirred under Ar for 16 hrs. the mixture was diluted with EA, washed with aq $NaHCO_3$ and brine, dried over anhydrous $Na_2SO_4$, concentrated under vacuum, purified by silica gel chromatography to furnish 3-bromo-2-methyl-5-(5-(trifluoromethyl)-4-((2-(trimethylsilyl)ethoxy)methyl)-4H-1,2,4-triazol-3-yl)pyridine (125 mg, yield 25.7%) as a yellow oil.

MS Calcd.: 436.0; MS Found: 437.1 $[M+H]^+$.

Several regio-isomers maybe exist. We choose A-1 as a representative structure.

A-1

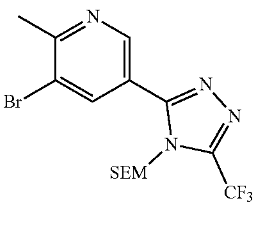

A-2

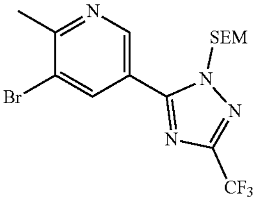

-continued

A-2

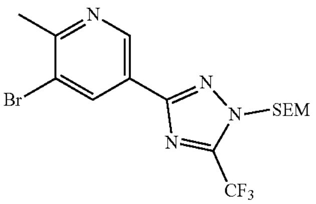

Similar cases also observed in other examples.

Step E: 3-(2,5-dihydrofuran-3-yl)-2-methyl-5-(5-(trifluoromethyl)-4-((2-(trimethylsilyl)ethoxy)methyl)-4H-1,2,4-triazol-3-yl)pyridine A mixture of 3-bromo-2-methyl-5-(5-(trifluoromethyl)-4-((2-(trimethylsilyl)ethoxy)methyl)-4H-1,2,4-triazol-3-yl) pyridine (30 mg, 0.068 mmol) and 2-(2,5-dihydrofuran-3-yl)-4,4,5,5-tetramethyl-1,3,2-dioxaborolane (16.1 mg, 0.082 mmol), $Pd(dppf)Cl_2$ (5 mg, 0.0068 mmol) and $K_2CO_3$ (28 mg, 0.204 mmol) in dioxane/$H_2O$ (1 mL/0.2 mL) was stirred at 90° C. under Ar for 16 hours. Upon cooled down to room temperature, the mixture was concentrated under vacuum, diluted with DCM, and purified by Prep-TLC (PE/EA=4/1) to furnish 3-(2,5-dihydrofuran-3-yl)-2-methyl-5-(5-(trifluoromethyl)-4-((2-(trimethylsilyl)ethoxy)methyl)-4H-1,2,4-triazol-3-yl)pyridine (30 mg, yield>99.9%) as a yellow oil.

MS Calcd.: 426.2; MS Found: 427.2 $[M+H]^+$.

Step F: 2-methyl-3-(tetrahydrofuran-3-yl)-5-(trifluoromethyl)-4-((2-(trimethylsilyl)ethoxy)methyl)-4H-1,2,4-triazol-3-yl)pyridine To a solution of 3-(2,5-dihydrofuran-3-yl)-2-methyl-5-(5-(trifluoromethyl)-4-((2-(trimethylsilyl)ethoxy)methyl)-4H-1,2,4-triazol-3-yl)pyridine (30 mg, 0.07 mmol) in McOH/EA (4 mL/4 mL) was added Pd/C (15 mg, 10% w/w), the mixture was stirred at rt under $H_2$ for 2 hours. The mixture was filtered, the filtrate was concentrated to furnish 2-methyl-3-(tetrahydrofuran-3-yl)-5-(5-(trifluoromethyl)-4-((2-(trimethylsilyl)ethoxy)methyl)-4H-1,2,4-triazol-3-yl) pyridine (29 mg, crude) as a yellow oil.

MS Calcd.: 428.2; MS Found: 429.2 $[M+H]^+$.

Step G: 3-(tetrahydrofuran-3-yl)-5-(5-trifluoromethyl)-4-((2-(trimethylsilyl)ethoxy)methyl)-4H-1,2,4-triazol-3-yl)picolinaldehyde To a solution of 2-methyl-3-(tetrahydrofuran-3-yl)-5-(5-(trifluoromethyl)-4-((2-(trimethylsilyl)ethoxy)methyl)-4H-1,2,4-triazol-3-yl)pyridine (29 mg) in dioxane (6 mL) was added $SeO_2$ (75.5 mg, 0.68 mmol), the mixture was stirred at 80° C. for 32 hours. The mixture was diluted with EA, washed with $H_2O$ and brine, dried over $Na_2SO_4$, concentrated to furnish 3-(tetrahydrofuran-3-yl)-5-(5-(trifluoromethyl)-4-((2-(trimethylsilyl)ethoxy)methyl)-4H-1,2,4-triazol-3-yl)picolinaldehyde (29 mg, crude) as a yellow oil.

MS Calcd.: 442.2; MS Found: 443.2 $[M+H]^+$.

Step H: 2-((4-((S)-2-(4-chloro-2-fluorophenyl)-2-methylbenzo[d][1,3]dioxol-4-yl)piperidin-1-yl) methyl)-3-(tetrahydrofuran-3-yl)-5-(5trifluoromethyl)-4-((2-(trimethylsilyl)ethoxy)methyl)-4H-1,2,4-triazol-3-yl)pyridine A mixture of (S)-4-(2-(4-chloro-2-fluorophenyl)-2-methylbenzo[d][1,3]dioxol-4-yl)piperidine 4-methylbenzenesulfonate (35 mg, 0.068 mmol) and TEA (34 mg, 0.34 mmol) in DCM (3 mL) was stirred at rt for 10 min. 3-(tetrahydrofuran-3-yl)-5-(5-(trifluoromethyl)-4-((2-(trimethylsilyl)ethoxy)methyl)-4H-1,2,4-triazol-3-yl)picolinaldehyde (30 mg, 0.068 mmol) in DCM (3 mL) was added, $NaBH(OAc)_3$ (58 mg, 0.27 mmol) was added, the mixture was stirred at rt for 2 hrs. The reaction was diluted with DCM, washed with $H_2O$ and brine, dried over sodium sulfate, concentrated in vacuum, purified by prep-TLC (PE/EA=2/1) to give 2-((4-((S)-2-(4-chloro-2-fluorophenyl)-2-methylbenzo [d][1,3]dioxol-4-yl)piperidin-1-yl)methyl)-3-(tetrahydrofuran-3-yl)-5-(5-(trifluoromethyl)-4-((2-(trimethylsilyl)ethoxy)methyl)-4H-1,2,4-triazol-3-yl) pyridine (12 mg, yield: 22.8%) as yellow oil.

MS Calcd.: 773.3; MS Found: 774.3 $[M+H]^+$.

Step I: 2-({4-[(2S)-2-(4-chloro-2-fluorophenyl)-2-methyl-2H-1,3-benzodioxol-4-yl]piperidin-1-yl}methyl)-3-(oxolan-3-yl)-5-[5-(trifluoromethyl)-4H-1,2,4-triazol-3-yl]pyridine (Compound 282)

To a solution of 2-((4-((S)-2-(4-chloro-2-fluorophenyl)-2-methylbenzo [d][1,3]dioxol-4-yl)piperidin-1-yl)methyl)-3-(tetrahydrofuran-3-yl)-5-(5-(trifluoromethyl)-4-((2-(trimethylsilyl)ethoxy)methyl)-4H-1,2,4-triazol-3-yl)pyridine (12 mg, 0.016 mmol) in THF (3 mL) was dropwise added TBAF (1.0 M, 2 mL), the mixture was stirred at 60° C. for 8 hrs. The mixture was diluted with EA, washed with $H_2O$ and brine, dried over $Na_2SO_4$, concentrated, purified by prep-HPLC (0.1% TFA) to give 2-({4-[(2S)-2-(4-chloro-2-fluorophenyl)-2-methyl-2H-1,3-benzodioxol-4-yl]piperidin-1-yl}methyl)-3-(oxolan-3-yl)-5-[5-(trifluoromethyl)-4H-1,2,4-triazol-3-yl]pyridine (4.69 mg, yield 44.6%) as a white solid.

MS Calcd.: 643.2; MS Found: 644.2 $[M+H]^+$.

$^1$H NMR (400 MHz, MeOD): δ 9.19 (s, 1H), 8.46 (s, 1H), 7.63 (t, J=8.4 Hz, 1H), 7.30 (d, J=10.8 Hz, 1H), 7.23 (d, J=8.8 Hz, 1H), 6.90-6.77 (m, 3H), 4.20-4.12 (m, 2H), 4.01-3.86 (m, 2H), 3.86-3.74 (m, 2H), 3.72-3.62 (m, 1H), 3.44-3.30 (m, 1H), 3.30-3.18 (m, 2H), 3.18-3.06 (m, 1H), 2.60-2.49 (m, 1H), 2.40-2.22 (m, 2H), 2.21-1.98 (m, 7H).

$^{19}$F-NMR (377 MHz): −66.70, −112.20

Example 78

2-({4-[(2 S)-2-(4-chloro-2-fluorophenyl)-2-methyl-2H-1,3-benzodioxol-4-yl]piperidin-1-yl}methyl)-3-(2-ethoxyethyl)-5-[5-(trifluoromethyl)-4H-1,2,4-triazol-3-yl]pyridine (Compound 287)

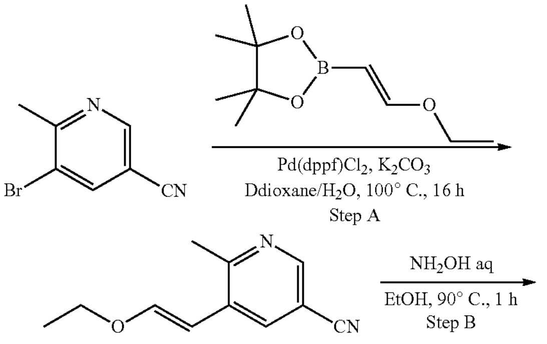

-continued

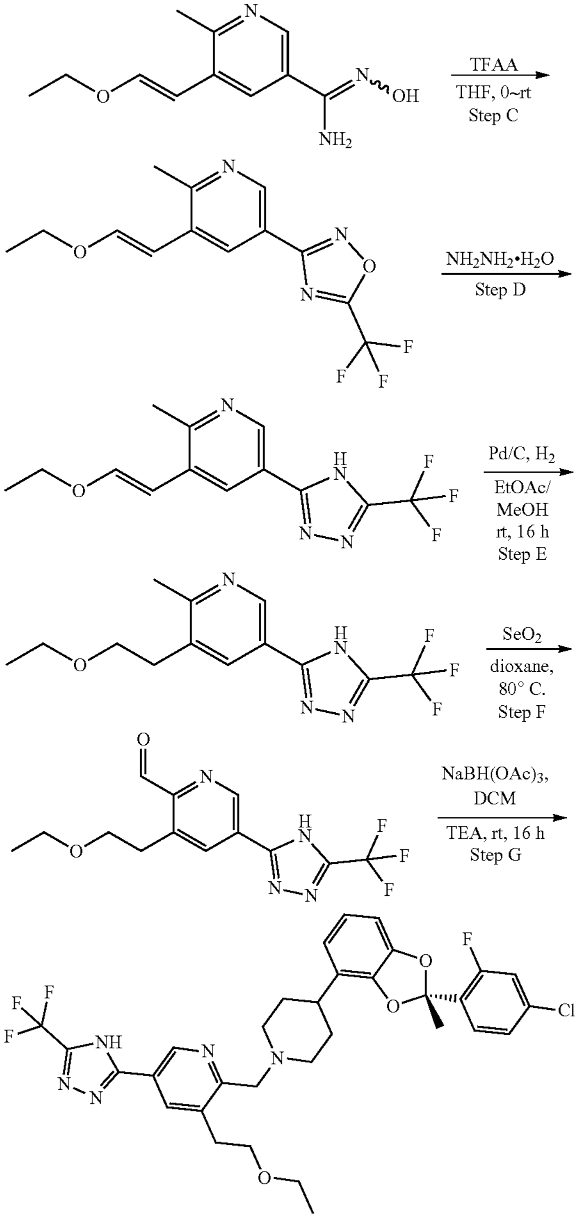

Compound 287

Step A: (E)-5-(2-ethoxyvinyl)-6-methylnicotinonitrile

A mixture of 5-bromo-6-methylnicotinonitrile (500 mg, 2.55 mmol) in dioxane/$H_2O$ (20 mL/5 mL), was added $K_2CO_3$ (1.4 g, 10.2 mmol), (E)-2-(2-ethoxyvinyl)-4,4,5,5-tetramethyl-1,3,2-dioxaborolane (1.22 g, 6.20 mmol) and $Pd(dppf)Cl_2$ (187 mg, 0.255 mmol) under $N_2$. The mixture was stirred at 100° C. for 16 h. The water and EtOAc were added to the mixture, the organic phase was washed by brine, dried with $Na_2SO_4$, The residue was purified by chromatography on silica gel to provide the product as a yellow solid (450 mg, yield: 93.9%).

MS Calcd: 188.1; MS Found: 189.2 $[M+H]^+$.

Step B: 5-((E)-2-ethoxyvinyl)-N'-hydroxy-6-methylnicotinimidamide

A mixture of (E)-5-(2-ethoxyvinyl)-6-methylnicotinonitrile (150 mg, 0.80 mmol), $NH_2OH$ aq (528 mg, 8.0 mmol) in EtOH (6 mL) was stirred at 90° C. for 1 hour. The mixture was concentrated to dryness to provide crude product (177 mg) as a yellow solid.

MS Calcd: 221.1; MS Found: 222.2 $[M+H]^+$.

Step C: (E)-3-(5-(2-ethoxyvinyl)-6-methylpyridin-3-yl)-5-(trifluoromethyl)-1,2,4-oxadiazole A mixture of 5-((E)-2-ethoxyvinyl)-N'-hydroxy-6-methylnicotinimidamide (177 mg) in THF (5 mL) at 0° C.; was added TFAA (840 mg, 4.0 mmol). Then, the mixture was stirred at 0° C. for 10 min. The mixture was warmed to room temperature and stirred for 16 hrs. The $NaHCO_3$ aq and EtOAc were added to the mixture, the organic phase was washed by brine, dried with $Na_2SO_4$. The solvent was concentrated to dryness to obtain (E)-3-(5-(2-ethoxyvinyl)-6-methylpyridin-3-yl)-5-(trifluoromethyl)-1,2,4-oxadiazole (183 mg, yield: 61.2%) as a yellow oil.

MS Calcd: 299.1; MS Found: 300.1 $[M+H]^+$.

Step D: (E)-3-(2-ethoxyvinyl)-2-methyl trifluoromethyl)-4H-1,2,4-triazol-3-yl)pyridine-2,2,2-trifluoroacetic acid A mixture of (E)-3-(5-(2-ethoxyvinyl)-6-methylpyridin-3-yl)-5-(trifluoromethyl)-1,2,4-oxadiazole (153 mg), $NH_2NH_2 \cdot H_2O$ (1.5 mL) in EtOH (10 mL) was stirred at 70° C.; for 1 h. The mixture was purified by flash chromatography (0.1% of TFA in $CH_3CN$) to obtain (E)-3-(2-ethoxyvinyl)-2-methyl-5-(5-(trifluoromethyl)-4H-1,2,4-triazol-3-yl) pyridine (210 mg) as a yellow oil.

MS Calcd: 298.1; MS Found: 299.1 $[M+H]^+$.

Step E: 3-(2-ethoxyethyl)-2-methyl-5-(5-(trifluoromethyl)-4H-1,2,4-triazol-3-1)pyridine A mixture of (E)-3-(2-ethoxyvinyl)-2-methyl-5-(5-(trifluoromethyl)-4H-1,2,4-triazol-3-yl)pyridine (110 mg, 0.27 mmol) in EtOAc/MeOH (12 mL/1 mL) was added Pd/C (30 mg, 0.027 mmol) under $H_2$ balloons for stirring at rt for 16 hours. The mixture was purified by flash chromatography (0.1% of $NH_3 \cdot H_2O$ in $CH_3CN$) to obtain 3-(2-ethoxyethyl)-2-methyl-5-(5-(trifluoromethyl)-4H-1,2,4-triazol-3-yl)pyridine (80 mg, yield: 99%) as a yellow oil.

MS Calcd: 300.1; MS Found: 301.1 $[M+H]^+$.

Step F: 3-(2-ethoxyethyl)-5-(5-(trifluoromethyl)-4H-1,2,4-triazol-3-yl)picolinaldehyde A mixture of (3-(2-ethoxyethyl)-2-methyl-5-(5-(trifluoromethyl)-4H-1,2,4-triazol-3-yl)pyridine (28 mg, 0.093 mmol) in dioxane (3 mL) was added $SeO_2$ (104 mg, 0.933 mmol) and the mixture was stirred at 80° C. for 16 hours. The mixture was filtered and the filtrate was concentrated to obtain 3-(2-ethoxyethyl)-2-methyl-5-(5-(trifluoromethyl)-4H-1,2,4-triazol-3-yl)pyridine (26 mg, yield: 89%) as a yellow oil, which was used directly without further purifications.

MS Calcd: 314.1; MS Found: 315.1 $[M+H]^+$.

Step G: 2-({4-[(2S)-2-(4-chloro-2-fluorophenyl)-2-methyl-2H-1,3-benzodioxol-4-yl]piperidin-1-yl}methyl)-3-(2-ethoxyethyl)-5-[5-(trifluoromethyl)-4H-1,2,4-triazol-3-yl]pyridine (Compound 287)

A mixture of (S)-4-(2-(4-chloro-2-fluorophenyl)-2-methylbenzo [d][1,3]dioxol-4-yl)-1-tosyl-1-piperidine (43 mg), TEA (0.04 mL, 0.249 mmol) in DCM (4 mL) was stirred at rt for 30 min. 3-(2-ethoxyethyl)-2-methyl-5-(5-(trifluoromethyl)-4H-1,2,4-triazol-3-yl)pyridine (26 mg, 0.083 mmol) was added, followed by the addition of $NaBH(OAc)_3$ (70 mg, 0.332 mol) in portions. The mixture was stirred at rt for 16 hrs. The water and DCM were added to the mixture, the organic phase was washed by brine, dried over $Na_2SO_4$. The solvent was concentrated to dryness. The residue was purified by pre-HPLC (0.1% $NH_3H_2O$) to obtain 2-({4-[(2S)-2-(4-chloro-2-fluorophenyl)-2-methyl-2H-1,3-benzodioxol-4-yl]piperidin-1-yl}methyl)-3-(2-ethoxyethyl)-5-[5-(trifluoromethyl)-4H-1,2,4-triazol-3-yl]pyridine (2.30 mg, yield: 4.31%) as a white solid.

MS Calcd: 645.2; MS Found: 646.2 $[M+H]^+$.

$^1H$ NMR (400 MHz, $CD_3OD-d_4$) δ 9.10 (s, 1H), 8.32 (d, J=2.0 Hz, 1H), 7.65-7.58 (m, 1H), 7.33-7.20 (m, 2H), 6.85-6.72 (m, 3H), 4.87 (s, 2H), 3.78 (t, J=6.4 Hz, 2H), 3.55-3.50 (m, 2H), 3.50-3.46 (m, 2H), 3.14-3.10 (m, 1H), 3.10-3.03 (m, 2H), 2.19 (t, J=7.6 Hz, 2H), 2.07 (s, 3H), 2.10-1.92 (m, 4H), 1.15 (t, J=7.2 Hz, 3H).

$^{19}F$-NMR (377 MHz): −64.57, −65.00, −112.25.

Example 79

3-fluoro-4-[(2S)-2-methyl-4-[1-({3-methyl-5-[5-(trifluoromethyl)-4H-1,2,4-triazol-3-yl]pyridin-2-yl}methyl)piperidin-4-yl]-2H-1,3-benzodioxol-2-yl] benzonitrile (Compound 286)

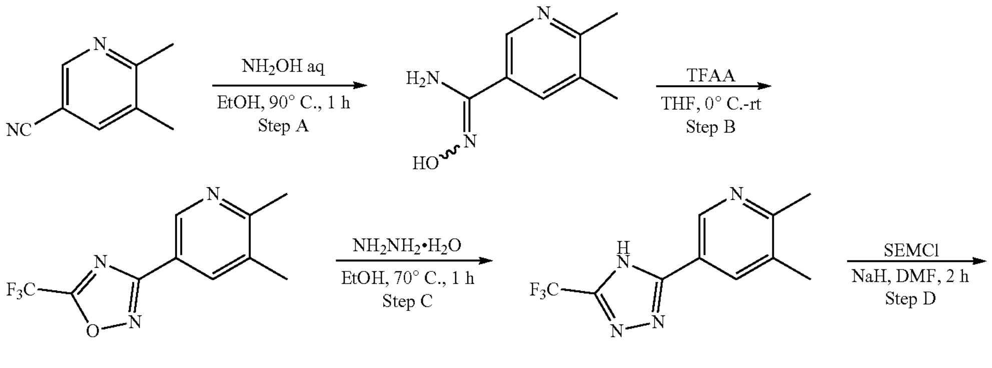

-continued

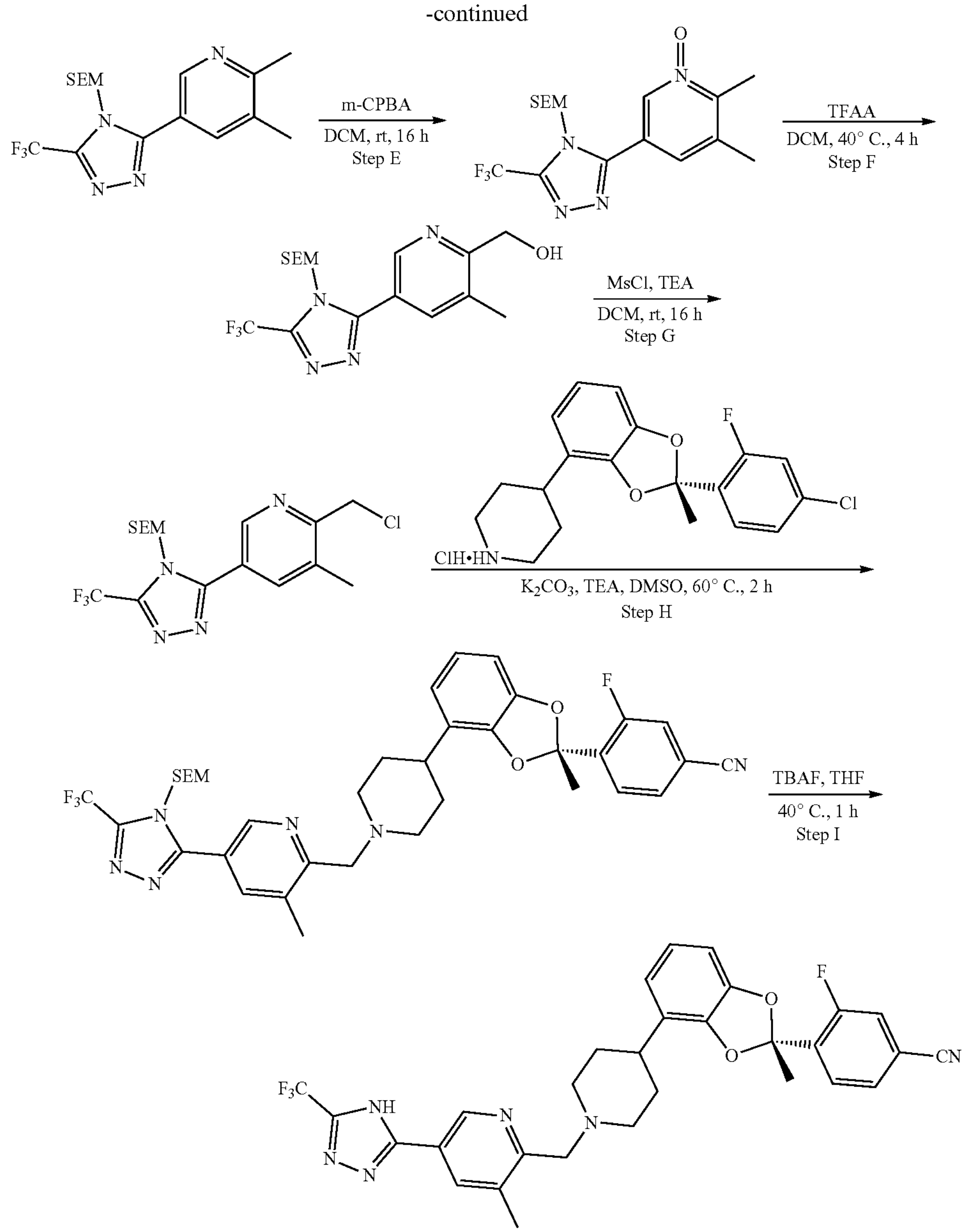

Compound 286

Step A: N'-hydroxy-5,6-dimethylnicotinimidamide

A mixture of 5-isocyano-2,3-dimethylpyridine (1 g, 7.57 mmol) and hydroxylamine aqueous solution (5 mL, 75.7 mmol) in EtOH (20 mL) was stirred at 90° C. for 1 hour. The mixture was concentrated to obtain N'-hydroxy-5,6-dimethylnicotinimidamide (1.25 g, crude) as a yellow solid.

MS Calcd: 165.1; MS Found: 166.2 $[M+H]^+$.

Step B: 3-(5,6-dimethylpyridin-3-yl)-5-(trifluoromethyl)-1,2,4-oxadiazole

To a solution of N'-hydroxy-5,6-dimethylnicotinimidamide (1.25 g) in THF (20 mL) were added dropwise TFAA (5.3 mL, 37.88 mmol) in THF (5 mL) at 0° C. The mixture was stirred at rt for 16 h. The mixture was poured into sodium bicarbonate aqueous solution (100 mL) and extracted with EtOAc (2×100 mL), the combined organic layer was washed with brine, dried over sodium sulfate, filtered and the residue was concentrated to obtain 3-(5,6-dimethylpyridin-3-yl)-5-(trifluoromethyl)-1,2,4-oxadiazole (1.55 g, yield: 84.2%) as a yellow solid.

MS Calcd: 243.1; MS Found: 244.1 $[M+H]^+$.

Step C: 2,3-dimethyl-5-(5-trifluoromethyl)-4H-1,2,4-triazol-3-yl)pyridine

A mixture of 3-(5,6-dimethylpyridin-3-yl)-5-(trifluoromethyl)-1,2,4-oxadiazole (750 mg) and hydrazine hydrate solution (4 mL) in EtOH (10 mL) was stirred at 70° C. for 1 h. The mixture was concentrated to obtain 2,3-dimethyl- 5-(5-(trifluoromethyl)-4H-1,2,4-triazol-3-yl)pyridine (750 mg, crude) as a white solid. MS Calcd: 242.1; MS Found: 243.1 $[M+H]^+$.

Step D: 2,3-dimethyl-5-(5-trifluoromethyl)-4-((2-(trimethylsilyl)ethoxy)methyl)-4H-1,2,4-triazol-3-yl) pyridine To a solution of 2,3-dimethyl-5-(5-(trifluoromethyl)-4H-1,2,4-triazol-3-yl)pyridine (1.55 g) in DMF (15 mL) was added NaH (60% w/w) (512 mg, 12.81 mmol) at 0° C. The mixture was stirred at 0° C. for 0.5 h and SEMCl (2.3 mL, 12.81 mmol) was added. The mixture was stirred at rt for 2 hours. The mixture was poured into water (200 mL) and extracted with EtOAc (2×200 mL), the combined organic layer was washed with brine, dried over sodium sulfate, filtered and the residue was concentrated. The residue was purified by column chromatography on silica gel to obtain 2,3-dimethyl-5-(5-(trifluoromethyl)-4-((2-(trimethylsilyl) ethoxy)methyl)-4H-1,2,4-triazol-3-yl)pyridine (1.6 g, yield: 77.1%) as yellow oil.

MS Calcd: 372.2; MS Found: 373.2 $[M+H]^+$.

Several regio-isomers maybe exist. We choose A-1 as a representative structure.

A-1

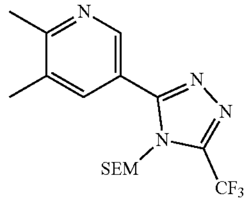

A-2

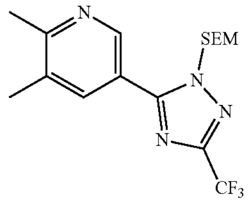

A-2

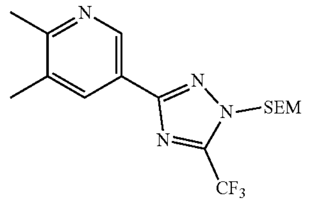

Similar cases also observed in other examples.

Step E: 2,3-dimethyl-5-(5-(trifluoromethyl)-4-((2-(trimethylsilyl)ethoxy)methyl)-4H-1,2,4-triazol-3-yl) pyridine 1-oxide To a solution of 2,3-dimethyl-5-(5-(trifluoromethyl)-4-((2-(trimethylsilyl)ethoxy)methyl)-4H-1,2,4-triazol-3-yl) pyridine (558 mg, 1.5 mmol) in DCM (10 mL) was added m-CPBA (518 mg, 3.0 mmol) at 0° C. The mixture was stirred at rt for 16 h. The mixture was poured into sodium bisulfite aqueous solution (100 mL) and extracted with DCM (2×100 mL), the combined organic layer was washed with brine, dried over sodium sulfate, filtered and concentrated. The residue was purified by column chromatography on silica gel to obtain 2,3-dimethyl-5-(5-(trifluoromethyl)-4-((2-(trimethylsilyl)ethoxy)methyl)-4H-1,2,4-triazol-3-yl) pyridine 1-oxide (300 mg, yield: 51.5%) as a yellow oil.

MS Calcd: 388.2; MS Found: 389.2 $[M+H]^+$

Step F: (3-methyl trifluoromethyl)-4-((2-(trimethylsilyl)ethoxy)methyl)-4H-1,2,4-triazol-3-yl)pyridin-2-yl)methanol To a solution of 2,3-dimethyl-5-(5-(trifluoromethyl)-4-((2-(trimethylsilyl)ethoxy)methyl)-4H-1,2,4-triazol-3-yl) pyridine 1-oxide (300 mg, 0.773 mmol) in DCM (10 mL) was added dropwise TFAA (0.54 mL, 3.86 mmol) at 0° C. The mixture was stirred at 40° C. for 4 h. The mixture was poured into sodium bicarbonate aqueous solution (100 mL) and extracted with DCM (2×100 mL), the combined organic layer was washed with brine, dried over sodium sulfate, filtered and the residue was concentrated to obtain (3-methyl-5-(5-(trifluoromethyl)-4-((2-(trimethylsilyl) ethoxy)methyl)-4H-1,2,4-triazol-3-yl)pyridin-2-yl)methanol (300 mg, crude) as a yellow oil.

MS Calcd: 388.2; MS Found: 389.1 [M+H]+

Step G: 2-(chloromethyl)-3-methyl-5-(5trifluoromethyl)-4-((2-(trimethylsilyl)ethoxy)methyl)-4H-1,2,4-triazol-3-yl)pyridine To a solution of (3-methyl-5-(5-(trifluoromethyl)-4-((2-(trimethylsilyl)ethoxy)methyl)-4H-1,2,4-triazol-3-yl)pyridin-2-yl)methanol (300 mg) in DCM (5 mL) were added dropwise TEA (0.32 mL, 2.31 mmol) and MsCl (0.12 mL, 1.55 mmol) at 0° C. The mixture was stirred at rt for 16 hours. The mixture was poured into water (100 mL) and extracted with DCM (2×100 mL), the combined organic layer was washed with brine, dried over sodium sulfate, filtered and the residue was concentrated. The residue was purified by column chromatography on silica gel to obtain 2-(chloromethyl)-3-methyl-5-(5-(trifluoromethyl)-4-((2-(trimethylsilyl)ethoxy)methyl)-4H-1,2,4-triazol-3-yl)pyridine (224 mg, yield: 71.4%) as a yellow oil.

MS Calcd: 406.1; MS Found: 407.1 $[M+H]^+$

Step H: (S)-3-fluoro-4-(2-methyl-4-(1-((3-methyl trifluoromethyl)-4-((2-(trimethylsilyl)ethoxy) methyl)-4H-1,2,4-triazol-3-yl)pyridin-2-yl)methyl) piperidin-4-yl)benzo[d][1,3]dioxol-2-yl)benzonitrile A mixture of (S)-3-fluoro-4-(2-methyl-4-(piperidin-4-yl) benzo[d][1,3]dioxol-2-yl)benzonitrile hydrochloride (51 mg, 0.136 mmol), $K_2CO_3$ (56 mg, 0.408 mmol) and TEA (41 mg, 0.408 mmol) in DMSO (2 mL) was stirred at rt for 1 h. The mixture was added 2-(chloromethyl)-3-methyl-5-(5-(trifluoromethyl)-4-((2-(trimethylsilyl)ethoxy)methyl)-4H-1,2,4-triazol-3-yl)pyridine (55 mg, 0.136 mmol). The mixture was stirred at 60° C. for 2 h. The mixture was purified by column chromatography on silica gel to obtain (S)-3-fluoro-4-(2-methyl-4-(1-((3-methyl-5-(5-(trifluoromethyl)-4-((2-(trimethylsilyl)ethoxy)methyl)-4H-1,2,4-triazol-3-yl) pyridin-2-yl)methyl)piperidin-4-yl)benzo[d][1,3]dioxol-2-yl)benzonitrile (68 mg, yield: 70.9%) as yellow oil.

MS Calcd: 708.3; MS Found: 709.3 $[M+H]^+$.

Step I: 2-({4-[(2S)-2-(4-chloro-2-fluorophenyl)-2-methyl-2H-1,3-benzodioxol-4-yl]piperidin-1-yl}methyl)-3-(2-ethoxvethyl)-5-[5-(trifluoromethyl)-4H-1,2,4-triazol-3-yl]pyridine (Compound 286)

A mixture of (S)-3-fluoro-4-(2-methyl-4-(1-((3-methyl-5-(5-(trifluoromethyl)-4-((2-(trimethylsilyl)ethoxy)methyl)-

4H-1,2,4-triazol-3-yl)pyridin-2-yl)methyl)piperidin-4-yl) benzo[d][1,3]dioxol-2-yl)benzonitrile (68 mg, 0.096 mmol) in TBAF (in THF, 1M) (1.5 mL) was stirred at 40° C. for 1 hour. The mixture was purified by prep-HPLC to obtain 3-fluoro-4-[(2S)-2-methyl-4-[1-({3-methyl-5-[5-(trifluoromethyl)-4H-1,2,4-triazol-3-yl]pyridin-2-yl}methyl)piperidin-4-yl]-2H-1,3-benzodioxol-2-yl]benzonitrile (17.40 mg, yield: 31.3%) as white solid.

MS Calcd: 578.2; MS Found: 579.1 $[M+H]^+$.

$^1H$ NMR (400 MHz, DMSO-$d_6$) δ 8.91 (s, 1H), 8.20 (brs, 1H), 7.98 (d, J=11.2 Hz, 1H), 7.80-7.70 (m, 2H), 6.81-6.72 (m, 3H), 3.70 (s, 2H), 3.00-2.90 (m, 2H), 2.72-2.60 (m, 1H), 2.47 (s, 3H), 2.29-2.18 (m, 2H), 2.05 (s, 3H), 1.78-1.67 (m, 4H).

$^{19}F$-NMR (377 MHz): −61.94, −111.09.

Example 80

1-{[2-({4-[(2S)-2-(5-chloropyridin-2-yl)-2-methyl-2H-1,3-benzodioxol-4-yl]piperidin-1-yl}methyl)-5-[5-(trifluoromethyl)-4H-1,2,4-triazol-3-yl]pyridin-3-yl]methyl}cyclopropane-1-carbonitrile (Compound 277)

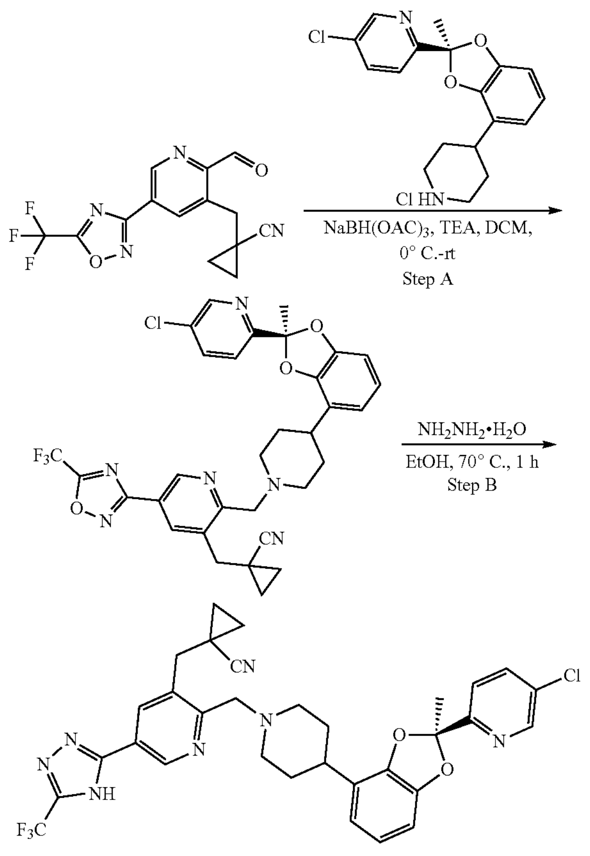

Compound 277

Step A: (S)-1-((2-((4-(2-(5-chloropyridin-2-yl)-2-methylbenzo[d][1,3]dioxol-4-yl)piperidin-1-yl)methyl)-5-(5-(trifluoromethyl)-1,2,4-oxadiazol-3-yl)pyridin-3-yl)methyl)cyclopropane-1-carbonitrile A mixture of (S)-5-chloro-2-(2-methyl-4-(piperidin-4-yl)benzo[d][1,3]dioxol-2-yl)pyridine hydrochloride (60 mg, 0.163 mmol) and TEA (82 mg, 0.815 mmol) in DCM (5 mL) was stirred at rt for 30 min. The mixture was added 1-((2-formyl-5-(5-(trifluoromethyl)-1,2,4-oxadiazol-3-yl)pyridin-3-yl)methyl)cyclopropane-1-carbonitrile (53 mg, 0.163 mmol). The mixture was added $NaBH(OAc)_3$ (138 mg, 0.652 mmol) at 0° C. and stirred at rt for 16 h. The mixture was poured into water (50 mL) and extracted with DCM (2×50 mL), the combined organic layer was washed with brine, dried over sodium sulfate, filtered and the residue was concentrated. The residue was purified by column chromatography on silica gel to obtain (S)-1-((2-((4-(2-(5-chloropyridin-2-yl)-2-methylbenzo[d][1,3]dioxol-4-yl)piperidin-1-yl)methyl)-5-(5-(trifluoromethyl)-1,2,4-oxadiazol-3-yl)pyridin-3-yl)methyl)cyclopropane-1-carbonitrile (100 mg) as a yellow solid.

MS Calcd: 636.2; MS Found: 637.3 $[M+H]^+$

Step B: 1-{[2-({4-[(2S)-2-(5-chloropyridin-2-yl)-2-methyl-2H-1,3-benzodioxol-4-yl]piperidin-1-yl}methyl)-5-[5-(trifluoromethyl)-4H-1,2,4-triazol-3-yl]pyridin-3-yl]methyl}cyclopropane-1-carbonitrile (Compound 277)

A mixture of (S)-1-((2-((4-(2-(5-chloropyridin-2-yl)-2-methylbenzo[d][1,3]dioxol-4-yl)piperidin-1-yl)methyl)-5-(5-(trifluoromethyl)-1,2,4-oxadiazol-3-yl)pyridin-3-yl)methyl)cyclopropane-1-carbonitrile (100 mg, 0.157 mmol) and $NH_2NH_2 \cdot H_2O$ (10 drops) in EtOH (3 mL) was stirred at 70° C. for 1 h. The mixture was purified by prep-HPLC to obtain 1-{[2-({4-[(2S)-2-(5-chloropyridin-2-yl)-2-methyl-2H-1,3-benzodioxol-4-yl]piperidin-1-yl}methyl)-5-[5-(trifluoromethyl)-4H-1,2,4-triazol-3-yl]pyridin-3-yl]methyl}cyclopropane-1-carbonitrile (38.0 mg, yield: 38.1%) as a white solid.

MS Calcd: 635.2; MS Found: 636.1 $[M+H]^+$ $^1H$ NMR (400 MHz, DMSO-$d_6$) δ 9.26 (s, 1H), 8.74 (d, J=2.4 Hz, 1H), 8.57 (d, J=2.0 Hz, 1H), 8.03 (dd, J=2.0 Hz, 8.4 Hz, 1H), 7.65 (d, J=8.4 Hz, 1H), 6.90-6.82 (m, 2H), 6.79-6.74 (m, 1H), 4.70 (s, 2H), 3.65-3.55 (m, 2H), 3.35-3.20 (m, 2H), 3.11 (s, 2H), 3.02-2.91 (m, 1H), 2.24-2.10 (m, 2H), 2.04 (s, 3H), 2.05-1.90 (m, 2H), 1.45-1.40 (m, 2H), 1.26-1.18 (m, 2H).

$^{19}F$-NMR (377 MHz): −63.69.

Example A: cAMP Assays

Activation of GLP-1 receptor is known to stimulate cyclic AMP (cAMP) production in cells which indicates primary coupling to the Gas subunit of the G protein heterotrimeric complex. Evidence suggests signaling through Gas induced cAMP stimulation elicits the desired pharmacological response regarding insulin release from pancreatic β-cells.

To optimize functional activity directed toward $G_{\alpha s}$ coupling, a HEK293/CRE-Luc cell line developed by HDB stably expressing the GLP-1 Receptor was used. 200× concentration of compound working solutions were prepared (Agilent Technologies Bravo) with ½ log serial dilution in 384-well Echo LDV plate (Labcyte, Cat #LP-0200). 50 nL/well 200× concentration of compound working solutions were moved to 384-well white low volume plate (Greiner, Cat #784075) using Labcyte ECHO550. $1\times10^5$ cells/mL HEK293/GLP 1R/CRE-LUC(HD Biosciences) cell suspensions prepared with assay buffer[DPBS containing 0.5 mM IBMX(Sigma, Cat #I5879) and 0.1% BSA (GENVIEW, Cat #FAO16-100 g)], 10 uL cell suspensions were added to each well of previous generated assay plate which already contains 50 nl compound at 200× concentration using ThermoFisher Multidrop Combi (1000cells/well). Seal the plate and incubate at 37° C. with 5% $CO_2$ for 30 min.

After incubation the cAMP assay signal was generated using cAMP dynamic 2 Kit (Cisbio). 5 μL cAMP-$d_2$ working solution was added to each well, followed with 5 μL Anti-cAMP antibody-cryptate working solution added to each well using ThermoFisher Multidrop Combi. Incubate at room temperature for 1 hour protected from light. Read the fluorescence at 665 and 615 nm with Reader PerkinElmer EnVision.

$$\%\ \text{Activity} = 100\% \times (\text{mean } RLU \text{ of test sample} - \text{mean } RLU \text{ of vehicle control}) / (\text{mean } RLU \text{ of MAX control} - \text{mean } RLU \text{ of vehicle control}))$$

Table 1 shows the biological activity of compounds in GLP-1R agonist cAMP stimulation assay ($EC_{50}$)

| Compound No. | GLP1R cAMP Stimulation DR: $EC_{50}$ (nM) |
|---|---|
| 101 | 227 |
| 102a | 1.6 |
| 103a | 0.093 |
| 104 | 3.45 (n = 2) |
| 105 | 59.2 (n = 2) |
| 106 | 0.364 (n = 2) |
| 107 | 4.4 |
| 108 | 28.2 (n = 2) |
| 109 | 86.4 |
| 110 | 5.5 |
| 112 | 2.01 |
| 113 | 34.9 |
| 114a | 9.4 |
| 115a | 3.2 |
| 116a | 0.71 |
| 117 | 3300 |
| 118 | >1000 |
| 119 | 1495 |
| 120 | 99 |
| 121 | >1000 |
| 122 | >1000 |
| 123 | 109 |
| 124 | >1000 |
| 125 | >1000 |
| 126 | 817 |
| 127 | 147 |
| 128 | 48.9 |
| 129 | 1500 |
| 130 | >1000 |
| 131a | 0.099 (n = 2) |
| 131b | 8.7 |
| 132a | 1.6 |
| 133a | 5.4 |
| 133b | 48 |
| 134a | 0.21 |
| 134b | 17 |
| 135a | 0.033 (n = 3) |
| 135b | 15 |
| 136a | 0.11 (n = 2) |
| 137a | 0.30 |
| 138a | 0.0023 |
| 138 | 0.0034 (n = 2) |
| 138b | 0.66 |
| 139a | 0.0012 (n = 2) |
| 139b | 0.20 |
| 140a | 0.090 (n = 2) |
| 141 | 0.012 |
| 142 | 0.012 (n = 2) |
| 143 | 0.0059 |
| 144 | 0.015 |
| 145 | 0.16 |

-continued

| Compound No. | GLP1R cAMP Stimulation DR: $EC_{50}$ (nM) |
|---|---|
| 146 | 1.9 |
| 147 | 0.045 (n = 2) |
| 148 | 0.98 |
| 149 | 0.12 |
| 150 | 0.054 (n = 2) |
| 151 | 0.043 (n = 3) |
| 152 | 0.53 |
| 153 | 18 |
| 154 | 0.012 (n = 4) |
| 155 | 0.0054 (n = 4) |
| 156 | 0.086 |
| 157 | 0.26 |
| 158 | 0.056 (n = 3) |
| 159 | 0.051 (n = 6) |
| 160 | 0.12 |
| 161 | 0.18 |
| 162 | 0.14 |
| 163 | 0.13 |
| 164 | 0.33 |
| 165 | 0.014 (n = 2) |
| 166 | 0.069 (n = 2) |
| 167 | 0.065 (n = 2) |
| 168 | 0.046 (n = 3) |
| 169a | 0.16 (n = 2) |
| 169b | 0.015 (n = 4) |
| 170b | 0.0067 (n = 3) |
| 170a | 2.5 |
| 171b | 17 |
| 171a | 10 |
| 172a | 0.048 (n = 2) |
| 172b | 0.021 (n = 3) |
| 173a | 0.0069 |
| 173b | 0.0014 |
| 174 | 6.4 |
| 175 | 0.047 (n = 2) |
| 176 | 0.058 (n = 2) |
| 177 | 0.18 (n = 4) |
| 178 | 1.2 |
| 179 | 0.036 (n = 3) |
| 180 | 0.026 (n = 4) |
| 181 | 4.1 |
| 182 | 93 |
| 183 | 0.015 (n = 2) |
| 184 | 0.24 |
| 185 | 20 |
| 186a | 0.41 (n = 3) |
| 187a | >1000 |
| 188 | 0.22 |
| 189 | 0.022 (n = 3) |
| 190 | 0.012 (n = 3) |
| 191 | 0.33 |
| 192 | 0.073 (n = 3) |
| 193 | 0.11 (n = 2) |
| 194 | 0.064 (n = 2) |
| 195 | 0.091 |
| 196 | 0.058 (n = 3) |
| 197 | 0.019 (n = 2) |
| 198a | 0.0095 (n = 2) |
| 199a | 1.6 (n = 2) |
| 200 | 0.22 |
| 201 | 0.034 (n = 4) |
| 202 | 0.26 |
| 203 | 0.058 |
| 204 | 0.012 |
| 205a | 0.26 (n = 4) |
| 206a | 0.19 |
| 207a | 0.016 (n = 3) |
| 208a | 0.011 |
| 209a | 0.54 (n = 2) |
| 210a | 0.43 (n = 2) |
| 211 | 0.54 (n = 2) |
| 212 | 6.4 |
| 213 | 4.2 (n = 2) |
| 214 | 0.0032 |
| 215a | 55 |
| 216a | 4.4 |

-continued

| Compound No. | GLP1R cAMP Stimulation DR: $EC_{50}$ (nM) |
|---|---|
| 217a | 46 (n = 2) |
| 218a | 1.4 (n = 3) |
| 219 | 0.0069 (n = 2) |
| 220 | 0.11 (n = 2) |
| 221 | 0.56 |
| 222a | 6.9 |
| 223 | 0.47 (n = 2) |
| 224 | 2.1 (n = 2) |
| 225a | 0.26 (n = 2) |
| 226a | 1.2 |
| 227 | 1.7 |
| 228 | 0.0048 (n = 2) |
| 229 | 2.7 |
| 230 | 41 |
| 231 | 0.88 (n = 2) |
| 232 | 1.2 (n = 2) |
| 233 | 26 |
| 234a | 0.026 (n = 4) |
| 235 | 10 |
| 236 | 38 |
| 237 | 0.29 (n = 2) |
| 238 | 0.43 |
| 239 | 0.45 |
| 240 | 0.38 |
| 241 | 0.21 |
| 242 | 0.63 |
| 243 | 0.87 |
| 244 | 0.023 (n = 3) |
| 245 | 0.15 (n = 4) |
| 246 | 0.38 |
| 247 | 310 |
| 248 | 35 |
| 249a | 3.7 |
| 250 | 1.6 |
| 251 | 13 |
| 252 | 11 |
| 253 | 4 |
| 254 | 10 |
| 255 | 8.3 |
| 256 | 5 |
| 257 | 14 |
| 258 | 0.0061 |
| 259 | 0.53 |
| 260 | 2.3 |
| 261 | 5.3 |
| 262 | 3 |
| 263 | 6.8 |
| 264 | 15 |
| 265 | 4.5 |
| 266 | 10 |
| 267 | 4.7 |
| 268 | 7.7 |
| 277 | 0.023 |
| 282 | 3.7 |
| 286 | 1.38 |
| 287 | 0.87 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound, or a pharmaceutically acceptable salt or solvate thereof, selected from the group consisting of:

145

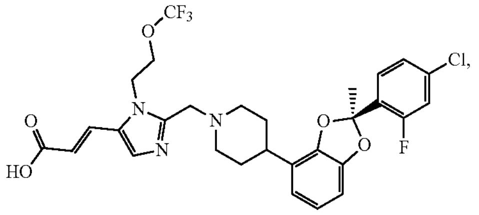 [SMILES: C[C@]1(c2ccc(Cl)cc2F)Oc2cccc(C3CCN(Cc4ncc(/C=C/C(=O)O)n4CCOC(F)(F)F)CC3)c2O1]

146

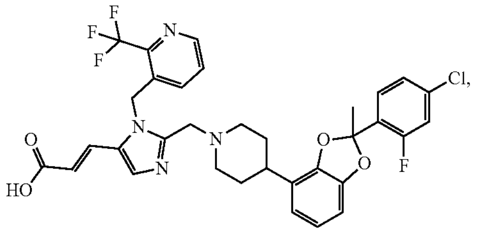 [SMILES: CC1(c2ccc(Cl)cc2F)Oc2cccc(C3CCN(Cc4ncc(/C=C/C(=O)O)n4Cc4cccnc4C(F)(F)F)CC3)c2O1]

147

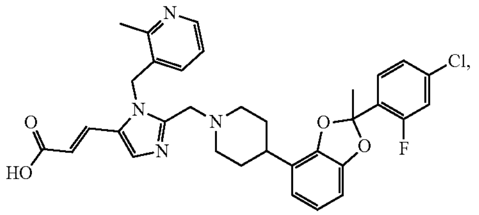 [SMILES: Cc1ncccc1Cn1c(/C=C/C(=O)O)cnc1CN1CCC(c2cccc3c2OC(C)(c2ccc(Cl)cc2F)O3)CC1]

148

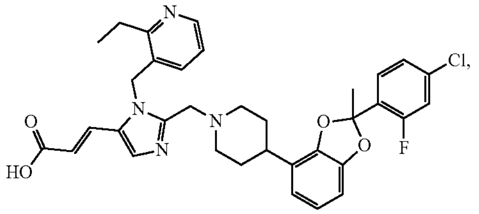 [SMILES: CCc1ncccc1Cn1c(/C=C/C(=O)O)cnc1CN1CCC(c2cccc3c2OC(C)(c2ccc(Cl)cc2F)O3)CC1]

149

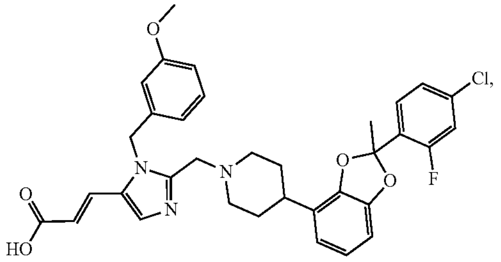 [SMILES: COc1cccc(Cn2c(/C=C/C(=O)O)cnc2CN2CCC(c3cccc4c3OC(C)(c3ccc(Cl)cc3F)O4)CC2)c1]

150

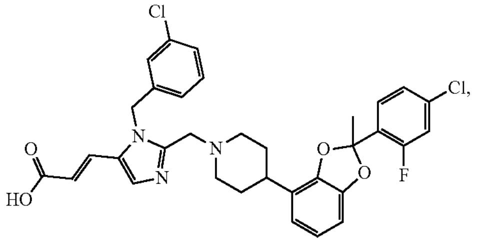 [SMILES: CC1(c2ccc(Cl)cc2F)Oc2cccc(C3CCN(Cc4ncc(/C=C/C(=O)O)n4Cc4cccc(Cl)c4)CC3)c2O1]

151

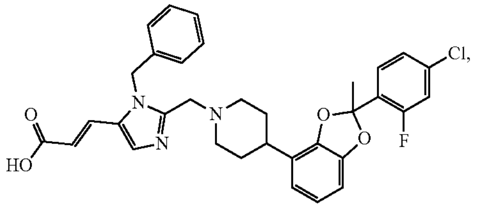 [SMILES: CC1(c2ccc(Cl)cc2F)Oc2cccc(C3CCN(Cc4ncc(/C=C/C(=O)O)n4Cc4ccccc4)CC3)c2O1]

-continued
152
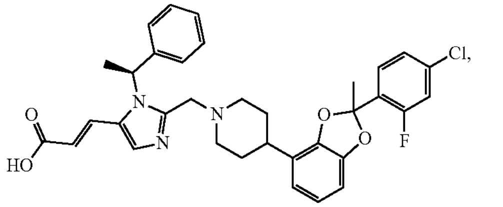 [SMILES: C[C@@H](c1ccccc1)n1c(/C=C/C(=O)O)cnc1CN1CCC(c2cccc3c2OC(C)(c2ccc(Cl)cc2F)O3)CC1]
153
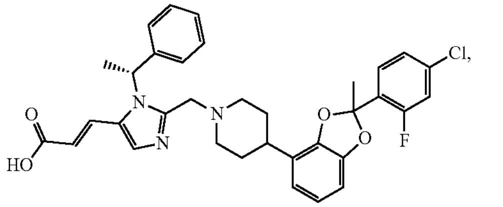 [SMILES: C[C@H](c1ccccc1)n1c(/C=C/C(=O)O)cnc1CN1CCC(c2cccc3c2OC(C)(c2ccc(Cl)cc2F)O3)CC1]
154
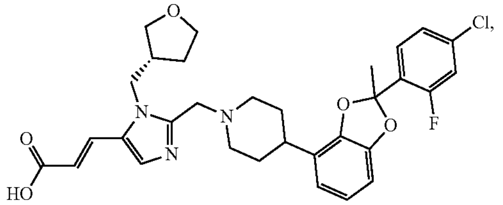 [SMILES: CC1(c2ccc(Cl)cc2F)Oc2cccc(C3CCN(Cc4ncc(/C=C/C(=O)O)n4C[C@H]4CCOC4)CC3)c2O1]
155
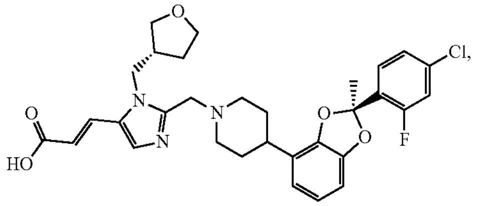 [SMILES: C[C@]1(c2ccc(Cl)cc2F)Oc2cccc(C3CCN(Cc4ncc(/C=C/C(=O)O)n4C[C@H]4CCOC4)CC3)c2O1]
156
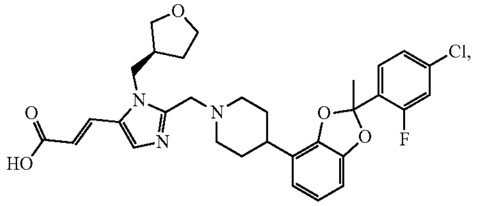 [SMILES: CC1(c2ccc(Cl)cc2F)Oc2cccc(C3CCN(Cc4ncc(/C=C/C(=O)O)n4C[C@@H]4CCOC4)CC3)c2O1]
157
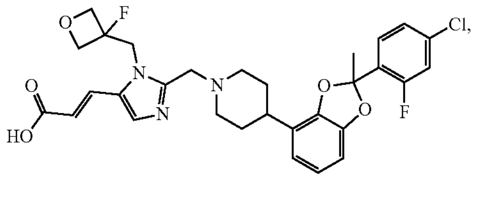 [SMILES: CC1(c2ccc(Cl)cc2F)Oc2cccc(C3CCN(Cc4ncc(/C=C/C(=O)O)n4CC4(F)COC4)CC3)c2O1]
158
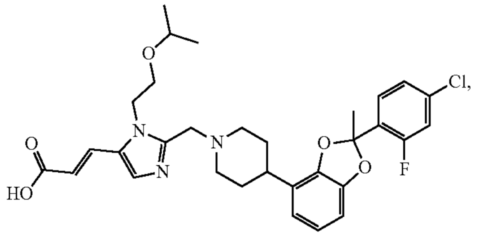 [SMILES: CC(C)OCCn1c(/C=C/C(=O)O)cnc1CN1CCC(c2cccc3c2OC(C)(c2ccc(Cl)cc2F)O3)CC1]
-continued
159
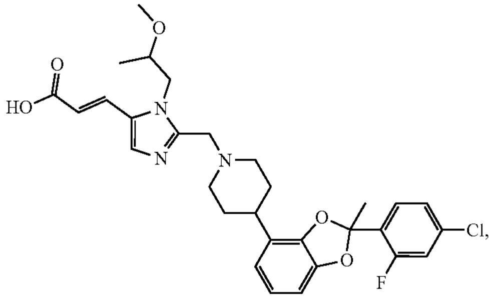 [SMILES: COC(C)Cn1c(/C=C/C(=O)O)cnc1CN1CCC(c2cccc3c2OC(C)(c2ccc(Cl)cc2F)O3)CC1]
160
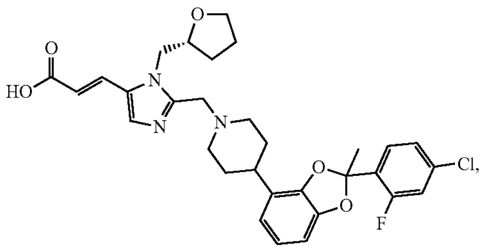 [SMILES: CC1(c2ccc(Cl)cc2F)Oc2cccc(C3CCN(Cc4ncc(/C=C/C(=O)O)n4C[C@H]4CCCO4)CC3)c2O1]
161
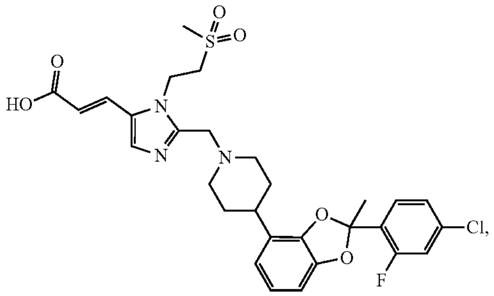 [SMILES: CC1(c2ccc(Cl)cc2F)Oc2cccc(C3CCN(Cc4ncc(/C=C/C(=O)O)n4CCS(C)(=O)=O)CC3)c2O1]
162
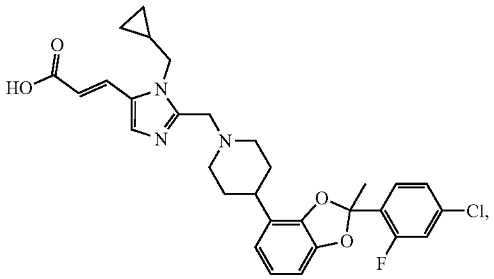 [SMILES: CC1(c2ccc(Cl)cc2F)Oc2cccc(C3CCN(Cc4ncc(/C=C/C(=O)O)n4CC4CC4)CC3)c2O1]
163
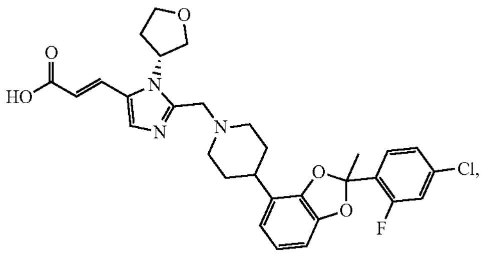 [SMILES: CC1(c2ccc(Cl)cc2F)Oc2cccc(C3CCN(Cc4ncc(/C=C/C(=O)O)n4[C@@H]4CCOC4)CC3)c2O1]
164
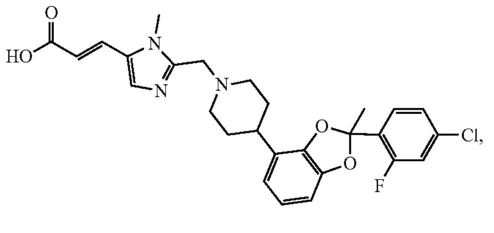 [SMILES: Cn1c(/C=C/C(=O)O)cnc1CN1CCC(c2cccc3c2OC(C)(c2ccc(Cl)cc2F)O3)CC1]

-continued
165
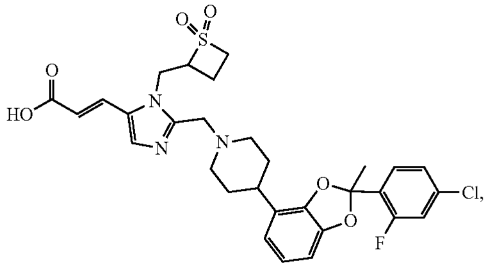 [SMILES: CC1(c2ccc(Cl)cc2F)Oc2cccc(C3CCN(Cc4ncc(/C=C/C(=O)O)n4CC4CCS4(=O)=O)CC3)c2O1]
,
166
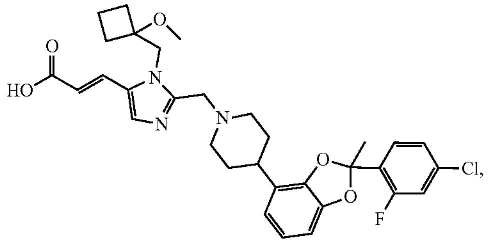 [SMILES: COC1(Cn2c(/C=C/C(=O)O)cnc2CN2CCC(c3cccc4c3OC(C)(c3ccc(Cl)cc3F)O4)CC2)CCC1]
,
167
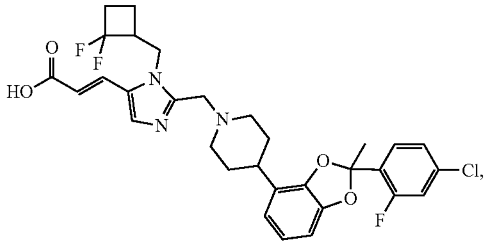 [SMILES: CC1(c2ccc(Cl)cc2F)Oc2cccc(C3CCN(Cc4ncc(/C=C/C(=O)O)n4CC4CCC4(F)F)CC3)c2O1]
,
168
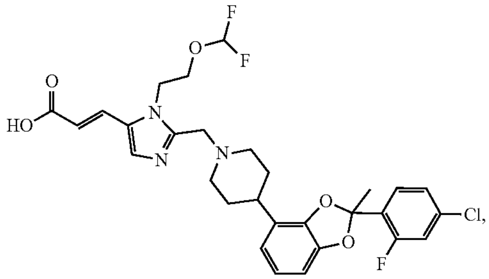 [SMILES: CC1(c2ccc(Cl)cc2F)Oc2cccc(C3CCN(Cc4ncc(/C=C/C(=O)O)n4CCOC(F)F)CC3)c2O1]
,
169a
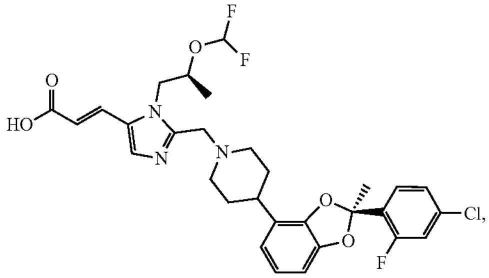 [SMILES: C[C@@H](Cn1c(/C=C/C(=O)O)cnc1CN1CCC(c2cccc3c2O[C@@](C)(c2ccc(Cl)cc2F)O3)CC1)OC(F)F]
,
169b
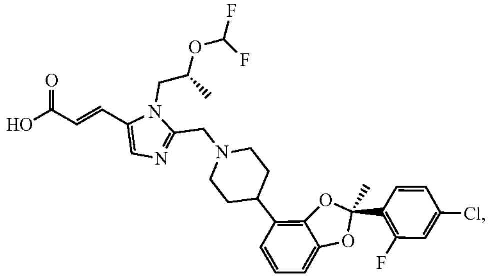 [SMILES: C[C@H](Cn1c(/C=C/C(=O)O)cnc1CN1CCC(c2cccc3c2O[C@@](C)(c2ccc(Cl)cc2F)O3)CC1)OC(F)F]
,
-continued
170b
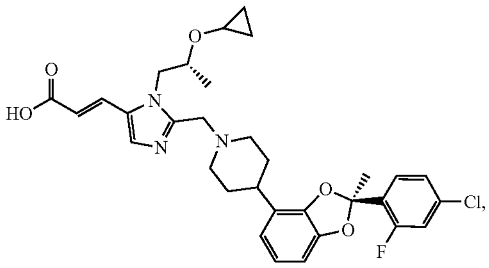 [SMILES: C[C@H](Cn1c(/C=C/C(=O)O)cnc1CN1CCC(c2cccc3c2O[C@@](C)(c2ccc(Cl)cc2F)O3)CC1)OC1CC1]
,
170a
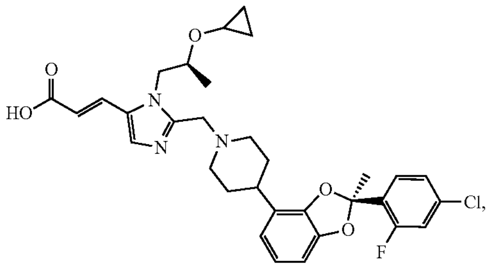 [SMILES: C[C@@H](Cn1c(/C=C/C(=O)O)cnc1CN1CCC(c2cccc3c2O[C@@](C)(c2ccc(Cl)cc2F)O3)CC1)OC1CC1]
,
171b
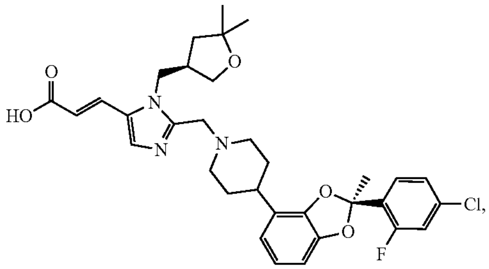 [SMILES: CC1(C)C[C@H](Cn2c(/C=C/C(=O)O)cnc2CN2CCC(c3cccc4c3O[C@@](C)(c3ccc(Cl)cc3F)O4)CC2)CO1]
,
171a
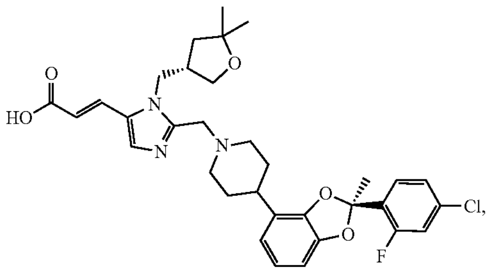 [SMILES: CC1(C)C[C@@H](Cn2c(/C=C/C(=O)O)cnc2CN2CCC(c3cccc4c3O[C@@](C)(c3ccc(Cl)cc3F)O4)CC2)CO1]
,
172a
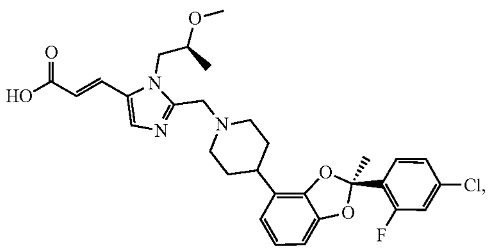 [SMILES: CO[C@@H](C)Cn1c(/C=C/C(=O)O)cnc1CN1CCC(c2cccc3c2O[C@@](C)(c2ccc(Cl)cc2F)O3)CC1]
,
172b
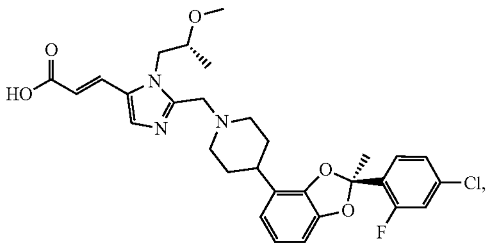 [SMILES: CO[C@H](C)Cn1c(/C=C/C(=O)O)cnc1CN1CCC(c2cccc3c2O[C@@](C)(c2ccc(Cl)cc2F)O3)CC1]
, 173a
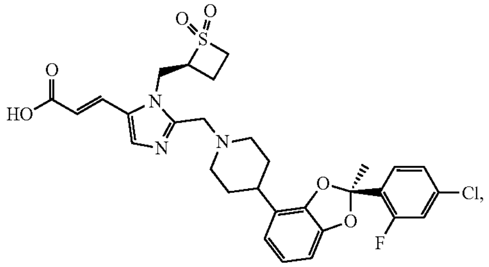 [SMILES: C[C@]1(c2ccc(Cl)cc2F)Oc2cccc(C3CCN(Cc4ncc(/C=C/C(=O)O)n4C[C@@H]4CCS4(=O)=O)CC3)c2O1]
,
173b
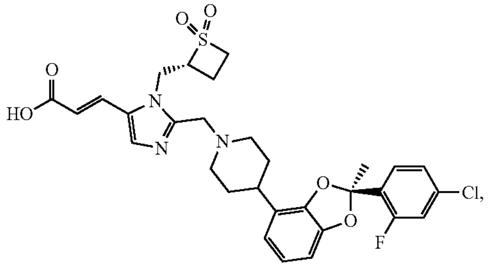 [SMILES: C[C@]1(c2ccc(Cl)cc2F)Oc2cccc(C3CCN(Cc4ncc(/C=C/C(=O)O)n4C[C@H]4CCS4(=O)=O)CC3)c2O1]
,
174
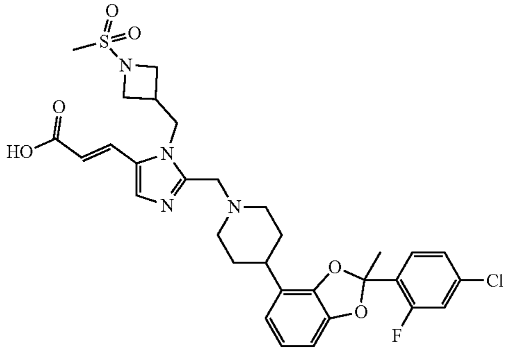 [SMILES: CC1(c2ccc(Cl)cc2F)Oc2cccc(C3CCN(Cc4ncc(/C=C/C(=O)O)n4CC4CN(S(C)(=O)=O)C4)CC3)c2O1]
175
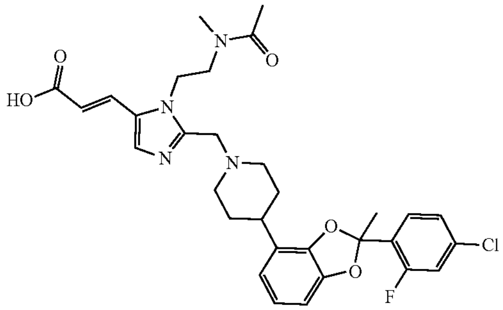 [SMILES: CC(=O)N(C)CCn1c(/C=C/C(=O)O)cnc1CN1CCC(c2cccc3c2OC(C)(c2ccc(Cl)cc2F)O3)CC1]
176
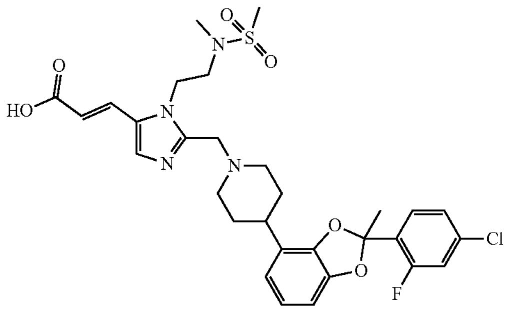 [SMILES: CN(CCn1c(/C=C/C(=O)O)cnc1CN1CCC(c2cccc3c2OC(C)(c2ccc(Cl)cc2F)O3)CC1)S(C)(=O)=O]
177
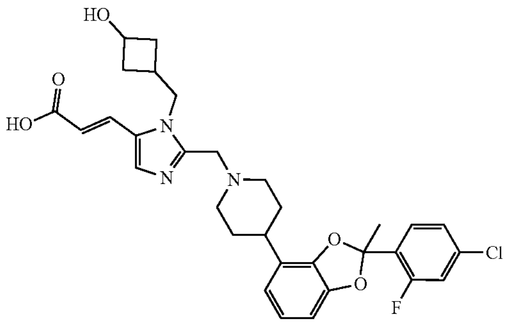 [SMILES: CC1(c2ccc(Cl)cc2F)Oc2cccc(C3CCN(Cc4ncc(/C=C/C(=O)O)n4CC4CC(O)C4)CC3)c2O1]
178
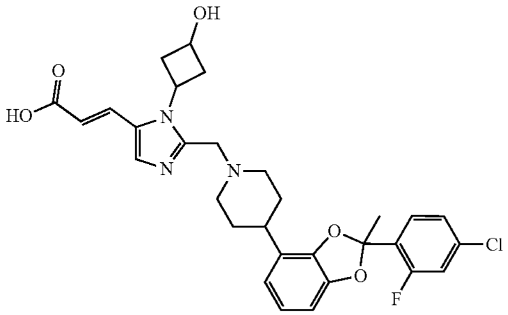 [SMILES: CC1(c2ccc(Cl)cc2F)Oc2cccc(C3CCN(Cc4ncc(/C=C/C(=O)O)n4C4CC(O)C4)CC3)c2O1]
179
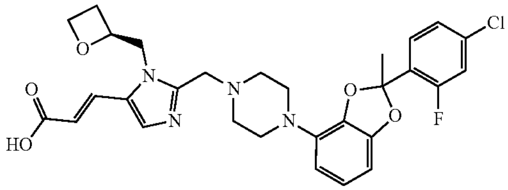 [SMILES: CC1(c2ccc(Cl)cc2F)Oc2cccc(N3CCN(Cc4ncc(/C=C/C(=O)O)n4C[C@@H]4CCO4)CC3)c2O1]
180
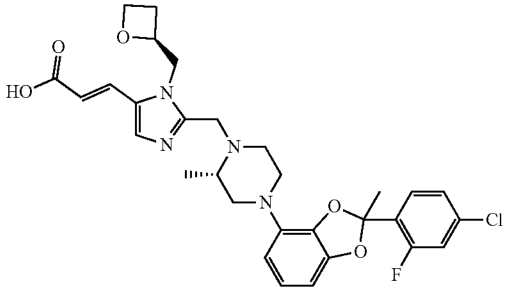 [SMILES: C[C@H]1CN(c2cccc3c2OC(C)(c2ccc(Cl)cc2F)O3)CCN1Cc1ncc(/C=C/C(=O)O)n1C[C@@H]1CCO1]
181
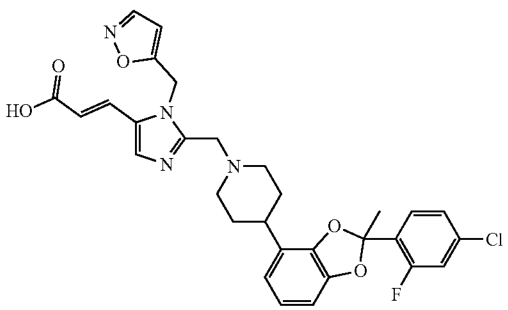 [SMILES: CC1(c2ccc(Cl)cc2F)Oc2cccc(C3CCN(Cc4ncc(/C=C/C(=O)O)n4Cc4ccno4)CC3)c2O1]

182
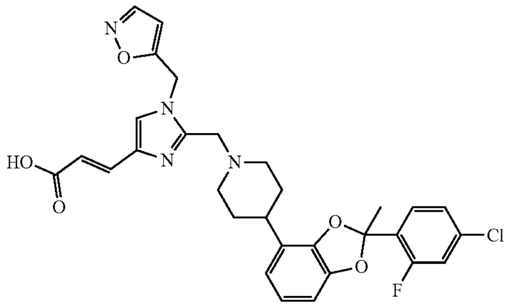 [SMILES: CC1(c2ccc(Cl)cc2F)Oc2cccc(C3CCN(Cc4nc(/C=C/C(=O)O)cn4Cc4ccno4)CC3)c2O1]
183
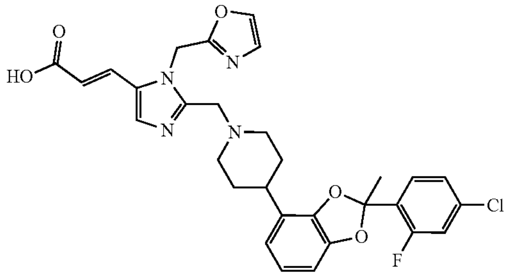 [SMILES: CC1(c2ccc(Cl)cc2F)Oc2cccc(C3CCN(Cc4ncc(/C=C/C(=O)O)n4Cc4ncco4)CC3)c2O1]
184
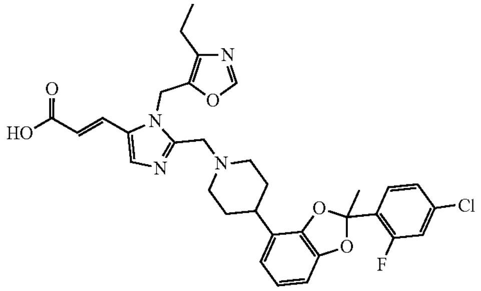 [SMILES: CCc1ncoc1Cn1c(/C=C/C(=O)O)cnc1CN1CCC(c2cccc3c2OC(C)(c2ccc(Cl)cc2F)O3)CC1]
185
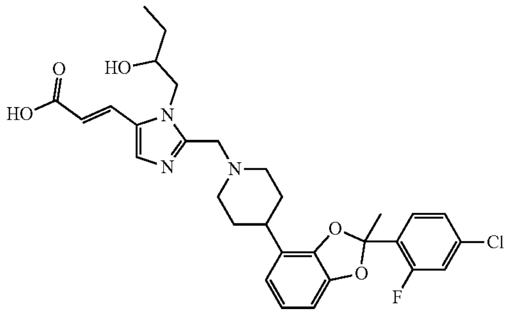 [SMILES: CCC(O)Cn1c(/C=C/C(=O)O)cnc1CN1CCC(c2cccc3c2OC(C)(c2ccc(Cl)cc2F)O3)CC1]
186a
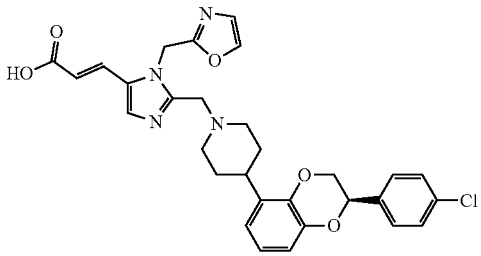 [SMILES: O=C(O)/C=C/c1cnc(CN2CCC(c3cccc4c3OC[C@@H](c3ccc(Cl)cc3)O4)CC2)n1Cc1ncco1]
187a
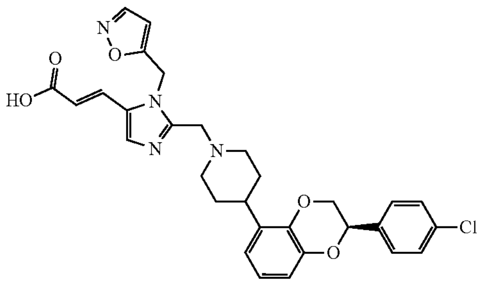 [SMILES: O=C(O)/C=C/c1cnc(CN2CCC(c3cccc4c3OC[C@@H](c3ccc(Cl)cc3)O4)CC2)n1Cc1ccno1]
188
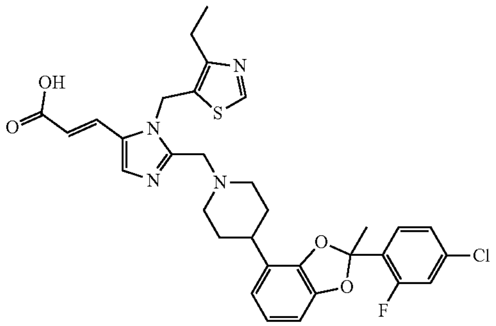 [SMILES: CCc1ncsc1Cn1c(/C=C/C(=O)O)cnc1CN1CCC(c2cccc3c2OC(C)(c2ccc(Cl)cc2F)O3)CC1]
189
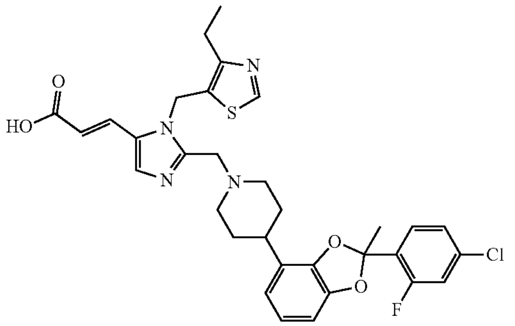 [SMILES: CCc1ncsc1Cn1c(/C=C/C(=O)O)cnc1CN1CCC(c2cccc3c2OC(C)(c2ccc(Cl)cc2F)O3)CC1]
190
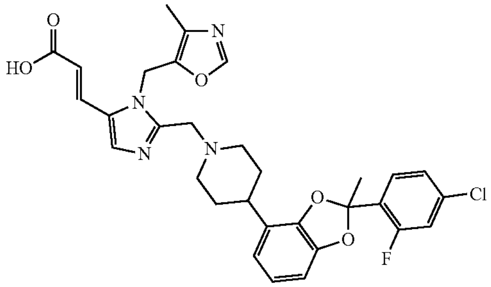 [SMILES: Cc1ncoc1Cn1c(/C=C/C(=O)O)cnc1CN1CCC(c2cccc3c2OC(C)(c2ccc(Cl)cc2F)O3)CC1]
191
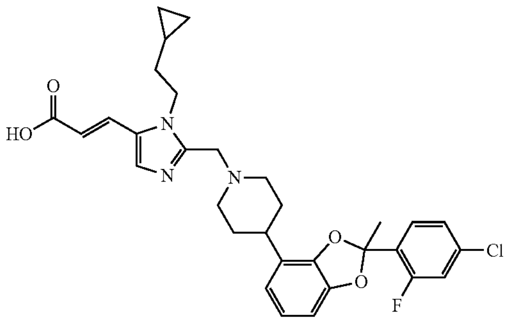 [SMILES: CC1(c2ccc(Cl)cc2F)Oc2cccc(C3CCN(Cc4ncc(/C=C/C(=O)O)n4CCC4CC4)CC3)c2O1]

-continued
192
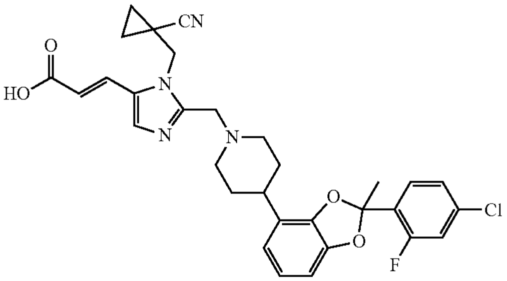 [SMILES: CC1(c2ccc(Cl)cc2F)Oc2cccc(C3CCN(Cc4ncc(/C=C/C(=O)O)n4CC4(C#N)CC4)CC3)c2O1]
193
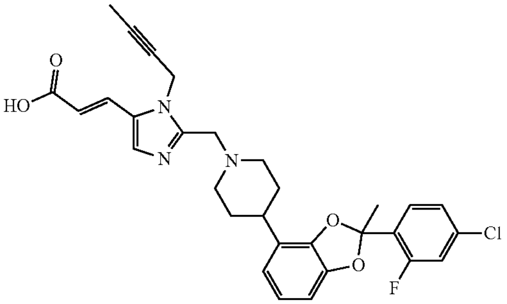 [SMILES: CC#CCn1c(/C=C/C(=O)O)cnc1CN1CCC(c2cccc3c2OC(C)(c2ccc(Cl)cc2F)O3)CC1]
195
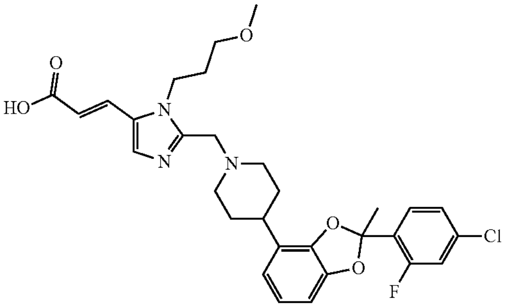 [SMILES: COCCCn1c(/C=C/C(=O)O)cnc1CN1CCC(c2cccc3c2OC(C)(c2ccc(Cl)cc2F)O3)CC1]
196
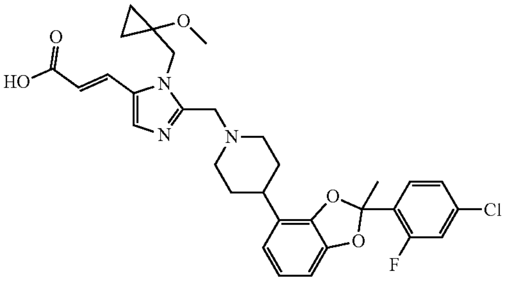 [SMILES: COC1(Cn2c(/C=C/C(=O)O)cnc2CN2CCC(c3cccc4c3OC(C)(c3ccc(Cl)cc3F)O4)CC2)CC1]
197
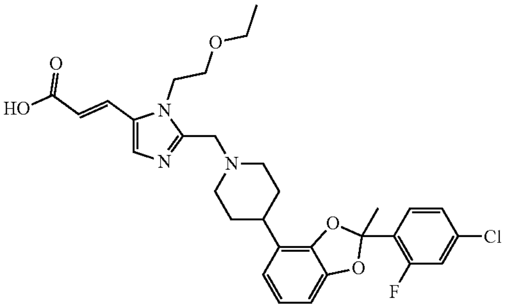 [SMILES: CCOCCn1c(/C=C/C(=O)O)cnc1CN1CCC(c2cccc3c2OC(C)(c2ccc(Cl)cc2F)O3)CC1]
-continued
198a
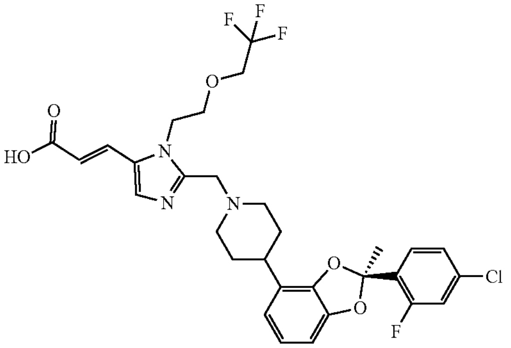 [SMILES: C[C@]1(c2ccc(Cl)cc2F)Oc2cccc(C3CCN(Cc4ncc(/C=C/C(=O)O)n4CCOCC(F)(F)F)CC3)c2O1]
199a
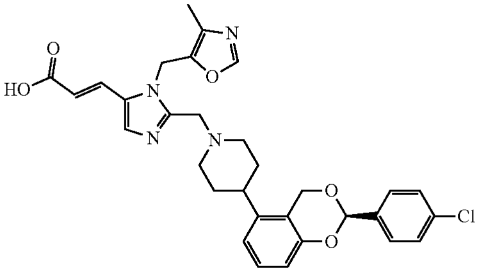 [SMILES: Cc1ncoc1Cn1c(/C=C/C(=O)O)cnc1CN1CCC(c2cccc3c2CO[C@@H](c2ccc(Cl)cc2)O3)CC1]
200
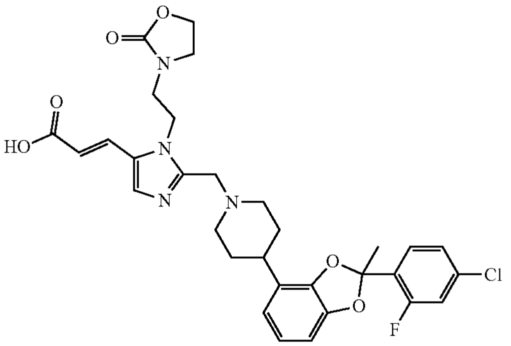 [SMILES: CC1(c2ccc(Cl)cc2F)Oc2cccc(C3CCN(Cc4ncc(/C=C/C(=O)O)n4CCN4CCOC4=O)CC3)c2O1]
201
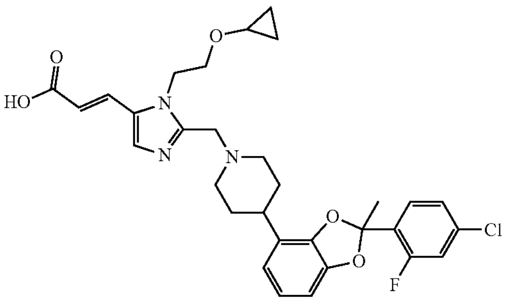 [SMILES: CC1(c2ccc(Cl)cc2F)Oc2cccc(C3CCN(Cc4ncc(/C=C/C(=O)O)n4CCOC4CC4)CC3)c2O1]
202
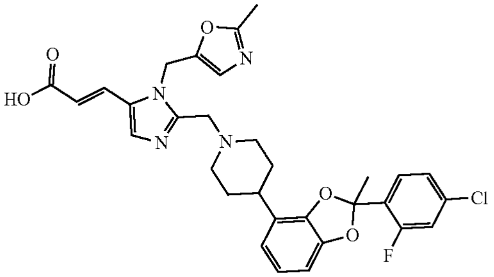 [SMILES: Cc1ncc(Cn2c(/C=C/C(=O)O)cnc2CN2CCC(c3cccc4c3OC(C)(c3ccc(Cl)cc3F)O4)CC2)o1]

-continued
203
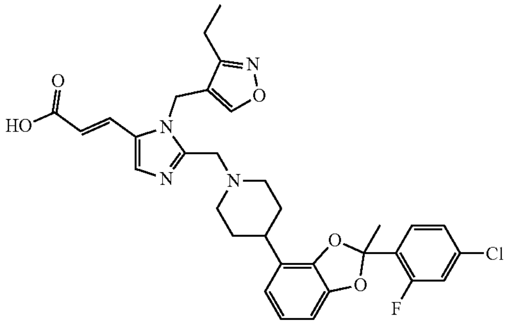 [SMILES: CCc1nocc1Cn1c(/C=C/C(=O)O)cnc1CN1CCC(c2cccc3c2OC(C)(c2ccc(Cl)cc2F)O3)CC1]
204
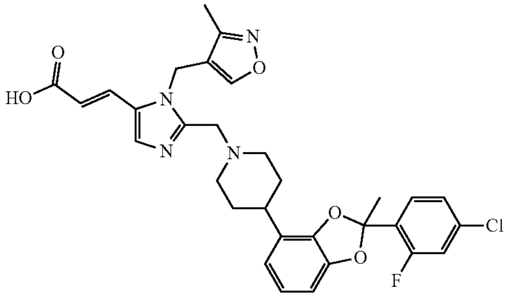 [SMILES: Cc1nocc1Cn1c(/C=C/C(=O)O)cnc1CN1CCC(c2cccc3c2OC(C)(c2ccc(Cl)cc2F)O3)CC1]
205a
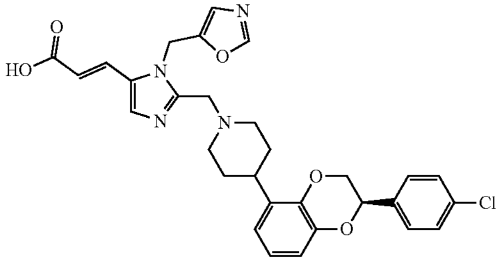 [SMILES: O=C(O)/C=C/c1cnc(CN2CCC(c3cccc4c3OC[C@@H](c3ccc(Cl)cc3)O4)CC2)n1Cc1cnco1]
206a
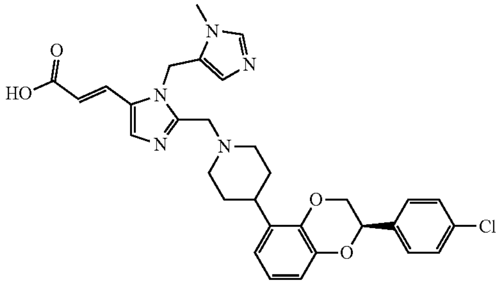 [SMILES: Cn1cncc1Cn1c(/C=C/C(=O)O)cnc1CN1CCC(c2cccc3c2OC[C@@H](c2ccc(Cl)cc2)O3)CC1]
207a
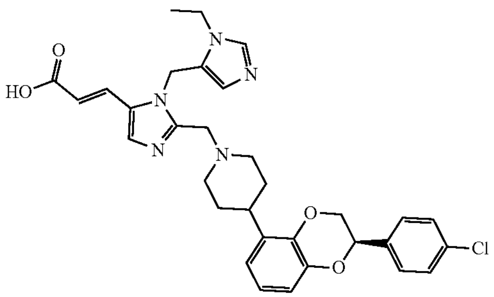 [SMILES: CCn1cncc1Cn1c(/C=C/C(=O)O)cnc1CN1CCC(c2cccc3c2OC[C@@H](c2ccc(Cl)cc2)O3)CC1]
-continued
208a
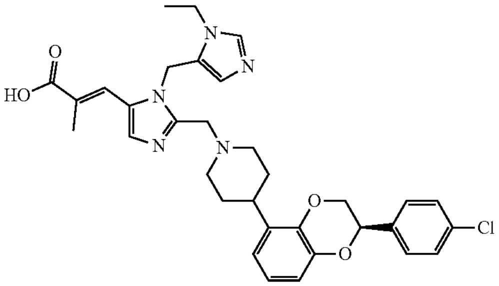 [SMILES: CCn1cncc1Cn1c(/C=C(\C)C(=O)O)cnc1CN1CCC(c2cccc3c2OC[C@@H](c2ccc(Cl)cc2)O3)CC1]
209a
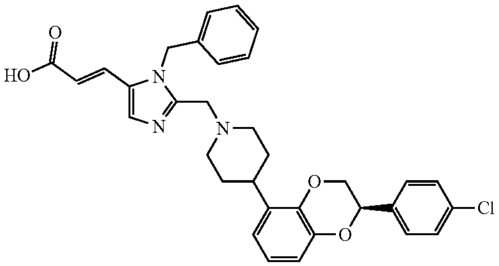 [SMILES: O=C(O)/C=C/c1cnc(CN2CCC(c3cccc4c3OC[C@@H](c3ccc(Cl)cc3)O4)CC2)n1Cc1ccccc1]
210a
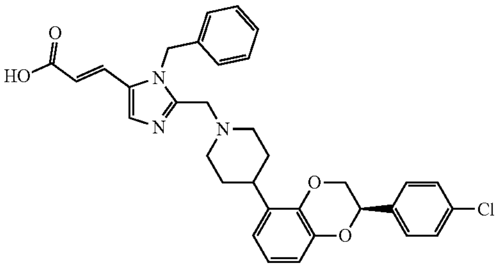 [SMILES: O=C(O)/C=C/c1cnc(CN2CCC(c3cccc4c3OC[C@@H](c3ccc(Cl)cc3)O4)CC2)n1Cc1ccccc1]
211
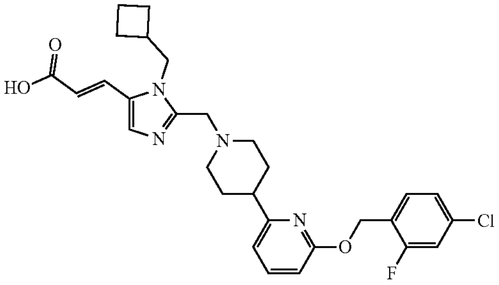 [SMILES: O=C(O)/C=C/c1cnc(CN2CCC(c3cccc(OCc4ccc(Cl)cc4F)n3)CC2)n1CC1CCC1]
212
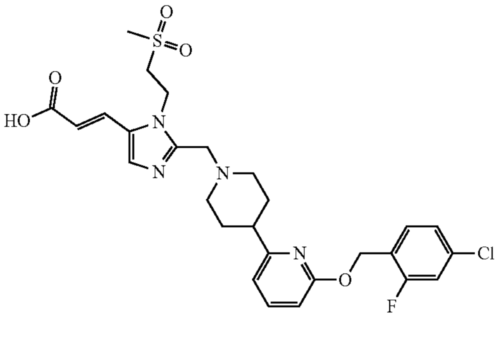 [SMILES: CS(=O)(=O)CCn1c(/C=C/C(=O)O)cnc1CN1CCC(c2cccc(OCc3ccc(Cl)cc3F)n2)CC1]

-continued
213
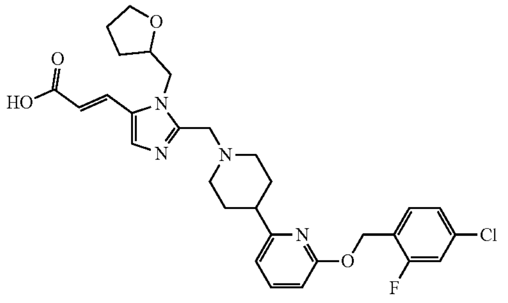 [SMILES: O=C(O)/C=C/c1cnc(CN2CCC(c3cccc(OCc4ccc(Cl)cc4F)n3)CC2)n1CC1CCCO1]
214
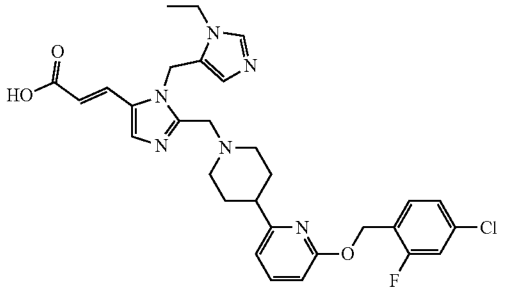 [SMILES: CCn1cncc1Cn1c(/C=C/C(=O)O)cnc1CN1CCC(c2cccc(OCc3ccc(Cl)cc3F)n2)CC1]
215a
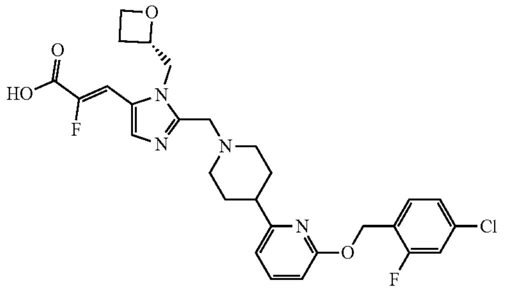 [SMILES: O=C(O)/C(F)=C/c1cnc(CN2CCC(c3cccc(OCc4ccc(Cl)cc4F)n3)CC2)n1C[C@@H]1CCO1]
216a
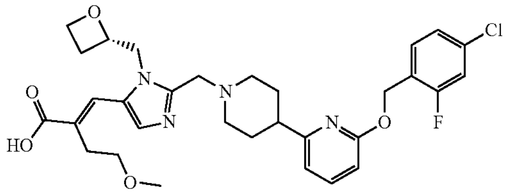 [SMILES: COCC/C(=C\c1cnc(CN2CCC(c3cccc(OCc4ccc(Cl)cc4F)n3)CC2)n1C[C@@H]1CCO1)C(=O)O]
217a
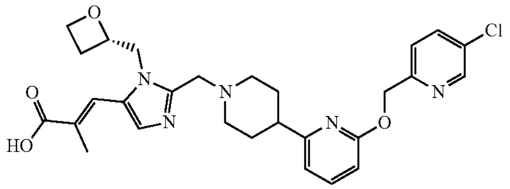 [SMILES: C/C(=C\c1cnc(CN2CCC(c3cccc(OCc4ccc(Cl)cn4)n3)CC2)n1C[C@@H]1CCO1)C(=O)O]
218a
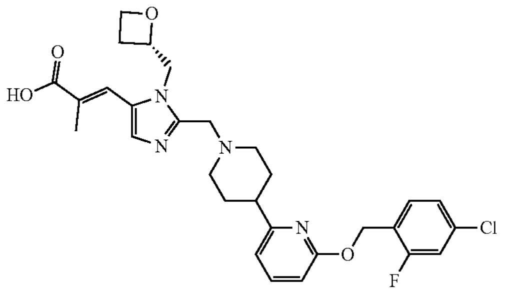 [SMILES: C/C(=C\c1cnc(CN2CCC(c3cccc(OCc4ccc(Cl)cc4F)n3)CC2)n1C[C@@H]1CCO1)C(=O)O]
-continued
219
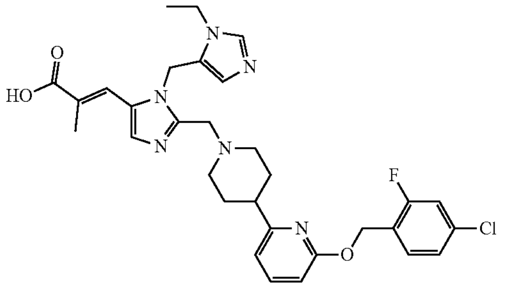 [SMILES: CCn1cncc1Cn1c(/C=C(\C)C(=O)O)cnc1CN1CCC(c2cccc(OCc3ccc(Cl)cc3F)n2)CC1]
220
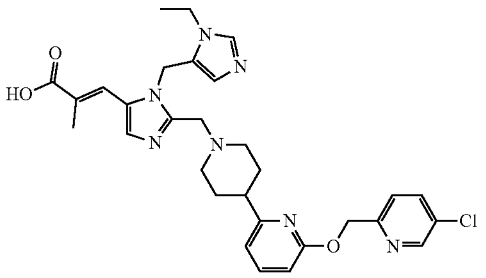 [SMILES: CCn1cncc1Cn1c(/C=C(\C)C(=O)O)cnc1CN1CCC(c2cccc(OCc3ccc(Cl)cn3)n2)CC1]
221
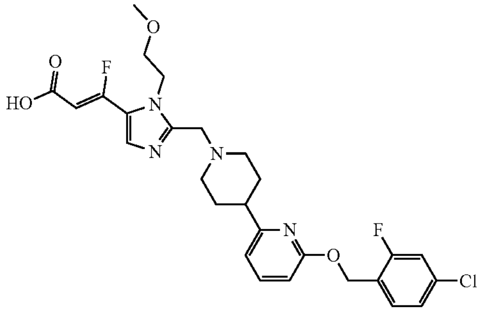 [SMILES: COCCn1c(/C(F)=C/C(=O)O)cnc1CN1CCC(c2cccc(OCc3ccc(Cl)cc3F)n2)CC1]
222a
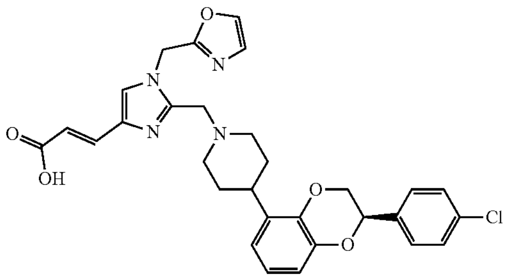 [SMILES: O=C(O)/C=C/c1cn(Cc2ncco2)c(CN2CCC(c3cccc4c3OC[C@@H](c3ccc(Cl)cc3)O4)CC2)n1]
223
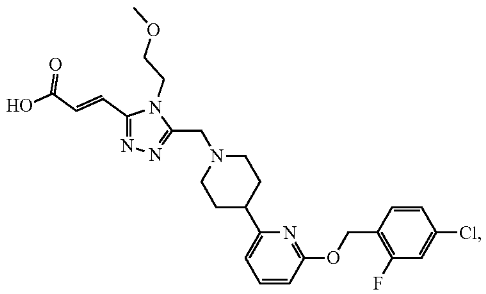 [SMILES: COCCn1c(/C=C/C(=O)O)nnc1CN1CCC(c2cccc(OCc3ccc(Cl)cc3F)n2)CC1]
, -continued
224
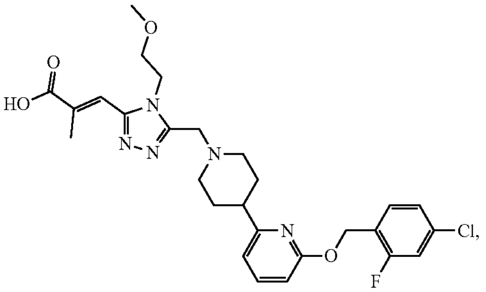 [SMILES: COCCn1c(/C=C(\C)C(=O)O)nnc1CN1CCC(c2cccc(OCc3ccc(Cl)cc3F)n2)CC1]
225a
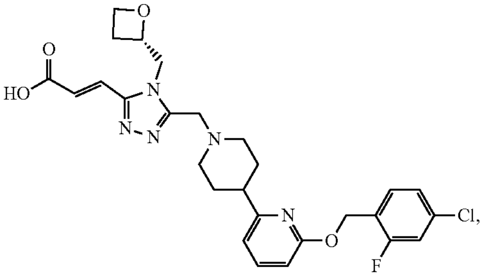 [SMILES: O=C(O)/C=C/c1nnc(CN2CCC(c3cccc(OCc4ccc(Cl)cc4F)n3)CC2)n1C[C@@H]1CCO1]
226a
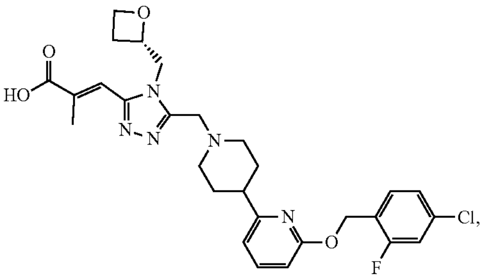
227
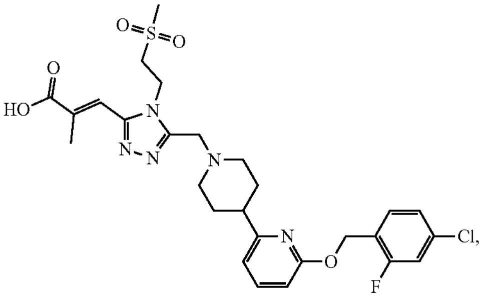 [SMILES: C/C(=C\c1nnc(CN2CCC(c3cccc(OCc4ccc(Cl)cc4F)n3)CC2)n1CCS(C)(=O)=O)C(=O)O]
228
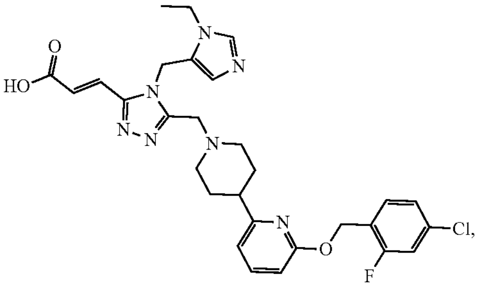 [SMILES: CCn1cncc1Cn1c(/C=C/C(=O)O)nnc1CN1CCC(c2cccc(OCc3ccc(Cl)cc3F)n2)CC1]
-continued
229
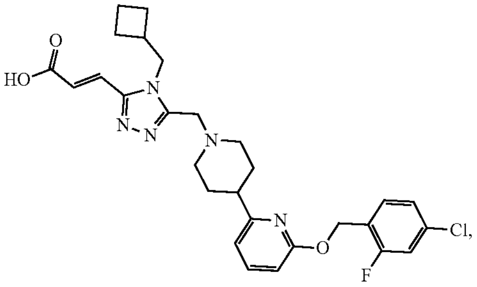 [SMILES: O=C(O)/C=C/c1nnc(CN2CCC(c3cccc(OCc4ccc(Cl)cc4F)n3)CC2)n1CC1CCC1]
230
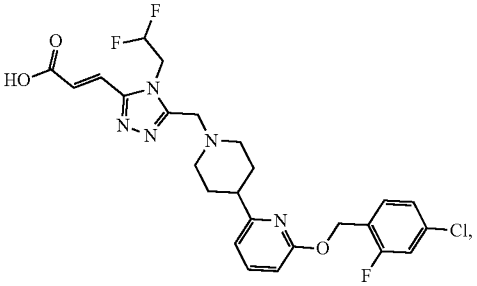 [SMILES: O=C(O)/C=C/c1nnc(CN2CCC(c3cccc(OCc4ccc(Cl)cc4F)n3)CC2)n1CC(F)F]
231
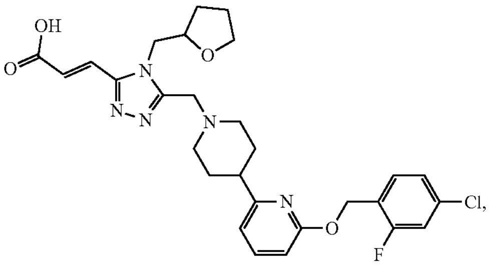 [SMILES: O=C(O)/C=C/c1nnc(CN2CCC(c3cccc(OCc4ccc(Cl)cc4F)n3)CC2)n1CC1CCCO1]
232
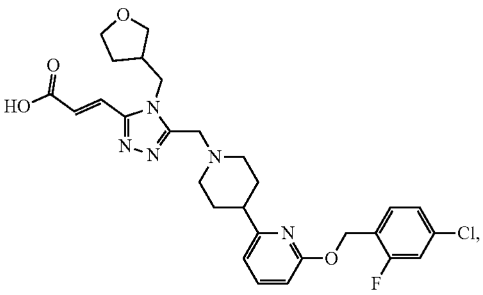 [SMILES: O=C(O)/C=C/c1nnc(CN2CCC(c3cccc(OCc4ccc(Cl)cc4F)n3)CC2)n1CC1CCOC1]
233
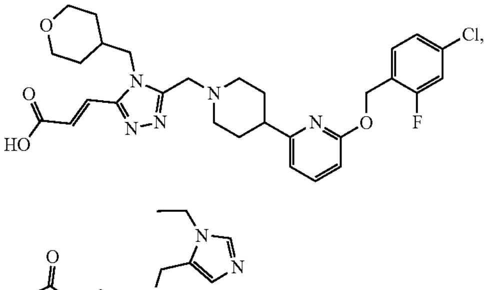
234a
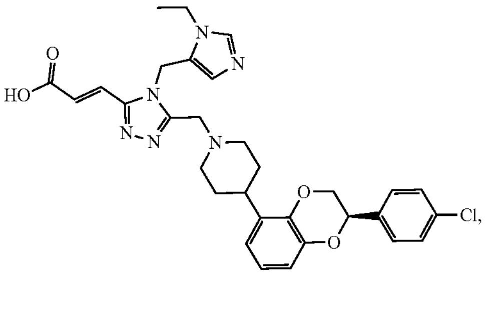 [SMILES: CCn1cncc1Cn1c(/C=C/C(=O)O)nnc1CN1CCC(c2cccc3c2OC[C@@H](c2ccc(Cl)cc2)O3)CC1]

-continued
235
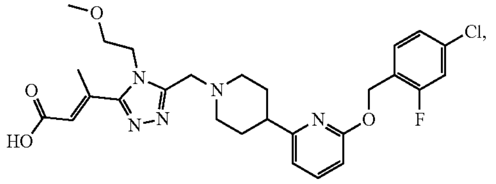 [SMILES: COCCn1c(CN2CCC(c3cccc(OCc4ccc(Cl)cc4F)n3)CC2)nnc1/C(C)=C/C(=O)O]
236
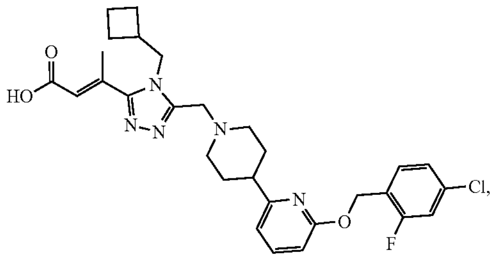 [SMILES: C/C(=C\C(=O)O)c1nnc(CN2CCC(c3cccc(OCc4ccc(Cl)cc4F)n3)CC2)n1CC1CCC1]
237
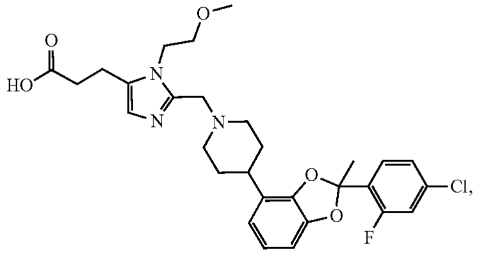 [SMILES: COCCn1c(CCC(=O)O)cnc1CN1CCC(c2cccc3c2OC(C)(c2ccc(Cl)cc2F)O3)CC1]
238
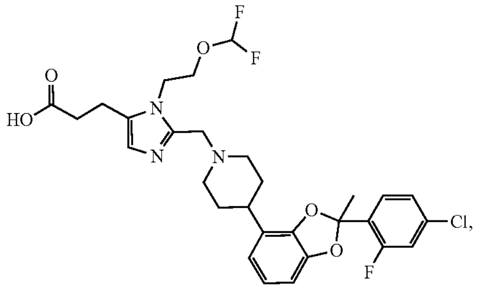 [SMILES: CC1(c2ccc(Cl)cc2F)Oc2cccc(C3CCN(Cc4ncc(CCC(=O)O)n4CCOC(F)F)CC3)c2O1]
239
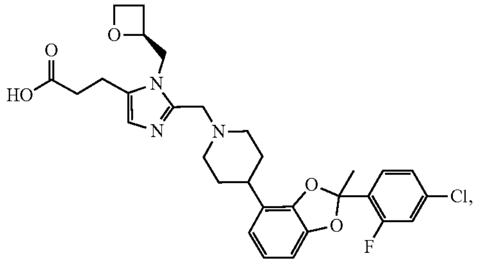 [SMILES: CC1(c2ccc(Cl)cc2F)Oc2cccc(C3CCN(Cc4ncc(CCC(=O)O)n4C[C@@H]4CCO4)CC3)c2O1]
240
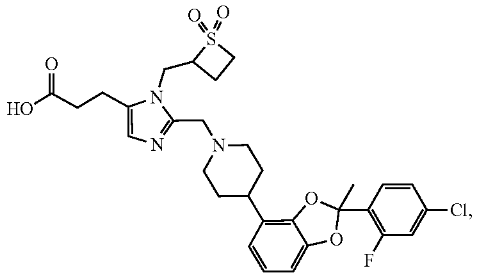 [SMILES: CC1(c2ccc(Cl)cc2F)Oc2cccc(C3CCN(Cc4ncc(CCC(=O)O)n4CC4CCS4(=O)=O)CC3)c2O1]
-continued
241
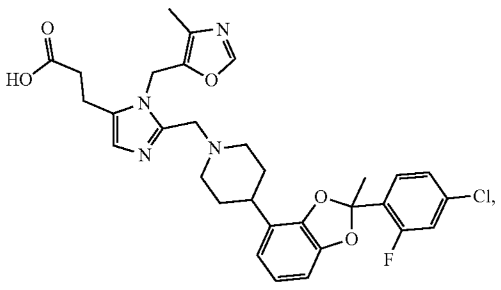 [SMILES: Cc1ncoc1Cn1c(CCC(=O)O)cnc1CN1CCC(c2cccc3c2OC(C)(c2ccc(Cl)cc2F)O3)CC1]
242
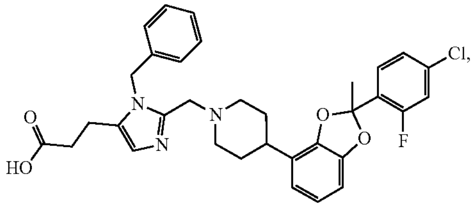 [SMILES: CC1(c2ccc(Cl)cc2F)Oc2cccc(C3CCN(Cc4ncc(CCC(=O)O)n4Cc4ccccc4)CC3)c2O1]
243
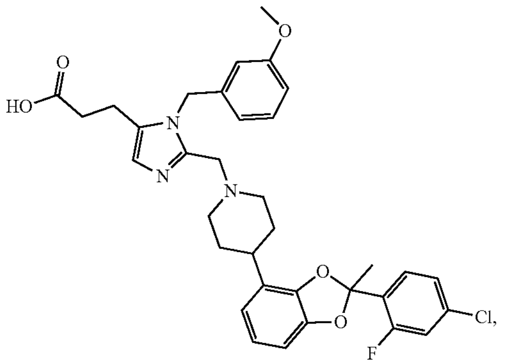 [SMILES: COc1cccc(Cn2c(CCC(=O)O)cnc2CN2CCC(c3cccc4c3OC(C)(c3ccc(Cl)cc3F)O4)CC2)c1]
244
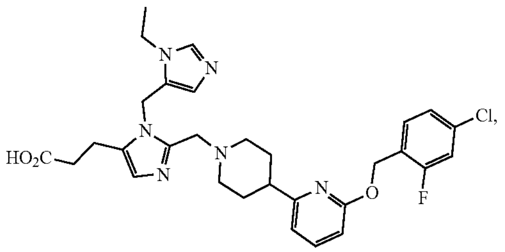 [SMILES: CCn1cncc1Cn1c(CCC(=O)O)cnc1CN1CCC(c2cccc(OCc3ccc(Cl)cc3F)n2)CC1]
245
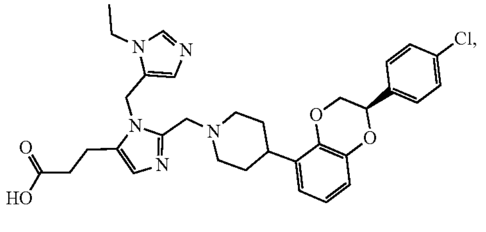 [SMILES: CCn1cncc1Cn1c(CCC(=O)O)cnc1CN1CCC(c2cccc3c2OC[C@@H](c2ccc(Cl)cc2)O3)CC1]
246
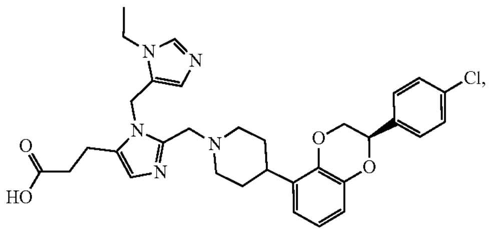 [SMILES: CCn1cncc1Cn1c(CCC(=O)O)cnc1CN1CCC(c2cccc3c2OC[C@@H](c2ccc(Cl)cc2)O3)CC1]

-continued
247
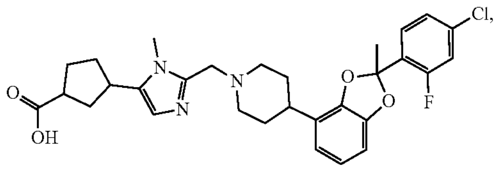 [SMILES: Cn1c(C2CCC(C(=O)O)C2)cnc1CN1CCC(c2cccc3c2OC(C)(c2ccc(Cl)cc2F)O3)CC1]
248
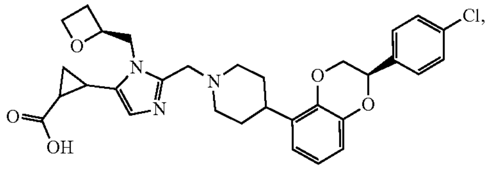 [SMILES: O=C(O)C1CC1c1cnc(CN2CCC(c3cccc4c3OC[C@@H](c3ccc(Cl)cc3)O4)CC2)n1C[C@@H]1CCO1]
249a
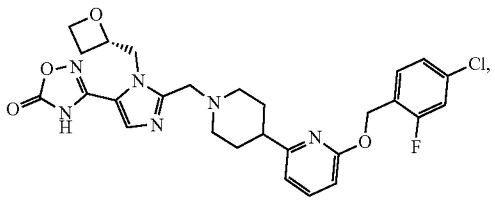 [SMILES: O=c1[nH]c(-c2cnc(CN3CCC(c4cccc(OCc5ccc(Cl)cc5F)n4)CC3)n2C[C@@H]2CCO2)no1]
250
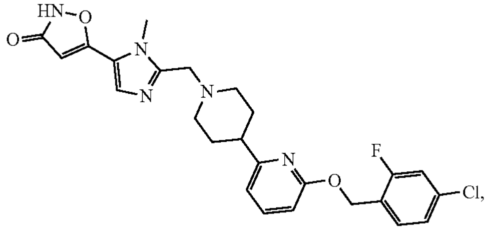 [SMILES: Cn1c(-c2cc(=O)[nH]o2)cnc1CN1CCC(c2cccc(OCc3ccc(Cl)cc3F)n2)CC1]
251
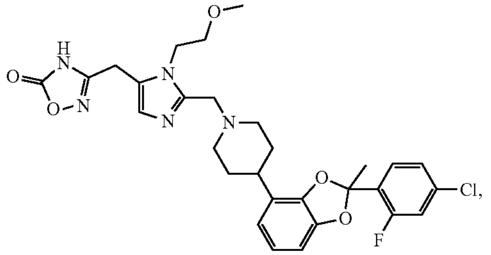 [SMILES: COCCn1c(Cc2noc(=O)[nH]2)cnc1CN1CCC(c2cccc3c2OC(C)(c2ccc(Cl)cc2F)O3)CC1]
252
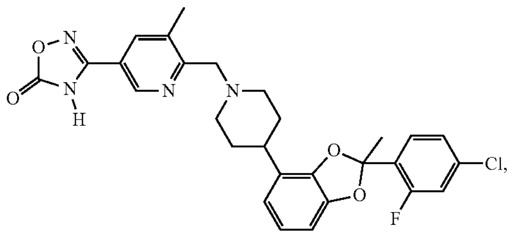 [SMILES: Cc1cc(-c2noc(=O)[nH]2)cnc1CN1CCC(c2cccc3c2OC(C)(c2ccc(Cl)cc2F)O3)CC1]
253
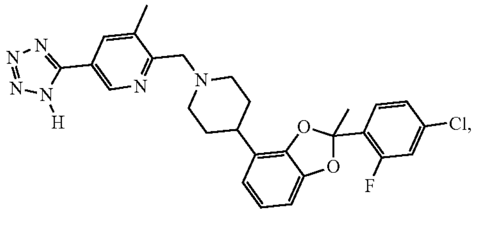 [SMILES: Cc1cc(-c2nnn[nH]2)cnc1CN1CCC(c2cccc3c2OC(C)(c2ccc(Cl)cc2F)O3)CC1]
-continued
254
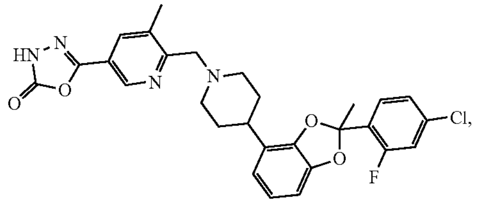 [SMILES: Cc1cc(-c2n[nH]c(=O)o2)cnc1CN1CCC(c2cccc3c2OC(C)(c2ccc(Cl)cc2F)O3)CC1]
255
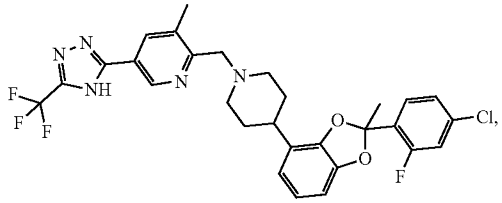 [SMILES: Cc1cc(-c2nnc(C(F)(F)F)[nH]2)cnc1CN1CCC(c2cccc3c2OC(C)(c2ccc(Cl)cc2F)O3)CC1]
256
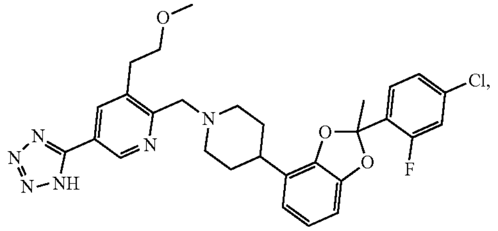 [SMILES: COCCc1cc(-c2nnn[nH]2)cnc1CN1CCC(c2cccc3c2OC(C)(c2ccc(Cl)cc2F)O3)CC1]
257
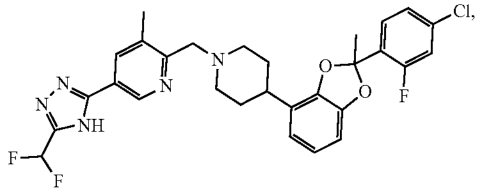 [SMILES: Cc1cc(-c2nnc(C(F)F)[nH]2)cnc1CN1CCC(c2cccc3c2OC(C)(c2ccc(Cl)cc2F)O3)CC1]
258
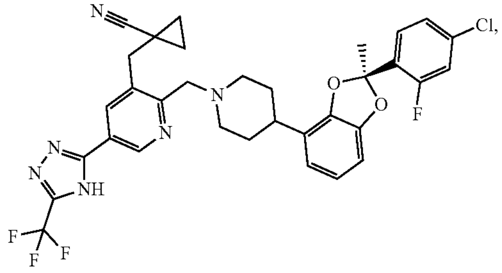 [SMILES: C[C@]1(c2ccc(Cl)cc2F)Oc2cccc(C3CCN(Cc4ncc(-c5nnc(C(F)(F)F)[nH]5)cc4CC4(C#N)CC4)CC3)c2O1]
259
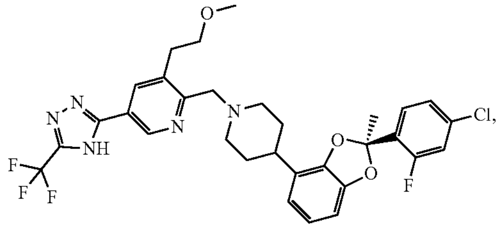 [SMILES: COCCc1cc(-c2nnc(C(F)(F)F)[nH]2)cnc1CN1CCC(c2cccc3c2O[C@@](C)(c2ccc(Cl)cc2F)O3)CC1]
260
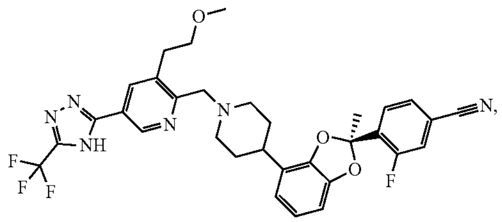 [SMILES: COCCc1cc(-c2nnc(C(F)(F)F)[nH]2)cnc1CN1CCC(c2cccc3c2O[C@@](C)(c2ccc(C#N)cc2F)O3)CC1]

-continued
261
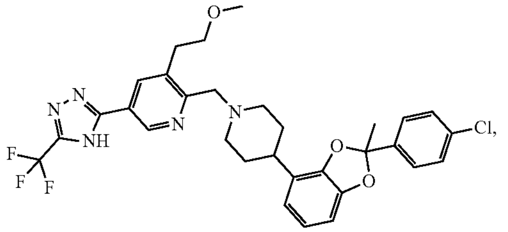 [SMILES: COCCc1cc(-c2nnc(C(F)(F)F)[nH]2)cnc1CN1CCC(c2cccc3c2OC(C)(c2ccc(Cl)cc2)O3)CC1]
262
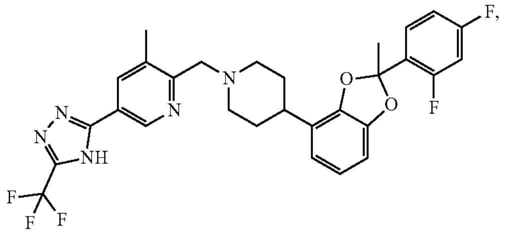 [SMILES: Cc1cc(-c2nnc(C(F)(F)F)[nH]2)cnc1CN1CCC(c2cccc3c2OC(C)(c2ccc(F)cc2F)O3)CC1]
263
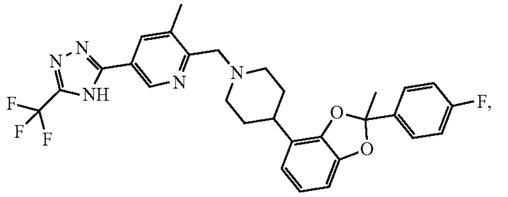 [SMILES: Cc1cc(-c2nnc(C(F)(F)F)[nH]2)cnc1CN1CCC(c2cccc3c2OC(C)(c2ccc(F)cc2)O3)CC1]
264
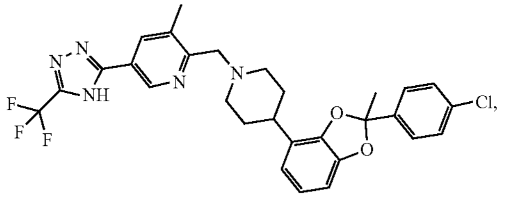 [SMILES: Cc1cc(-c2nnc(C(F)(F)F)[nH]2)cnc1CN1CCC(c2cccc3c2OC(C)(c2ccc(Cl)cc2)O3)CC1]
265
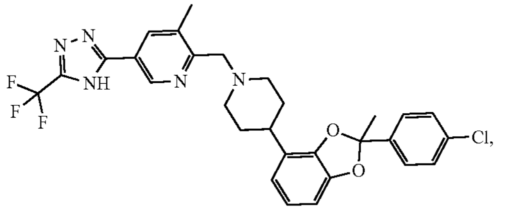 [SMILES: Cc1cc(-c2nnc(C(F)(F)F)[nH]2)cnc1CN1CCC(c2cccc3c2OC(C)(c2ccc(Cl)cc2)O3)CC1]
266
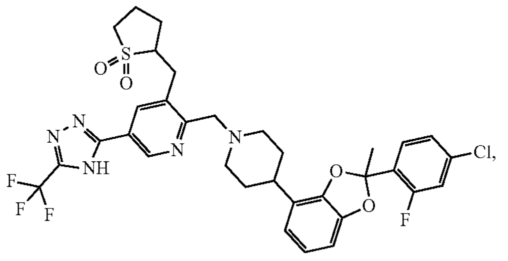 [SMILES: CC1(c2ccc(Cl)cc2F)Oc2cccc(C3CCN(Cc4ncc(-c5nnc(C(F)(F)F)[nH]5)cc4CC4CCCS4(=O)=O)CC3)c2O1]
267
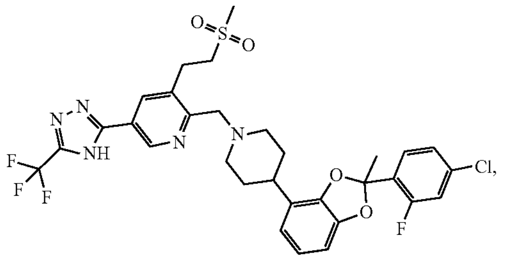 [SMILES: CC1(c2ccc(Cl)cc2F)Oc2cccc(C3CCN(Cc4ncc(-c5nnc(C(F)(F)F)[nH]5)cc4CCS(C)(=O)=O)CC3)c2O1]
-continued
268
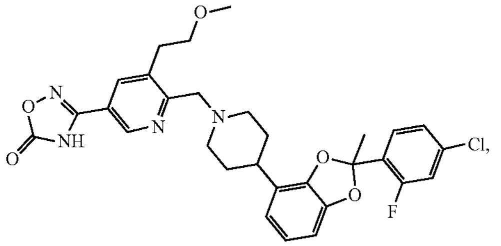 [SMILES: COCCc1cc(-c2noc(=O)[nH]2)cnc1CN1CCC(c2cccc3c2OC(C)(c2ccc(Cl)cc2F)O3)CC1]
269
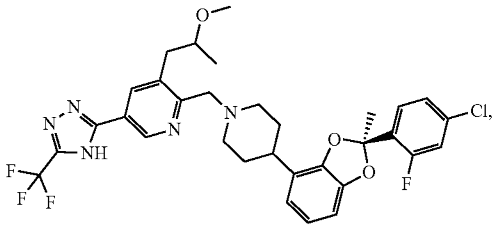 [SMILES: COC(C)Cc1cc(-c2nnc(C(F)(F)F)[nH]2)cnc1CN1CCC(c2cccc3c2O[C@@](C)(c2ccc(Cl)cc2F)O3)CC1]
269a
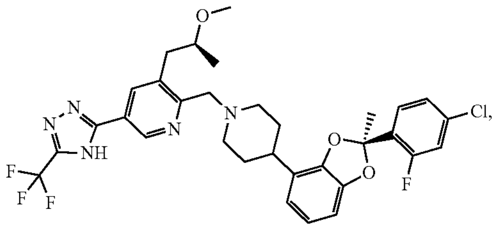 [SMILES: CO[C@@H](C)Cc1cc(-c2nnc(C(F)(F)F)[nH]2)cnc1CN1CCC(c2cccc3c2O[C@@](C)(c2ccc(Cl)cc2F)O3)CC1]
269b
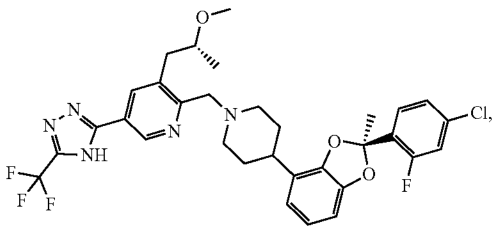 [SMILES: CO[C@H](C)Cc1cc(-c2nnc(C(F)(F)F)[nH]2)cnc1CN1CCC(c2cccc3c2O[C@@](C)(c2ccc(Cl)cc2F)O3)CC1]
270
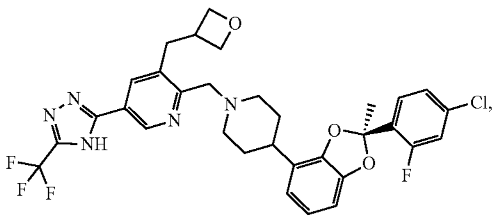 [SMILES: C[C@]1(c2ccc(Cl)cc2F)Oc2cccc(C3CCN(Cc4ncc(-c5nnc(C(F)(F)F)[nH]5)cc4CC4COC4)CC3)c2O1]
271
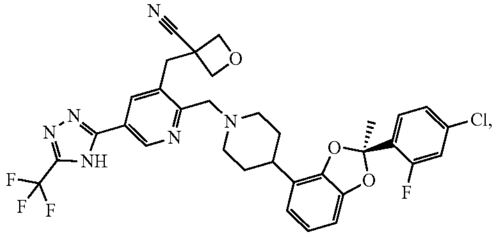 [SMILES: C[C@]1(c2ccc(Cl)cc2F)Oc2cccc(C3CCN(Cc4ncc(-c5nnc(C(F)(F)F)[nH]5)cc4CC4(C#N)COC4)CC3)c2O1]

-continued
272
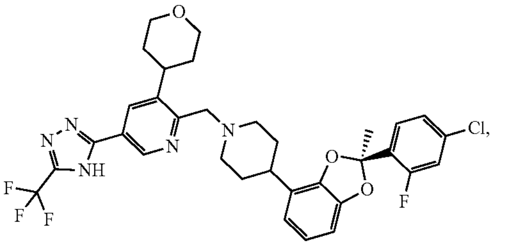 [SMILES: C[C@]1(c2ccc(Cl)cc2F)Oc2cccc(C3CCN(Cc4ncc(-c5nnc(C(F)(F)F)[nH]5)cc4C4CCOCC4)CC3)c2O1]
273
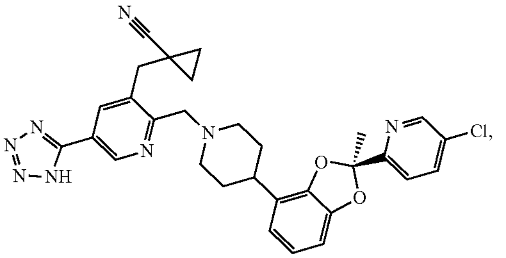 [SMILES: C[C@]1(c2ccc(Cl)cn2)Oc2cccc(C3CCN(Cc4ncc(-c5nnn[nH]5)cc4CC4(C#N)CC4)CC3)c2O1]
274
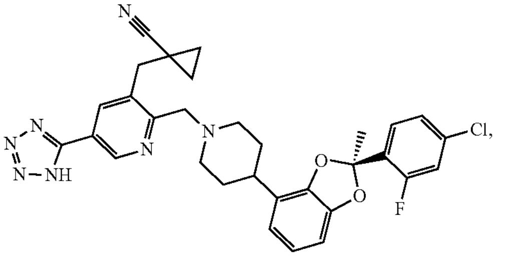 [SMILES: C[C@]1(c2ccc(Cl)cc2F)Oc2cccc(C3CCN(Cc4ncc(-c5nnn[nH]5)cc4CC4(C#N)CC4)CC3)c2O1]
275
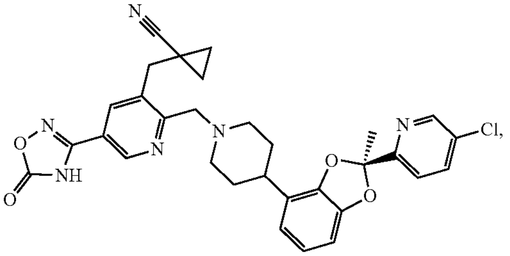 [SMILES: C[C@]1(c2ccc(Cl)cn2)Oc2cccc(C3CCN(Cc4ncc(-c5noc(=O)[nH]5)cc4CC4(C#N)CC4)CC3)c2O1]
276
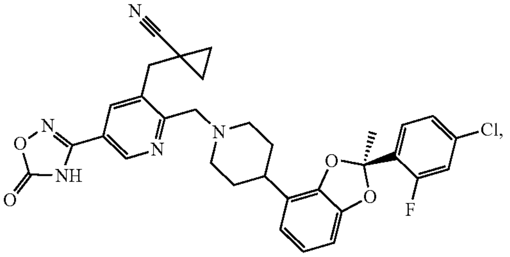 [SMILES: C[C@]1(c2ccc(Cl)cc2F)Oc2cccc(C3CCN(Cc4ncc(-c5noc(=O)[nH]5)cc4CC4(C#N)CC4)CC3)c2O1]
277
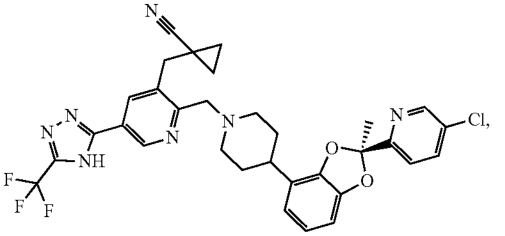 [SMILES: C[C@]1(c2ccc(Cl)cn2)Oc2cccc(C3CCN(Cc4ncc(-c5nnc(C(F)(F)F)[nH]5)cc4CC4(C#N)CC4)CC3)c2O1]
-continued
278
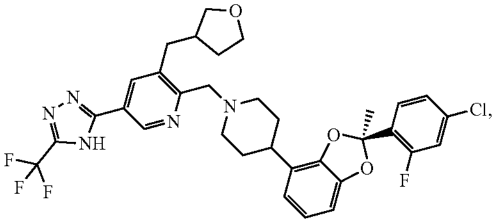 [SMILES: C[C@]1(c2ccc(Cl)cc2F)Oc2cccc(C3CCN(Cc4ncc(-c5nnc(C(F)(F)F)[nH]5)cc4CC4CCOC4)CC3)c2O1]
279
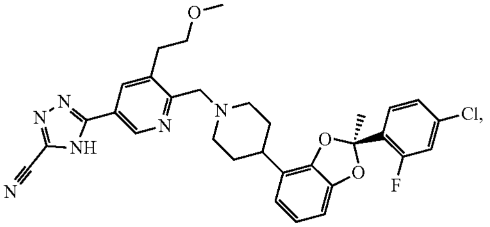 [SMILES: COCCc1cc(-c2nnc(C#N)[nH]2)cnc1CN1CCC(c2cccc3c2O[C@@](C)(c2ccc(Cl)cc2F)O3)CC1]
280
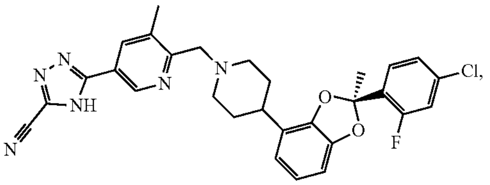 [SMILES: Cc1cc(-c2nnc(C#N)[nH]2)cnc1CN1CCC(c2cccc3c2O[C@@](C)(c2ccc(Cl)cc2F)O3)CC1]
281
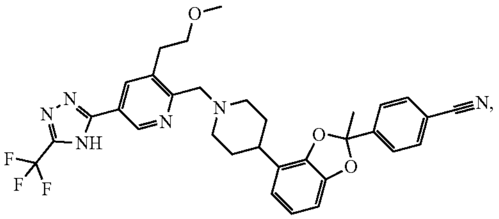 [SMILES: COCCc1cc(-c2nnc(C(F)(F)F)[nH]2)cnc1CN1CCC(c2cccc3c2OC(C)(c2ccc(C#N)cc2)O3)CC1]
282
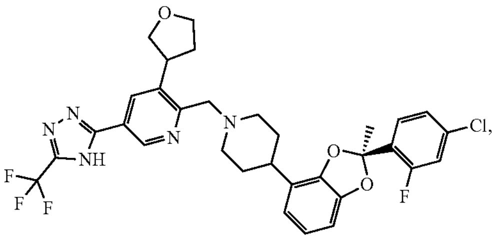 [SMILES: C[C@]1(c2ccc(Cl)cc2F)Oc2cccc(C3CCN(Cc4ncc(-c5nnc(C(F)(F)F)[nH]5)cc4C4CCOC4)CC3)c2O1]
283
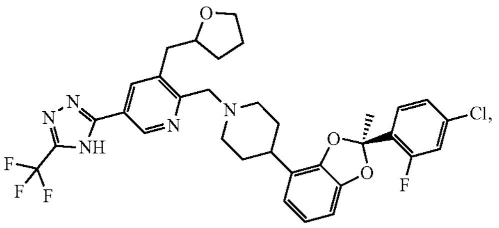 [SMILES: C[C@]1(c2ccc(Cl)cc2F)Oc2cccc(C3CCN(Cc4ncc(-c5nnc(C(F)(F)F)[nH]5)cc4CC4CCCO4)CC3)c2O1]
284
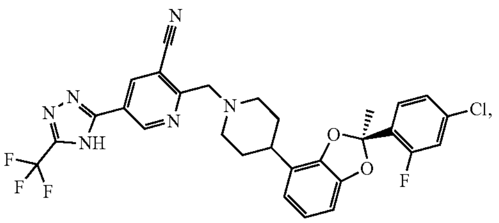 [SMILES: C[C@]1(c2ccc(Cl)cc2F)Oc2cccc(C3CCN(Cc4ncc(-c5nnc(C(F)(F)F)[nH]5)cc4C#N)CC3)c2O1]

-continued
285
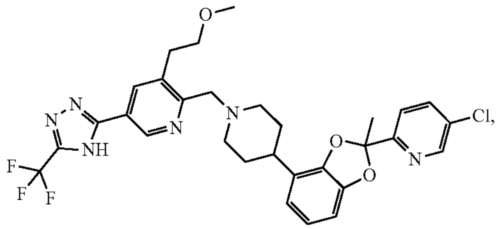 [SMILES: COCCc1cc(-c2nnc(C(F)(F)F)[nH]2)cnc1CN1CCC(c2cccc3c2OC(C)(c2ccc(Cl)cn2)O3)CC1]
286
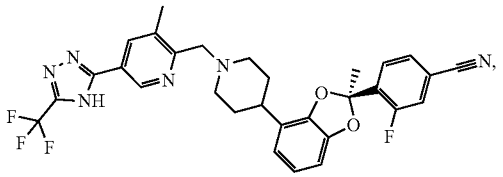 [SMILES: Cc1cc(-c2nnc(C(F)(F)F)[nH]2)cnc1CN1CCC(c2cccc3c2O[C@@](C)(c2ccc(C#N)cc2F)O3)CC1]
287
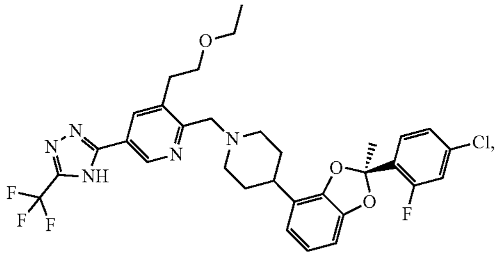 [SMILES: CCOCCc1cc(-c2nnc(C(F)(F)F)[nH]2)cnc1CN1CCC(c2cccc3c2O[C@@](C)(c2ccc(Cl)cc2F)O3)CC1]
288
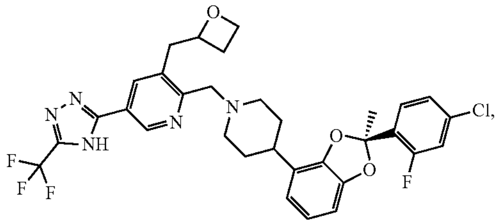 [SMILES: C[C@]1(c2ccc(Cl)cc2F)Oc2cccc(C3CCN(Cc4ncc(-c5nnc(C(F)(F)F)[nH]5)cc4CC4CCO4)CC3)c2O1]
289
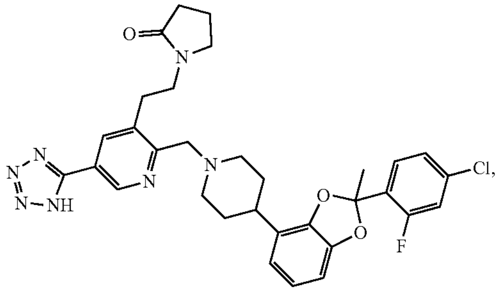 [SMILES: CC1(c2ccc(Cl)cc2F)Oc2cccc(C3CCN(Cc4ncc(-c5nnn[nH]5)cc4CCN4CCCC4=O)CC3)c2O1]
290
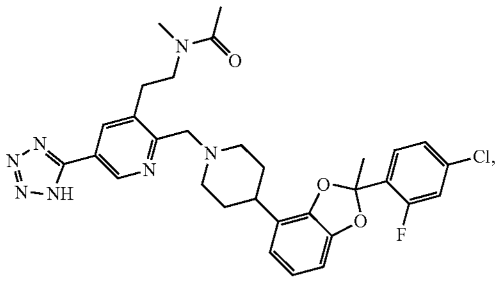 [SMILES: CC(=O)N(C)CCc1cc(-c2nnn[nH]2)cnc1CN1CCC(c2cccc3c2OC(C)(c2ccc(Cl)cc2F)O3)CC1]
-continued
291
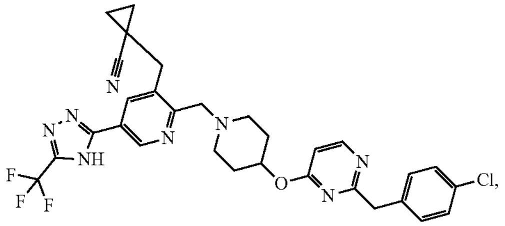 [SMILES: N#CC1(Cc2cc(-c3nnc(C(F)(F)F)[nH]3)cnc2CN2CCC(Oc3ccnc(Cc4ccc(Cl)cc4)n3)CC2)CC1]
292
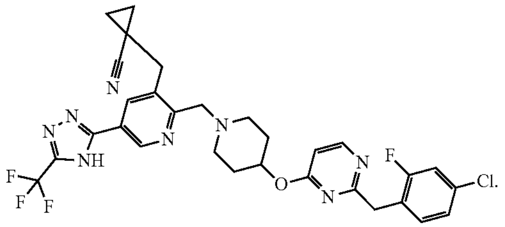 [SMILES: N#CC1(Cc2cc(-c3nnc(C(F)(F)F)[nH]3)cnc2CN2CCC(Oc3ccnc(Cc4ccc(Cl)cc4F)n3)CC2)CC1]
2. A pharmaceutical composition comprising a compound of claim 1, or a pharmaceutically acceptable salt or solvate thereof, and a pharmaceutically acceptable excipient.
3. The compound of claim 1, or a pharmaceutically acceptable salt thereof, wherein the compound is selected from the group consisting of:
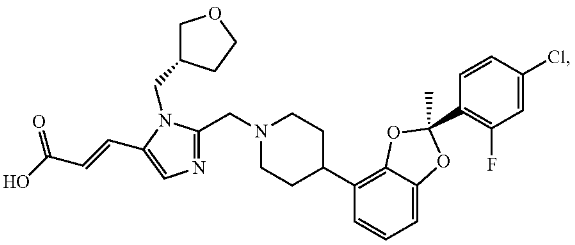
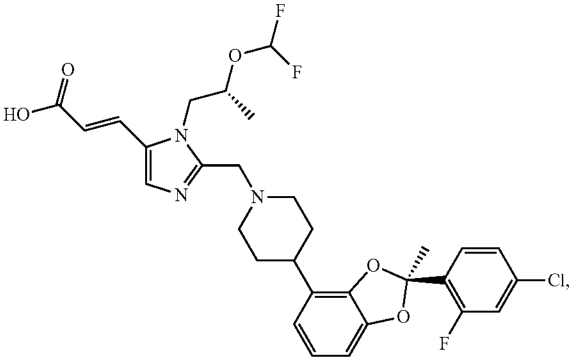
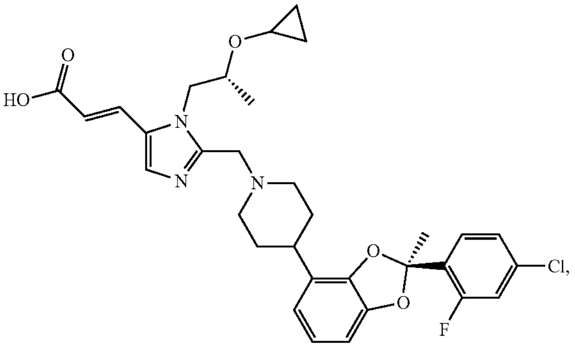

-continued

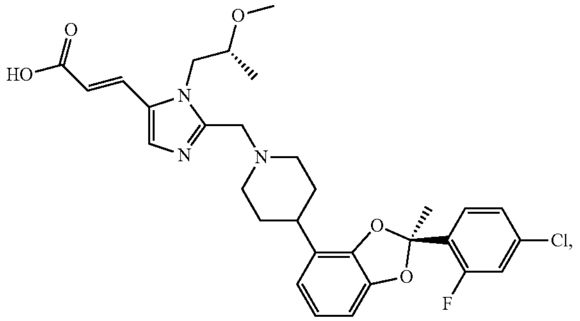

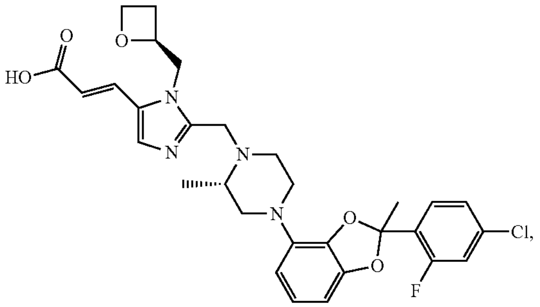

and

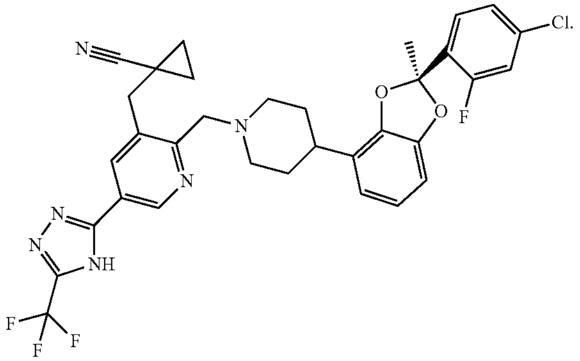 [SMILES: C[C@]1(c2ccc(Cl)cc2F)Oc2cccc(C3CCN(Cc4ncc(-c5nnc(C(F)(F)F)[nH]5)cc4CC4(C#N)CC4)CC3)c2O1]

4. A compound which is:

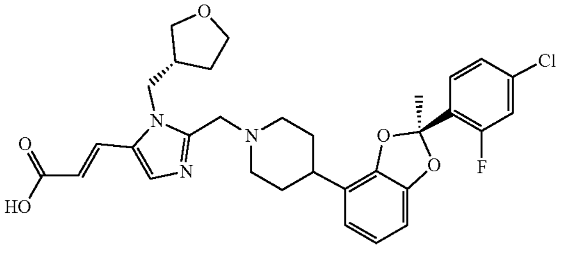 [SMILES: C[C@]1(c2ccc(Cl)cc2F)Oc2cccc(C3CCN(Cc4ncc(/C=C/C(=O)O)n4C[C@H]4CCOC4)CC3)c2O1]

or a pharmaceutically acceptable salt thereof.

5. A compound which is:

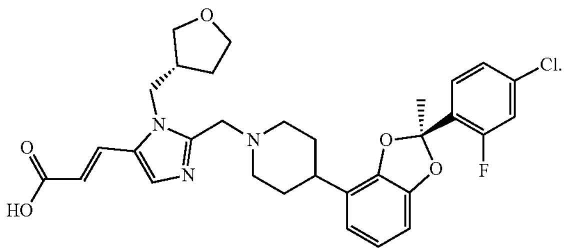 [SMILES: C[C@]1(c2ccc(Cl)cc2F)Oc2cccc(C3CCN(Cc4ncc(/C=C/C(=O)O)n4C[C@H]4CCOC4)CC3)c2O1]

6. A pharmaceutical composition comprising the compound of claim 4, or a pharmaceutically acceptable salt thereof, and a pharmaceutically acceptable excipient.

7. A compound which is:

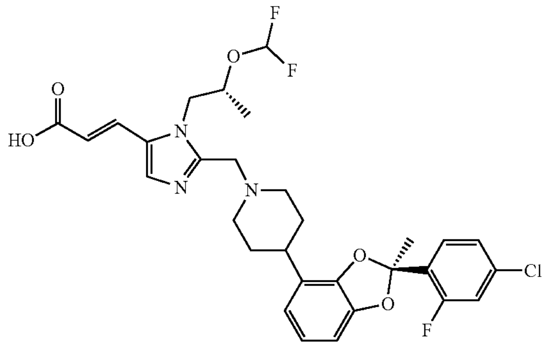 [SMILES: C[C@H](Cn1c(/C=C/C(=O)O)cnc1CN1CCC(c2cccc3c2O[C@@](C)(c2ccc(Cl)cc2F)O3)CC1)OC(F)F]

or a pharmaceutically acceptable salt thereof.

8. A compound which is:

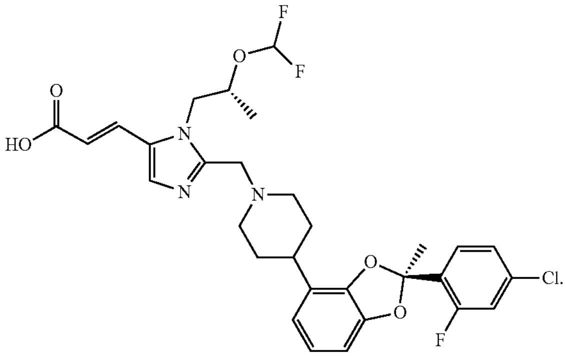 [SMILES: C[C@H](Cn1c(/C=C/C(=O)O)cnc1CN1CCC(c2cccc3c2O[C@@](C)(c2ccc(Cl)cc2F)O3)CC1)OC(F)F]

9. A pharmaceutical composition comprising the compound of claim 7, or a pharmaceutically acceptable salt thereof, and a pharmaceutically acceptable excipient.

10. A compound which is:

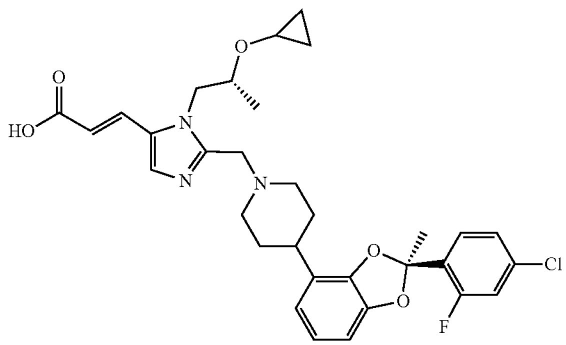 [SMILES: C[C@H](Cn1c(/C=C/C(=O)O)cnc1CN1CCC(c2cccc3c2O[C@@](C)(c2ccc(Cl)cc2F)O3)CC1)OC1CC1]

or a pharmaceutically acceptable salt thereof.

11. A compound which is:

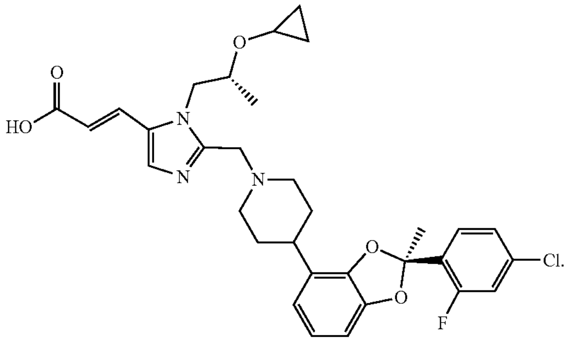 [SMILES: C[C@H](Cn1c(/C=C/C(=O)O)cnc1CN1CCC(c2cccc3c2O[C@@](C)(c2ccc(Cl)cc2F)O3)CC1)OC1CC1]

12. A pharmaceutical composition comprising the compound of claim 10, or a pharmaceutically acceptable salt thereof, and a pharmaceutically acceptable excipient.

13. A compound which is:

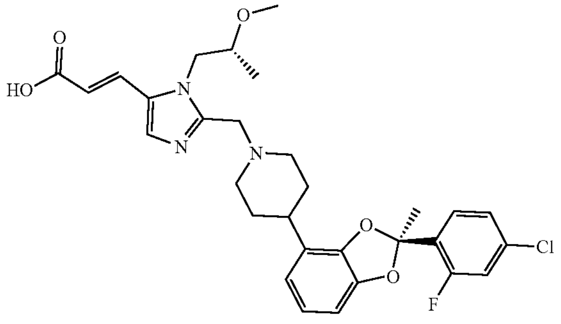 [SMILES: CO[C@H](C)Cn1c(/C=C/C(=O)O)cnc1CN1CCC(c2cccc3c2O[C@@](C)(c2ccc(Cl)cc2F)O3)CC1]

or a pharmaceutically acceptable salt thereof.

14. A compound which is:

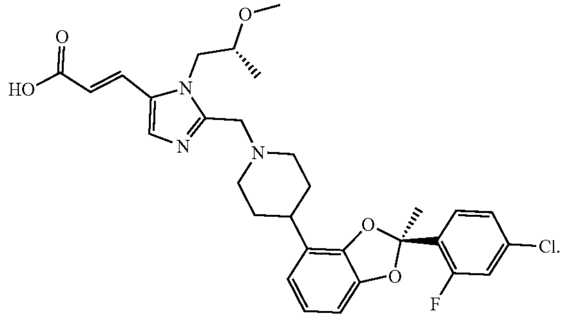 [SMILES: CO[C@H](C)Cn1c(/C=C/C(=O)O)cnc1CN1CCC(c2cccc3c2O[C@@](C)(c2ccc(Cl)cc2F)O3)CC1]

15. A pharmaceutical composition comprising the compound of claim 13, or a pharmaceutically acceptable salt thereof, and a pharmaceutically acceptable excipient.

16. A compound which is:

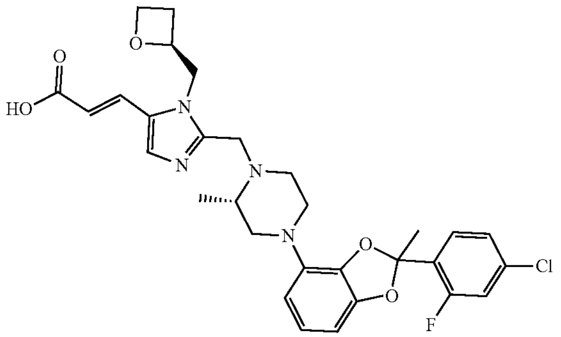 [SMILES: C[C@H]1CN(c2cccc3c2OC(C)(c2ccc(Cl)cc2F)O3)CCN1Cc1ncc(/C=C/C(=O)O)n1C[C@@H]1CCO1]

or a pharmaceutically acceptable salt thereof.

17. A compound which is:

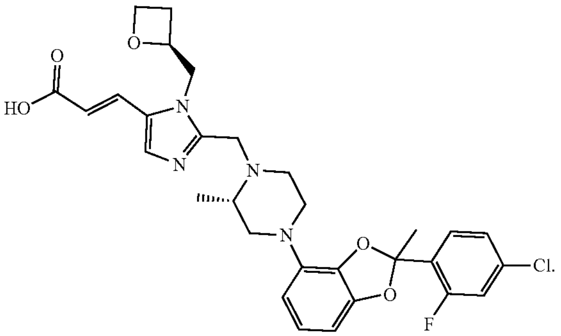 [SMILES: C[C@H]1CN(c2cccc3c2OC(C)(c2ccc(Cl)cc2F)O3)CCN1Cc1ncc(/C=C/C(=O)O)n1C[C@@H]1CCO1]

18. A pharmaceutical composition comprising the compound of claim 16, or a pharmaceutically acceptable salt thereof, and a pharmaceutically acceptable excipient.

19. A compound which is:
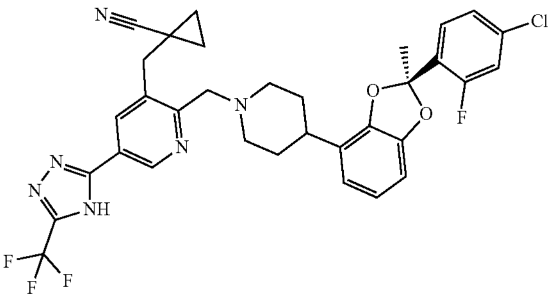 [SMILES: C[C@]1(c2ccc(Cl)cc2F)Oc2cccc(C3CCN(Cc4ncc(-c5nnc(C(F)(F)F)[nH]5)cc4CC4(C#N)CC4)CC3)c2O1]
or a pharmaceutically acceptable salt thereof.
20. A compound which is:
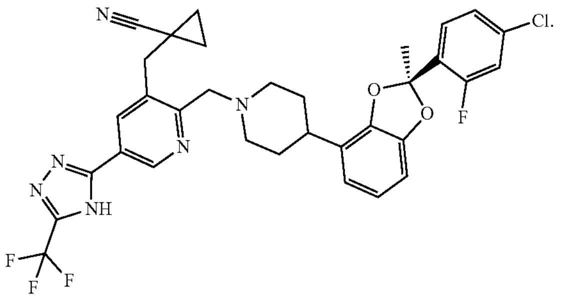 [SMILES: C[C@]1(c2ccc(Cl)cc2F)Oc2cccc(C3CCN(Cc4ncc(-c5nnc(C(F)(F)F)[nH]5)cc4CC4(C#N)CC4)CC3)c2O1]
21. A pharmaceutical composition comprising the compound of claim 19, or a pharmaceutically acceptable salt thereof, and a pharmaceutically acceptable excipient.
* * * * *